(12) United States Patent
Crawford et al.

(10) Patent No.: US 11,731,943 B2
(45) Date of Patent: Aug. 22, 2023

(54) THERAPEUTIC COMPOUNDS, COMPOSITIONS AND METHODS OF USE THEREOF

(71) Applicant: Genentech, Inc., South San Francisco, CA (US)

(72) Inventors: James John Crawford, San Francisco, CA (US); Mark Zak, Davidsonville, MD (US); Terry Kellar, Burlingame, CA (US); Yun-Xing Cheng, Montreal (CA); Wei Li, Beijing (CN); F. Anthony Romero, Redwood City, CA (US); Paul Gibbons, San Francisco, CA (US); Guiling Zhao, San Mateo, CA (US); Gregory Hamilton, Atlanta, GA (US); Simon Charles Goodacre, Harlow (GB)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 17/177,356

(22) Filed: Feb. 17, 2021

(65) Prior Publication Data
US 2021/0179564 A1     Jun. 17, 2021

Related U.S. Application Data

(63) Continuation of application No. 16/181,228, filed on Nov. 5, 2018, now abandoned, which is a continuation of application No. PCT/EP2017/060349, filed on May 2, 2017.

(60) Provisional application No. 62/418,500, filed on Nov. 7, 2016.

(30) Foreign Application Priority Data

May 5, 2016   (WO) ............... PCT/CN2016/081093
May 10, 2016  (WO) ............... PCT/CN2016/081566

(51) Int. Cl.
| | |
|---|---|
| *C07D 231/40* | (2006.01) |
| *C07D 401/04* | (2006.01) |
| *C07D 401/14* | (2006.01) |
| *C07D 403/08* | (2006.01) |
| *C07D 405/04* | (2006.01) |
| *C07D 405/12* | (2006.01) |
| *C07D 405/14* | (2006.01) |
| *C07D 409/14* | (2006.01) |
| *C07D 413/14* | (2006.01) |
| *C07D 417/14* | (2006.01) |

(52) U.S. Cl.
CPC ......... *C07D 231/40* (2013.01); *C07D 401/04* (2013.01); *C07D 401/14* (2013.01); *C07D 403/08* (2013.01); *C07D 405/04* (2013.01); *C07D 405/12* (2013.01); *C07D 405/14* (2013.01); *C07D 409/14* (2013.01); *C07D 413/14* (2013.01); *C07D 417/14* (2013.01)

(58) Field of Classification Search
CPC .. C07D 231/40; C07D 401/04; C07D 401/14; C07D 403/08; C07D 405/04; C07D 405/12; C07D 409/14
See application file for complete search history.

(56) References Cited

U.S. PATENT DOCUMENTS

| | | | |
|---|---|---|---|
| 2014/0228348 A1* | 8/2014 | Brubaker ............. | C07D 403/12 514/210.18 |
| 2014/0243309 A1 | 8/2014 | Brubaker et al. | |

FOREIGN PATENT DOCUMENTS

| | | |
|---|---|---|
| JP | 2014526523 | 10/2014 |
| JP | 2014530203 | 11/2014 |
| WO | 2010/014453 A1 | 2/2010 |
| WO | 2013/043962 | 3/2013 |
| WO | 2015/184305 A1 | 12/2015 |

OTHER PUBLICATIONS

International Preliminary Report on Patentability—PCT/EP2017/060349 dated Nov. 6, 2018, pp. 1-10.
PCT ISR and Written Opinion for PCT/EP2017/060349.

* cited by examiner

*Primary Examiner* — Timothy R Rozof
(74) *Attorney, Agent, or Firm* — Robert C. Hall

(57) ABSTRACT

Compounds of Formula (I):

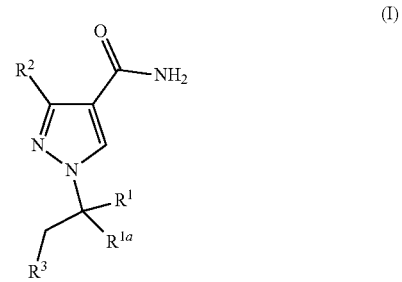

and salts thereof, and methods of use as Janus kinase inhibitors are described herein.

8 Claims, No Drawings

THERAPEUTIC COMPOUNDS, COMPOSITIONS AND METHODS OF USE THEREOF

CROSS-REFERENCE TO RELATED APPLICATIONS

This application is a continuation of U.S. application Ser. No. 16/181,228 filed on Nov. 5, 2018, which is a continuation of International Application No. PCT/EP2017/060349, filed May 2, 2017, which claims priority to International Application No. PCT/CN2016/081093, filed May 5, 2016, International Application No. PCT/CN2016/081566, filed May 10, 2016, and U.S. provisional application Ser. No. 62/418,500, filed Nov. 7, 2016, each of which is incorporated by reference in its entirety.

FIELD OF THE INVENTION

The field of the invention pertains to compounds that are inhibitors of a Janus kinase, such as JAK1, as well as compositions containing these compounds, and methods of use including, but not limited to, diagnosis or treatment of patients suffering from a condition responsive to the inhibition of a JAK kinase.

BACKGROUND OF INVENTION

Cytokine pathways mediate a broad range of biological functions, including many aspects of inflammation and immunity. Janus kinases (JAK), including JAK1, JAK2, JAK3 and TYK2, are cytoplasmic protein kinases that associate with type I and type II cytokine receptors and regulate cytokine signal transduction. Cytokine engagement with cognate receptors triggers activation of receptor associated JAKs and this leads to JAK-mediated tyrosine phosphorylation of signal transducer and activator of transcription (STAT) proteins and ultimately transcriptional activation of specific gene sets (Schindler et al., 2007, J. Biol. Chem. 282: 20059-63). JAK1, JAK2 and TYK2 exhibit broad patterns of gene expression, while JAK3 expression is limited to leukocytes. Cytokine receptors are typically functional as heterodimers, and as a result, more than one type of JAK kinase is usually associated with cytokine receptor complexes. The specific JAKs associated with different cytokine receptor complexes have been determined in many cases through genetic studies and corroborated by other experimental evidence. Exemplary therapeutic benefits of the inhibition of JAK enzymes are discussed, for example, in International Application No. WO 2013/014567.

JAK1 was initially identified in a screen for novel kinases (Wilks A. F., 1989, Proc. Natl. Acad. Sci. U.S.A. 86:1603-1607). Genetic and biochemical studies have shown that JAK1 is functionally and physically associated with the type I interferon (e.g., IFNalpha), type II interferon (e.g., IFN-gamma), and IL-2 and IL-6 cytokine receptor complexes (Kisseleva et al., 2002, Gene 285:1-24; Levy et al., 2005, Nat. Rev. Mol. Cell Biol. 3:651-662; O'Shea et al., 2002, Cell, 109 (suppl.): S121-S131). JAK1 knockout mice die perinatally due to defects in LIF receptor signalling (Kisseleva et al., 2002, Gene 285:1-24; O'Shea et al., 2002, Cell, 109 (suppl.): S121-S131). Characterization of tissues derived from JAK1 knockout mice demonstrated critical roles for this kinase in the IFN, IL-10, IL-2/IL-4 and IL-6 pathways. A humanized monoclonal antibody targeting the IL-6 pathway (Tocilizumab) is approved in many countries for the treatment of moderate-to-severe rheumatoid arthritis (Scheinecker et al., 2009, Nat. Rev. Drug Discov. 8:273-274).

CD4 T cells play an important role in asthma pathogenesis through the production of TH2 cytokines within the lung, including IL-4, IL-9 and IL-13 (Cohn et al., 2004, Annu. Rev. Immunol. 22:789-815). IL-4 and IL-13 induce increased mucus production, recruitment of eosinophils to the lung, and increased production of IgE (Kasaian et al., 2008, Biochem. Pharmacol. 76 (2): 147-155). IL-9 leads to mast cell activation, which exacerbates the asthma symptoms (Kearley et al., 2011, Am. J. Resp. Crit. Care Med., 183(7): 865-875). The IL-4Rα chain activates JAK1 and binds to either IL-4 or IL-13 when combined with the common gamma chain or the IL-13Rα1 chain, respectively (Pernis et al., 2002, J. Clin. Invest. 109 (10):1279-1283). The common gamma chain can also combine with IL-9Rα to bind to IL-9, and IL-9Rα activates JAK1 as well (Demoulin et al., 1996, Mol. Cell Biol. 16 (9):4710-4716). While the common gamma chain activates JAK3, it has been shown that JAK1 is dominant over JAK3, and inhibition of JAK1 is sufficient to inactivate signaling through the common gamma chain despite JAK3 activity (Haan et al., 2011, Chem. Biol. 18 (3):314-323). Inhibition of IL-4, IL-13 and IL-9 signaling by blocking the JAK/STAT signaling pathway can alleviate asthmatic symptoms in pre-clinical lung inflammation models (Mathew et al., 2001, J. Exp. Med. 193 (9): 1087-1096; Kudlacz et. al., 2008, Eur. J. Pharmacol. 582 (1-3): 154-161).

Biochemical and genetic studies have shown an association between JAK2 and single-chain (e.g., EPO), IL-3 and interferon gamma cytokine receptor families (Kisseleva et al., 2002, Gene 285:1-24; Levy et al., 2005, Nat. Rev. Mol. Cell Biol. 3:651-662; O'Shea et al., 2002, Cell, 109 (suppl.): S121-S131). Consistent with this, JAK2 knockout mice die of anemia (O'Shea et al., 2002, Cell, 109 (suppl.): S121-S131). Kinase activating mutations in JAK2 (e.g., JAK2 V617F) are associated with myeloproliferative disorders in humans.

JAK3 associates exclusively with the gamma common cytokine receptor chain, which is present in the IL-2, IL-4, IL-7, IL-9, IL-15 and IL-21 cytokine receptor complexes. JAK3 is critical for lymphoid cell development and proliferation and mutations in JAK3 result in severe combined immunodeficiency (SCID) (O'Shea et al., 2002, Cell, 109 (suppl.): S121-S131). Based on its role in regulating lymphocytes, JAK3 and JAK3-mediated pathways have been targeted for immunosuppressive indications (e.g., transplantation rejection and rheumatoid arthritis) (Baslund et al., 2005, Arthritis & Rheumatism 52:2686-2692; Changelian et al., 2003, Science 302: 875-878).

TYK2 associates with the type I interferon (e.g., IFNalpha), IL-6, IL-10, IL-12 and IL-23 cytokine receptor complexes (Kisseleva et al., 2002, Gene 285:1-24; Watford, W. T. & O'Shea, J. J., 2006, Immunity 25:695-697). Consistent with this, primary cells derived from a TYK2 deficient human are defective in type I interferon, IL-6, IL-10, IL-12 and IL-23 signalling. A fully human monoclonal antibody targeting the shared p40 subunit of the IL-12 and IL-23 cytokines (Ustekinumab) is approved in several countries for the treatment of moderate-to-severe plaque psoriasis (Krueger et al., 2007, N. Engl. J. Med. 356:580-92; Reich et al., 2009, Nat. Rev. Drug Discov. 8:355-356). In addition, an antibody targeting the IL-12 and IL-23 pathways underwent clinical trials for treating Crohn's Disease (Mannon et al., 2004, N. Engl. J. Med. 351:2069-79).

Currently there remains a need for additional compounds that are inhibitors of Janus kinases. For example, there is a need for compounds that possess useful potency as inhibitors of one or more Janus kinase (e.g., JAK1) in combination with other pharmacological properties that are necessary to achieve a useful therapeutic benefit. For example, there is a need for potent compounds that demonstrate selectivity for one Janus kinase over other kinases in general (e.g., selectivity for JAK1 over other kinases such as leucine-rich repeat kinase 2 LRRK2). There is also a need for potent compounds that demonstrate selectivity for one Janus kinase over other Janus kinases (e.g., selectivity for JAK1 over other Janus kinases). Kinases demonstrating selectivity for JAK1 could provide a therapeutic benefit, with fewer side effects, in conditions responsive to the inhibition of JAK1. Additionally there is currently a need for potent JAK1 inhibitors that possess other properties (e.g., melting point, pK, solubility, etc.) necessary for formulation and administration by inhalation. Such compounds would be particularly useful for treating conditions such as, for example, asthma.

SUMMARY OF INVENTION

One aspect of the invention includes a compound of the invention, which is a compound of Formula (I):

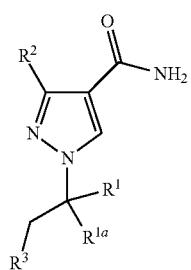

(I)

or a salt thereof, wherein:

$R^1$ and $R^{1a}$ taken together with the atom to which they are attached form a 3-10 membered carbocycle optionally substituted with $R^a$ and optionally substituted with $R^b$; or $R^1$ and $R^{1a}$ taken together with the atom to which they are attached form a 3-15 membered heterocycle optionally substituted with RC and optionally substituted with $R^d$;

$R^2$ is —$NR^eR^f$;

$R^3$ is —$CH_3$ or —CN;

$R^a$ is —$NR^rR^s$ or —$OR^r$;

each $R^b$ is independently selected from the group consisting of halo, cyano, hydroxy, oxo, $C_1$-$C_6$alkyl, $C_1$-$C_6$alkoxy, —$NH_2$, —$NHCH_3$, —$N(CH_3)_2$, —SH, and —$SCH_3$, wherein any $C_1$-$C_6$alkyl, and $C_1$-$C_6$alkoxy is optionally substituted with halo, cyano, hydroxy, oxo, $C_{1-3}$alkyl, $C_{1-3}$alkoxy, —$NH_2$, —$NHCH_3$, —$N(CH_3)_2$, —SH, or —$SCH_3$, wherein any $C_{1-3}$alkyl and $C_{1-3}$alkoxy is optionally substituted with halo, hydroxy, cyano or oxo;

$R^c$ is —$OR^m$, —$SR^m$, —$NR^mR^n$, —$C(O)R^m$, —$C(O)OR^m$, —$C(O)NR^mR^n$, —$NR^mC(O)R^n$, —$S(O)_{1-2}R^m$, —$NR^mS(O)_{1-2}R^n$, —$S(O)_{1-2}NR^mR^n$, $C_1$-$C_6$alkyl, $C_2$-$C_6$alkenyl, $C_2$-$C_6$alkynyl, 3-10 membered carbocyclyl, 3-10 membered heterocyclyl, 6-10 membered aryl, or 5-10 membered heteroaryl, wherein any $C_1$-$C_6$alkyl, $C_2$-$C_6$alkenyl, $C_2$-$C_6$alkynyl of $R^c$ is optionally substituted with $R^x$;

each $R^d$ is independently selected from the group consisting of halo, cyano, $C_1$-$C_6$alkyl, and $C_1$-$C_6$alkoxy, wherein any $C_1$-$C_6$alkyl, and $C_1$-$C_6$alkoxy is optionally substituted with halo, hydroxy, cyano or oxo;

$R^e$ is H or $C_1$-$C_4$alkyl;

$R^f$ is —C(=O)—$R^g$, or aryl that is optionally substituted with one or more groups selected from the group consisting of halo, cyano, nitro, trifluoromethyl, trifluoromethoxy, —$S(O)_2R^h$, and —$P(=O)(OR^k)_2$;

$R^g$ is H, hydroxy, $C_1$-$C_6$alkyl, $C_1$-$C_6$alkoxy, —$NR^rR^u$, or a 3-10 membered carbocyclyl that is optionally substituted with halo, hydroxy, cyano, oxo, $C_1$-$C_3$alkyl, $C_2$-$C_3$alkynyl, 6-10 membered aryl, 5-6 membered heteroaryl, or 3-5 membered carbocyclyl, wherein any $C_1$-$C_3$ alkyl, 6-10 membered aryl, 5-6 membered heteroaryl, or 3-5 membered carbocyclyl is optionally substituted with halo, hydroxy, cyano, or $C_1$-$C_3$alkyl;

each $R^h$ is independently selected from the group consisting of $C_1$-$C_6$alkyl that is optionally substituted with halo;

each $R^k$ is independently selected from the group consisting of H and $C_1$-$C_6$alkyl that is optionally substituted with halo;

$R^m$ and $R^n$ are independently selected from the group consisting of hydrogen, 3-6 membered heterocyclyl, 3-6 membered carbocyclyl, 6-10 membered aryl, 5-10 membered heteroaryl, and $C_1$-$C_6$alkyl, wherein any 3-6 membered heterocyclyl, 3-6 membered carbocyclyl, 6-10 membered aryl, 5-10 membered heteroaryl, and $C_1$-$C_6$alkyl of $R^m$ and $R^n$ is optionally substituted with $R^w$; or $R^m$ and $R^n$ are taken together with the atom to which they are attached to form a 3-8 membered heterocyclyl that is optionally substituted with $R^w$;

each $R^r$ and $R^s$ is independently selected from the group consisting of hydrogen, 3-6 membered heterocyclyl, 3-6 membered carbocyclyl, 6-10 membered aryl, 5-10 membered heteroaryl and $C_1$-$C_3$alkyl, wherein any 3-6 membered heterocyclyl, 3-6 membered carbocyclyl, 6-10 membered aryl, 5-10 membered heteroaryl and $C_1$-$C_3$alkyl of $R^r$ and $R^s$ is optionally substituted with $R^v$; or $R^r$ and $R^s$ are taken together with the atom to which they are attached to form a 3-8 membered heterocyclyl or 5-10 membered heteroaryl, which 3-8 membered heterocyclyl and 5-10 membered heteroaryl is optionally substituted with $R^v$;

$R^t$ and $R^u$ are independently selected from the group consisting of hydrogen, 3-6 membered heterocyclyl, 3-6 membered carbocyclyl, 6-10 membered aryl, 5-10 membered heteroaryl and $C_1$-$C_3$alkyl, wherein any 3-6 membered heterocyclyl, 3-6 membered carbocyclyl, 6-10 membered aryl, 5-10 membered heteroaryl and $C_1$-$C_3$alkyl of $R^t$ and $R^u$ is optionally substituted with halo, hydroxy, cyano or oxo; or $R^t$ and $R^u$ are taken together with the atom to which they are attached to form a 3-6 membered heterocyclyl, optionally substituted with halo, hydroxy, cyano or oxo, or $C_1$-$C_6$alkyl that is optionally substituted with halo, hydroxy, cyano or oxo;

each $R^v$ is independently selected from the group consisting of halo, hydroxy, cyano, oxo, 6-10 membered aryl, 5-10 membered heteroaryl, $C_1$-$C_6$alkyl, $C_2$-$C_3$alkenyl, $C_2$-$C_3$alkynyl, 3-6 membered carbocyclyl, 3-6 membered heterocyclyl, (6-10 membered aryl)—O—, (5-10 membered heteroaryl)—O—, (3-6 membered carbocyclyl)—O—, (3-6 membered heterocyclyl)—O—, and $C_1$-$C_6$alkoxy, wherein any 6-10 membered aryl, 5-10 membered heteroaryl, $C_1$-$C_6$alkyl, 3-6 membered carbocyclyl, 3-6 membered heterocyclyl, (6-10 membered aryl)—O—, (5-10 membered heteroaryl)—O—, (3-6 membered carbocyclyl)—O—, (3-6 membered heterocyclyl)—O—, and $C_1$-$C_6$alkoxy of $R^v$ is optionally substituted with halo, hydroxy, cyano, $C_1$-$C_6$alkyl, $C_2$-$C_3$alkynyl, oxo, 3-6 membered carbocycle, 3-6 membered heterocyclyl, $C_1$-$C_6$alkoxy, 5-10 membered heteroaryl or 6-10 membered aryl, each of which is optionally substituted with halo, hydroxy, cyano, oxo $C_1$-$C_3$alkyl or $C_1$-$C_3$alkoxy;

each $R^w$ is independently selected from the group consisting of halo, hydroxy, cyano, oxo, 6-10 membered aryl, 5-10 membered heteroaryl, $C_1$-$C_6$alkyl, 3-6 membered carbocyclyl, 3-6 membered heterocyclyl and $C_1$-$C_6$alkoxy, wherein any 6-10 membered aryl, 5-10 membered heteroaryl, $C_1$-$C_6$alkyl, 3-6 membered carbocyclyl, 3-6 membered heterocyclyl and $C_1$-$C_6$alkoxy of $R^w$ is optionally substituted with halo, hydroxy, cyano, $C_1$-$C_6$alkyl, oxo, 3-6 membered carbocyclyl, 3-6 membered heterocyclyl $C_1$-$C_6$alkoxy, 5-10 membered heteroaryl, or 6-10 membered aryl, each optionally substituted with halo, hydroxy, cyano, oxo, $C_1$-$C_3$alkyl or $C_1$-$C_3$alkoxy; and each $R^x$ is independently selected from the group consisting of halo, hydroxy, cyano, nitro, oxo, —$OR'''$, —$SR'''$, —$NR'''R''$, —$C(O)R'''$, —$C(O)OR'''$, —$C(O)NR'''R''$, —$NR'''C(O)R''$, —$S(O)_{1-2}R'''$, —$NR'''S(O)_{1-2}R''$, —$S(O)_{1-2}NR'''R''$, 3-10 membered carbocyclyl, 3-15 membered heterocyclyl, 6-10 membered aryl, and 5-15 membered heteroaryl, wherein any 3-10 membered carbocyclyl, 3-15 membered heterocyclyl, 6-10 membered aryl, and 5-15 membered heteroaryl, is optionally substituted with halo, hydroxy, cyano, nitro, $C_2$-$C_6$alkenyl, $C_2$-$C_6$alkynyl, —$OR'''$, —$SR'''$, —$NR'''R''$, —$C(O)R'''$, —$C(O)OR'''$, —$C(O)NR'''R''$, —$NR'''C(O)R''$, —$S(O)_{1-2}R'''$, —$NR'''S(O)_{1-2}R''$, —$S(O)_{1-2}NR'''R''$, $C_1$-$C_6$alkyl, oxo, 3-10 membered carbocyclyl, 3-10 membered heterocyclyl, 6-10 membered aryl, or 5-10 membered heteroaryl, wherein any $C_1$-$C_6$alkyl, $C_2$-$C_6$alkenyl, $C_2$-$C_6$alkynyl, 3-10 membered carbocyclyl, 3-10 membered heterocyclyl, 6-10 membered aryl, and 5-10 membered heteroaryl is optionally substituted with halo, hydroxy, cyano, oxo, —$OR'''$, —$NR'''R''$, —$C(O)R'''$, —$C(O)OR'''$, —$C(O)NR'''R''$, 3-6 membered carbocyclyl, 6-10 membered aryl, or $C_1$-$C_6$alkyl that is optionally substituted with halo, hydroxy, cyano, oxo or $C_1$-$C_6$alkoxy.

Also provided is a pharmaceutical composition that comprises a compound of the invention or a salt thereof (e.g., a pharmaceutically acceptable salt) and a pharmaceutically acceptable carrier, diluent or excipient.

Another aspect includes a compound of the invention or a salt thereof (e.g., a pharmaceutically acceptable salt) for use in therapy, such as the treatment of an inflammatory disease or cancer. The inflammatory disease may be asthma.

Another aspect includes a method of preventing, treating or lessening the severity of a disease or condition responsive to the inhibition of a Janus kinase, such as JAK1 kinase, in a patient. The method can comprise administering to the patient a therapeutically effective amount of a compound of the invention or a salt thereof (e.g., a pharmaceutically acceptable salt).

Another aspect includes the use of a compound of the invention or a salt thereof (e.g., a pharmaceutically acceptable salt) in the manufacture of a medicament for the treatment of a disease responsive to the inhibition of a Janus kinase, such as JAK1 kinase.

Another aspect includes a kit for treating a disease or disorder responsive to the inhibition of a Janus kinase, such as JAK1 kinase. The kit can comprise a first pharmaceutical composition comprising a compound of the invention or a salt thereof (e.g., a pharmaceutically acceptable salt), and instructions for use.

Certain compounds of the invention possess beneficial potency as inhibitors of one or more Janus kinase (e.g., JAK1). Certain compounds are also, a) selective for one Janus kinase over other kinases, b) selective for JAK1 over other Janus kinases, and/or c) possess other properties (e.g., melting point, pK, solubility, etc.) necessary for formulation and administration by inhalation. Certain compounds of Formula (I) may be particularly useful for treating conditions such as asthma.

DETAILED DESCRIPTION OF THE INVENTION

Definitions

"Halogen" or "halo" refers to F, Cl, Br or I. Additionally, terms such as "haloalkyl," are meant to include monohaloalkyl and polyhaloalkyl.

The term "alkyl" refers to a saturated linear or branched-chain monovalent hydrocarbon radical, wherein the alkyl radical may be optionally substituted. In one example, the alkyl radical is one to eighteen carbon atoms ($C_1$-$C_{18}$). In other examples, the alkyl radical is $C_0$-$C_6$, $C_0$-$C_5$, $C_0$-$C_3$, $C_1$-$C_{12}$, $C_1$-$C_{10}$, $C_1$-$C_8$, $C_1$-$C_6$, $C_1$-$C_5$, $C_1$-$C_4$, or $C_1$-$C_3$. $C_0$ alkyl refers to a bond. Examples of alkyl groups include methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl and 1-octyl. In some embodiments, substituents for "optionally substituted alkyls" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, phenyl and heterocyclic portions thereof may be optionally substituted, such as by one to four instances of substituents selected from this same list.

"Aryl" refers to a carbocyclic aromatic group, whether or not fused to one or more groups, having the number of carbon atoms designated, or if no number is designated, up to 14 carbon atoms. One example includes aryl groups having 6-14 carbon atoms. Another example includes aryl groups having 6-10 carbon atoms. Examples of aryl groups include phenyl, naphthyl, biphenyl, phenanthrenyl, naphthacenyl, 1,2,3,4-tetrahydronaphthalenyl, 1H-indenyl, 2,3-dihydro-1H-indenyl, and the like (see, e.g., Lang's Handbook of Chemistry (Dean, J. A., ed.) 13th ed. Table 7-2 [1985]). A particular aryl is phenyl. Substituted phenyl or substituted aryl means a phenyl group or aryl group substituted with one, two, three, four or five substituents, for example, 1-2, 1-3 or 1-4 substituents, such as chosen from groups specified herein (see "optionally substituted" definition), such as F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, phenyl and heterocyclic portions thereof may be optionally substituted, such as by one to four instances of substituents selected from this same list. Examples of the term "substituted phenyl" include a mono- or di(halo)phenyl group such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl, 2,4-difluorophenyl and the like; a mono- or di(hydroxy) phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(alkyl)phenyl group such as 4-methylphenyl, 2,4-dimethylphenyl, 2-methylphenyl, 4-(isopropyl)phenyl, 4-ethylphenyl, 3-(n-propyl)phenyl and the like; a mono or di(alkoxy)phenyl group, for example, 3,4-dimethoxyphenyl, 3-methoxy-4-benzyloxyphenyl, 3-ethoxyphenyl, 4-(isopropoxy)phenyl, 4-(t-butoxy)phenyl, 3-ethoxy-4-methoxyphenyl and the like; 3- or 4-trifluoromethylphenyl; a mono- or dicarboxyphenyl or (protected carboxy)phenyl group such 4-carboxyphenyl, a mono- or di(hydroxymethyl) phenyl or (protected hydroxymethyl)phenyl such as 3-(protected hydroxymethyl)phenyl or 3,4-di(hydroxymethyl)phenyl; a mono- or di(aminomethyl)phenyl or (protected aminomethyl)phenyl such as 2-(aminomethyl)phenyl or 2,4-(protected aminomethyl)phenyl; or a mono- or di(N-(methylsulfonylamino))phenyl such as 3-(N-methylsulfonylamino))phenyl. Also, the term "substituted phenyl" represents disubstituted phenyl groups where the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, 2-chloro-5-difluoromethoxy and the like, as well as trisubstituted phenyl groups where the substituents are different, for example 3-methoxy-4-benzyloxy-6-methyl sulfonylamino, 3-methoxy-4-benzyloxy-6-phenyl sulfonylamino, and tetrasubstituted phenyl groups where the substituents are different such as 3-methoxy-4-benzyloxy-5-methyl-6-phenyl sulfonylamino.

The terms "compound(s) of the invention," and "compound(s) of the present invention" and the like, unless otherwise indicated, include compounds of formulae (I), (Ia), (Ib), (Ic), and (Id), and the compounds of the Examples herein, including stereoisomers (including atropisomers), geometric isomers, tautomers, solvates, metabolites, isotopes, salts (e.g., pharmaceutically acceptable salts), and prodrugs thereof. In some embodiments, solvates, metabolites, isotopes or prodrugs are excluded, or any combination thereof.

The term "aryl" as used herein refers to a single all carbon aromatic ring or a multiple condensed all carbon ring system wherein at least one of the rings is aromatic. For example, in certain embodiments, an aryl group has 6 to 20 carbon atoms, 6 to 15 carbon atoms, 6 to 12 or 6 to 10 carbon atoms. Aryl includes a phenyl radical. Aryl also includes multiple condensed ring systems (e.g., ring systems comprising 2, 3 or 4 rings) having 9 to 20 carbon atoms in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Non-limiting examples of aryl groups include, but are not limited to, phenyl, indenyl, naphthyl, 1, 2, 3, 4-tetrahydronaphthyl, anthracenyl, and the like.

The term "carbocycle" or "carbocyclyl" refers to a single saturated (i.e., cycloalkyl) or a single partially unsaturated (e.g., cycloalkenyl, cycloalkadienyl, etc.) all carbon ring having 3 to 7 carbon atoms (i.e., $(C_3-C_7)$carbocycle). The term "carbocycle" or "carbocyclyl" also includes multiple condensed, saturated and partially unsaturated all carbon ring systems (e.g., ring systems comprising 2, 3 or 4 carbocyclic rings).

Accordingly, carbocycle includes multicyclic carbocyles such as a bicyclic carbocycles (e.g., bicyclic carbocycles having about 6 to 12 carbon atoms such as bicyclo[3.1.0] hexane and bicyclo[2.1.1]hexane), and polycyclic carbocycles (e.g., tricyclic and tetracyclic carbocycles with up to about 20 carbon atoms). The rings of the multiple condensed ring system can be connected to each other via fused, spiro and bridged bonds when allowed by valency requirements. For example, multicyclic carbocyles can be connected to each other via a single carbon atom to form a spiro connection (e.g., spiropentane, spiro[4,5]decane, etc), via two adjacent carbon atoms to form a fused connection (e.g., carbocycles such as decahydronaphthalene, norsabinane, norcarane) or via two non-adjacent carbon atoms to form a bridged connection (e.g., norbornane, bicyclo[2.2.2]octane, etc). The "carbocycle" or "carbocyclyl" can also be optionally substituted with one or more (e.g., 1, 2 or 3) oxo groups. In one embodiment the term carbocycle includes 3-20 membered carbocycles. In another embodiment the term carbocycle includes 3-15 membered carbocycles. In another embodiment the term carbocycle includes 3-10 membered carbocycles. In one embodiment the term carbocycle includes a 3-8 membered carbocycle. In one embodiment the term carbocycle includes a 3-6 membered carbocycle. In one embodiment the term carbocycle includes a 3-5 carbocycle. Non-limiting examples of carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, bicyclo[2.2.1]heptane, pinane, adamantane, norborene, spirocyclic $C_{5-12}$ alkane, and 1-cyclohex-3-enyl.

The term "heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. For example, in certain embodiments, a heteroaryl group has 5 to 20 members, 5 to 15 members, 5 to 12 members, or 5 to 10 members. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from heteroaryls (to form for example a naphthyridinyl such as 1,8-naphthyridinyl), heterocycles, (to form for example a 1, 2, 3, 4-tetrahydronaphthyridinyl such as 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has about 1-20 carbon atoms and about 1-6 heteroatoms within the heteroaryl ring. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heteroaryl) can be at any position of the multiple condensed ring system including a heteroaryl, heterocycle, aryl or carbocycle portion of the multiple condensed ring system. It is also to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thianaphthenyl, pyrrolo[2,3-b]pyridinyl, quinazolinyl-4(3H)-one, triazolyl, 4,5,6,7-tetrahydro-1H-indazole and 3b,4,4a,5-tetrahydro-1H-cyclopropa[3,4]cyclopenta[1,2-c]pyrazole.

The term "heterocyclyl" or "heterocycle" as used herein refers to a single saturated or partially unsaturated ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems are further described below. Thus, the term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The ring may be substituted with one or more (e.g., 1, 2 or 3) oxo groups and the sulfur and nitrogen atoms may also be present in their oxidized forms. Exemplary heterocycles include but are not limited to azetidinyl, tetrahydrofuranyl and piperidinyl. The term "heterocycle" also includes multiple condensed ring systems (e.g., ring systems comprising 2, 3 or 4 rings) wherein a single heterocycle ring (as defined above) can be condensed with one or more groups selected from heterocycles (to form for example a 1,8-decahydronapthyridinyl), carbocycles (to form for example a decahydroquinolyl) and aryls to form the multiple condensed ring system. Thus, a heterocycle (a single saturated or single partially unsaturated ring or multiple condensed ring system) has about 2-20 carbon atoms and 1-6 heteroatoms within the heterocycle ring. Such multiple condensed ring systems may be optionally substituted with one or more (e.g., 1, 2, 3 or 4) oxo groups on the carbocycle or heterocycle portions of the multiple condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heterocycle) can be at any position of the multiple condensed ring system including a heterocycle, aryl and carbocycle portion of the ring. It is also to be understood that the point of attachment for a heterocycle or heterocycle multiple condensed ring system can be at any suitable atom of the heterocycle or heterocycle multiple condensed ring system including a carbon atom and a heteroatom (e.g., a nitrogen). In one embodiment the term heterocycle includes a $C_{2-20}$ heterocycle. In one embodiment the term heterocycle includes a $C_{2-7}$ heterocycle. In one embodiment the term heterocycle includes a $C_{2-5}$ heterocycle. In one embodiment the term heterocycle includes a $C_{2-4}$ heterocycle. In one embodiment the term heterocycle includes 3-20 membered heterocycles. In another embodiment the term heterocycle includes 3-15 membered heterocycles. In another embodiment the term heterocycle includes 3-10 membered heterocycles. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, spiro[cyclopropane-1,1'-isoindolinyl]-3'-one, isoindolinyl-1-one, 2-oxa-6-azaspiro[3.3]heptanyl, imidazolidin-2-one N-methylpiperidine, imidazolidine, pyrazolidine, butyrolactam, valerolactam, imidazolidinone, hydantoin, dioxolane, phthalimide, 1,4-dioxane, thiomorpholine, thiomorpholine-S-oxide, thiomorpholine-S,S-oxide, pyran, 3-pyrroline, thiopyran, pyrone, tetrhydrothiophene, quinuclidine, tropane, 2-azaspiro[3.3]heptane, (1R,5S)-3-azabicyclo[3.2.1]octane, (1s,4s)-2-azabicyclo[2.2.2]octane, (1R,4R)-2-oxa-5-azabicyclo[2.2.2]octane and pyrrolidin-2-one.

The term "alkoxy" refers to a linear or branched monovalent radical represented by the formula —OR in which R is alkyl, as defined herein. Alkoxy groups include methoxy, ethoxy, propoxy, isopropoxy, mono-, di- and tri-fluoromethoxy and cyclopropoxy.

The term "alkanoyl" refers to group (alkyl)—C(═O)—, wherein alkyl is as defined herein. For example, $C_1$-$C_6$alkanoyl refers to a group of formula ($C_1$-$C_5$alkyl)—C(═O)—. Alkanoyl groups include, formyl, acetyl, propanoyl, isopropanoyl, butanoyl, isobutanoyl, pentanoyl, 3-methylpentanoyl, and hexanoyl.

"Optionally substituted" unless otherwise specified means that a group may be unsubstituted or substituted by one or more (e.g., 0, 1, 2, 3, 4, or 5 or more, or any range derivable therein) of the substituents listed for that group in which said substituents may be the same or different. In an embodiment, an optionally substituted group has 1 substituent. In another embodiment an optionally substituted group has 2 substituents. In another embodiment an optionally substituted group has 3 substituents. In another embodiment an optionally substituted group has 4 substituents. In another embodiment an optionally substituted group has 5 substituents.

As used herein a wavy line "⁓" that intersects a bond in a chemical structure indicate the point of attachment of the atom to which the wavy bond is connected in the chemical structure to the remainder of a molecule, or to the remainder of a fragment of a molecule. In some embodiments, an arrow together with an asterisk is used in the manner of a wavy line to indicate a point of attachment.

In certain embodiments, divalent groups are described generically without specific bonding configurations. It is understood that the generic description is meant to include both bonding configurations, unless specified otherwise. For example, in the group $R^1$—$R^2$—$R^3$, if the group $R^2$ is described as —$CH_2C(O)$—, then it is understood that this group can be bonded both as $R^1$—$CH_2C(O)$—$R^3$, and as $R^1$—$C(O)CH_2$—$R^3$, unless specified otherwise.

The phrase "pharmaceutically acceptable" refers to molecular entities and compositions that do not produce an adverse, allergic or other untoward reaction when administered to an animal, such as, for example, a human, as appropriate.

Compounds of the invention may be in the form of a salt, such as a pharmaceutically acceptable salt. "Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particular base addition salts are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particular organic non-toxic bases include isopropylamine, diethylamine, ethanolamine, tromethamine, dicyclohexylamine, choline, and caffeine.

In some embodiments, a salt is selected from a hydrochloride, hydrobromide, trifluoroacetate, sulphate, phosphate, acetate, fumarate, maleate, tartrate, lactate, citrate, pyruvate, succinate, oxalate, methanesulphonate, p-toluenesulphonate, bisulphate, benzenesulphonate, ethanesulphonate, malonate, xinafoate, ascorbate, oleate, nicotinate, saccharinate, adipate, formate, glycolate, palmitate, L-lactate, D-lactate, aspartate, malate, L-tartrate, D-tartrate, stearate, furoate (e.g., 2-furoate or 3-furoate), napadisylate (naphthalene-1,5-disulfonate or naphthalene-1-(sulfonic acid)-5-sulfonate), edisylate (ethane-1,2-disulfonate or ethane-1-(sulfonic acid)-2-sulfonate), isethionate (2-hydroxyethylsulfonate), 2-mesitylenesulphonate, 2-naphthalenesulphonate, 2,5-dichlorobenzenesulphonate, D-mandelate, L-mandelate, cinnamate, benzoate, adipate, esylate, malonate, mesitylate (2-mesitylenesulphonate), napsylate (2-naphthalenesulfonate), camsylate (camphor-10-sulphonate, for example (1S)-(+)-10-camphorsulfonic acid salt), glutamate, glutarate, hippurate (2-(benzoylamino)acetate), orotate, xylate (p-xylene-2-sulphonate), and pamoic (2,2'-dihydroxy-1,1'-dinaphthylmethane-3,3'-dicarboxylate).

A "sterile" formulation is aseptic or free from all living microorganisms and their spores.

"Stereoisomers" refer to compounds that have identical chemical constitution, but differ with regard to the arrangement of the atoms or groups in space. Stereoisomers include diastereomers, enantiomers, conformers and the like.

"Chiral" refers to molecules which have the property of non-superimposability of the mirror image partner, while the term "achiral" refers to molecules which are superimposable on their mirror image partner.

"Diastereomer" refers to a stereoisomer with two or more centers of chirality and whose molecules are not mirror images of one another. Diastereomers have different physical properties, e.g., melting points, boiling points, spectral properties or biological activities. Mixtures of diastereomers may separate under high resolution analytical procedures such as electrophoresis and chromatography such as HPLC.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., N.Y., 1994. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Certain compounds of the invention can exist in unsolvated forms as well as solvated forms, including hydrated forms. A "solvate" refers to an association or complex of one or more solvent molecules and a compound of the present invention. Examples of solvents that form solvates include water, isopropanol, ethanol, methanol, DMSO, ethyl acetate, acetic acid, and ethanolamine. Certain compounds of the invention can exist in multiple crystalline or amorphous forms. In general, all physical forms are intended to be within the scope of the present invention. The term "hydrate" refers to the complex where the solvent molecule is water.

A "metabolite" refers to a product produced through metabolism in the body of a specified compound or salt thereof. Such products can result, for example, from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}C$ or $^{3}H$) isotope of a compound of the invention, administering it in a detectable dose (e.g., greater than about 0.5 mg/kg) to an animal such as rat, mouse, guinea pig, monkey, or to a human, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

"Amino-protecting group" as used herein refers to a derivative of the groups commonly employed to block or protect an amino group while reactions are carried out on other functional groups on the compound. Examples of such protecting groups include carbamates, amides, alkyl and aryl groups, and imines, as well as many N-heteroatom derivatives which can be removed to regenerate the desired amine group. Particular amino protecting groups are Pmb (p-Methoxybenzyl), Boc (tert-Butyloxycarbonyl), Fmoc (9-Fluorenylmethyloxycarbonyl) and Cbz (Carbobenzyloxy). Further examples of these groups are found in T. W. Greene and P. G. M. Wuts, "Protecting Groups in Organic Synthesis, $3^{rd}$ ed., John Wiley & Sons, Inc., 1999. The term "protected amino" refers to an amino group substituted with one of the above amino-protecting groups.

"Carboxy-protecting group" as used herein refers to those groups that are stable to the conditions of subsequent reaction(s) at other positions of the molecule, which may be removed at the appropriate point without disrupting the remainder of the molecule, to give the unprotected carboxy-group. Examples of carboxy protecting groups include, ester groups and heterocyclyl groups. Ester derivatives of the carboxylic acid group may be employed to block or protect the carboxylic acid group while reactions are carried out on other functional groups on the compound. Examples of such ester groups include substituted arylalkyl, including substituted benzyls, such as 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, alkyl or substituted alkyl esters such as methyl, ethyl, t-butyl allyl or t-amyl, triphenylmethyl (trityl), 4-methoxytrityl, 4,4'-dimethoxytrityl, 4,4',4''-trimethoxytrityl, 2-phenylprop-2-yl, thioesters such as t-butyl thioester, silyl esters such as trimethylsilyl, t-butyldimethylsilyl esters, phenacyl, 2,2,2-trichloroethyl, beta-(trimethylsilyl)ethyl, beta-(di(n-butyl) methylsilyl)ethyl, p-toluenesulfonyl ethyl, 4-nitrobenzylsulfonylethyl, allyl, cinnamyl, 1-(trimethylsilylmethyl) prop-1-en-3-yl, and like moieties. Another example of carboxy-protecting groups are heterocyclyl groups such as 1,3-oxazolinyl. Further examples of these groups are found in T. W. Greene and P. G. M. Wuts, "Protecting Groups in Organic Synthesis, $3^{rd}$ ed., John Wiley & Sons, Inc., 1999. The term "protected carboxy" refers to a carboxy group substituted with one of the above carboxy-protecting groups.

"Hydroxy-protecting group" as used herein refers to a derivative of the hydroxy group commonly employed to block or protect the hydroxy group while reactions are carried out on other functional groups on the compound. Examples of such protecting groups include tetrahydropyranyloxy, benzoyl, acetoxy, carbamoyloxy, benzyl, and silylethers (e.g., TBS, TBDPS) groups. Further examples of these groups are found in T. W. Greene and P. G. M. Wuts, "Protecting Groups in Organic Synthesis, $3^{rd}$ ed., John Wiley & Sons, Inc., 1999. The term "protected hydroxy" refers to a hydroxy group substituted with one of the above hydroxy-protecting groups.

Compounds of the invention may contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Mixtures of particular diastereomeric compounds may be separated, or enriched in one or more particular diastereomers, by chromatographic or crystallization methods. Similarly, enantiomeric mixtures may be separated, or enantiomerically enriched, using the same techniques or others known in the art. Each of the asymmetric carbon or nitrogen atoms may be in the R or S configuration and both of these configurations are within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined. Unless otherwise specified, if solid wedges or dashed lines are used, relative stereochemistry is intended. In some instances, the stereochemistry has not been determined or has been provisionally assigned.

Another aspect includes prodrugs of the compounds of the invention including known amino-protecting and carboxy-protecting groups which are released, for example hydrolyzed, to yield the compound of the present invention under physiologic conditions.

The term "prodrug" refers to a precursor or derivative form of a pharmaceutically active substance that is less efficacious to the patient compared to the parent drug and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). Prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, and 5-fluorocytosine and 5-fluorouridine prodrugs.

A particular class of prodrugs are compounds in which a nitrogen atom in an amino, amidino, aminoalkyleneamino, iminoalkyleneamino or guanidino group is substituted with a hydroxy group, an alkylcarbonyl (—CO—R) group, an alkoxycarbonyl (—CO—OR), or an acyloxyalkyl-alkoxycarbonyl (—CO—O—R—O—CO—R) group where R is a monovalent or divalent group, for example alkyl, alkylene or aryl, or a group having the Formula —C(O)—O—CP1P2-haloalkyl, where P1 and P2 are the same or different and are hydrogen, alkyl, alkoxy, cyano, halogen, alkyl or aryl. In a particular embodiment, the nitrogen atom is one of the nitrogen atoms of the amidino group of the compounds of the invention. Prodrugs may be prepared by reacting a compound of the present invention with an activated group, such as acyl groups, to bond, for example, a nitrogen atom in the compound to the exemplary carbonyl of the activated acyl group. Examples of activated carbonyl compounds are those containing a leaving group bonded to the carbonyl group, and include, for example, acyl halides, acyl amines, acyl pyridinium salts, acyl alkoxides, acyl phenoxides such as p-nitrophenoxy acyl, dinitrophenoxy acyl, fluorophenoxy acyl, and difluorophenoxy acyl. The reactions are generally carried out in inert solvents at reduced temperatures such as −78 to about 50° C. The reactions may also be carried out in the presence of an inorganic base, for example potassium carbonate or sodium bicarbonate, or an organic base such as an amine, including pyridine, trimethylamine, triethylamine, triethanolamine, or the like.

Additional types of prodrugs are also encompassed. For instance, a free carboxyl group of a compound of the invention can be derivatized as an amide or alkyl ester. As another example, compounds of the invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_1-C_6)$alkanoyloxymethyl, 1-$((C_1-C_6)$alkanoyloxy)ethyl, 1-methyl-1-$((C_1-C_6)$ alkanoyloxy)ethyl, $(C_1-C_6)$alkoxycarbonyloxymethyl, N—$(C_1-C_6)$ alkoxycarbonylaminomethyl, succinoyl, $(C_1-C_6)$alkanoyl, alpha-amino$(C_1-C_4)$ alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_1-C_6)$alkyl$)_2$ or glycosyl (the radical resulting from the removal of a hydroxyl group of the hemiacetal form of a carbohydrate).

"Leaving group" refers to a portion of a first reactant in a chemical reaction that is displaced from the first reactant in the chemical reaction. Examples of leaving groups include, but are not limited to, halogen atoms, alkoxy and sulfonyloxy groups. Example sulfonyloxy groups include, but are not limited to, alkylsulfonyloxy groups (for example methyl sulfonyloxy (mesylate group) and trifluoromethylsulfonyloxy (triflate group)) and arylsulfonyloxy groups (for example p-toluenesulfonyloxy (tosylate group) and p-nitrosulfonyloxy (nosylate group)).

A "subject," "individual," or "patient" is a vertebrate. In certain embodiments, the vertebrate is a mammal. Mammals include, but are not limited to, farm animals (such as cows), sport animals, pets (such as guinea pigs, cats, dogs, rabbits and horses), primates, mice and rats. In certain embodiments, a mammal is a human. In embodiments comprising administration of a compound of to a patient, the patient is typically in need thereof.

The term "Janus kinase" refers to JAK1, JAK2, JAK3 and TYK2 protein kinases. In some embodiments, a Janus kinase may be further defined as one of JAK1, JAK2, JAK3 or TYK2. In any embodiment, any one of JAK1, JAK2, JAK3 and TYK2 may be specifically excluded as a Janus kinase. In some embodiments, a Janus kinase is JAK1. In some embodiments, a Janus kinase is a combination of JAK1 and JAK2.

The terms "inhibiting" and "reducing," or any variation of these terms, includes any measurable decrease or complete inhibition to achieve a desired result. For example, there may be a decrease of about, at most about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of activity (e.g., JAK1 activity) compared to normal.

In some embodiments, a compound of Formula (I) is selective for inhibition of JAK1 over JAK3 and TYK2. In some embodiments, a compound of Formula (I) is selective for inhibition of JAK1 over JAK2, JAK3, or TYK2, or any combination of JAK2, JAK3, or TYK2. In some embodiments, a compound of Formula (I) is selective for inhibition of JAK1 and JAK2 over JAK3 and TYK2. In some embodiments, a compound of Formula (I) is selective for inhibition of JAK1 over JAK3. By "selective for inhibition" it is meant that the compound is at least a 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, better inhibitor of a particular Janus kinase (e.g., JAK1) activity compared to another particular Janus kinase (e.g., JAK3) activity, or is at least a 2-, 3-, 4-, 5-, 10-, 25-, 50-, 100-, 250-, or 500-fold better inhibitor of a particular Janus kinase (e.g., JAK1) activity compared to another particular Janus kinase (e.g., JAK3) activity.

"Therapeutically effective amount" means an amount of a compound of the present invention, such as a compound of Formula (I), that (i) treats or prevents the particular disease, condition or disorder, or (ii) attenuates, ameliorates or eliminates one or more symptoms of the particular disease, condition, or disorder, and optionally (iii) prevents or delays the onset of one or more symptoms of the particular disease, condition or disorder described herein. In some embodiments, the therapeutically effective amount is an amount sufficient to decrease or alleviate the symptoms of an autoimmune or inflammatory disease (e.g., asthma). In some embodiments, a therapeutically effective amount is an amount of a chemical entity described herein sufficient to significantly decrease the activity or number of B-cells. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; or relieve to some extent one or more of the symptoms associated with the cancer. To the extent the drug may prevent growth or kill existing cancer cells, it may be cytostatic or cytotoxic. For cancer therapy, efficacy can, for example, be measured by assessing the time to disease progression (TTP) or determining the response rate (RR).

"Treatment" (and variations such as "treat" or "treating") refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, stabilized (i.e., not worsening) state of disease, decreasing the rate of disease progression, amelioration or palliation of the disease state, prolonging survival as compared to expected survival if not receiving treatment and remission or improved prognosis. In some embodiments, compounds of the invention, are used to delay development of a disease or disorder or to slow the progression of a disease or disorder. Those in need of treatment include those already with the condition or disorder as well as those prone to have the condition or disorder, (for example, through a genetic mutation) or those in which the condition or disorder is to be prevented.

"Inflammatory disorder" refers to any disease, disorder or syndrome in which an excessive or unregulated inflammatory response leads to excessive inflammatory symptoms, host tissue damage, or loss of tissue function. "Inflammatory disorder" also refers to a pathological state mediated by influx of leukocytes or neutrophil chemotaxis.

"Inflammation" refers to a localized, protective response elicited by injury or destruction of tissues, which serves to destroy, dilute, or wall off (sequester) both the injurious agent and the injured tissue. Inflammation is notably associated with influx of leukocytes or neutrophil chemotaxis. Inflammation can result from infection with pathogenic organisms and viruses and from noninfectious means such as trauma or reperfusion following myocardial infarction or stroke, immune responses to foreign antigens, and autoimmune responses. Accordingly, inflammatory disorders amenable to treatment with a compound of the present invention, such as a compound of Formula (I), encompass disorders associated with reactions of the specific defense system as well as with reactions of the nonspecific defense system.

"Specific defense system" refers to the component of the immune system that reacts to the presence of specific antigens. Examples of inflammation resulting from a response of the specific defense system include the classical response to foreign antigens, autoimmune diseases, and delayed type hypersensitivity responses mediated by T-cells. Chronic inflammatory diseases, the rejection of solid transplanted tissue and organs, e.g., kidney and bone marrow transplants, and graft versus host disease (GVHD), are further examples of inflammatory reactions of the specific defense system.

The term "nonspecific defense system" refers to inflammatory disorders that are mediated by leukocytes that are incapable of immunological memory (e.g., granulocytes, and macrophages). Examples of inflammation that result, at least in part, from a reaction of the nonspecific defense system include inflammation associated with conditions such as adult (acute) respiratory distress syndrome (ARDS) or multiple organ injury syndromes; reperfusion injury; acute glomerulonephritis; reactive arthritis; dermatoses with acute inflammatory components; acute purulent meningitis or other central nervous system inflammatory disorders such as stroke; thermal injury; inflammatory bowel disease; granulocyte transfusion associated syndromes; and cytokine-induced toxicity.

"Autoimmune disease" refers to any group of disorders in which tissue injury is associated with humoral or cell-mediated responses to the body's own constituents. Non-limiting examples of autoimmune diseases include rheumatoid arthritis, lupus and multiple sclerosis.

"Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies. "Transplant rejection" as used herein refers to any immune reaction directed against grafted tissue, such as organs or cells (e.g., bone marrow), characterized by a loss of function of the grafted and surrounding tissues, pain, swelling, leukocytosis, and thrombocytopenia. The therapeutic methods of the present invention include methods for the treatment of disorders associated with inflammatory cell activation.

"Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatability antigens or cell adhesion molecules) in inflammatory cells (including but not limited to monocytes, macrophages, T lymphocytes, B lymphocytes, granulocytes (i.e., polymorphonuclear leukocytes such as neutrophils, basophils, and eosinophils), mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory disorder.

In some embodiments, inflammatory disorders which can be treated according to the methods of this invention include, but are not limited to, asthma, rhinitis (e.g., allergic rhinitis), allergic airway syndrome, atopic dermatitis, bronchitis, rheumatoid arthritis, psoriasis, contact dermatitis, chronic obstructive pulmonary disease and delayed hypersensitivity reactions.

The terms "cancer" and "cancerous", "neoplasm", and "tumor" and related terms refer to or describe the physiological condition in mammals that is typically characterized by unregulated cell growth. A "tumor" comprises one or more cancerous cells. Examples of cancer include carcinoma, blastoma, sarcoma, seminoma, glioblastoma, melanoma, leukemia, and myeloid or lymphoid malignancies. More particular examples of such cancers include squamous cell cancer (e.g., epithelial squamous cell cancer) and lung cancer including small-cell lung cancer, non-small cell lung cancer ("NSCLC"), adenocarcinoma of the lung and squamous carcinoma of the lung. Other cancers include skin, keratoacanthoma, follicular carcinoma, hairy cell leukemia, buccal cavity, pharynx (oral), lip, tongue, mouth, salivary gland, esophageal, larynx, hepatocellular, gastric, stomach, gastrointestinal, small intestine, large intestine, pancreatic, cervical, ovarian, liver, bladder, hepatoma, breast, colon, rectal, colorectal, genitourinary, biliary passage, thyroid, papillary, hepatic, endometrial, uterine, salivary gland, kidney or renal, prostate, testis, vulval, peritoneum, anal, penile, bone, multiple myeloma, B-cell lymphoma, central nervous system, brain, head and neck, Hodgkin's, and associated metastases. Examples of neoplastic disorders include myeloproliferative disorders, such as polycythemia vera, essential thrombocytosis, myelofibrosis, such as primary myelofibrosis, and chronic myelogenous leukemia (CML).

A "chemotherapeutic agent" is an agent useful in the treatment of a given disorder, for example, cancer or inflammatory disorders. Examples of chemotherapeutic agents are well-known in the art and include examples such as those disclosed in U.S. Publ. Appl. No. 2010/0048557, incorporated herein by reference. Additionally, chemotherapeutic agents include pharmaceutically acceptable salts, acids or derivatives of any of chemotherapeutic agents, as well as combinations of two or more of them.

"Package insert" is used to refer to instructions customarily included in commercial packages of therapeutic products that contain information about the indications, usage, dosage, administration, contraindications or warnings concerning the use of such therapeutic products.

Unless otherwise stated, structures depicted herein are also meant to include compounds that differ only in the presence of one or more isotopically enriched atoms.

Exemplary isotopes that can be incorporated into compounds of the invention, include isotopes of hydrogen, carbon, nitrogen, oxygen, phosphorus, sulfur, fluorine, chlorine, and iodine such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$, and $^{125}I$, respectively. Isotopically-labeled compounds (e.g., those labeled with $^{3}H$ and $^{14}C$) can be useful in compound or substrate tissue distribution assays. Tritiated (i.e., $^{3}H$) and carbon-14 (i.e., $^{14}C$) isotopes can be useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements). In some embodiments, in compounds of the invention, one or more carbon atoms are replaced by $^{13}C$- or $^{14}C$-enriched carbon. Positron emitting isotopes such as $^{15}O$, $^{13}N$, $^{11}C$, and $^{18}F$ are useful for positron emission tomography (PET) studies to examine substrate receptor occupancy. Isotopically labeled compounds can generally be prepared by following procedures analogous to those disclosed in the Schemes or in the Examples herein, by substituting an isotopically labeled reagent for a non-isotopically labeled reagent.

It is specifically contemplated that any limitation discussed with respect to one embodiment of the invention may apply to any other embodiment of the invention. Furthermore, any compound or composition of the invention may be used in any method of the invention, and any method of the invention may be used to produce or to utilize any compound or composition of the invention.

The use of the term "or" is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device or method being employed to determine the value.

As used herein, "a" or "an" means one or more, unless clearly indicated otherwise. As used herein, "another" means at least a second or more.

Headings used herein are intended only for organizational purposes.

Inhibitors of Janus Kinases

In one embodiment, the invention provides a compound of Formula (I) as an inhibitor of Janus kinase (e.g., JAK1):

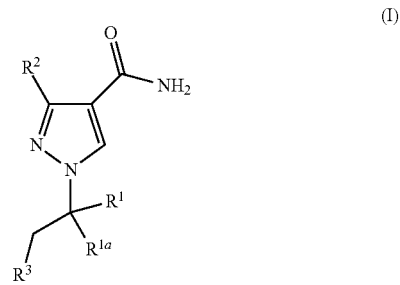

or a salt thereof, wherein:

$R^1$ and $R^{1a}$ taken together with the atom to which they are attached form a 3-10 membered carbocycle optionally substituted with $R^a$ and optionally substituted with $R^b$; or $R^1$ and $R^{1a}$ taken together with the atom to which they are attached form a 3-10 membered heterocycle optionally substituted with $R^c$ and optionally substituted with $R^d$;

$R^2$ is —$NR^eR^f$;

$R^3$ is —$CH_3$ or —CN;

$R^a$ is —$NR^rR^s$;

each $R^b$ is independently selected from the group consisting of halo, cyano, hydroxy, oxo, $C_1$-$C_6$alkyl, $C_1$-$C_6$alkoxy, —$NH_2$, —$NHCH_3$, —$N(CH_3)_2$, —SH, and —$SCH_3$, wherein any $C_1$-$C_6$alkyl, and $C_1$-$C_6$alkoxy is optionally substituted with halo, cyano, hydroxy, oxo, $C_{1-3}$alkyl, $C_{1-3}$alkoxy, —$NH_2$, —$NHCH_3$, —$N(CH_3)_2$, —SH, or —$SCH_3$, wherein any $C_{1-3}$alkyl and $C_{1-3}$alkoxy is optionally substituted with halo, hydroxy, cyano or oxo;

$R^c$ is —$OR^m$, —$SR^m$, —$NR^mR^n$, —$C(O)R^m$, —$C(O)OR^m$, —$C(O)NR^mR^n$, —$NR^mC(O)R^n$, —$S(O)_{1-2}R^m$, —$NR^mS(O)_{1-2}R^n$, —$S(O)_{1-2}NR^mR^n$, $C_1$-$C_6$alkyl, $C_2$-$C_6$alkenyl, $C_2$-$C_6$alkynyl, 3-10 membered carbocyclyl, 3-10 membered heterocyclyl, 6-10 membered aryl, or 5-10 membered heteroaryl, wherein any $C_1$-$C_6$alkyl, $C_2$-$C_6$alkenyl, $C_2$-$C_6$alkynyl of $R^c$ is optionally substituted with $R^x$;

each $R^d$ is independently selected from the group consisting of halo, cyano, $C_1$-$C_6$alkyl, and $C_1$-$C_6$alkoxy, wherein any $C_1$-$C_6$alkyl, and $C_1$-$C_6$alkoxy is optionally substituted with halo, hydroxy, cyano or oxo;

$R^e$ is H or $C_1$-$C_4$alkyl;

$R^f$ is —C(=O)—$R^g$, wherein $R^g$ is H, hydroxy, $C_1$-$C_6$alkyl, $C_1$-$C_6$alkoxy, —$NR^tR^u$, or a 3-10 membered carbocyclyl that is optionally substituted with halo, hydroxy, cyano, oxo, $C_1$-$C_3$alkyl or 3-5 membered carbocyclyl;

$R^m$ and $R^n$ are independently selected from the group consisting of hydrogen, 3-6 s membered heterocyclyl, 3-6 membered carbocyclyl, 6-10 membered aryl, 5-10 membered heteroaryl, and $C_1$-$C_6$alkyl, wherein any 3-6 membered heterocyclyl, 3-6 membered carbocyclyl, 6-10 membered aryl, 5-10 membered heteroaryl, and $C_1$-$C_6$alkyl of $R^m$ and $R^n$ is optionally substituted with $R^w$; or $R^m$ and $R^n$ are taken together with the atom to which they are attached to form a 3-8 membered heterocyclyl that is optionally substituted with $R^w$;

each $R^r$ and $R^s$ is independently selected from the group consisting of hydrogen, 3-6 membered heterocyclyl, 3-6 membered carbocyclyl, 6-10 membered aryl, 5-10 membered heteroaryl and $C_1$-$C_3$alkyl, wherein any 3-6 membered heterocyclyl, 3-6 membered carbocyclyl, 6-10 membered aryl, 5-10 membered heteroaryl and $C_1$-$C_3$alkyl of $R^r$ and $R^s$ is optionally substituted with $R^v$; or $R^r$ and $R^s$ are taken together with the atom to which they are attached to form a 3-8 membered heterocyclyl or 5-10 membered heteroaryl, which 3-8 membered heterocyclyl and 5-10 membered heteroaryl is optionally substituted with $R^v$;

$R^t$ and $R^u$ are independently selected from the group consisting of hydrogen, 3-6 membered heterocyclyl, 3-6 membered carbocyclyl, 6-10 membered aryl, 5-10 membered heteroaryl and $C_1$-$C_3$alkyl, wherein any 3-6 membered heterocyclyl, 3-6 membered carbocyclyl, 6-10 membered aryl, 5-10 membered heteroaryl and $C_1$-$C_3$alkyl of $R^t$ and $R^u$ is optionally substituted with halo, hydroxy, cyano or oxo; or $R^t$ and $R^u$ are taken together with the atom to which they are attached to form a 3-6 membered heterocyclyl, optionally substituted with halo, hydroxy, cyano or oxo, or $C_1$-$C_6$alkyl that is optionally substituted with halo, hydroxy, cyano or oxo;

each $R^v$ is independently selected from the group consisting of halo, hydroxy, cyano, oxo, 6-10 membered aryl, 5-10 membered heteroaryl, $C_1$-$C_6$alkyl, $_3$-6 membered carbocyclyl, 3-6 membered heterocyclyl and $C_1$-$C_6$alkoxy, wherein any 6-10 membered aryl, 5-10 membered heteroaryl, $C_1$-$C_6$alkyl, 3-6 membered carbocyclyl, 3-6 membered heterocyclyl and $C_1$-$C_6$alkoxy of $R^v$ is optionally substituted with halo, hydroxy, cyano, $C_1$-$C_6$alkyl, oxo, 3-6 membered carbocycle, 3-6 membered heterocyclyl, $C_1$-$C_6$alkoxy, 5-10 membered heteroaryl or 6-10 membered aryl, each of which is optionally substituted with halo, hydroxy, cyano, oxo $C_1$-$C_3$alkyl or $C_1$-$C_3$alkoxy;

each $R^w$ is independently selected from the group consisting of halo, hydroxy, cyano, oxo, 6-10 membered aryl, 5-10 membered heteroaryl, $C_1$-$C_6$alkyl, 3-6 membered carbocyclyl, 3-6 membered heterocyclyl and $C_1$-$C_6$alkoxy, wherein any 6-10 membered aryl, 5-10 membered heteroaryl, $C_1$-$C_6$alkyl, 3-6 membered carbocyclyl, 3-6 membered heterocyclyl and $C_1$-$C_6$alkoxy of $R^w$ is optionally substituted with halo, hydroxy, cyano, $C_1$-$C_6$alkyl, oxo, 3-6 membered carbocyclyl, 3-6 membered heterocyclyl $C_1$-$C_6$alkoxy, 5-10 membered heteroaryl, or 6-10 membered aryl, each optionally substituted with halo, hydroxy, cyano, oxo, $C_1$-$C_3$alkyl or $C_1$-$C_3$alkoxy; and each $R^x$ is independently selected from the group consisting of halo, hydroxy, cyano, nitro, oxo, —$OR'''$, —$SR'''$, —$NR'''R''$, —$C(O)R'''$, —$C(O)OR'''$, —$C(O)NR'''R''$, —$NR'''C(O)R''$, —$S(O)_{1-2}R'''$, —$NR'''S(O)_{1-2}R''$, —$S(O)_{1-2}NR'''R''$, 3-10 membered carbocyclyl, 3-10 membered heterocyclyl, 6-10 membered aryl, and 5-10 membered heteroaryl, wherein any 3-10 membered carbocyclyl, 3-10 membered heterocyclyl, 6-10 membered aryl, and 5-10 membered heteroaryl, is optionally substituted with halo, hydroxy, cyano, nitro, $C_2$-$C_3$ alkynyl, —$OR'''$, —$SR'''$, —$NR'''R''$, —$C(O)R'''$, —$C(O)OR'''$, —$C(O)NR'''R''$, —$NR'''C(O)R''$, —$S(O)_{1-2}R'''$, —$NR'''S(O)_{1-2}R''$, —$S(O)_{1-2}NR'''R''$, $C_1$-$C_6$alkyl, oxo, 3-10 membered carbocyclyl, 3-10 membered heterocyclyl, 6-10 membered aryl, or 5-10 membered heteroaryl, wherein any $C_1$-$C_6$alkyl, $C_2$-$C_3$ alkynyl, 3-10 membered carbocyclyl, 3-10 membered heterocyclyl, 6-10 membered aryl, and 5-10 membered heteroaryl is optionally substituted with halo, hydroxy, cyano, oxo, —$OR'''$, —$NR'''R''$, —$C(O)R'''$, —$C(O)OR'''$, —$C(O)NR'''R''$, 3-6 membered carbocyclyl, 6-10 membered aryl, or $C_1$-$C_6$alkyl that is optionally substituted with halo, hydroxy, cyano, oxo or $C_1$-$C_6$alkoxy.

In some embodiments, $R^g$ is H, $C_1$-$C_6$alkyl, $C_1$-$C_6$alkoxy, —$NR^tR^u$, or a 3-10 membered carbocyclyl that is optionally substituted with halo, hydroxy, cyano, oxo, $C_1$-$C_3$alkyl or 3-5 membered carbocyclyl In some embodiments, each $R^x$ is independently selected from the group consisting of halo, hydroxy, cyano, nitro, oxo, —$OR'''$, —$SR'''$, —$NR'''R''$, —$C(O)R'''$, —$C(O)OR'''$, —$C(O)NR'''R''$, —$NR'''C(O)R''$, —$S(O)_{1-2}R'''$, —$NR'''S(O)_{1-2}R''$, —$S(O)_{1-2}NR'''R''$, 3-10 membered carbocyclyl, 3-10 membered heterocyclyl, 6-10 membered aryl, and 5-10 s membered heteroaryl, wherein any 3-10 membered carbocyclyl, 3-10 membered heterocyclyl, 6-10 membered aryl, and 5-10 membered heteroaryl, is optionally substituted with halo, hydroxy, cyano, nitro, —$OR'''$, —$SR'''$, —$NR'''R''$, —$C(O)R'''$, —$C(O)OR'''$, —$C(O)NR'''R''$, —$NR'''C(O)R''$, —$S(O)_{1-2}R'''$, —$NR'''S(P)_{1-2}R''$, —$S(O)_{1-2}NR'''R''$, $C_1$-$C_6$alkyl, oxo, 3-10 membered carbocyclyl, 3-10 membered heterocyclyl, 6-10 membered aryl, or 5-10 membered heteroaryl, wherein any $C_1$-$C_6$alkyl, 3-10 membered carbocyclyl, $_3$-10 membered heterocyclyl, 6-10 membered aryl, and 5-10 membered heteroaryl is optionally substituted with halo, hydroxy, cyano, oxo, —$OR'''$, —$NR'''R''$, —$C(O)R'''$, —$C(O)OR'''$, —$C(O)NR'''R''$, 6-10 membered aryl, or $C_1$-$C_6$alkyl that is optionally substituted with halo, hydroxy, cyano, oxo or $C_1$-$C_6$alkoxy.

In some embodiments, $R^3$ is —$CH_3$.

In some embodiments, $R^3$ is —CN.

In some embodiments, a compound of Formula (I) is further defined as a compound of Formula (Ia):

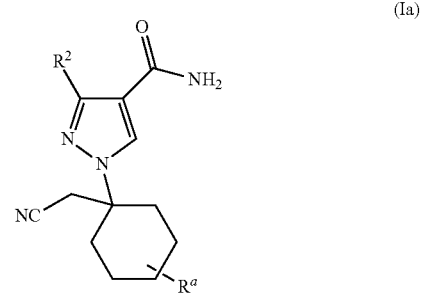

(Ia)

or a salt thereof.

In some embodiments, a compound of Formula (I) is further defined as a compound of Formula (Ib):

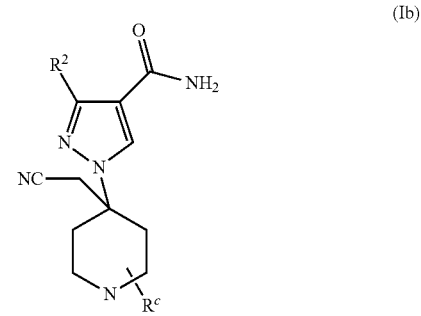

(Ib)

In some embodiments, a compound of Formula (I) is further defined as a compound of Formula (Ic):

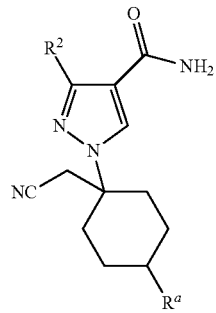

(Ic)

or a salt thereof.

In some embodiments, a compound of Formula (I) is further defined as a compound of Formula (Id):

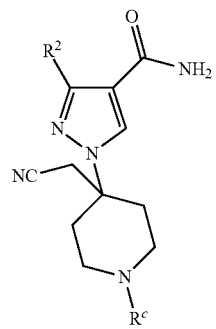

(Id)

or a salt thereof.

In some embodiments, R² is selected from the group consisting of:

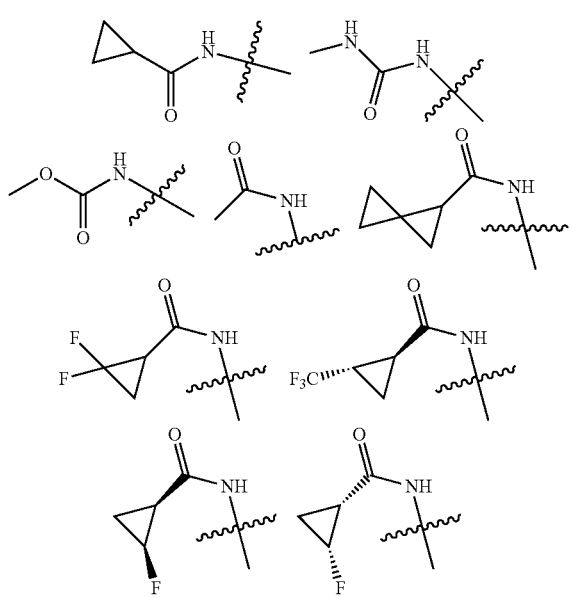

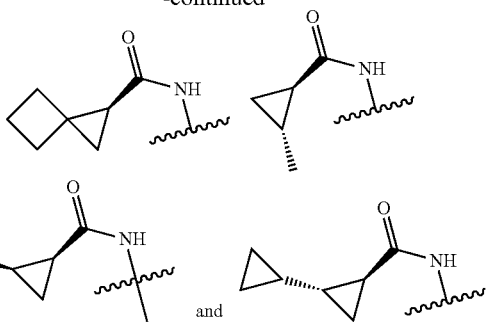

In some embodiments, R² is selected from the group consisting of:

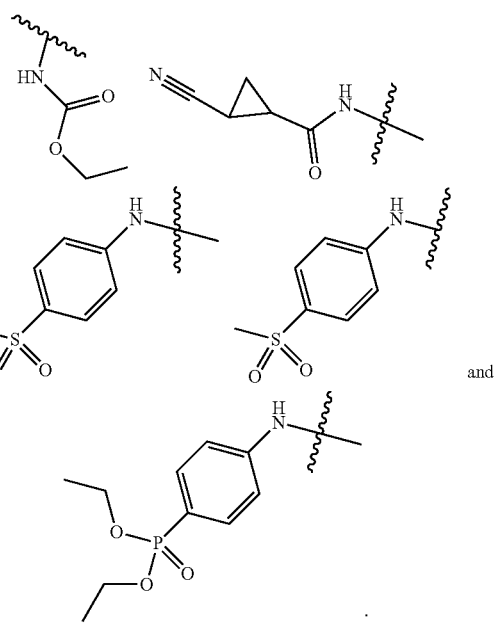

In some embodiments, R² is cyclopropylcarbonylamino.

In some embodiments, the group

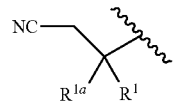

is selected from the group consisting of:

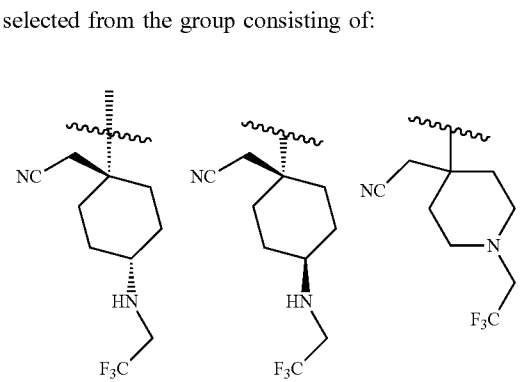

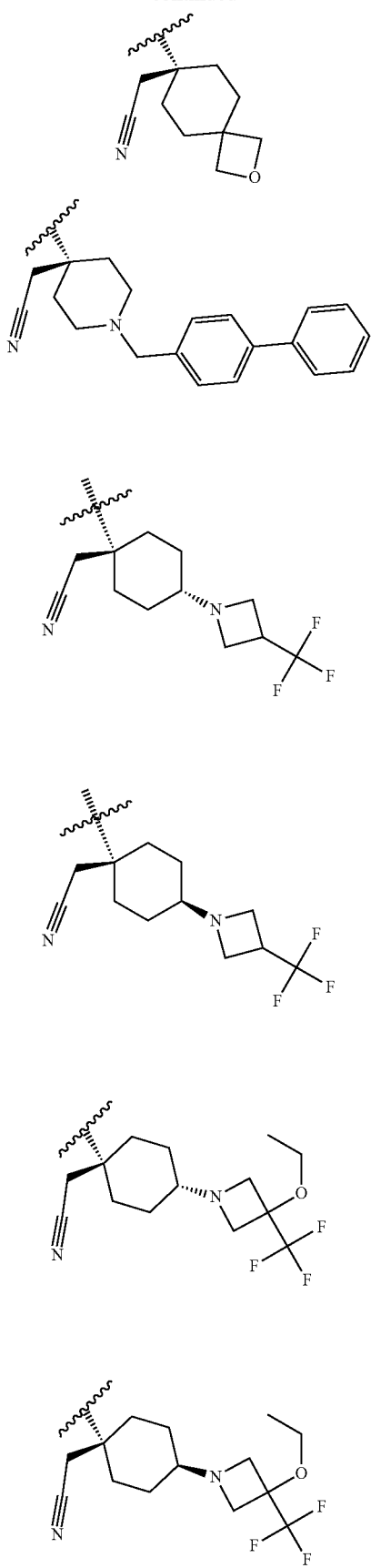
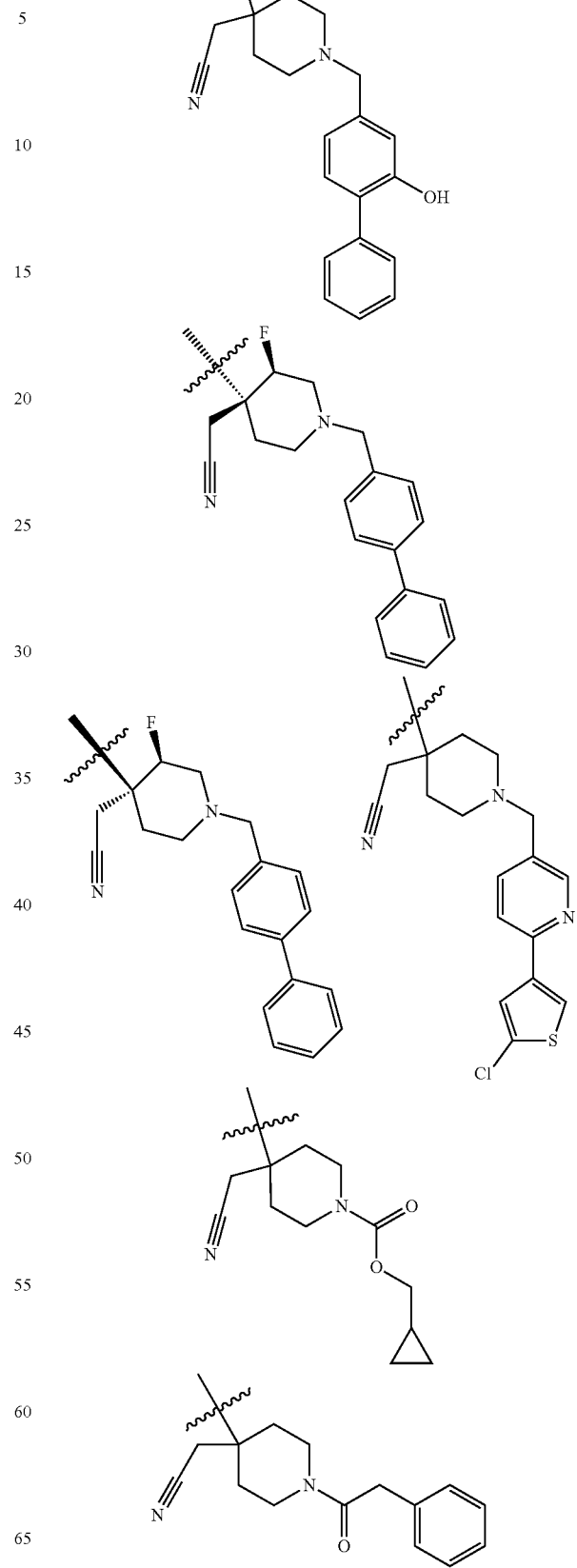

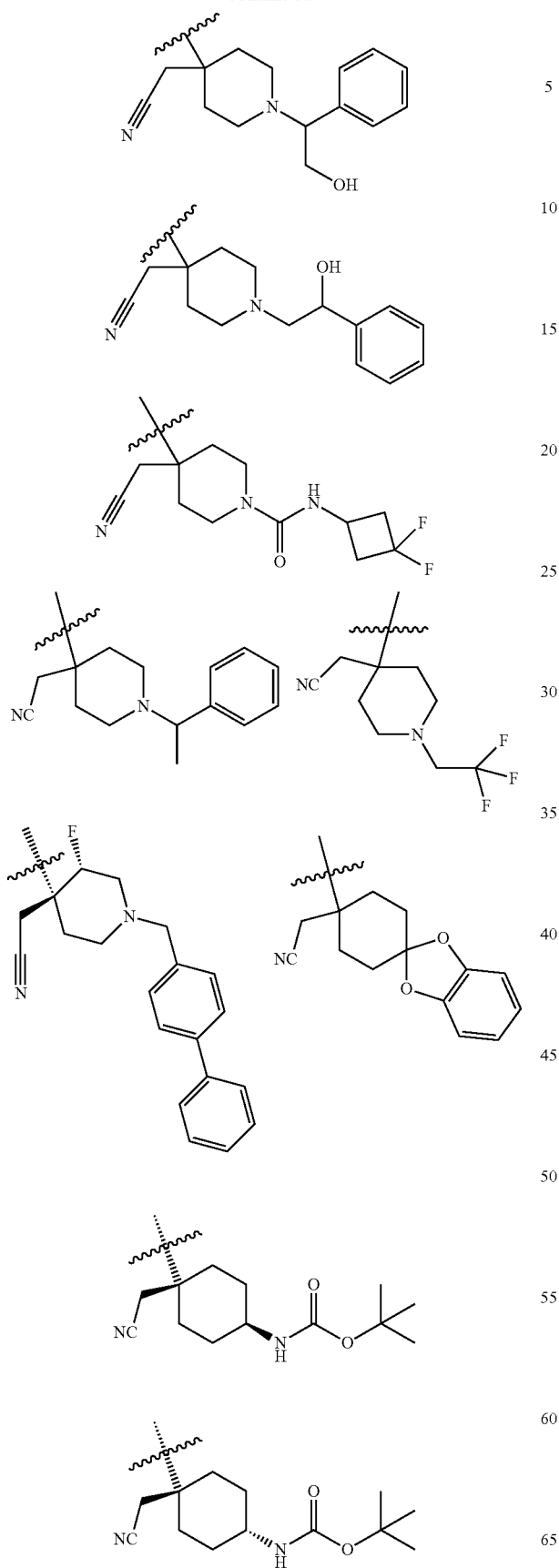
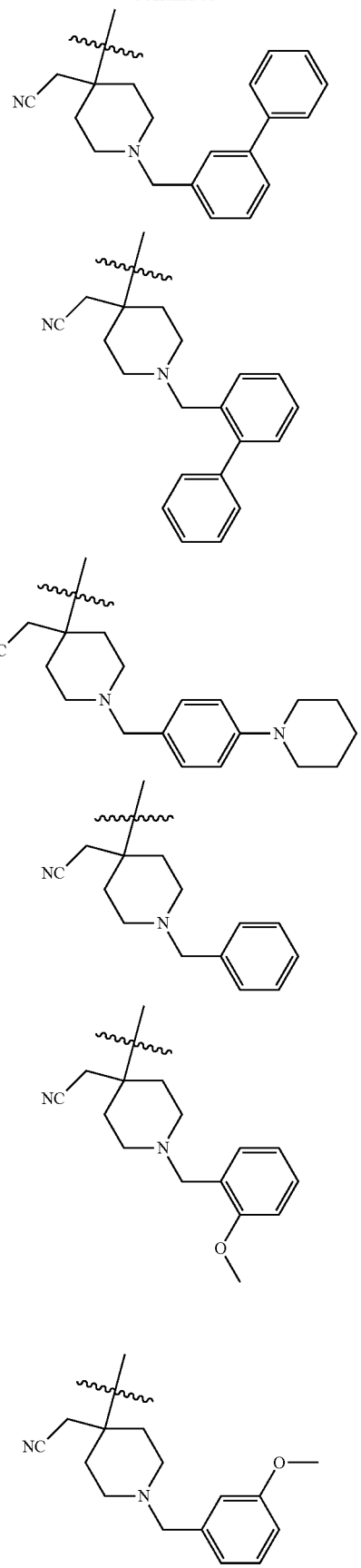

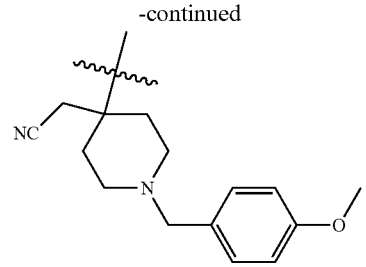
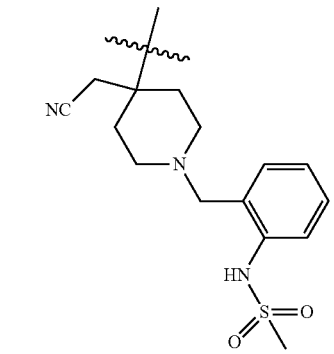
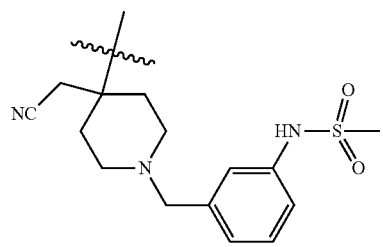
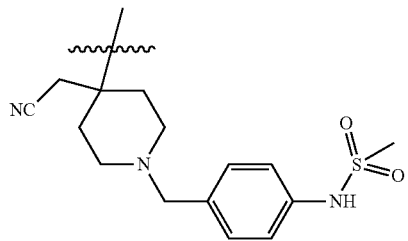
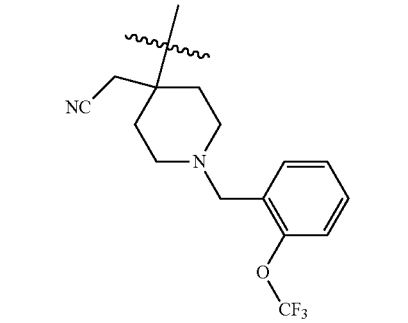
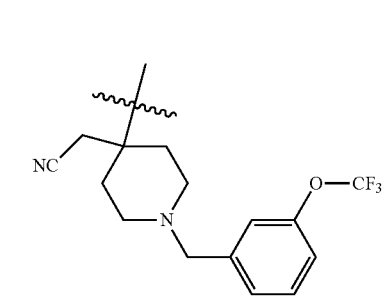
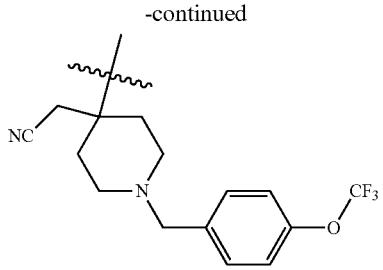
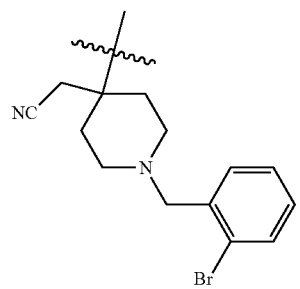
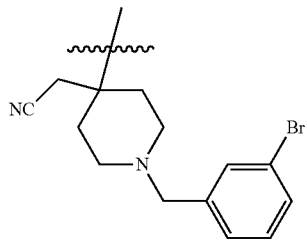
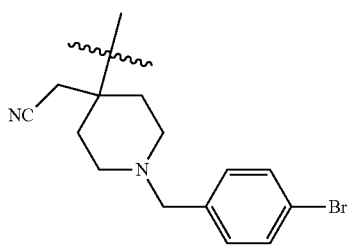
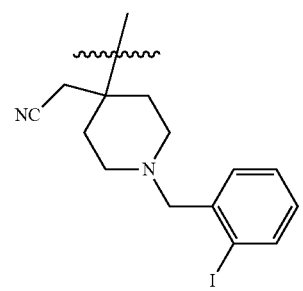
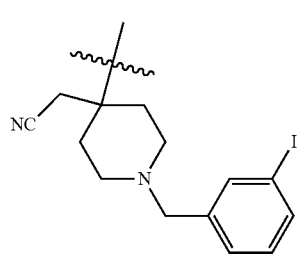

31
-continued
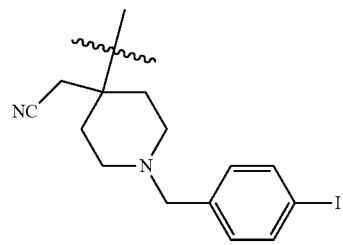
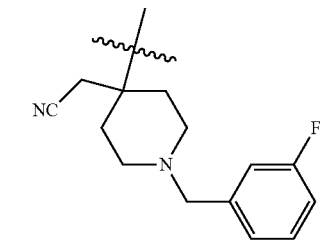
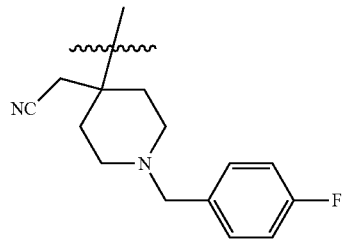
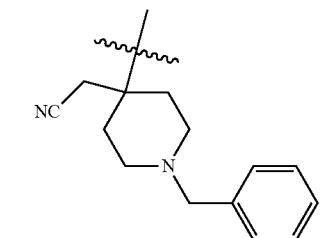
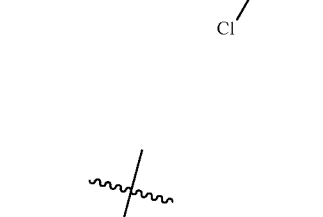
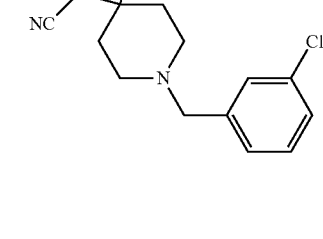
32
-continued
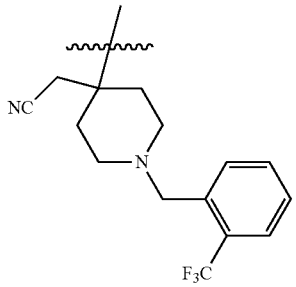
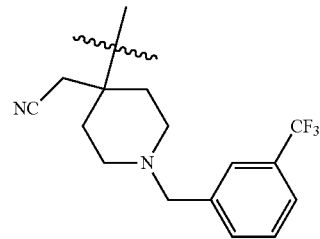
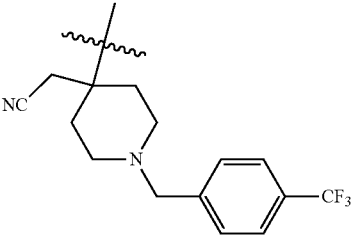
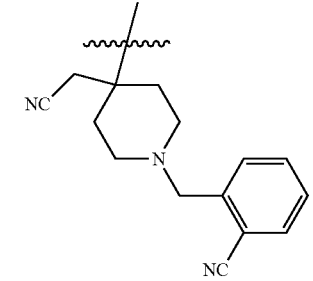
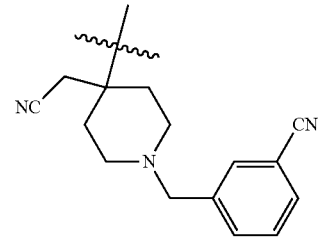
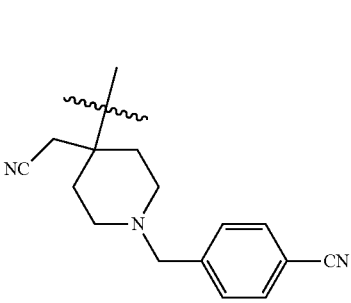

-continued
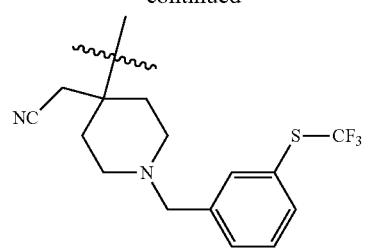
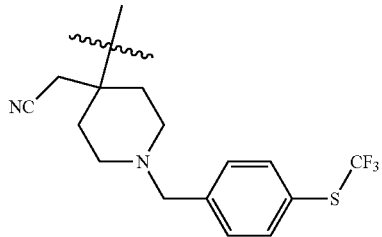
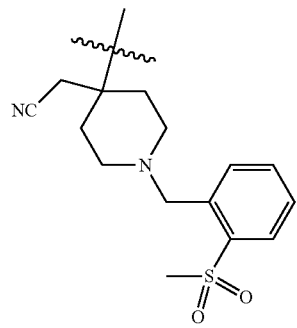
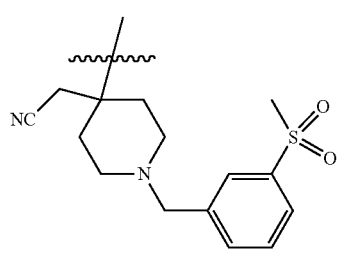
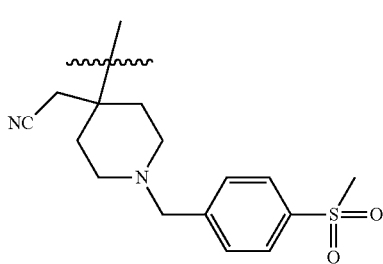
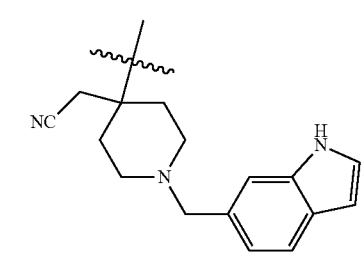
-continued
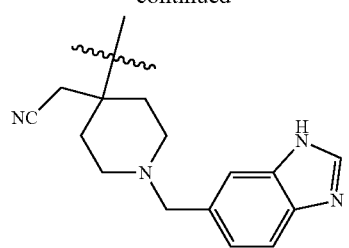
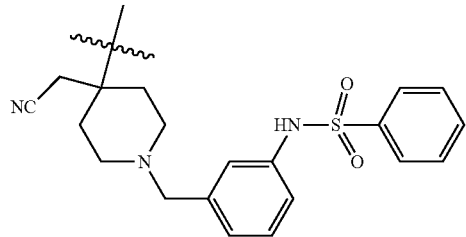
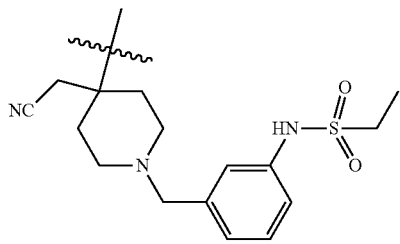
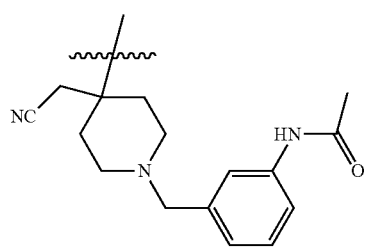
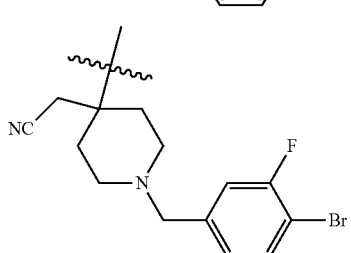
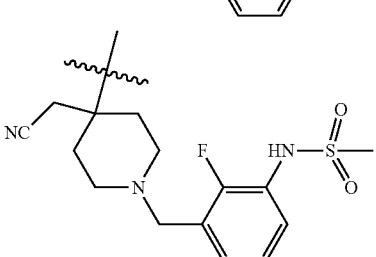
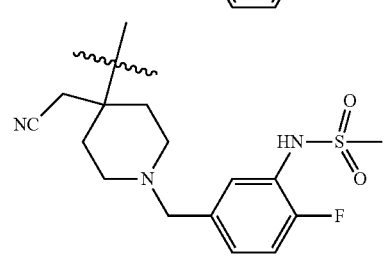

35
-continued
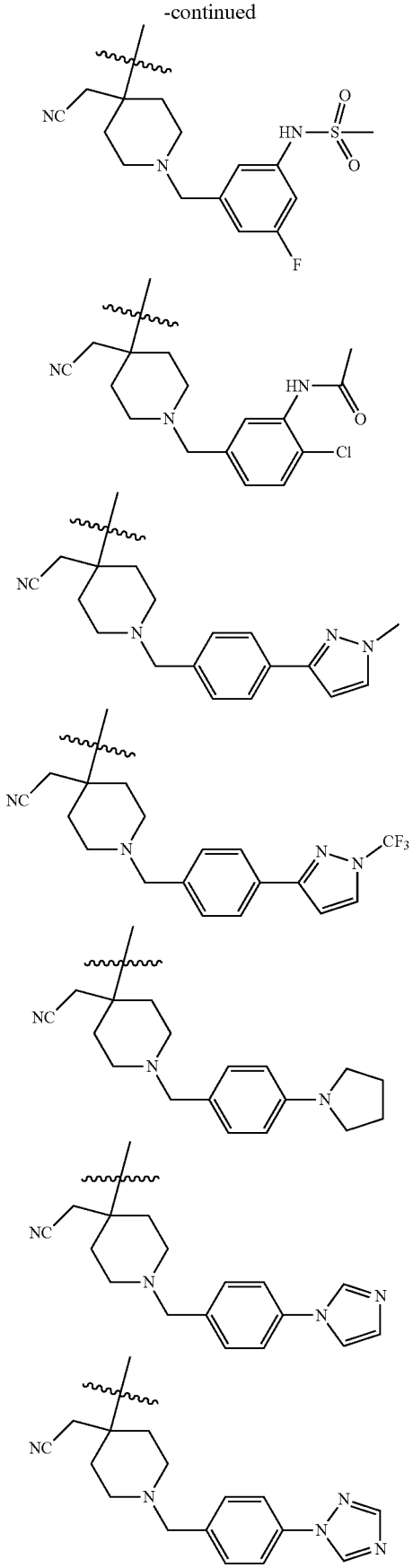
36
-continued
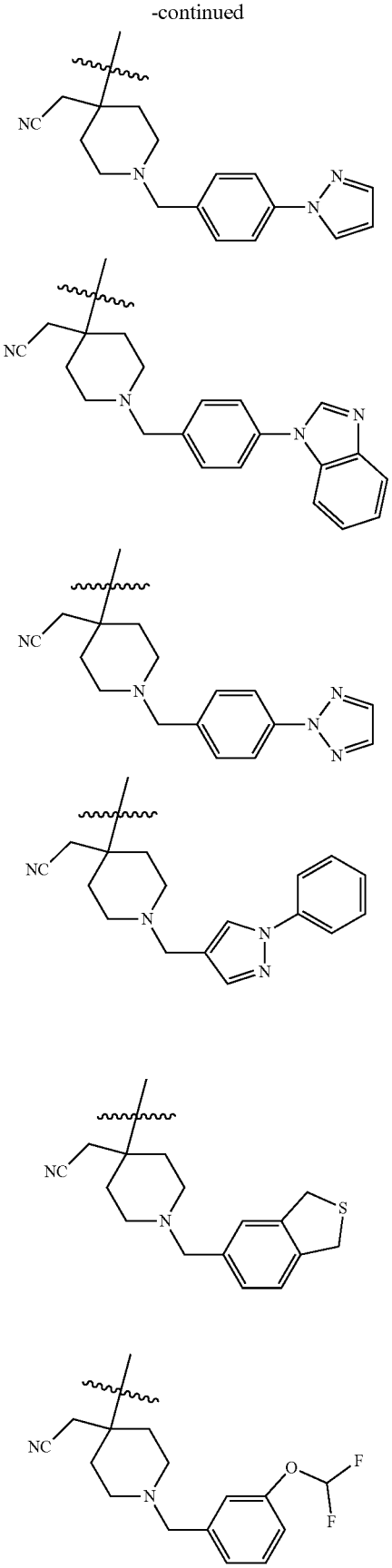

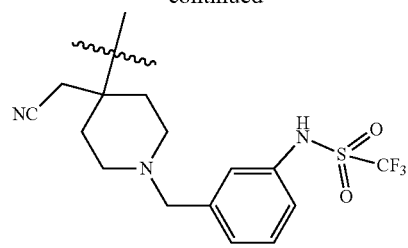
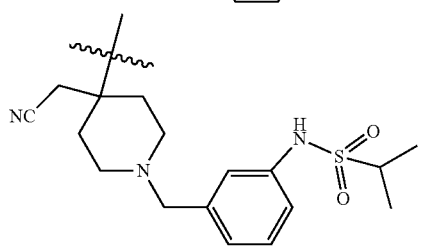
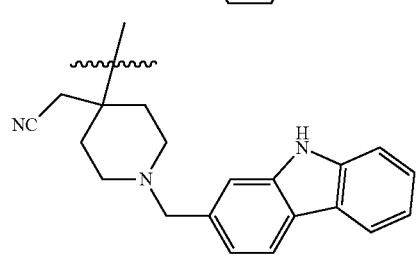
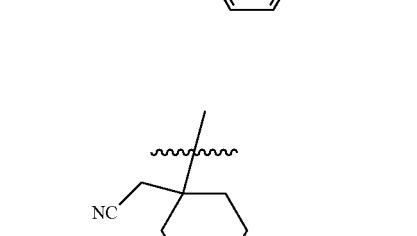
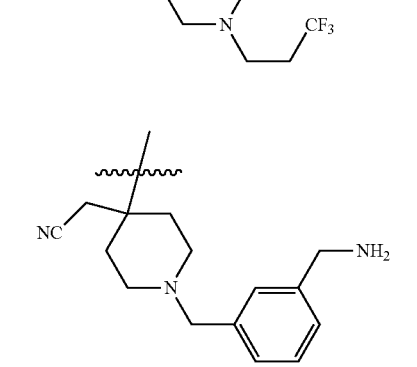
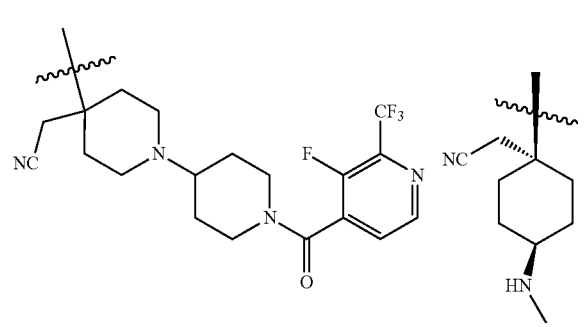
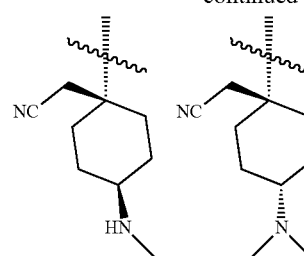
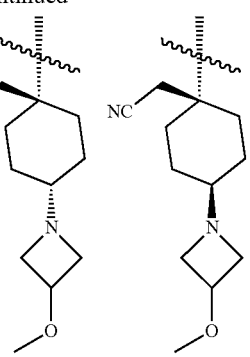
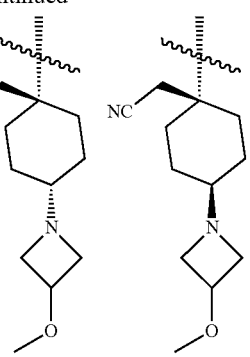
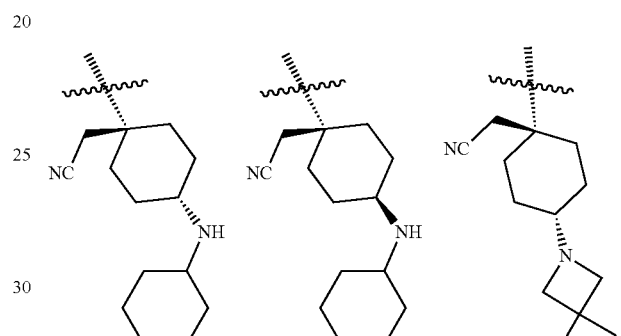
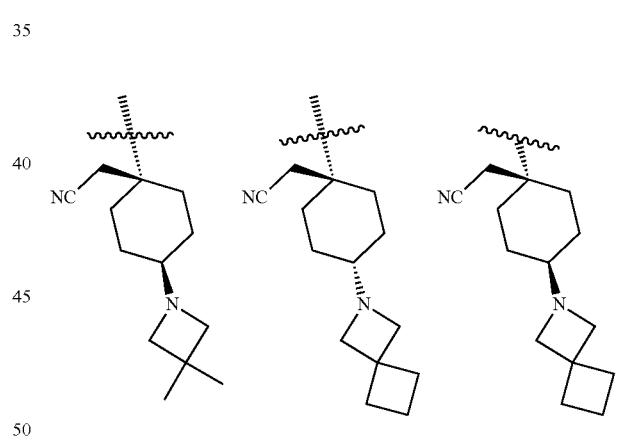
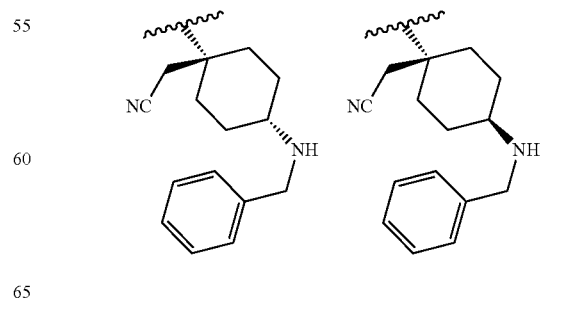

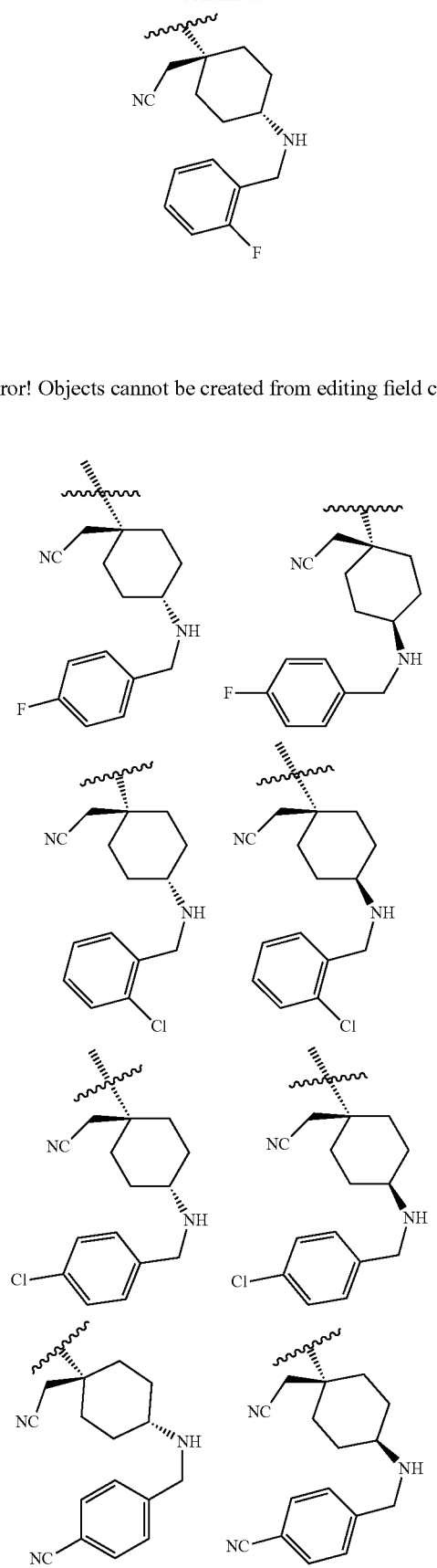
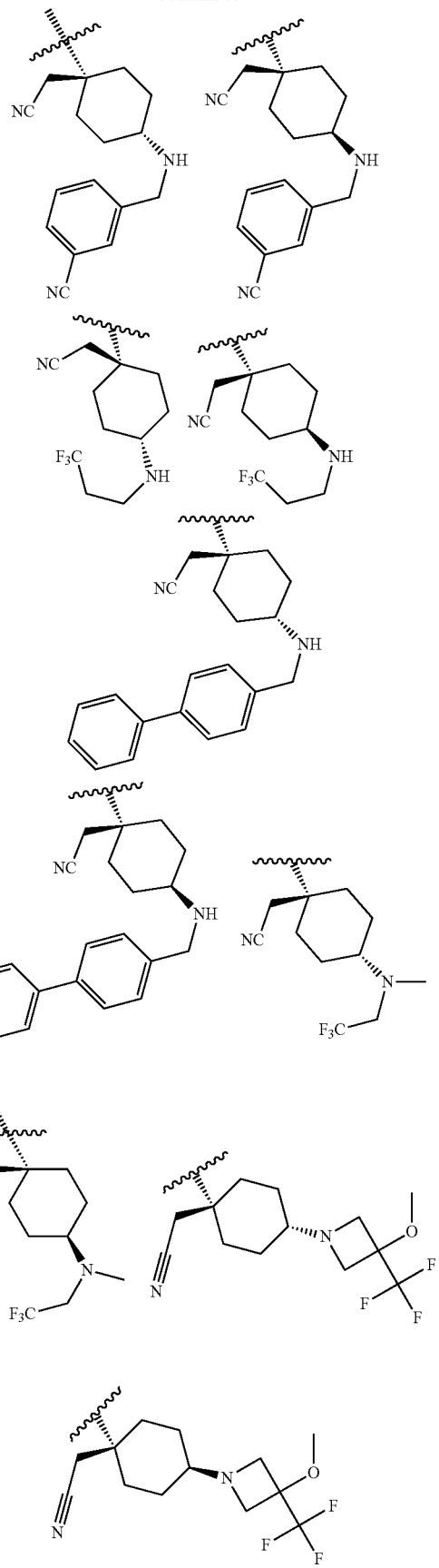
Error! Objects cannot be created from editing field codes.

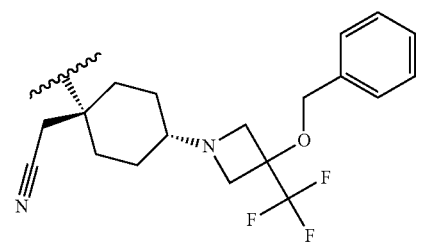
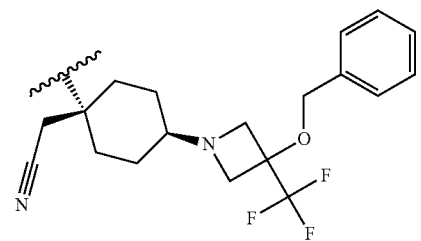
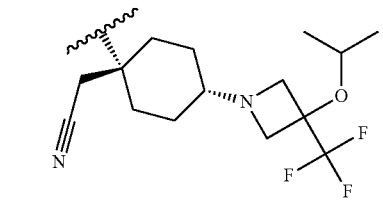
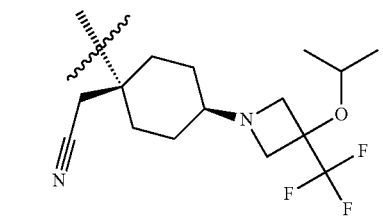
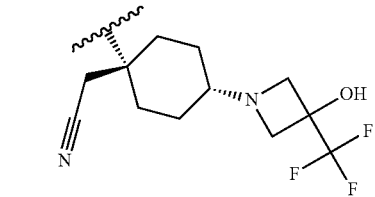
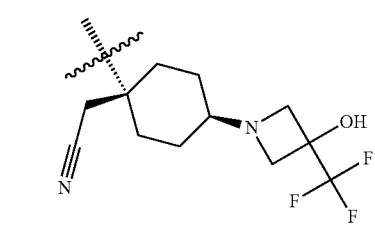
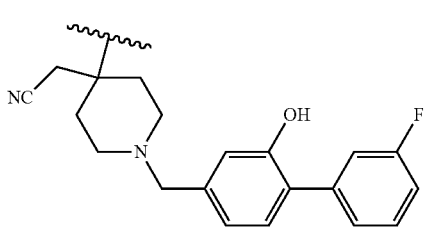
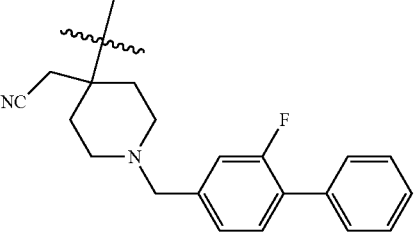
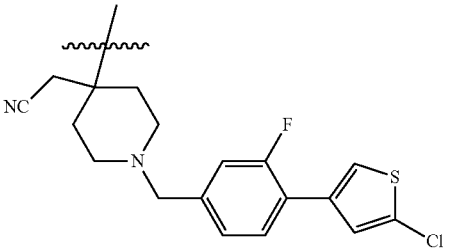
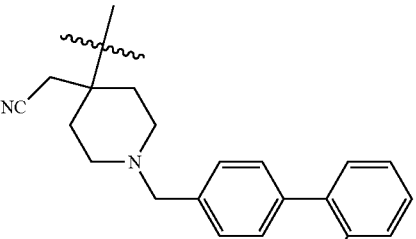
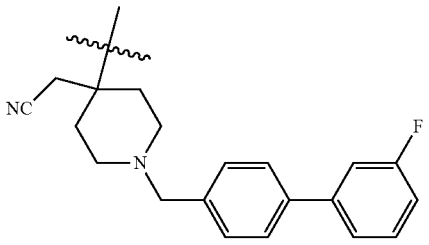
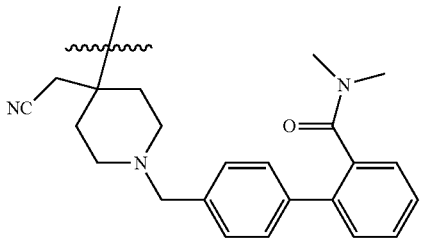
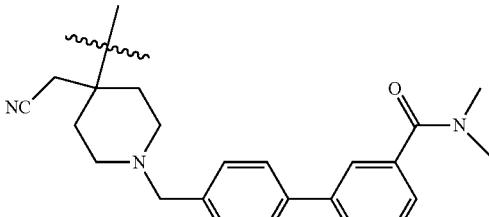
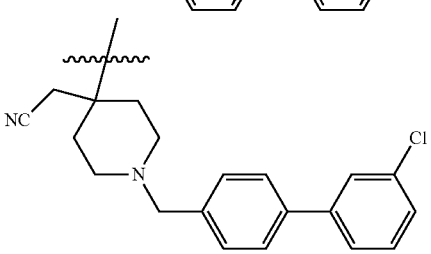

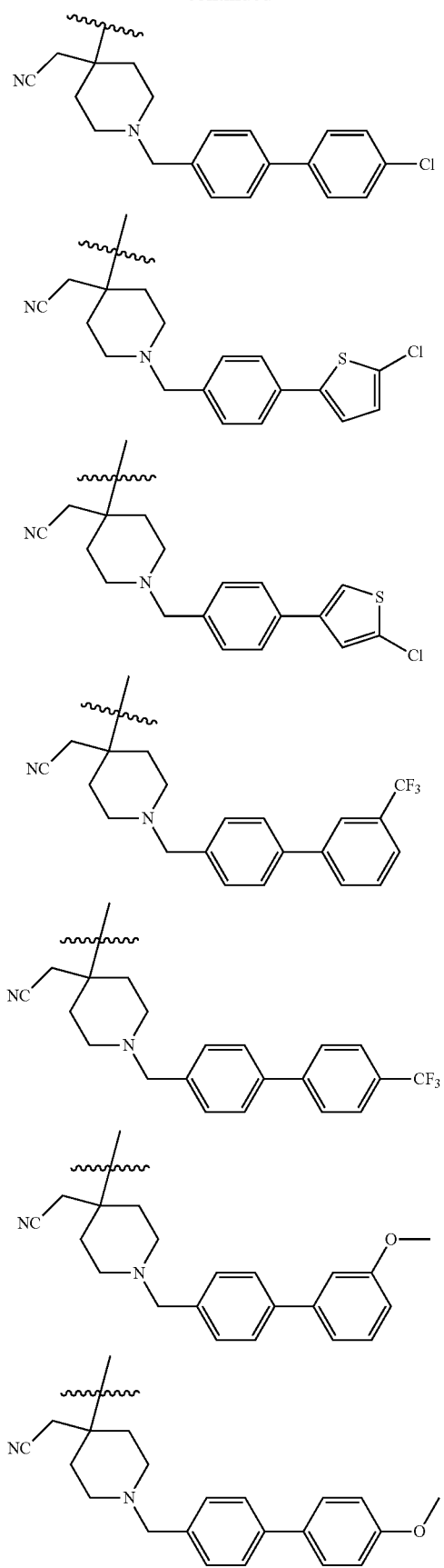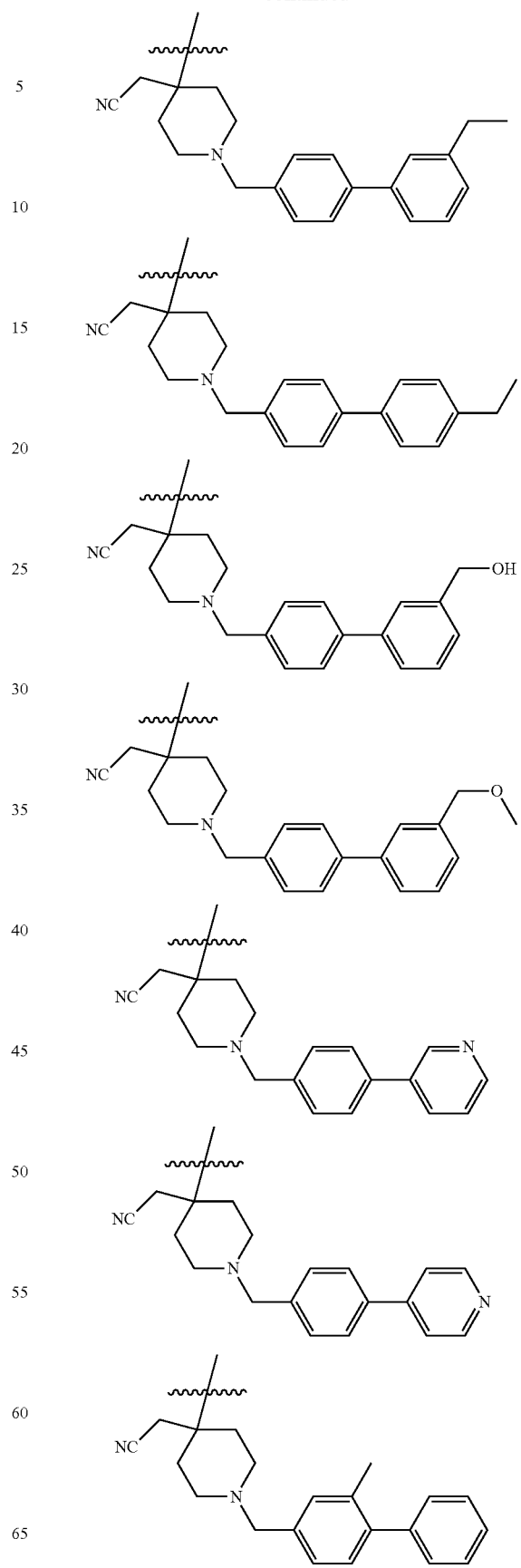

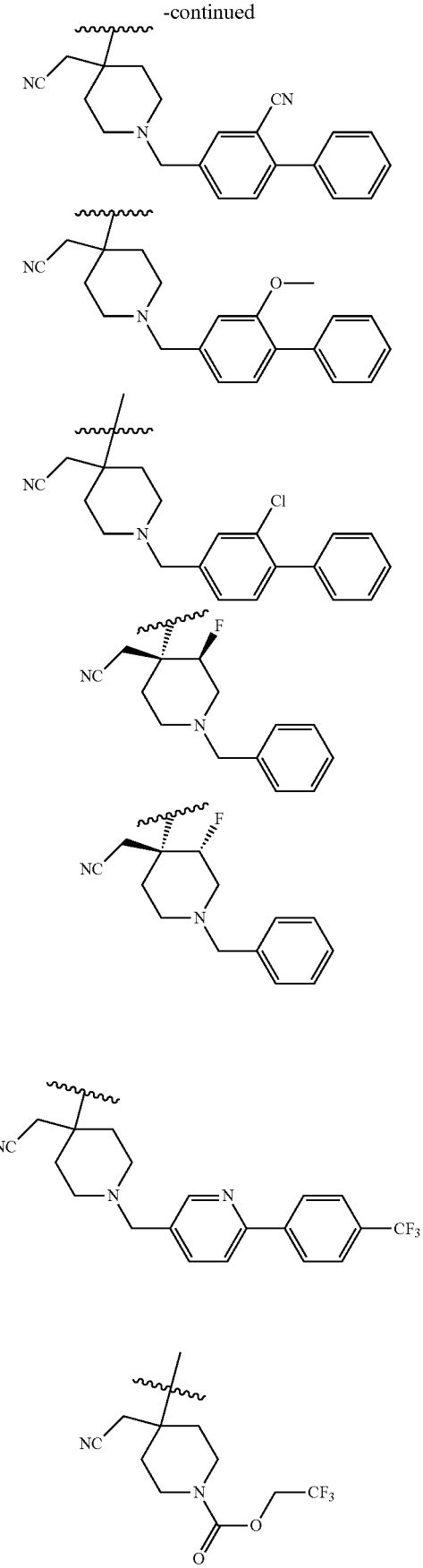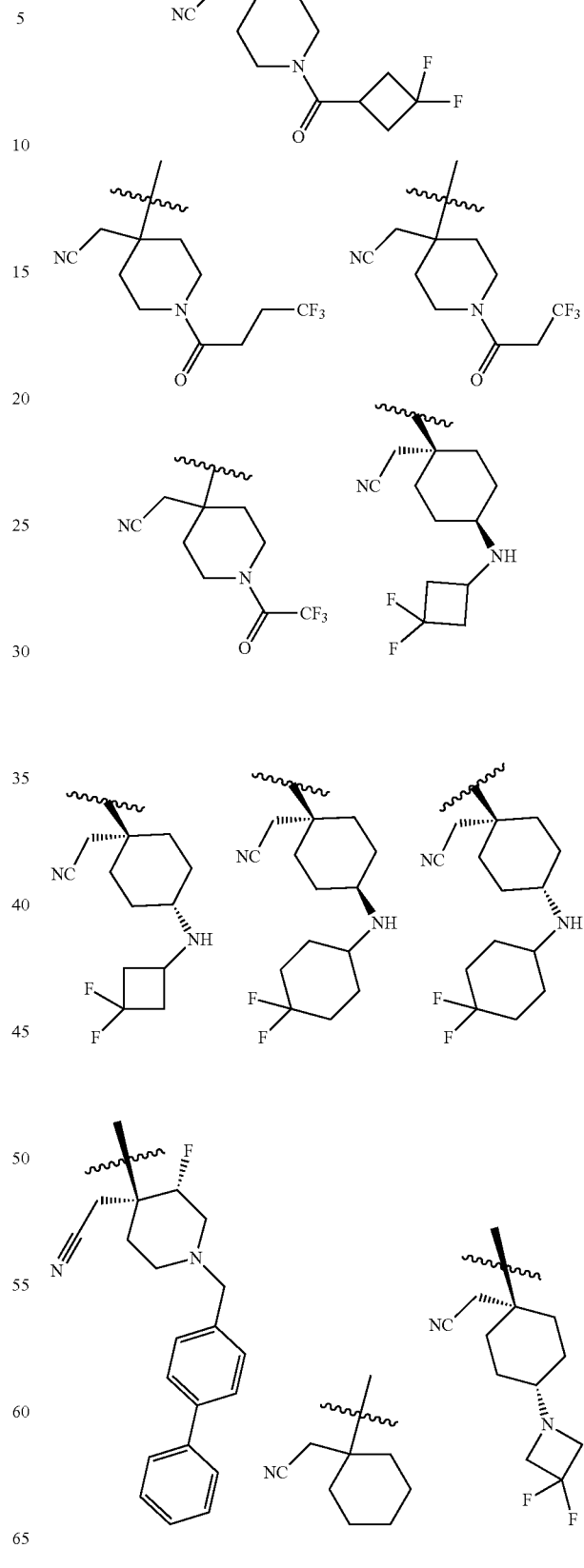

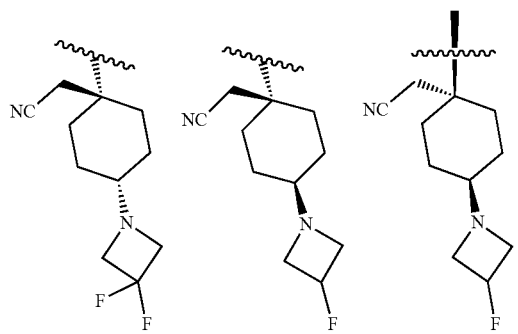
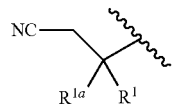
is selected from the group consisting of:
and optionally may further include
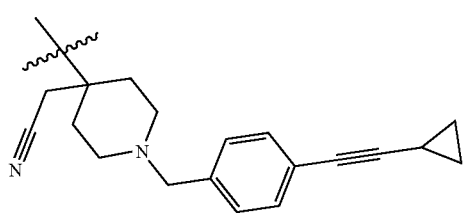
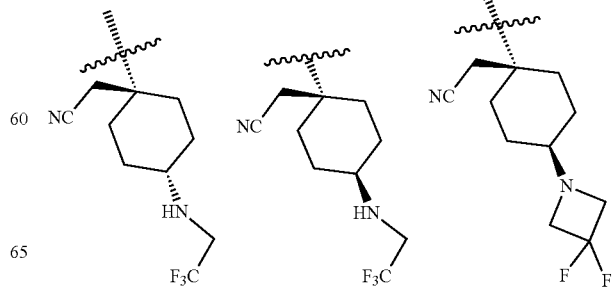

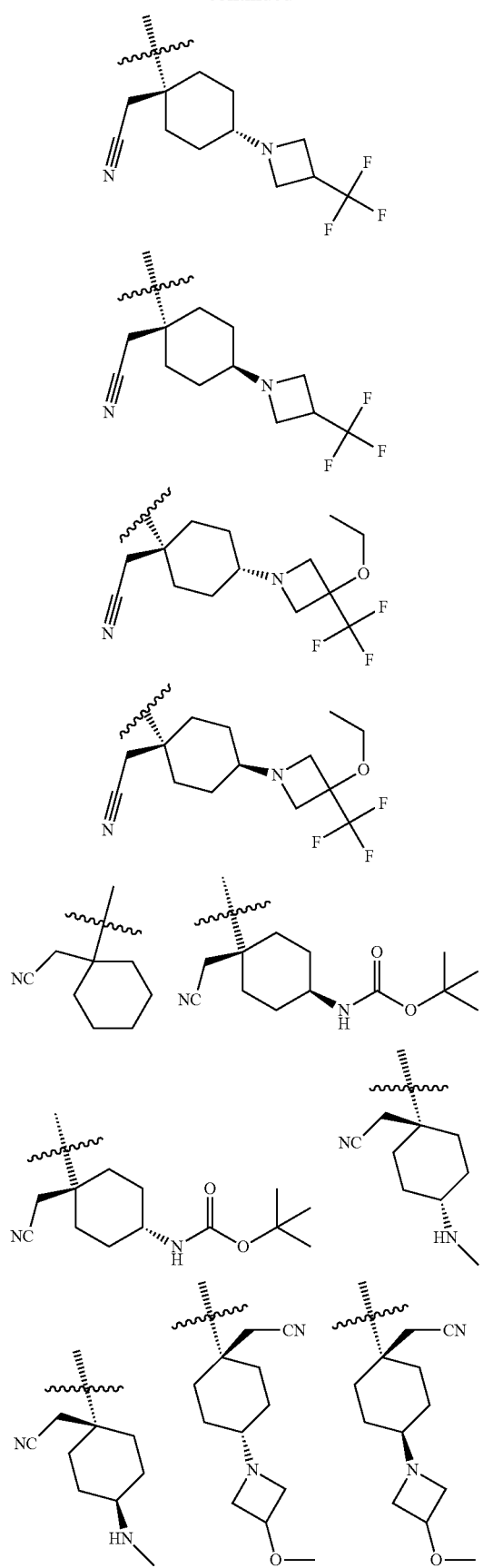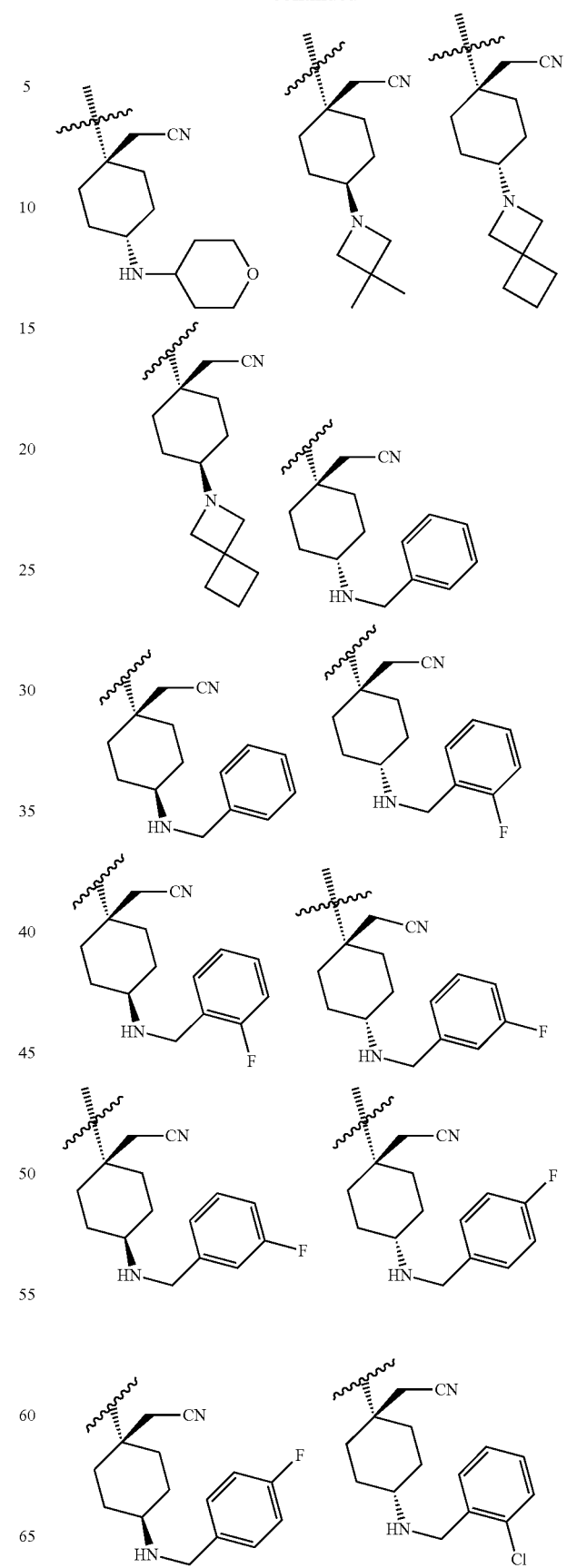

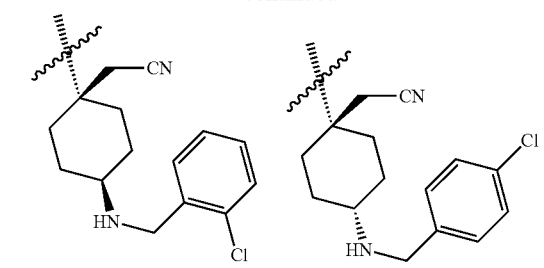
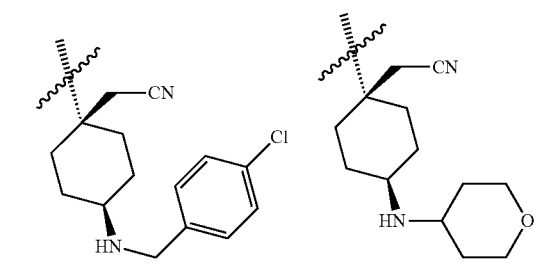
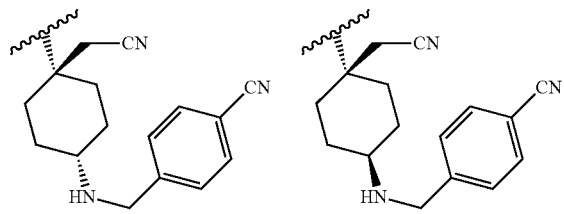
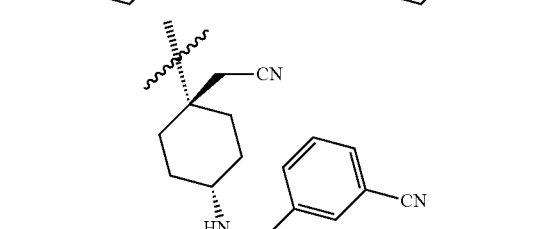
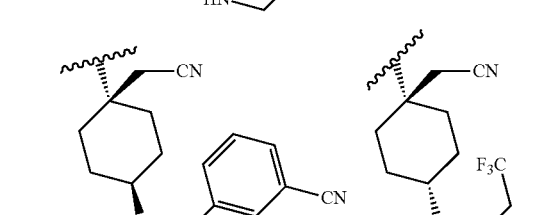
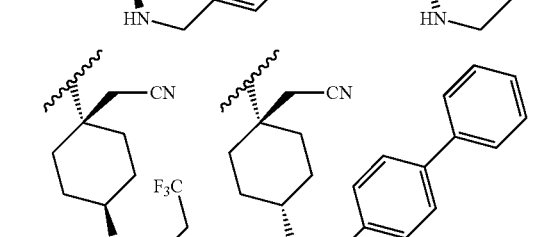
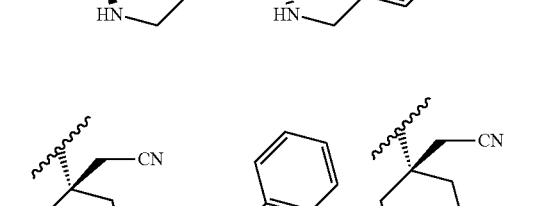
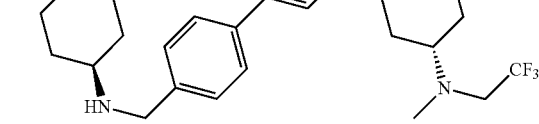
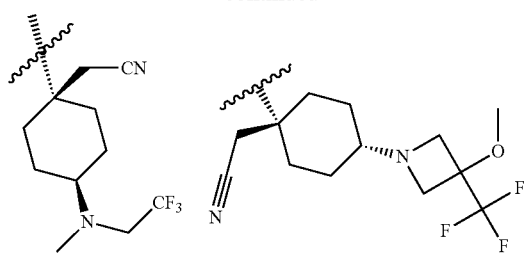
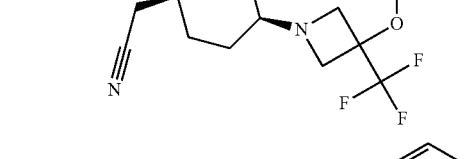
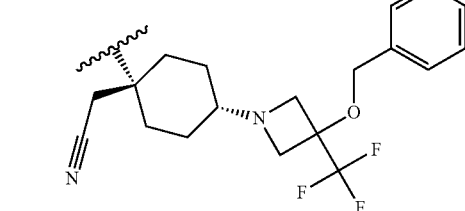
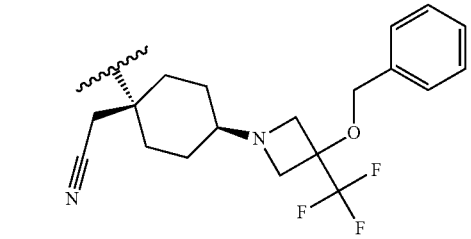
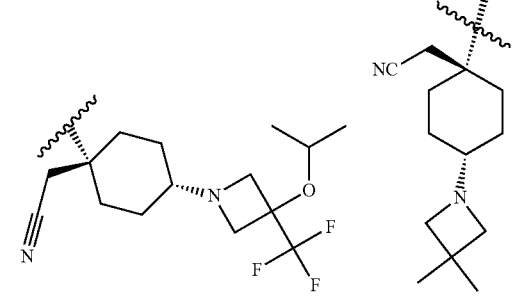
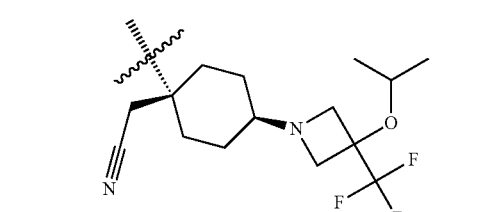
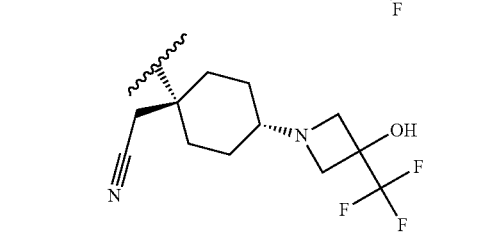

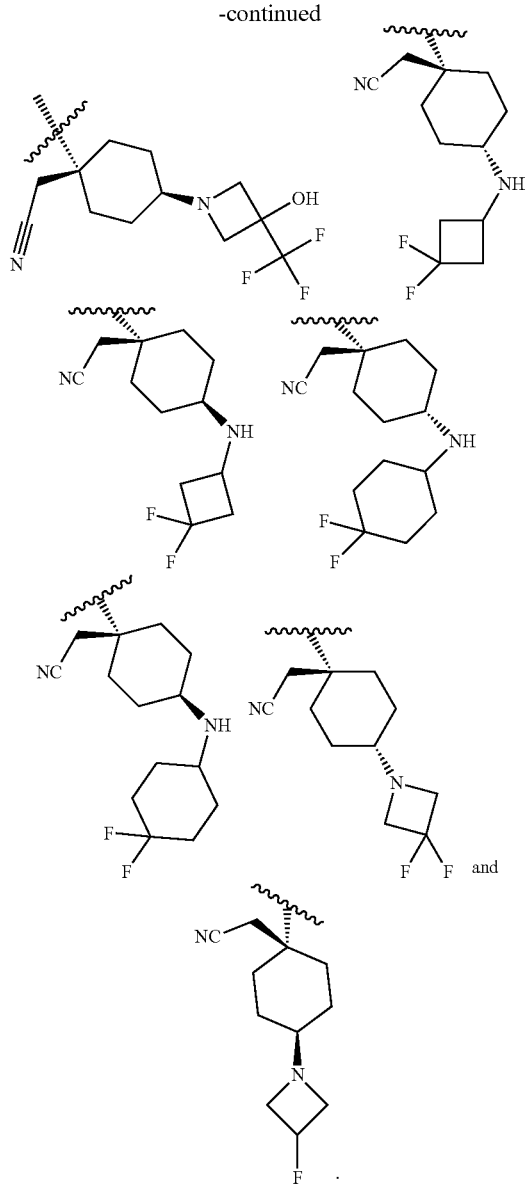
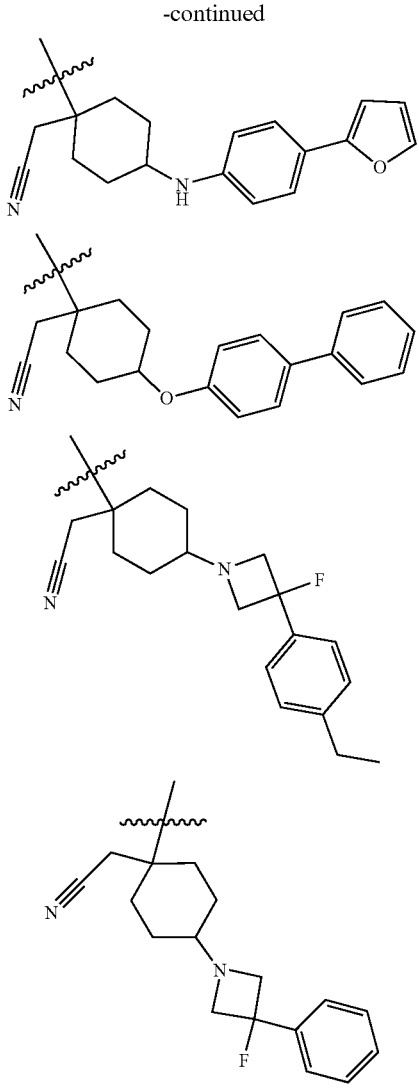
In some embodiments, the group
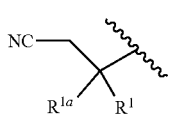
is selected from the group consisting of:
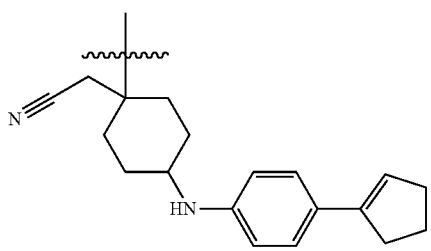
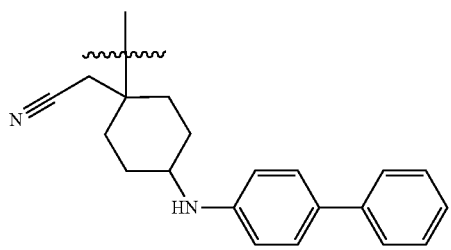
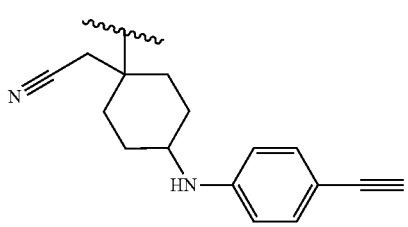

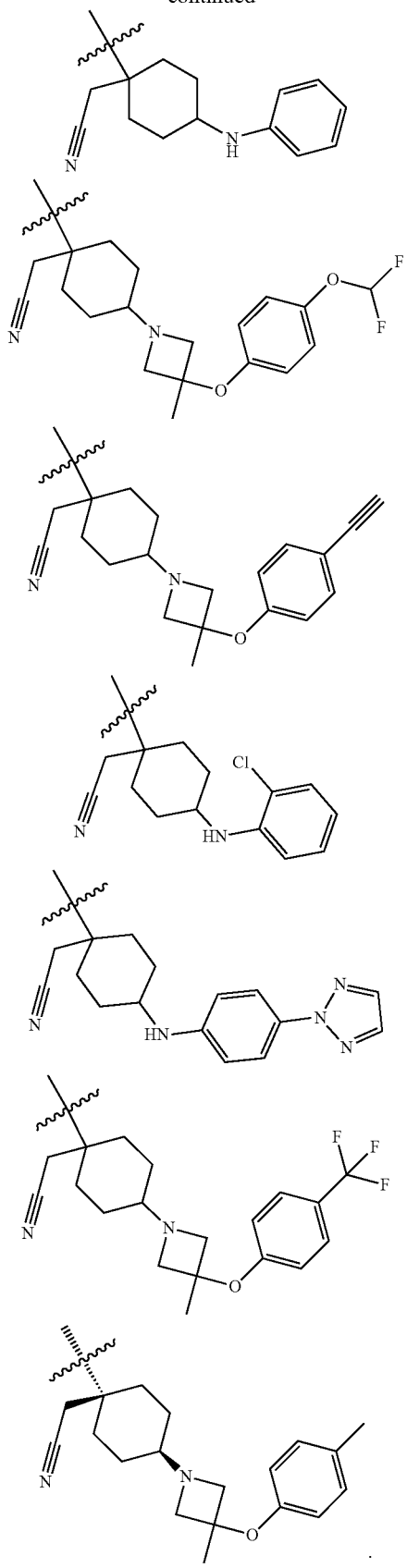
In some embodiments, the group
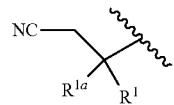
is selected from the group consisting of:
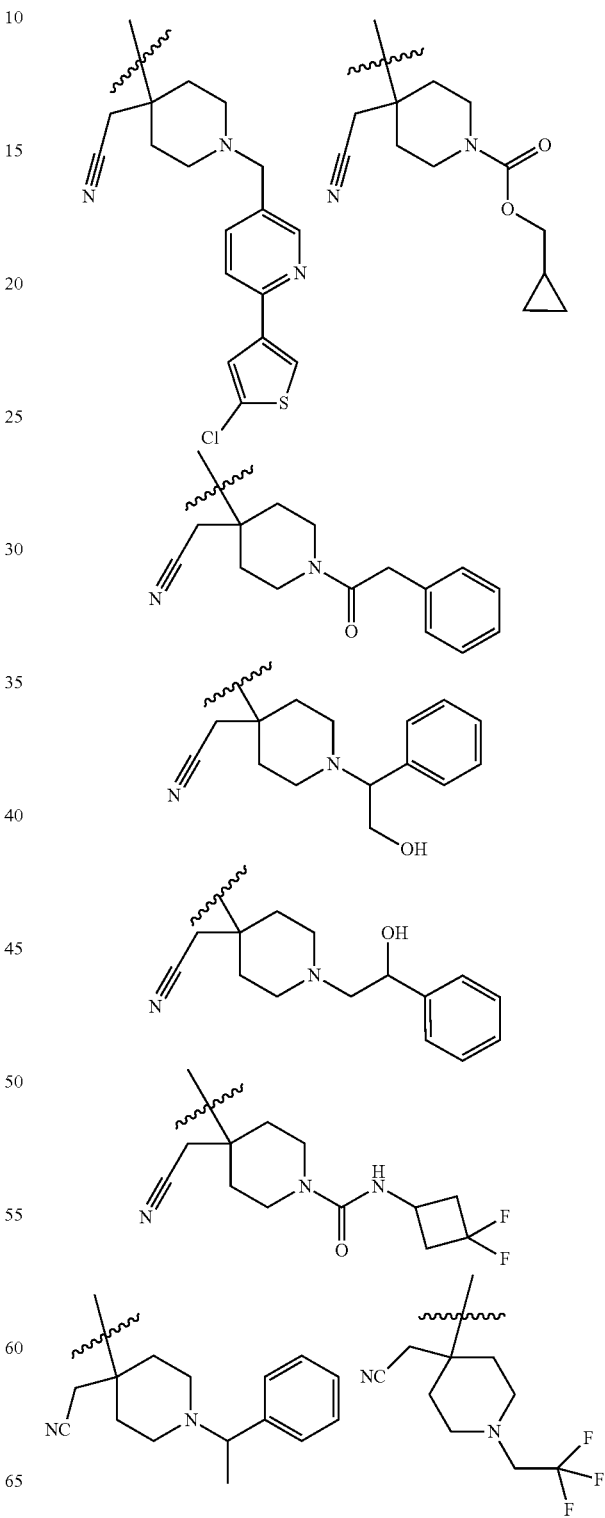

57
-continued
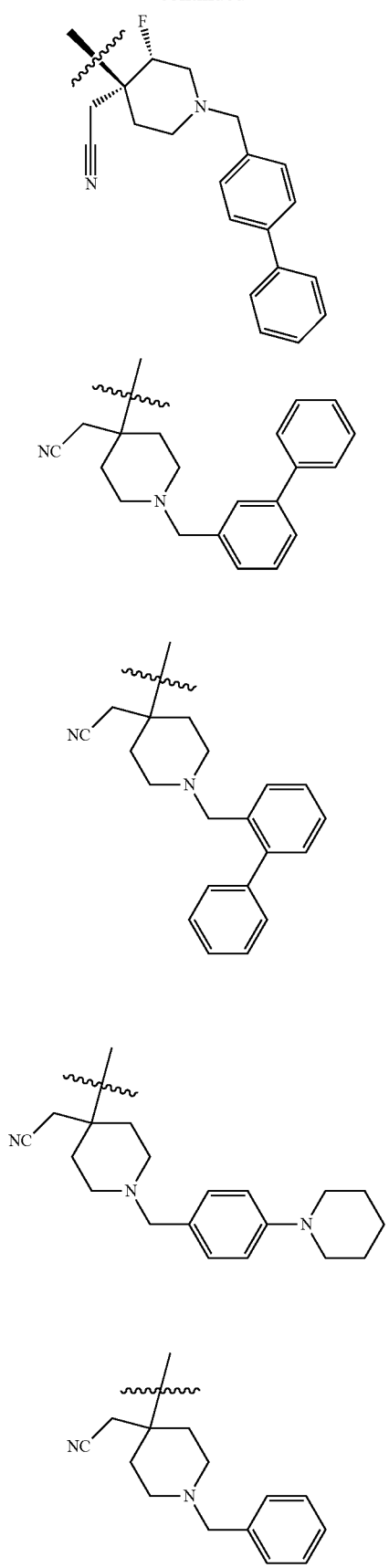
58
-continued
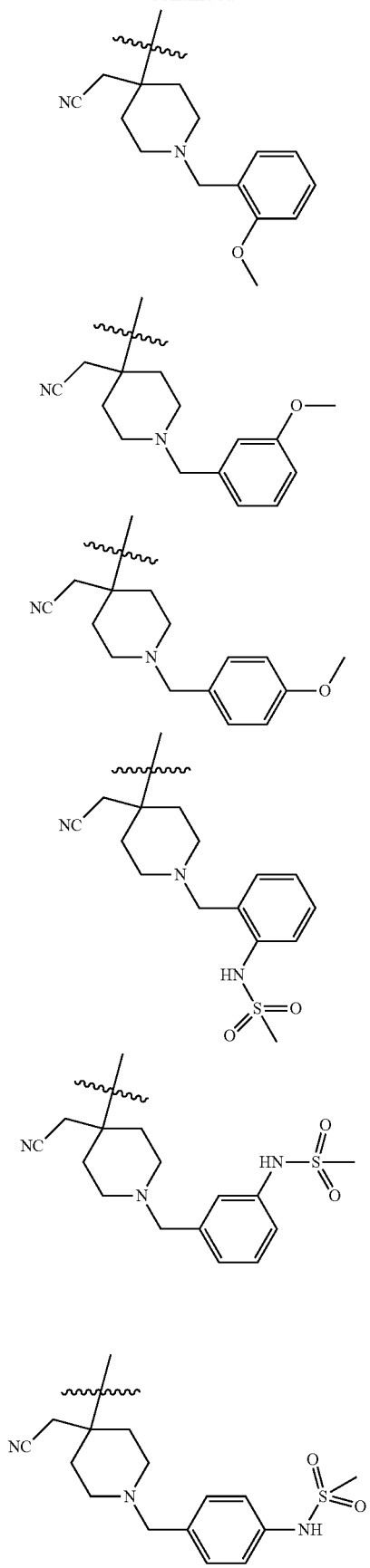

-continued
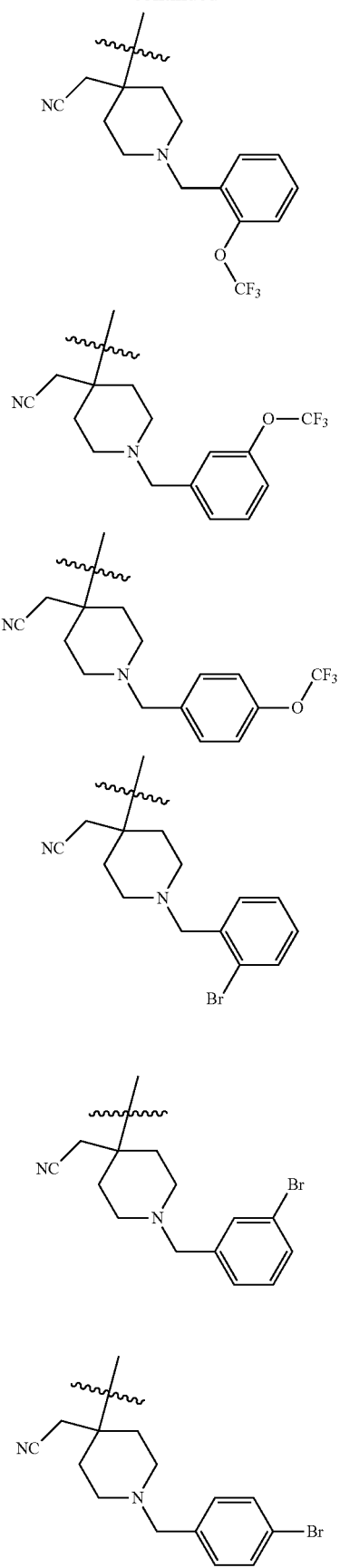
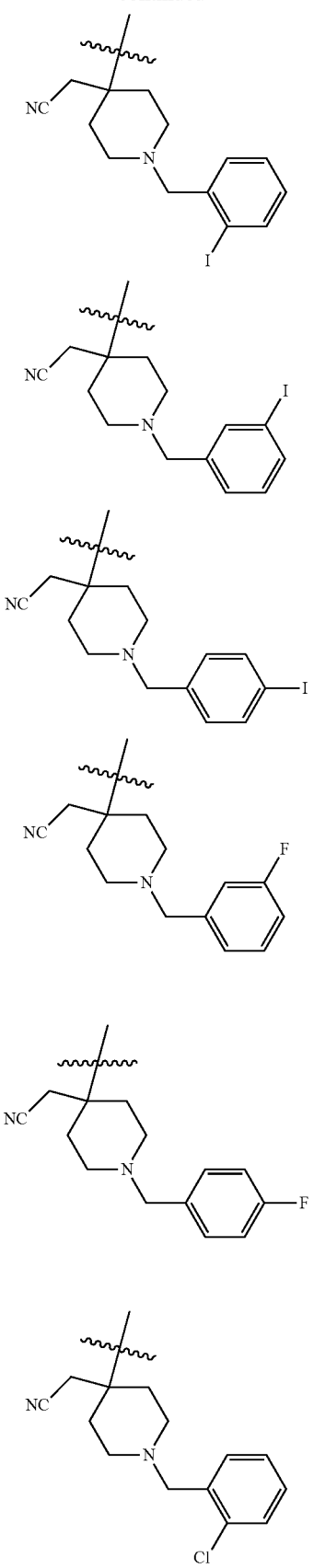

-continued
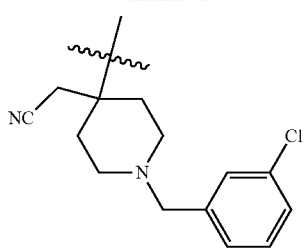
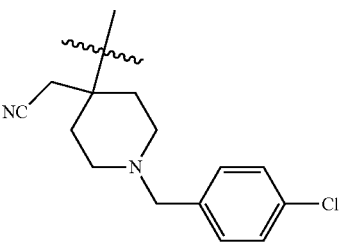
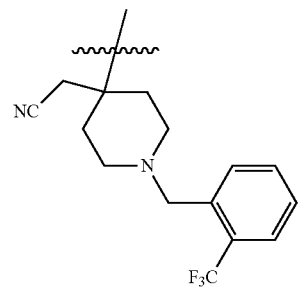
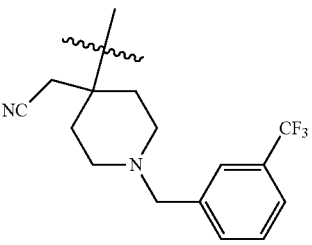
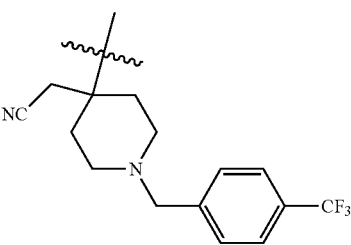
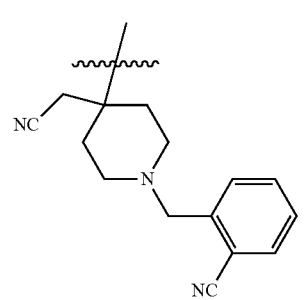
-continued
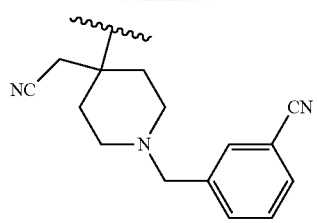
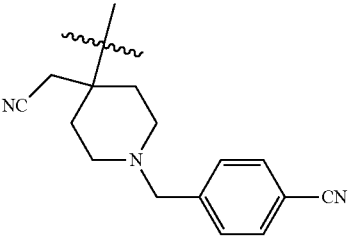
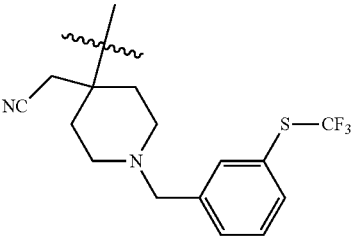
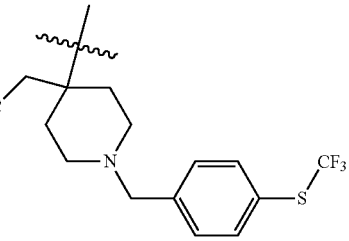
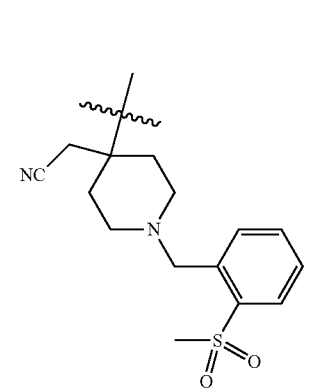
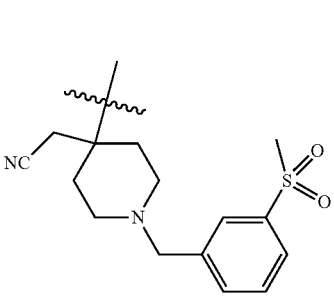

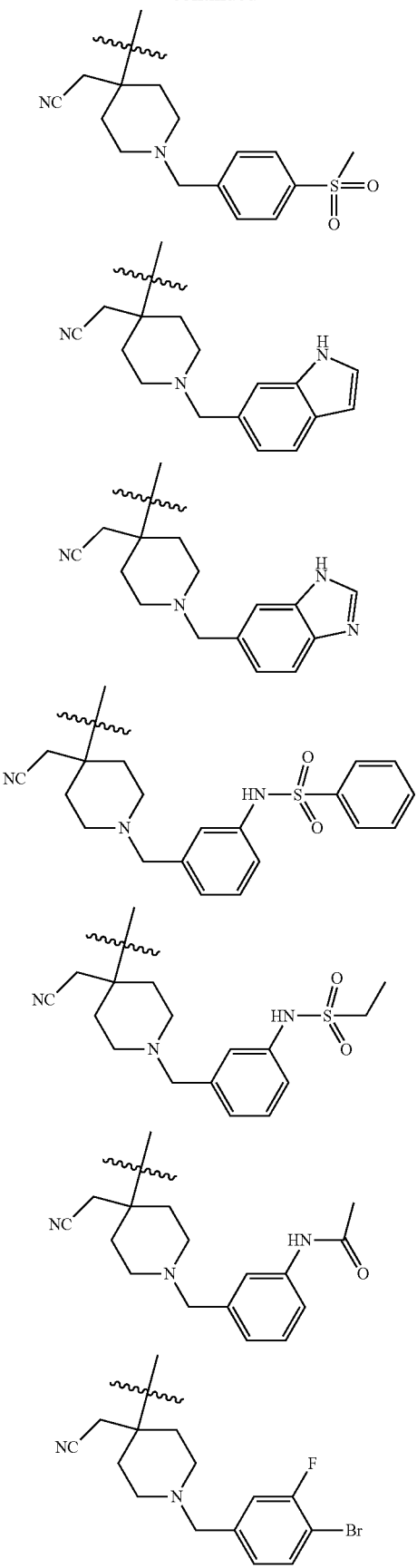
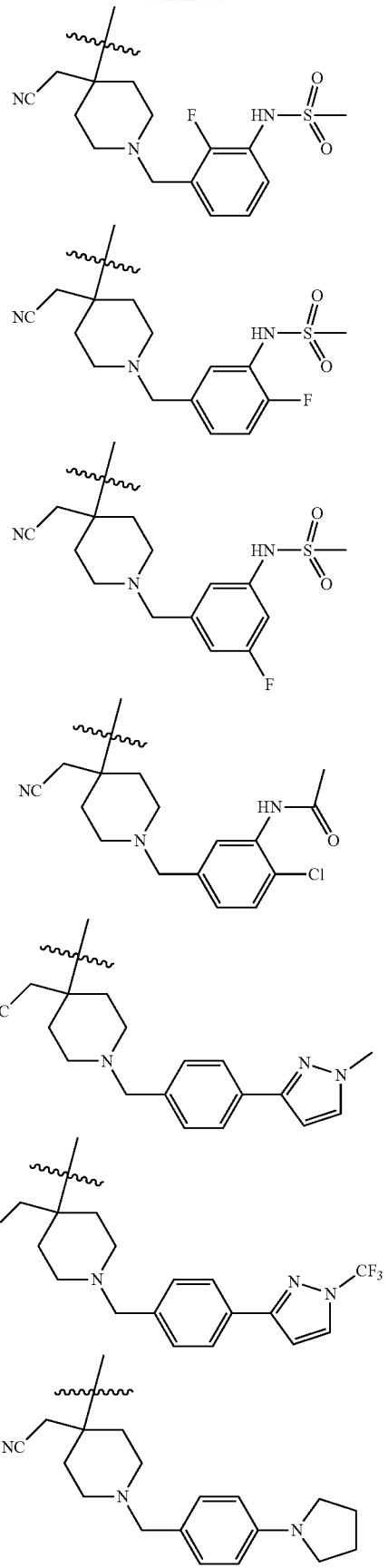

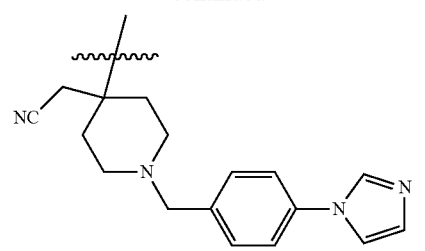
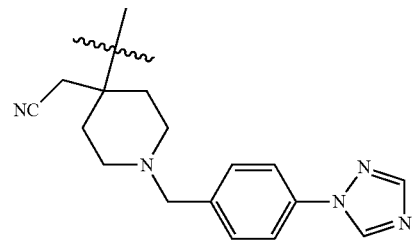
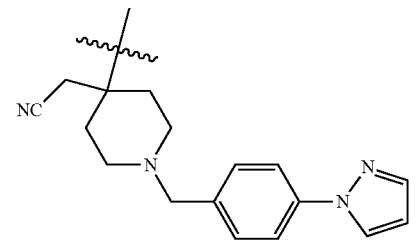
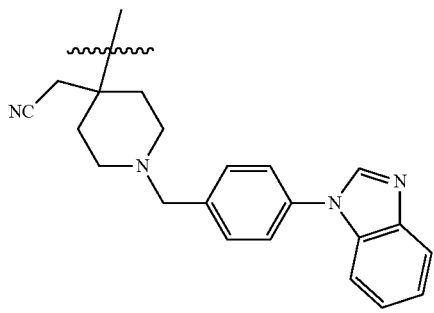
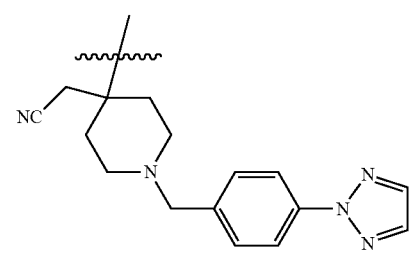
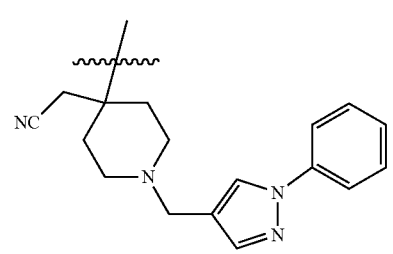
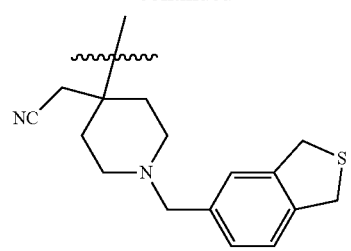
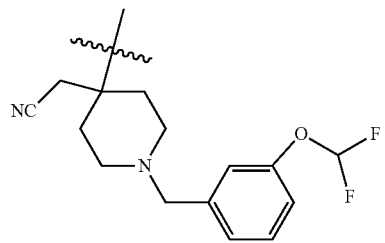
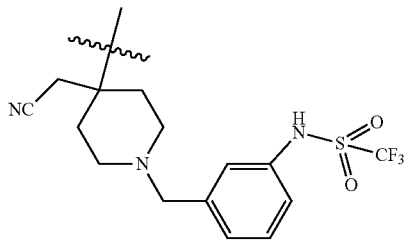
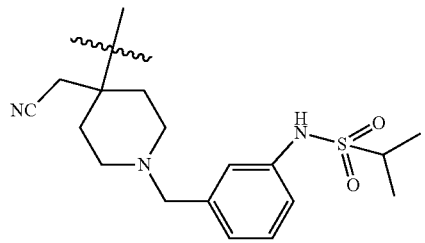
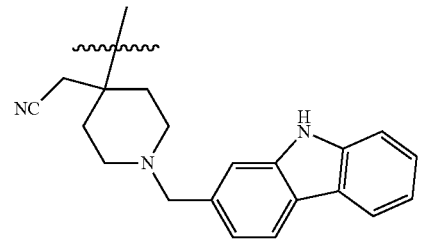
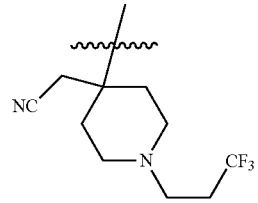
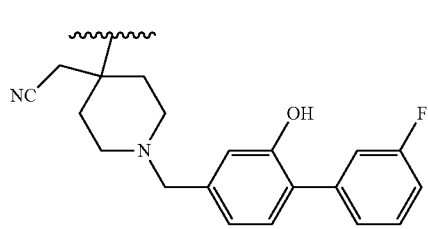

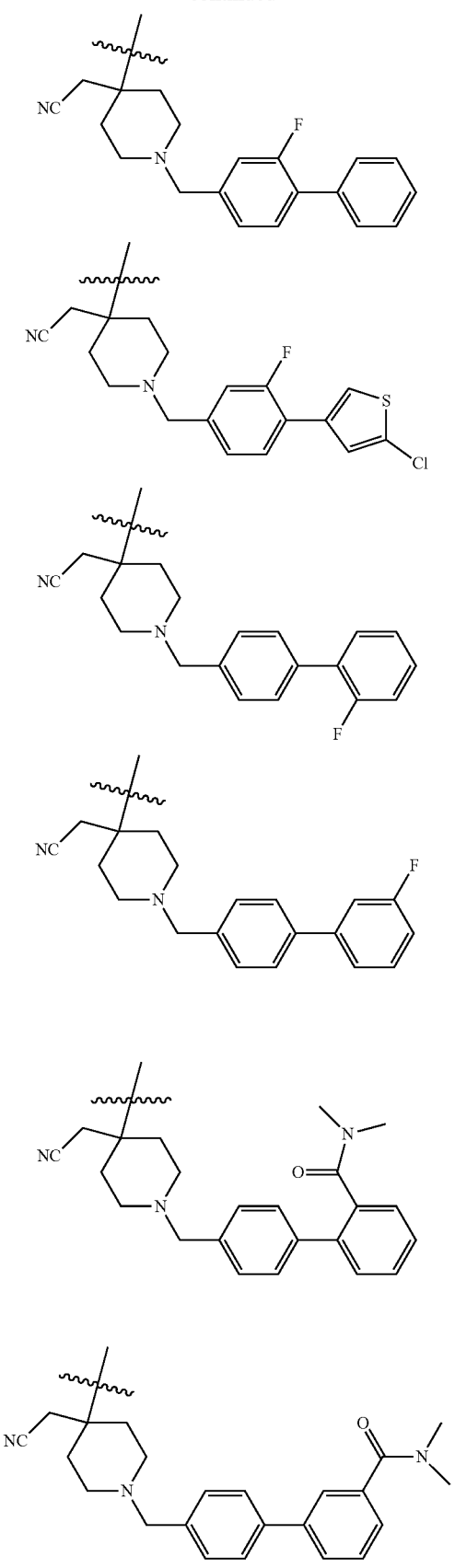
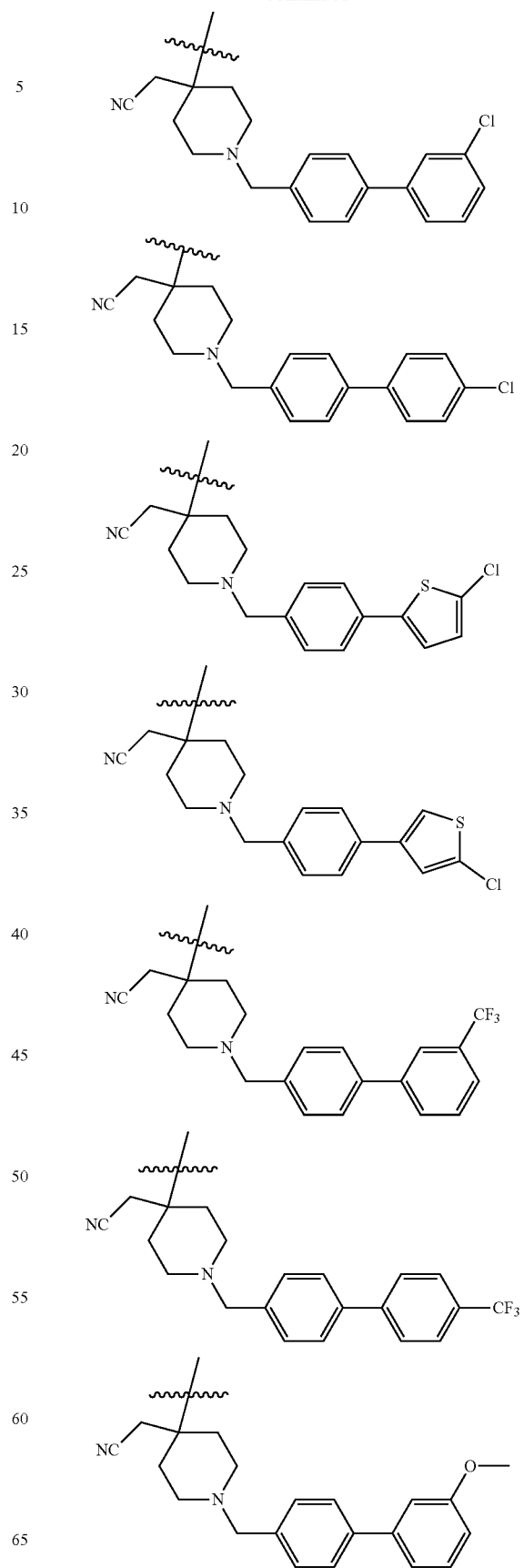

69
-continued
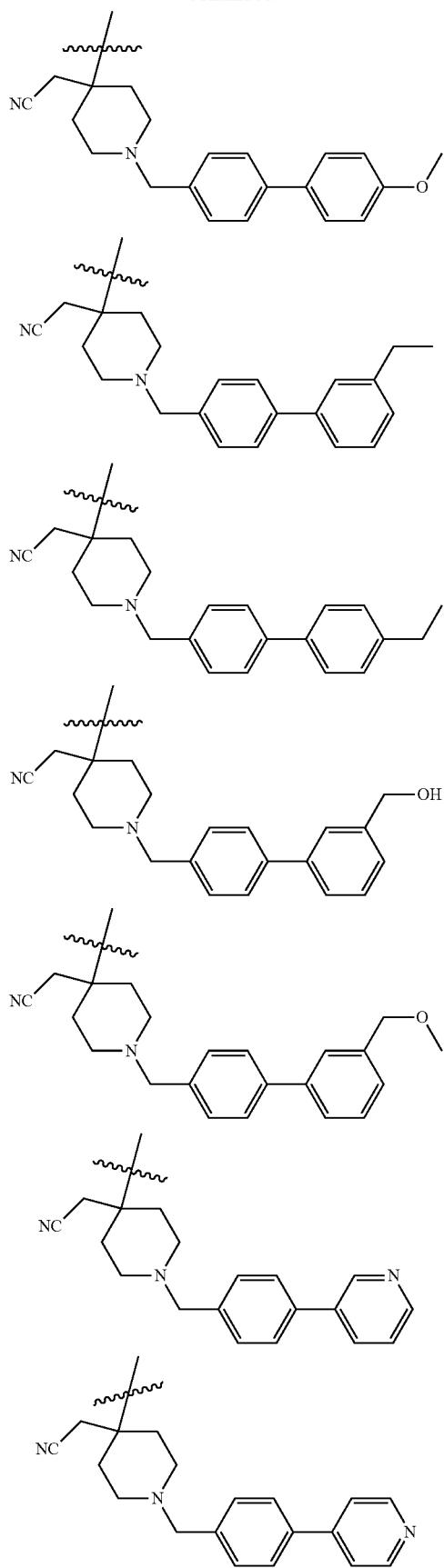
70
-continued
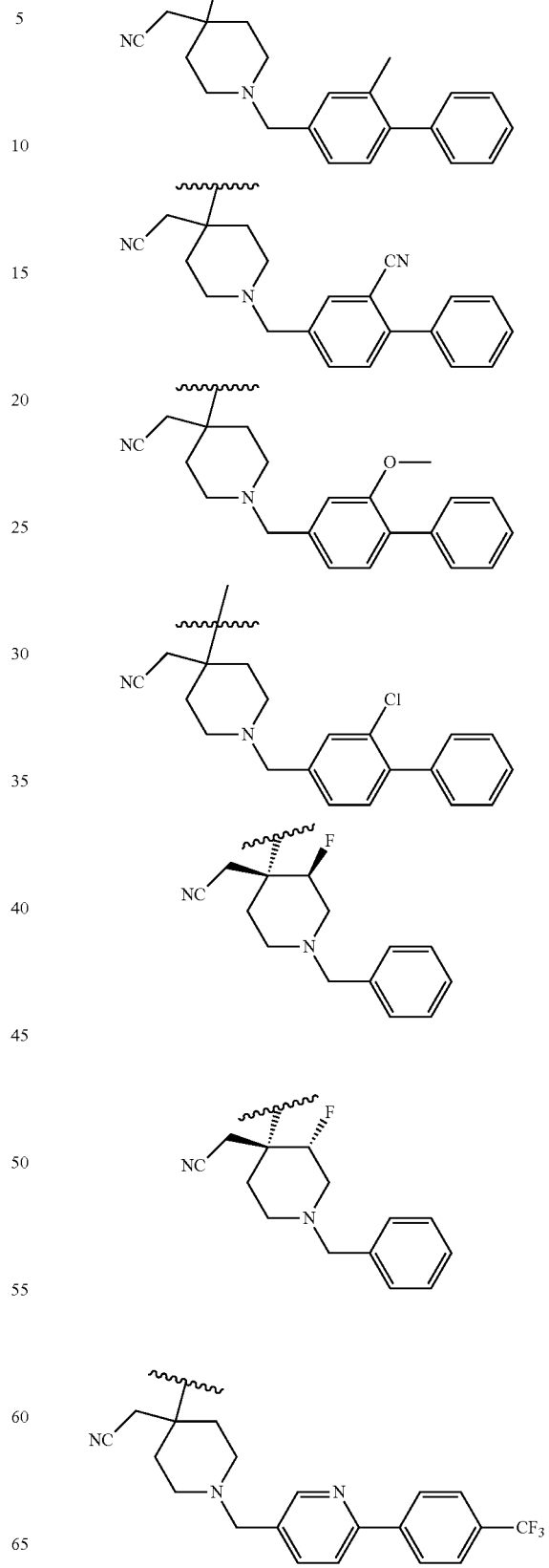

-continued
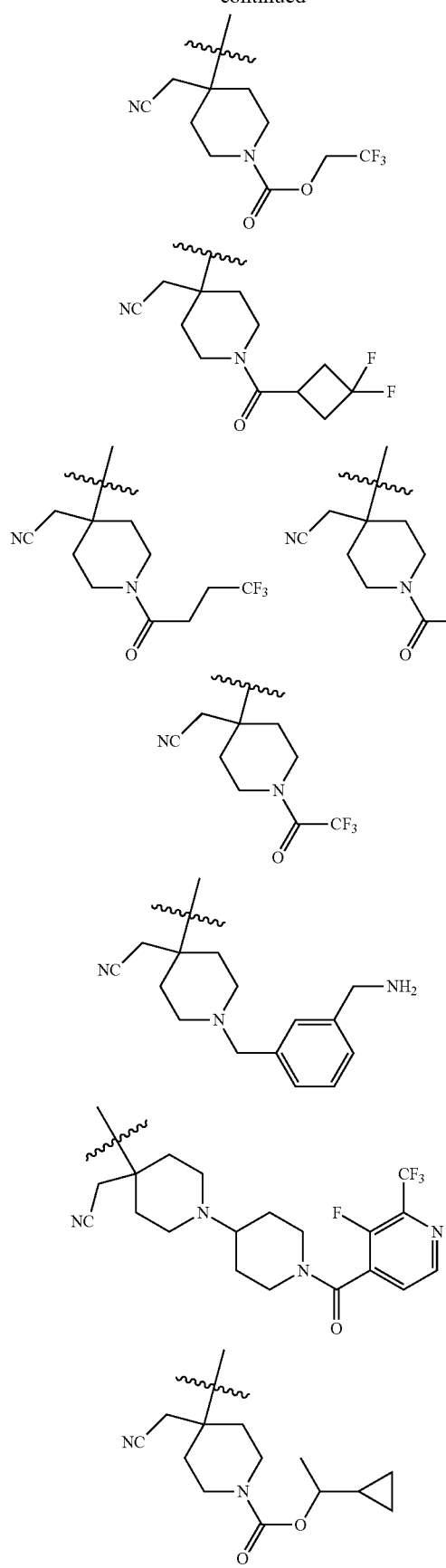
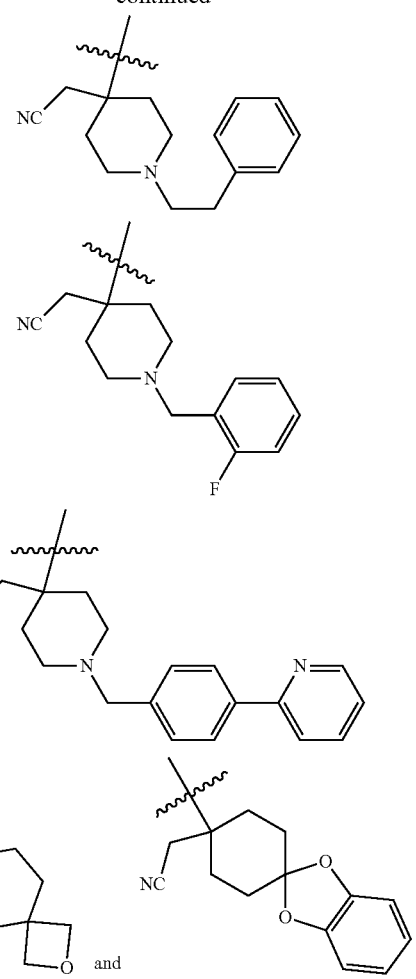
and
In some embodiments, the group
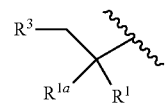
is selected from the group consisting of:
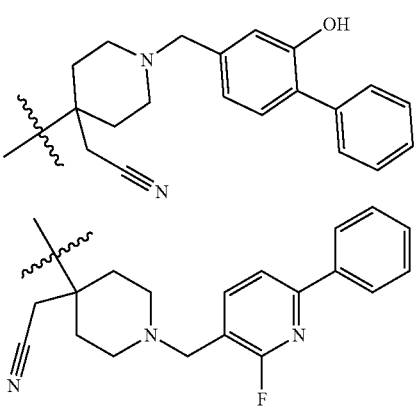

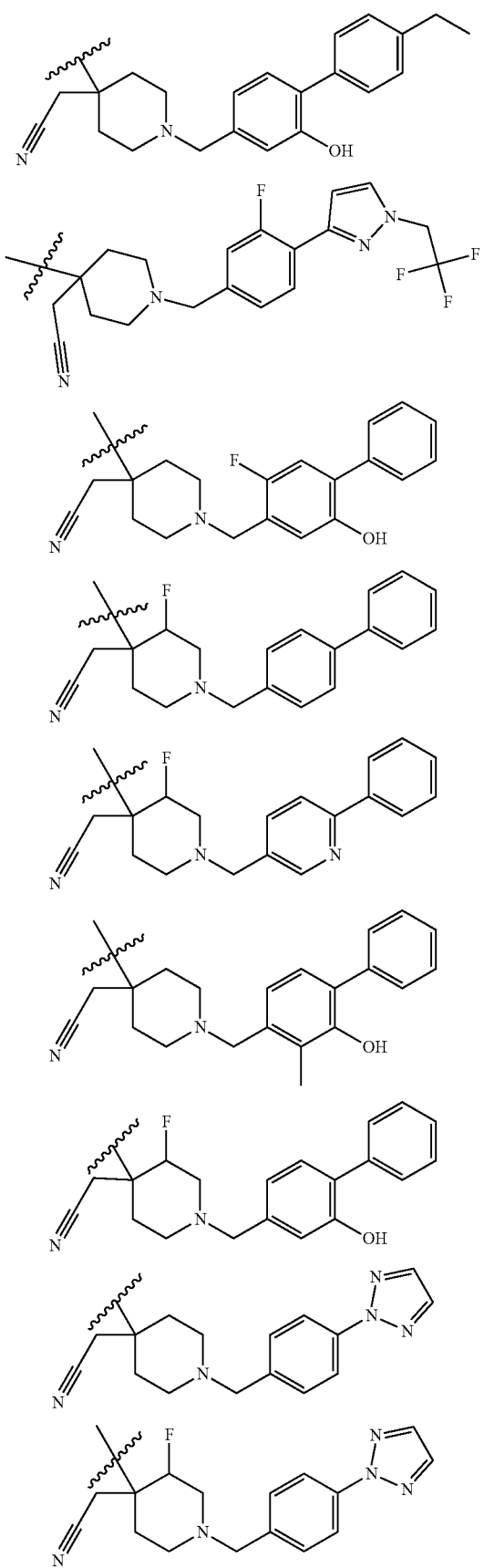
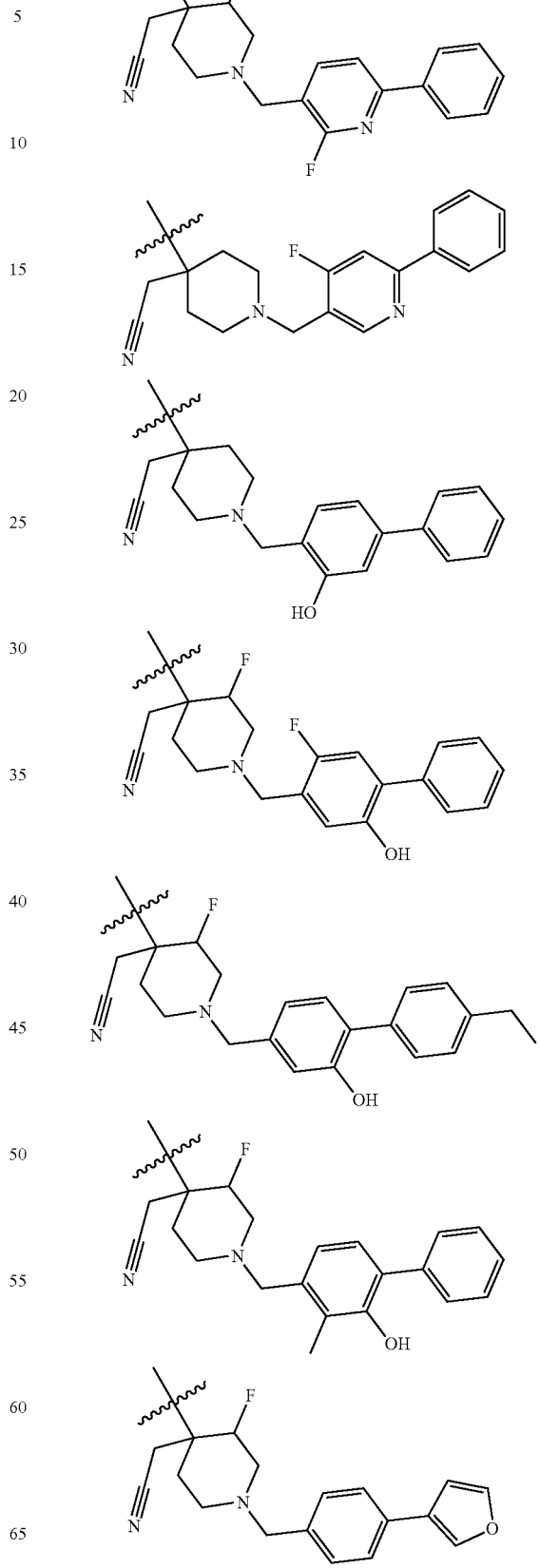

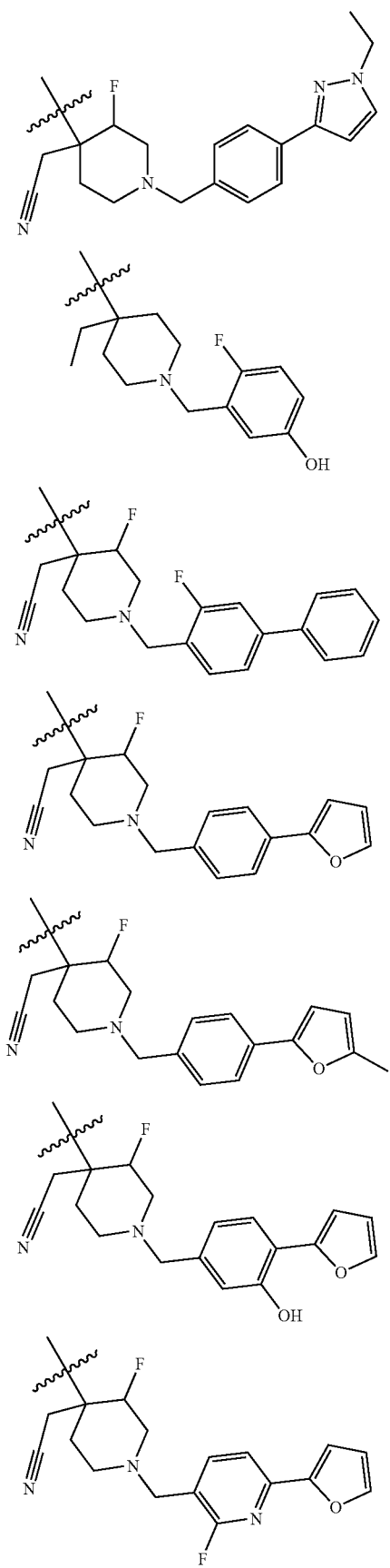
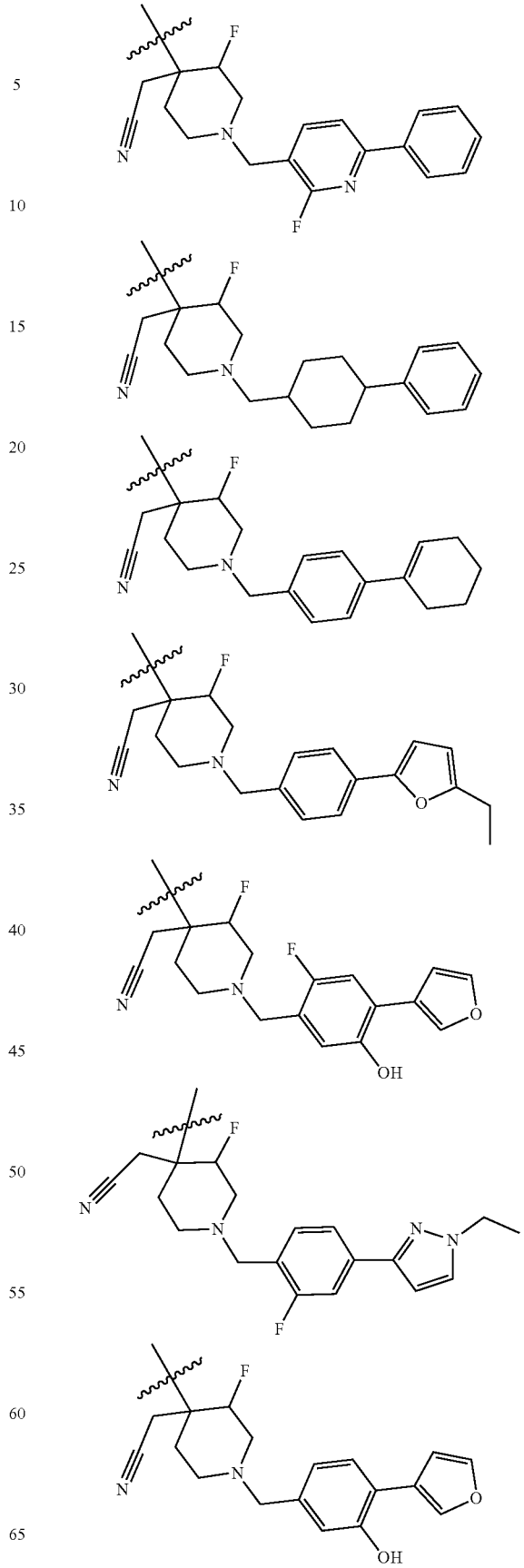

77
-continued
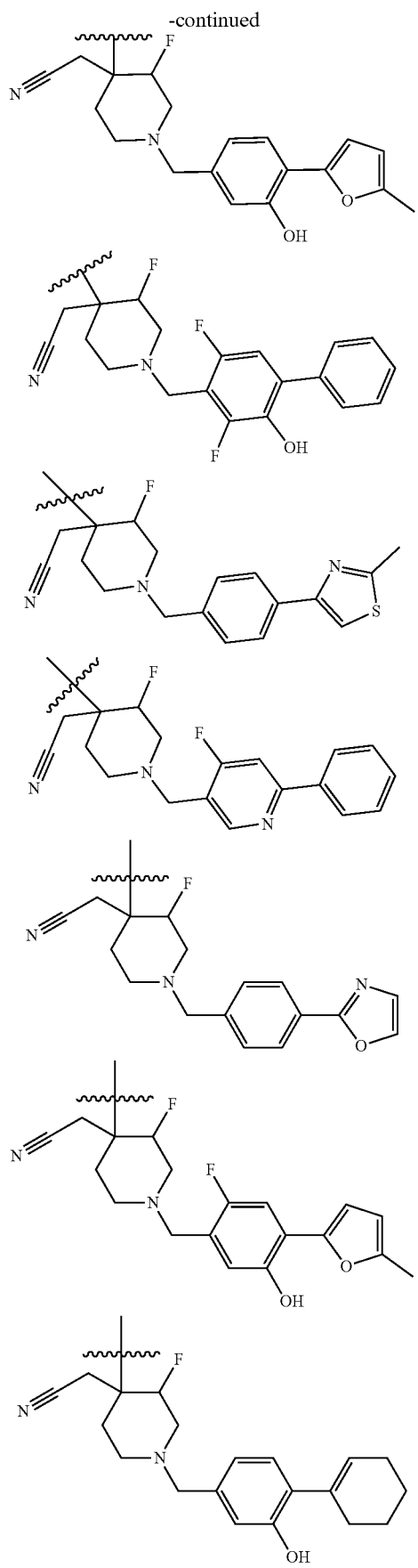
78
-continued
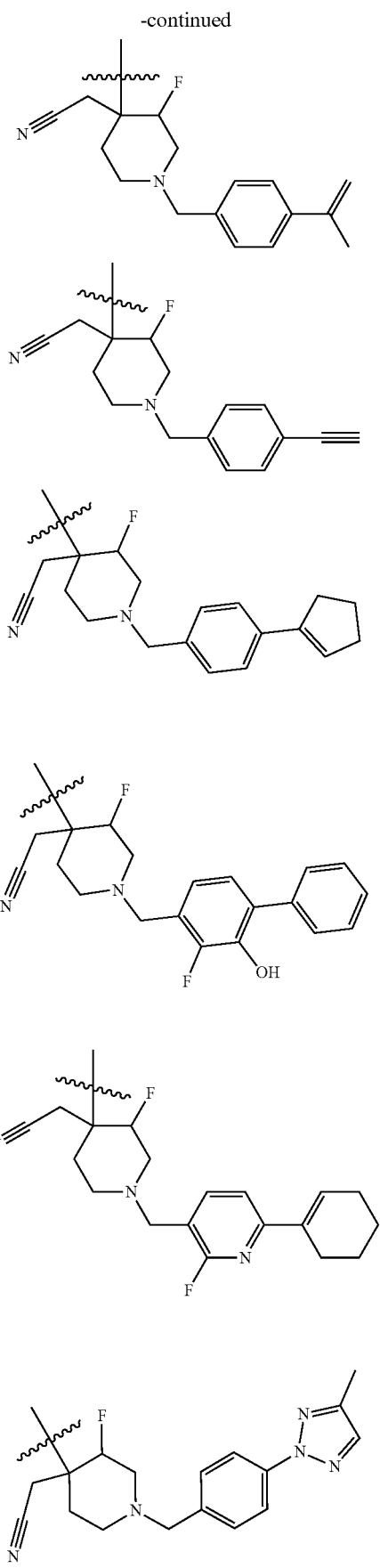

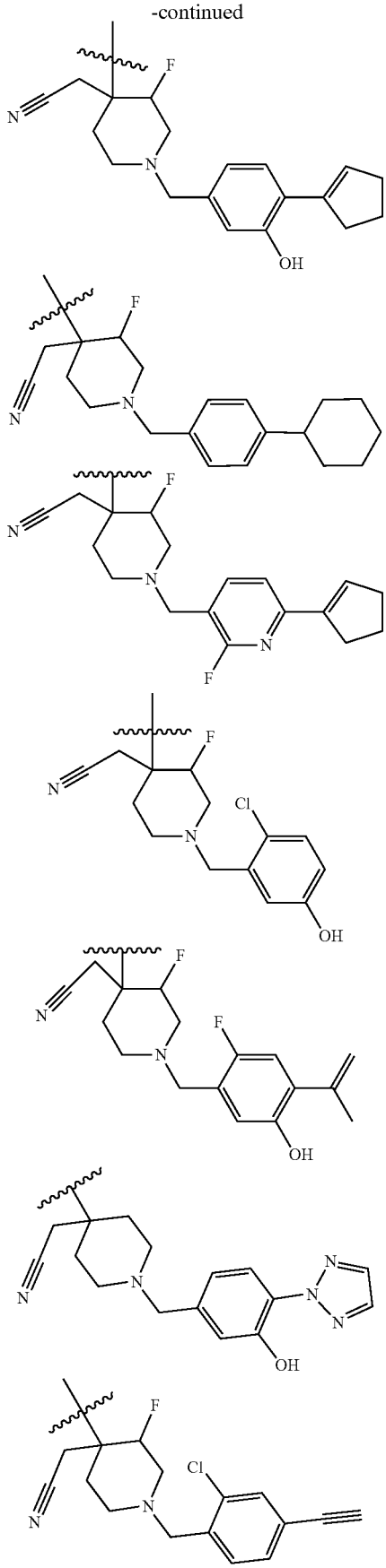
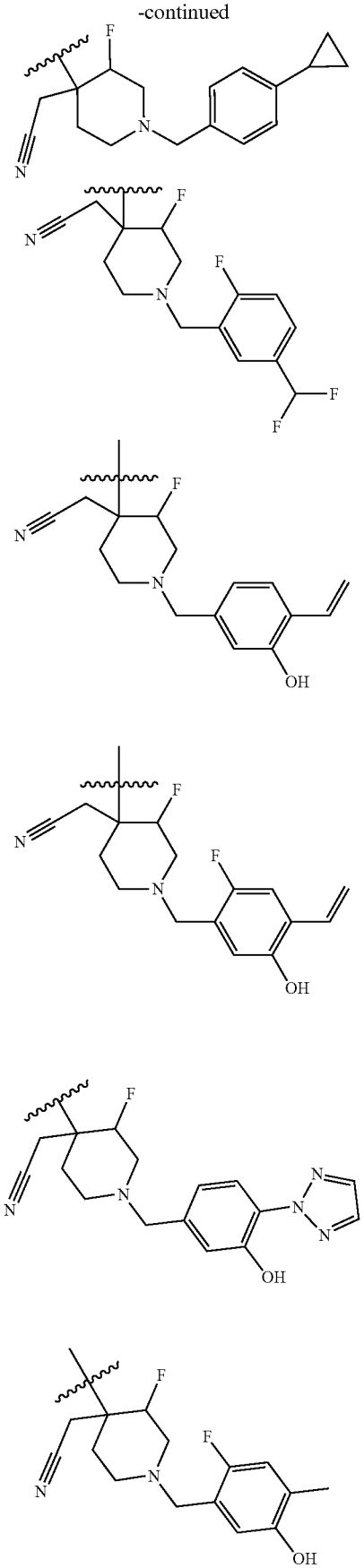

-continued
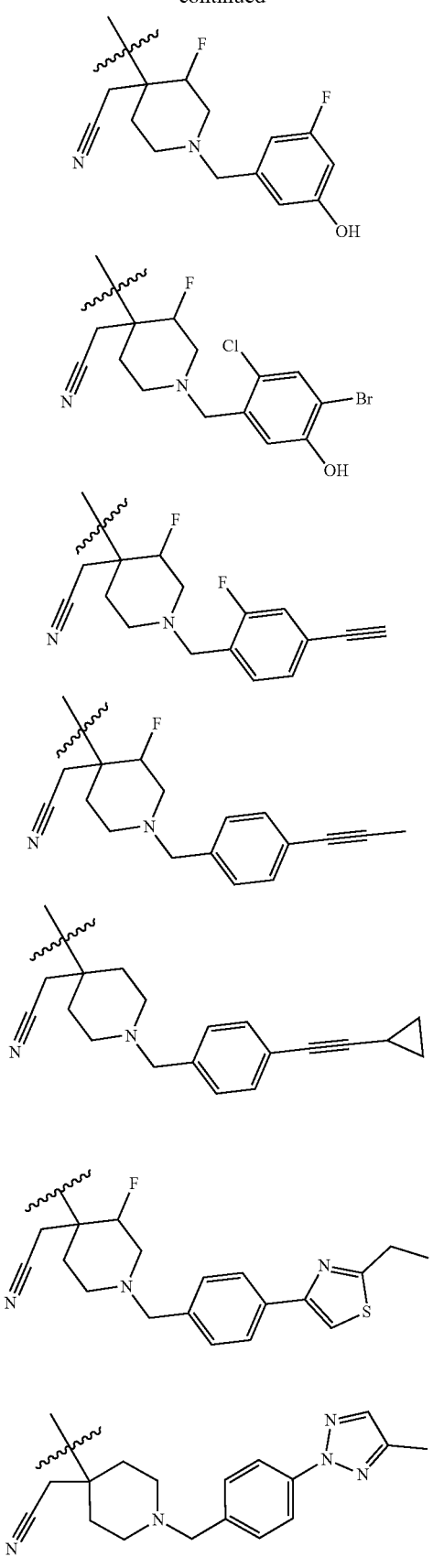
-continued
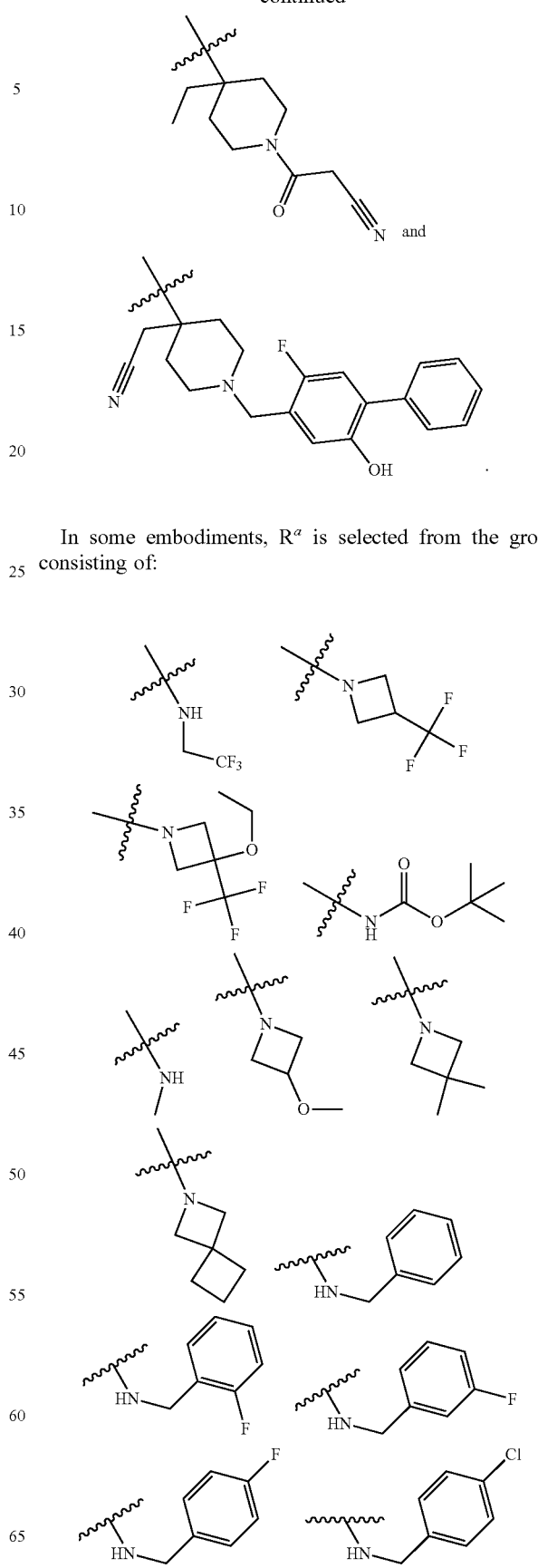
In some embodiments, $R^a$ is selected from the group consisting of:

83

-continued

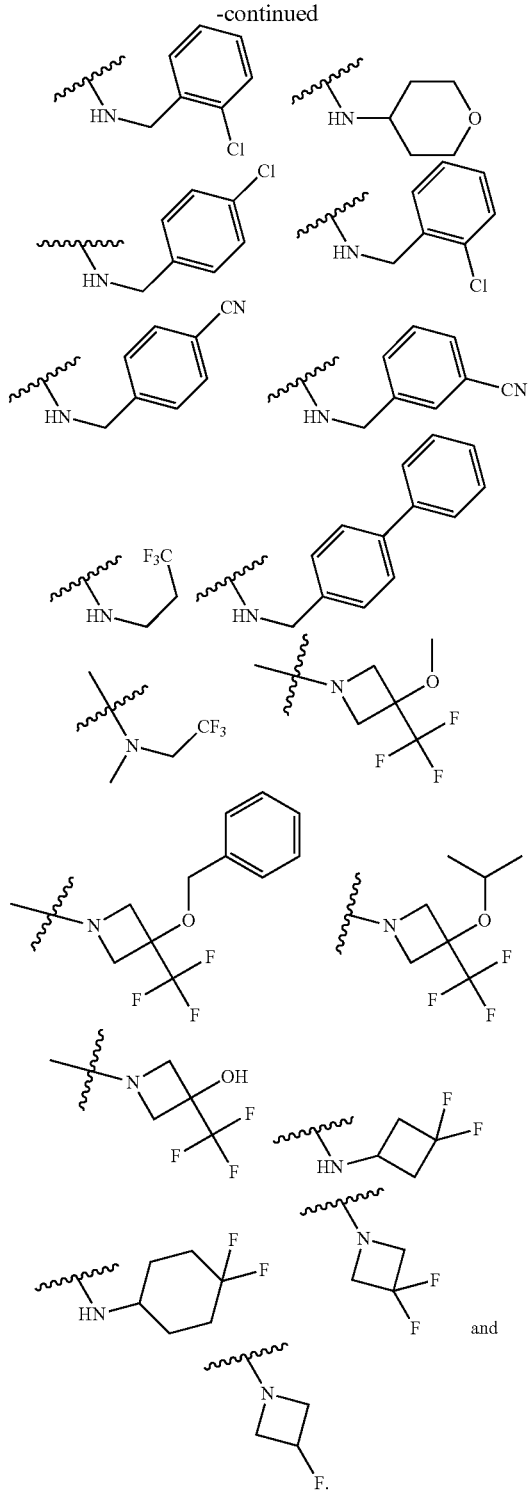

In some embodiments, $R^a$ is selected from the group consisting of:

84

-continued

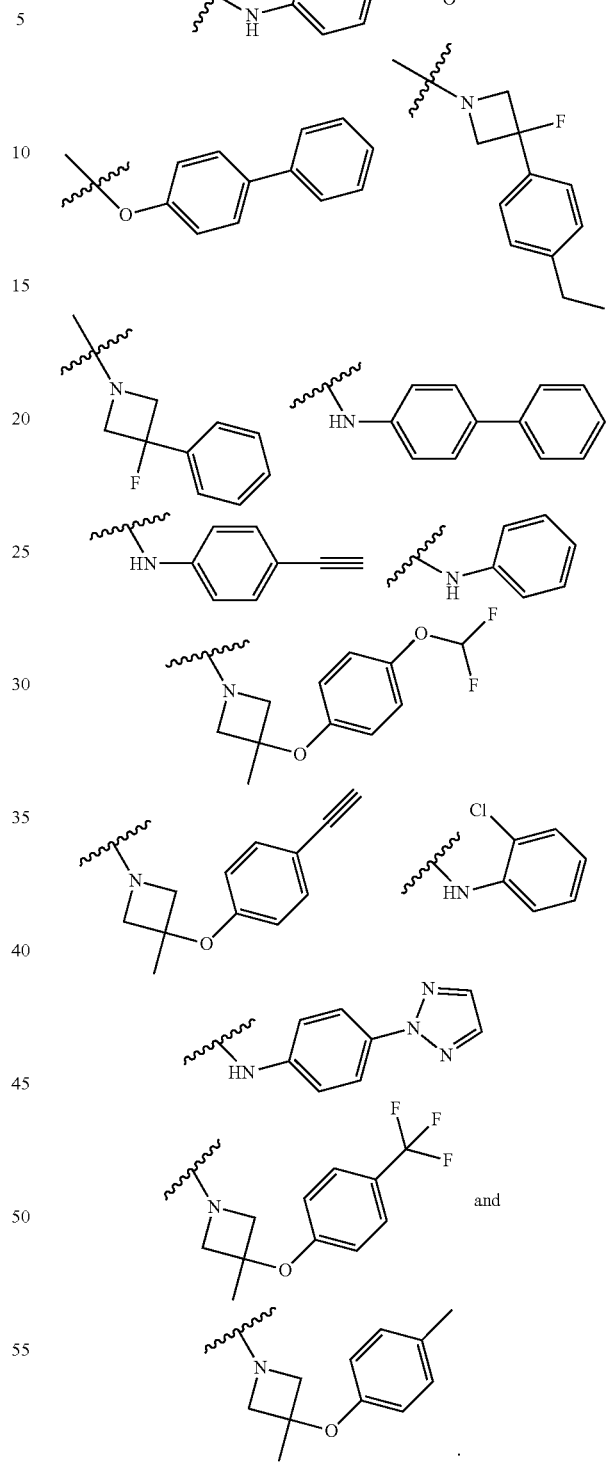

In some embodiments, $R^c$ is $C_1$-$C_6$alkyl that is substituted with $R^x$; and $R^x$ is selected from the group consisting of 3-10 membered carbocyclyl, 3-10 membered heterocycle, 6-10 membered aryl, and 5-10 membered heteroaryl, wherein any 3-10 membered carbocyclyl, 3-10 membered heterocycle, 6-10 membered aryl, and 5-10 membered heteroaryl is optionally substituted with 3-10 membered carbocyclyl, 3-10 membered heterocycle, 6-10 membered aryl, or 5-10 membered heteroaryl, wherein any 3-10 membered carbocyclyl, 3-10 membered heterocycle, 6-10 membered aryl, and 5-10 membered heteroaryl is optionally substituted with halo, hydroxy, cyano, oxo, —OR$^m$, —NR$^m$R$^n$, —C(O)R$^m$, —C(O)OR$^m$, —C(O)NR$^m$R$^n$, or $C_1$-$C_6$alkyl that is optionally substituted with halo, hydroxy, cyano, oxo or $C_1$-$C_6$alkoxy.

In some embodiments, RC is selected from the group consisting of:

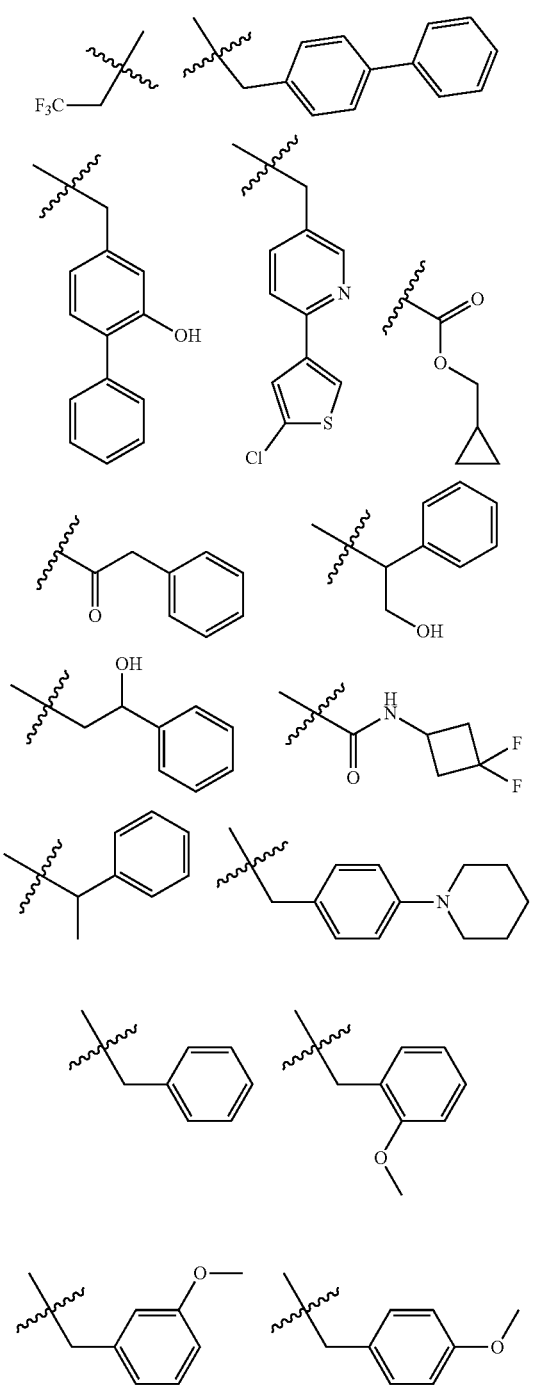
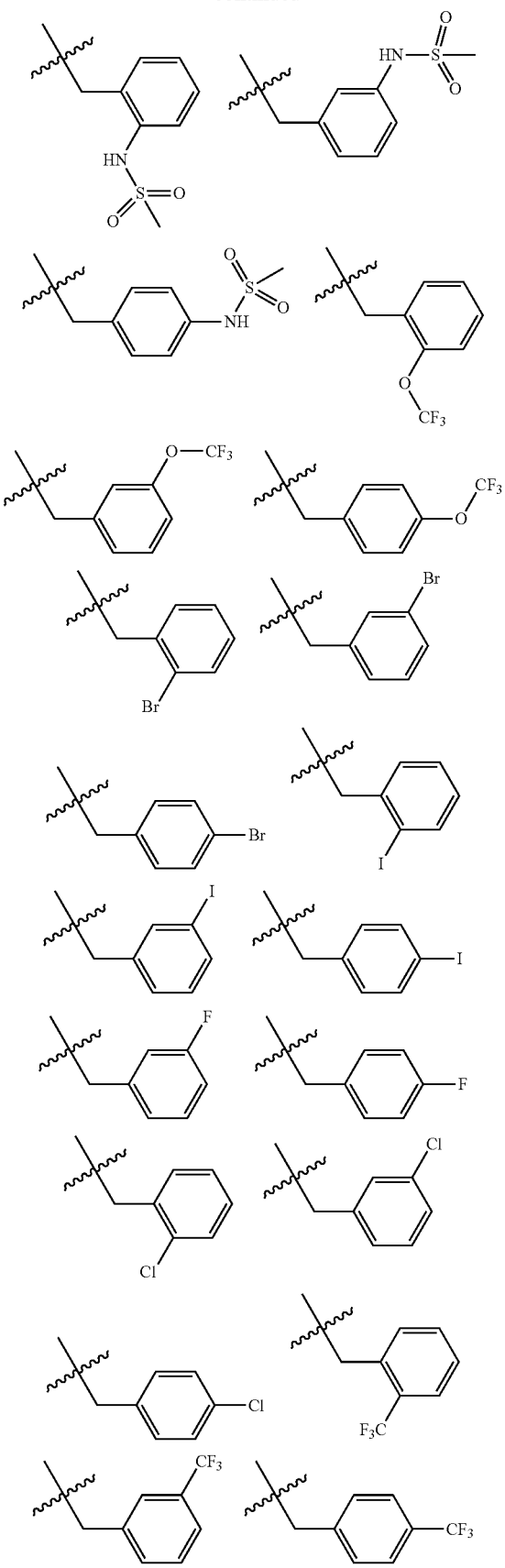

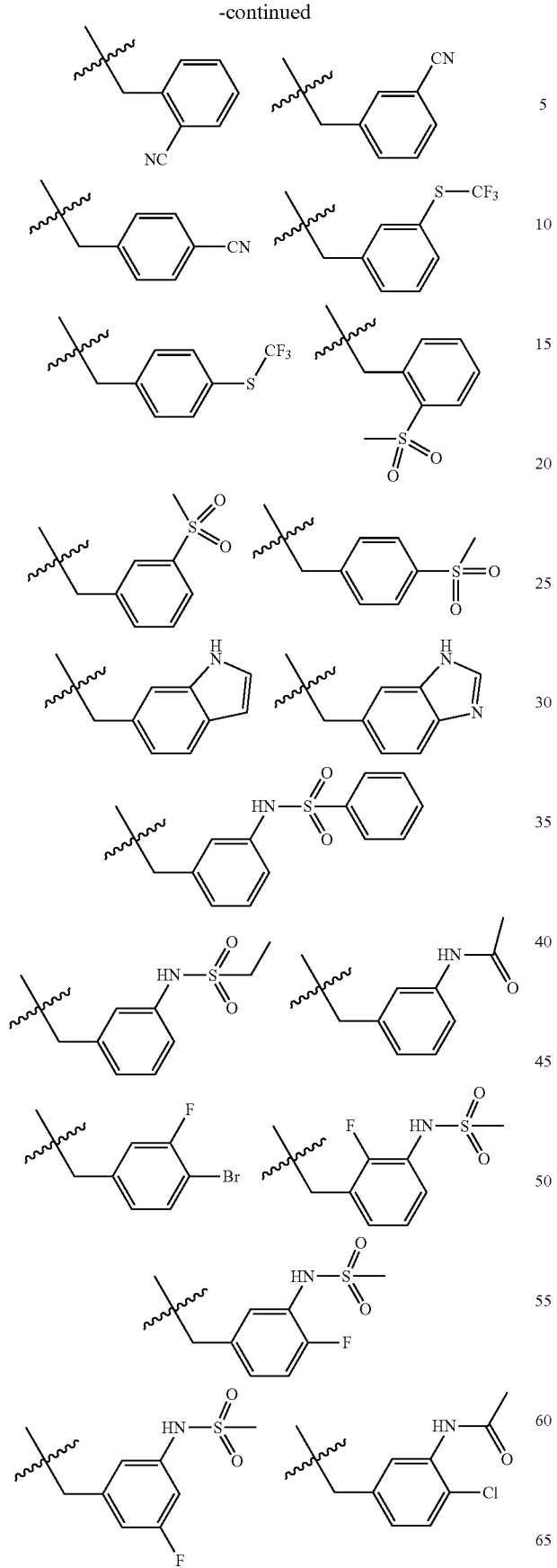
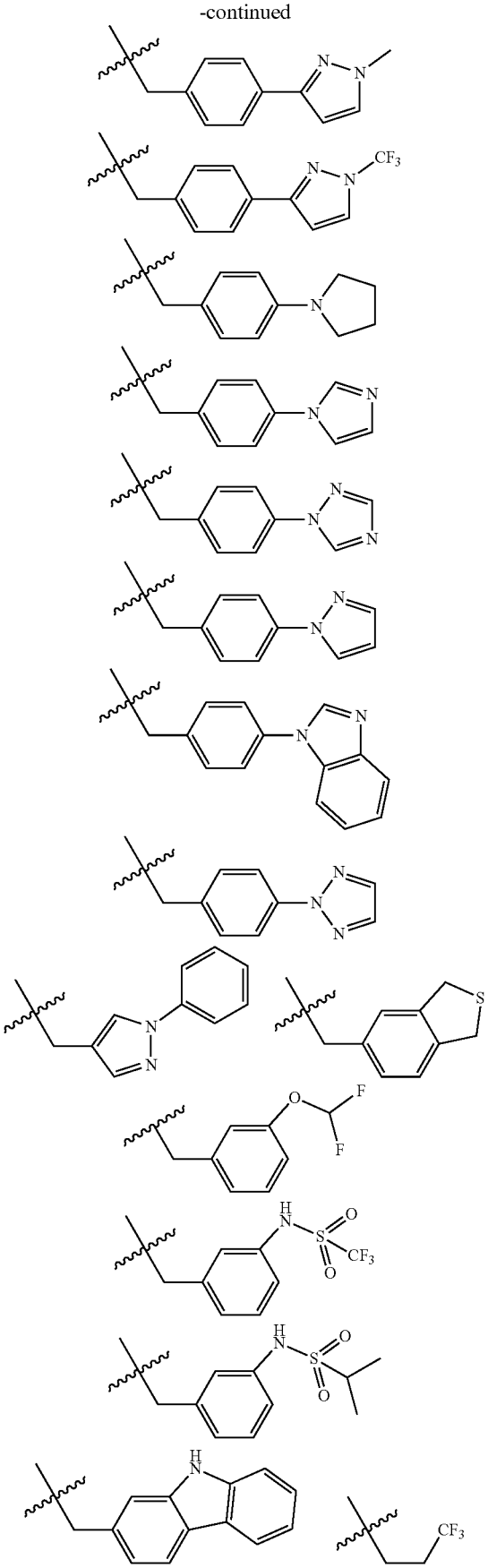

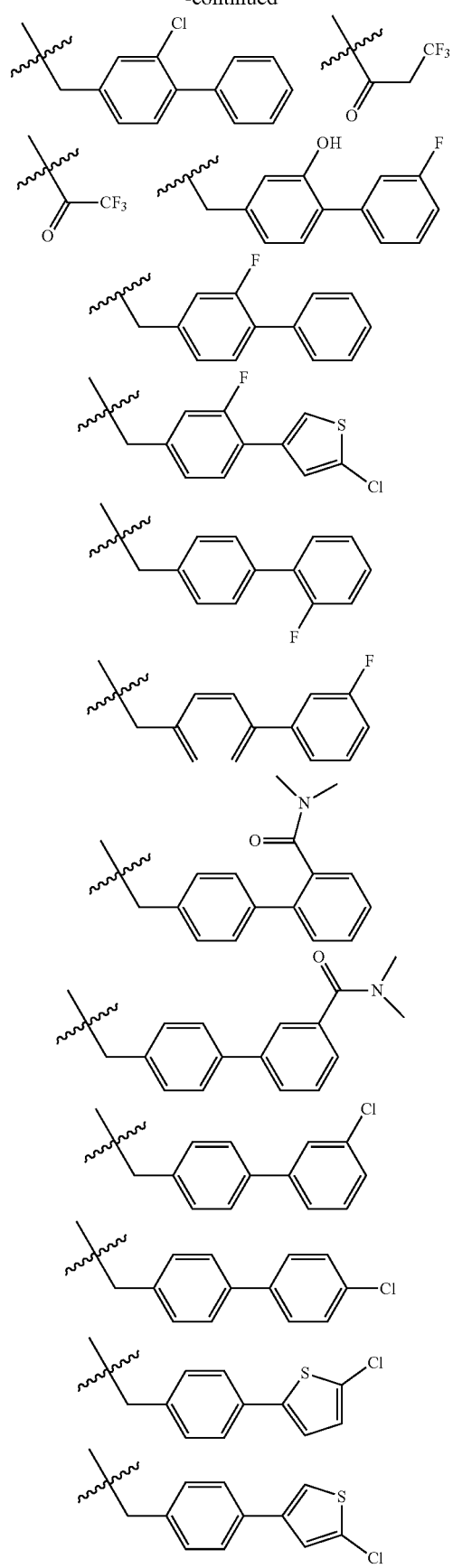
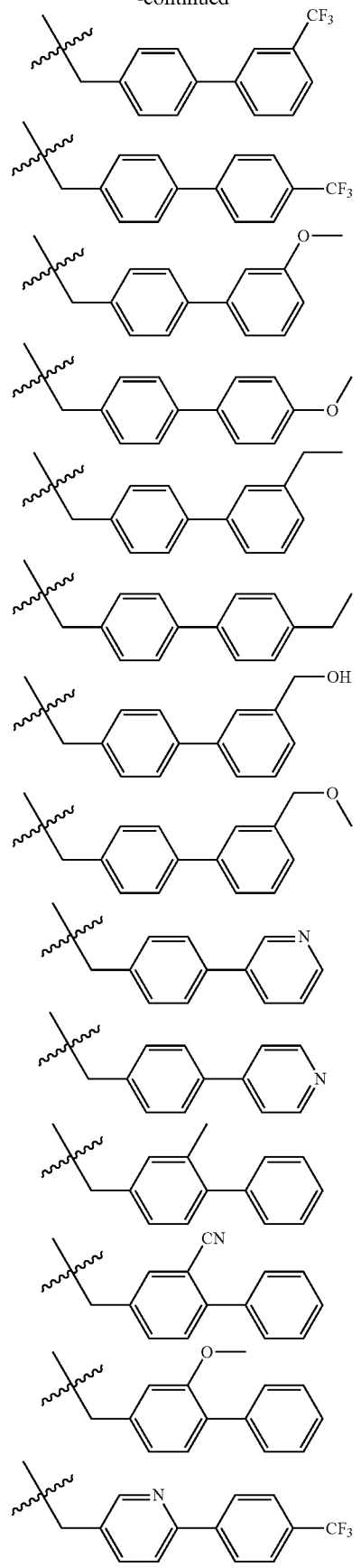

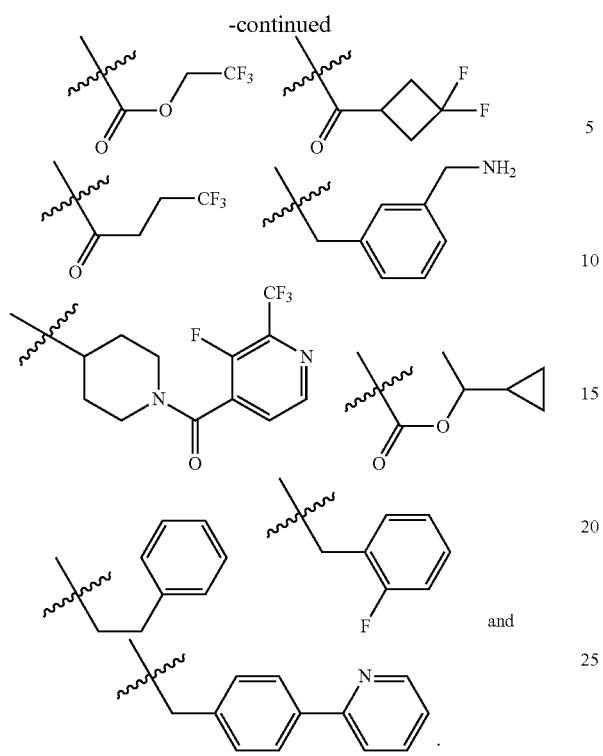
In some embodiments, RC is selected from the group consisting of:
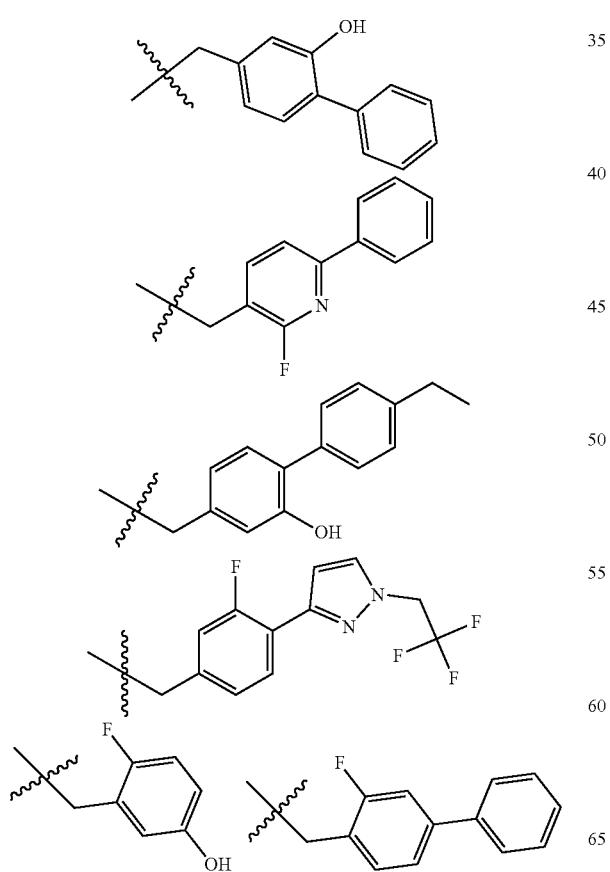
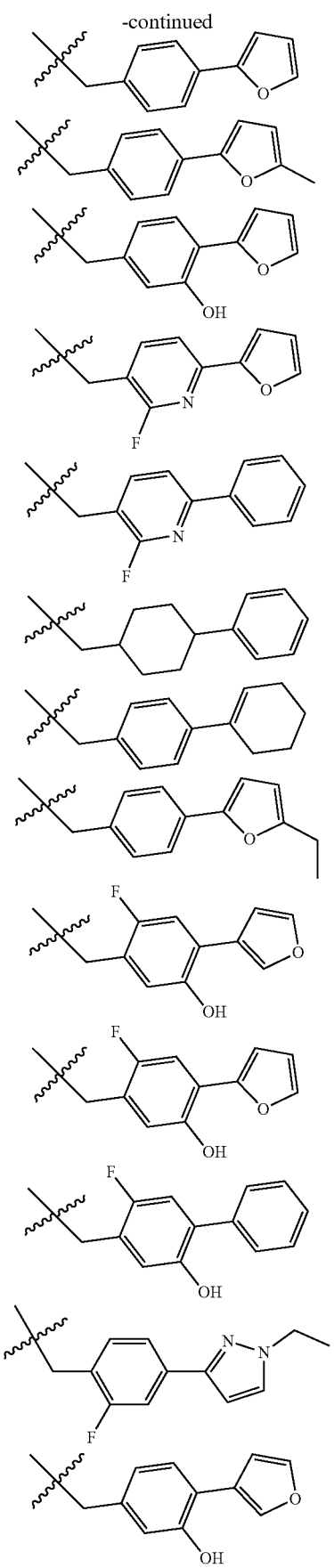

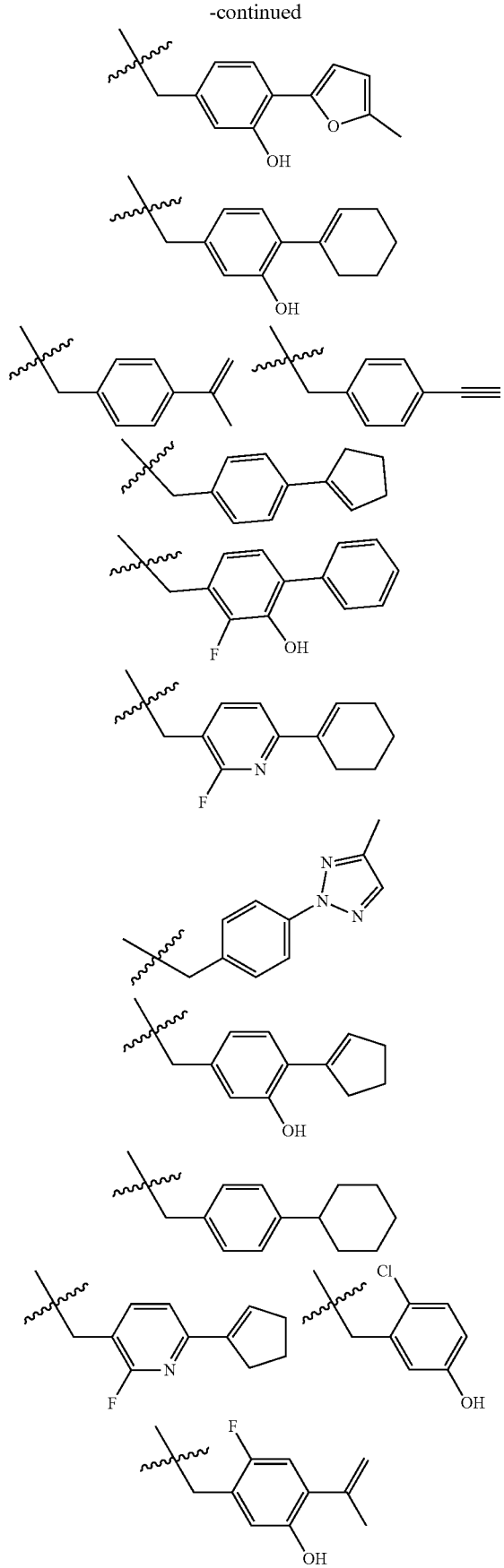
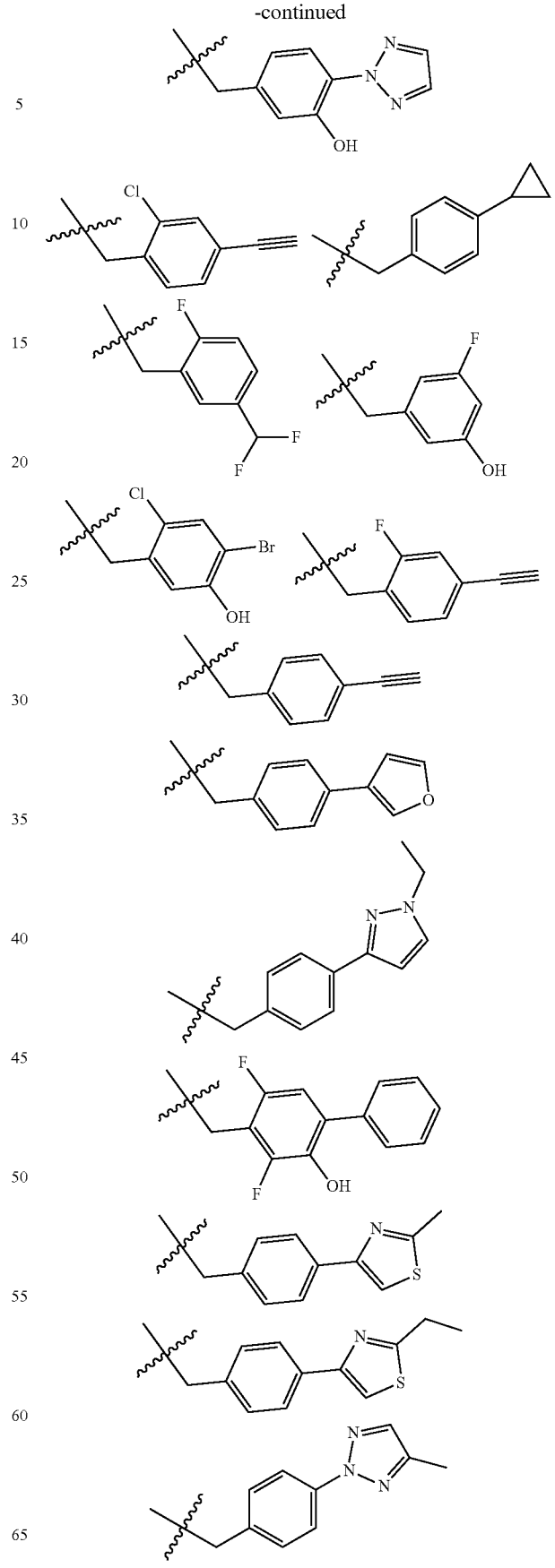

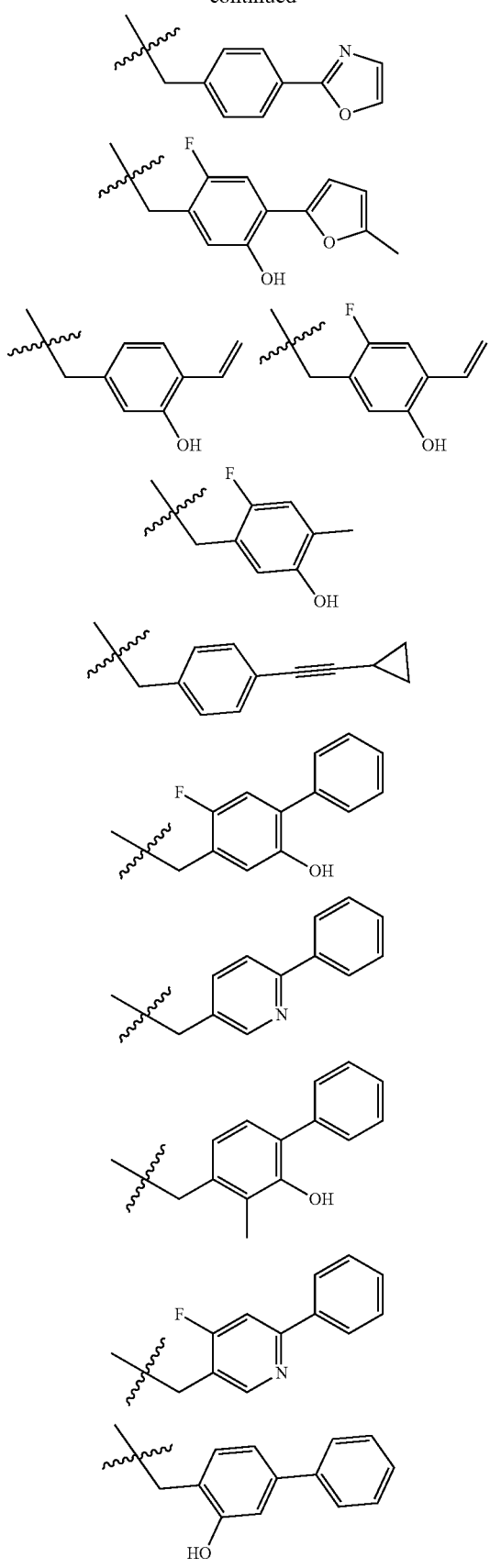
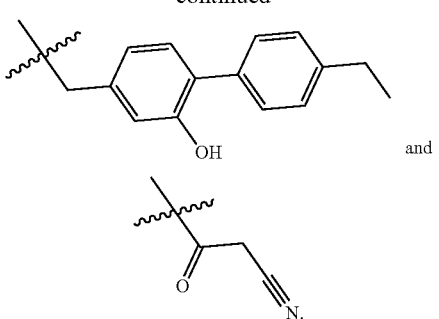
and
In some embodiments, a compound of the invention is selected from the group consisting of:
Error! Objects cannot be created from editing field codes.
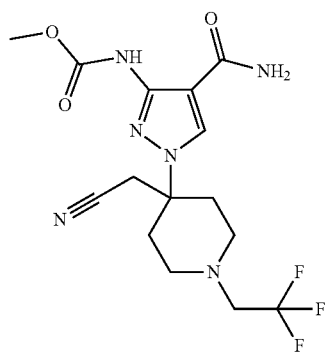
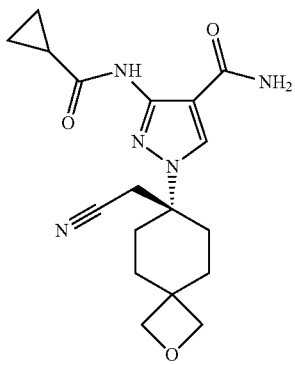
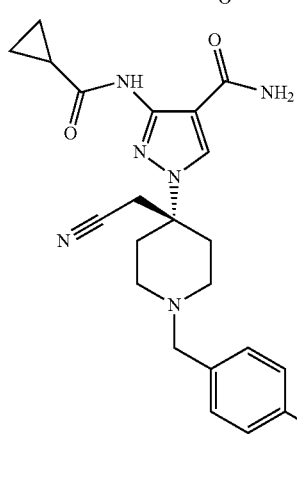

97
-continued
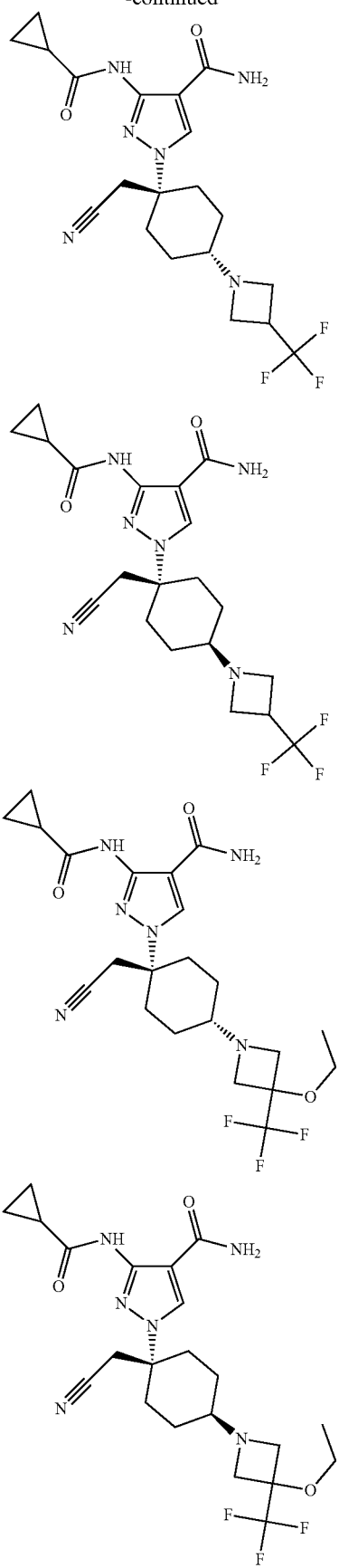
98
-continued
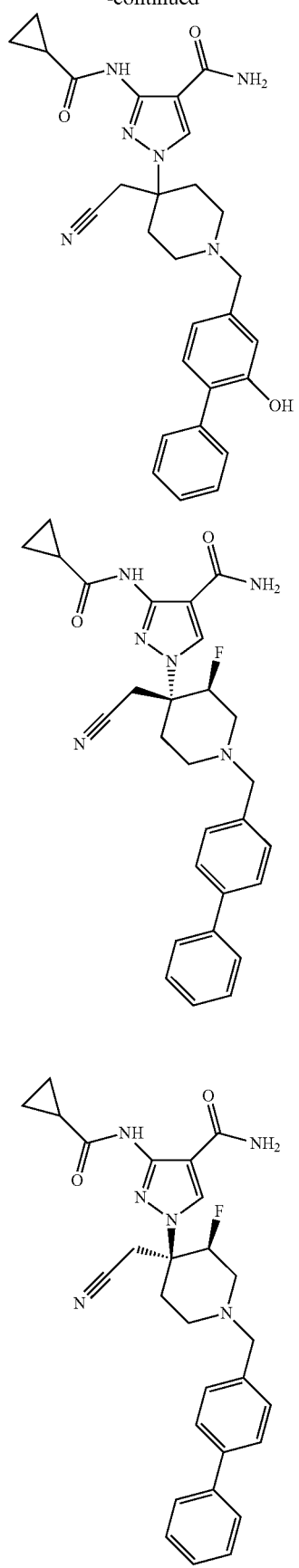

99
-continued
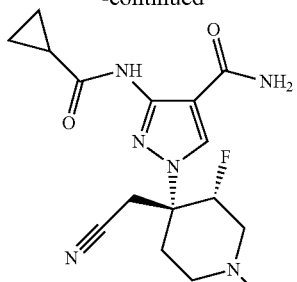
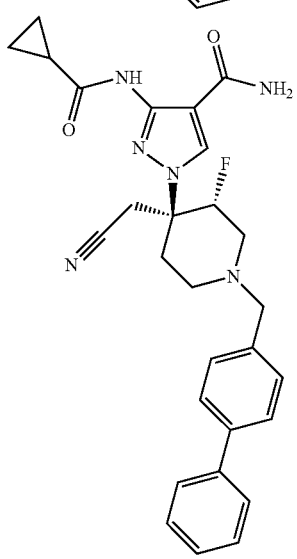
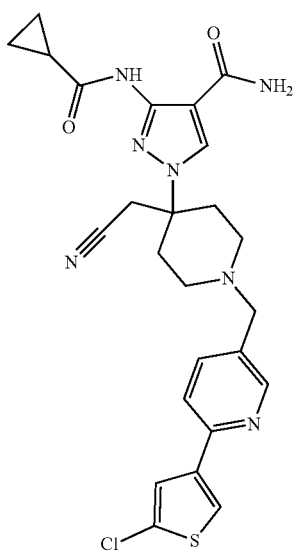
100
-continued
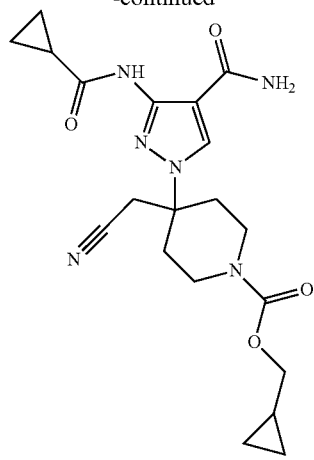
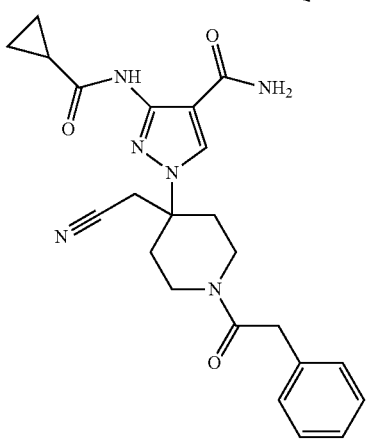
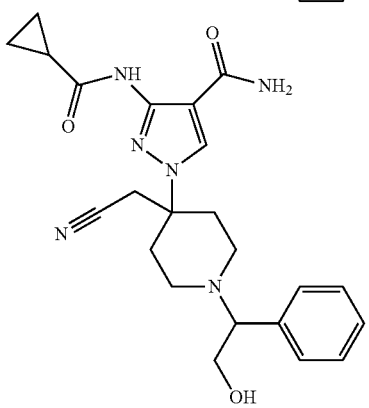
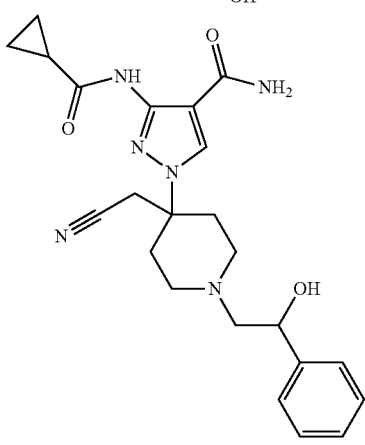

101
-continued
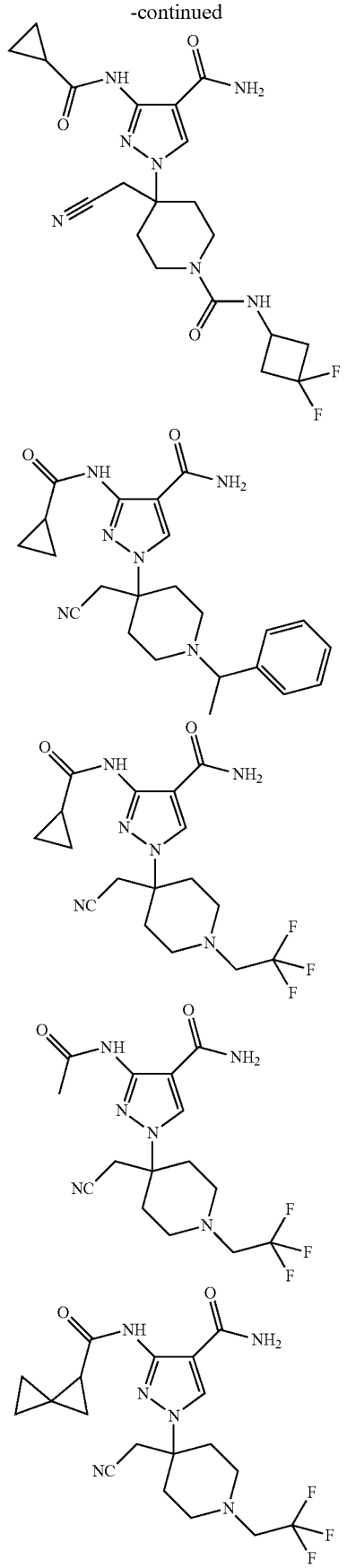
102
-continued
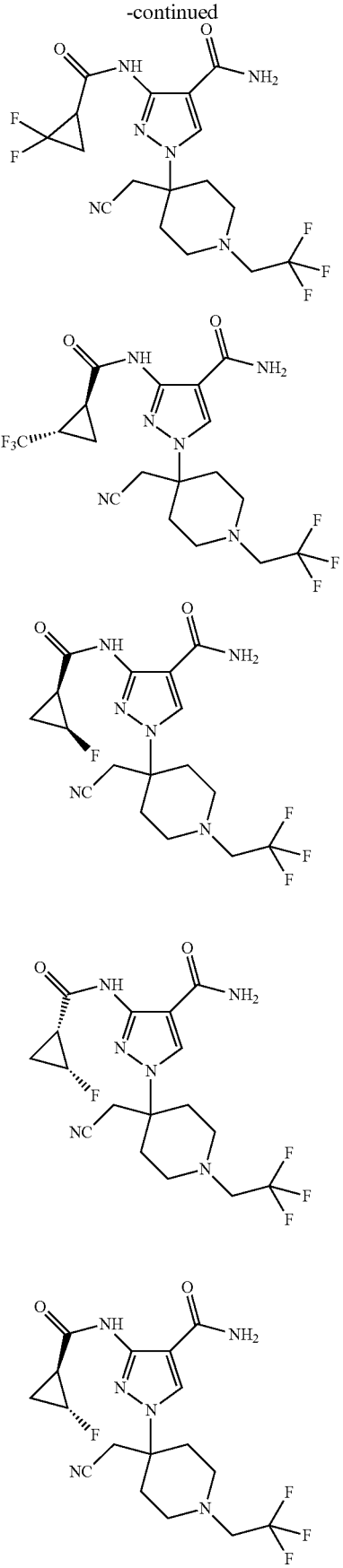

103
-continued
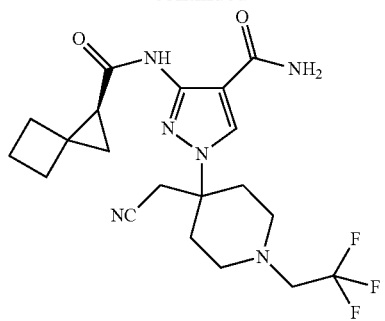
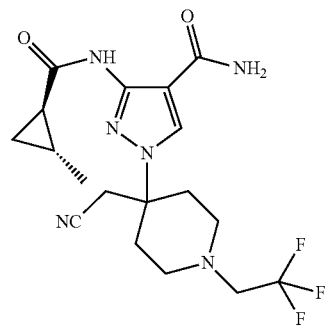
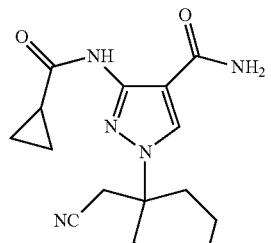
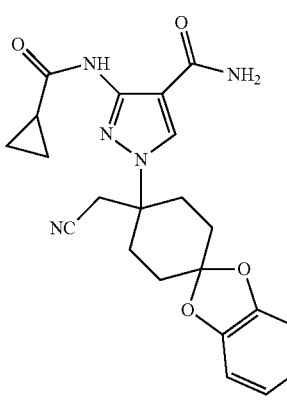
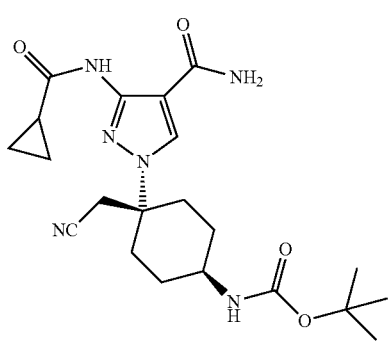
104
-continued
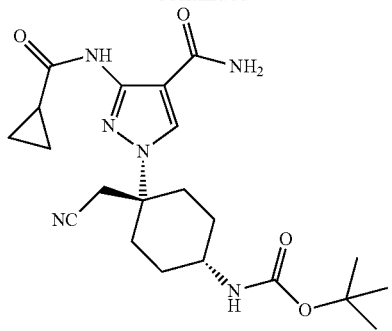
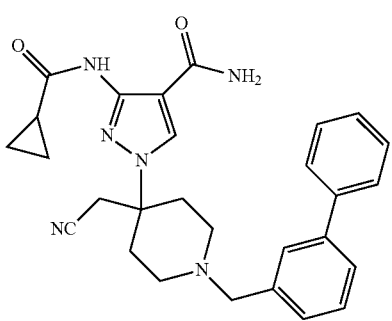
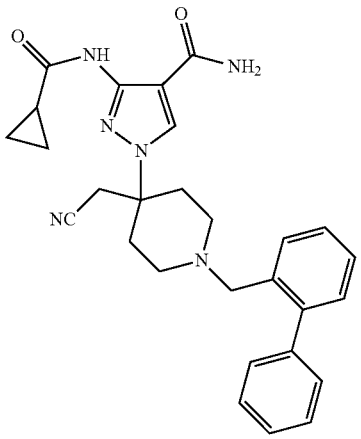
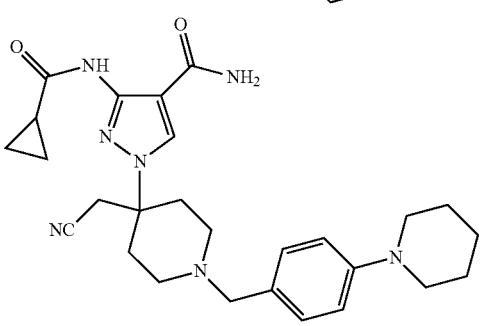
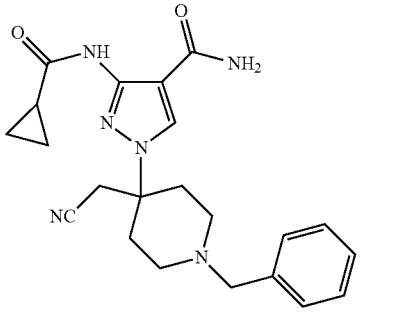

-continued
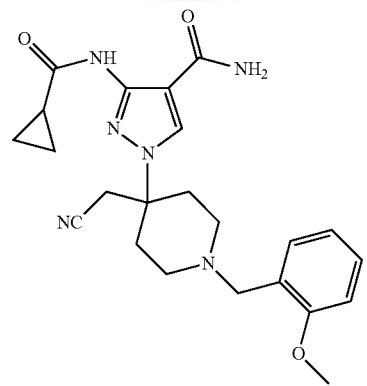
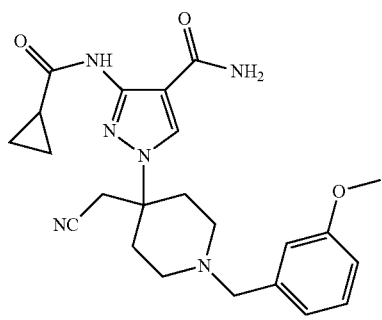
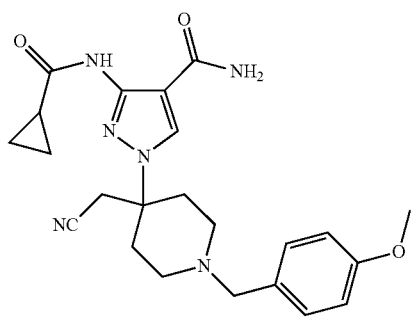
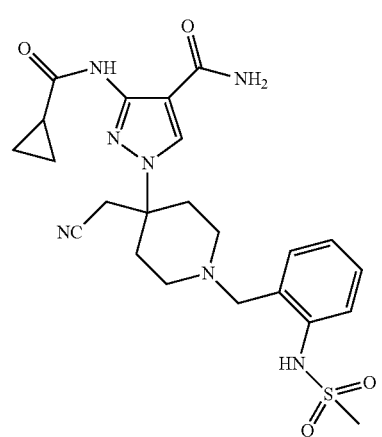
-continued
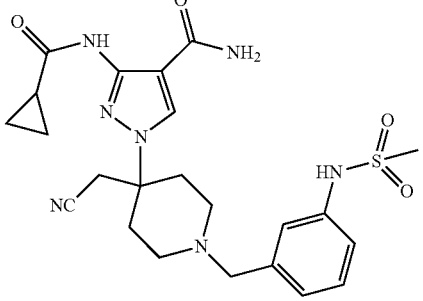
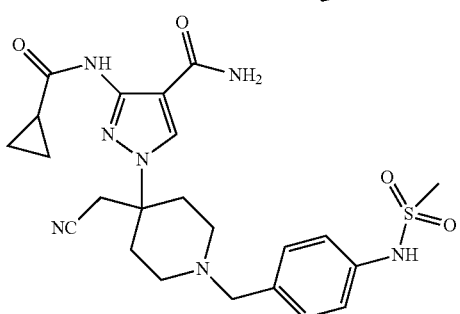
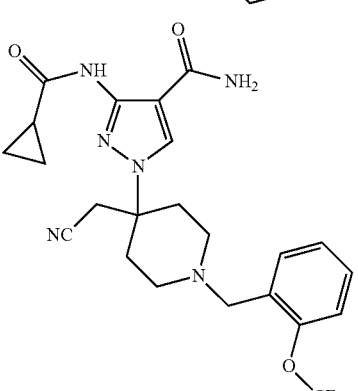
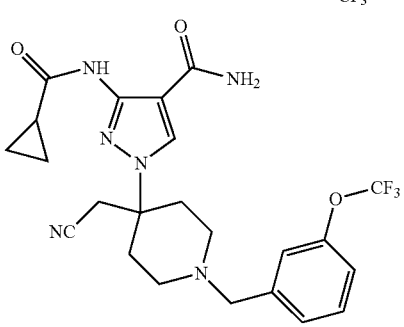
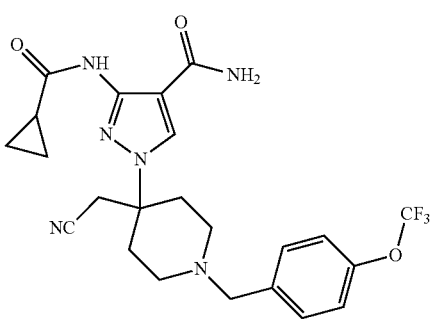

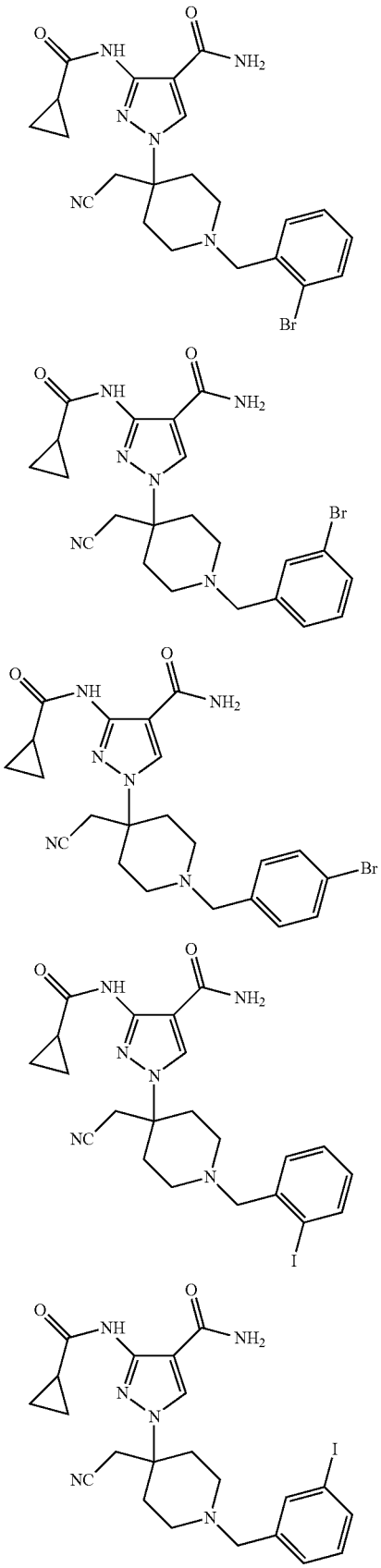
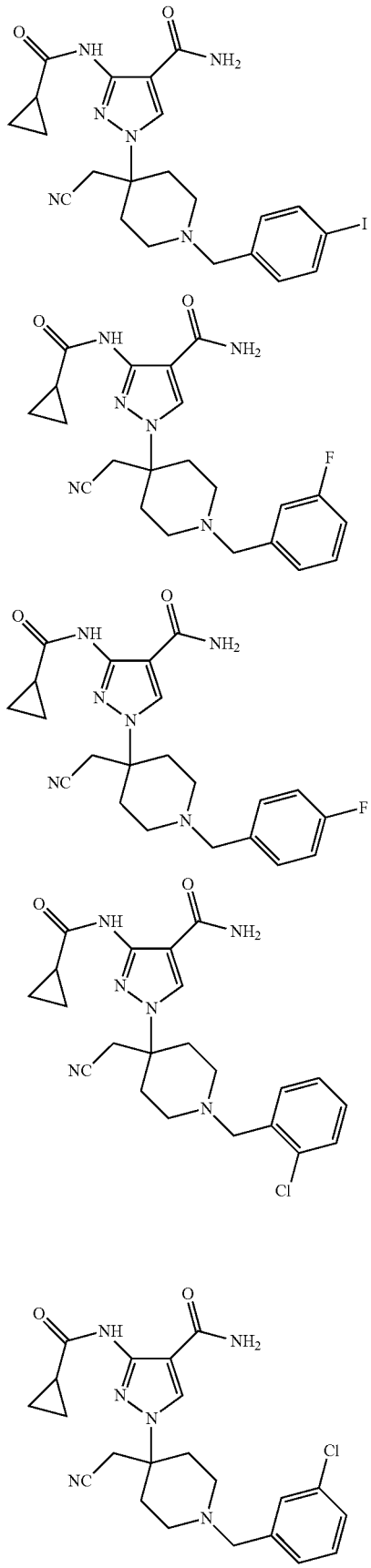

-continued
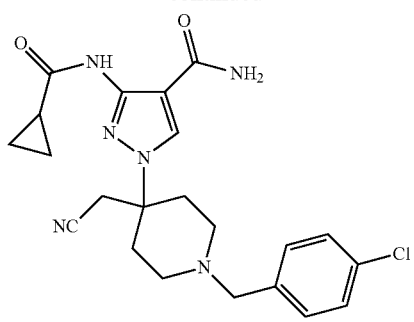
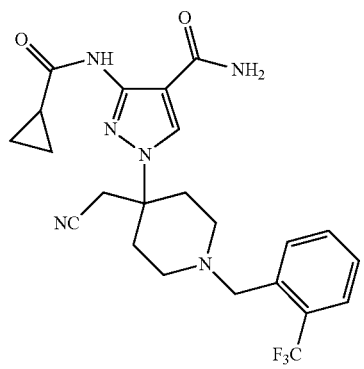
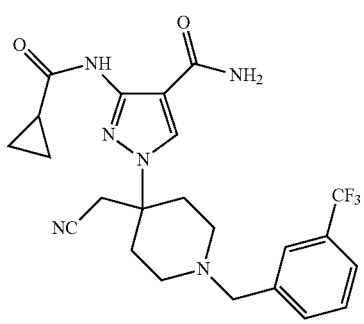
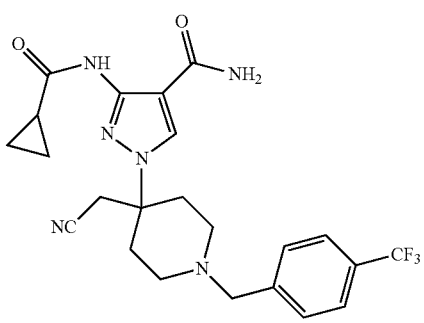
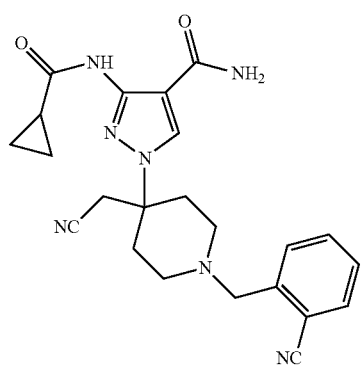
-continued
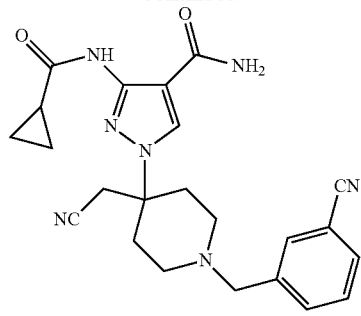
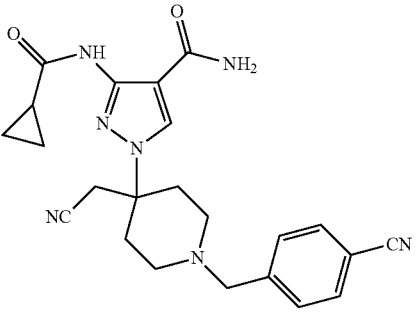
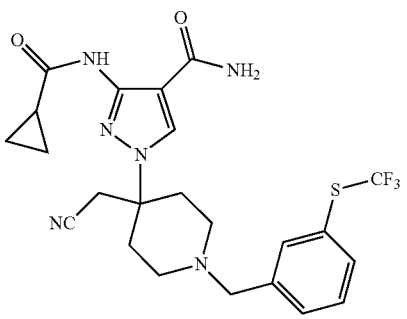
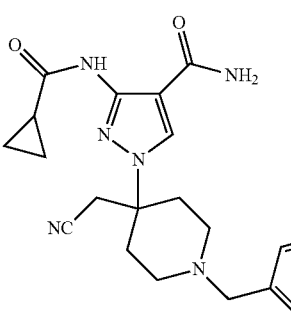
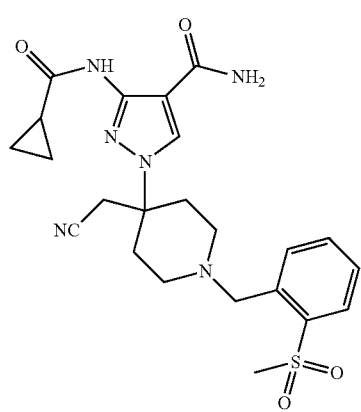

111    112
-continued    -continued
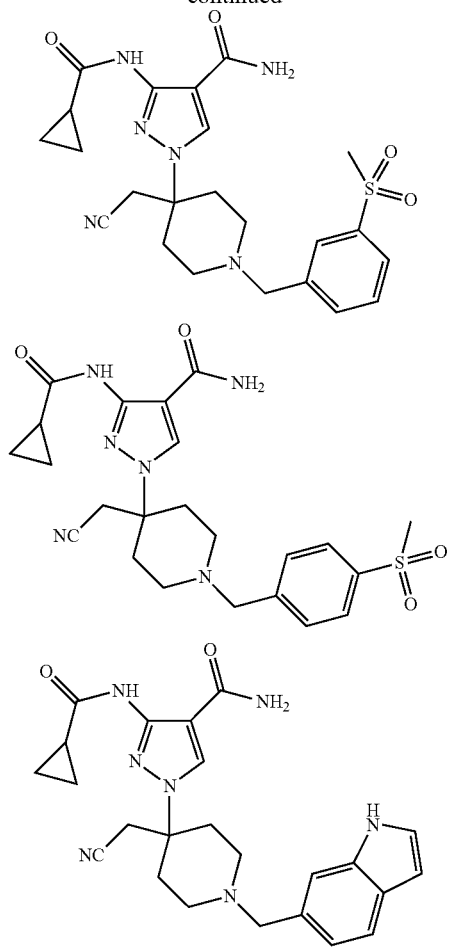
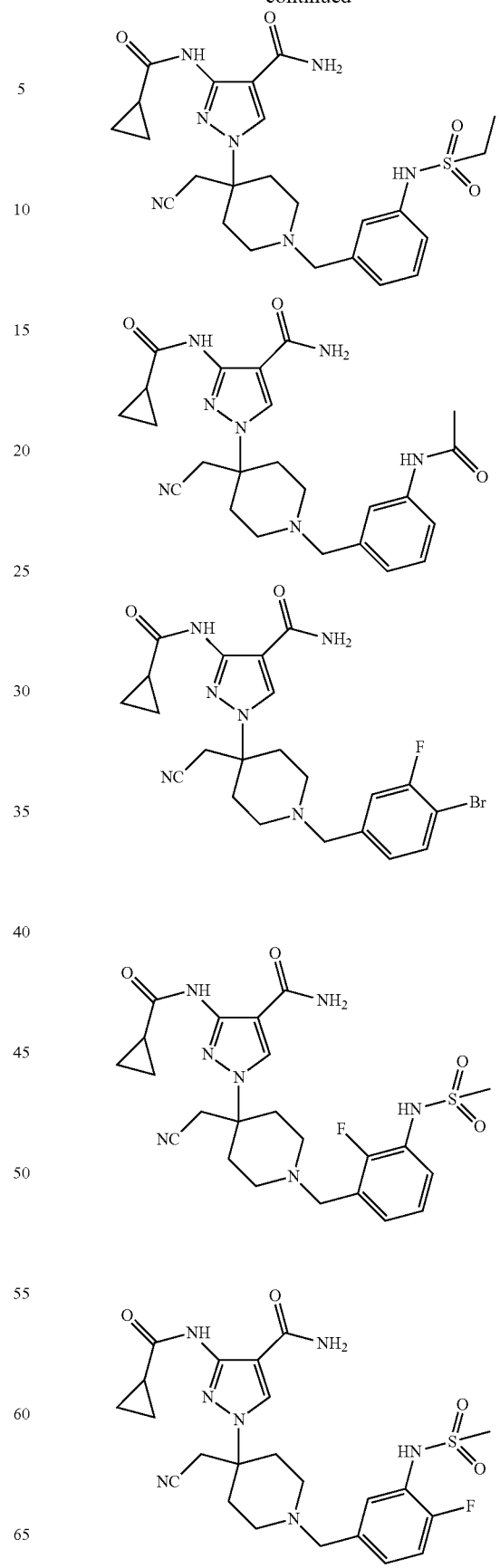

113
-continued
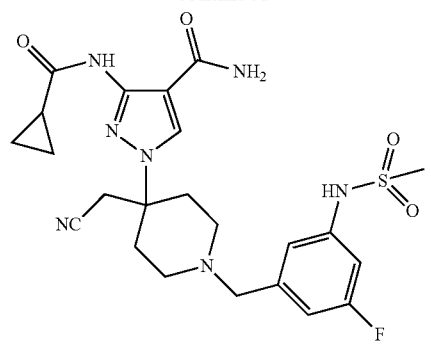
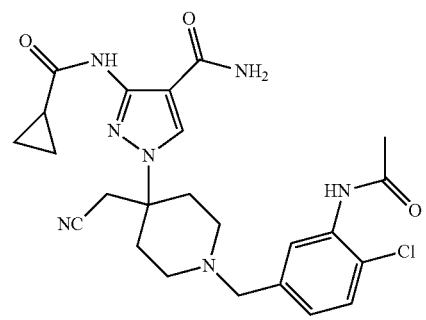
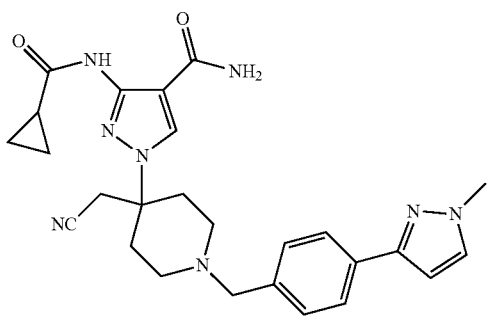
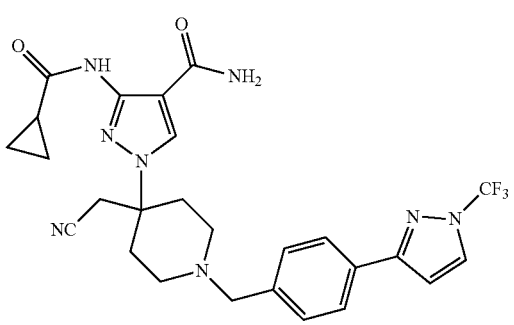
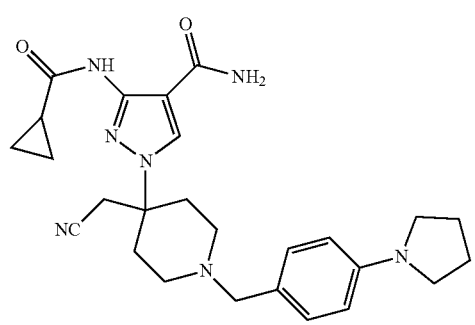
114
-continued
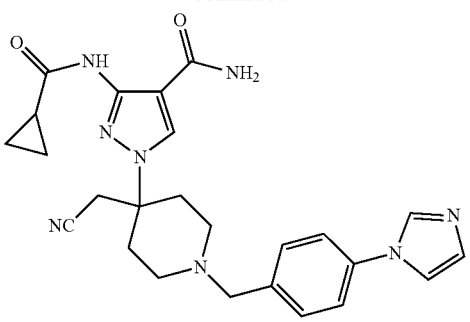
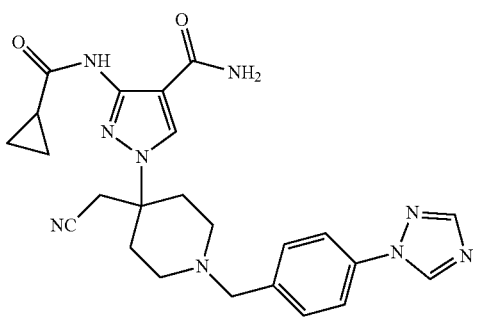
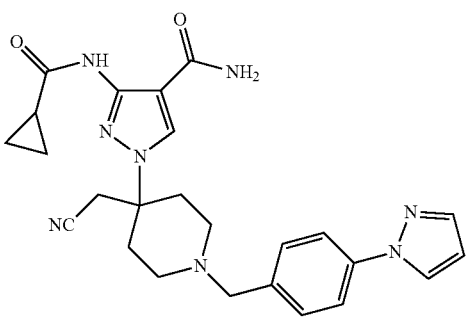
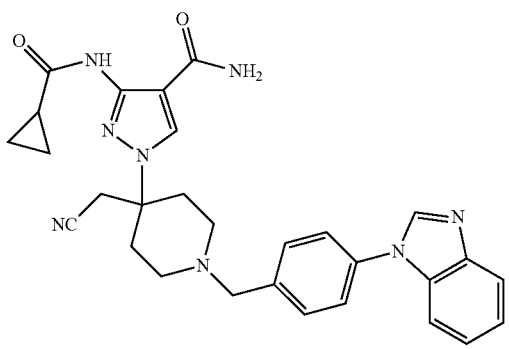
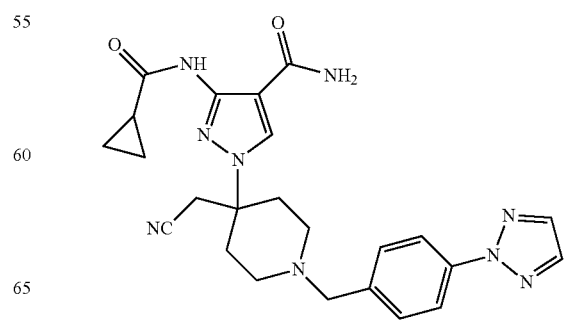

115
-continued
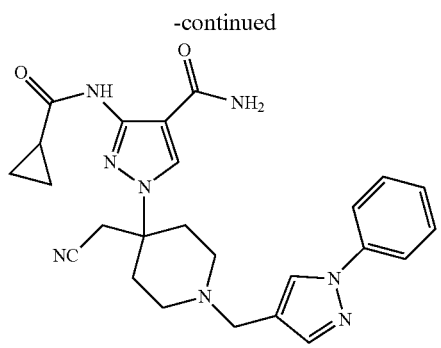
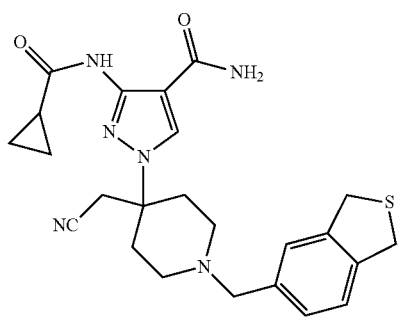
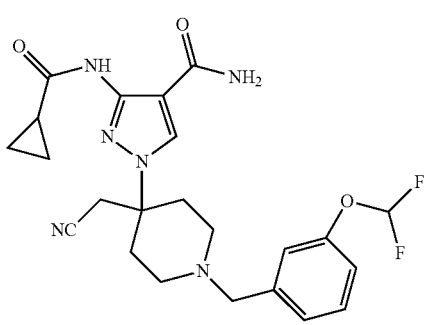
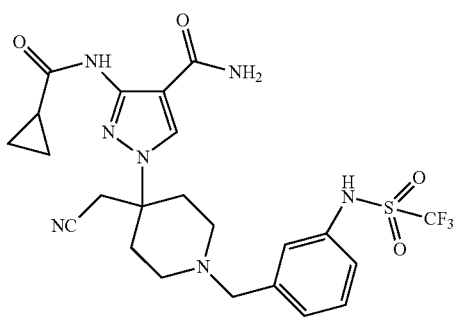
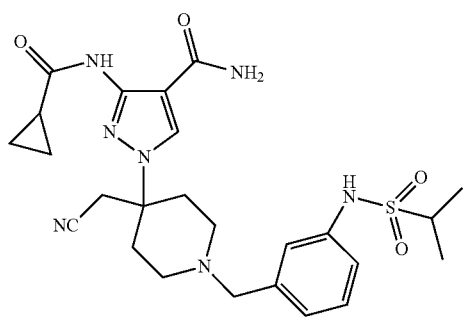
116
-continued
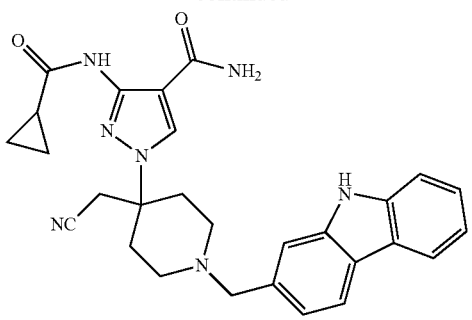
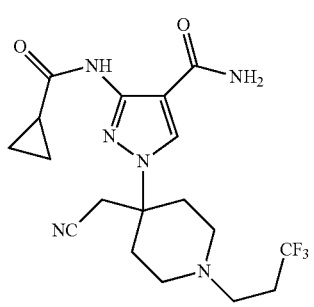
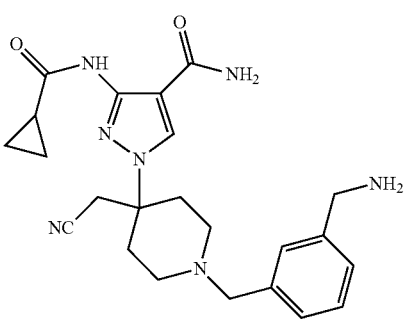
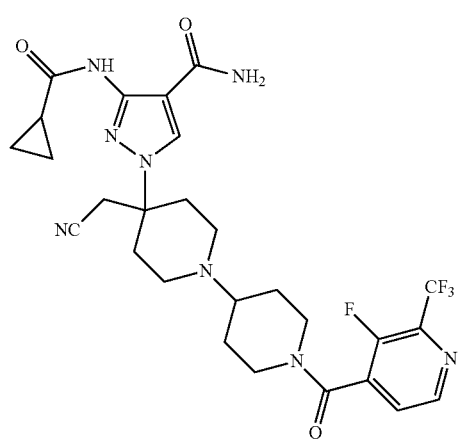

117
-continued
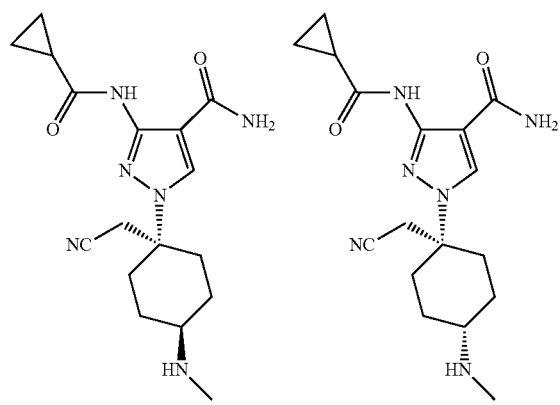
118
-continued
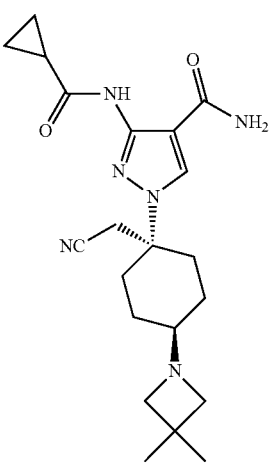
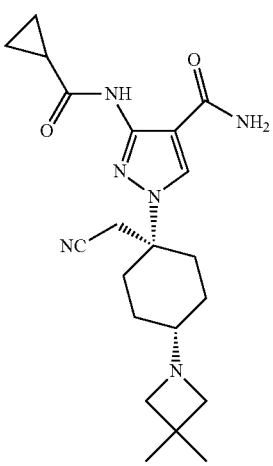
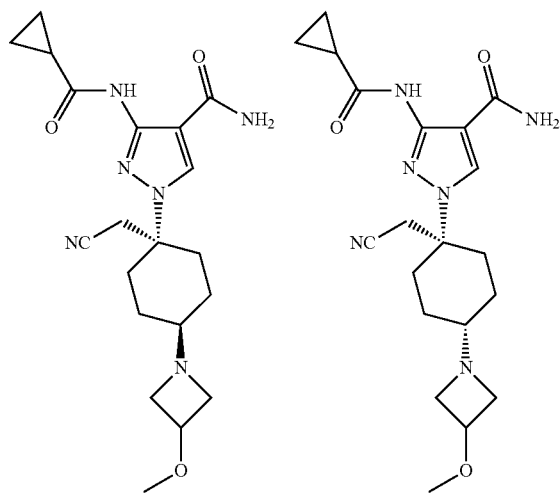
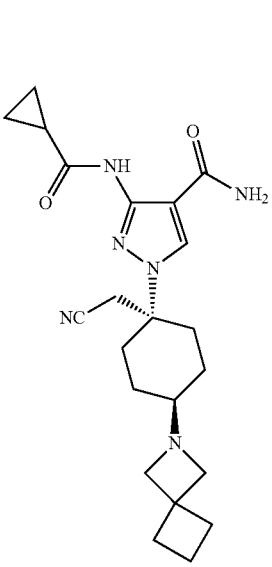
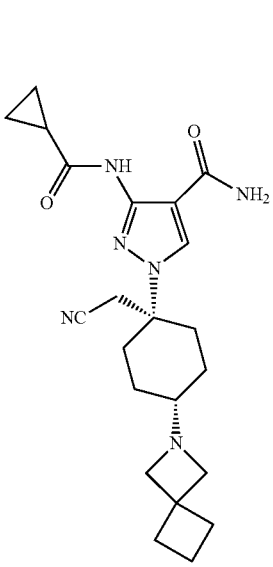
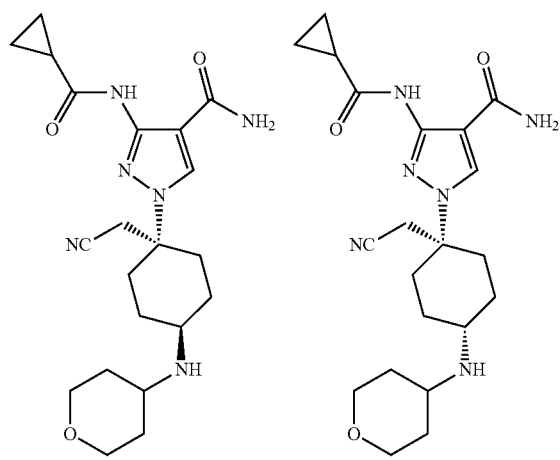
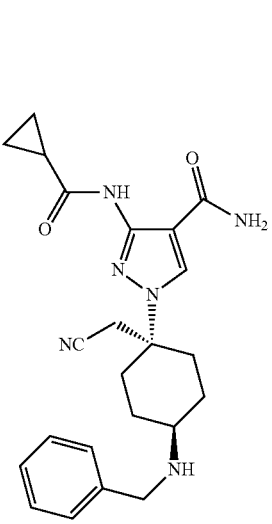
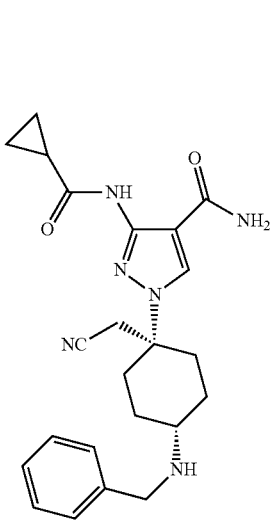

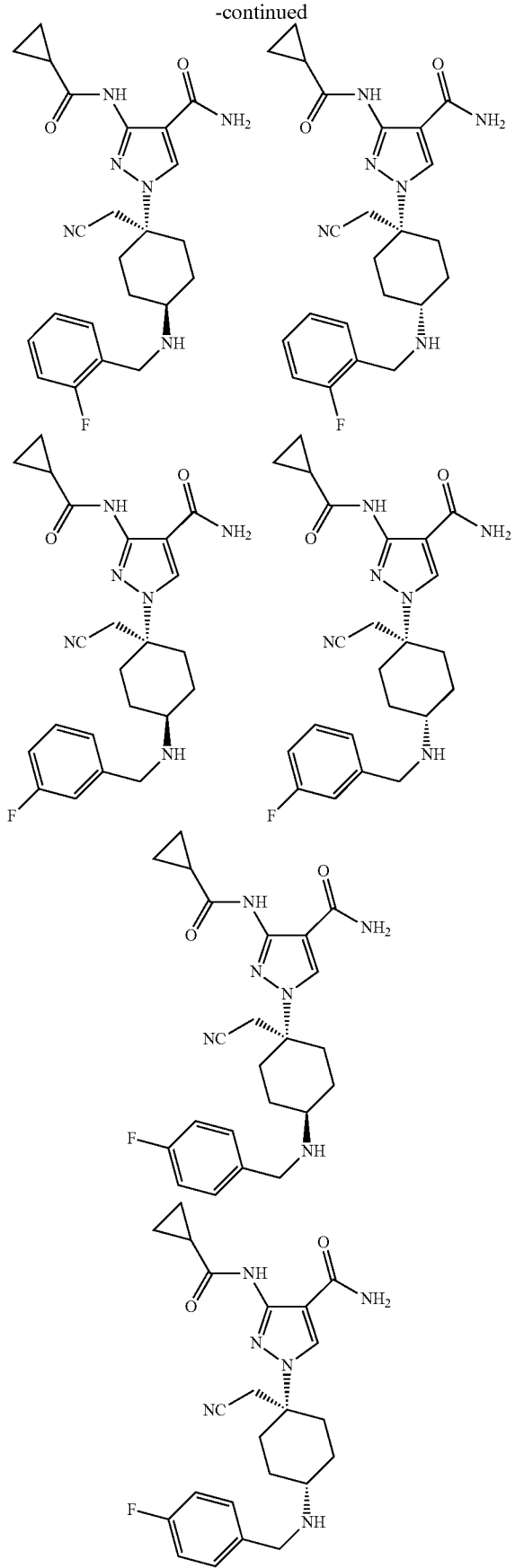
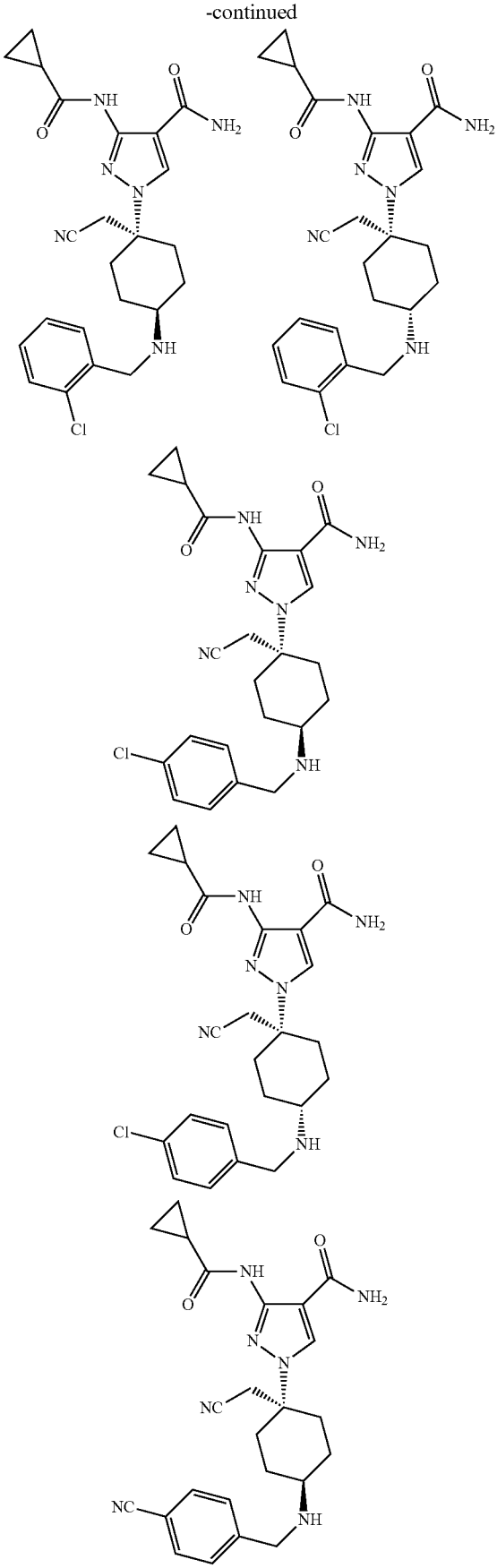

121
-continued
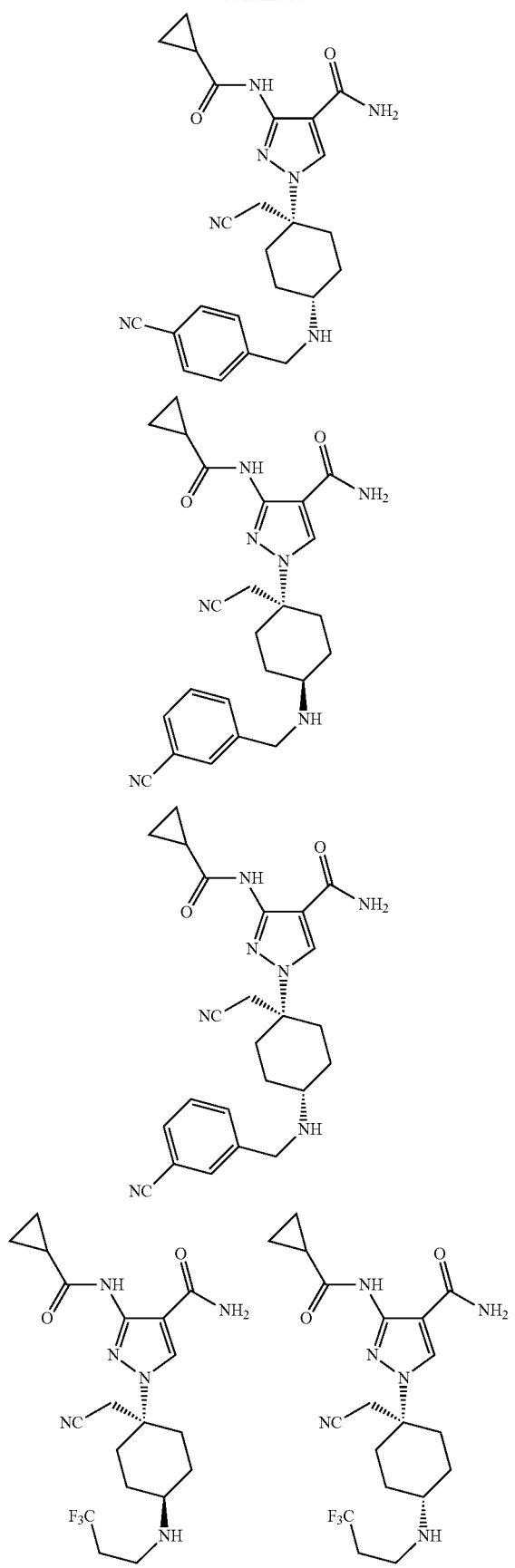
122
-continued
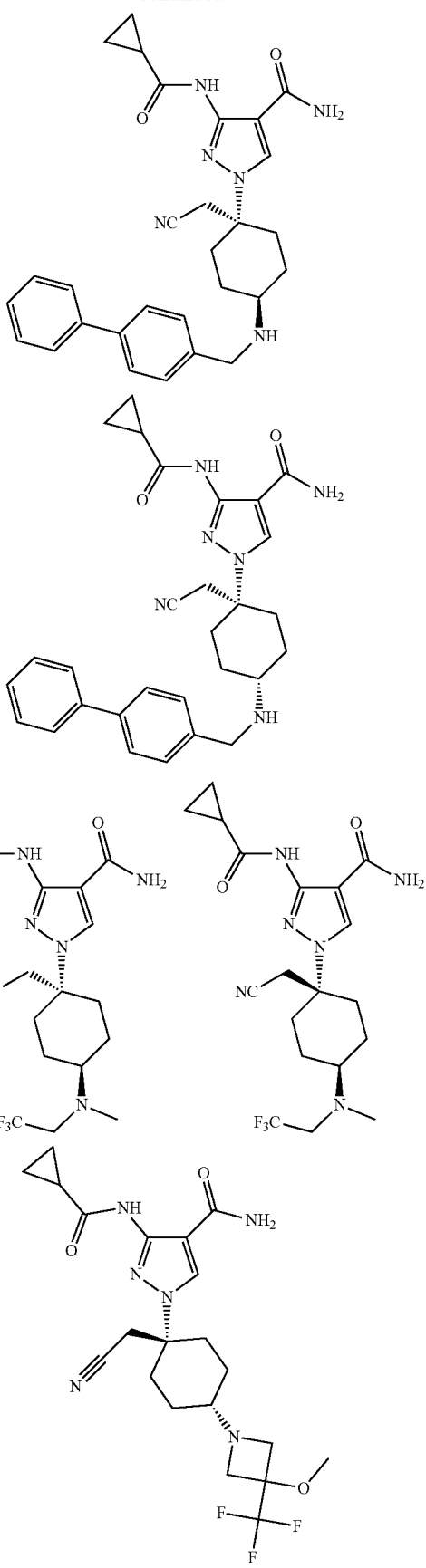

123
-continued
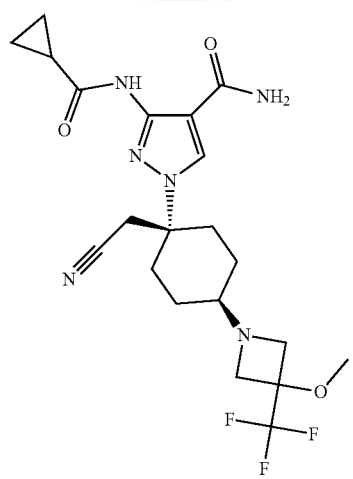
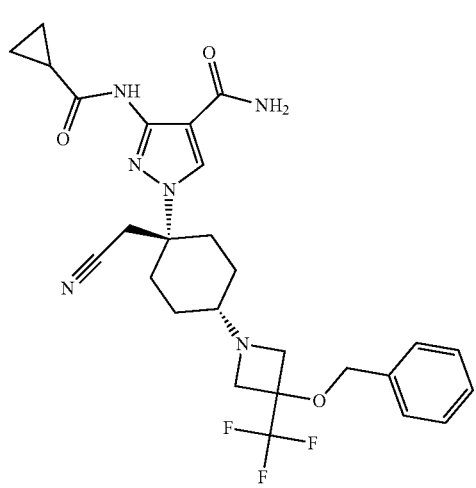
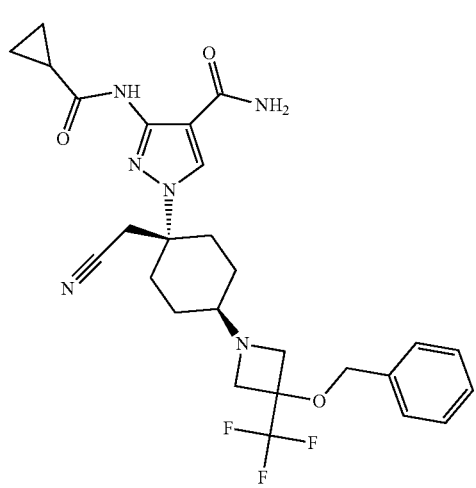
124
-continued
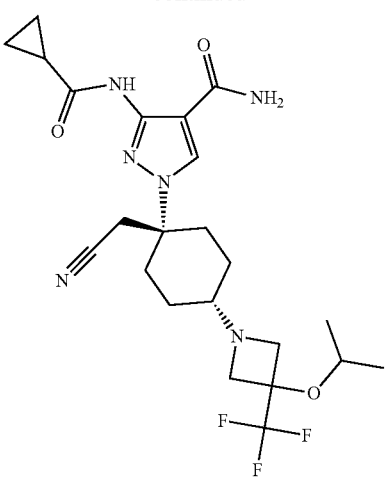
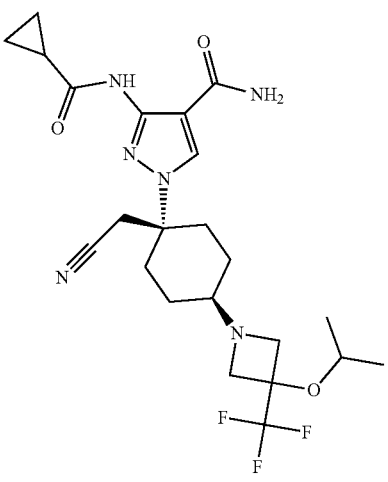
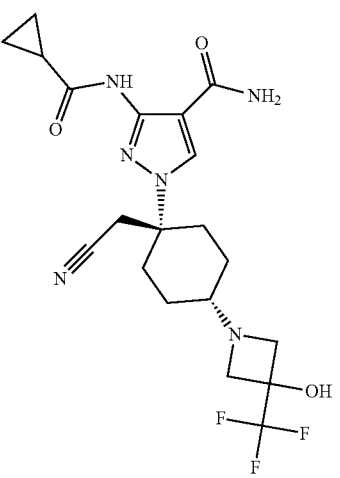

125
-continued
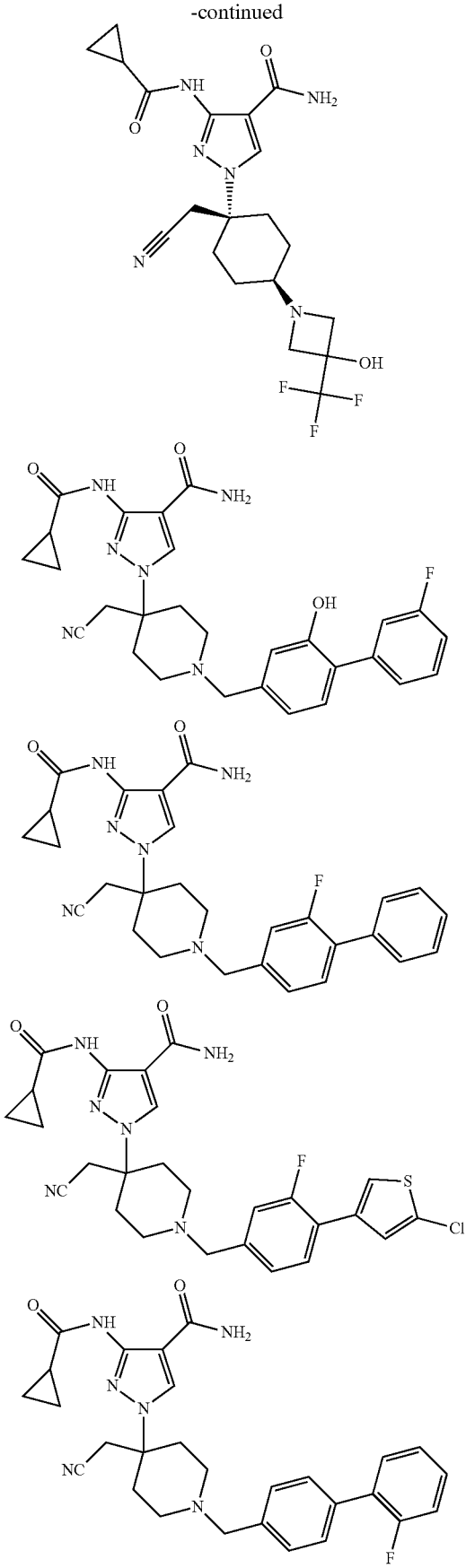
126
-continued
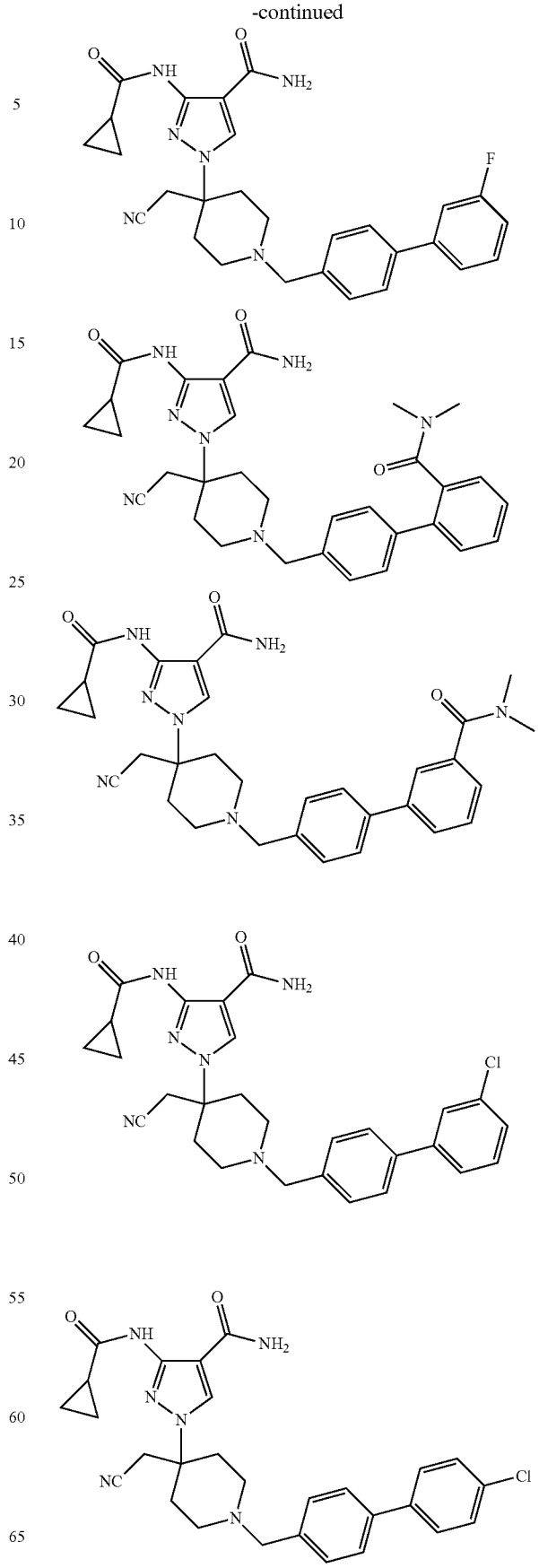

127
-continued
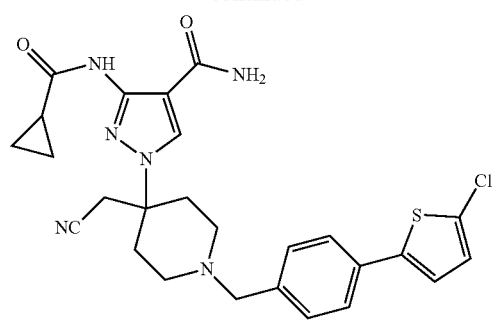
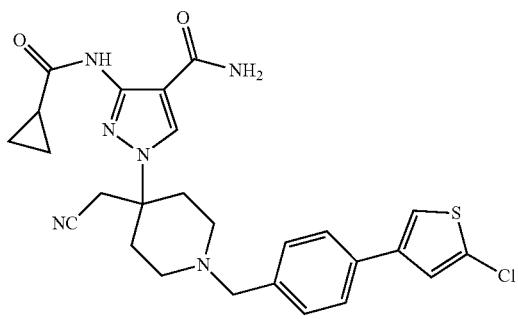
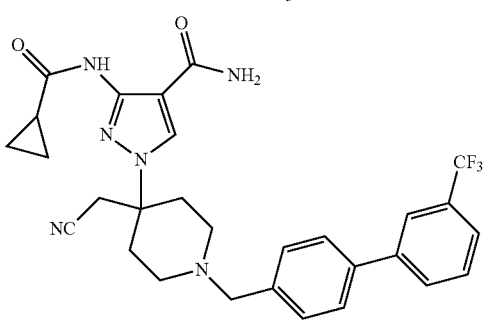
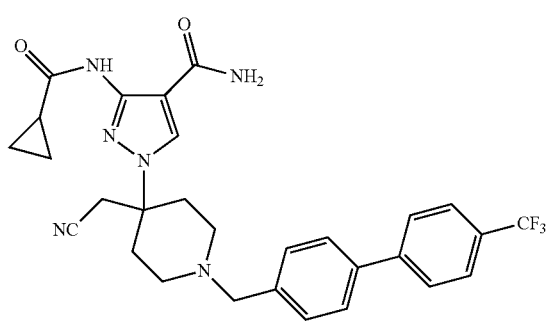
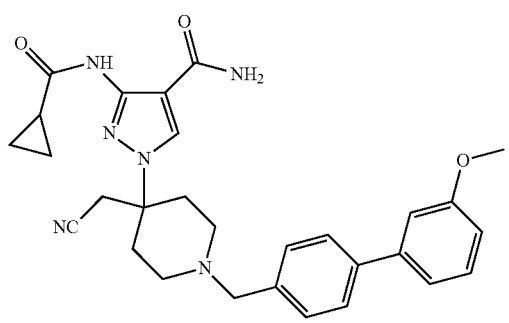
128
-continued
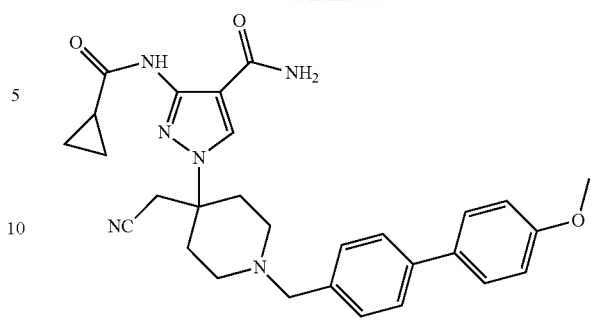
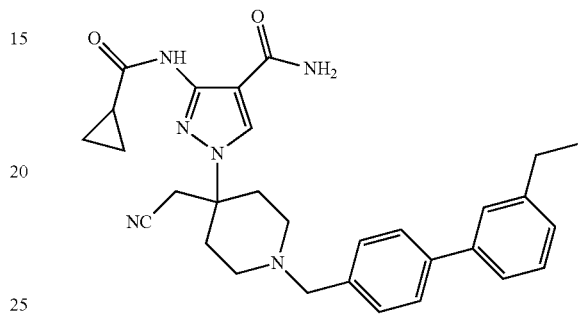
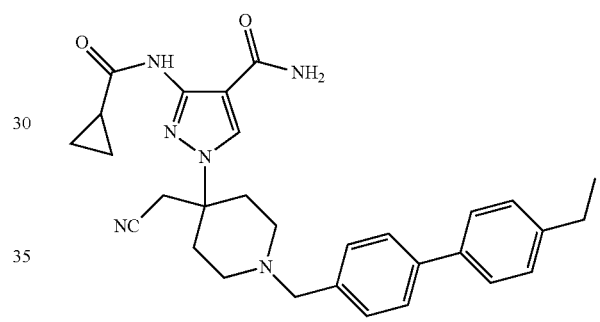
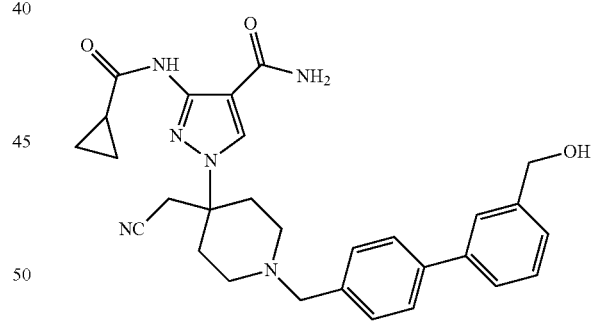
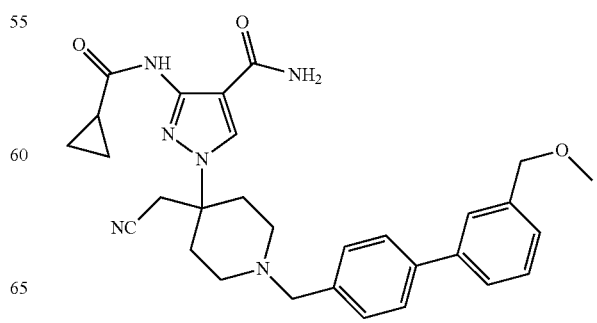

129
-continued
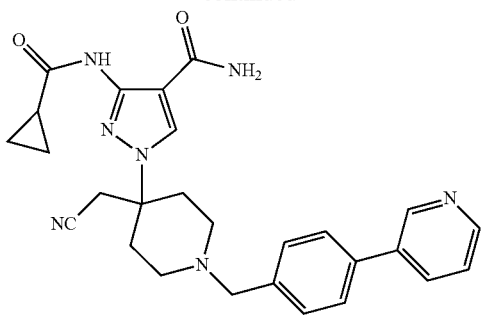
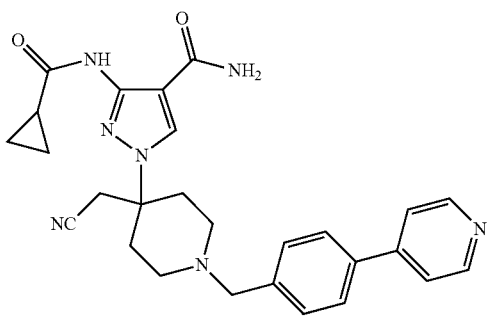
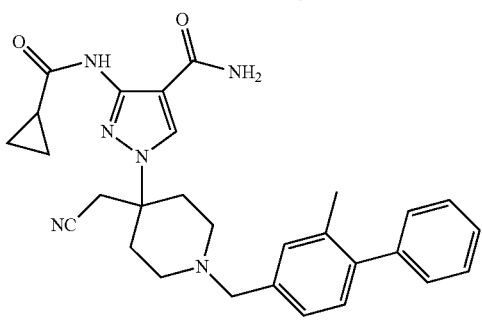
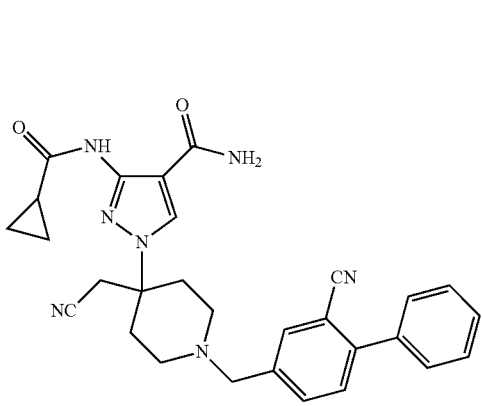
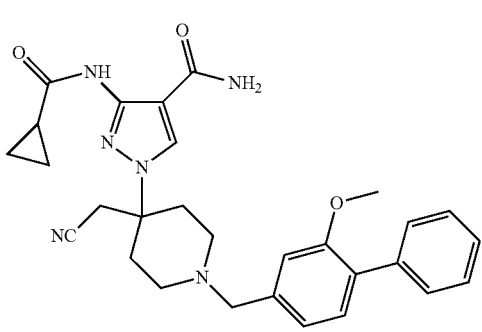
130
-continued
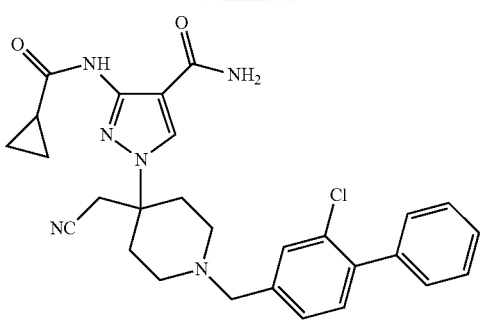
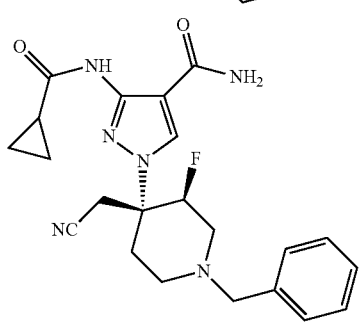
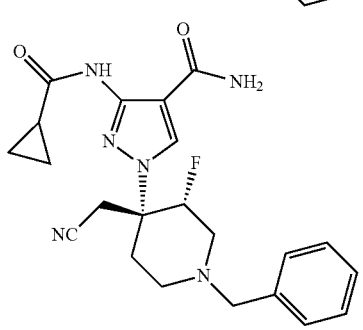
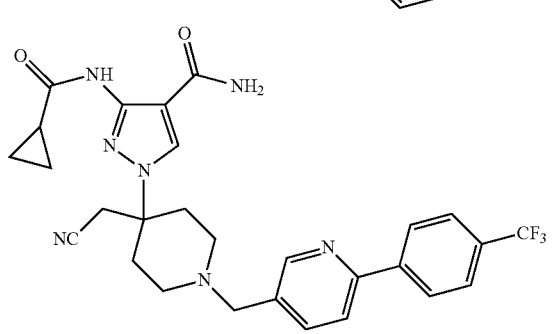
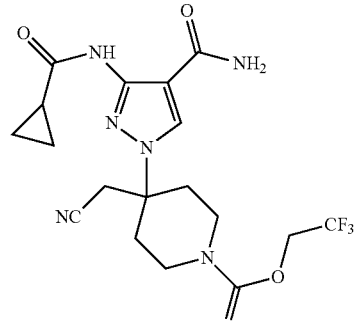

-continued
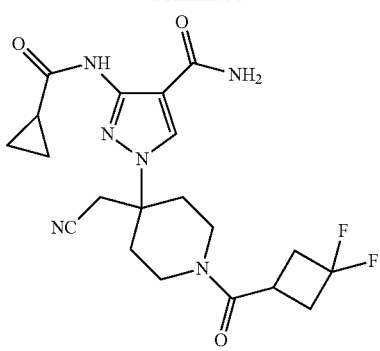
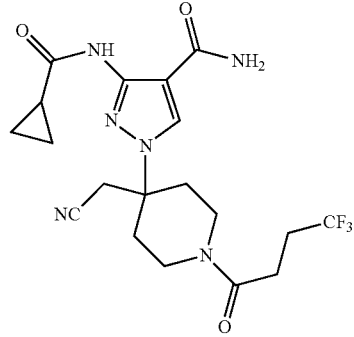
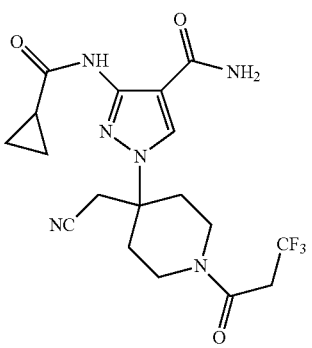
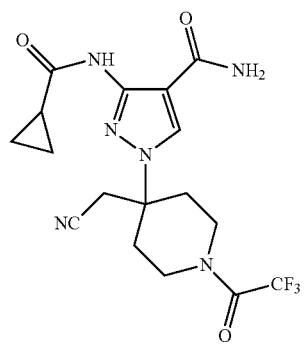
-continued
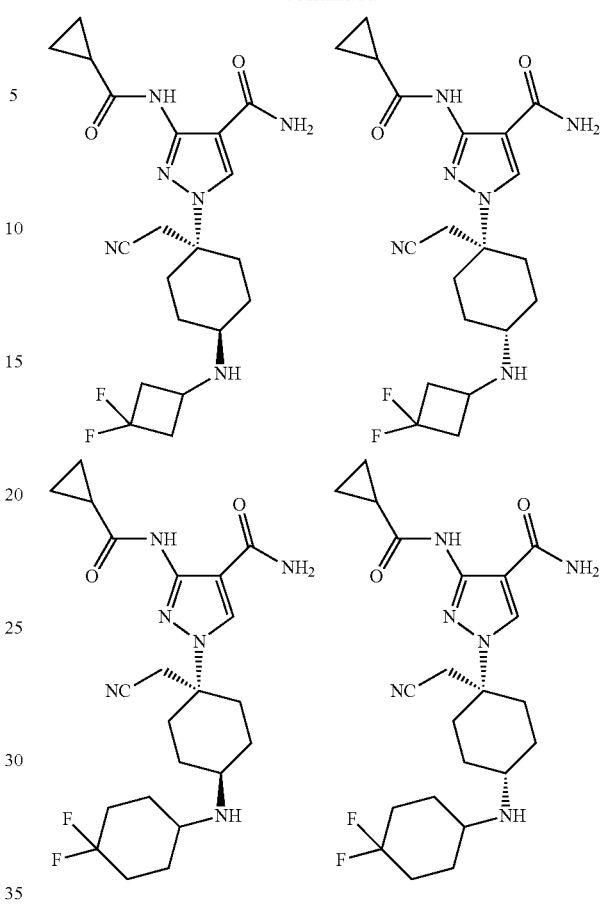
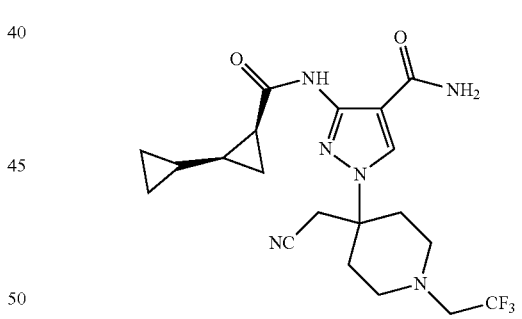
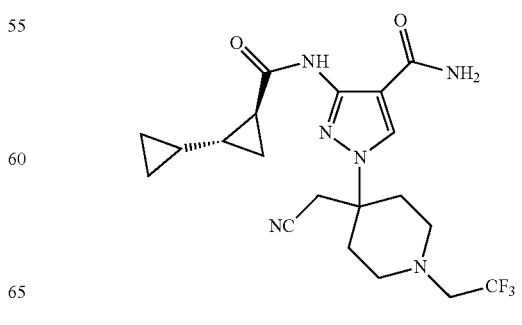

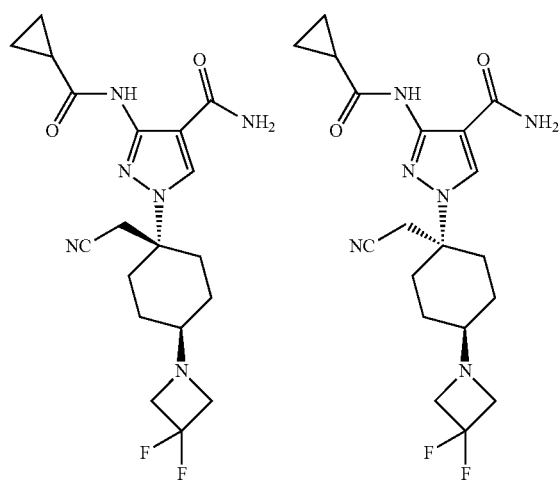
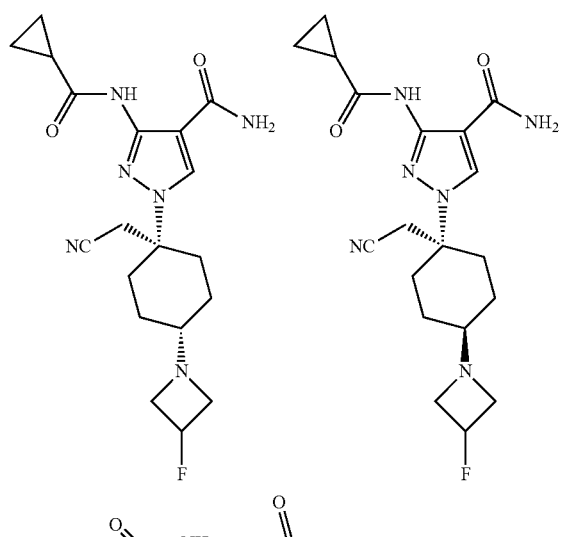
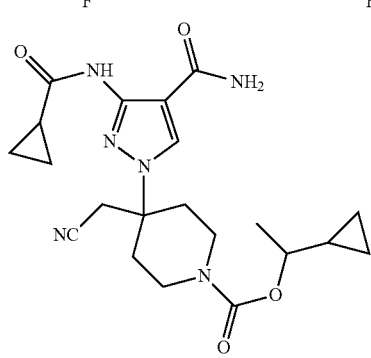
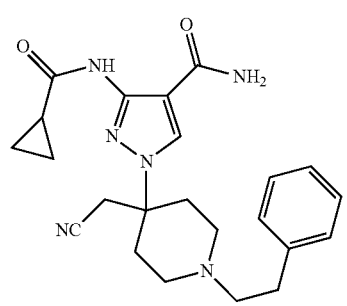
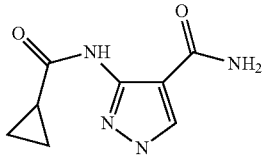
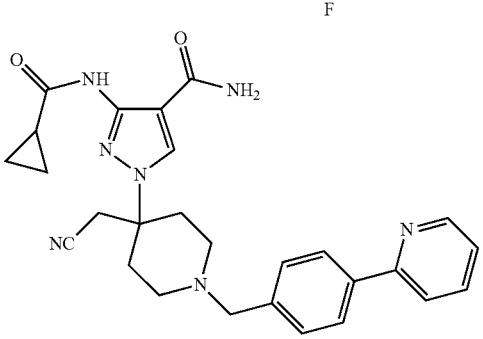
and salts thereof.
In some embodiments, a compound of the invention is selected from the group consisting of:
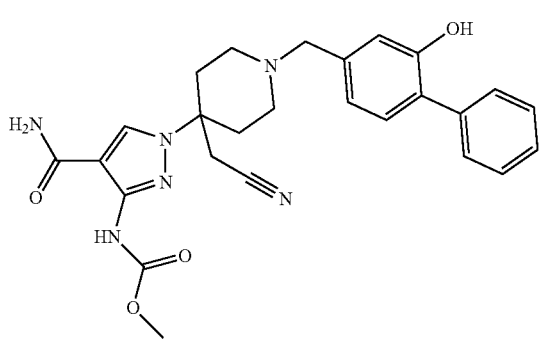
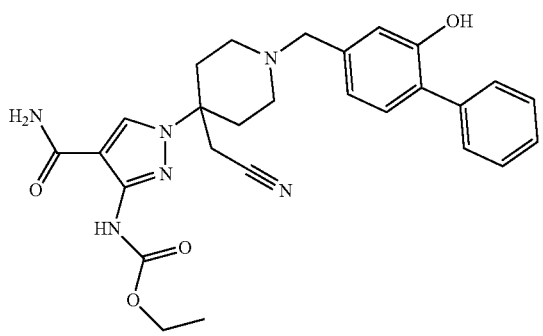

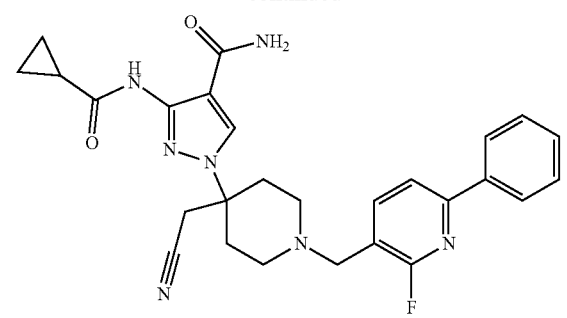
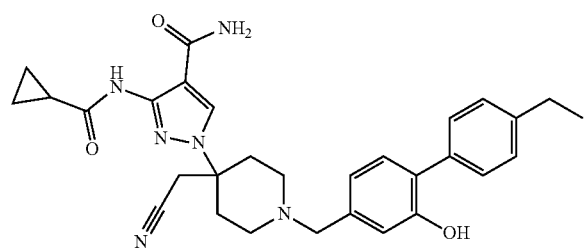
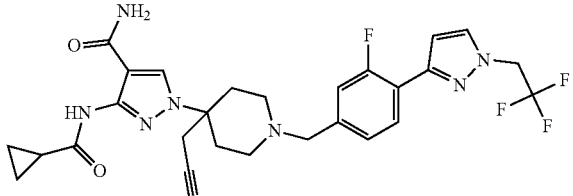
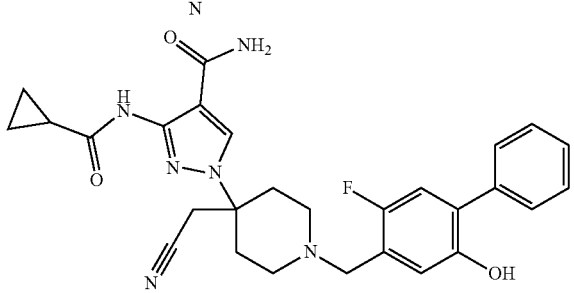
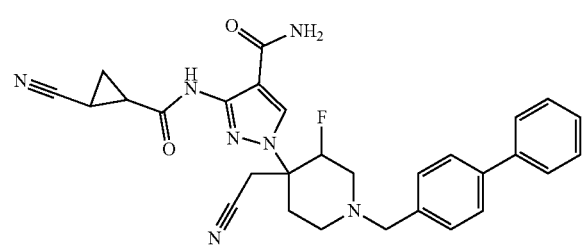
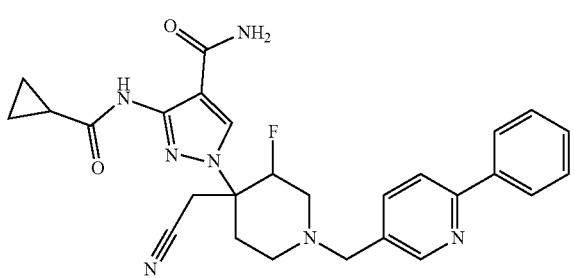
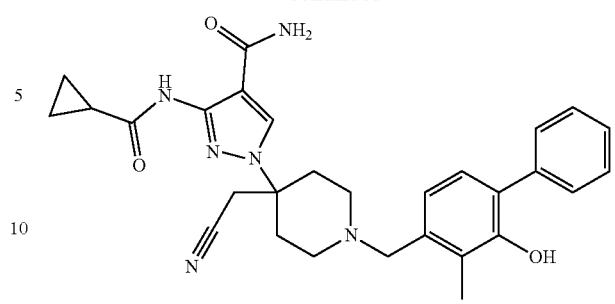
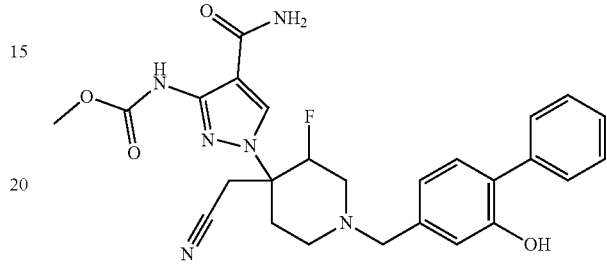
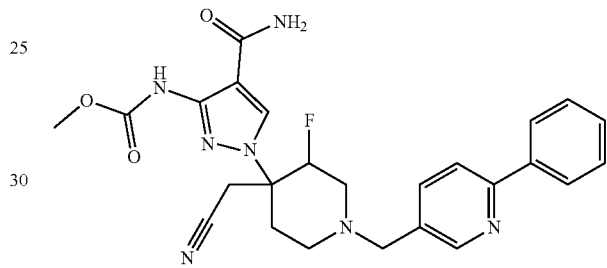
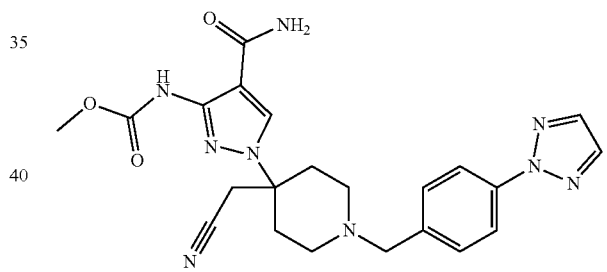
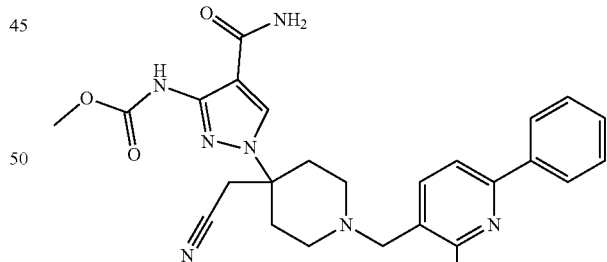
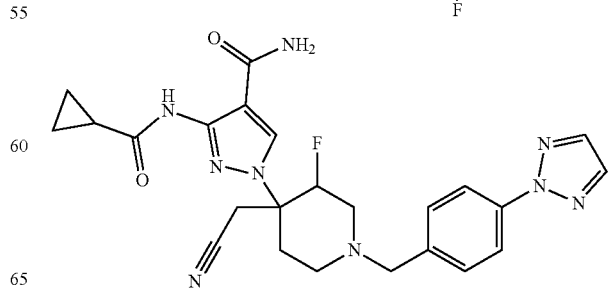

137
-continued
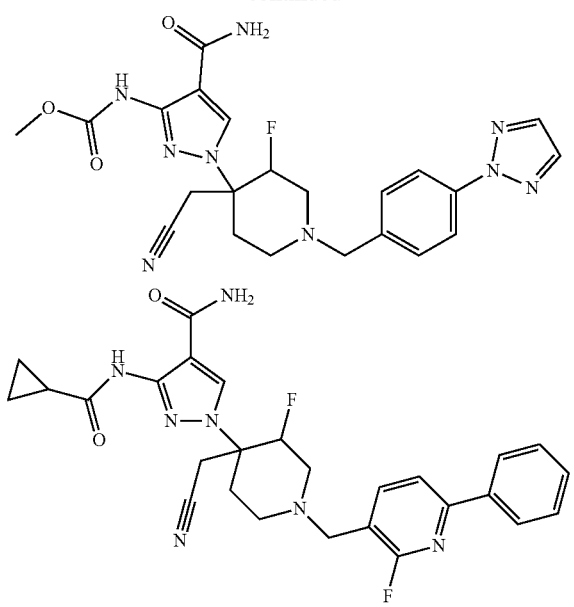
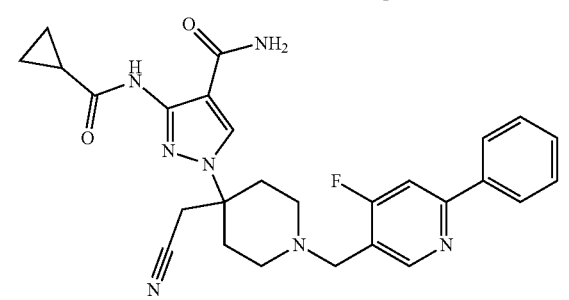
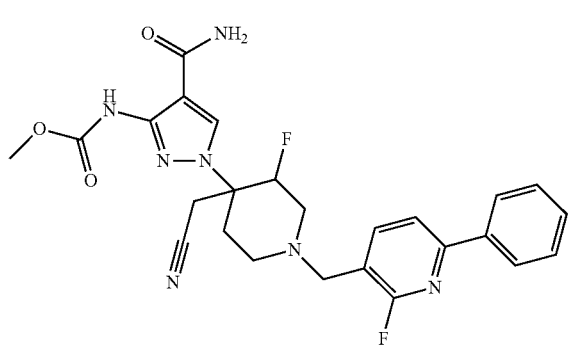
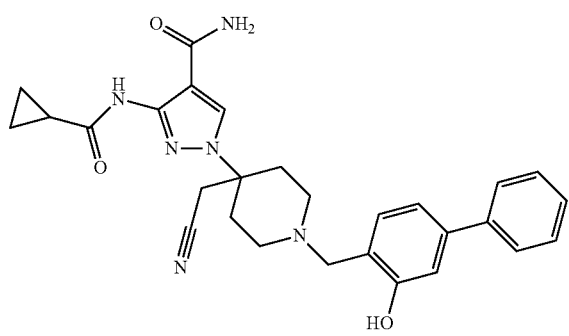
138
-continued
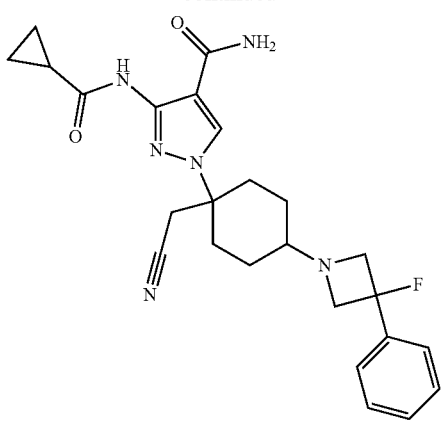
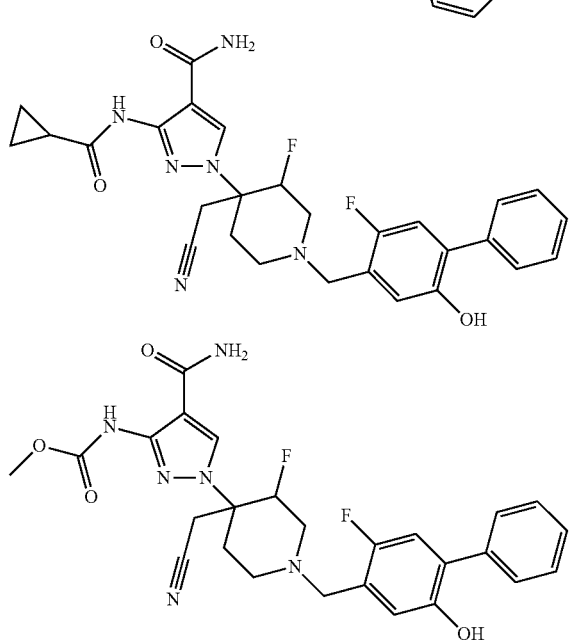
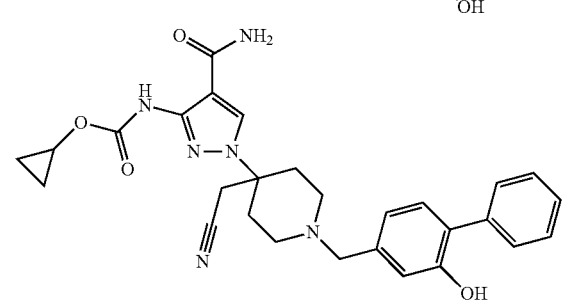
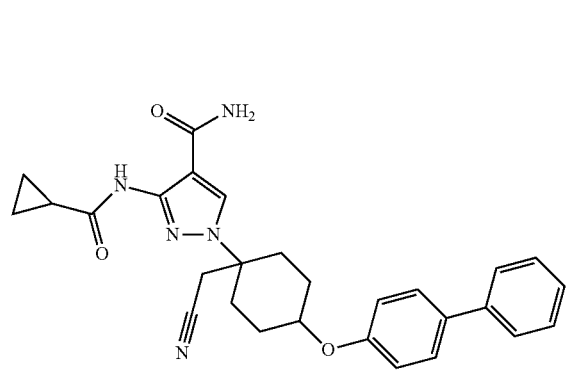

139
-continued
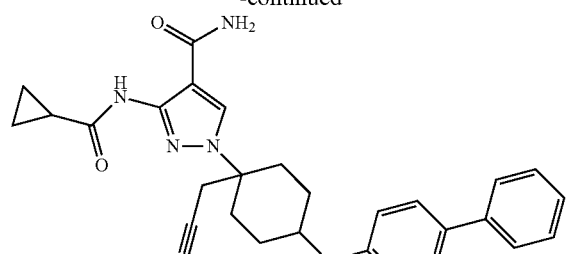
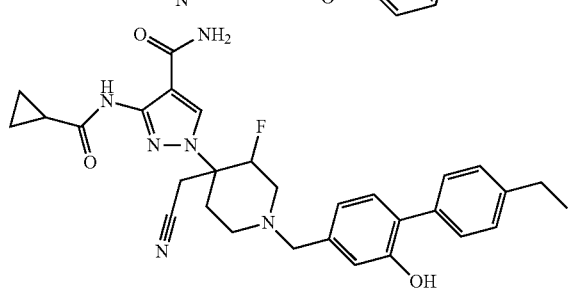
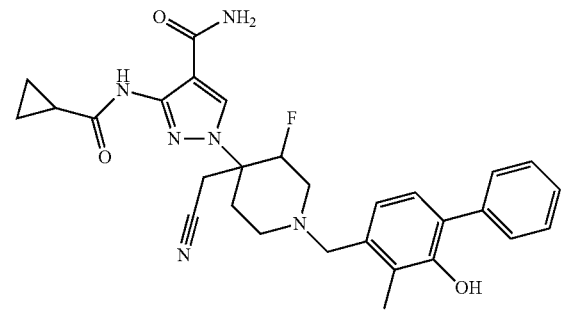
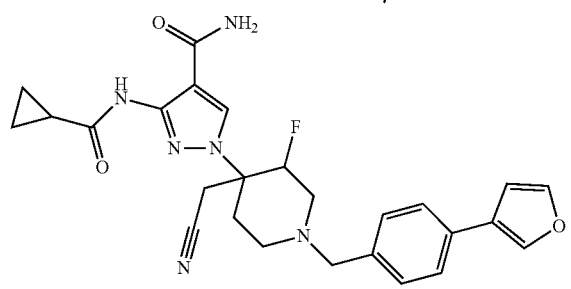
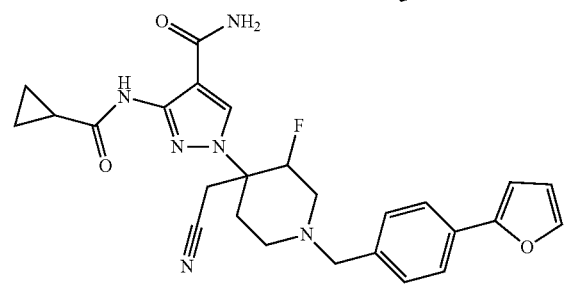
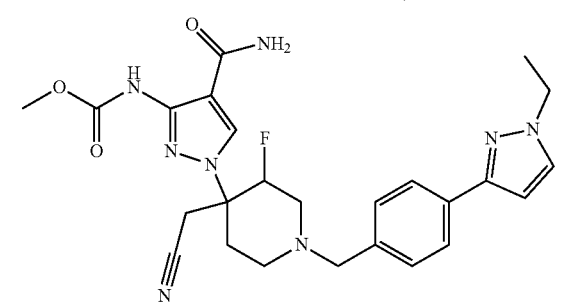
140
-continued
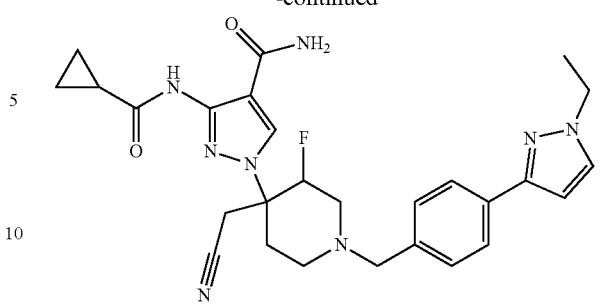
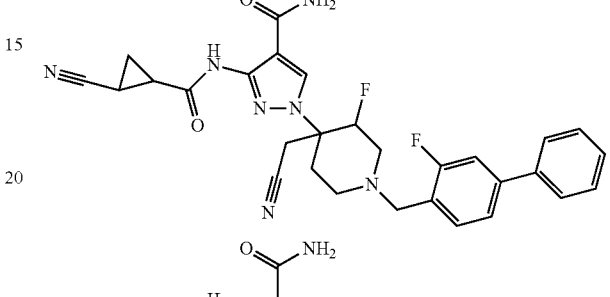
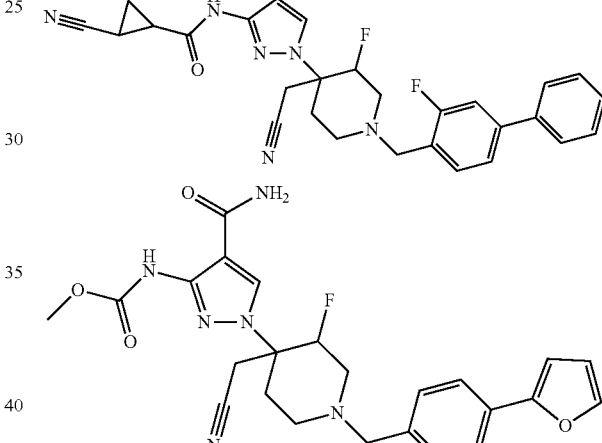
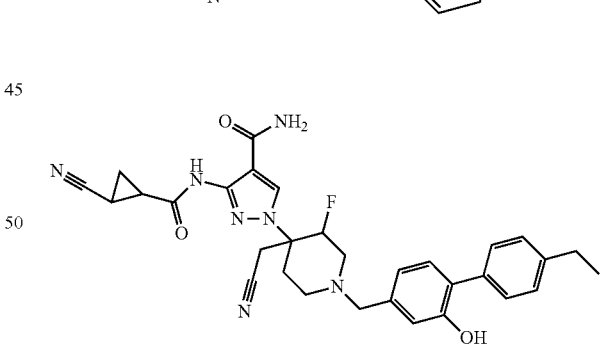
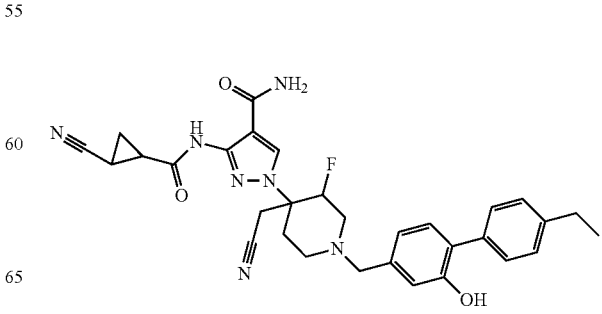

141
-continued
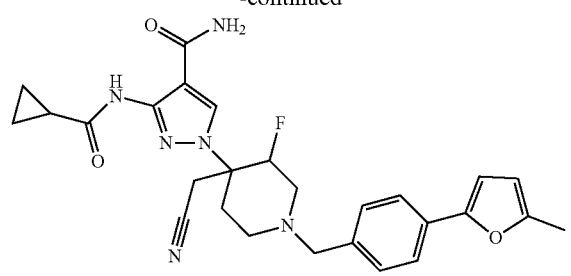
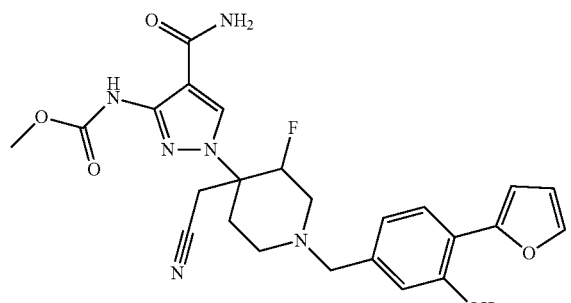
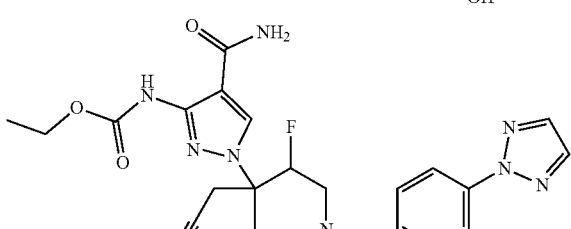
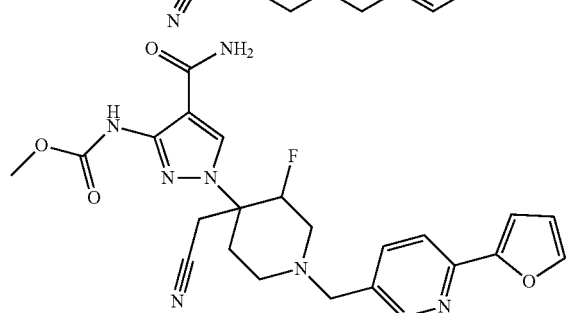
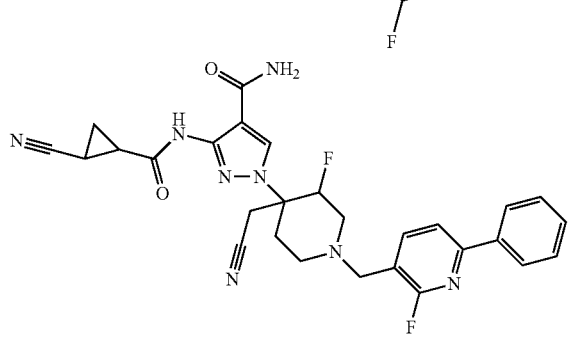
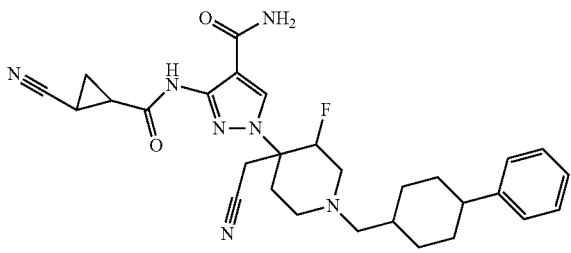
142
-continued
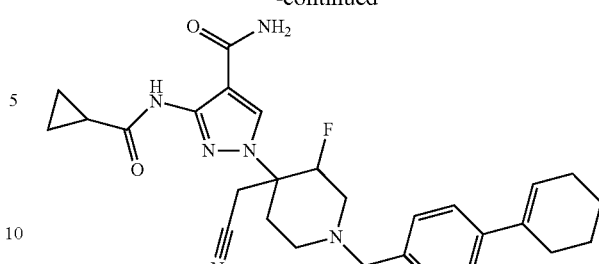
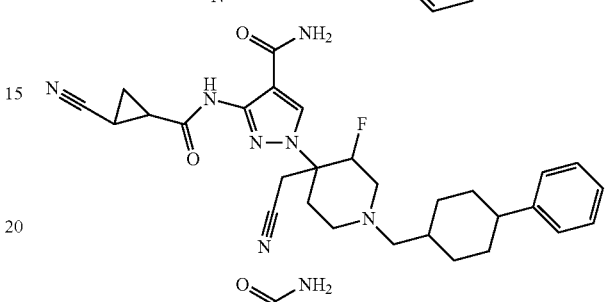
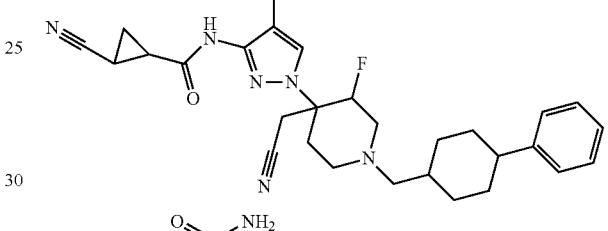
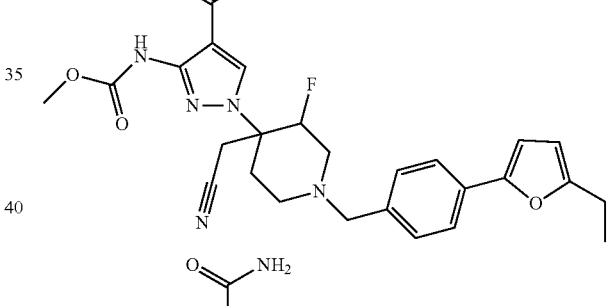
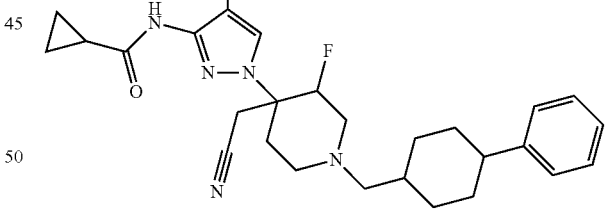
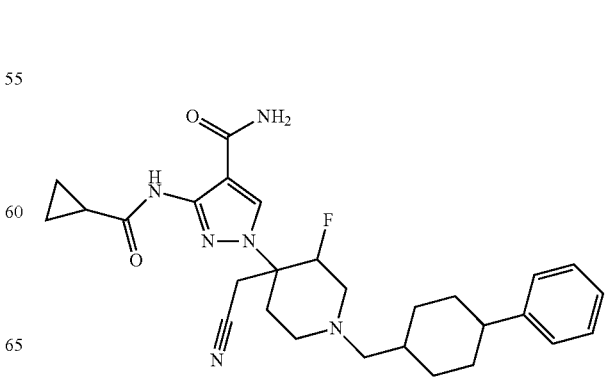

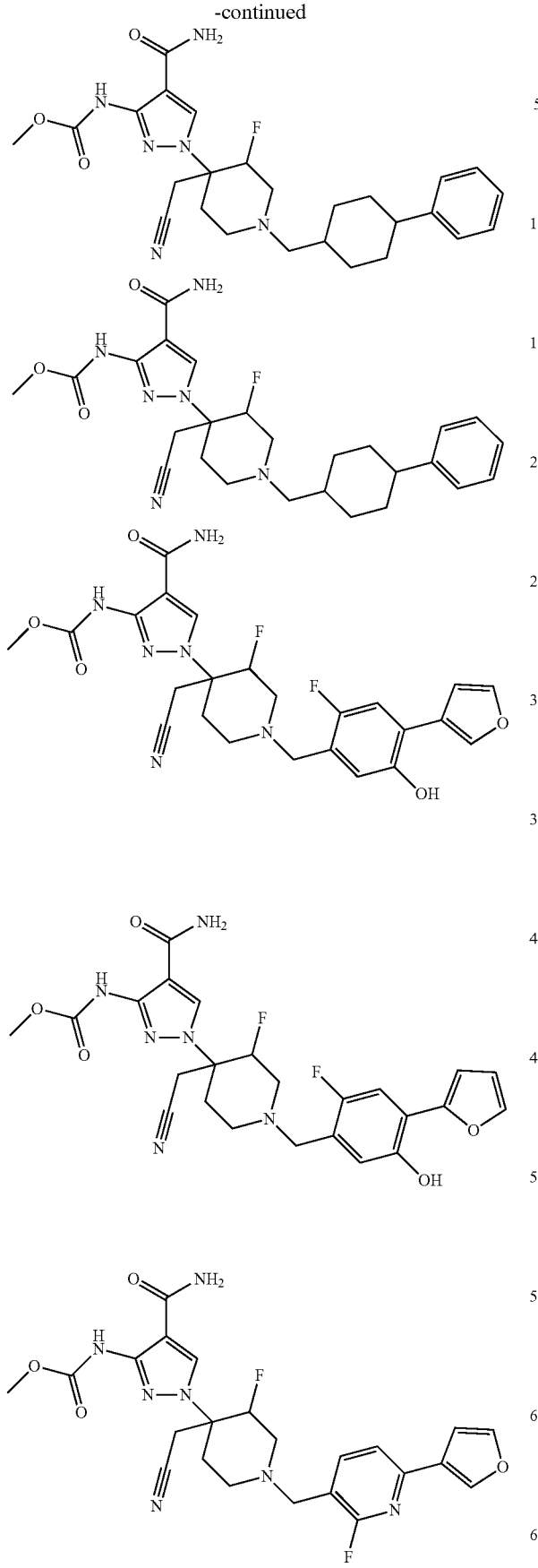
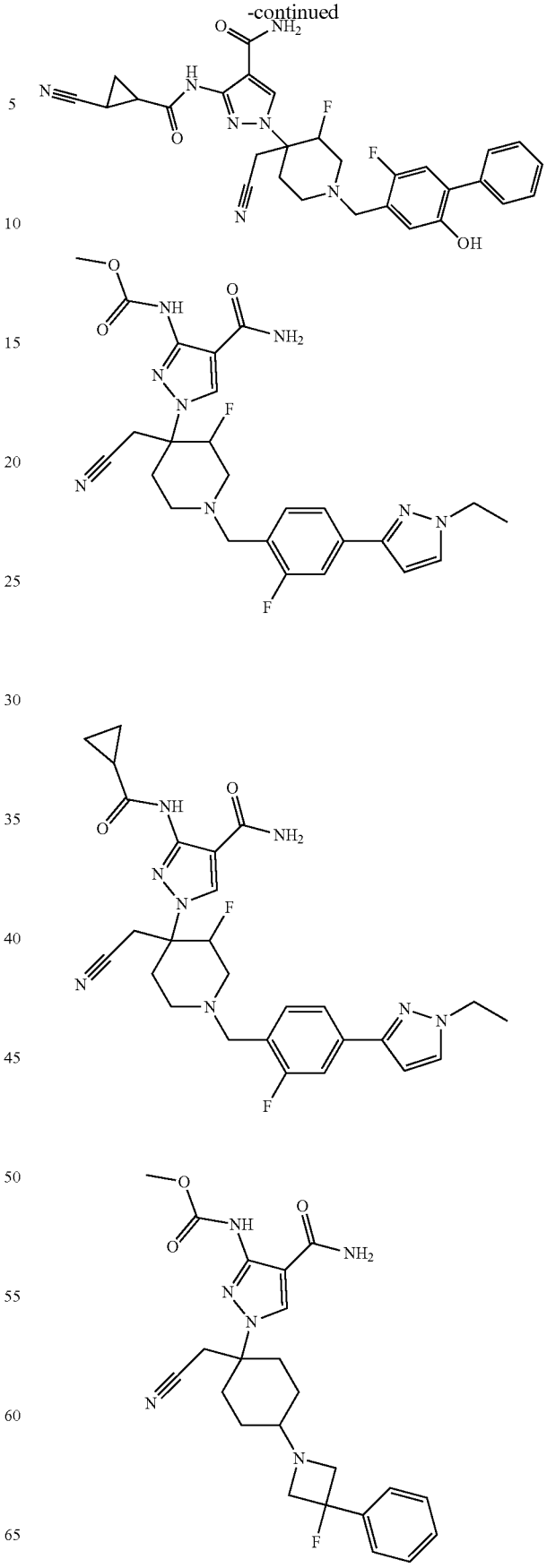

145
-continued
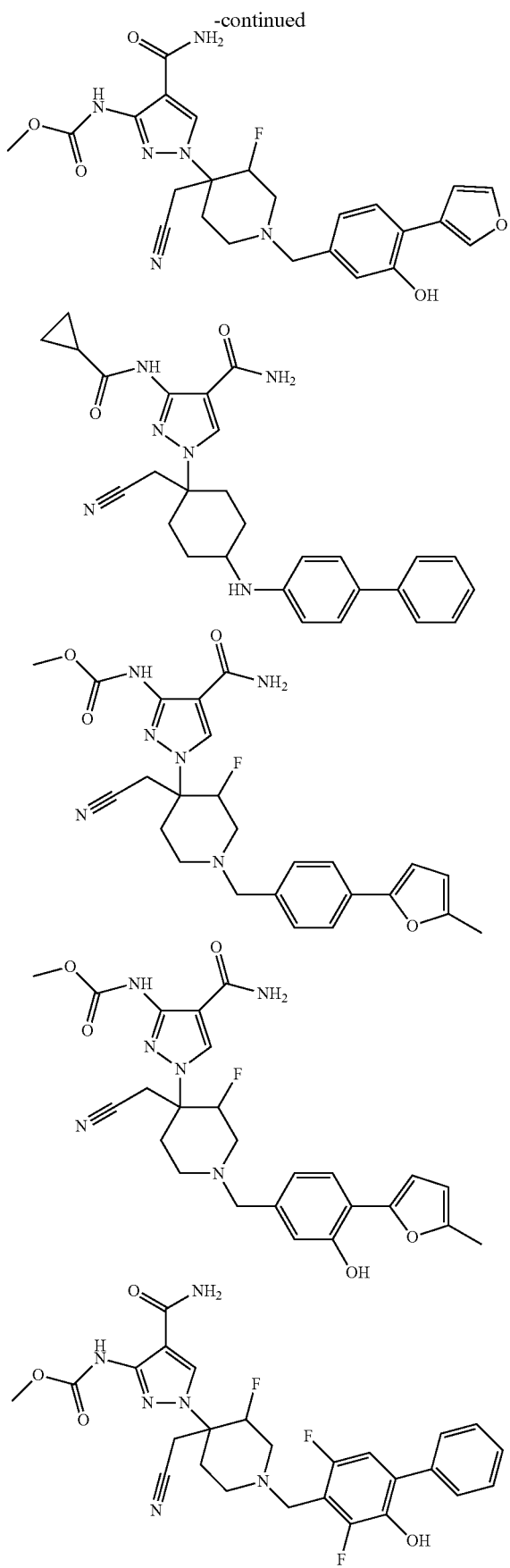
146
-continued
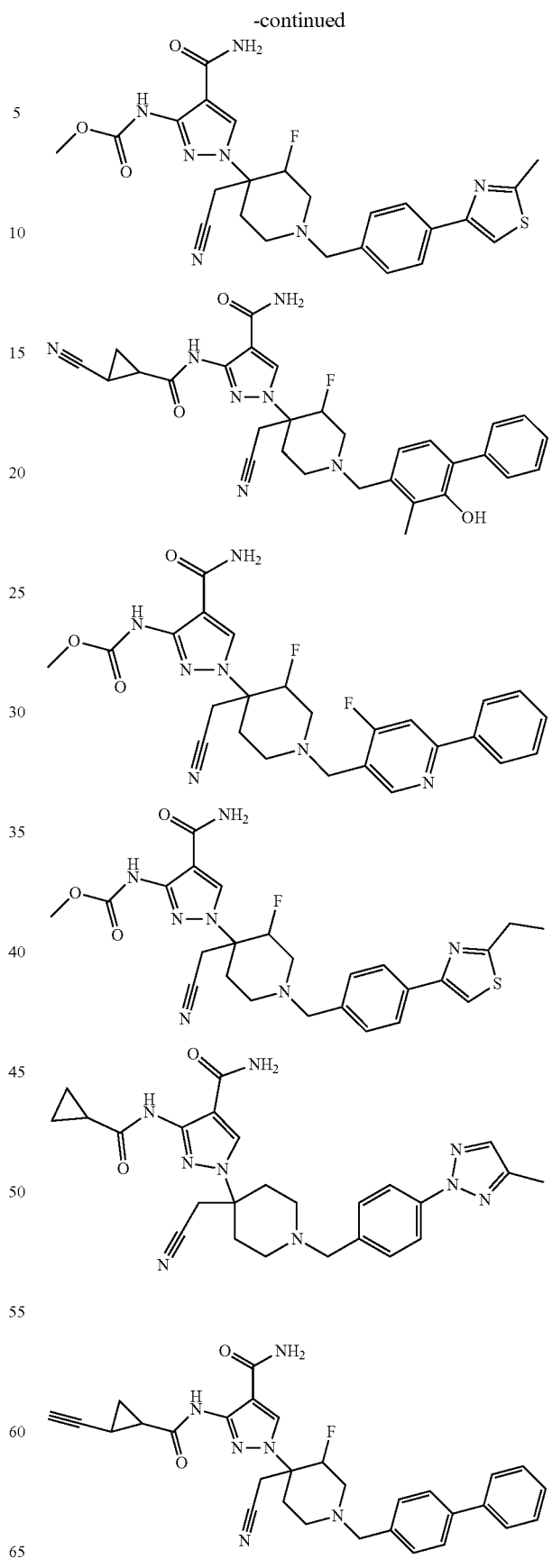

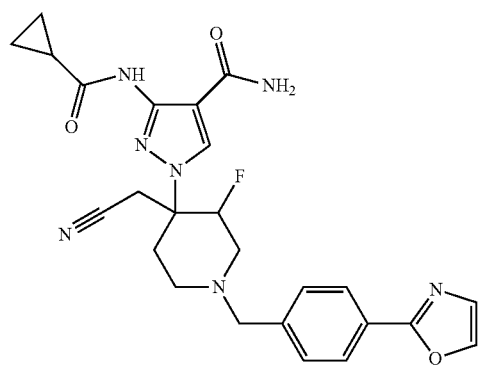
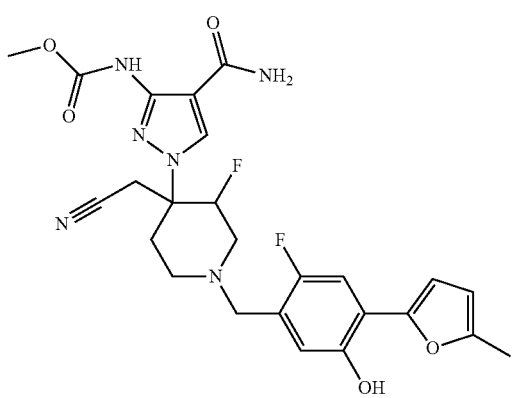
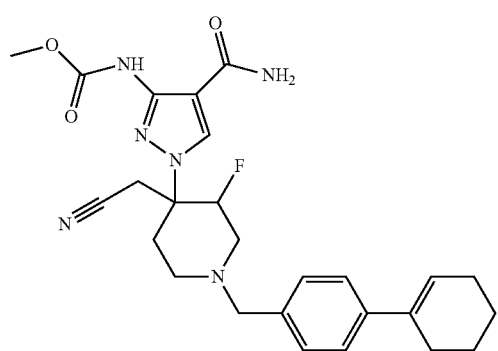
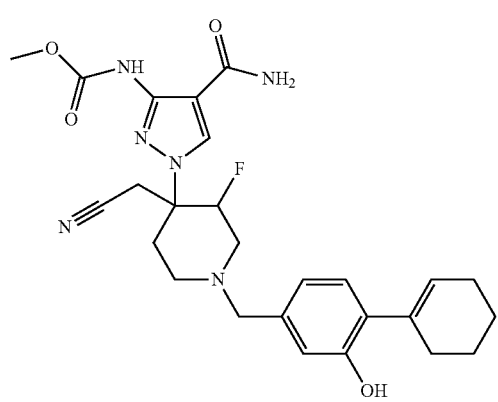
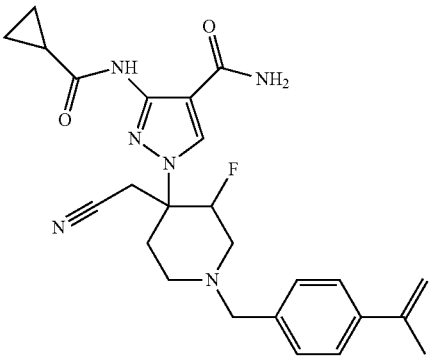
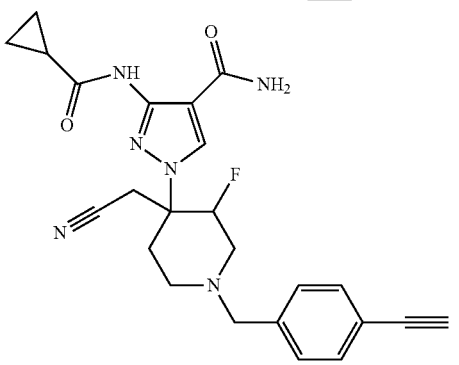
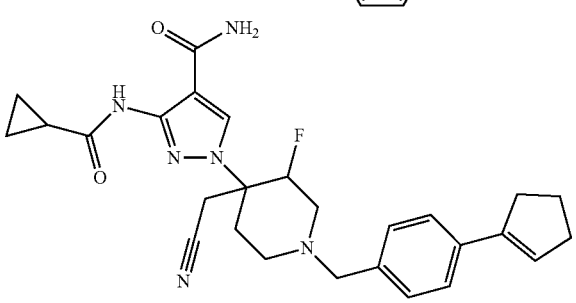
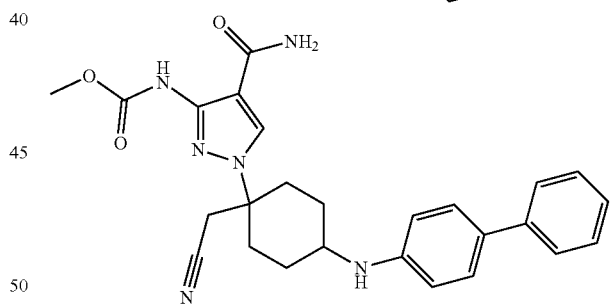
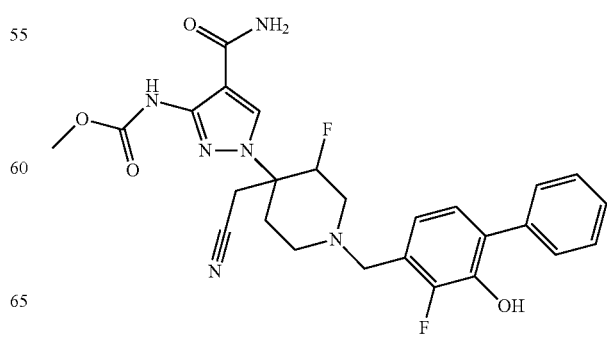

149
-continued
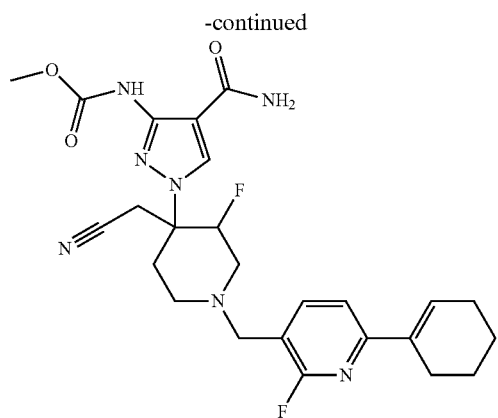
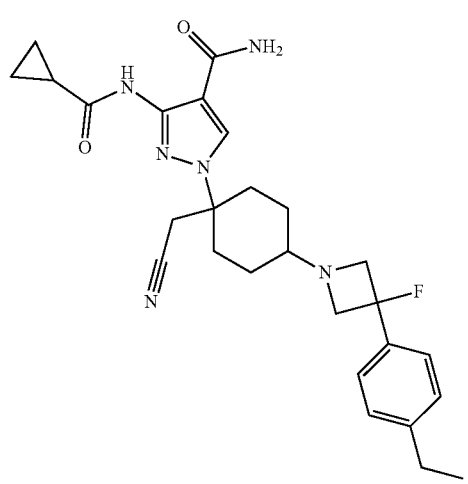
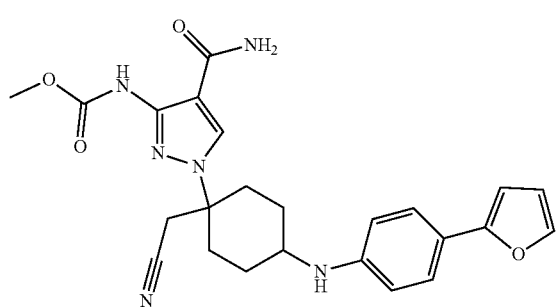
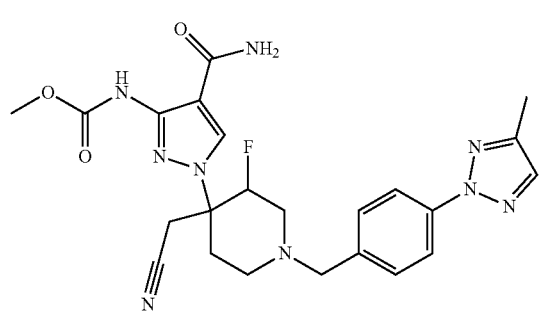
150
-continued
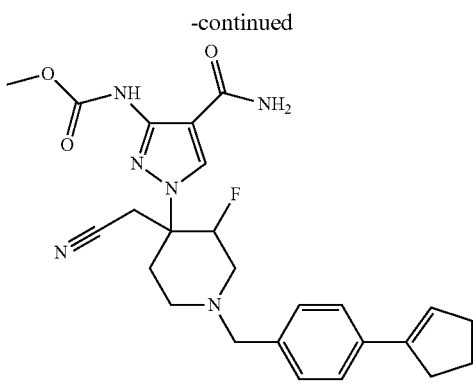
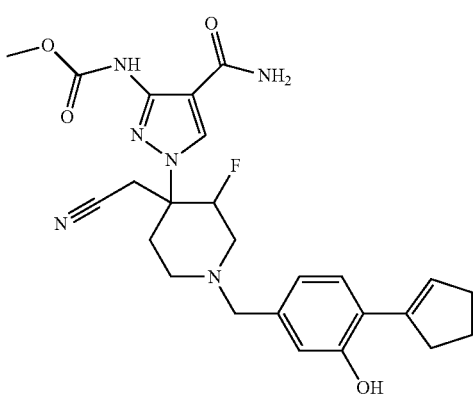
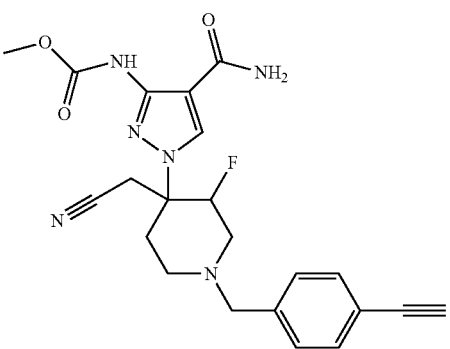
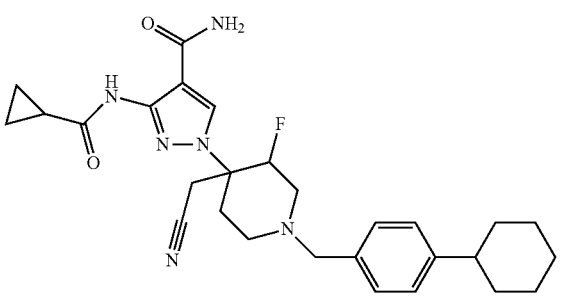

151
-continued
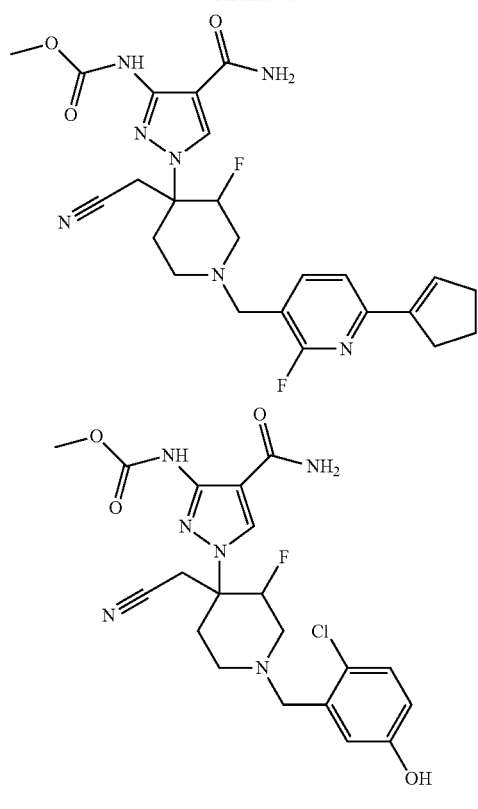
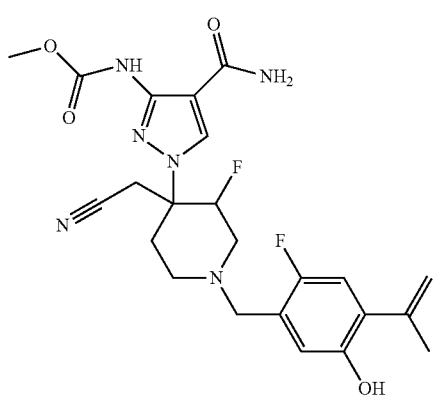
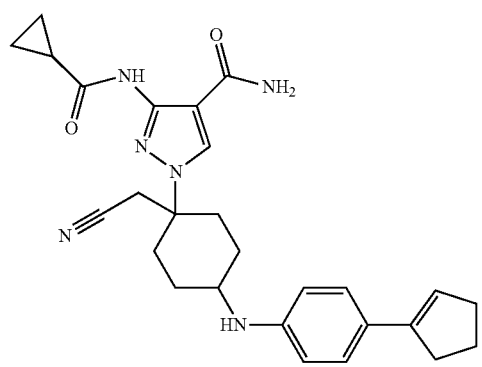
152
-continued
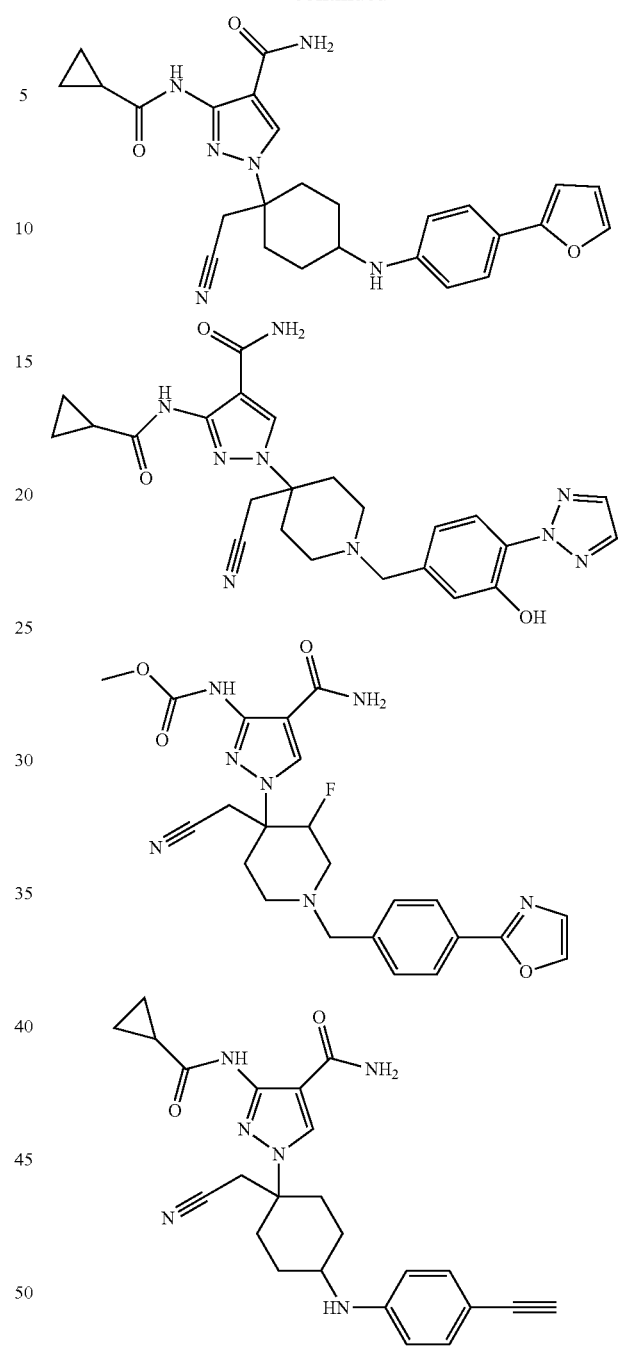
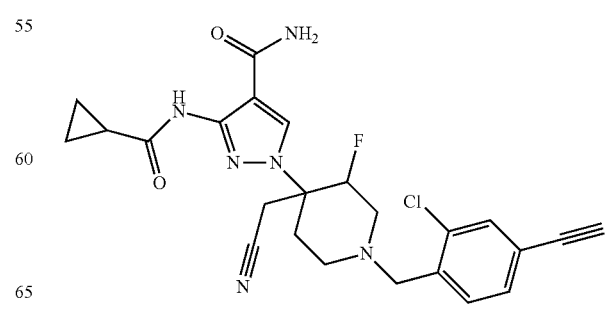

153
-continued
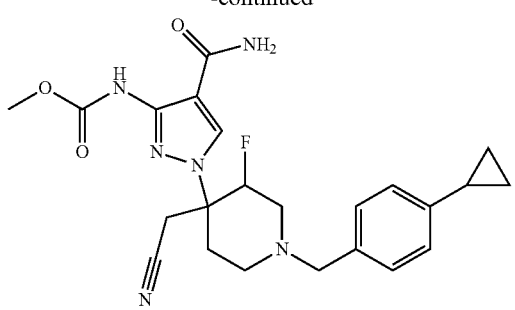
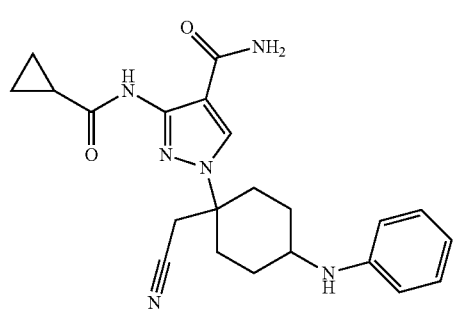
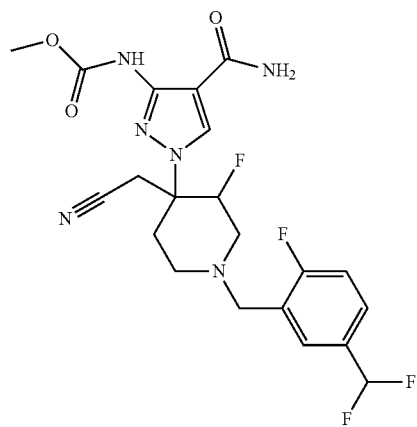
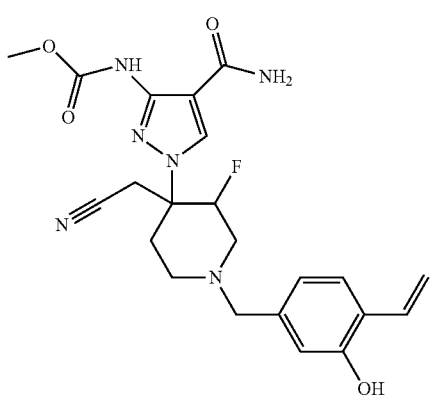
154
-continued
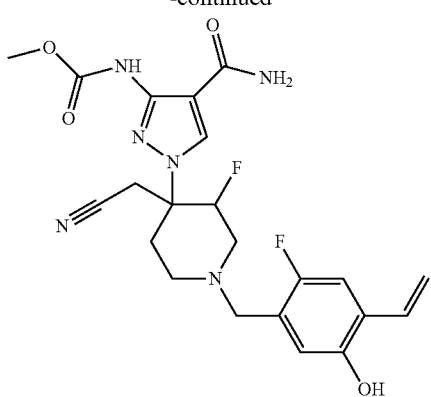
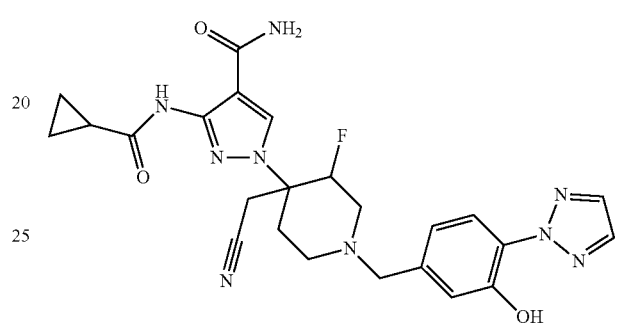
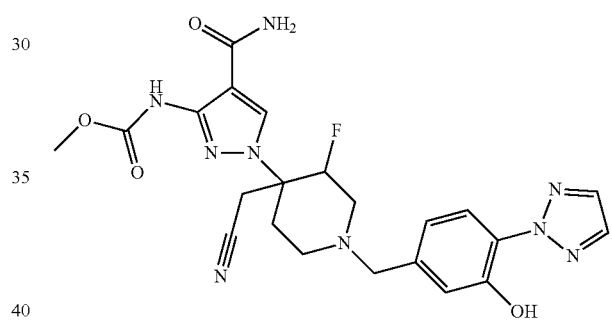
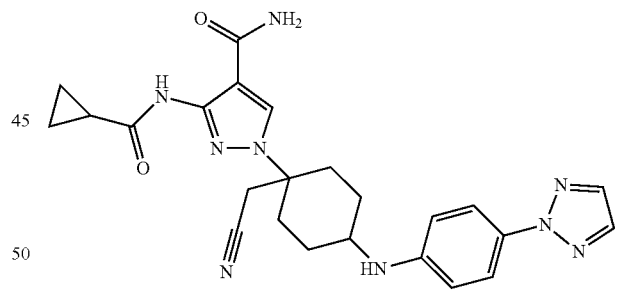
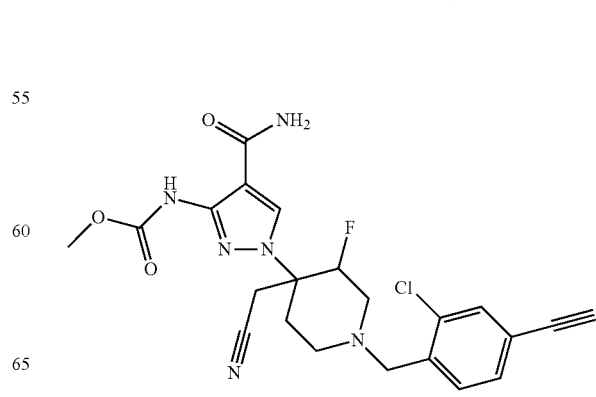

155
-continued
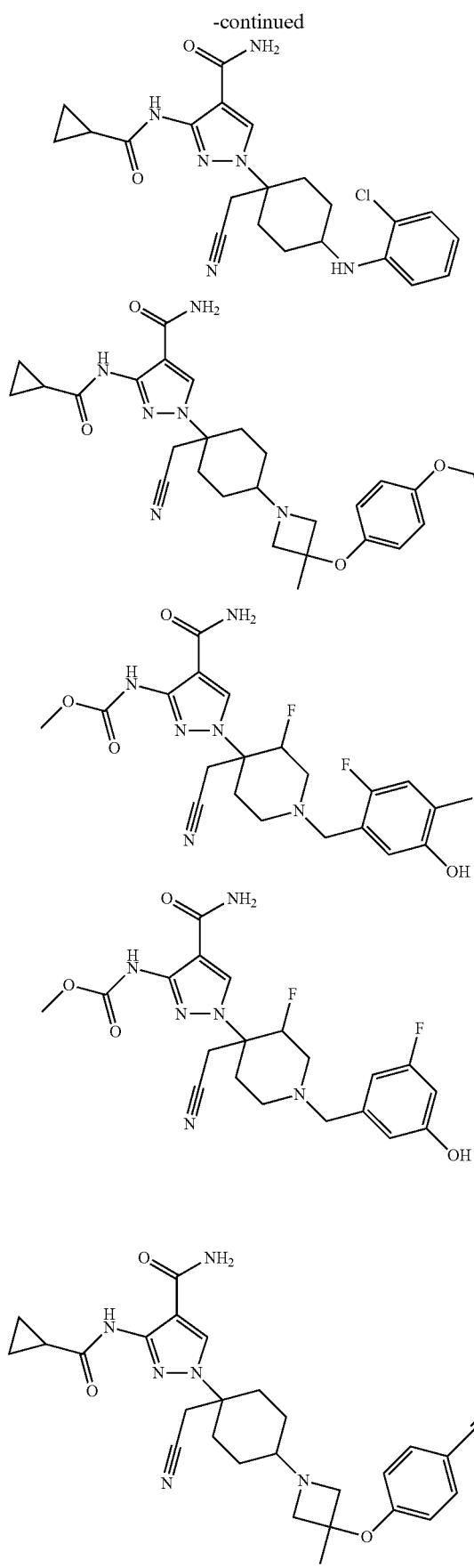
156
-continued
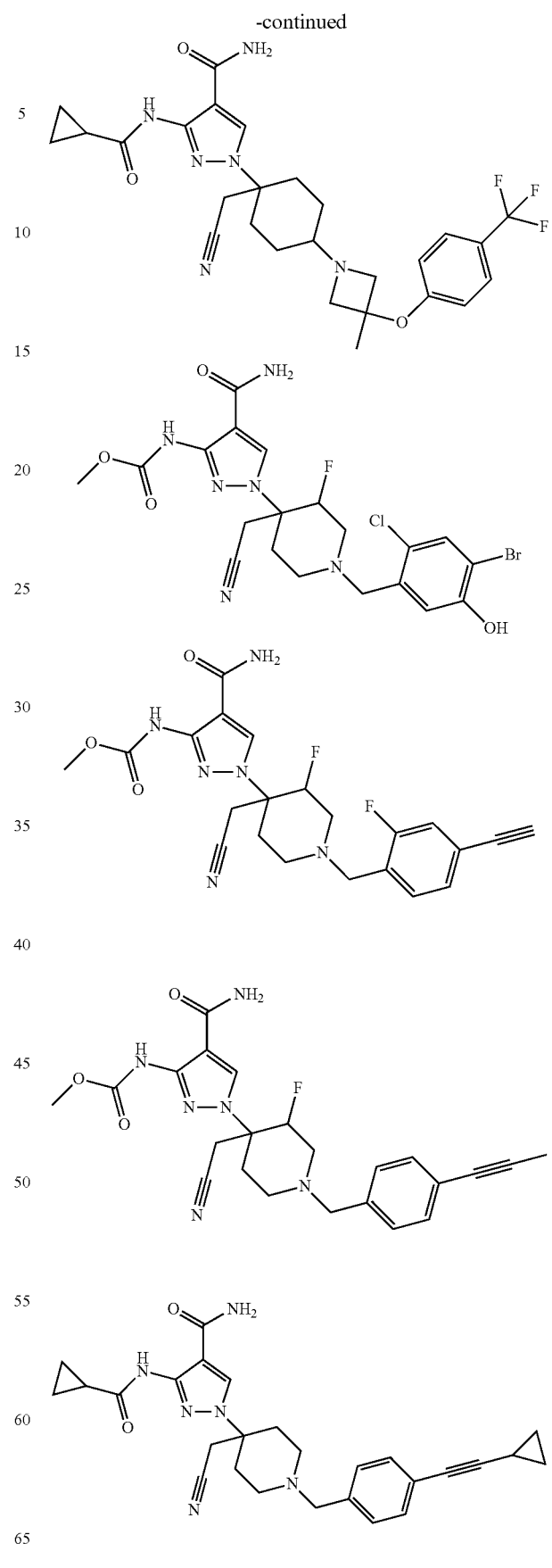

157
-continued
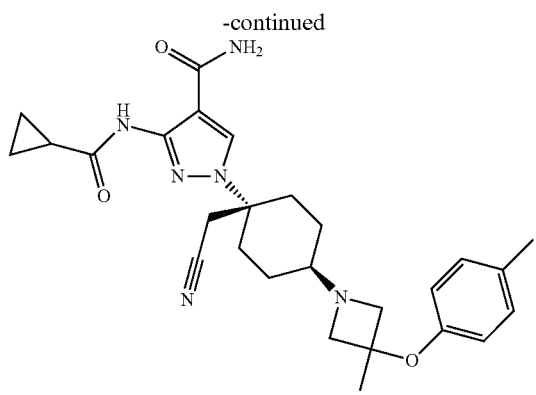
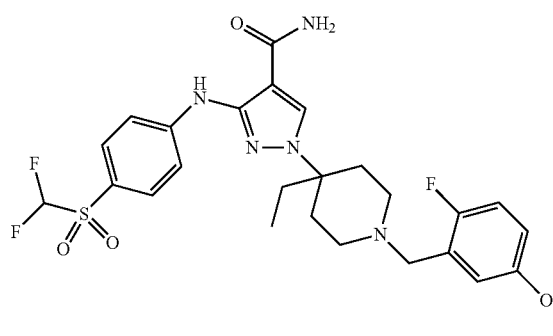
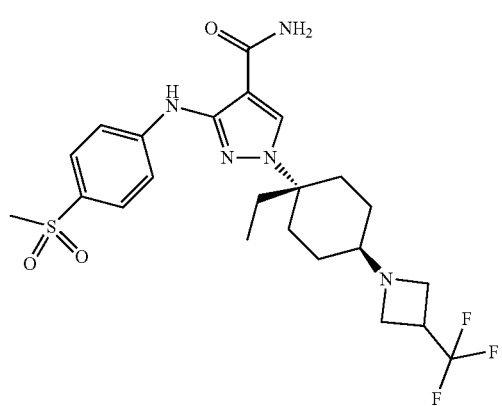
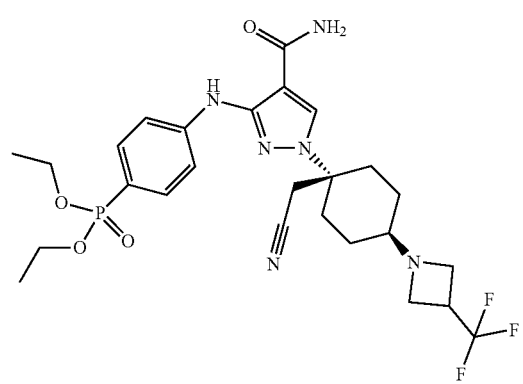
and
158
-continued
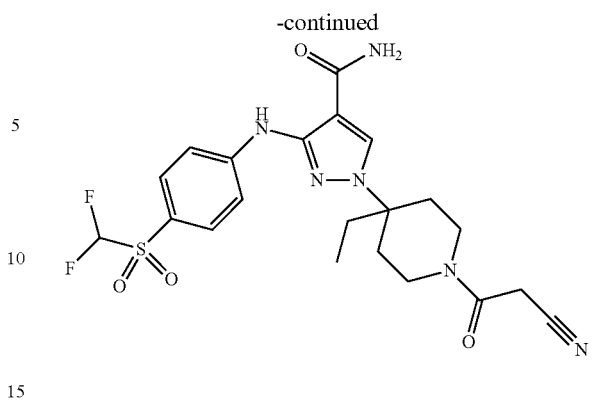
and salts thereof.
In some embodiments, a compound of the invention is selected from the group consisting of:
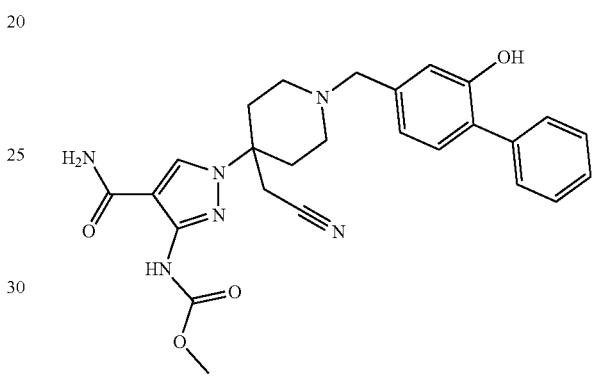
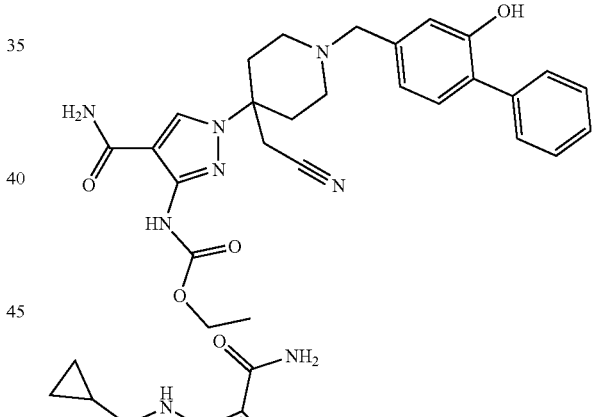
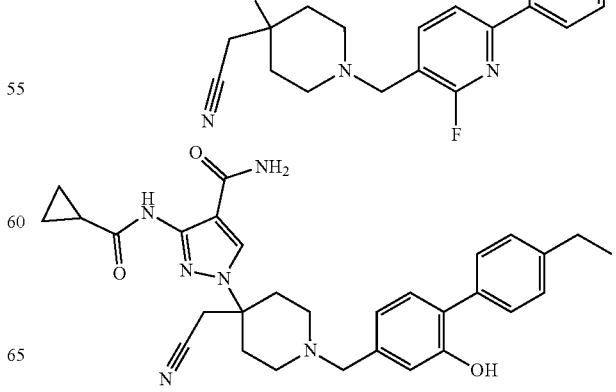

159
-continued
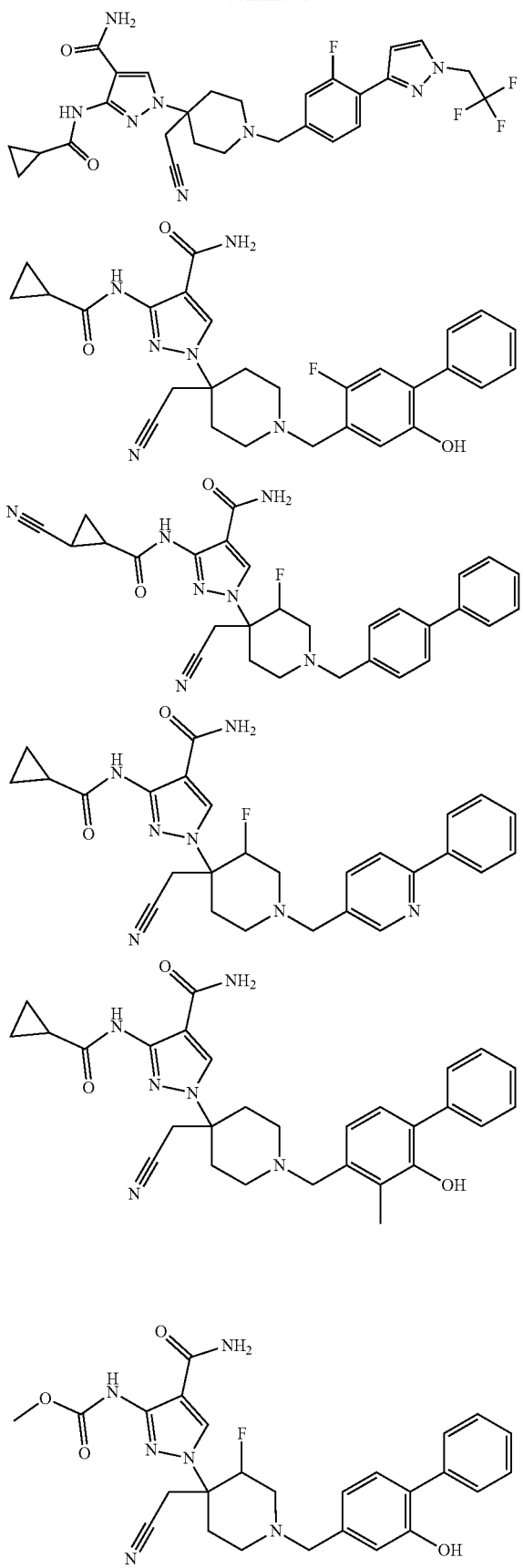
160
-continued
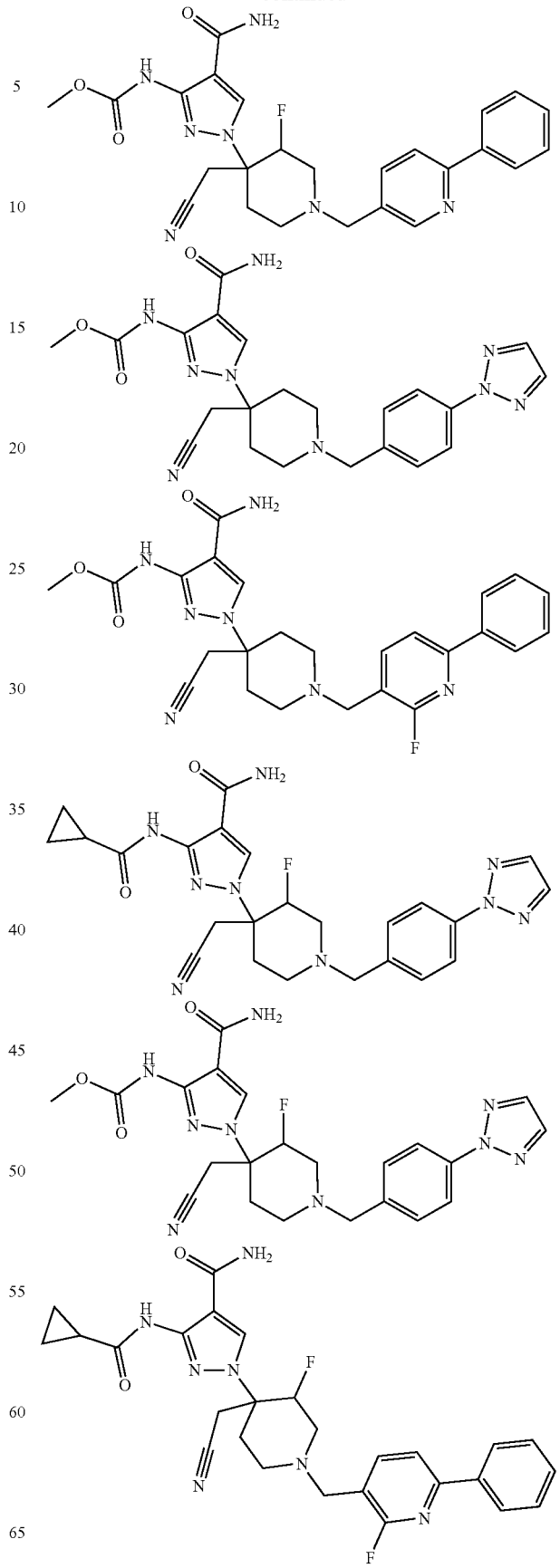

161
-continued
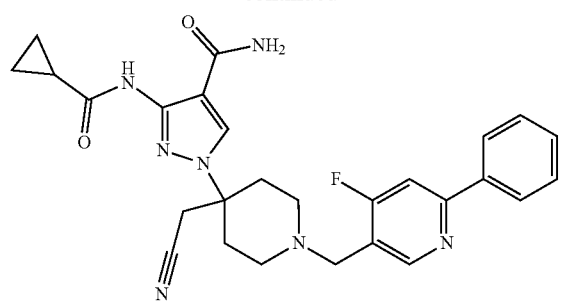
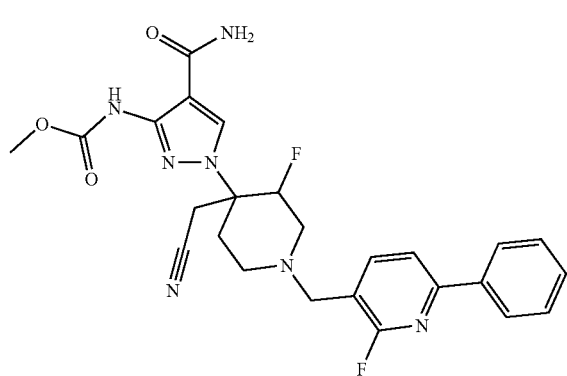
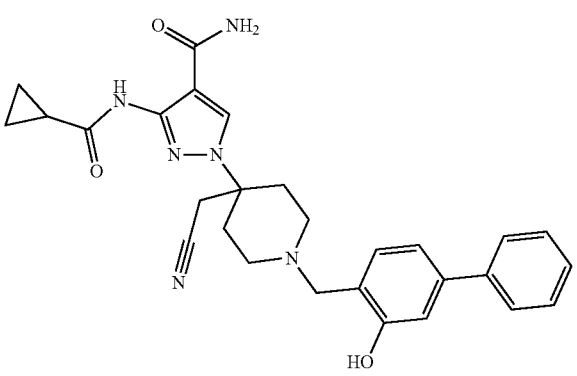
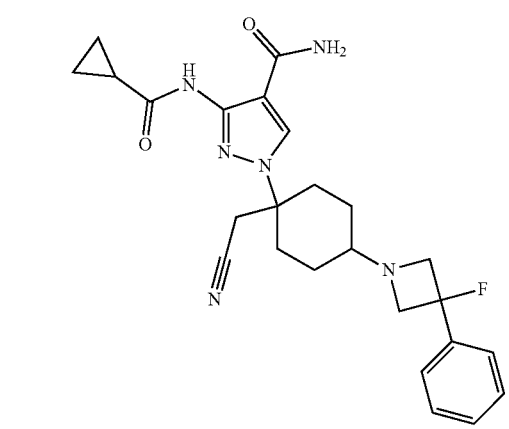
162
-continued
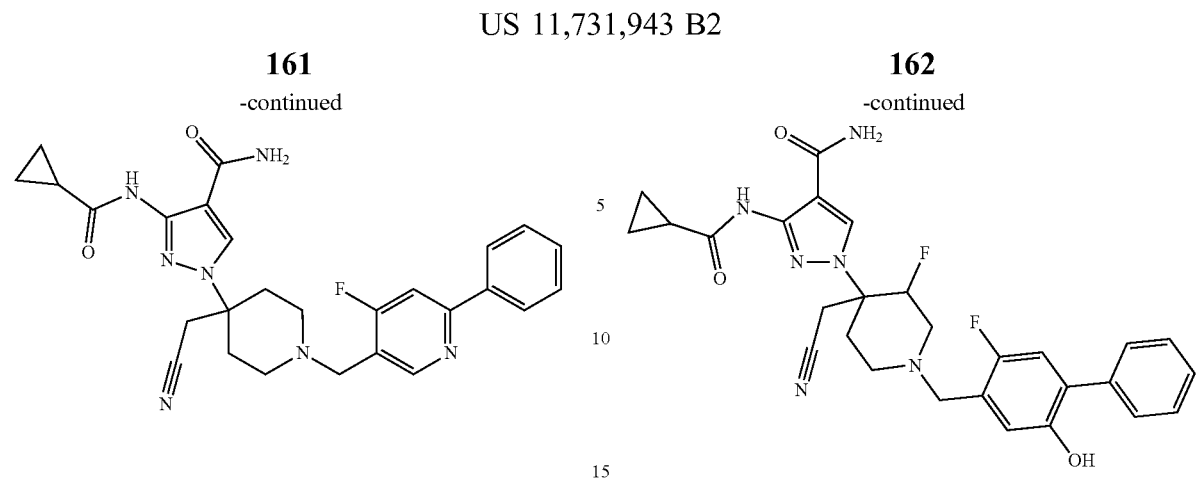
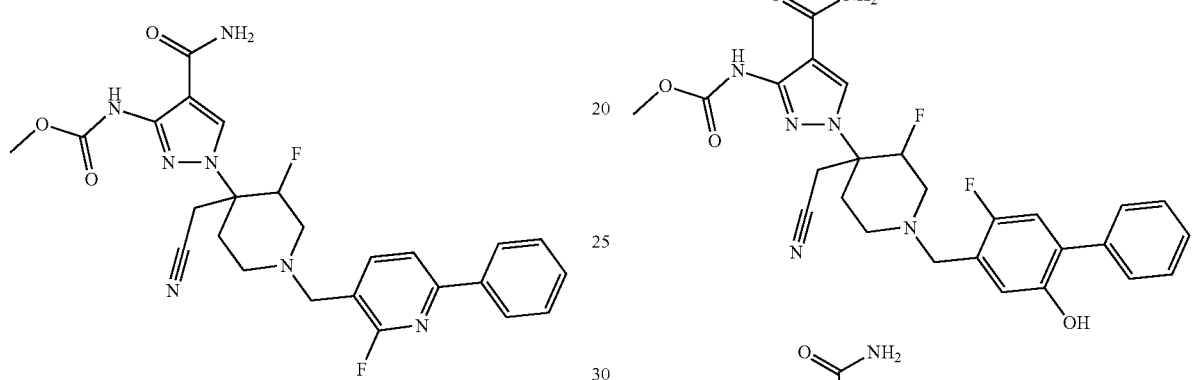
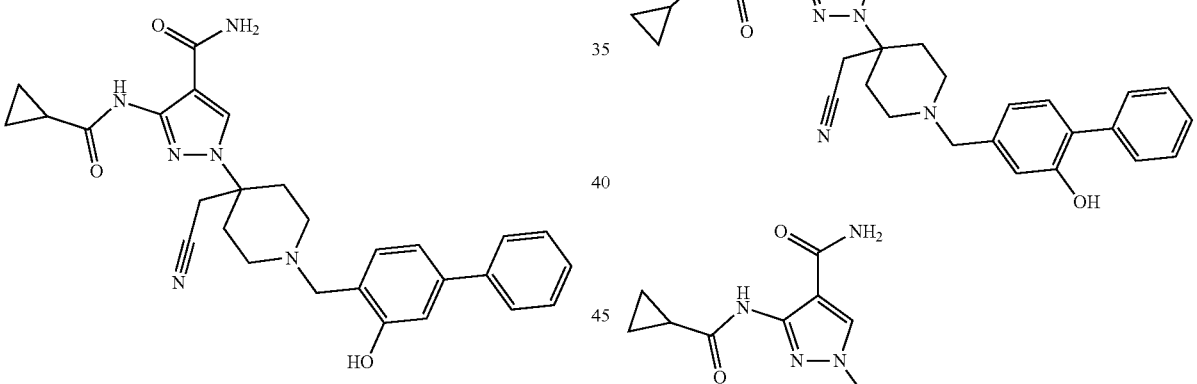
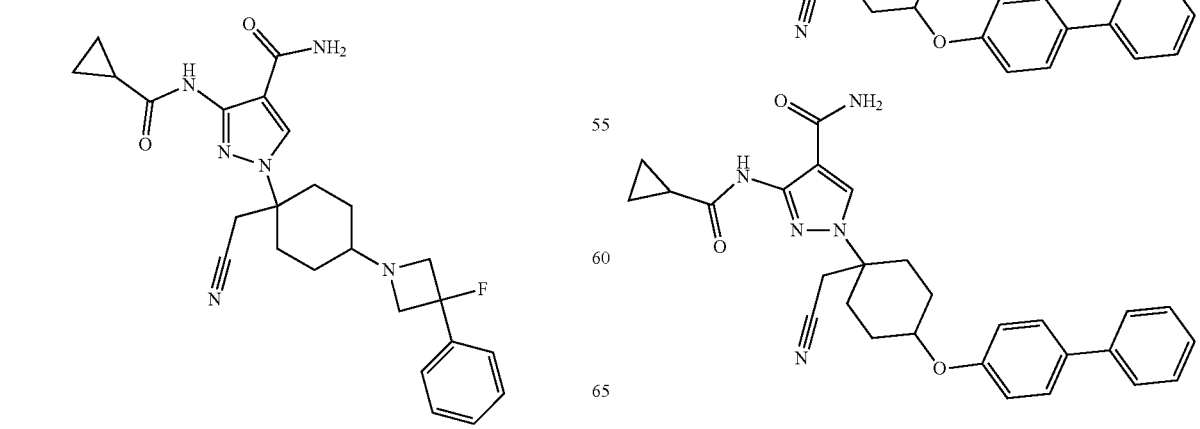

163
-continued
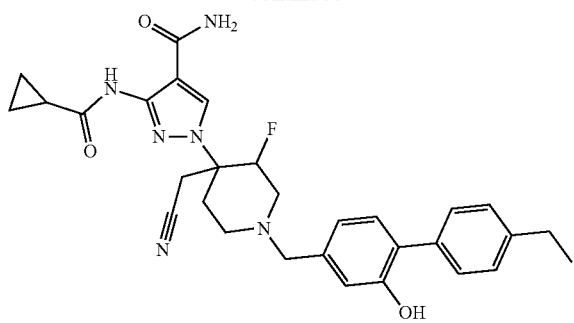
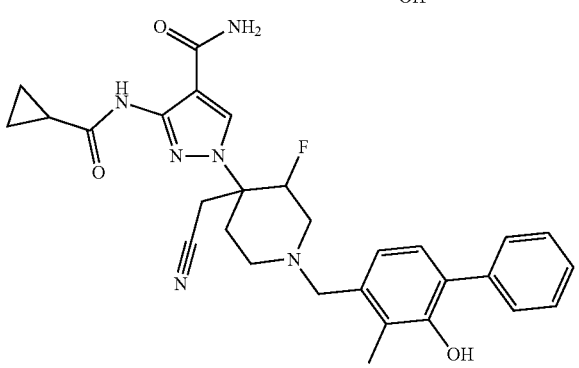
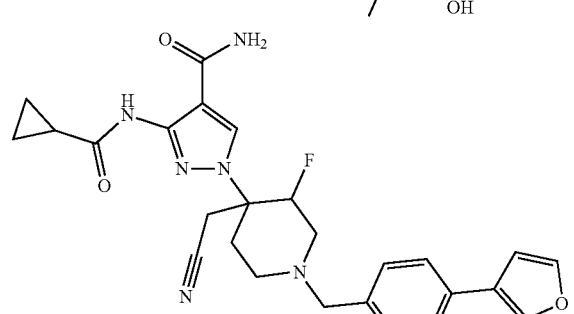
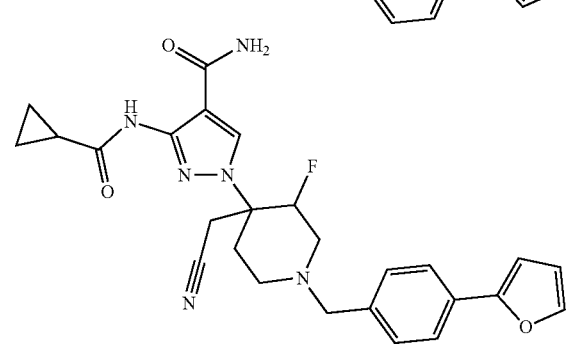
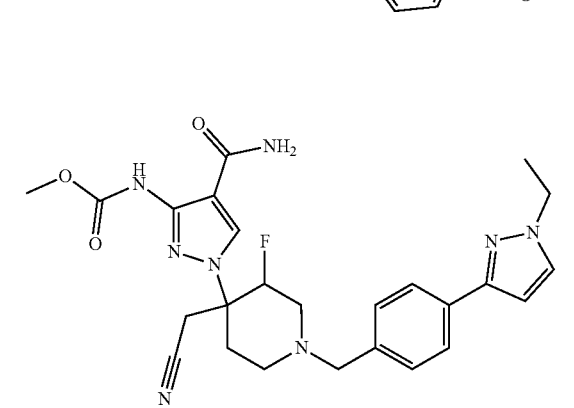
164
-continued
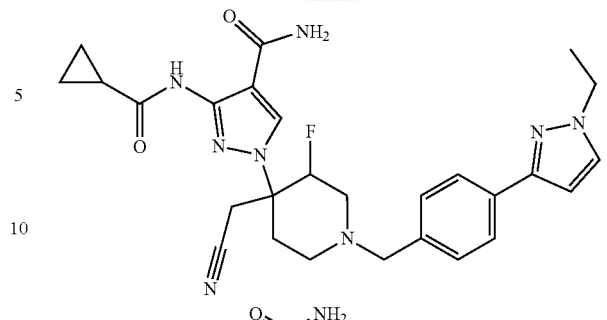
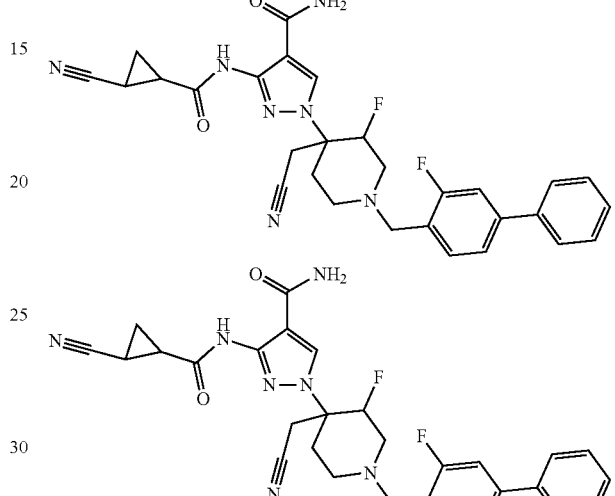
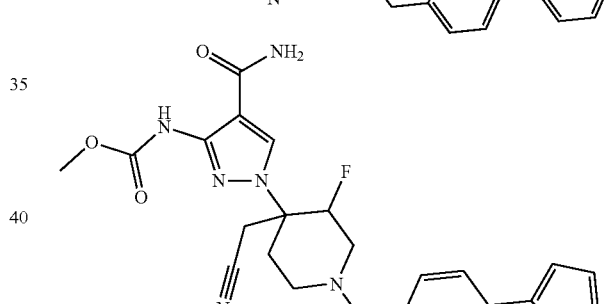

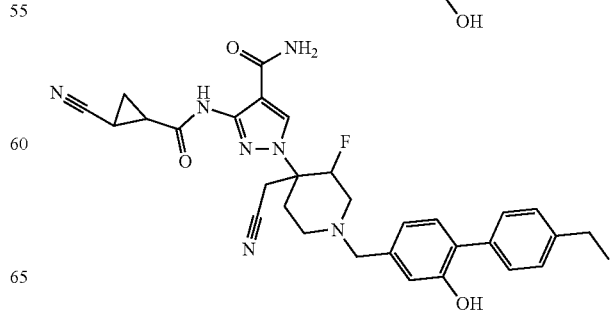

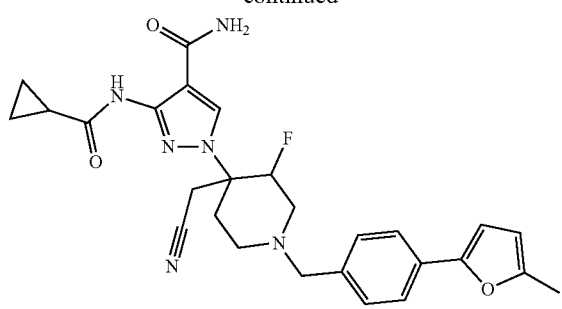
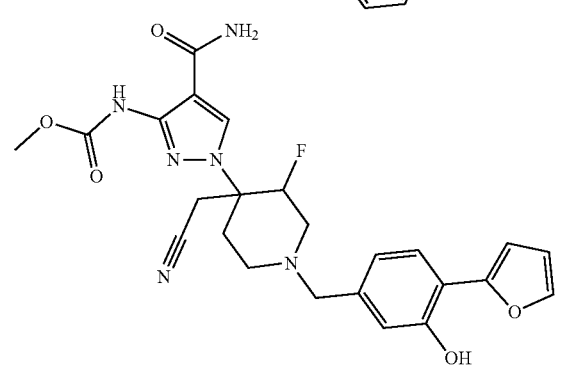
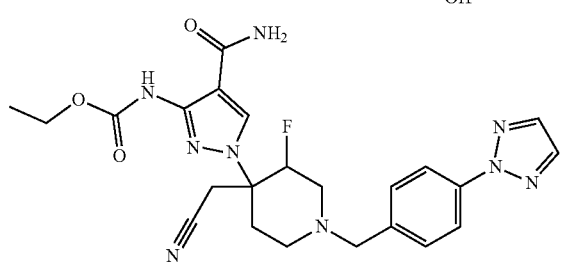
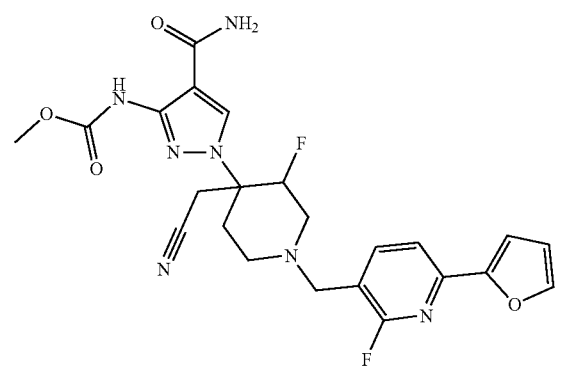
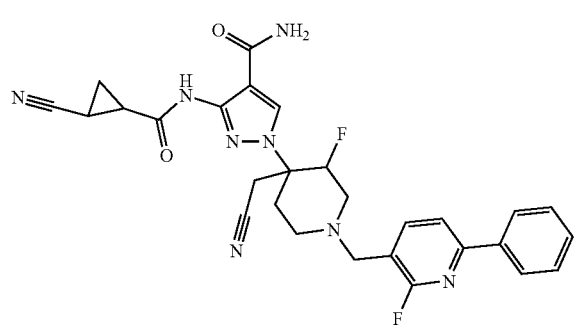
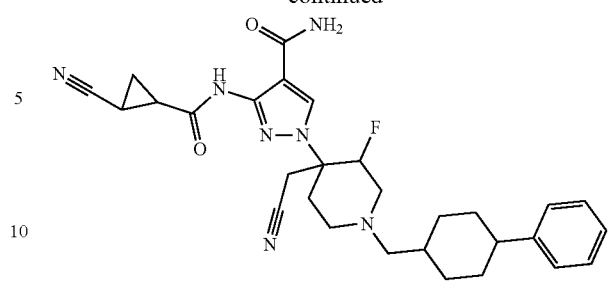
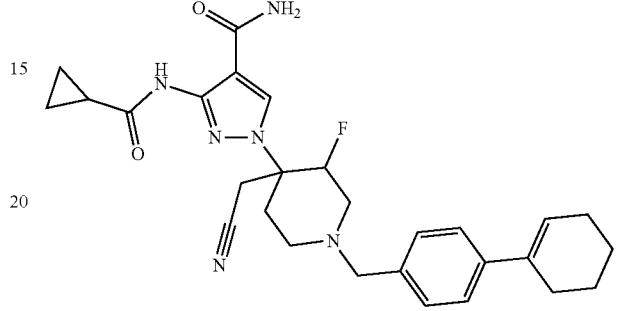
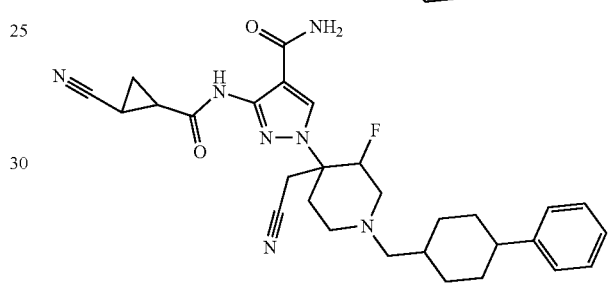
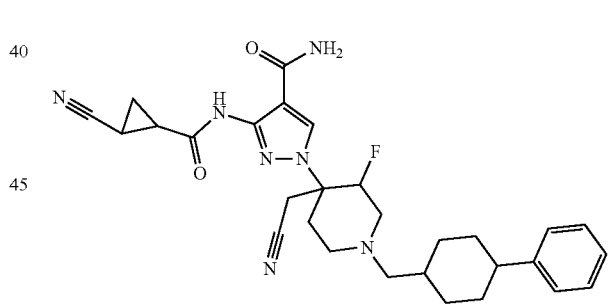
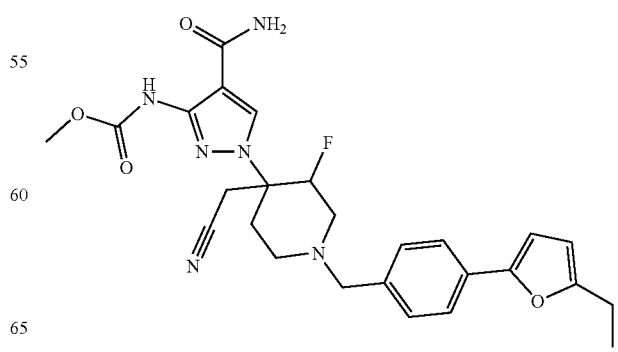

167
-continued
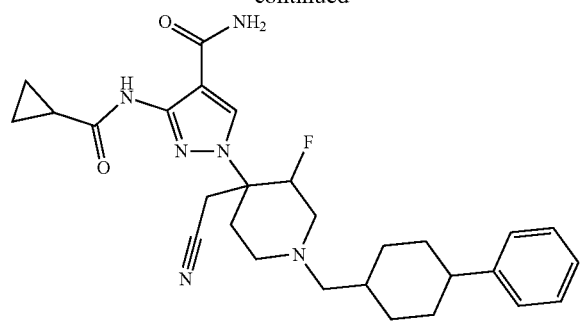
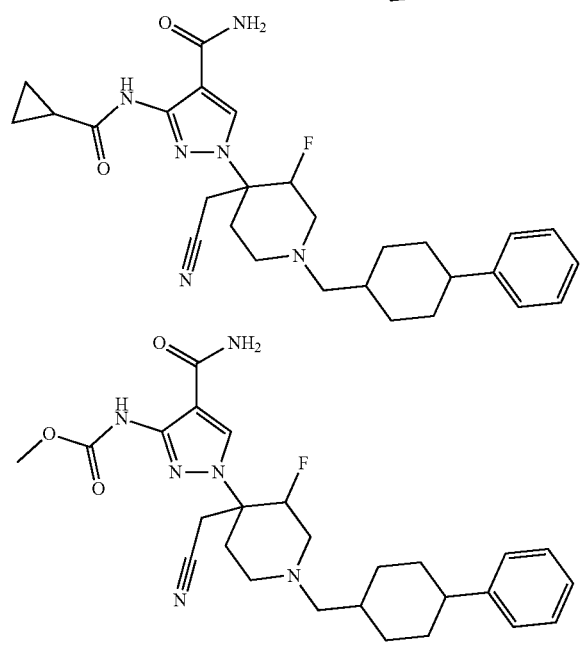
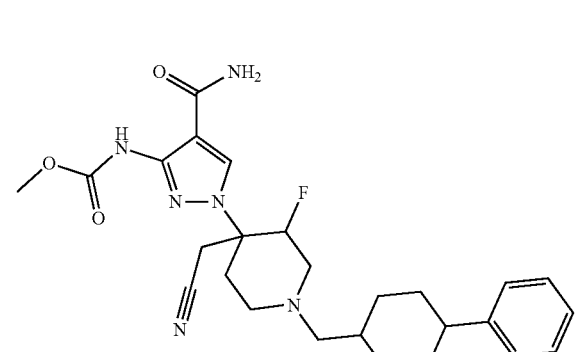
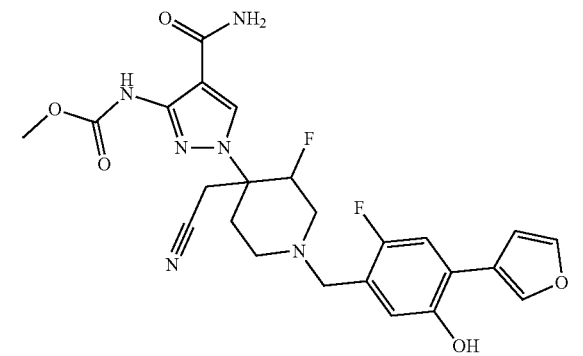
168
-continued
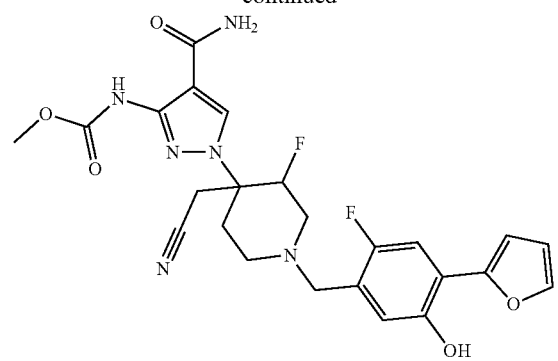
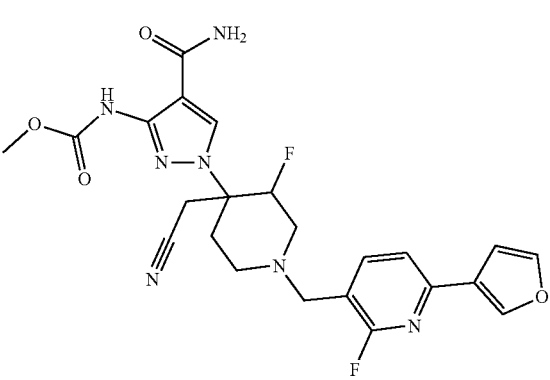
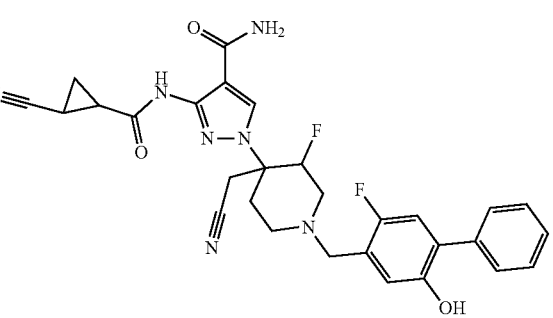
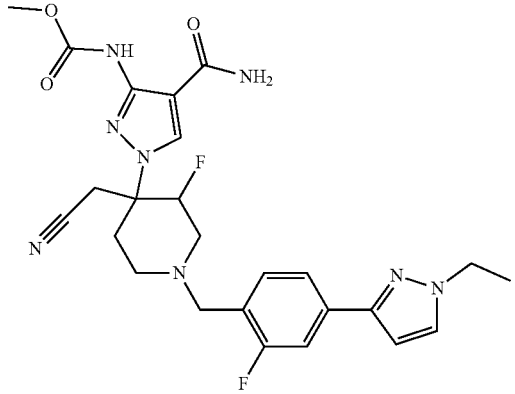

169
-continued
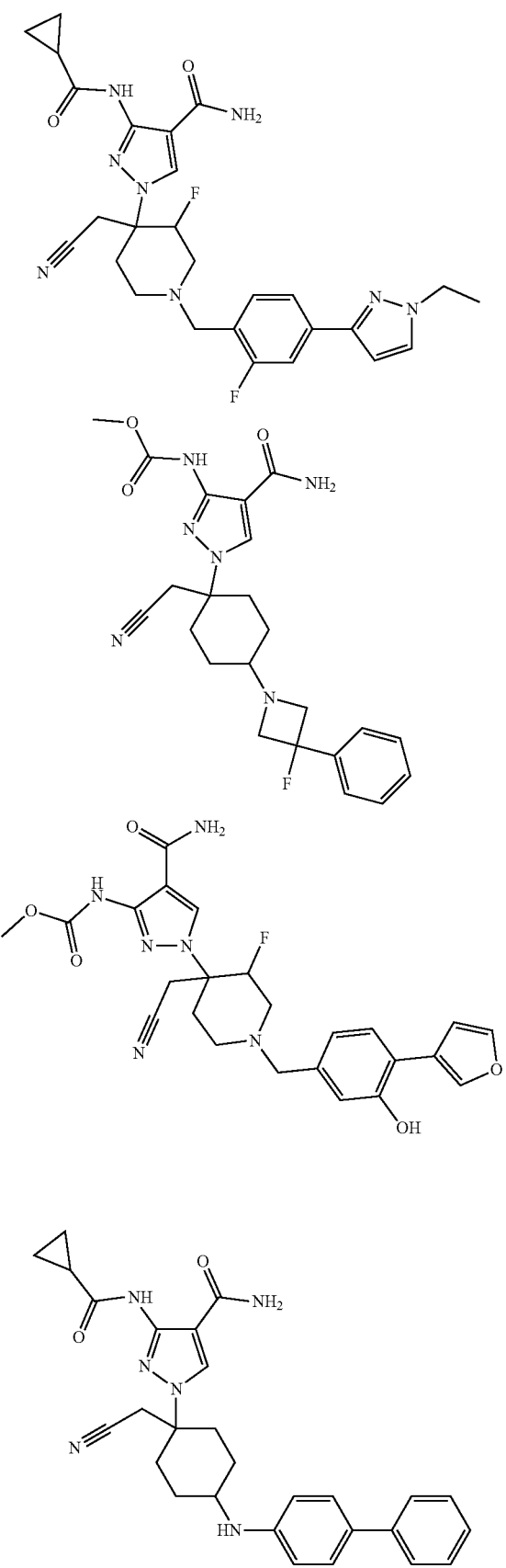
170
-continued
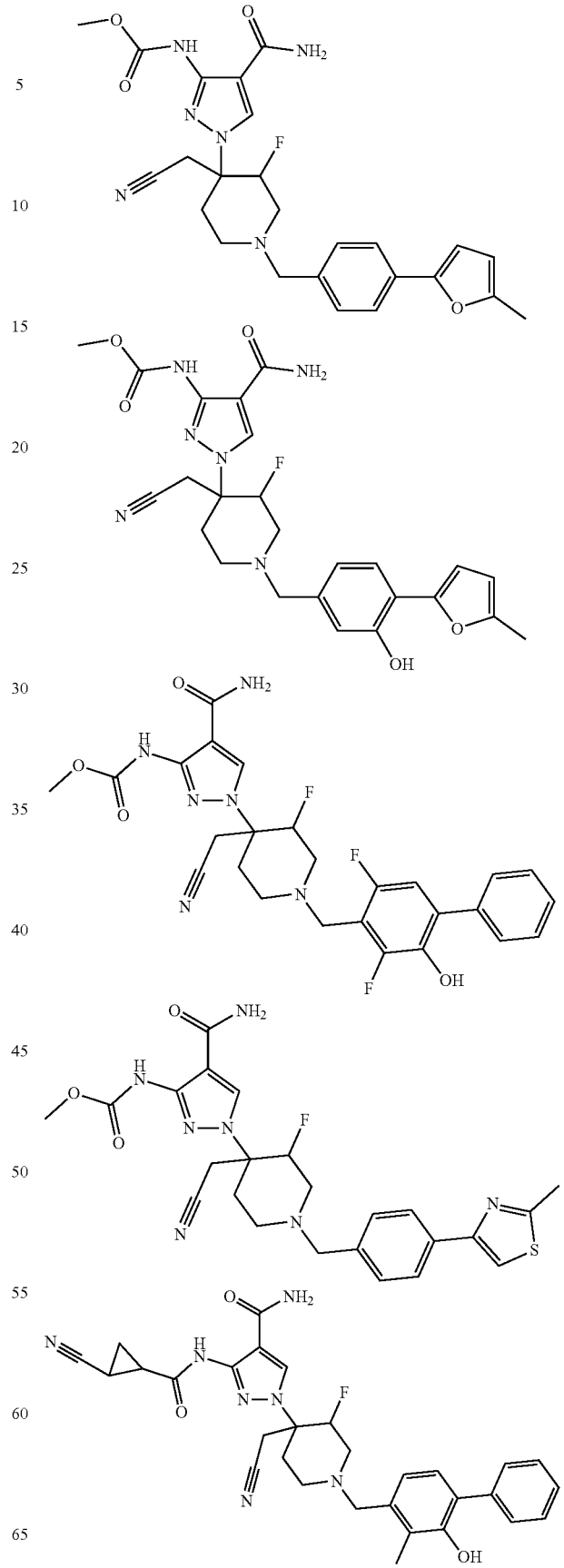

171
-continued
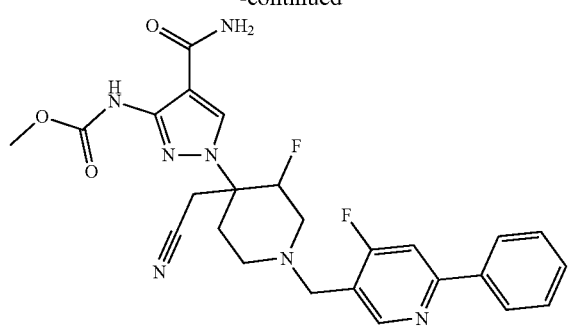
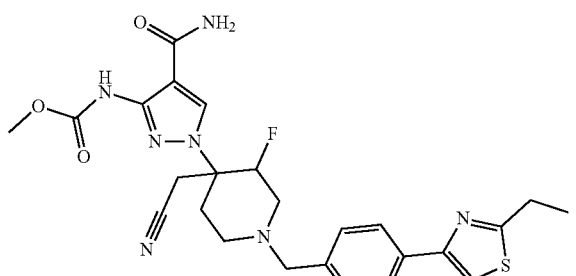
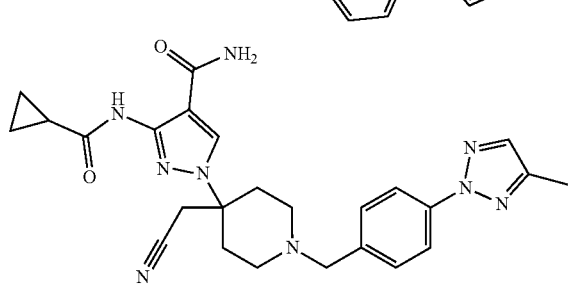
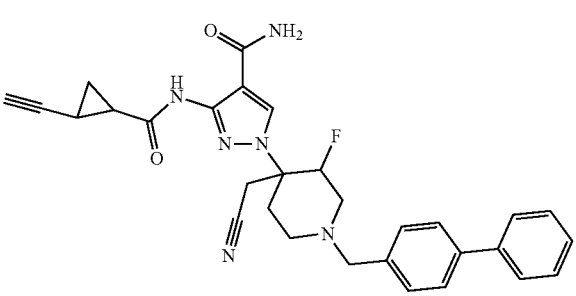
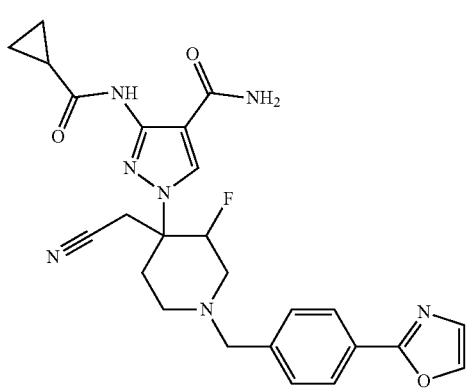
172
-continued
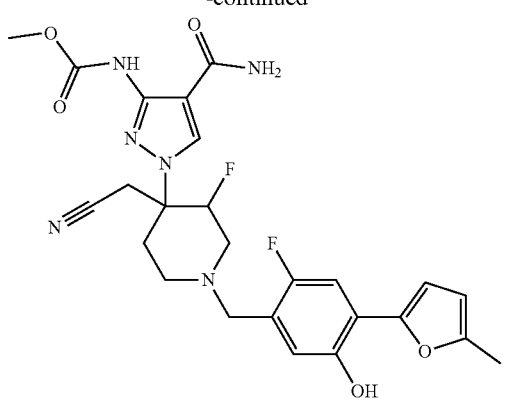
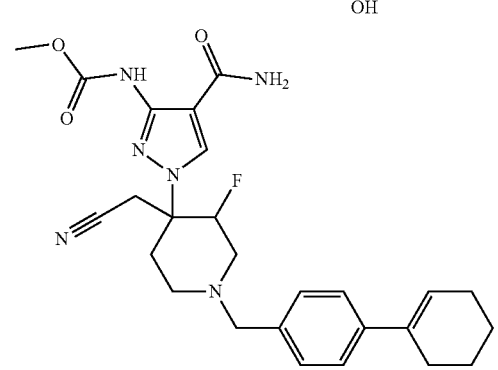
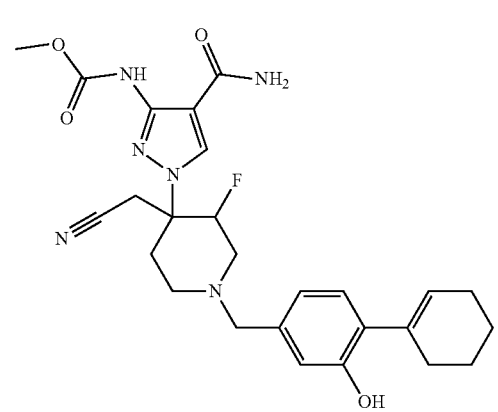
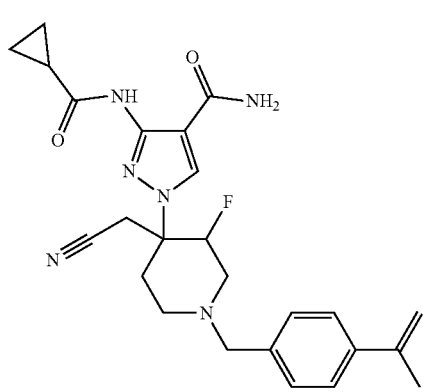

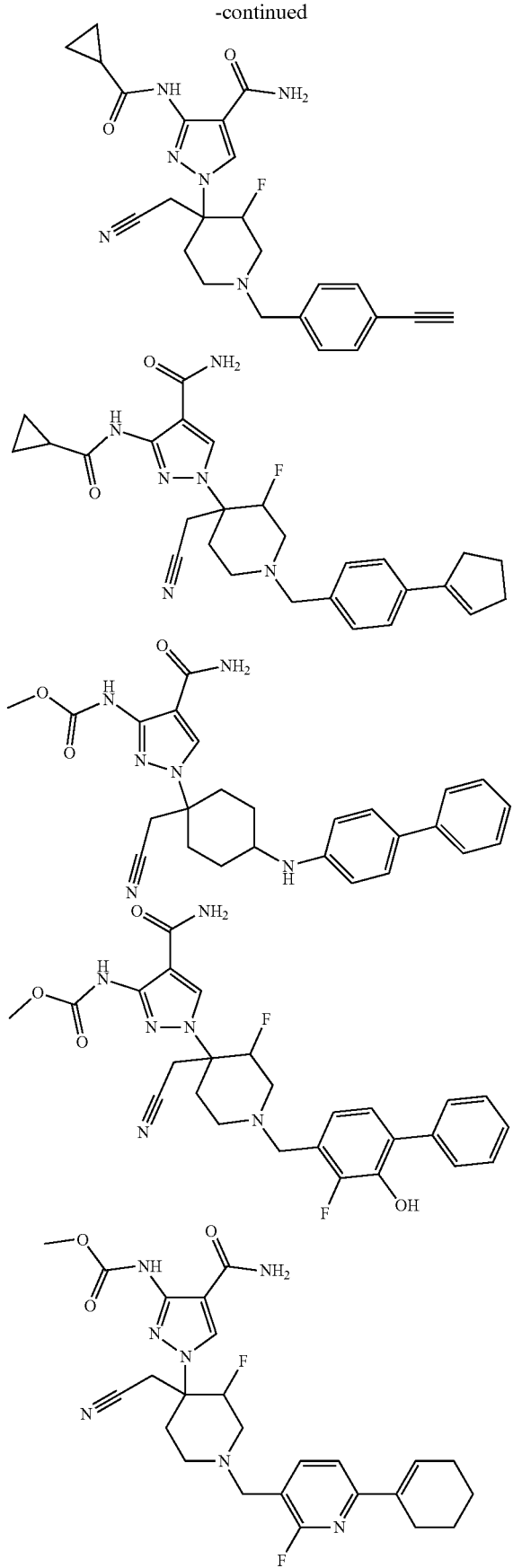
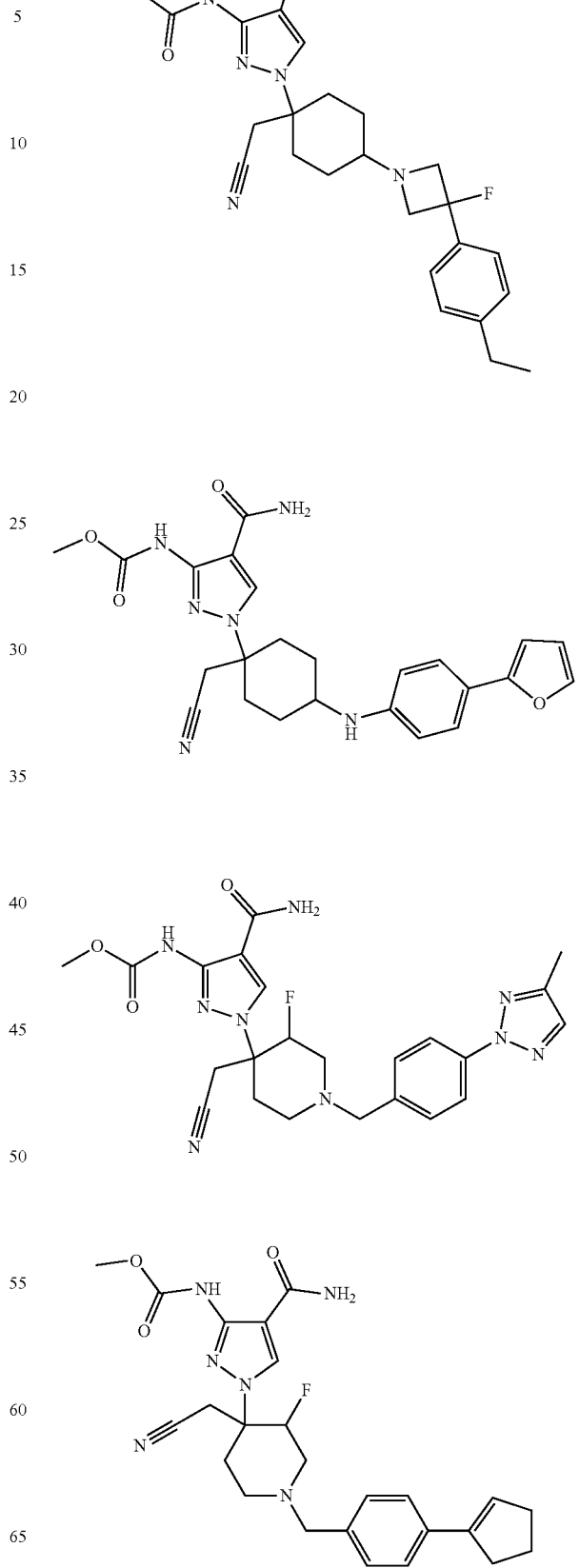

175
-continued
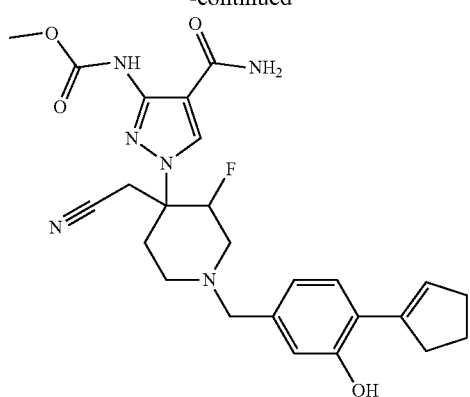
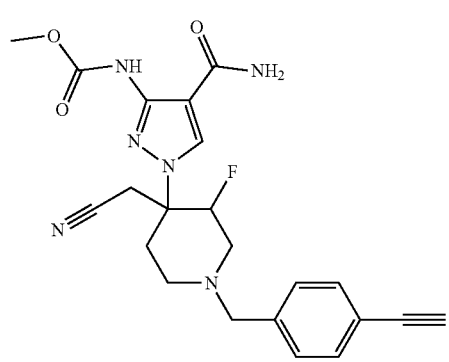
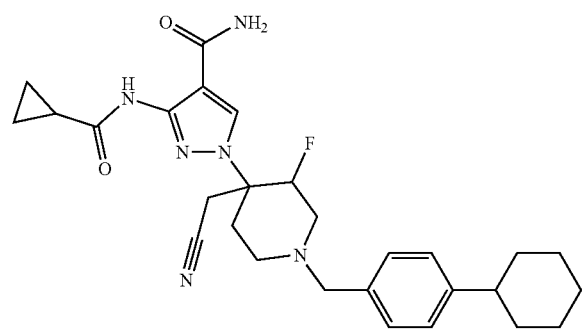
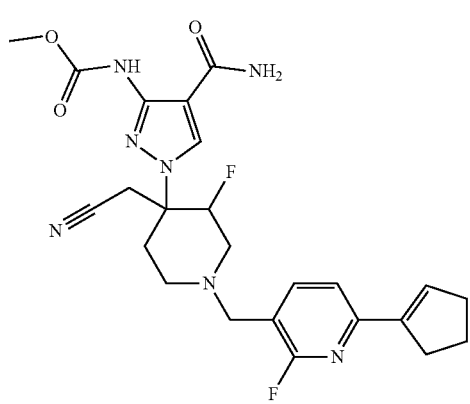
176
-continued
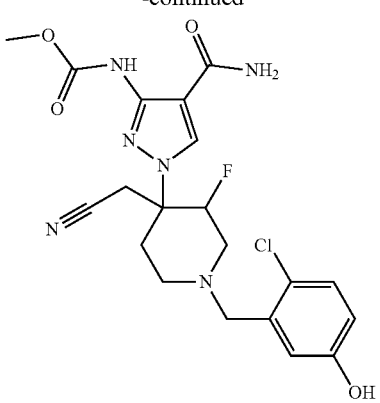
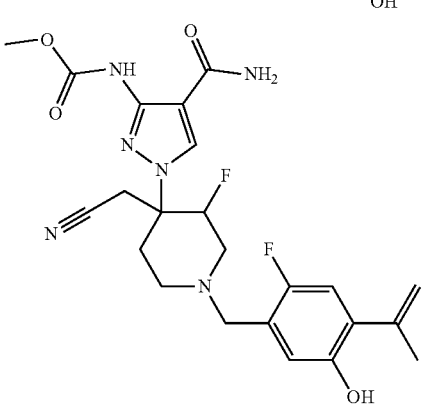
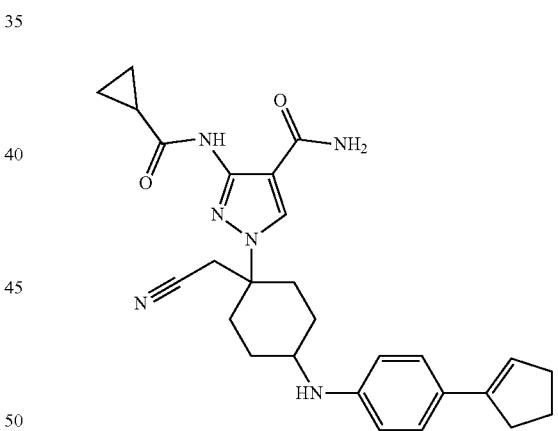
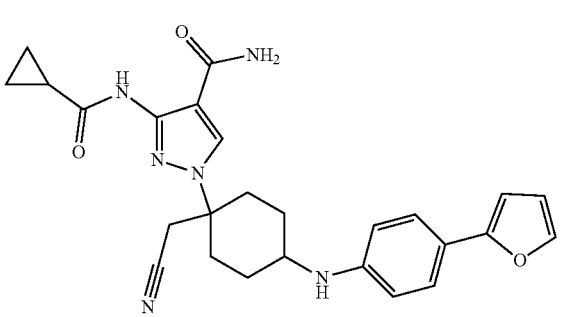

177
-continued
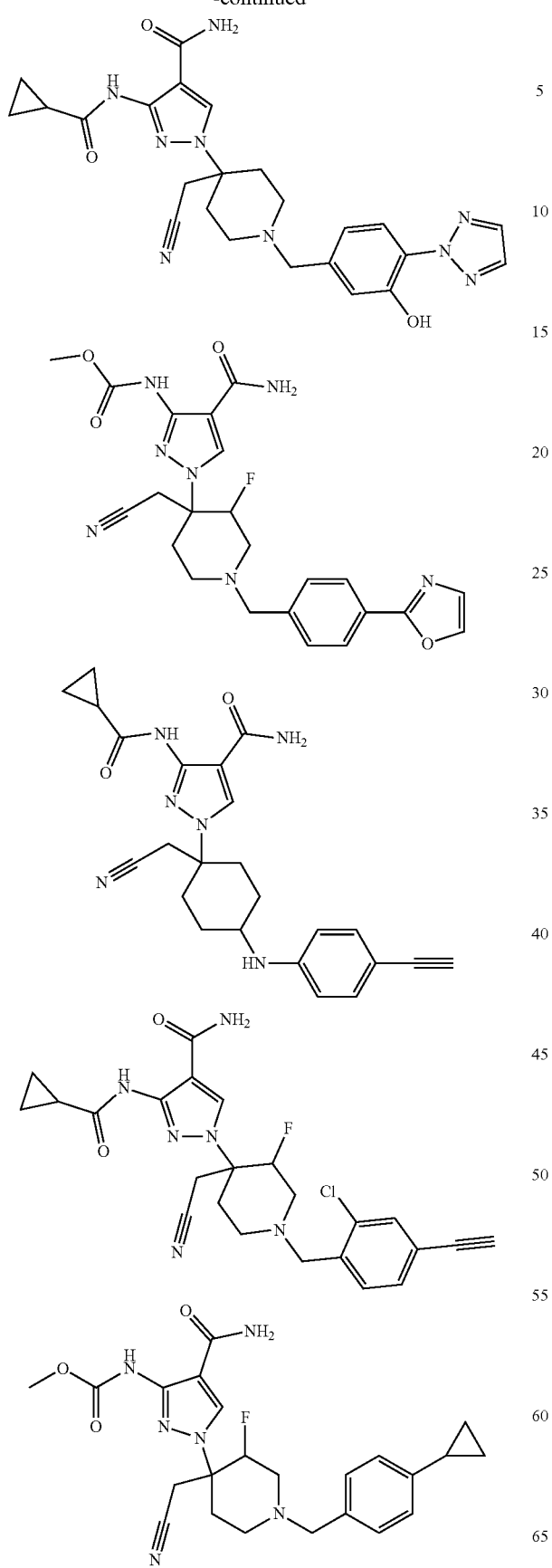
178
-continued
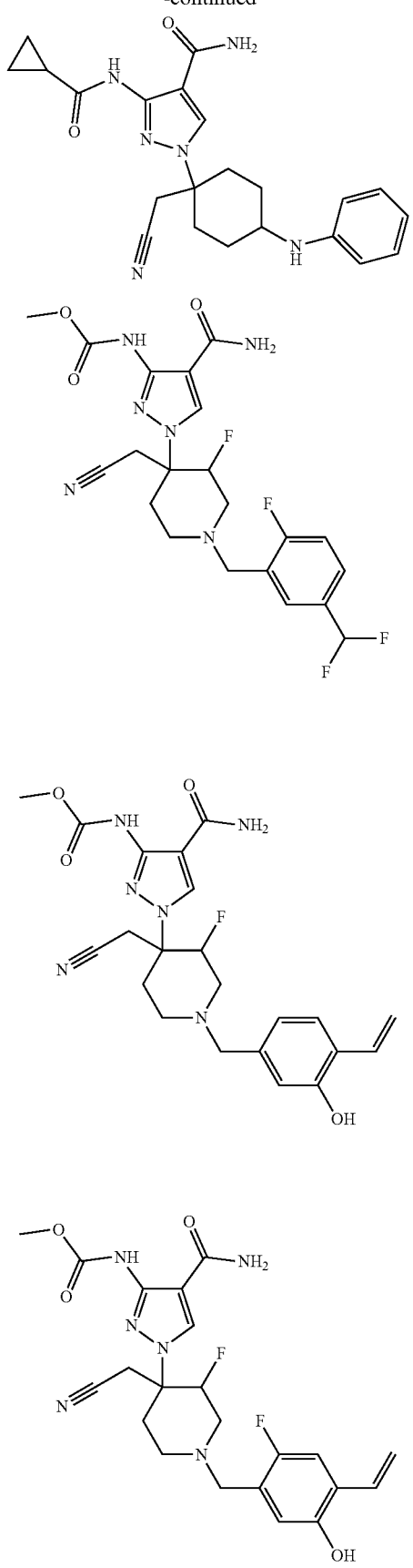

-continued
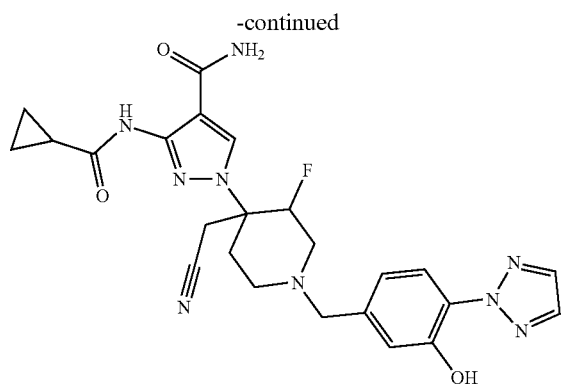
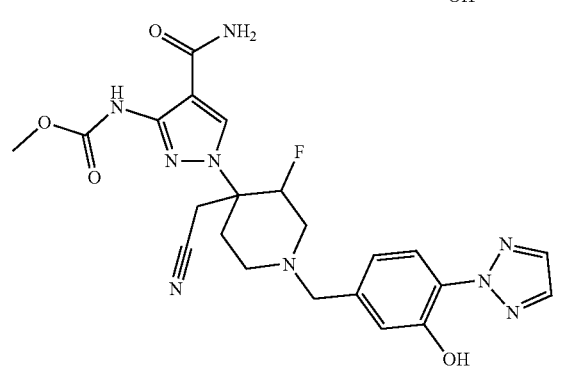
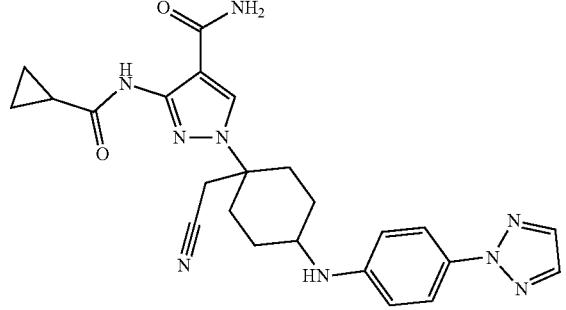
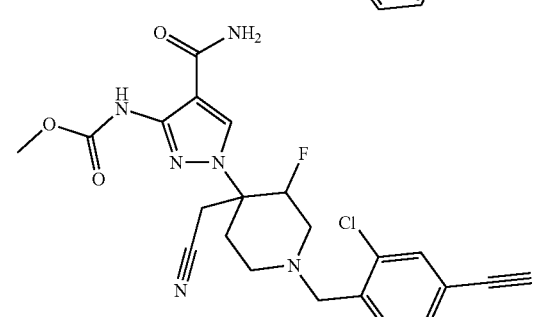
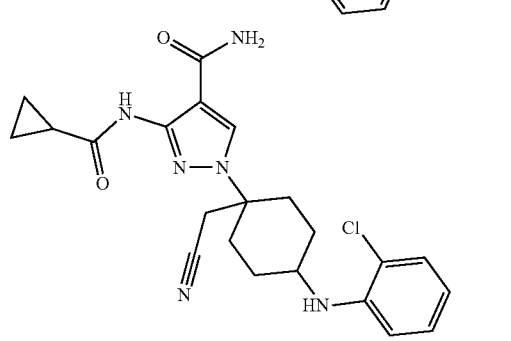
-continued
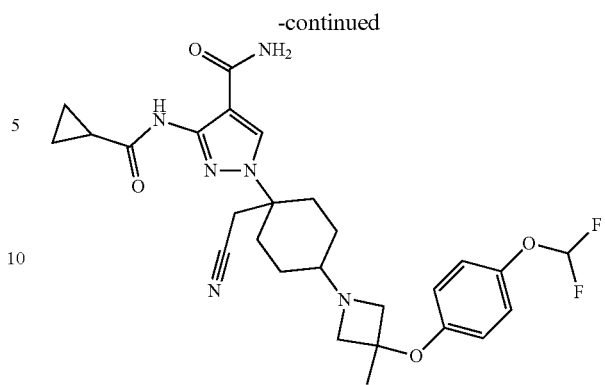
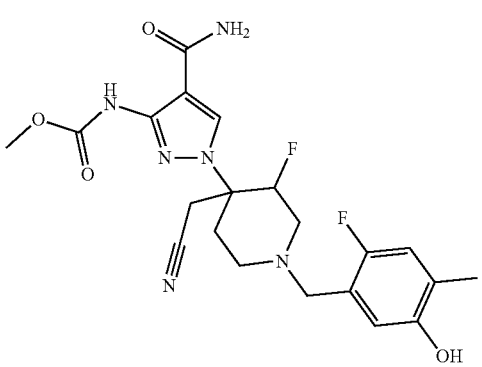
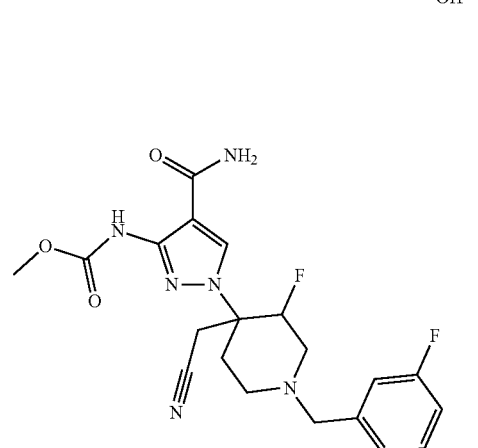
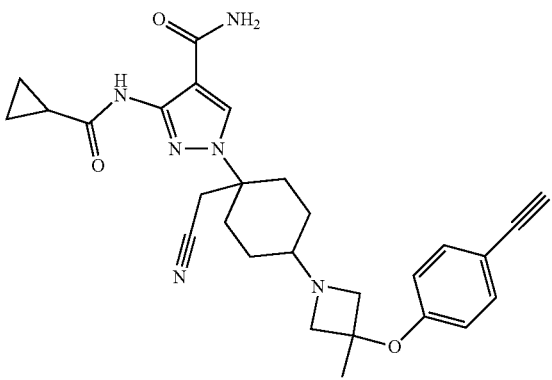

181
-continued
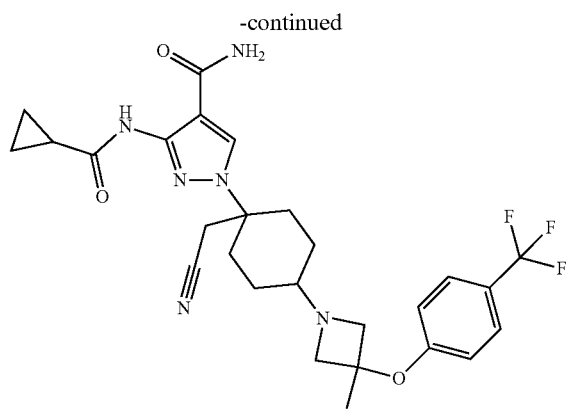
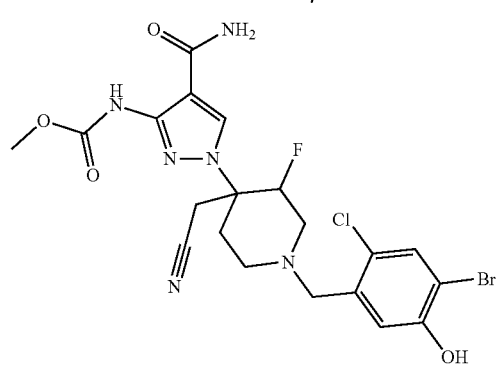
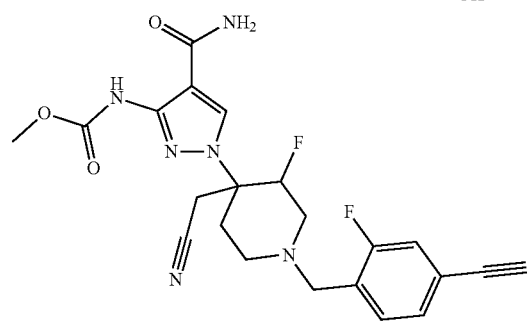
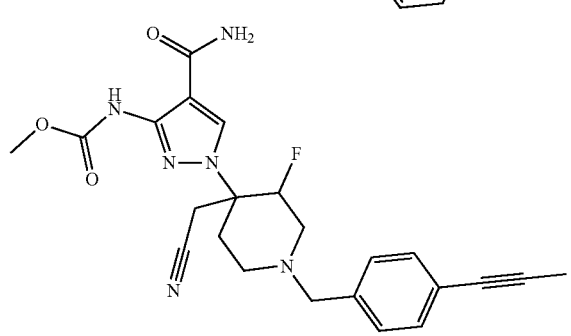
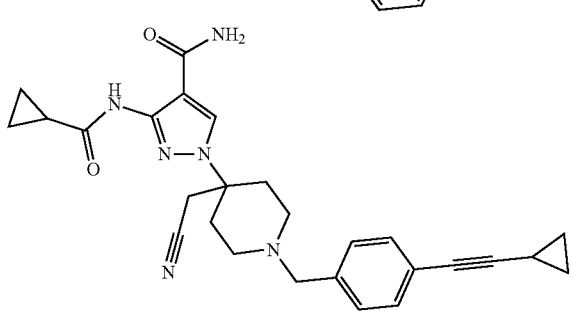
182
-continued
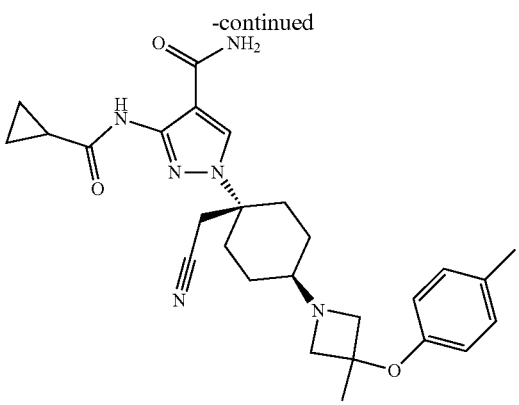
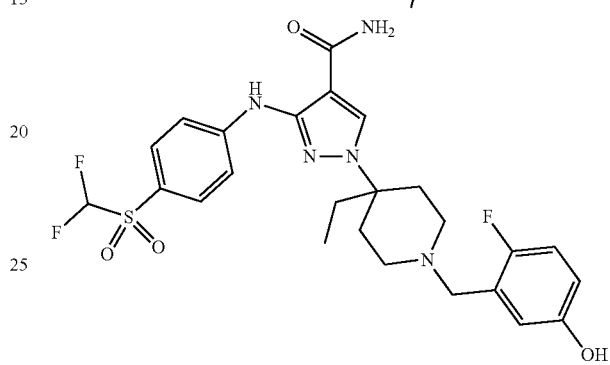
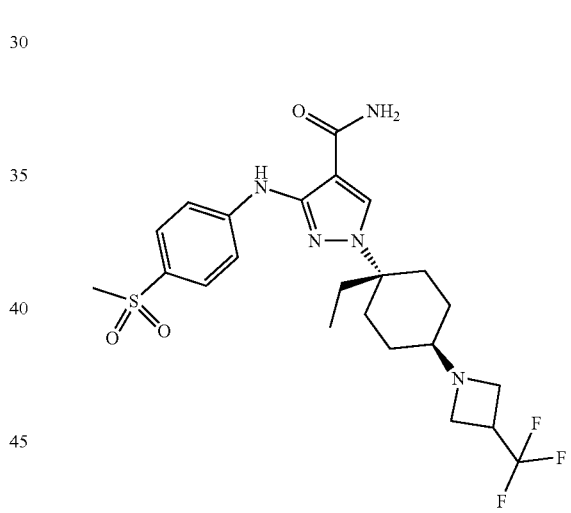
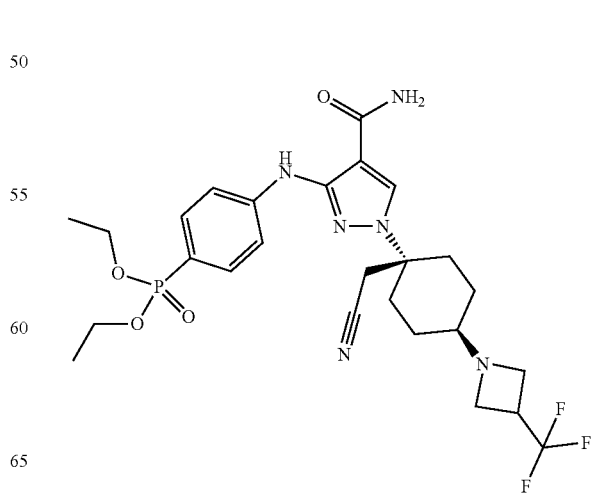

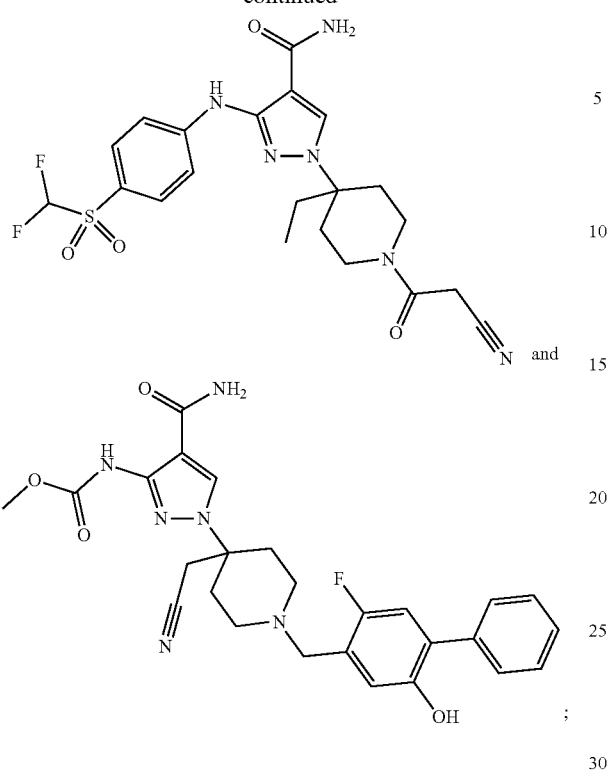
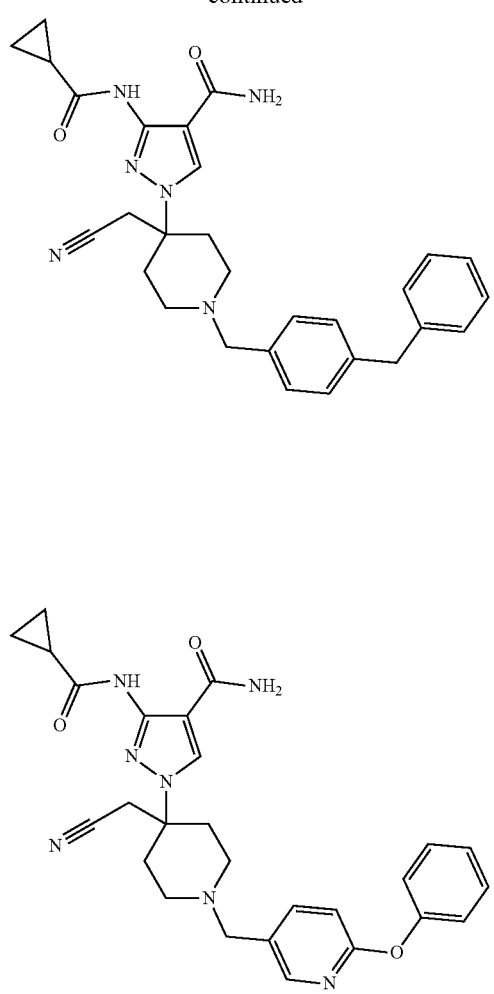
and salts thereof.
In some embodiments, a compound of the invention is selected from the group consisting of:
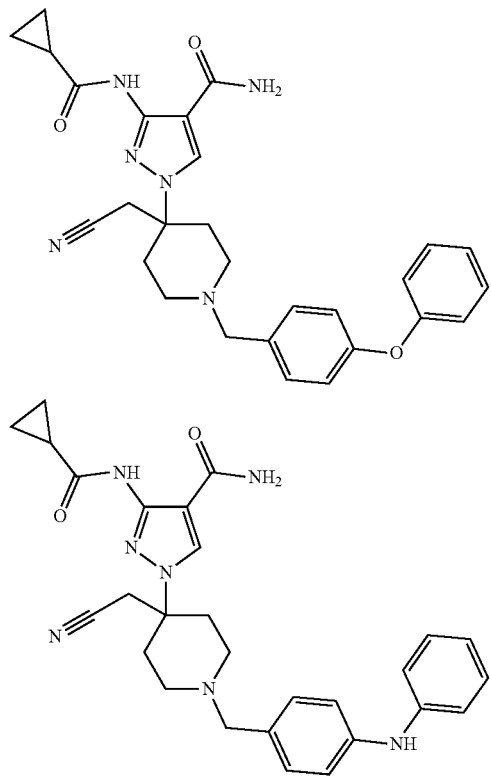
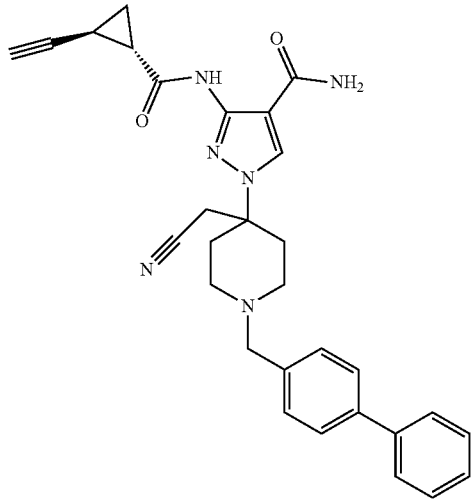

185
-continued
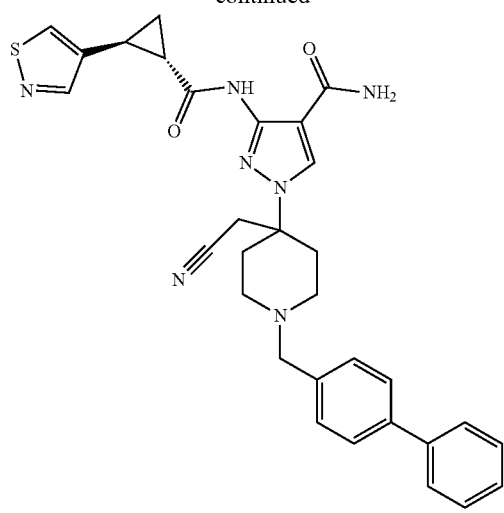
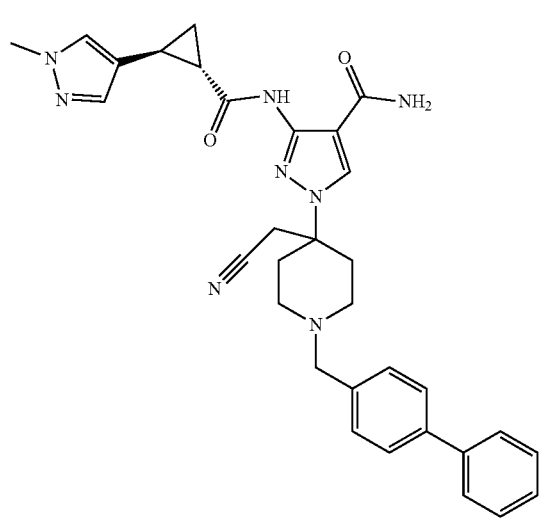
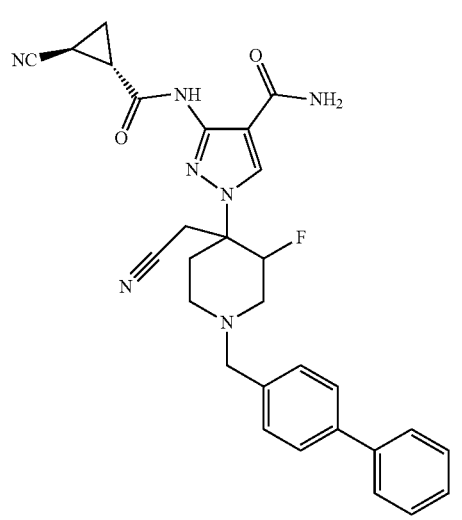
186
-continued
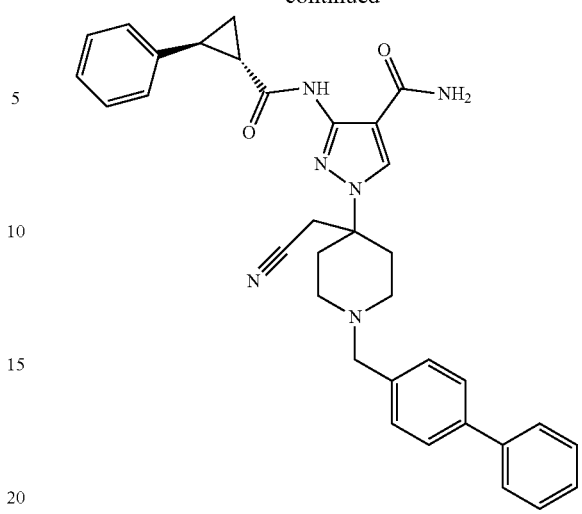
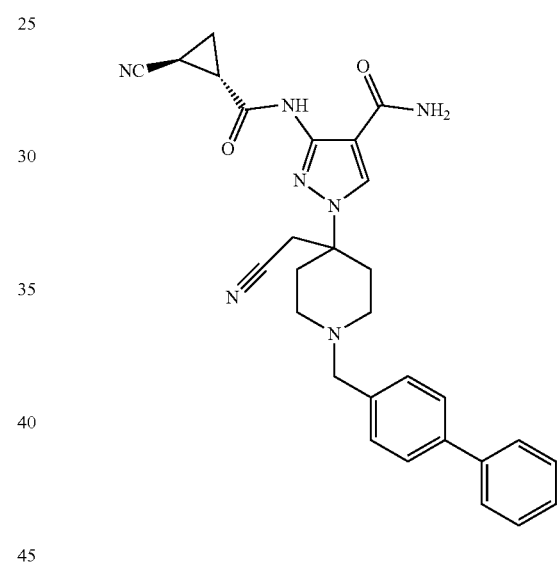
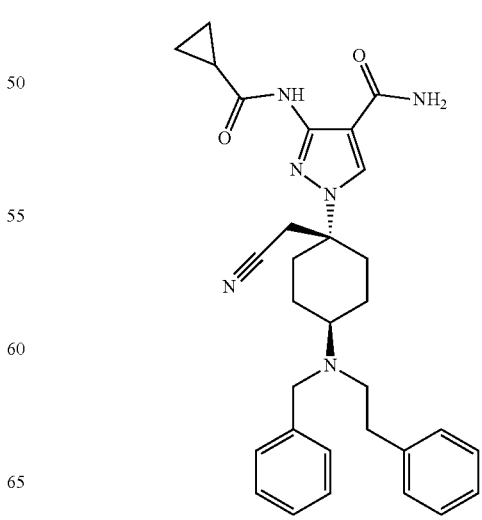

187
-continued
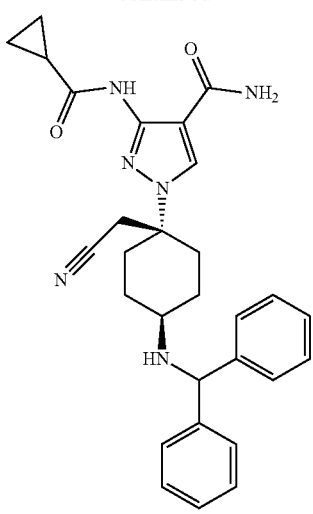
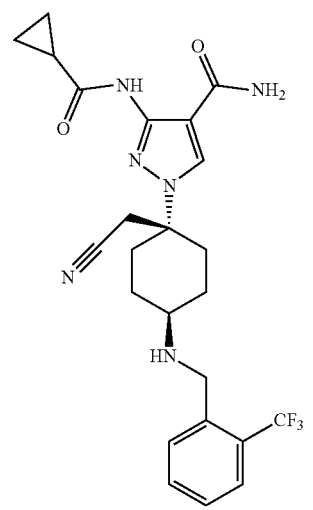
188
-continued
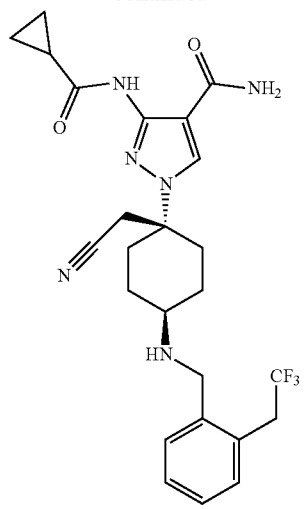
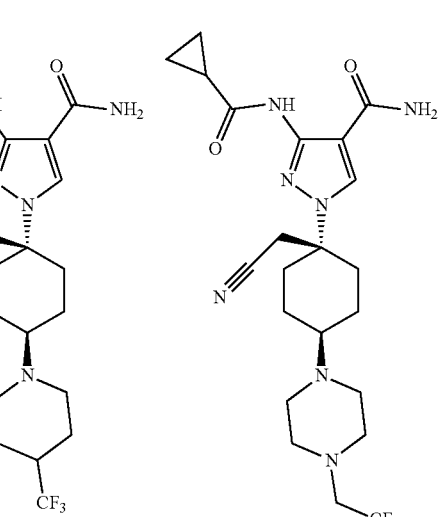

189
-continued
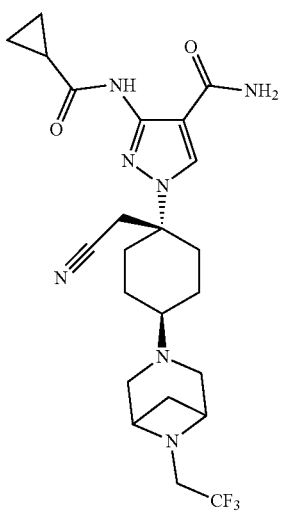
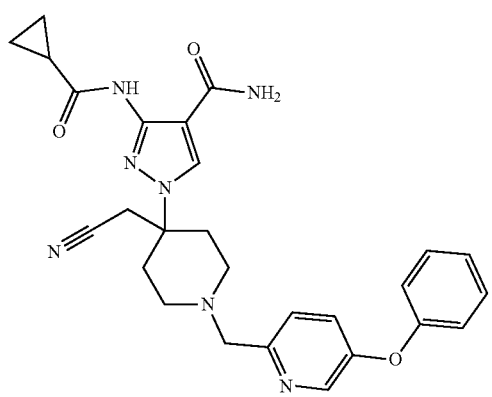
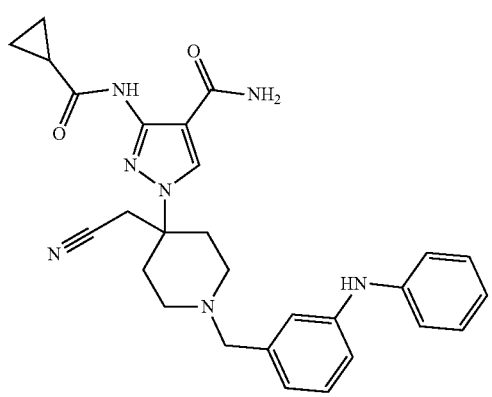
190
-continued
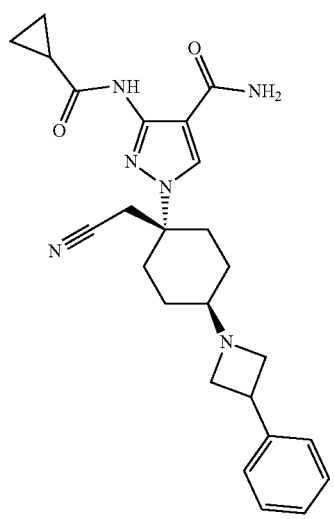
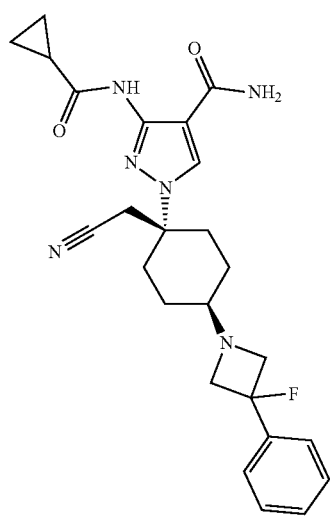
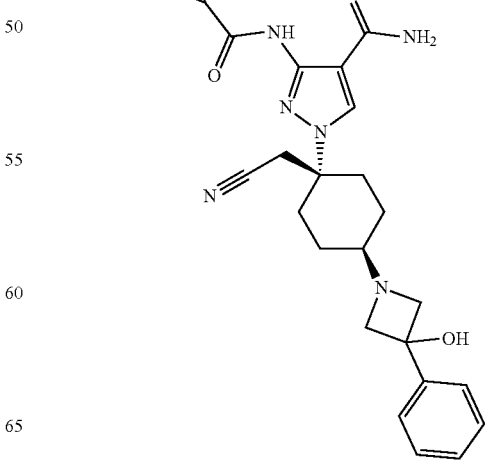

-continued
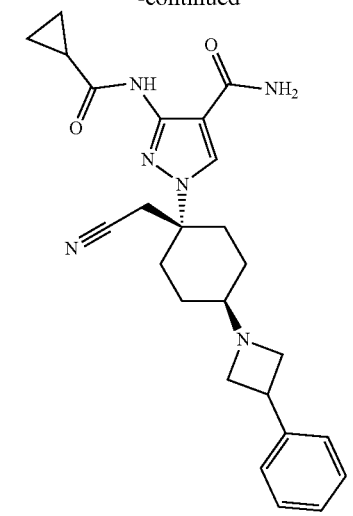
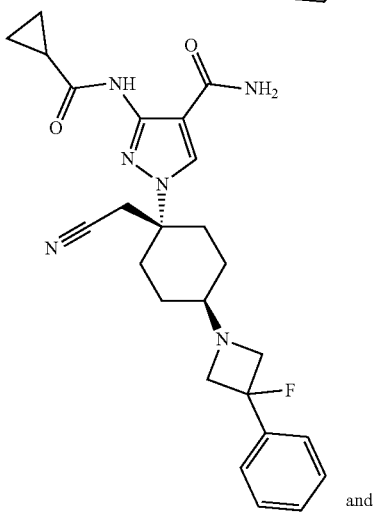
and
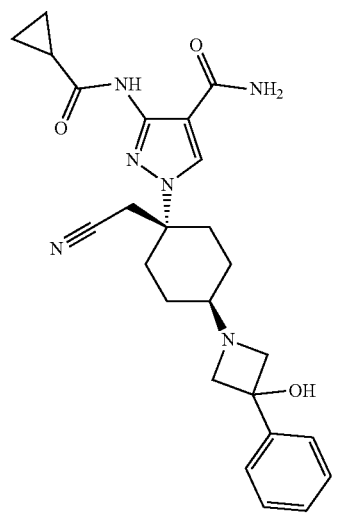 [SMILES: N#CC[C@]1(n2cc(C(N)=O)c(NC(=O)C3CC3)n2)CC[C@H](N2CC(O)(c3ccccc3)C2)CC1]
and salts thereof.
In some embodiments, the group
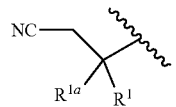
is selected from the group consisting of:
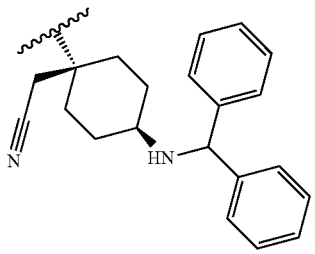
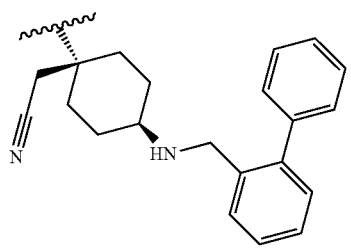
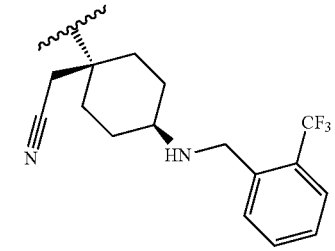
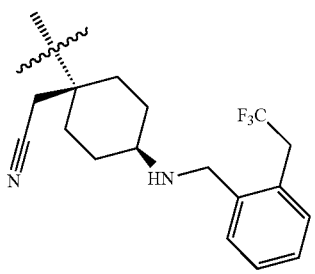
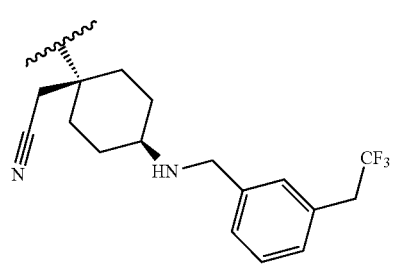

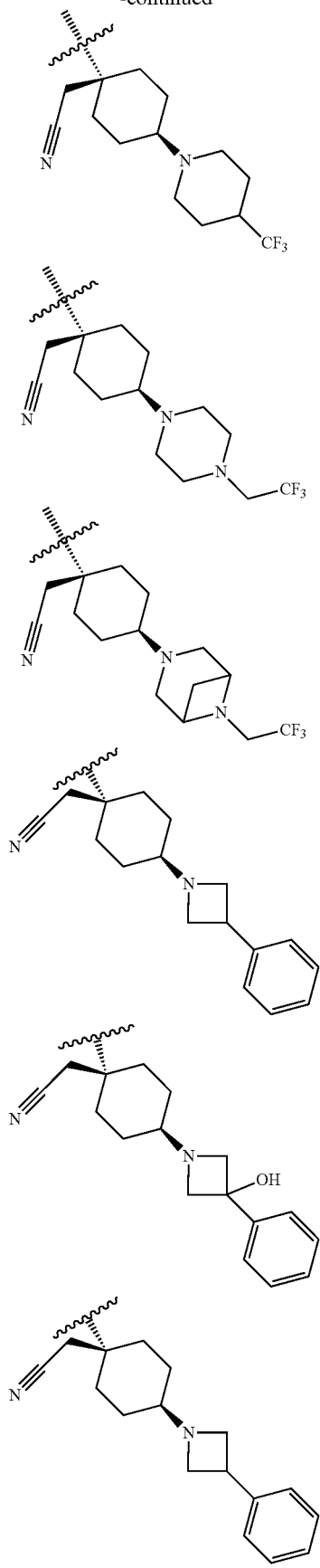
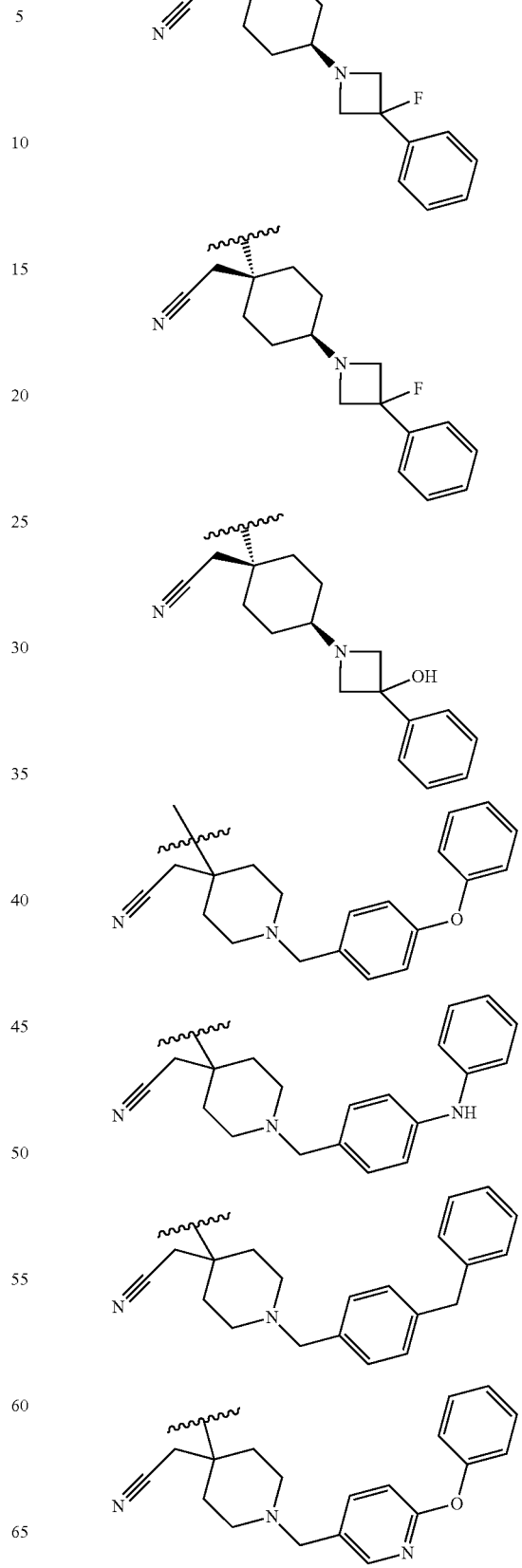

-continued
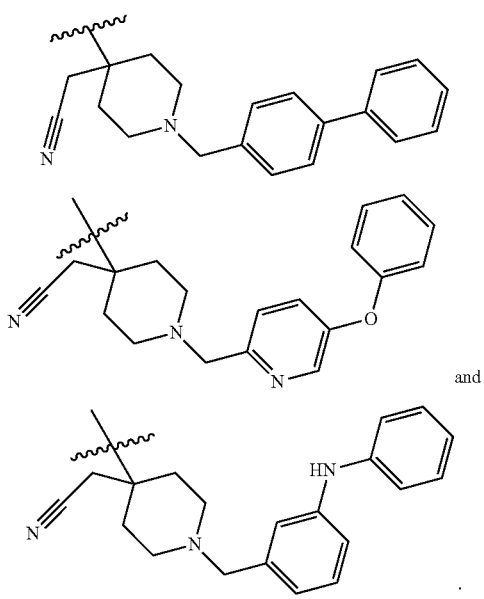
In some embodiments, $R^a$ is selected from the group consisting of:
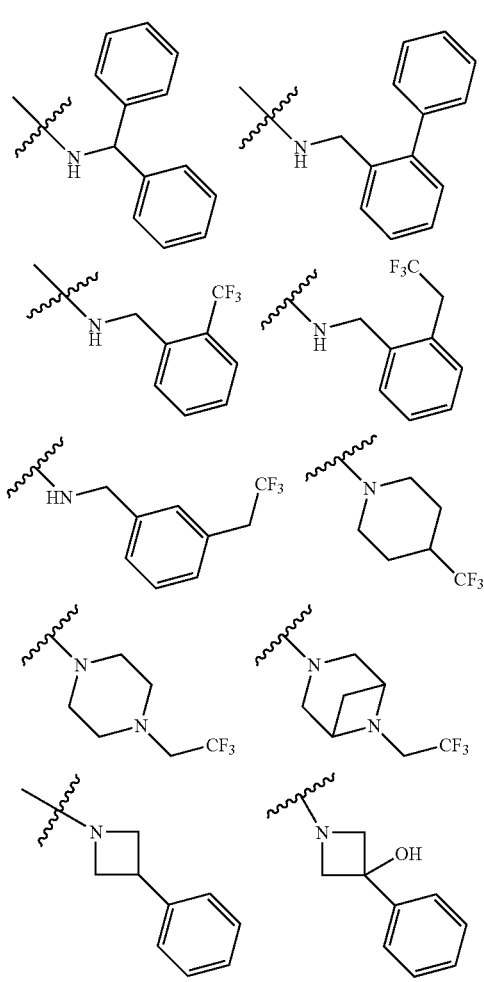
-continued
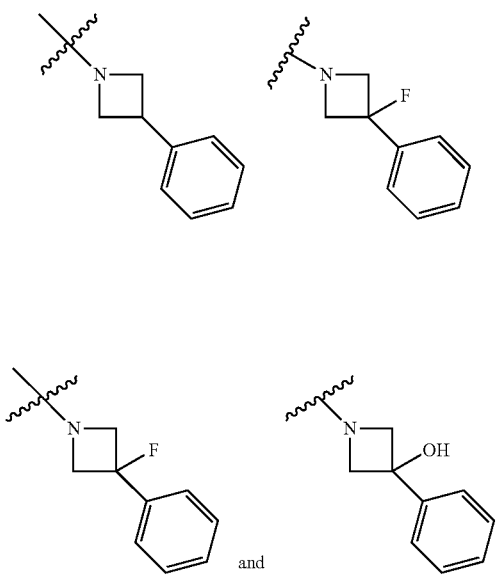
In some embodiments, $R^c$ is selected from the group consisting of:
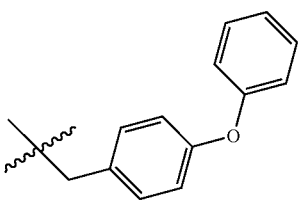
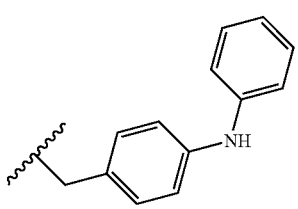
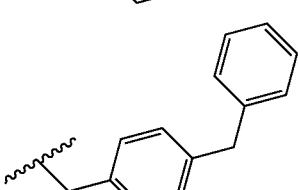
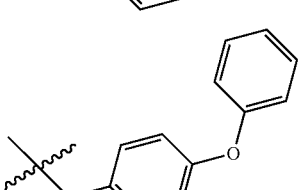
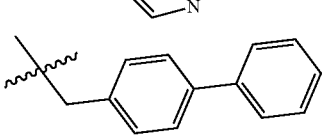

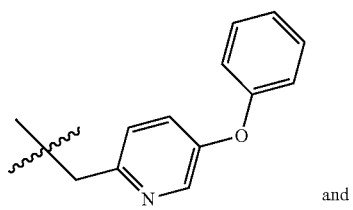 and 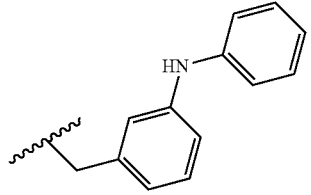

Also provided is a compound selected from Examples 1-304, and salts thereof.

Also provided is a compound selected from Table 1 below, or any combination thereof, and any salt thereof.

TABLE 1

Exemplary Compounds of the Present Invention

| Ex. | Structure | Name |
|---|---|---|
| 1, 2 | 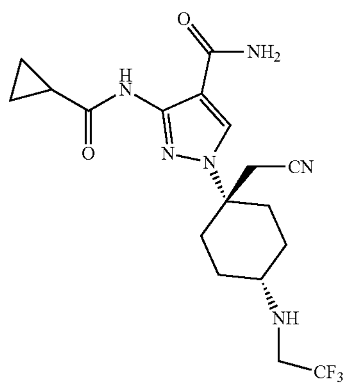 [SMILES: N#CC[C@]1(n2cc(C(N)=O)c(NC(=O)C3CC3)n2)CC[C@@H](NCC(F)(F)F)CC1] | 1-[1-(cyanomethyl)-4-(2,2,2-trifluoroethylamino)cyclohexyl]-3-(cyclopropanecarbonylamino)pyrazole-4-carboxamide |
| | | |
| 3 | 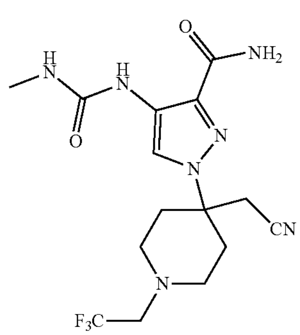 [SMILES: CNC(=O)Nc1cn(C2(CC#N)CCN(CC(F)(F)F)CC2)nc1C(N)=O] | 1-[1-(cyanomethyl)-4-(2,2,2-trifluoroethylamino)cyclohexyl]-3-(cyclopropanecarbonylamino)pyrazole-4-carboxamide |

TABLE 1-continued

Exemplary Compounds of the Present Invention

| Ex. | Structure | Name |
|---|---|---|
| 4 | 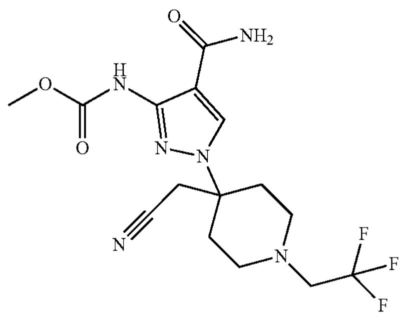 [SMILES: COC(=O)Nc1nn(C2(CC#N)CCN(CC(F)(F)F)CC2)cc1C(N)=O] | 1-[4-(cyanomethyl)-1-(2,2,2-trifluoroethyl)-4-piperidyl]-3-(methylcarbamoylamino)pyrazole-4-carboxamide |
| 5 | 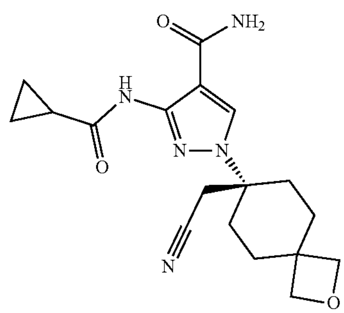 | methyl N-[4-carbamoyl-1-[4-(cyanomethyl)-1-(2,2,2-trifluoroethyl)-4-piperidyl]pyrazol-3-yl]carbamate |
| 6 | 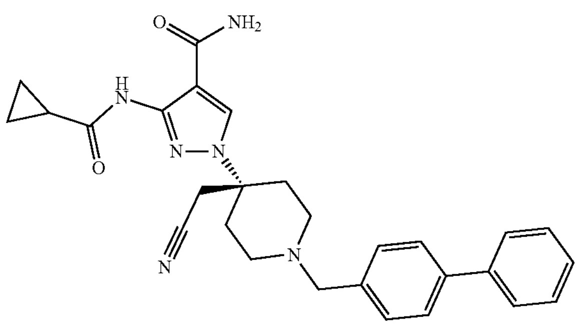 | 1-[7-(cyanomethyl)-2-oxaspiro[3.5]nonan-7-yl]-3-(cyclopropanecarbonylamino)pyrazole-4-carboxamide |
| 7, 8 | 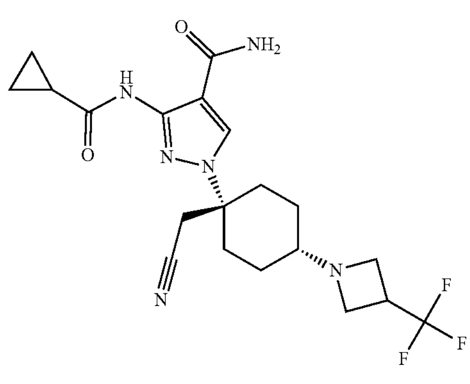 [SMILES: N#CC[C@]1(n2cc(C(N)=O)c(NC(=O)C3CC3)n2)CC[C@@H](N2CC(C(F)(F)F)C2)CC1] | 1-[4-(cyanomethyl)-1-[(4-phenylphenyl)methyl]-4-piperidyl]-3-(cyclopropanecarbonylamino)pyrazole-4-carboxamide |

TABLE 1-continued

Exemplary Compounds of the Present Invention

| Ex. | Structure | Name |
|---|---|---|
| 9, 10 | | 1-[1-(cyanomethyl)-4-[3-(trifluoromethyl)azetidin-1-yl]cyclohexyl]-3-(cyclopropanecarbonylamino)pyrazole-4-carboxamide |
| | | |
| 11 | 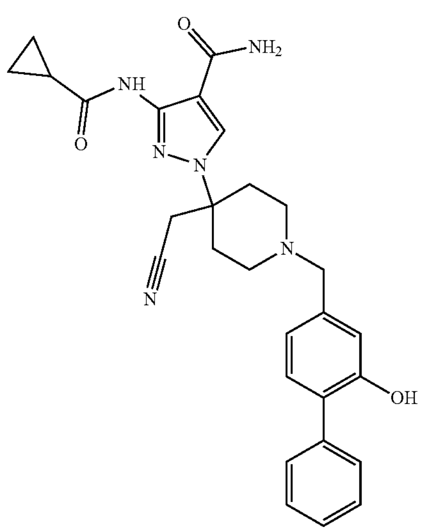 [SMILES: N#CCC1(n2cc(C(N)=O)c(NC(=O)C3CC3)n2)CCN(Cc2ccc(-c3ccccc3)c(O)c2)CC1] | 1-[1-(cyanomethyl)-4-[3-(trifluoromethyl)azetidin-1-yl]cyclohexyl]-3-(cyclopropanecarbonylamino)pyrazole-4-carboxamide |

TABLE 1-continued
Exemplary Compounds of the Present Invention
| Ex. | Structure | Name |
|---|---|---|
| 12, 13, 14, 15 | 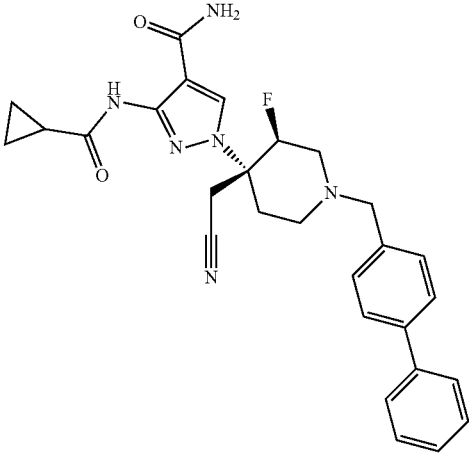 [SMILES: N#CC[C@]1(n2cc(C(N)=O)c(NC(=O)C3CC3)n2)CCN(Cc2ccc(-c3ccccc3)cc2)C[C@@H]1F]<br>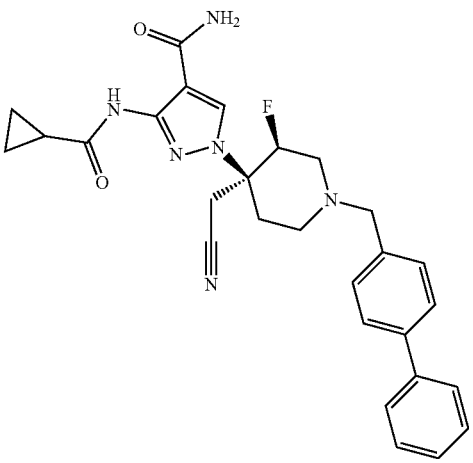 [SMILES: N#CC[C@@]1(n2cc(C(N)=O)c(NC(=O)C3CC3)n2)CCN(Cc2ccc(-c3ccccc3)cc2)C[C@@H]1F]<br>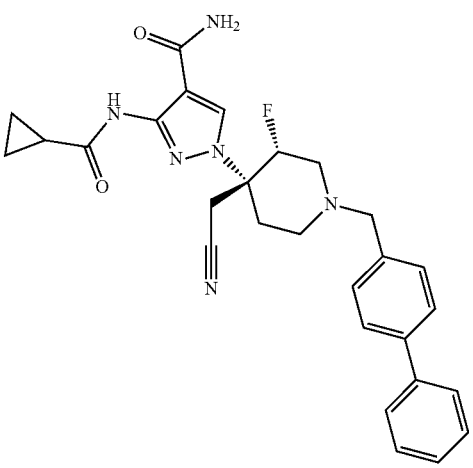 [SMILES: N#CC[C@]1(n2cc(C(N)=O)c(NC(=O)C3CC3)n2)CCN(Cc2ccc(-c3ccccc3)cc2)C[C@H]1F] | 1-[1-(cyanomethyl)-4-[3-ethoxy-3-(trifluoromethyl)azetidin-1-yl]cyclohexyl]-3-(cyclopropanecarbonylamino)pyrazole-4-carboxamide |

TABLE 1-continued
Exemplary Compounds of the Present Invention
| Ex. | Structure | Name |
|---|---|---|
| | 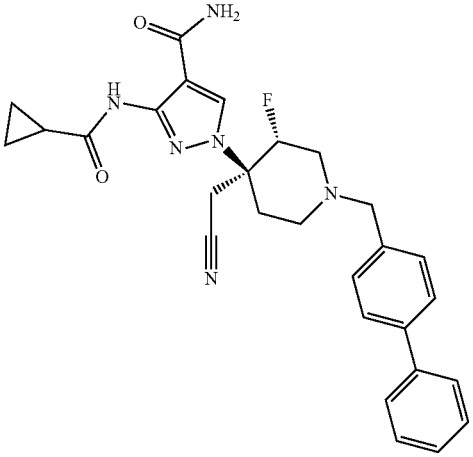 [SMILES: N#CC[C@@]1(n2cc(C(N)=O)c(NC(=O)C3CC3)n2)CCN(Cc2ccc(-c3ccccc3)cc2)C[C@H]1F] | |
| 16 | 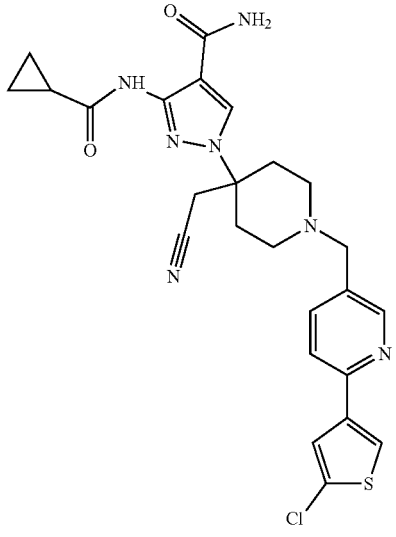 [SMILES: N#CCC1(n2cc(C(N)=O)c(NC(=O)C3CC3)n2)CCN(Cc2ccc(-c3csc(Cl)c3)nc2)CC1] | 1-[1-(cyanomethyl)-4-[3-ethoxy-3-(trifluoromethyl)azetidin-1-yl]cyclohexyl]-3-(cyclopropanecarbonylamino)pyrazole-4-carboxamide |
| 17 | 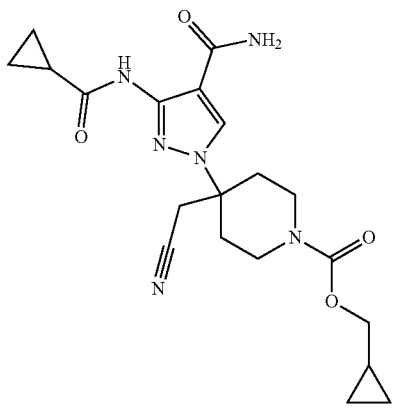 [SMILES: N#CCC1(n2cc(C(N)=O)c(NC(=O)C3CC3)n2)CCN(C(=O)OCC2CC2)CC1] | 1-[4-(cyanomethyl)-1-[(3-hydroxy-4-phenyl-phenyl)methyl]-4-piperidyl]-3-(cyclopropanecarbonylamino)pyrazole-4-carboxamide |

TABLE 1-continued

Exemplary Compounds of the Present Invention

| Ex. | Structure | Name |
|---|---|---|
| 18 | 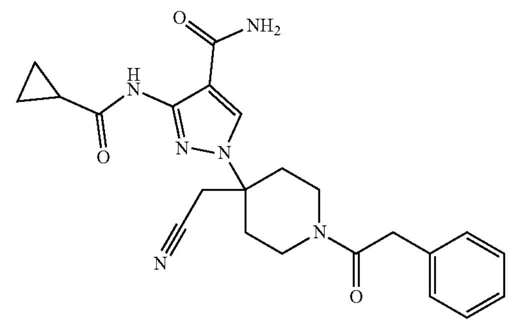 [SMILES: N#CCC1(n2cc(C(N)=O)c(NC(=O)C3CC3)n2)CCN(C(=O)Cc2ccccc2)CC1] | 1-[4-(cyanomethyl)-3-fluoro-1-[(4-phenylphenyl)methyl]-4-piperidyl]-3-(cyclopropanecarbonylamino)pyrazole-4-carboxamide |
| 19, 20 | | 1-[4-(cyanomethyl)-3-fluoro-1-[(4-phenylphenyl)methyl]-4-piperidyl]-3-(cyclopropanecarbonylamino)pyrazole-4-carboxamide |
| | | |
| 21 | 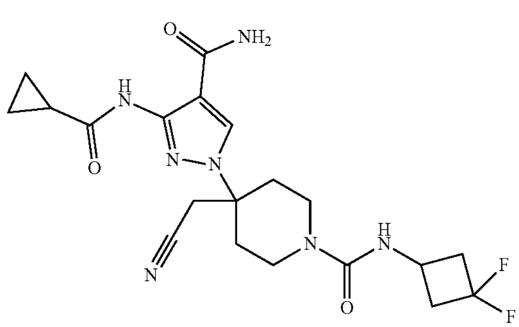 [SMILES: N#CCC1(n2cc(C(N)=O)c(NC(=O)C3CC3)n2)CCN(C(=O)NC2CC(F)(F)C2)CC1] | 1-[4-(cyanomethyl)-3-fluoro-1-[(4-phenylphenyl)methyl]-4-piperidyl]-3-(cyclopropanecarbonylamino)pyrazole-4-carboxamide |

TABLE 1-continued

Exemplary Compounds of the Present Invention

| Ex. | Structure | Name |
|---|---|---|
| 22 | 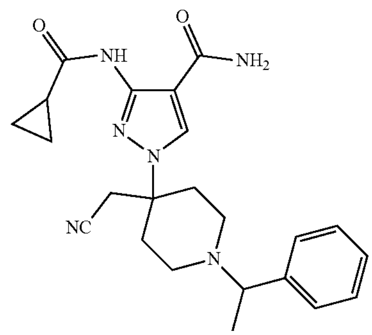 [SMILES: CC(c1ccccc1)N1CCC(CC#N)(n2cc(C(N)=O)c(NC(=O)C3CC3)n2)CC1] | 1-[4-(cyanomethyl)-3-fluoro-1-[(4-phenylphenyl)methyl]-4-piperidyl]-3-(cyclopropanecarbonylamino)pyrazole-4-carboxamide |
| 23 | 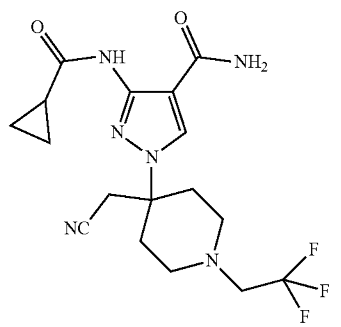 [SMILES: N#CCC1(n2cc(C(N)=O)c(NC(=O)C3CC3)n2)CCN(CC(F)(F)F)CC1] | 1-[1-[[6-(5-chloro-3-thienyl)-3-pyridyl]methyl]-4-(cyanomethyl)-4-piperidyl]-3-(cyclopropanecarbonylamino)pyrazole-4-carboxamide |
| 24 | 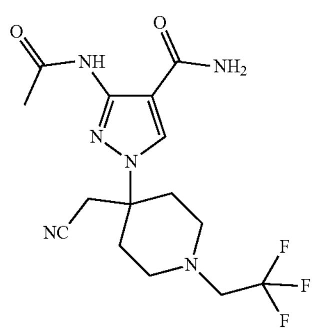 [SMILES: CC(=O)Nc1nn(C2(CC#N)CCN(CC(F)(F)F)CC2)cc1C(N)=O] | cyclopropylmethyl 4-[4-carbamoyl-3-(cyclopropanecarbonylamino)pyrazol-1-yl]-4-(cyanomethyl)piperidine-1-carboxylate |
| 25 | 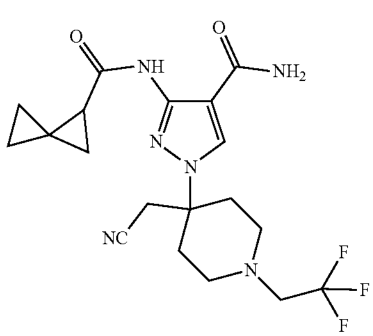 [SMILES: N#CCC1(n2cc(C(N)=O)c(NC(=O)C3CC34CC4)n2)CCN(CC(F)(F)F)CC1] | 1-[4-(cyanomethyl)-1-(2-phenylacetyl)-4-piperidyl]-3-(cyclopropanecarbonylamino)pyrazole-4-carboxamide |

TABLE 1-continued

Exemplary Compounds of the Present Invention

| Ex. | Structure | Name |
|---|---|---|
| 26 | 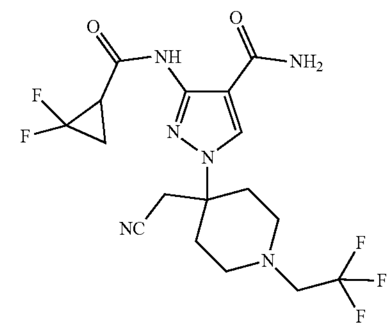 [SMILES: N#CCC1(n2cc(C(N)=O)c(NC(=O)C3CC3(F)F)n2)CCN(CC(F)(F)F)CC1] | 1-[4-(cyanomethyl)-1-(2-hydroxy-1-phenyl-ethyl)-4-piperidyl]-3-(cyclopropanecarbonylamino)pyrazole-4-carboxamide |
| 27 | 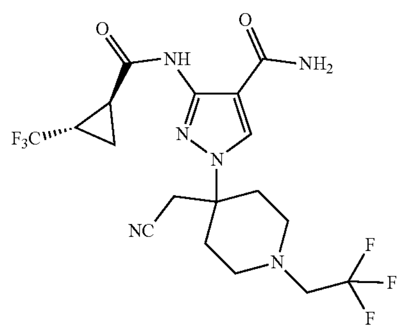 [SMILES: N#CCC1(n2cc(C(N)=O)c(NC(=O)[C@H]3C[C@@H]3C(F)(F)F)n2)CCN(CC(F)(F)F)CC1] | 1-[4-(cyanomethyl)-1-(2-hydroxy-2-phenyl-ethyl)-4-piperidyl]-3-(cyclopropanecarbonylamino)pyrazole-4-carboxamide |
| 28 | 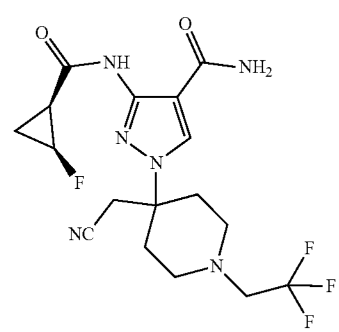 [SMILES: N#CCC1(n2cc(C(N)=O)c(NC(=O)[C@@H]3C[C@@H]3F)n2)CCN(CC(F)(F)F)CC1] | 4-[4-carbamoyl-3-(cyclopropanecarbonylamino)pyrazol-1-yl]-4-(cyanomethyl)-N-(3,3-difluorocyclobutyl)piperidine-1-carboxamide |
| 29 | 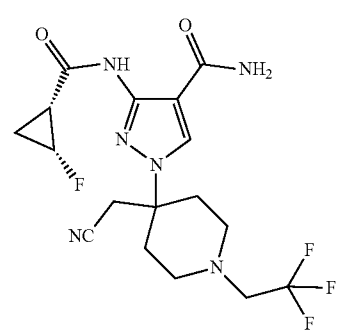 [SMILES: N#CCC1(n2cc(C(N)=O)c(NC(=O)[C@H]3C[C@H]3F)n2)CCN(CC(F)(F)F)CC1] | 1-[4-(cyanomethyl)-1-(1-phenylethyl)-4-piperidyl]-3-(cyclopropanecarbonylamino)pyrazole-4-carboxamide |

US 11,731,943 B2

TABLE 1-continued

Exemplary Compounds of the Present Invention

| Ex. | Structure | Name |
|---|---|---|
| 30 | 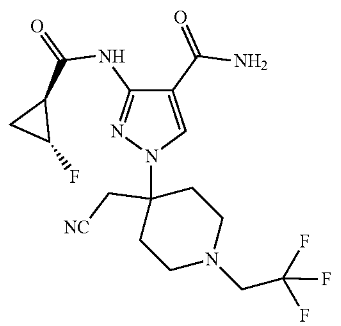 [SMILES: N#CCC1(n2cc(C(N)=O)c(NC(=O)[C@@H]3C[C@H]3F)n2)CCN(CC(F)(F)F)CC1] | 1-[4-(cyanomethyl)-1-(2,2,2-trifluoroethyl)-4-piperidyl]-3-(cyclopropanecarbonylamino)pyrazole-4-carboxamide |
| 31 | 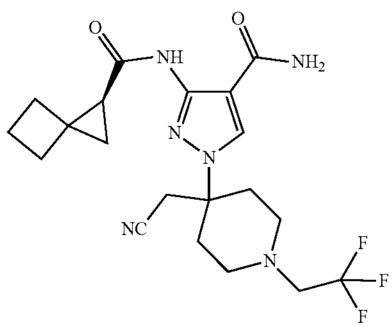 [SMILES: N#CCC1(n2cc(C(N)=O)c(NC(=O)[C@H]3CC34CCC4)n2)CCN(CC(F)(F)F)CC1] | 3-acetamido-1-[4-(cyanomethyl)-1-(2,2,2-trifluoroethyl)-4-piperidyl]pyrazole-4-carboxamide |
| 32 | 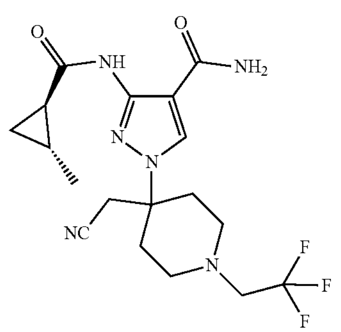 | 1-[4-(cyanomethyl)-1-(2,2,2-trifluoroethyl)-4-piperidyl]-3-(spiro[2.2]pentane-2-carbonylamino)pyrazole-4-carboxamide |
| 33 | 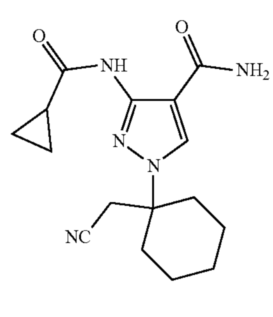 [SMILES: N#CCC1(n2cc(C(N)=O)c(NC(=O)C3CC3)n2)CCCCC1] | 1-[4-(cyanomethyl)-1-(2,2,2-trifluoroethyl)-4-piperidyl]-3-[(2,2-difluorocyclopropanecarbonyl)amino]pyrazole-4-carboxamide |

TABLE 1-continued

Exemplary Compounds of the Present Invention

| Ex. | Structure | Name |
|---|---|---|
| 34 | 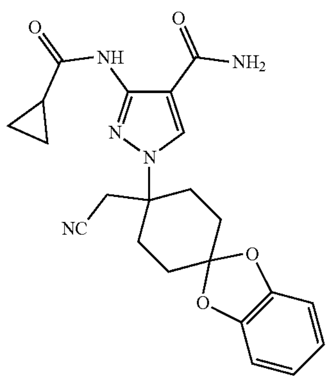 [SMILES: N#CCC1(n2cc(C(N)=O)c(NC(=O)C3CC3)n2)CCC2(CC1)Oc1ccccc1O2] | 1-[4-(cyanomethyl)-1-(2,2,2-trifluoroethyl)-4-piperidyl]-3-[[rac-(1R,2R)-2-(trifluoromethyl)cyclopropanecarbonyl]amino]pyrazole-4-carboxamide |
| 35 | 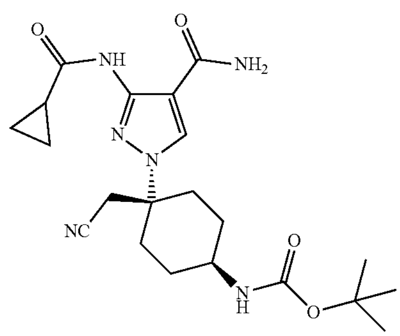 | 1-[4-(cyanomethyl)-1-(2,2,2-trifluoroethyl)-4-piperidyl]-3-[[rac-(1S,2S)-2-fluorocyclopropanecarbonyl]amino]pyrazole-4-carboxamide |
| 36 | 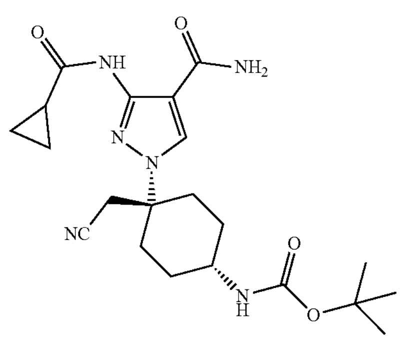 | 1-[4-(cyanomethyl)-1-(2,2,2-trifluoroethyl)-4-piperidyl]-3-[[rac-(1R,2R)-2-fluorocyclopropanecarbonyl]amino]pyrazole-4-carboxamide |
| 37 | 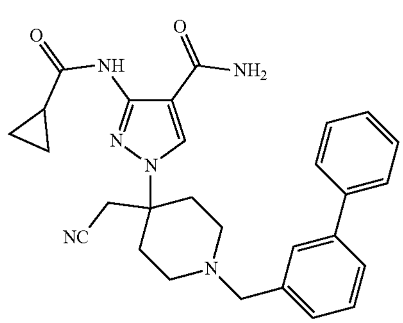 [SMILES: N#CCC1(n2cc(C(N)=O)c(NC(=O)C3CC3)n2)CCN(Cc2cccc(-c3ccccc3)c2)CC1] | 1-[4-(cyanomethyl)-1-(2,2,2-trifluoroethyl)-4-piperidyl]-3-[[rac-(1S,2R)-2-fluorocyclopropanecarbonyl]amino]pyrazole-4-carboxamide |

TABLE 1-continued

Exemplary Compounds of the Present Invention

| Ex. | Structure | Name |
|---|---|---|
| 38 | 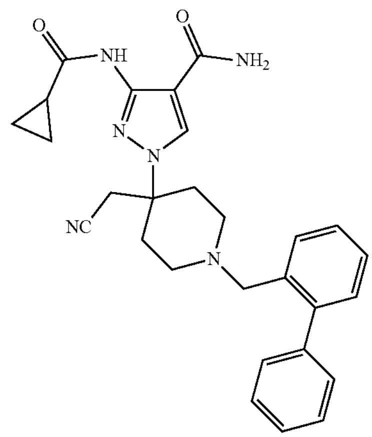 [SMILES: N#CCC1(n2cc(C(N)=O)c(NC(=O)C3CC3)n2)CCN(Cc2ccccc2-c2ccccc2)CC1] | 1-[4-(cyanomethyl)-1-(2,2,2-trifluoroethyl)-4-piperidyl]-3-(spiro[2.3]hexane-2-carbonylamino)pyrazole-4-carboxamide |
| 39 | 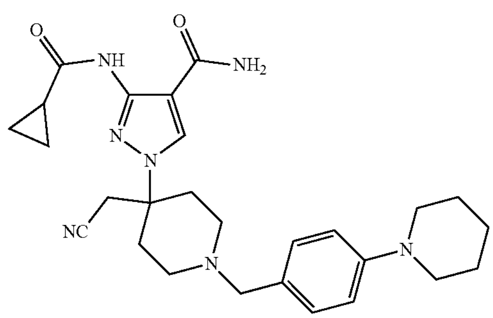 [SMILES: N#CCC1(n2cc(C(N)=O)c(NC(=O)C3CC3)n2)CCN(Cc2ccc(N3CCCCC3)cc2)CC1] | 1-[4-(cyanomethyl)-1-(2,2,2-trifluoroethyl)-4-piperidyl]-3-[[rac-(1R,2R)-2-methylcyclopropanecarbonyl]amino]pyrazole-4-carboxamide |
| 40 | 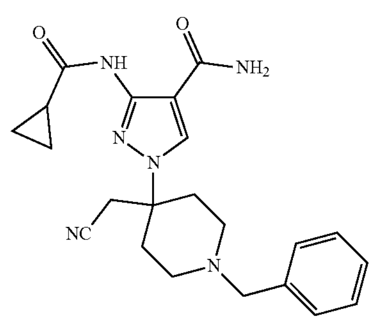 [SMILES: N#CCC1(n2cc(C(N)=O)c(NC(=O)C3CC3)n2)CCN(Cc2ccccc2)CC1] | 1-[1-(cyanomethyl)cyclohexyl]-3-(cyclopropanecarbonylamino)pyrazole-4-carboxamide |
| 41 | 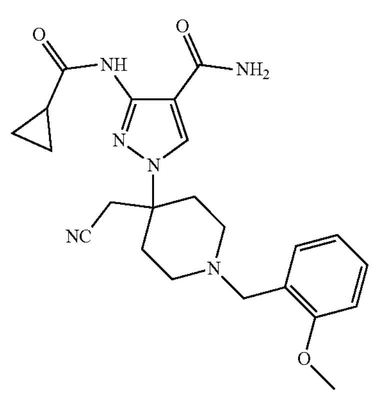 [SMILES: COc1ccccc1CN1CCC(CC#N)(n2cc(C(N)=O)c(NC(=O)C3CC3)n2)CC1] | 1-[1'-(cyanomethyl)spiro[1,3-benzodioxole-2,4'-cyclohexane]-1'-yl]-3-(cyclopropanecarbonylamino)pyrazole-4-carboxamide |

TABLE 1-continued

Exemplary Compounds of the Present Invention

| Ex. | Structure | Name |
|---|---|---|
| 42 | 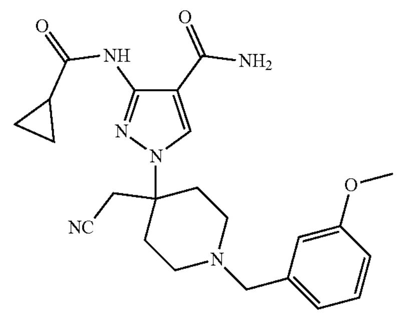 [SMILES: COc1cccc(CN2CCC(CC#N)(n3cc(C(N)=O)c(NC(=O)C4CC4)n3)CC2)c1] | tert-butyl N-[4-[4-carbamoyl-3-(cyclopropanecarbonylamino)pyrazol-1-yl]-4-(cyanomethyl)cyclohexyl] carbamate |
| 43 | 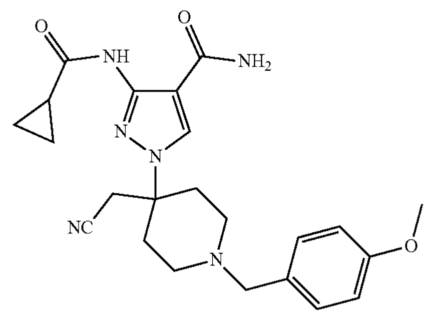 [SMILES: COc1ccc(CN2CCC(CC#N)(n3cc(C(N)=O)c(NC(=O)C4CC4)n3)CC2)cc1] | tert-butyl N-[4-[4-carbamoyl-3-(cyclopropanecarbonylamino)pyrazol-1-yl]-4-(cyanomethyl)cyclohexyl] carbamate |
| 44 | 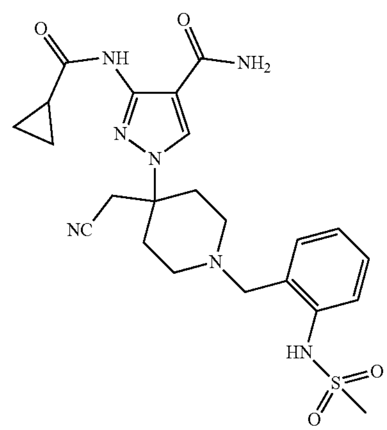 [SMILES: CS(=O)(=O)Nc1ccccc1CN1CCC(CC#N)(n2cc(C(N)=O)c(NC(=O)C3CC3)n2)CC1] | 1-[4-(cyanomethyl)-1-[(3-phenylphenyl)methyl]-4-piperidyl]-3-(cyclopropanecarbonylamino)pyrazole-4-carboxamide |
| 45 | 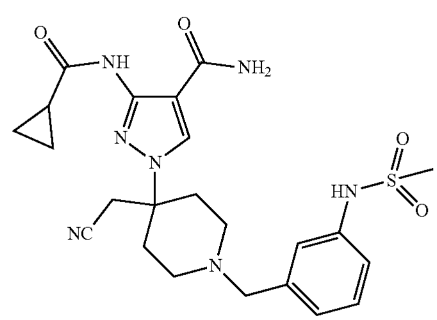 [SMILES: CS(=O)(=O)Nc1cccc(CN2CCC(CC#N)(n3cc(C(N)=O)c(NC(=O)C4CC4)n3)CC2)c1] | 1-[4-(cyanomethyl)-1-[(2-phenylphenyl)methyl]-4-piperidyl]-3-(cyclopropanecarbonylamino)pyrazole-4-carboxamide |

TABLE 1-continued

Exemplary Compounds of the Present Invention

| Ex. | Structure | Name |
| --- | --- | --- |
| 46 | 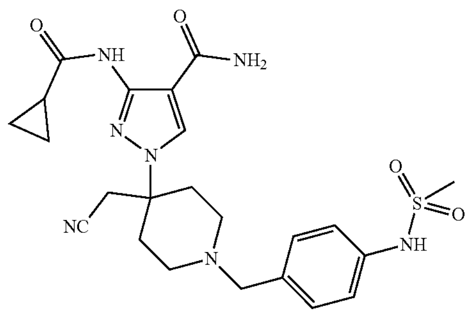 [SMILES: CS(=O)(=O)Nc1ccc(CN2CCC(CC#N)(n3cc(C(N)=O)c(NC(=O)C4CC4)n3)CC2)cc1] | 1-[4-(cyanomethyl)-1-[[4-(1-piperidyl)phenyl]methyl]-4-piperidyl]-3-(cyclopropanecarbonylamino)pyrazole-4-carboxamide |
| 47 | 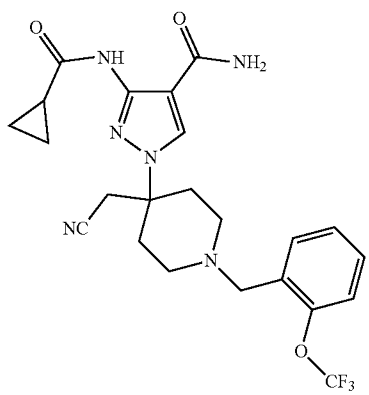 [SMILES: N#CCC1(n2cc(C(N)=O)c(NC(=O)C3CC3)n2)CCN(Cc2ccccc2OC(F)(F)F)CC1] | 1-[1-benzyl-4-(cyanomethyl)-4-piperidyl]-3-(cyclopropanecarbonylamino)pyrazole-4-carboxamide |
| 48 | 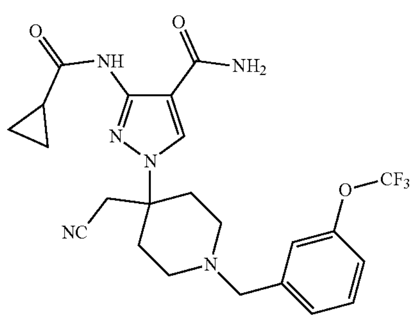 [SMILES: N#CCC1(n2cc(C(N)=O)c(NC(=O)C3CC3)n2)CCN(Cc2cccc(OC(F)(F)F)c2)CC1] | 1-[4-(cyanomethyl)-1-[(2-methoxyphenyl)methyl]-4-piperidyl]-3-(cyclopropanecarbonylamino)pyrazole-4-carboxamide |
| 49 | 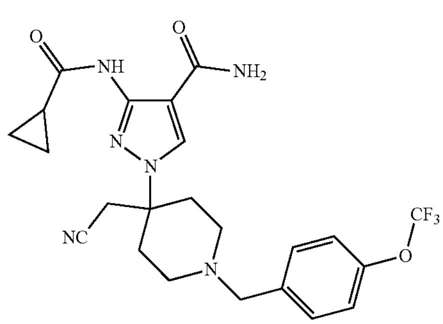 [SMILES: N#CCC1(n2cc(C(N)=O)c(NC(=O)C3CC3)n2)CCN(Cc2ccc(OC(F)(F)F)cc2)CC1] | 1-[4-(cyanomethyl)-1-[(3-methoxyphenyl)methyl]-4-piperidyl]-3-(cyclopropanecarbonylamino)pyrazole-4-carboxamide |

TABLE 1-continued

Exemplary Compounds of the Present Invention

| Ex. | Structure | Name |
|---|---|---|
| 50 | 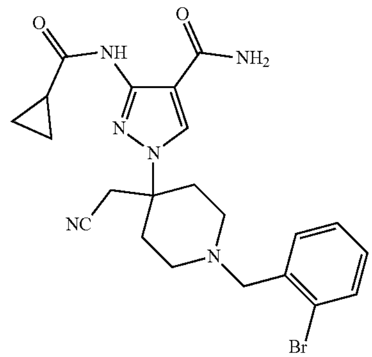 | 1-[4-(cyanomethyl)-1-[(4-methoxyphenyl)methyl]-4-piperidyl]-3-(cyclopropanecarbonylamino)pyrazole-4-carboxamide |
| 51 | 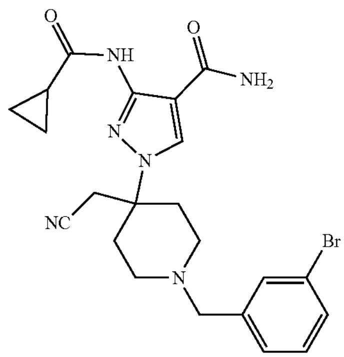 [SMILES: N#CCC1(n2cc(C(N)=O)c(NC(=O)C3CC3)n2)CCN(Cc2cccc(Br)c2)CC1] | 1-[4-(cyanomethyl)-1-[[2-(methanesulfonamido)phenyl]methyl]-4-piperidyl]-3-(cyclopropanecarbonylamino)pyrazole-4-carboxamide |
| 52 | 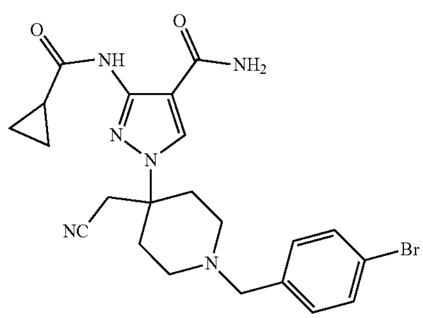 [SMILES: N#CCC1(n2cc(C(N)=O)c(NC(=O)C3CC3)n2)CCN(Cc2ccc(Br)cc2)CC1] | 1-[4-(cyanomethyl)-1-[[3-(methanesulfonamido)phenyl]methyl]-4-piperidyl]-3-(cyclopropanecarbonylamino)pyrazole-4-carboxamide |
| 53 | 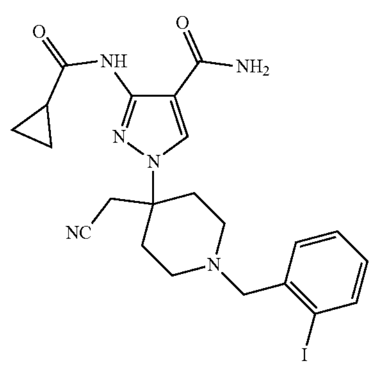 [SMILES: N#CCC1(n2cc(C(N)=O)c(NC(=O)C3CC3)n2)CCN(Cc2ccccc2I)CC1] | 1-[4-(cyanomethyl)-1-[[4-(methanesulfonamido)phenyl]methyl]-4-piperidyl]-3-(cyclopropanecarbonylamino)pyrazole-4-carboxamide |

TABLE 1-continued

Exemplary Compounds of the Present Invention

| Ex. | Structure | Name |
|---|---|---|
| 54 | 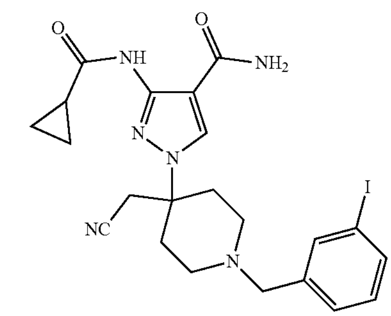 [SMILES: N#CCC1(n2cc(C(N)=O)c(NC(=O)C3CC3)n2)CCN(Cc2cccc(I)c2)CC1] | 1-[4-(cyanomethyl)-1-[[2-(trifluoromethoxy)phenyl]methyl]-4-piperidyl]-3-(cyclopropanecarbonylamino)pyrazole-4-carboxamide |
| 55 | 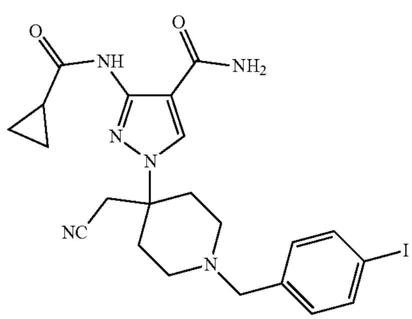 [SMILES: N#CCC1(n2cc(C(N)=O)c(NC(=O)C3CC3)n2)CCN(Cc2ccc(I)cc2)CC1] | 1-[4-(cyanomethyl)-1-[[3-(trifluoromethoxy)phenyl]methyl]-4-piperidyl]-3-(cyclopropanecarbonylamino)pyrazole-4-carboxamide |
| 56 | 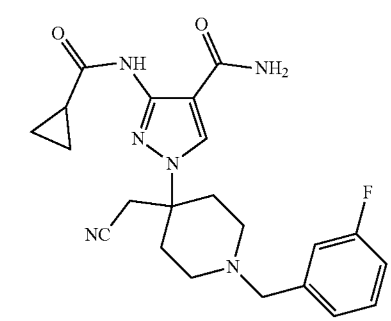 | 1-[4-(cyanomethyl)-1-[[4-(trifluoromethoxy)phenyl]methyl]-4-piperidyl]-3-(cyclopropanecarbonylamino)pyrazole-4-carboxamide |
| 57 | 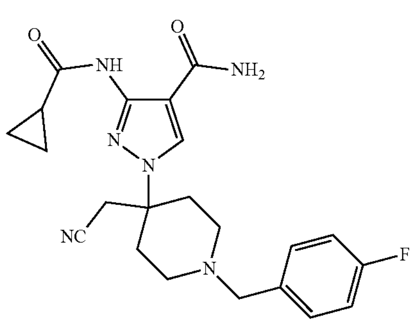 [SMILES: N#CCC1(n2cc(C(N)=O)c(NC(=O)C3CC3)n2)CCN(Cc2ccc(F)cc2)CC1] | 1-[1-[(2-bromophenyl)methyl]-4-(cyanomethyl)-4-piperidyl]-3-(cyclopropanecarbonylamino)pyrazole-4-carboxamide |

TABLE 1-continued

Exemplary Compounds of the Present Invention

| Ex. | Structure | Name |
|---|---|---|
| 58 | 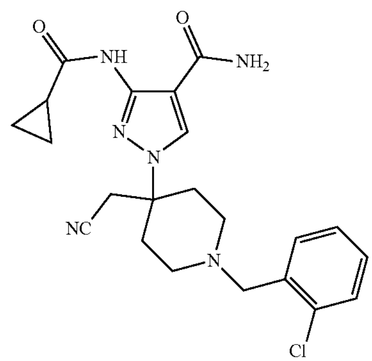 | 1-[1-[(3-bromophenyl)methyl]-4-(cyanomethyl)-4-piperidyl]-3-(cyclopropanecarbonylamino)pyrazole-4-carboxamide |
| 59 | 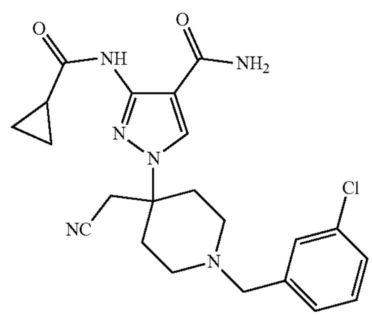 [SMILES: N#CCC1(n2cc(C(N)=O)c(NC(=O)C3CC3)n2)CCN(Cc2cccc(Cl)c2)CC1] | 1-[1-[(4-bromophenyl)methyl]-4-(cyanomethyl)-4-piperidyl]-3-(cyclopropanecarbonylamino)pyrazole-4-carboxamide |
| 60 | 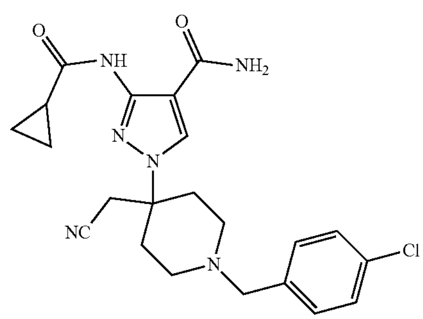 [SMILES: N#CCC1(n2cc(C(N)=O)c(NC(=O)C3CC3)n2)CCN(Cc2ccc(Cl)cc2)CC1] | 1-[4-(cyanomethyl)-1-[(2-iodophenyl)methyl]-4-piperidyl]-3-(cyclopropanecarbonylamino)pyrazole-4-carboxamide |
| 61 | 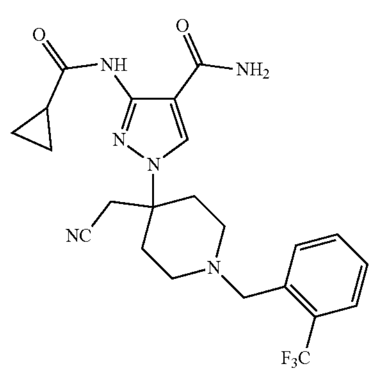 [SMILES: N#CCC1(n2cc(C(N)=O)c(NC(=O)C3CC3)n2)CCN(Cc2ccccc2C(F)(F)F)CC1] | 1-[4-(cyanomethyl)-1-[(3-iodophenyl)methyl]-4-piperidyl]-3-(cyclopropanecarbonylamino)pyrazole-4-carboxamide |

TABLE 1-continued

Exemplary Compounds of the Present Invention

| Ex. | Structure | Name |
|---|---|---|
| 62 | 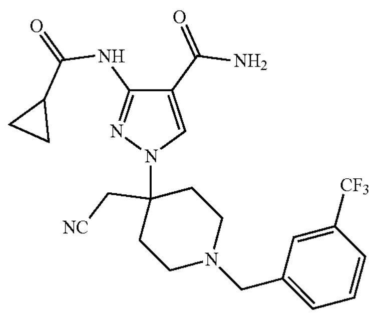 [SMILES: N#CCC1(n2cc(C(N)=O)c(NC(=O)C3CC3)n2)CCN(Cc2cccc(C(F)(F)F)c2)CC1] | 1-[4-(cyanomethyl)-1-[(4-iodophenyl)methyl]-4-piperidyl]-3-(cyclopropanecarbonylamino)pyrazole-4-carboxamide |
| 63 | 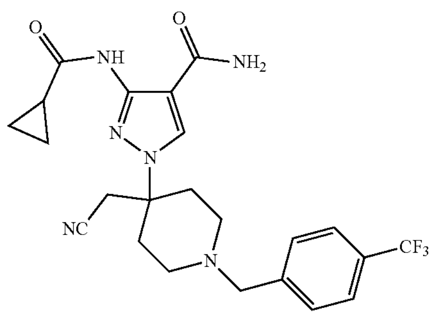 [SMILES: N#CCC1(n2cc(C(N)=O)c(NC(=O)C3CC3)n2)CCN(Cc2ccc(C(F)(F)F)cc2)CC1] | 1-[4-(cyanomethyl)-1-[(3-fluorophenyl)methyl]-4-piperidyl]-3-(cyclopropanecarbonylamino)pyrazole-4-carboxamide |
| 64 | 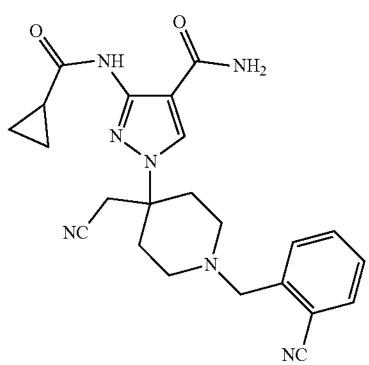 [SMILES: N#CCC1(n2cc(C(N)=O)c(NC(=O)C3CC3)n2)CCN(Cc2ccccc2C#N)CC1] | 1-[4-(cyanomethyl)-1-[(4-fluorophenyl)methyl]-4-piperidyl]-3-(cyclopropanecarbonylamino)pyrazole-4-carboxamide |
| 65 | 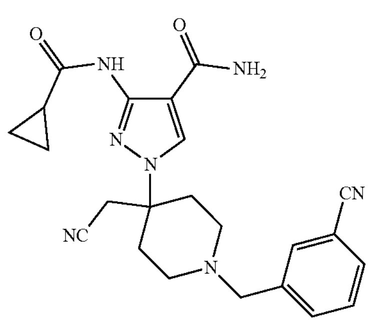 [SMILES: N#CCC1(n2cc(C(N)=O)c(NC(=O)C3CC3)n2)CCN(Cc2cccc(C#N)c2)CC1] | 1-[1-[(2-chlorophenyl)methyl]-4-(cyanomethyl)-4-piperidyl]-3-(cyclopropanecarbonylamino)pyrazole-4-carboxamide |

TABLE 1-continued

Exemplary Compounds of the Present Invention

| Ex. | Structure | Name |
|---|---|---|
| 66 | 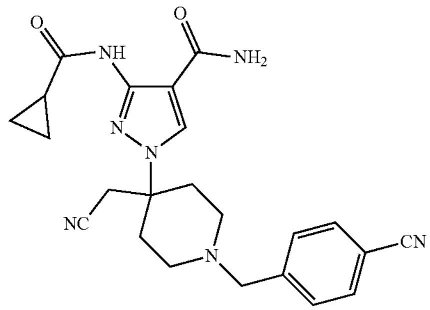 [SMILES: N#CCC1(n2cc(C(N)=O)c(NC(=O)C3CC3)n2)CCN(Cc2ccc(C#N)cc2)CC1] | 1-[1-[(3-chlorophenyl)methyl]-4-(cyanomethyl)-4-piperidyl]-3-(cyclopropanecarbonylamino)pyrazole-4-carboxamide |
| 67 | 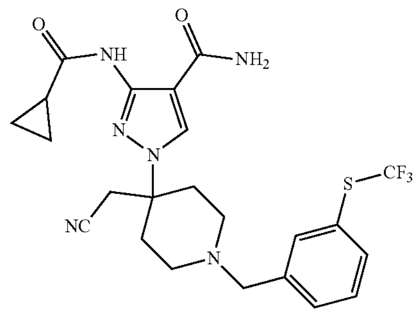 | 1-[1-[(4-chlorophenyl)methyl]-4-(cyanomethyl)-4-piperidyl]-3-(cyclopropanecarbonylamino)pyrazole-4-carboxamide |
| 68 | 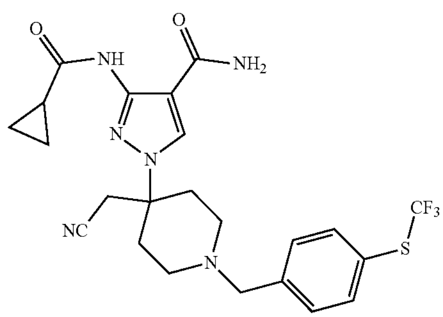 | 1-[4-(cyanomethyl)-1-[[2-(trifluoromethyl)phenyl]methyl]-4-piperidyl]-3-(cyclopropanecarbonylamino)pyrazole-4-carboxamide |
| 69 | 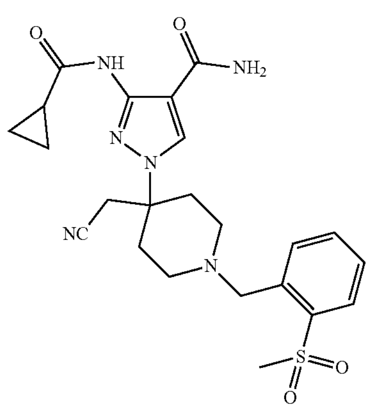 [SMILES: CS(=O)(=O)c1ccccc1CN1CCC(CC#N)(n2cc(C(N)=O)c(NC(=O)C3CC3)n2)CC1] | 1-[4-(cyanomethyl)-1-[[3-(trifluoromethyl)phenyl]methyl]-4-piperidyl]-3-(cyclopropanecarbonylamino)pyrazole-4-carboxamide |

TABLE 1-continued

Exemplary Compounds of the Present Invention

| Ex. | Structure | Name |
|---|---|---|
| 70 | 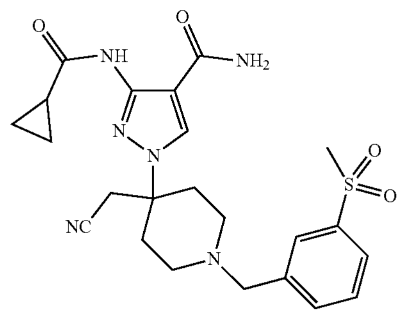 [SMILES: CS(=O)(=O)c1cccc(CN2CCC(CC#N)(n3cc(C(N)=O)c(NC(=O)C4CC4)n3)CC2)c1] | 1-[4-(cyanomethyl)-1-[[4-(trifluoromethyl)phenyl]methyl]-4-piperidyl]-3-(cyclopropanecarbonylamino)pyrazole-4-carboxamide |
| 71 | 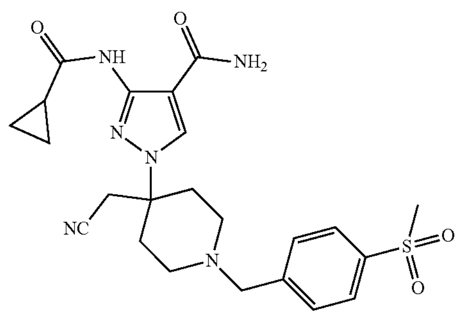 [SMILES: CS(=O)(=O)c1ccc(CN2CCC(CC#N)(n3cc(C(N)=O)c(NC(=O)C4CC4)n3)CC2)cc1] | 1-[4-(cyanomethyl)-1-[(2-cyanophenyl)methyl]-4-piperidyl]-3-(cyclopropanecarbonylamino)pyrazole-4-carboxamide |
| 72 | 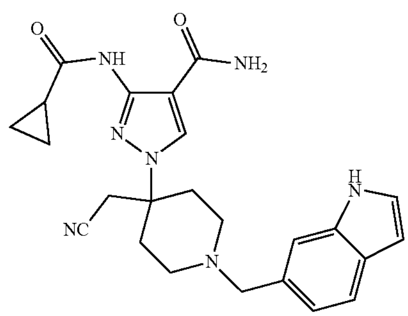 [SMILES: N#CCC1(n2cc(C(N)=O)c(NC(=O)C3CC3)n2)CCN(Cc2ccc3cc[nH]c3c2)CC1] | 1-[4-(cyanomethyl)-1-[(3-cyanophenyl)methyl]-4-piperidyl]-3-(cyclopropanecarbonylamino)pyrazole-4-carboxamide |
| 73 | 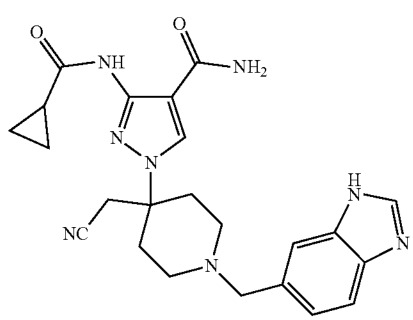 [SMILES: N#CCC1(n2cc(C(N)=O)c(NC(=O)C3CC3)n2)CCN(Cc2ccc3nc[nH]c3c2)CC1] | 1-[4-(cyanomethyl)-1-[(4-cyanophenyl)methyl]-4-piperidyl]-3-(cyclopropanecarbonylamino)pyrazole-4-carboxamide |
| 74 | 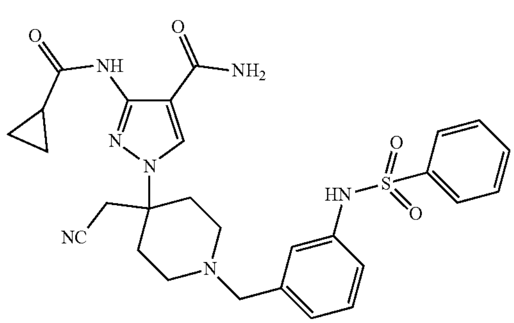 [SMILES: N#CCC1(n2cc(C(N)=O)c(NC(=O)C3CC3)n2)CCN(Cc2cccc(NS(=O)(=O)c3ccccc3)c2)CC1] | 1-[4-(cyanomethyl)-1-[[3-(trifluoromethylsulfanyl)phenyl]methyl]-4-piperidyl]-3-(cyclopropanecarbonylamino)pyrazole-4-carboxamide |

TABLE 1-continued

Exemplary Compounds of the Present Invention

| Ex. | Structure | Name |
|---|---|---|
| 75 | 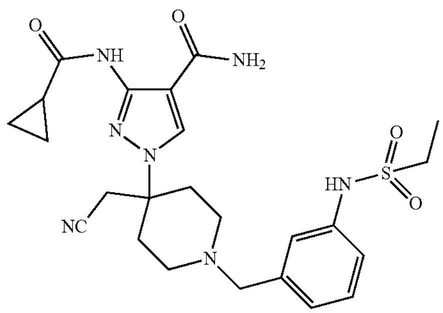 [SMILES: CCS(=O)(=O)Nc1cccc(CN2CCC(CC#N)(n3cc(C(N)=O)c(NC(=O)C4CC4)n3)CC2)c1] | 1-[4-(cyanomethyl)-1-[[4-(trifluoromethylsulfanyl)phenyl]methyl]-4-piperidyl]-3-(cyclopropanecarbonylamino)pyrazole-4-carboxamide |
| 76 | 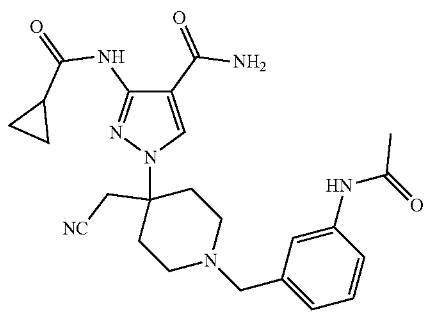 [SMILES: CC(=O)Nc1cccc(CN2CCC(CC#N)(n3cc(C(N)=O)c(NC(=O)C4CC4)n3)CC2)c1] | 1-[4-(cyanomethyl)-1-[(2-methylsulfonylphenyl)methyl]-4-piperidyl]-3-(cyclopropanecarbonylamino)pyrazole-4-carboxamide |
| 77 | 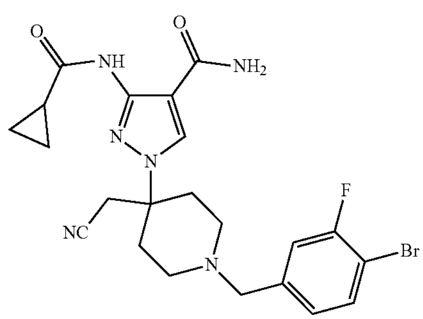 [SMILES: N#CCC1(n2cc(C(N)=O)c(NC(=O)C3CC3)n2)CCN(Cc2ccc(Br)c(F)c2)CC1] | 1-[4-(cyanomethyl)-1-[(3-methylsulfonylphenyl)methyl]-4-piperidyl]-3-(cyclopropanecarbonylamino)pyrazole-4-carboxamide |
| 78 | 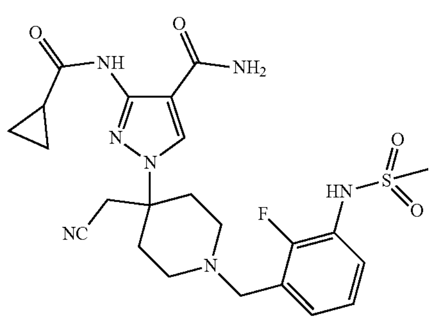 [SMILES: CS(=O)(=O)Nc1cccc(CN2CCC(CC#N)(n3cc(C(N)=O)c(NC(=O)C4CC4)n3)CC2)c1F] | 1-[4-(cyanomethyl)-1-[(4-methylsulfonylphenyl)methyl]-4-piperidyl]-3-(cyclopropanecarbonylamino)pyrazole-4-carboxamide |

TABLE 1-continued

Exemplary Compounds of the Present Invention

| Ex. | Structure | Name |
|---|---|---|
| 79 | 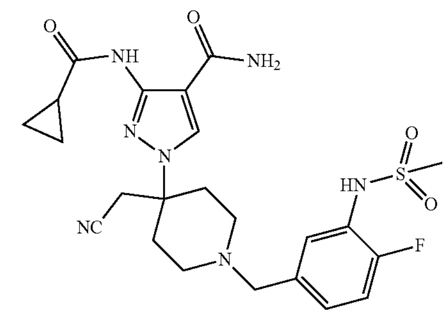 [SMILES: CS(=O)(=O)Nc1cc(CN2CCC(CC#N)(n3cc(C(N)=O)c(NC(=O)C4CC4)n3)CC2)ccc1F] | 1-[4-(cyanomethyl)-1-(1H-indol-6-ylmethyl)-4-piperidyl]-3-(cyclopropanecarbonylamino)pyrazole-4-carboxamide; formic acid |
| 80 | 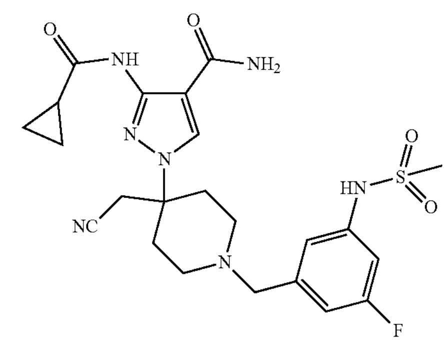 [SMILES: CS(=O)(=O)Nc1cc(F)cc(CN2CCC(CC#N)(n3cc(C(N)=O)c(NC(=O)C4CC4)n3)CC2)c1] | 1-[1-(3H-benzimidazol-5-ylmethyl)-4-(cyanomethyl)-4-piperidyl]-3-(cyclopropanecarbonylamino)pyrazole-4-carboxamide |
| 81 | 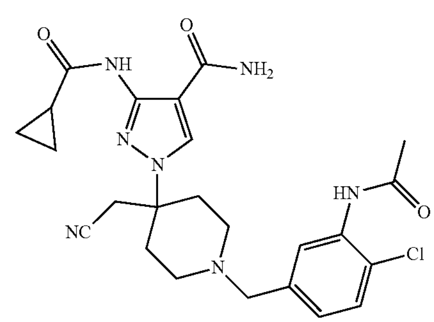 [SMILES: CC(=O)Nc1cc(CN2CCC(CC#N)(n3cc(C(N)=O)c(NC(=O)C4CC4)n3)CC2)ccc1Cl] | 1-[1-[[3-(benzenesulfonamido)phenyl]methyl]-4-(cyanomethyl)-4-piperidyl]-3-(cyclopropanecarbonylamino)pyrazole-4-carboxamide |
| 82 | 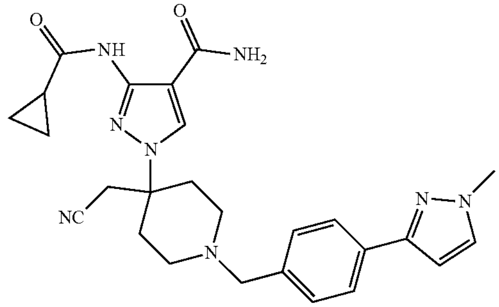 [SMILES: Cn1ccc(-c2ccc(CN3CCC(CC#N)(n4cc(C(N)=O)c(NC(=O)C5CC5)n4)CC3)cc2)n1] | 1-[4-(cyanomethyl)-1-[[3-(ethylsulfonylamino)phenyl]methyl]-4-piperidyl]-3-(cyclopropanecarbonylamino)pyrazole-4-carboxamide; formic acid |

TABLE 1-continued

Exemplary Compounds of the Present Invention

| Ex. | Structure | Name |
|---|---|---|
| 83 | 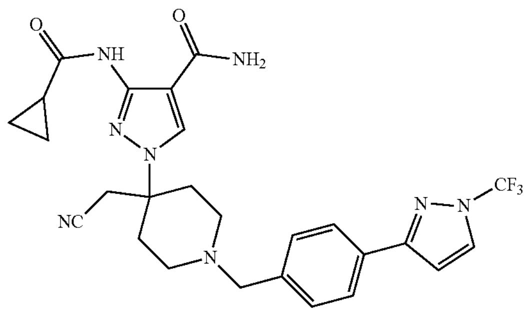 [SMILES: N#CCC1(n2cc(C(N)=O)c(NC(=O)C3CC3)n2)CCN(Cc2ccc(-c3ccn(C(F)(F)F)n3)cc2)CC1] | 1-[1-[(3-acetamidophenyl)methyl]-4-(cyanomethyl)-4-piperidyl]-3-(cyclopropanecarbonylamino)pyrazole-4-carboxamide |
| 84 | 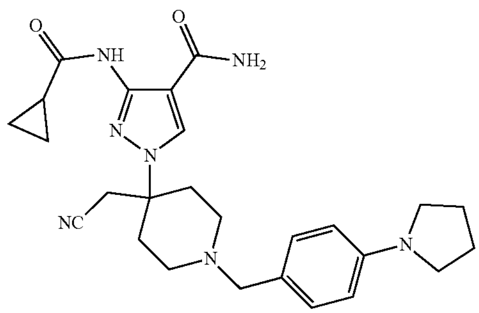 [SMILES: N#CCC1(n2cc(C(N)=O)c(NC(=O)C3CC3)n2)CCN(Cc2ccc(N3CCCC3)cc2)CC1] | 1-[1-[(4-bromo-3-fluoro-phenyl)methyl]-4-(cyanomethyl)-4-piperidyl]-3-(cyclopropanecarbonylamino)pyrazole-4-carboxamide |
| 85 | 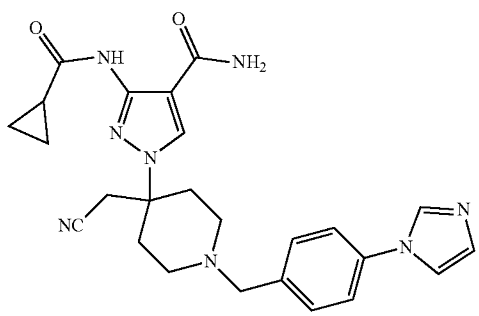 [SMILES: N#CCC1(n2cc(C(N)=O)c(NC(=O)C3CC3)n2)CCN(Cc2ccc(-n3ccnc3)cc2)CC1] | 1-[4-(cyanomethyl)-1-[[2-fluoro-3-(methanesulfonamido)phenyl]methyl]-4-piperidyl]-3-(cyclopropanecarbonylamino)pyrazole-4-carboxamide |
| 86 | 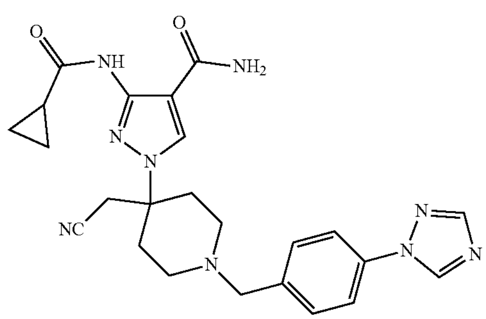 [SMILES: N#CCC1(n2cc(C(N)=O)c(NC(=O)C3CC3)n2)CCN(Cc2ccc(-n3cncn3)cc2)CC1] | 1-[4-(cyanomethyl)-1-[[4-fluoro-3-(methanesulfonamido)phenyl]methyl]-4-piperidyl]-3-(cyclopropanecarbonylamino)pyrazole-4-carboxamide |
| 87 | 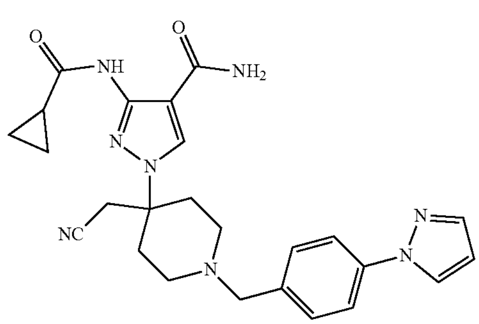 [SMILES: N#CCC1(n2cc(C(N)=O)c(NC(=O)C3CC3)n2)CCN(Cc2ccc(-n3cccn3)cc2)CC1] | 1-[4-(cyanomethyl)-1-[[3-fluoro-5-(methanesulfonamido)phenyl]methyl]-4-piperidyl]-3-(cyclopropanecarbonylamino)pyrazole-4-carboxamide |

TABLE 1-continued

Exemplary Compounds of the Present Invention

| Ex. | Structure | Name |
|---|---|---|
| 88 | 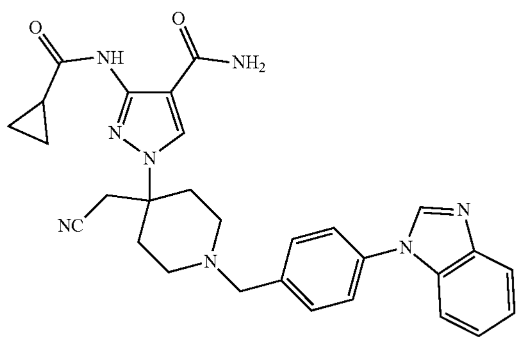 [SMILES: N#CCC1(n2cc(C(N)=O)c(NC(=O)C3CC3)n2)CCN(Cc2ccc(-n3cnc4ccccc43)cc2)CC1] | 1-[1-[(3-acetamido-4-chlorophenyl)methyl]-4-(cyanomethyl)-4-piperidyl]-3-(cyclopropanecarbonylamino)pyrazole-4-carboxamide |
| 89 | 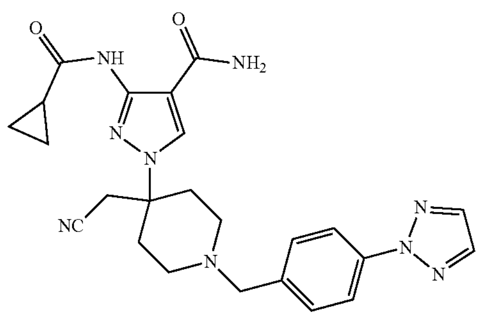 [SMILES: N#CCC1(n2cc(C(N)=O)c(NC(=O)C3CC3)n2)CCN(Cc2ccc(-n3nccn3)cc2)CC1] | 1-[4-(cyanomethyl)-1-[[4-(1-methylpyrazol-3-yl)phenyl]methyl]-4-piperidyl]-3-(cyclopropanecarbonylamino)pyrazole-4-carboxamide |
| 90 | 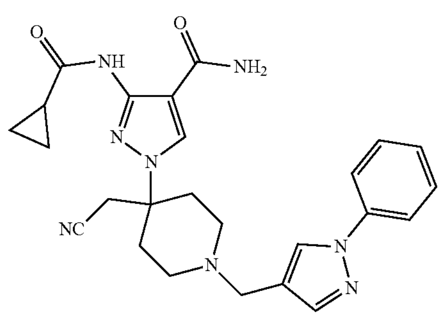 [SMILES: N#CCC1(n2cc(C(N)=O)c(NC(=O)C3CC3)n2)CCN(Cc2cnn(-c3ccccc3)c2)CC1] | 1-[4-(cyanomethyl)-1-[[4-[3-(trifluoromethyl)pyrazol-1-yl]phenyl]methyl]-4-piperidyl]-3-(cyclopropanecarbonylamino)pyrazole-4-carboxamide |
| 91 | 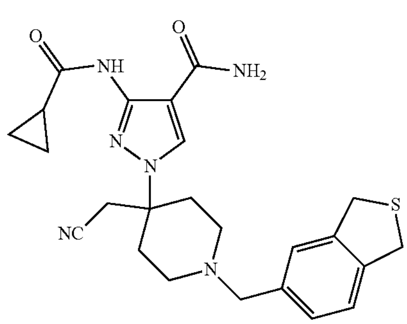 [SMILES: N#CCC1(n2cc(C(N)=O)c(NC(=O)C3CC3)n2)CCN(Cc2ccc3c(c2)CSC3)CC1] | 1-[4-(cyanomethyl)-1-[(4-pyrrolidin-1-ylphenyl)methyl]-4-piperidyl]-3-(cyclopropanecarbonylamino)pyrazole-4-carboxamide |

TABLE 1-continued

Exemplary Compounds of the Present Invention

| Ex. | Structure | Name |
|---|---|---|
| 92 | 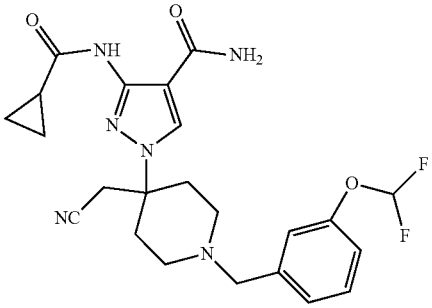 [SMILES: N#CCC1(n2cc(C(N)=O)c(NC(=O)C3CC3)n2)CCN(Cc2cccc(OC(F)F)c2)CC1] | 1-[4-(cyanomethyl)-1-[(4-imidazol-1-ylphenyl)methyl]-4-piperidyl]-3-(cyclopropanecarbonylamino)pyrazole-4-carboxamide |
| 93 | 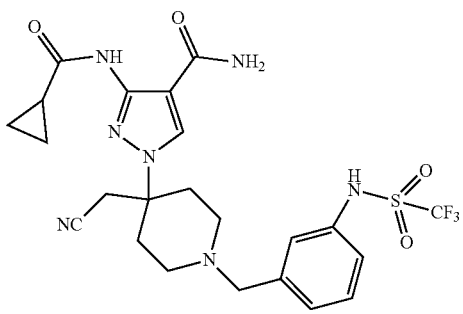 [SMILES: N#CCC1(n2cc(C(N)=O)c(NC(=O)C3CC3)n2)CCN(Cc2cccc(NS(=O)(=O)C(F)(F)F)c2)CC1] | 1-[4-(cyanomethyl)-1-[[4-(1,2,4-triazol-1-yl)phenyl]methyl]-4-piperidyl]-3-(cyclopropanecarbonylamino)pyrazole-4-carboxamide |
| 94 | 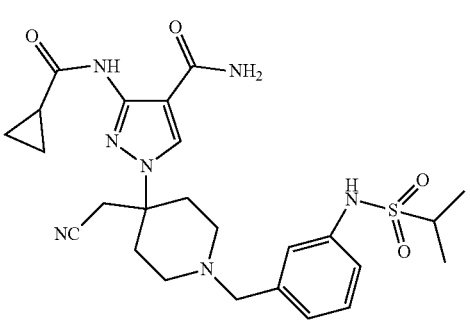 [SMILES: CC(C)S(=O)(=O)Nc1cccc(CN2CCC(CC#N)(n3cc(C(N)=O)c(NC(=O)C4CC4)n3)CC2)c1] | 1-[4-(cyanomethyl)-1-[(4-pyrazol-1-ylphenyl)methyl]-4-piperidyl]-3-(cyclopropanecarbonylamino)pyrazole-4-carboxamide |
| 95 | 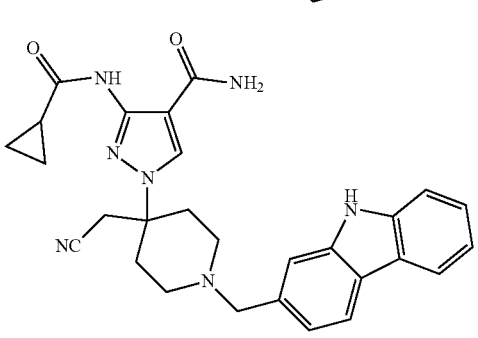 | 1-[1-[[4-(benzimidazol-1-yl)phenyl]methyl]-4-(cyanomethyl)-4-piperidyl]-3-(cyclopropanecarbonylamino)pyrazole-4-carboxamide |
| 96 | 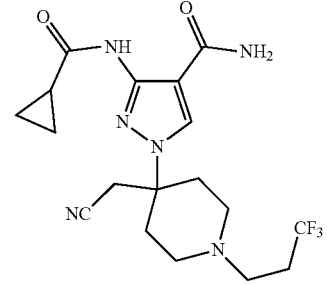 [SMILES: N#CCC1(n2cc(C(N)=O)c(NC(=O)C3CC3)n2)CCN(CCC(F)(F)F)CC1] | 1-[4-(cyanomethyl)-1-[[4-(triazol-2-yl)phenyl]methyl]-4-piperidyl]-3-(cyclopropanecarbonylamino)pyrazole-4-carboxamide |

TABLE 1-continued

Exemplary Compounds of the Present Invention

| Ex. | Structure | Name |
|---|---|---|
| 97 | 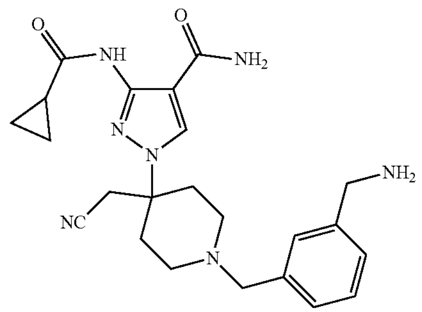 [SMILES: N#CCC1(n2cc(C(N)=O)c(NC(=O)C3CC3)n2)CCN(Cc2cccc(CN)c2)CC1] | 1-[4-(cyanomethyl)-1-[(1-phenylpyrazol-4-yl)methyl]-4-piperidyl]-3-(cyclopropanecarbonylamino)pyrazole-4-carboxamide |
| 98 | 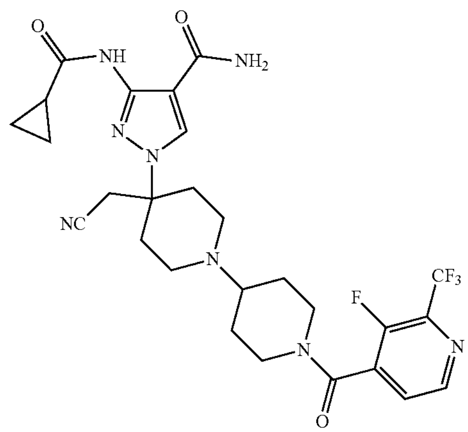 [SMILES: N#CCC1(n2cc(C(N)=O)c(NC(=O)C3CC3)n2)CCN(C2CCN(C(=O)c3ccnc(C(F)(F)F)c3F)CC2)CC1] | 1-[4-(cyanomethyl)-1-(1,3-dihydro-2-benzothiophen-5-ylmethyl)-4-piperidyl]-3-(cyclopropanecarbonylamino)pyrazole-4-carboxamide |
| 99 | 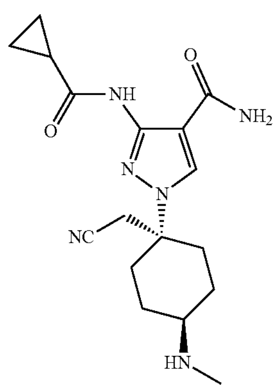 [SMILES: CN[C@H]1CC[C@](CC#N)(n2cc(C(N)=O)c(NC(=O)C3CC3)n2)CC1] | 1-[4-(cyanomethyl)-1-[[3-(difluoromethoxy)phenyl]methyl]-4-piperidyl]-3-(cyclopropanecarbonylamino)pyrazole-4-carboxamide |
| 100 | 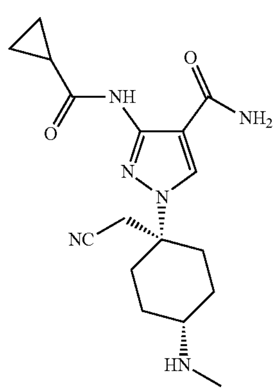 [SMILES: CN[C@H]1CC[C@@](CC#N)(n2cc(C(N)=O)c(NC(=O)C3CC3)n2)CC1] | 1-[4-(cyanomethyl)-1-[[3-(trifluoromethylsulfonylamino)phenyl]methyl]-4-piperidyl]-3-(cyclopropanecarbonylamino)pyrazole-4-carboxamide |

TABLE 1-continued

Exemplary Compounds of the Present Invention

| Ex. | Structure | Name |
| --- | --- | --- |
| 101 | 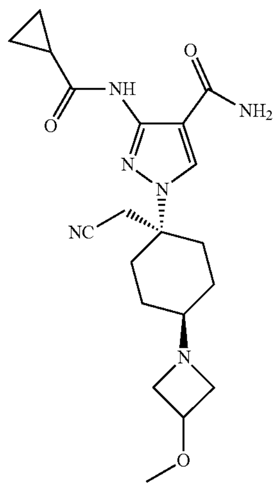 [SMILES: COC1CN([C@H]2CC[C@](CC#N)(n3cc(C(N)=O)c(NC(=O)C4CC4)n3)CC2)C1] | 1-[4-(cyanomethyl)-1-[[3-(isopropylsulfonylamino)phenyl]methyl]-4-piperidyl]-3-(cyclopropanecarbonylamino)pyrazole-4-carboxamide |
| 102 | 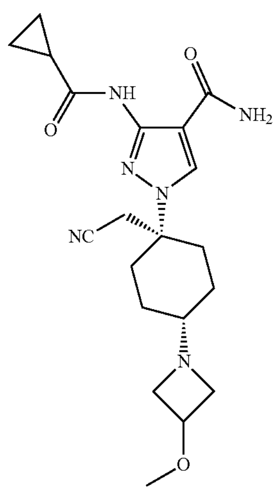 [SMILES: COC1CN([C@H]2CC[C@@](CC#N)(n3cc(C(N)=O)c(NC(=O)C4CC4)n3)CC2)C1] | 1-[1-(9H-carbazol-2-ylmethyl)-4-(cyanomethyl)-4-piperidyl]-3-(cyclopropanecarbonylamino)pyrazole-4-carboxamide |
| 103 | 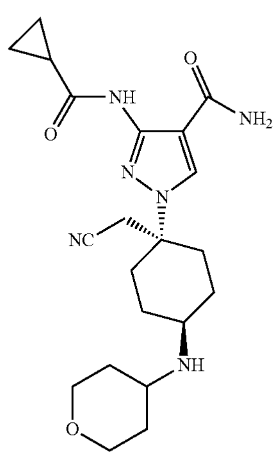 [SMILES: N#CC[C@]1(n2cc(C(N)=O)c(NC(=O)C3CC3)n2)CC[C@H](NC2CCOCC2)CC1] | 1-[4-(cyanomethyl)-1-(3,3,3-trifluoropropyl)-4-piperidyl]-3-(cyclopropanecarbonylamino)pyrazole-4-carboxamide |

TABLE 1-continued

Exemplary Compounds of the Present Invention

| Ex. | Structure | Name |
|---|---|---|
| 104 | 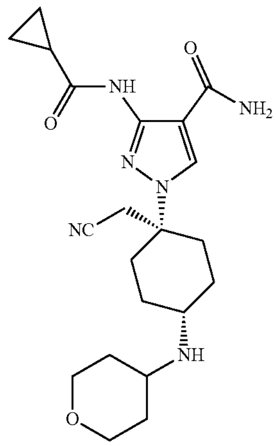 [SMILES: N#CC[C@]1(n2cc(C(N)=O)c(NC(=O)C3CC3)n2)CC[C@@H](NC2CCOCC2)CC1] | 1-[1-[[3-(aminomethyl)phenyl]methyl]-4-(cyanomethyl)-4-piperidyl]-3-(cyclopropanecarbonylamino)pyrazole-4-carboxamide |
| 105 | 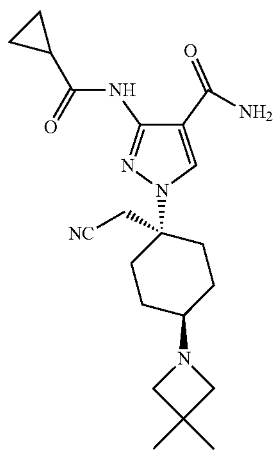 [SMILES: CC1(C)CN([C@H]2CC[C@](CC#N)(n3cc(C(N)=O)c(NC(=O)C4CC4)n3)CC2)C1] | 1-[4-(cyanomethyl)-1-[1-[3-fluoro-2-(trifluoromethyl)pyridine-4-carbonyl]-4-piperidyl]-4-piperidyl]-3-(cyclopropanecarbonylamino)pyrazole-4-carboxamide |
| 106 | 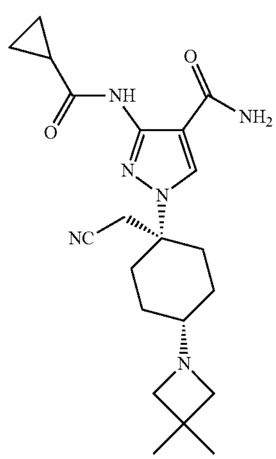 [SMILES: CC1(C)CN([C@H]2CC[C@@](CC#N)(n3cc(C(N)=O)c(NC(=O)C4CC4)n3)CC2)C1] | 1-[1-(cyanomethyl)-4-(methylamino)cyclohexyl]-3-(cyclopropanecarbonylamino)pyrazole-4-carboxamide |

TABLE 1-continued

Exemplary Compounds of the Present Invention

| Ex. | Structure | Name |
|---|---|---|
| 107 | 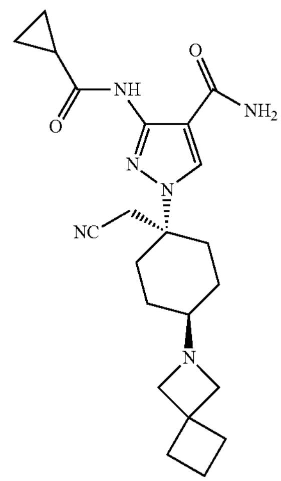 [SMILES: N#CC[C@]1(n2cc(C(N)=O)c(NC(=O)C3CC3)n2)CC[C@H](N2CC3(CCC3)C2)CC1] | 1-[1-(cyanomethyl)-4-(methylamino)cyclohexyl]-3-(cyclopropanecarbonylamino)pyrazole-4-carboxamide |
| 108 | 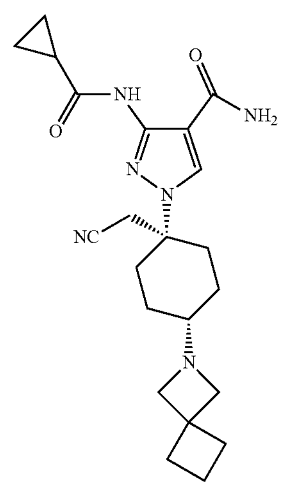 [SMILES: N#CC[C@]1(n2cc(C(N)=O)c(NC(=O)C3CC3)n2)CC[C@@H](N2CC3(CCC3)C2)CC1] | 1-[1-(cyanomethyl)-4-(3-methoxyazetidin-1-yl)cyclohexyl]-3-(cyclopropanecarbonylamino)pyrazole-4-carboxamide |
| 109 | 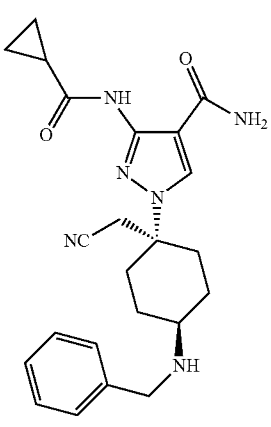 [SMILES: N#CC[C@]1(n2cc(C(N)=O)c(NC(=O)C3CC3)n2)CC[C@H](NCc2ccccc2)CC1] | 1-[1-(cyanomethyl)-4-(3-methoxyazetidin-1-yl)cyclohexyl]-3-(cyclopropanecarbonylamino)pyrazole-4-carboxamide |

TABLE 1-continued

Exemplary Compounds of the Present Invention

| Ex. | Structure | Name |
|---|---|---|
| 110 | 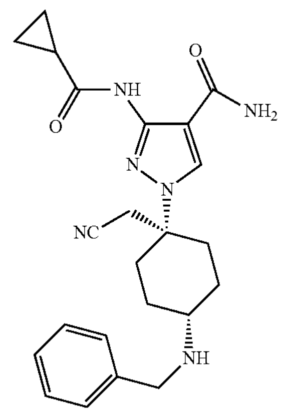 [SMILES: N#CC[C@]1(n2cc(C(N)=O)c(NC(=O)C3CC3)n2)CC[C@@H](NCc2ccccc2)CC1] | 1-[1-(cyanomethyl)-4-(tetrahydropyran-4-ylamino)cyclohexyl]-3-(cyclopropanecarbonylamino)pyrazole-4-carboxamide |
| 111 | 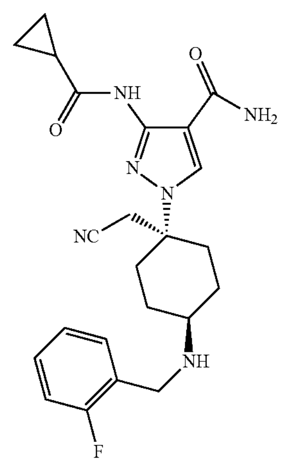 [SMILES: N#CC[C@]1(n2cc(C(N)=O)c(NC(=O)C3CC3)n2)CC[C@H](NCc2ccccc2F)CC1] | 1-[1-(cyanomethyl)-4-(tetrahydropyran-4-ylamino)cyclohexyl]-3-(cyclopropanecarbonylamino)pyrazole-4-carboxamide |
| 112 | 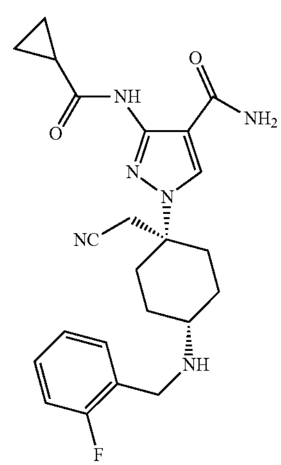 [SMILES: N#CC[C@]1(n2cc(C(N)=O)c(NC(=O)C3CC3)n2)CC[C@@H](NCc2ccccc2F)CC1] | 1-[1-(cyanomethyl)-4-(3,3-dimethylazetidin-1-yl)cyclohexyl]-3-(cyclopropanecarbonylamino)pyrazole-4-carboxamide; formic acid |

TABLE 1-continued

Exemplary Compounds of the Present Invention

| Ex. | Structure | Name |
|---|---|---|
| 113 | 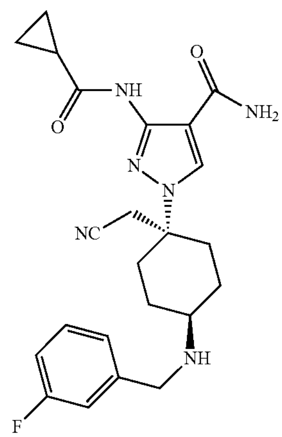 [SMILES: N#CC[C@]1(n2cc(C(N)=O)c(NC(=O)C3CC3)n2)CC[C@H](NCc2cccc(F)c2)CC1] | 1-[1-(cyanomethyl)-4-(3,3-dimethylazetidin-1-yl)cyclohexyl]-3-(cyclopropanecarbonylamino)pyrazole-4-carboxamide |
| 114 | 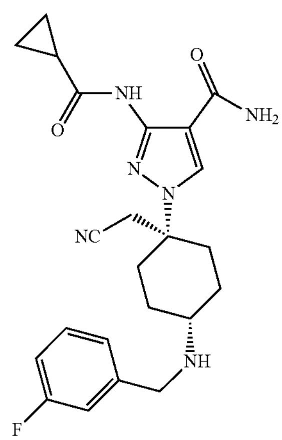 [SMILES: N#CC[C@]1(n2cc(C(N)=O)c(NC(=O)C3CC3)n2)CC[C@@H](NCc2cccc(F)c2)CC1] | 1-[4-(2-azaspiro[3.3]heptan-2-yl)-1-(cyanomethyl)cyclohexyl]-3-(cyclopropanecarbonylamino)pyrazole-4-carboxamide; formic acid |
| 115 | 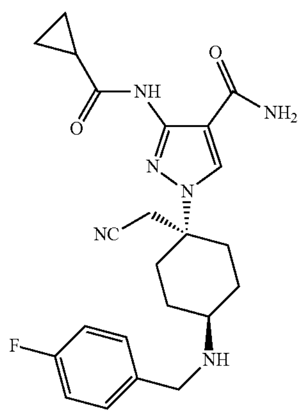 [SMILES: N#CC[C@]1(n2cc(C(N)=O)c(NC(=O)C3CC3)n2)CC[C@H](NCc2ccc(F)cc2)CC1] | 1-[4-(2-azaspiro[3.3]heptan-2-yl)-1-(cyanomethyl)cyclohexyl]-3-(cyclopropanecarbonylamino)pyrazole-4-carboxamide |

TABLE 1-continued

Exemplary Compounds of the Present Invention

| Ex. | Structure | Name |
| --- | --- | --- |
| 116 | 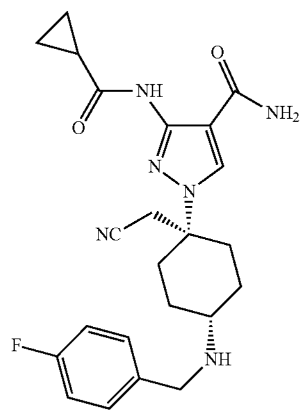 [SMILES: N#CC[C@]1(n2cc(C(N)=O)c(NC(=O)C3CC3)n2)CC[C@@H](NCc2ccc(F)cc2)CC1] | 1-[4-(benzylamino)-1-(cyanomethyl)cyclohexyl]-3-(cyclopropanecarbonylamino)pyrazole-4-carboxamide; formic acid |
| 117 | 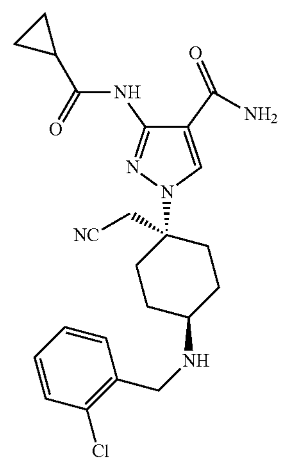 [SMILES: N#CC[C@]1(n2cc(C(N)=O)c(NC(=O)C3CC3)n2)CC[C@H](NCc2ccccc2Cl)CC1] | 1-[4-(benzylamino)-1-(cyanomethyl)cyclohexyl]-3-(cyclopropanecarbonylamino)pyrazole-4-carboxamide; formic acid |
| 118 | 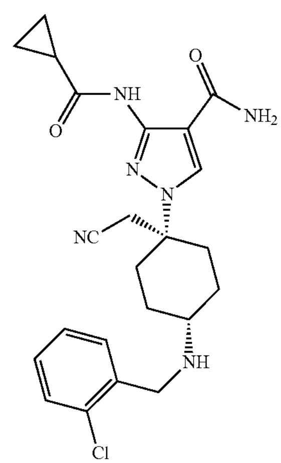 [SMILES: N#CC[C@]1(n2cc(C(N)=O)c(NC(=O)C3CC3)n2)CC[C@@H](NCc2ccccc2Cl)CC1] | 1-[1-(cyanomethyl)-4-[(2-fluorophenyl)methylamino]cyclohexyl]-3-(cyclopropanecarbonylamino)pyrazole-4-carboxamide |

TABLE 1-continued

Exemplary Compounds of the Present Invention

| Ex. | Structure | Name |
|---|---|---|
| 119 | 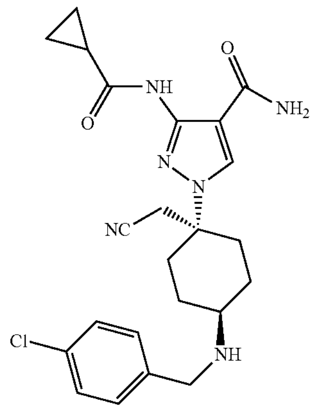 [SMILES: N#CC[C@]1(n2cc(C(N)=O)c(NC(=O)C3CC3)n2)CC[C@H](NCc2ccc(Cl)cc2)CC1] | 1-[1-(cyanomethyl)-4-[(2-fluorophenyl)methylamino]cyclohexyl]-3-(cyclopropanecarbonylamino)pyrazole-4-carboxamide |
| 120 | 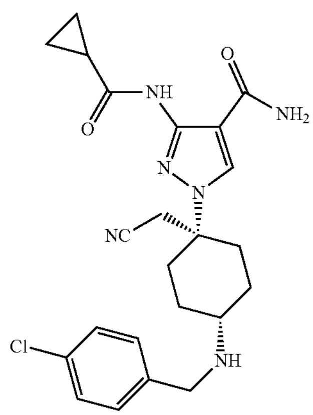 [SMILES: N#CC[C@]1(n2cc(C(N)=O)c(NC(=O)C3CC3)n2)CC[C@@H](NCc2ccc(Cl)cc2)CC1] | 1-[1-(cyanomethyl)-4-[(3-fluorophenyl)methylamino]cyclohexyl]-3-(cyclopropanecarbonylamino)pyrazole-4-carboxamide |
| 121 | 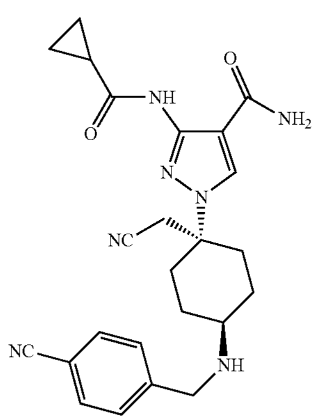 [SMILES: N#CC[C@]1(n2cc(C(N)=O)c(NC(=O)C3CC3)n2)CC[C@H](NCc2ccc(C#N)cc2)CC1] | 1-[1-(cyanomethyl)-4-[(3-fluorophenyl)methylamino]cyclohexyl]-3-(cyclopropanecarbonylamino)pyrazole-4-carboxamide |

TABLE 1-continued

Exemplary Compounds of the Present Invention

| Ex. | Structure | Name |
| --- | --- | --- |
| 122 | 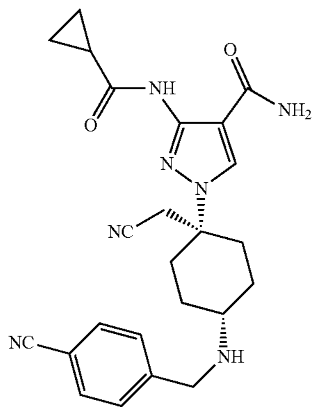 [SMILES: N#CC[C@]1(n2cc(C(N)=O)c(NC(=O)C3CC3)n2)CC[C@@H](NCc2ccc(C#N)cc2)CC1] | 1-[1-(cyanomethyl)-4-[(4-fluorophenyl)methylamino]cyclohexyl]-3-(cyclopropanecarbonylamino)pyrazole-4-carboxamide |
| 123 | 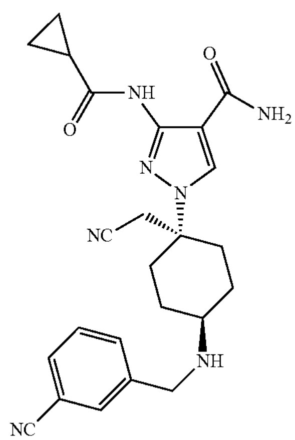 [SMILES: N#CC[C@]1(n2cc(C(N)=O)c(NC(=O)C3CC3)n2)CC[C@H](NCc2cccc(C#N)c2)CC1] | 1-[1-(cyanomethyl)-4-[(4-fluorophenyl)methylamino]cyclohexyl]-3-(cyclopropanecarbonylamino)pyrazole-4-carboxamide |
| 124 | 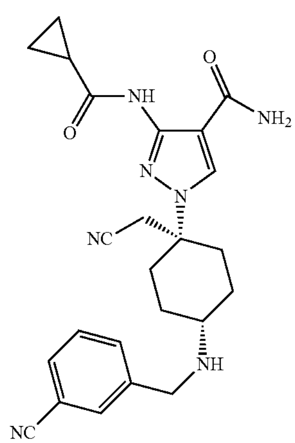 [SMILES: N#CC[C@]1(n2cc(C(N)=O)c(NC(=O)C3CC3)n2)CC[C@@H](NCc2cccc(C#N)c2)CC1] | 1-[4-[(2-chlorophenyl)methylamino]-1-(cyanomethyl)cyclohexyl]-3-(cyclopropanecarbonylamino)pyrazole-4-carboxamide |

TABLE 1-continued

Exemplary Compounds of the Present Invention

| Ex. | Structure | Name |
|---|---|---|
| 125 | 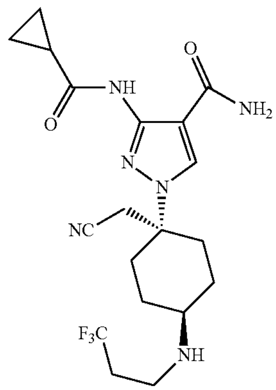 [SMILES: N#CC[C@]1(n2cc(C(N)=O)c(NC(=O)C3CC3)n2)CC[C@H](NCCC(F)(F)F)CC1] | 1-[4-[(2-chlorophenyl)methylamino]-1-(cyanomethyl)cyclohexyl]-3-(cyclopropanecarbonylamino)pyrazole-4-carboxamide |
| 126 | 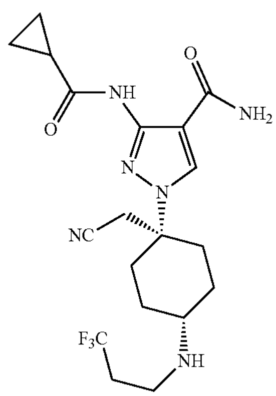 [SMILES: N#CC[C@]1(n2cc(C(N)=O)c(NC(=O)C3CC3)n2)CC[C@@H](NCCC(F)(F)F)CC1] | 1-[4-[(4-chlorophenyl)methylamino]-1-(cyanomethyl)cyclohexyl]-3-(cyclopropanecarbonylamino)pyrazole-4-carboxamide |
| 127 | 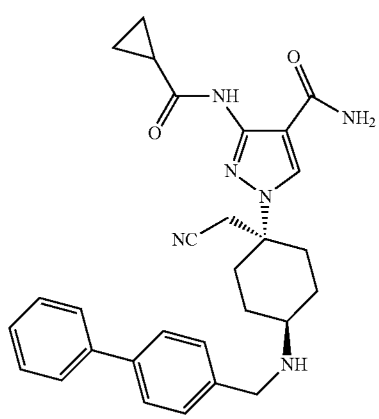 [SMILES: N#CC[C@]1(n2cc(C(N)=O)c(NC(=O)C3CC3)n2)CC[C@H](NCc2ccc(-c3ccccc3)cc2)CC1] | 1-[4-[(4-chlorophenyl)methylamino]-1-(cyanomethyl)cyclohexyl]-3-(cyclopropanecarbonylamino)pyrazole-4-carboxamide |

TABLE 1-continued

Exemplary Compounds of the Present Invention

| Ex. | Structure | Name |
|---|---|---|
| 128 | 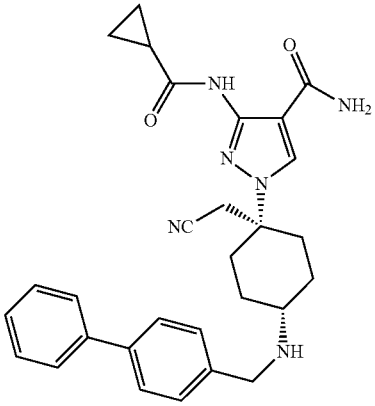 [SMILES: N#CC[C@]1(n2cc(C(N)=O)c(NC(=O)C3CC3)n2)CC[C@@H](NCc2ccc(-c3ccccc3)cc2)CC1] | 1-[1-(cyanomethyl)-4-[(4-cyanophenyl)methylamino]cyclohexyl]-3-(cyclopropanecarbonylamino)pyrazole-4-carboxamide |
| 129 | 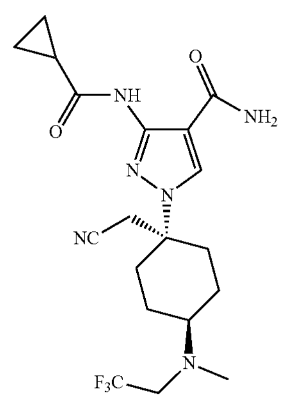 [SMILES: CN(CC(F)(F)F)[C@H]1CC[C@](CC#N)(n2cc(C(N)=O)c(NC(=O)C3CC3)n2)CC1] | 1-[1-(cyanomethyl)-4-[(4-cyanophenyl)methylamino]cyclohexyl]-3-(cyclopropanecarbonylamino)pyrazole-4-carboxamide |
| 130 | 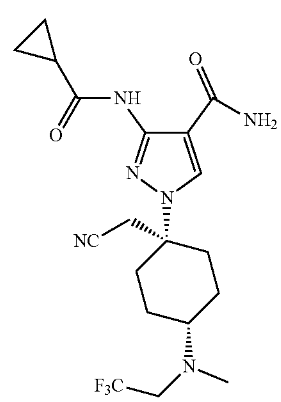 [SMILES: CN(CC(F)(F)F)[C@H]1CC[C@@](CC#N)(n2cc(C(N)=O)c(NC(=O)C3CC3)n2)CC1] | 1-[1-(cyanomethyl)-4-[(3-cyanophenyl)methylamino]cyclohexyl]-3-(cyclopropanecarbonylamino)pyrazole-4-carboxamide |

TABLE 1-continued

Exemplary Compounds of the Present Invention

| Ex. | Structure | Name |
|---|---|---|
| 131 | 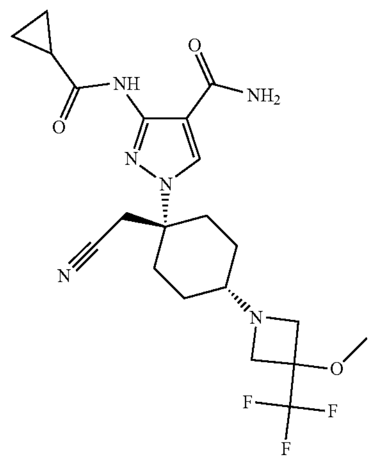 [SMILES: COC1(C(F)(F)F)CN([C@H]2CC[C@@](CC#N)(n3cc(C(N)=O)c(NC(=O)C4CC4)n3)CC2)C1] | 1-[1-(cyanomethyl)-4-[(3-cyanophenyl)methylamino]cyclohexyl]-3-(cyclopropanecarbonylamino)pyrazole-4-carboxamide |
| 132 | 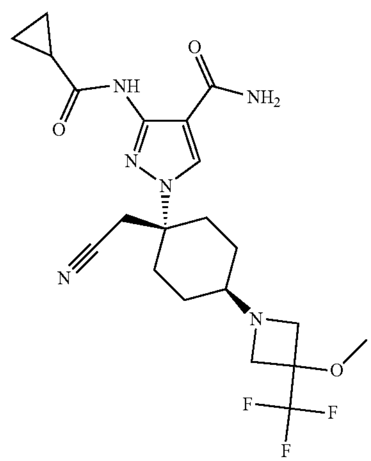 [SMILES: COC1(C(F)(F)F)CN([C@H]2CC[C@](CC#N)(n3cc(C(N)=O)c(NC(=O)C4CC4)n3)CC2)C1] | 1-[1-(cyanomethyl)-4-(3,3,3-trifluoropropylamino)cyclohexyl]-3-(cyclopropanecarbonylamino)pyrazole-4-carboxamide |
| 133 | 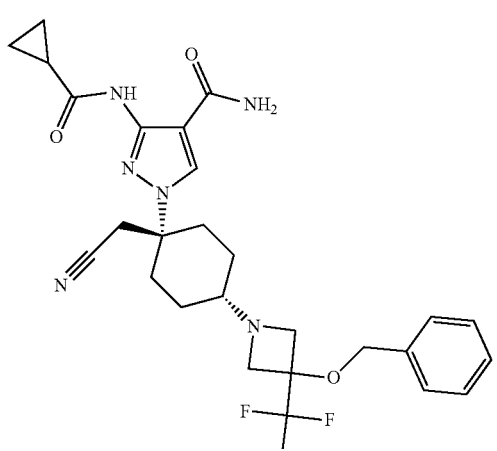 | 1-[1-(cyanomethyl)-4-(3,3,3-trifluoropropylamino)cyclohexyl]-3-(cyclopropanecarbonylamino)pyrazole-4-carboxamide |

TABLE 1-continued

Exemplary Compounds of the Present Invention

| Ex. | Structure | Name |
|---|---|---|
| 134 | 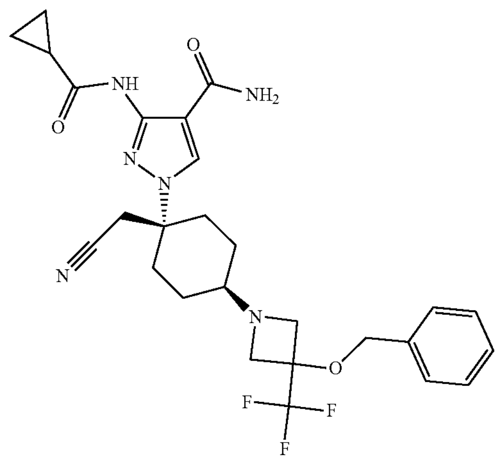 [SMILES: N#CC[C@]1(n2cc(C(N)=O)c(NC(=O)C3CC3)n2)CC[C@H](N2CC(OCc3ccccc3)(C(F)(F)F)C2)CC1] | 1-[1-(cyanomethyl)-4-[(4-phenylphenyl)methylamino]cyclohexyl]-3-(cyclopropanecarbonylamino)pyrazole-4-carboxamide |
| 135 | 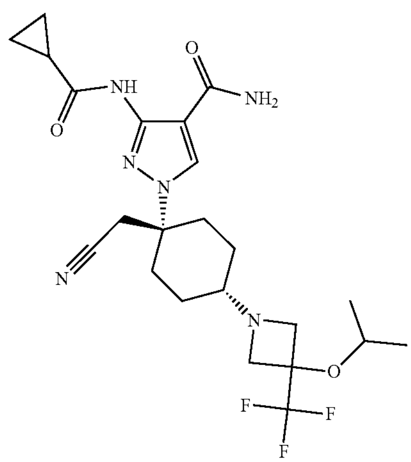 [SMILES: CC(C)OC1(C(F)(F)F)CN([C@H]2CC[C@@](CC#N)(n3cc(C(N)=O)c(NC(=O)C4CC4)n3)CC2)C1] | 1-[1-(cyanomethyl)-4-[(4-phenylphenyl)methylamino]cyclohexyl]-3-(cyclopropanecarbonylamino)pyrazole-4-carboxamide |
| 136 | 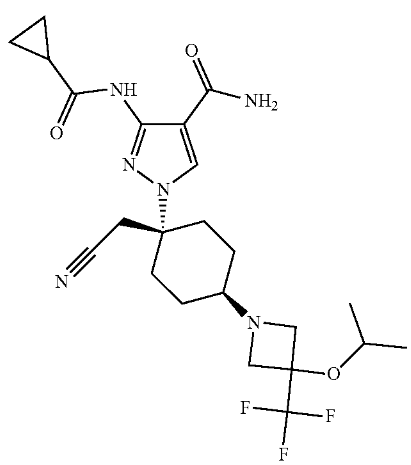 [SMILES: CC(C)OC1(C(F)(F)F)CN([C@H]2CC[C@](CC#N)(n3cc(C(N)=O)c(NC(=O)C4CC4)n3)CC2)C1] | 1-[1-(cyanomethyl)-4-[methyl(2,2,2-trifluoroethyl)amino]cyclohexyl]-3-(cyclopropanecarbonylamino)pyrazole-4-carboxamide |

TABLE 1-continued

Exemplary Compounds of the Present Invention

| Ex. | Structure | Name |
|---|---|---|
| 137 | 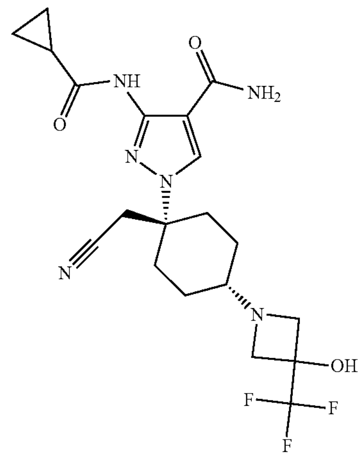 [SMILES: N#CC[C@]1(n2cc(C(N)=O)c(NC(=O)C3CC3)n2)CC[C@@H](N2CC(O)(C(F)(F)F)C2)CC1] | 1-[1-(cyanomethyl)-4-[3-hydroxy-3-(trifluoromethyl)azetidin-1-yl]cyclohexyl]-3-(cyclopropanecarbonylamino)pyrazole-4-carboxamide |
| 138 | 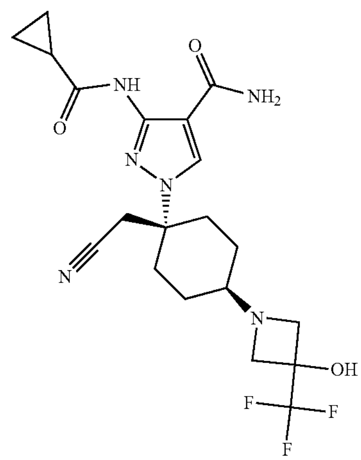 [SMILES: N#CC[C@]1(n2cc(C(N)=O)c(NC(=O)C3CC3)n2)CC[C@H](N2CC(O)(C(F)(F)F)C2)CC1] | 1-[1-(cyanomethyl)-4-[3-hydroxy-3-(trifluoromethyl)azetidin-1-yl]cyclohexyl]-3-(cyclopropanecarbonylamino)pyrazole-4-carboxamide |
| 139 | 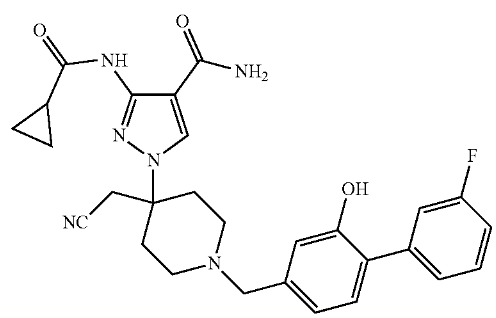 [SMILES: N#CCC1(n2cc(C(N)=O)c(NC(=O)C3CC3)n2)CCN(Cc2ccc(-c3cccc(F)c3)c(O)c2)CC1] | 1-[4-(cyanomethyl)-1-[[4-(3-fluorophenyl)-3-hydroxy-phenyl]methyl]-4-piperidyl]-3-(cyclopropanecarbonylamino)pyrazole-4-carboxamide |
| 140 | 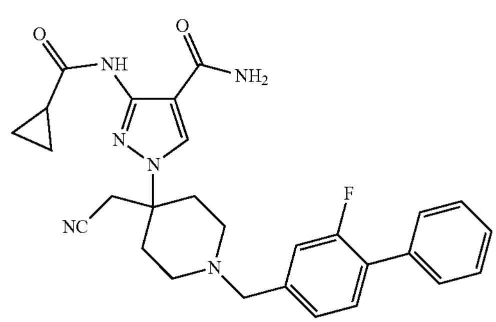 [SMILES: N#CCC1(n2cc(C(N)=O)c(NC(=O)C3CC3)n2)CCN(Cc2ccc(-c3ccccc3)c(F)c2)CC1] | 1-[4-(cyanomethyl)-1-[(3-fluoro-4-phenyl-phenyl)methyl]-4-piperidyl]-3-(cyclopropanecarbonylamino)pyrazole-4-carboxamide |

TABLE 1-continued

Exemplary Compounds of the Present Invention

| Ex. | Structure | Name |
|---|---|---|
| 141 | 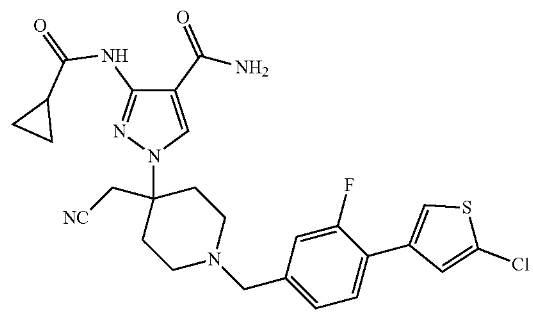 [SMILES: N#CCC1(n2cc(C(N)=O)c(NC(=O)C3CC3)n2)CCN(Cc2ccc(-c3csc(Cl)c3)c(F)c2)CC1] | 1-[1-[[4-(5-chloro-3-thienyl)-3-fluoro-phenyl]methyl]-4-(cyanomethyl)-4-piperidyl]-3-(cyclopropanecarbonylamino)pyrazole-4-carboxamide |
| 142 | 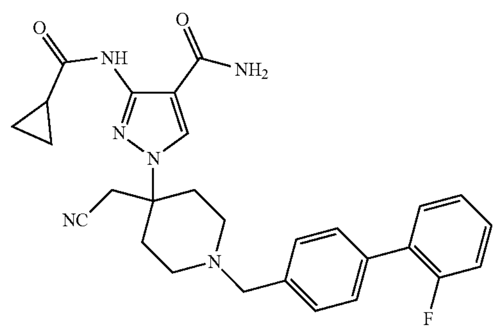 [SMILES: N#CCC1(n2cc(C(N)=O)c(NC(=O)C3CC3)n2)CCN(Cc2ccc(-c3ccccc3F)cc2)CC1] | 1-[4-(cyanomethyl)-1-[[4-(2-fluorophenyl)phenyl]methyl]-4-piperidyl]-3-(cyclopropanecarbonylamino)pyrazole-4-carboxamide |
| 143 | 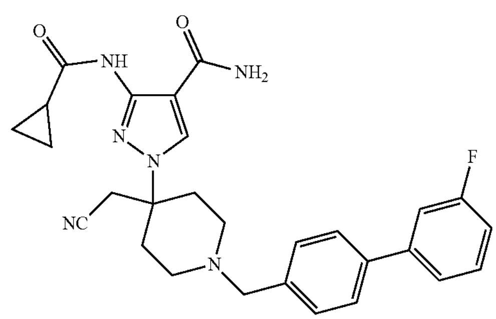 | 1-[4-(cyanomethyl)-1-[[4-(3-fluorophenyl)phenyl]methyl]-4-piperidyl]-3-(cyclopropanecarbonylamino)pyrazole-4-carboxamide |
| 144 | 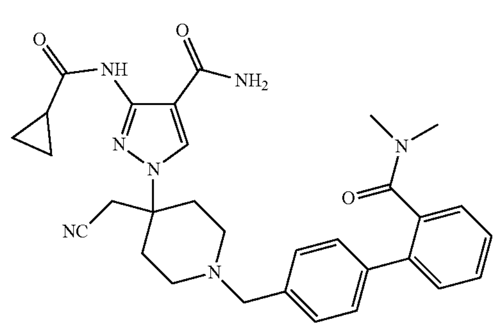 [SMILES: CN(C)C(=O)c1ccccc1-c1ccc(CN2CCC(CC#N)(n3cc(C(N)=O)c(NC(=O)C4CC4)n3)CC2)cc1] | 1-[4-(cyanomethyl)-1-[[4-[2-(dimethylcarbamoyl)phenyl]phenyl]methyl]-4-piperidyl]-3-(cyclopropanecarbonylamino)pyrazole-4-carboxamide |

TABLE 1-continued

Exemplary Compounds of the Present Invention

| Ex. | Structure | Name |
|---|---|---|
| 145 | 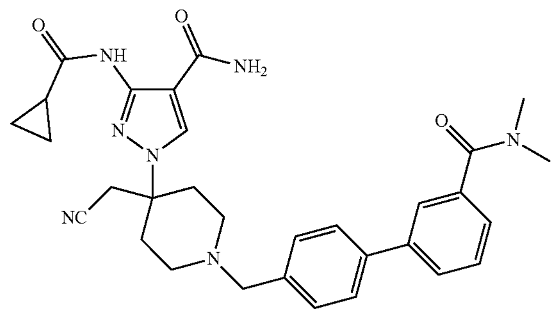 [SMILES: CN(C)C(=O)c1cccc(-c2ccc(CN3CCC(CC#N)(n4cc(C(N)=O)c(NC(=O)C5CC5)n4)CC3)cc2)c1] | 1-[4-(cyanomethyl)-1-[[4-[3-(dimethylcarbamoyl)phenyl]phenyl]methyl]-4-piperidyl]-3-(cyclopropanecarbonylamino)pyrazole-4-carboxamide |
| 146 | 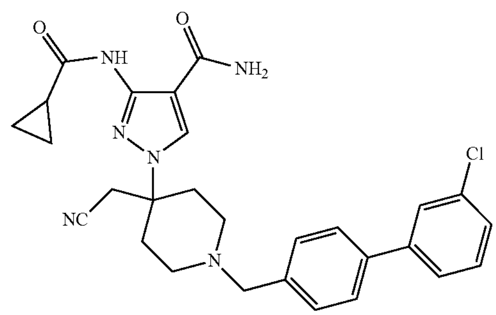 [SMILES: N#CCC1(n2cc(C(N)=O)c(NC(=O)C3CC3)n2)CCN(Cc2ccc(-c3cccc(Cl)c3)cc2)CC1] | 1-[1-[[4-(3-chlorophenyl)phenyl]methyl]-4-(cyanomethyl)-4-piperidyl]-3-(cyclopropanecarbonylamino)pyrazole-4-carboxamide |
| 147 | 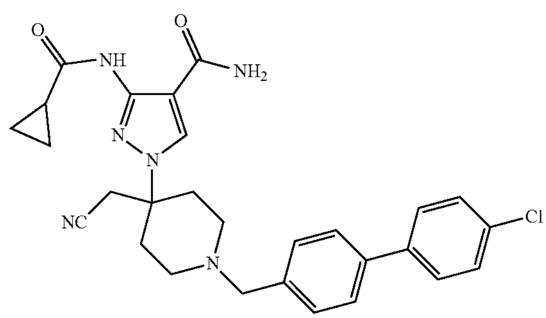 [SMILES: N#CCC1(n2cc(C(N)=O)c(NC(=O)C3CC3)n2)CCN(Cc2ccc(-c3ccc(Cl)cc3)cc2)CC1] | 1-[1-[[4-(4-chlorophenyl)phenyl]methyl]-4-(cyanomethyl)-4-piperidyl]-3-(cyclopropanecarbonylamino)pyrazole-4-carboxamide |
| 148 | 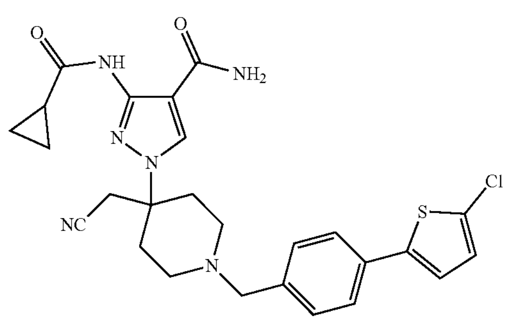 [SMILES: N#CCC1(n2cc(C(N)=O)c(NC(=O)C3CC3)n2)CCN(Cc2ccc(-c3ccc(Cl)s3)cc2)CC1] | 1-[1-[[4-(5-chloro-2-thienyl)phenyl]methyl]-4-(cyanomethyl)-4-piperidyl]-3-(cyclopropanecarbonylamino)pyrazole-4-carboxamide |
| 149 | 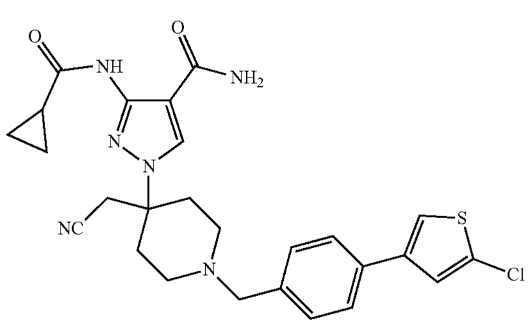 [SMILES: N#CCC1(n2cc(C(N)=O)c(NC(=O)C3CC3)n2)CCN(Cc2ccc(-c3csc(Cl)c3)cc2)CC1] | 1-[1-[[4-(5-chloro-3-thienyl)phenyl]methyl]-4-(cyanomethyl)-4-piperidyl]-3-(cyclopropanecarbonylamino)pyrazole-4-carboxamide |

TABLE 1-continued

Exemplary Compounds of the Present Invention

| Ex. | Structure | Name |
|---|---|---|
| 150 | 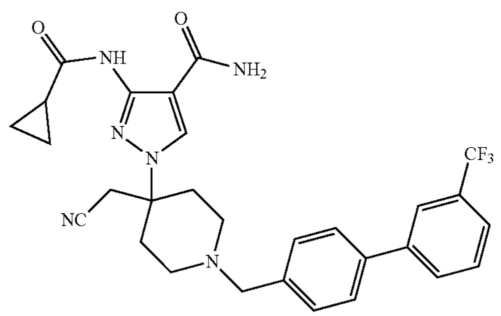 [SMILES: N#CCC1(n2cc(C(N)=O)c(NC(=O)C3CC3)n2)CCN(Cc2ccc(-c3cccc(C(F)(F)F)c3)cc2)CC1] | 1-[4-(cyanomethyl)-1-[[4-[3-(trifluoromethyl)phenyl]phenyl]methyl]-4-piperidyl]-3-(cyclopropanecarbonylamino)pyrazole-4-carboxamide |
| 151 | 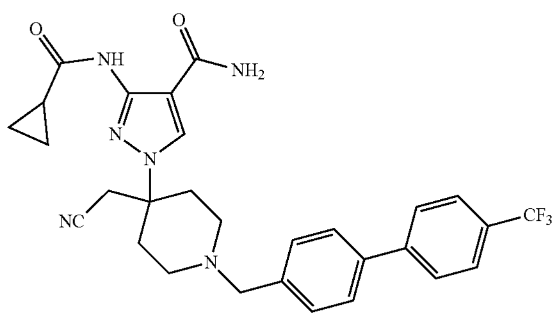 [SMILES: N#CCC1(n2cc(C(N)=O)c(NC(=O)C3CC3)n2)CCN(Cc2ccc(-c3ccc(C(F)(F)F)cc3)cc2)CC1] | 1-[4-(cyanomethyl)-1-[[4-[4-(trifluoromethyl)phenyl]phenyl]methyl]-4-piperidyl]-3-(cyclopropanecarbonylamino)pyrazole-4-carboxamide |
| 152 | 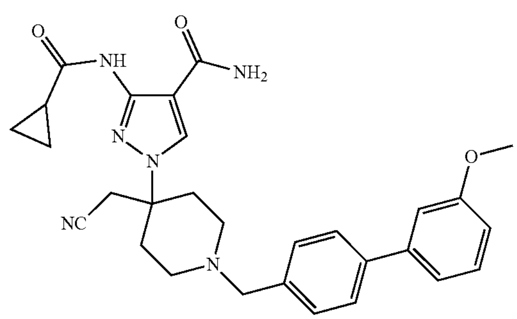 [SMILES: COc1cccc(-c2ccc(CN3CCC(CC#N)(n4cc(C(N)=O)c(NC(=O)C5CC5)n4)CC3)cc2)c1] | 1-[4-(cyanomethyl)-1-[[4-(3-methoxyphenyl)phenyl]methyl]-4-piperidyl]-3-(cyclopropanecarbonylamino)pyrazole-4-carboxamide |
| 153 | 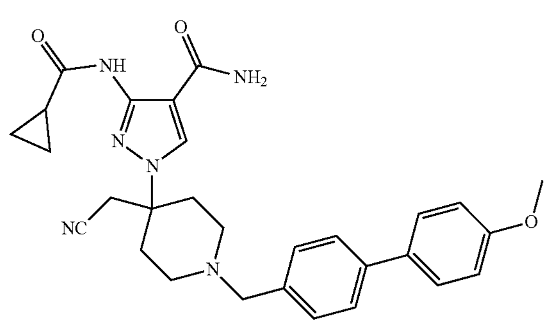 [SMILES: COc1ccc(-c2ccc(CN3CCC(CC#N)(n4cc(C(N)=O)c(NC(=O)C5CC5)n4)CC3)cc2)cc1] | 1-[4-(cyanomethyl)-1-[[4-(4-methoxyphenyl)phenyl]methyl]-4-piperidyl]-3-(cyclopropanecarbonylamino)pyrazole-4-carboxamide |

TABLE 1-continued

Exemplary Compounds of the Present Invention

| Ex. | Structure | Name |
|---|---|---|
| 154 | 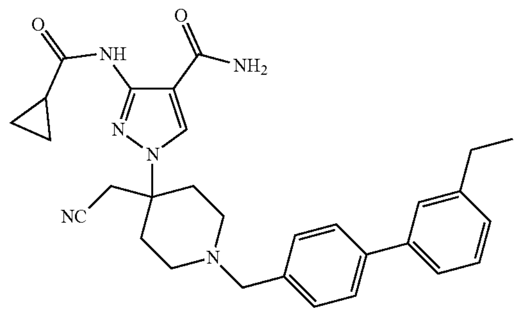 [SMILES: CCc1cccc(-c2ccc(CN3CCC(CC#N)(n4cc(C(N)=O)c(NC(=O)C5CC5)n4)CC3)cc2)c1] | 1-[4-(cyanomethyl)-1-[[4-(3-ethylphenyl)phenyl]methyl]-4-piperidyl]-3-(cyclopropanecarbonylamino)pyrazole-4-carboxamide |
| 155 | 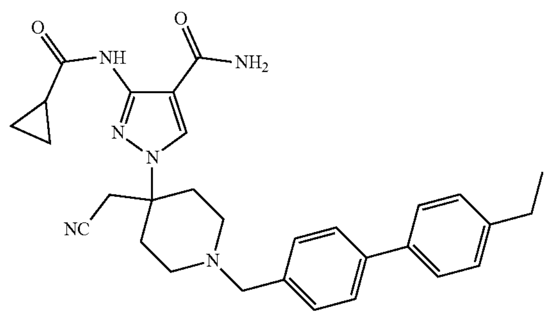 [SMILES: CCc1ccc(-c2ccc(CN3CCC(CC#N)(n4cc(C(N)=O)c(NC(=O)C5CC5)n4)CC3)cc2)cc1] | 1-[4-(cyanomethyl)-1-[[4-(4-ethylphenyl)phenyl]methyl]-4-piperidyl]-3-(cyclopropanecarbonylamino)pyrazole-4-carboxamide |
| 156 | 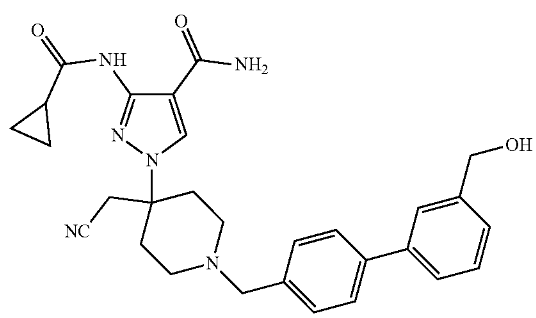 [SMILES: N#CCC1(n2cc(C(N)=O)c(NC(=O)C3CC3)n2)CCN(Cc2ccc(-c3cccc(CO)c3)cc2)CC1] | 1-[4-(cyanomethyl)-1-[[4-[3-(hydroxymethyl)phenyl]phenyl]methyl]-4-piperidyl]-3-(cyclopropanecarbonylamino)pyrazole-4-carboxamide |
| 157 | 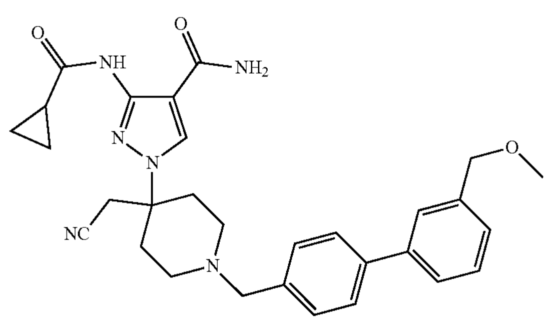 [SMILES: COCc1cccc(-c2ccc(CN3CCC(CC#N)(n4cc(C(N)=O)c(NC(=O)C5CC5)n4)CC3)cc2)c1] | 1-[4-(cyanomethyl)-1-[[4-[3-(methoxymethyl)phenyl]phenyl]methyl]-4-piperidyl]-3-(cyclopropanecarbonylamino)pyrazole-4-carboxamide |
| 158 | 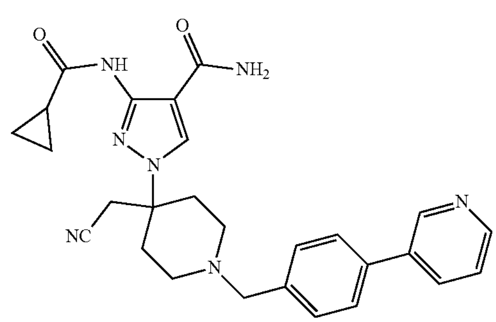 [SMILES: N#CCC1(n2cc(C(N)=O)c(NC(=O)C3CC3)n2)CCN(Cc2ccc(-c3cccnc3)cc2)CC1] | 1-[4-(cyanomethyl)-1-[[4-(3-pyridyl)phenyl]methyl]-4-piperidyl]-3-(cyclopropanecarbonylamino)pyrazole-4-carboxamide pyridyl)phenyl]methyl]-4-piperidyl]-3-(cyclopropanecarbonylamino)pyrazole-4-carboxamide |

TABLE 1-continued

Exemplary Compounds of the Present Invention

| Ex. | Structure | Name |
|---|---|---|
| 159 | 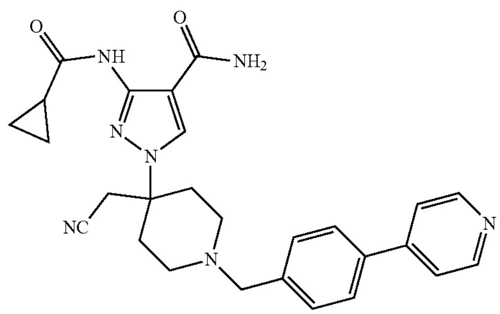 [SMILES: N#CCC1(n2cc(C(N)=O)c(NC(=O)C3CC3)n2)CCN(Cc2ccc(-c3ccncc3)cc2)CC1] | 1-[4-(cyanomethyl)-1-[[4-(4-pyridyl)phenyl]methyl]-4-piperidyl]-3-(cyclopropanecarbonylamino)pyrazole-4-carboxamide |
| 160 | 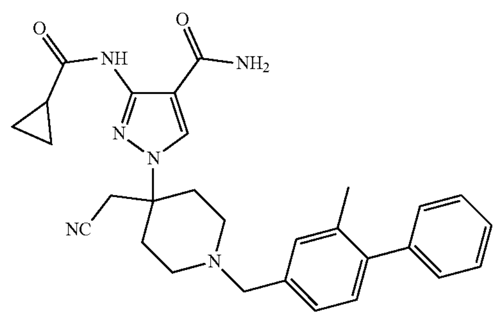 | 1-[4-(cyanomethyl)-1-[(3-methyl-4-phenyl-phenyl)methyl]-4-piperidyl]-3-(cyclopropanecarbonylamino)pyrazole-4-carboxamide |
| 161 | 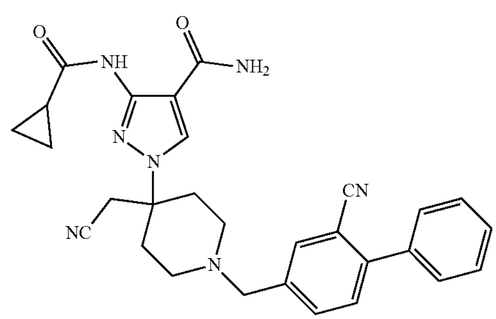 [SMILES: N#CCC1(n2cc(C(N)=O)c(NC(=O)C3CC3)n2)CCN(Cc2ccc(-c3ccccc3)c(C#N)c2)CC1] | 1-[4-(cyanomethyl)-1-[(3-cyano-4-phenyl-phenyl)methyl]-4-piperidyl]-3-(cyclopropanecarbonylamino)pyrazole-4-carboxamide |
| 162 | 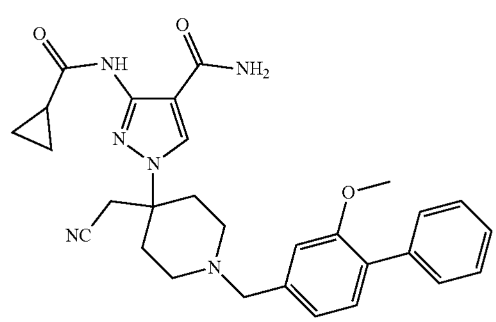 [SMILES: COc1cc(CN2CCC(CC#N)(n3cc(C(N)=O)c(NC(=O)C4CC4)n3)CC2)ccc1-c1ccccc1] | 1-[4-(cyanomethyl)-1-[(3-methoxy-4-phenyl-phenyl)methyl]-4-piperidyl]-3-(cyclopropanecarbonylamino)pyrazole-4-carboxamide |

TABLE 1-continued

Exemplary Compounds of the Present Invention

| Ex. | Structure | Name |
|---|---|---|
| 163 | 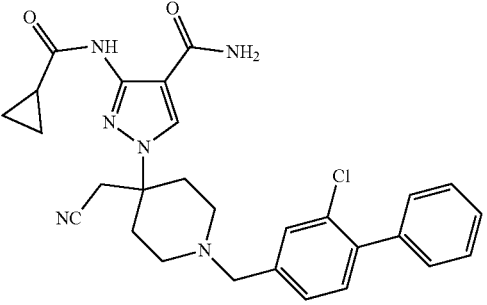 | 1-[1-[(3-chloro-4-phenyl-phenyl)methyl]-4-(cyanomethyl)-4-piperidyl]-3-(cyclopropanecarbonylamino)pyrazole-4-carboxamide |
| 164 | 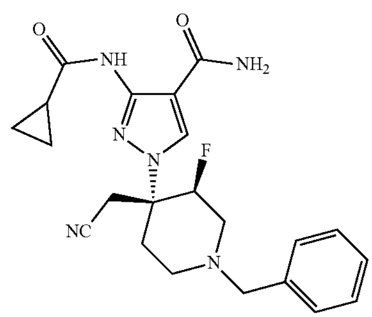 [SMILES: N#CC[C@]1(n2cc(C(N)=O)c(NC(=O)C3CC3)n2)CCN(Cc2ccccc2)C[C@@H]1F] | 1-[1-benzyl-4-(cyanomethyl)-3-fluoro-4-piperidyl]-3-(cyclopropanecarbonylamino)pyrazole-4-carboxamide |
| 165 | 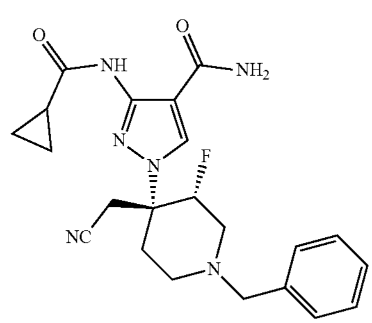 [SMILES: N#CC[C@]1(n2cc(C(N)=O)c(NC(=O)C3CC3)n2)CCN(Cc2ccccc2)C[C@H]1F] | tert-butyl 4-[4-carbamoyl-3-(cyclopropanecarbonylamino)pyrazol-1-yl]-4-(cyanomethyl)-3-fluoro-piperidine-1-carboxylate |
| 166 | 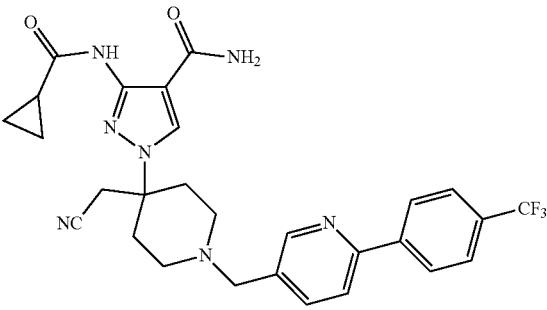 [SMILES: N#CCC1(n2cc(C(N)=O)c(NC(=O)C3CC3)n2)CCN(Cc2ccc(-c3ccc(C(F)(F)F)cc3)nc2)CC1] | 1-[4-(cyanomethyl)-1-[[6-[4-(trifluoromethyl)phenyl]-3-pyridyl]methyl]-4-piperidyl]-3-(cyclopropanecarbonylamino)pyrazole-4-carboxamide |

TABLE 1-continued

Exemplary Compounds of the Present Invention

| Ex. | Structure | Name |
|---|---|---|
| 167 | 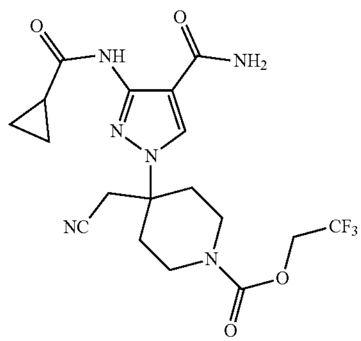 [SMILES: N#CCC1(n2cc(C(N)=O)c(NC(=O)C3CC3)n2)CCN(C(=O)OCC(F)(F)F)CC1] | 2,2,2-trifluoroethyl 4-[4-carbamoyl-3-(cyclopropanecarbonylamino)pyrazol-1-yl]-4-(cyanomethyl)piperidine-1-carboxylate |
| 168 | 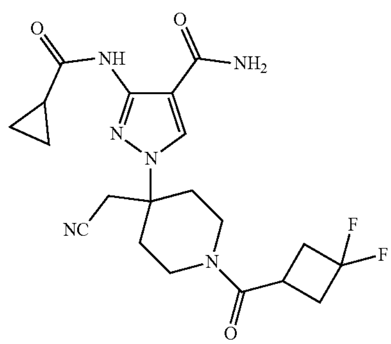 [SMILES: N#CCC1(n2cc(C(N)=O)c(NC(=O)C3CC3)n2)CCN(C(=O)C2CC(F)(F)C2)CC1] | 1-[4-(cyanomethyl)-1-(3,3-difluorocyclobutanecarbonyl)-4-piperidyl]-3-(cyclopropanecarbonylamino)pyrazole-4-carboxamide |
| 169 | 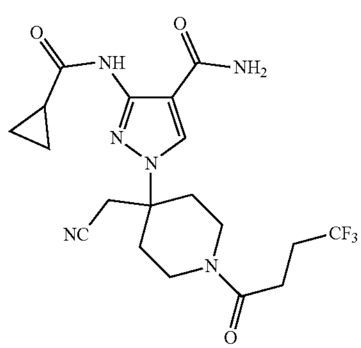 [SMILES: N#CCC1(n2cc(C(N)=O)c(NC(=O)C3CC3)n2)CCN(C(=O)CCC(F)(F)F)CC1] | 1-[4-(cyanomethyl)-1-(4,4,4-trifluorobutanoyl)-4-piperidyl]-3-(cyclopropanecarbonylamino)pyrazole-4-carboxamide |
| 170 | 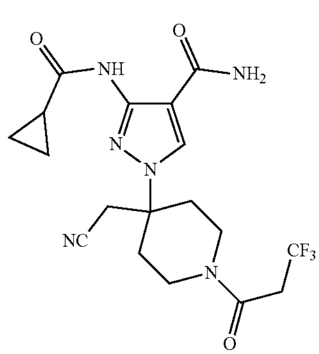 [SMILES: N#CCC1(n2cc(C(N)=O)c(NC(=O)C3CC3)n2)CCN(C(=O)CC(F)(F)F)CC1] | 1-[4-(cyanomethyl)-1-(3,3,3-trifluoropropanoyl)-4-piperidyl]-3-(cyclopropanecarbonylamino)pyrazole-4-carboxamide |

TABLE 1-continued

Exemplary Compounds of the Present Invention

| Ex. | Structure | Name |
|---|---|---|
| 171 | 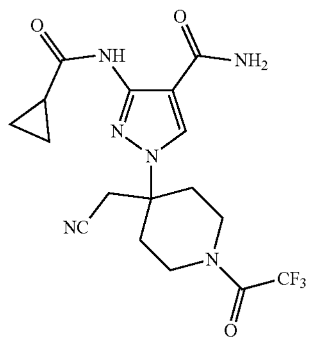 [SMILES: N#CCC1(n2cc(C(N)=O)c(NC(=O)C3CC3)n2)CCN(C(=O)C(F)(F)F)CC1] | 1-[4-(cyanomethyl)-1-(2,2-difluoropropanoyl)-4-piperidyl]-3-(cyclopropanecarbonylamino)pyrazole-4-carboxamide |
| 172 | 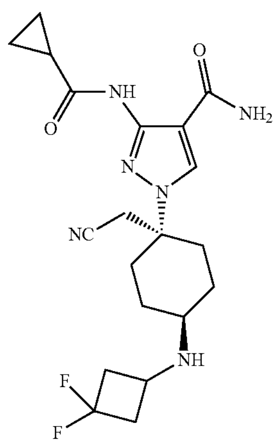 [SMILES: N#CC[C@]1(n2cc(C(N)=O)c(NC(=O)C3CC3)n2)CC[C@H](NC2CC(F)(F)C2)CC1] | 1-[1-(cyanomethyl)-4-[(3,3-difluorocyclobutyl)amino]cyclohexyl]-3-(cyclopropanecarbonylamino)pyrazole-4-carboxamide |
| 173 | 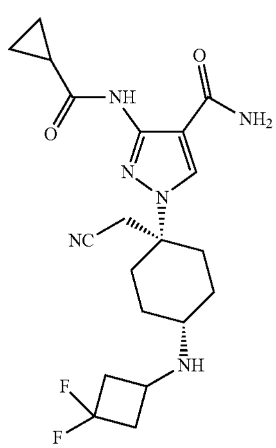 [SMILES: N#CC[C@]1(n2cc(C(N)=O)c(NC(=O)C3CC3)n2)CC[C@@H](NC2CC(F)(F)C2)CC1] | 1-[1-(cyanomethyl)-4-[(3,3-difluorocyclobutyl)amino]cyclohexyl]-3-(cyclopropanecarbonylamino)pyrazole-4-carboxamide |

TABLE 1-continued

Exemplary Compounds of the Present Invention

| Ex. | Structure | Name |
|---|---|---|
| 174 | 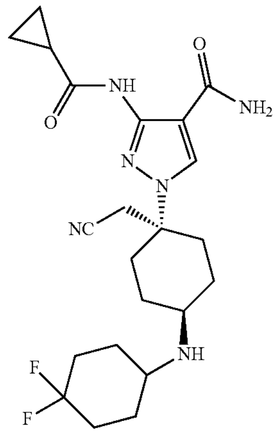 [SMILES: N#CC[C@]1(n2cc(C(N)=O)c(NC(=O)C3CC3)n2)CC[C@H](NC2CCC(F)(F)CC2)CC1] | 1-[1-(cyanomethyl)-4-[(4,4-difluorocyclohexyl)amino]cyclohexyl]-3-(cyclopropanecarbonylamino)pyrazole-4-carboxamide |
| 175 | 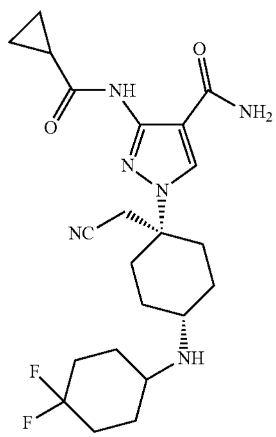 [SMILES: N#CC[C@]1(n2cc(C(N)=O)c(NC(=O)C3CC3)n2)CC[C@@H](NC2CCC(F)(F)CC2)CC1] | 1-[1-(cyanomethyl)-4-[(4,4-difluorocyclohexyl)amino]cyclohexyl]-3-(cyclopropanecarbonylamino)pyrazole-4-carboxamide |
| 176 | 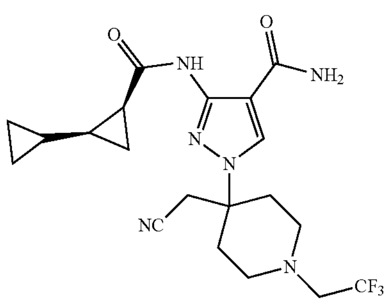 [SMILES: N#CCC1(n2cc(C(N)=O)c(NC(=O)[C@H]3C[C@H]3C3CC3)n2)CCN(CC(F)(F)F)CC1] | 1-[4-(cyanomethyl)-1-(2,2,2-trifluoroethyl)-4-piperidyl]-3-[(2-cyclopropylcyclopropanecarbonyl)amino]pyrazole-4-carboxamide |
| 177 | 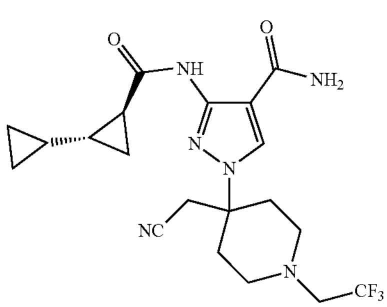 [SMILES: N#CCC1(n2cc(C(N)=O)c(NC(=O)[C@H]3C[C@@H]3C3CC3)n2)CCN(CC(F)(F)F)CC1] | 1-[4-(cyanomethyl)-1-(2,2,2-trifluoroethyl)-4-piperidyl]-3-[(2-cyclopropylcyclopropanecarbonyl)amino]pyrazole-4-carboxamide |

TABLE 1-continued

Exemplary Compounds of the Present Invention

| Ex. | Structure | Name |
| --- | --- | --- |
| 178 | 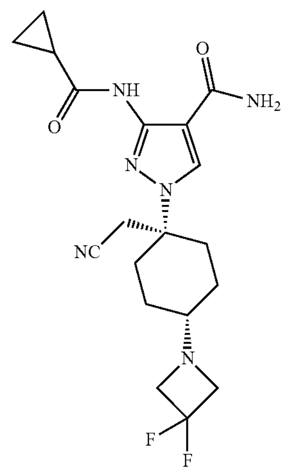 [SMILES: N#CC[C@]1(n2cc(C(N)=O)c(NC(=O)C3CC3)n2)CC[C@@H](N2CC(F)(F)C2)CC1] | 1-[1-(cyanomethyl)-4-(3,3-difluoroazetidin-1-yl)cyclohexyl]-3-(cyclopropanecarbonylamino)pyrazole-4-carboxamide |
| 179 | 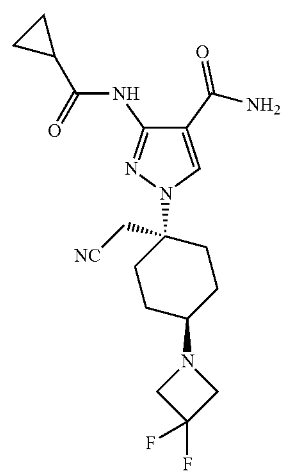 [SMILES: N#CC[C@]1(n2cc(C(N)=O)c(NC(=O)C3CC3)n2)CC[C@H](N2CC(F)(F)C2)CC1] | 1-[1-(cyanomethyl)-4-(3,3-difluoroazetidin-1-yl)cyclohexyl]-3-(cyclopropanecarbonylamino)pyrazole-4-carboxamide |
| 180 | 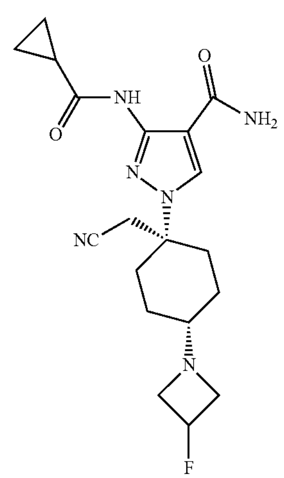 [SMILES: N#CC[C@]1(n2cc(C(N)=O)c(NC(=O)C3CC3)n2)CC[C@@H](N2CC(F)C2)CC1] | 1-[1-(cyanomethyl)-4-(3-fluoroazetidin-1-yl)cyclohexyl]-3-(cyclopropanecarbonylamino)pyrazole-4-carboxamide |

TABLE 1-continued

Exemplary Compounds of the Present Invention

| Ex. | Structure | Name |
|---|---|---|
| 181 | 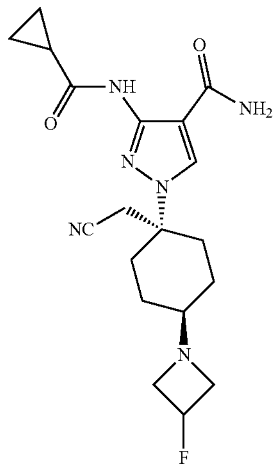 [SMILES: N#CC[C@]1(n2cc(C(N)=O)c(NC(=O)C3CC3)n2)CC[C@H](N2CC(F)C2)CC1] | 1-[1-(cyanomethyl)-4-(3-fluoroazetidin-1-yl)cyclohexyl]-3-(cyclopropanecarbonylamino)pyrazole-4-carboxamide |
| 182 | 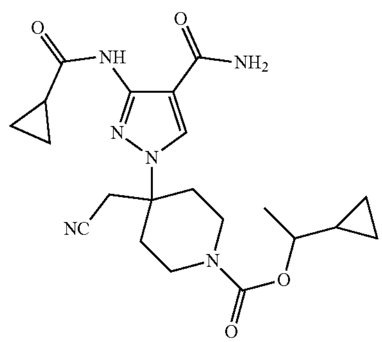 [SMILES: CC(OC(=O)N1CCC(CC#N)(n2cc(C(N)=O)c(NC(=O)C3CC3)n2)CC1)C1CC1] | 1-cyclopropylethyl 4-[4-carbamoyl-3-(cyclopropanecarbonylamino)pyrazol-1-yl]-4-(cyanomethyl)piperidine-1-carboxylate |
| 183 | 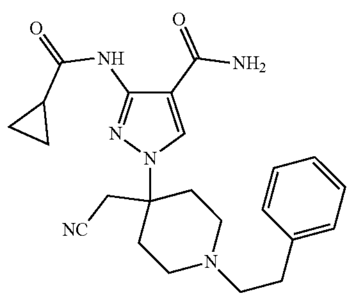 [SMILES: N#CCC1(n2cc(C(N)=O)c(NC(=O)C3CC3)n2)CCN(CCc2ccccc2)CC1] | 1-[4-(cyanomethyl)-1-(2-phenylethyl)-4-piperidyl]-3-(cyclopropanecarbonylamino)pyrazole-4-carboxamide |
| 184 | 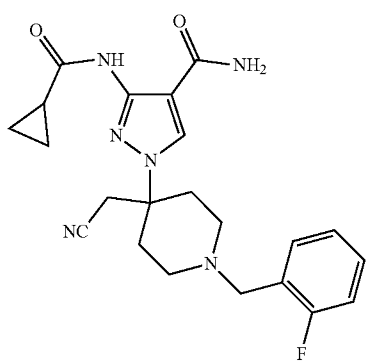 | 1-[4-(cyanomethyl)-1-[(2-fluorophenyl)methyl]-4-piperidyl]-3-(cyclopropanecarbonylamino)pyrazole-4-carboxamide |

TABLE 1-continued

Exemplary Compounds of the Present Invention

| Ex. | Structure | Name |
|---|---|---|
| 185 | 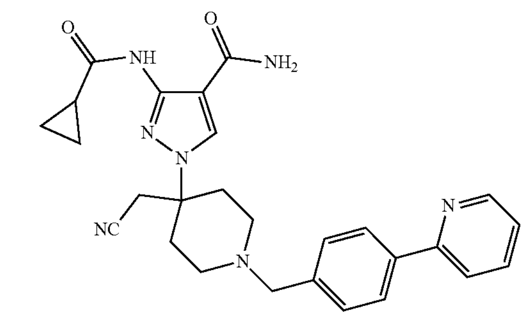 [SMILES: N#CCC1(n2cc(C(N)=O)c(NC(=O)C3CC3)n2)CCN(Cc2ccc(-c3ccccn3)cc2)CC1] | 1-[4-(cyanomethyl)-1-[[4-(2-pyridyl)phenyl]methyl]-4-piperidyl]-3-(cyclopropanecarbonylamino)pyrazole-4-carboxamide |
| 186 | 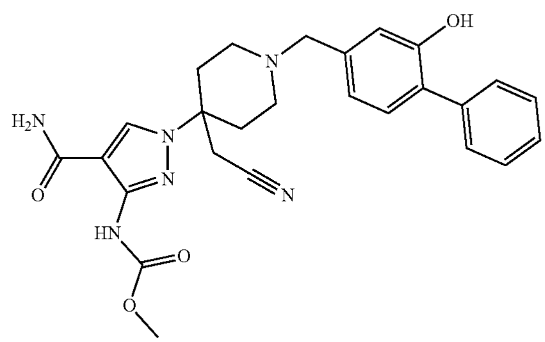 [SMILES: COC(=O)Nc1nn(C2(CC#N)CCN(Cc3ccc(-c4ccccc4)c(O)c3)CC2)cc1C(N)=O] | methyl N-[4-carbamoyl-1-[4-(cyanomethyl)-1-[(3-hydroxy-4-phenyl-phenyl)methyl]-4-piperidyl]pyrazol-3-yl]carbamate |
| 187 | 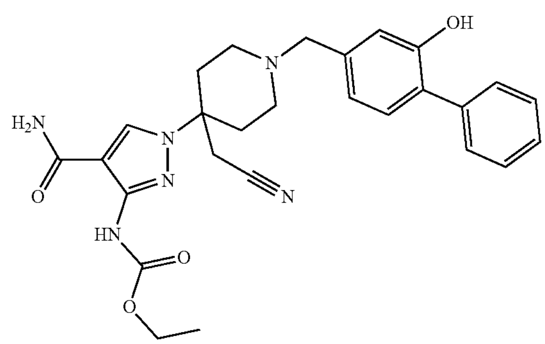 [SMILES: CCOC(=O)Nc1nn(C2(CC#N)CCN(Cc3ccc(-c4ccccc4)c(O)c3)CC2)cc1C(N)=O] | ethyl N-[4-carbamoyl-1-[4-(cyanomethyl)-1-[(3-hydroxy-4-phenyl-phenyl)methyl]-4-piperidyl]pyrazol-3-yl]carbamate |
| 188 | 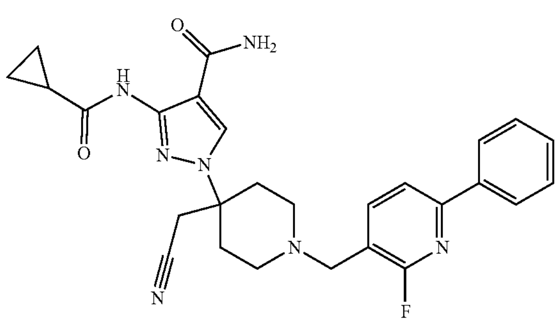 [SMILES: N#CCC1(n2cc(C(N)=O)c(NC(=O)C3CC3)n2)CCN(Cc2ccc(-c3ccccc3)nc2F)CC1] | 1-[4-(cyanomethyl)-1-[(2-fluoro-6-phenyl-3-pyridyl)methyl]-4-piperidyl]-3-(cyclopropanecarbonylamino)pyrazole-4-carboxamide |

TABLE 1-continued

Exemplary Compounds of the Present Invention

| Ex. | Structure | Name |
|---|---|---|
| 189 | 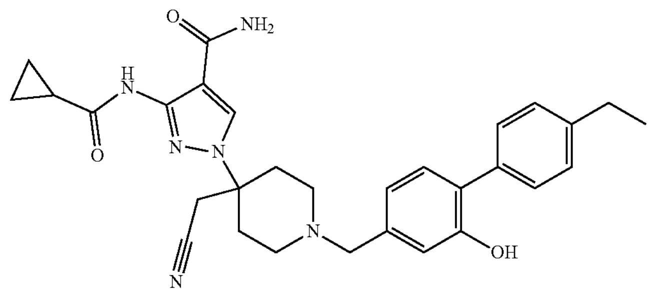 [SMILES: CCc1ccc(-c2ccc(CN3CCC(CC#N)(n4cc(C(N)=O)c(NC(=O)C5CC5)n4)CC3)cc2O)cc1] | 1-[4-(cyanomethyl)-1-[[4-(4-ethylphenyl)-3-hydroxyphenyl]methyl]-4-piperidyl]-3-(cyclopropanecarbonylamino)pyrazole-4-carboxamide |
| 190 | 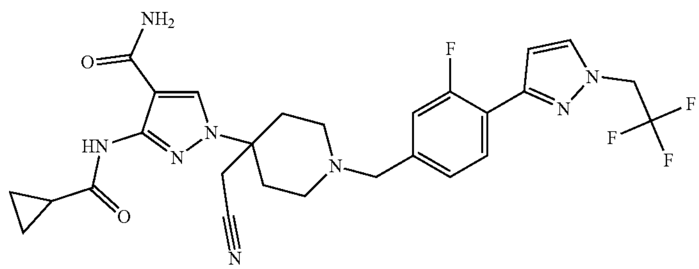 [SMILES: N#CCC1(n2cc(C(N)=O)c(NC(=O)C3CC3)n2)CCN(Cc2ccc(-c3ccn(CC(F)(F)F)n3)c(F)c2)CC1] | 1-[4-(cyanomethyl)-1-[[3-fluoro-4-[1-(2,2,2-trifluoroethyl)pyrazol-3-yl]phenyl]methyl]-4-piperidyl]-3-(cyclopropanecarbonylamino)pyrazole-4-carboxamide |
| 191 | 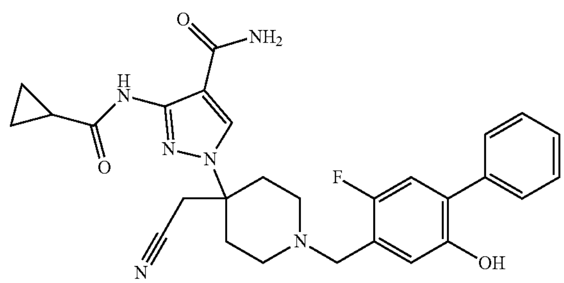 [SMILES: N#CCC1(n2cc(C(N)=O)c(NC(=O)C3CC3)n2)CCN(Cc2cc(O)c(-c3ccccc3)cc2F)CC1] | 1-[4-(cyanomethyl)-1-[(2-fluoro-5-hydroxy-4-phenyl-phenyl)methyl]-4-piperidyl]-3-(cyclopropanecarbonylamino)pyrazole-4-carboxamide |
| 192 | 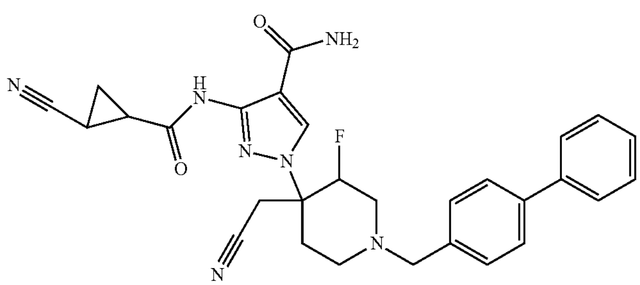 [SMILES: N#CCC1(n2cc(C(N)=O)c(NC(=O)C3CC3C#N)n2)CCN(Cc2ccc(-c3ccccc3)cc2)CC1F] | 3-[(2-cyanocyclopropanecarbonyl)amino]-1-[4-(cyanomethyl)-3-fluoro-1-[(4-phenylphenyl)methyl]-4-piperidyl]pyrazole-4-carboxamide |
| 193 | 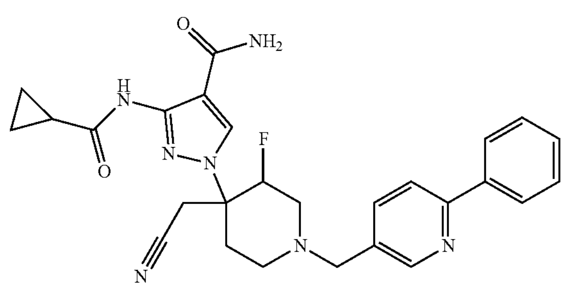 [SMILES: N#CCC1(n2cc(C(N)=O)c(NC(=O)C3CC3)n2)CCN(Cc2ccc(-c3ccccc3)nc2)CC1F] | 1-[4-(cyanomethyl)-3-fluoro-1-[(6-phenyl-3-pyridyl)methyl]-4-piperidyl]-3-(cyclopropanecarbonylamino)pyrazole-4-carboxamide |

TABLE 1-continued

Exemplary Compounds of the Present Invention

| Ex. | Structure | Name |
|---|---|---|
| 194 | 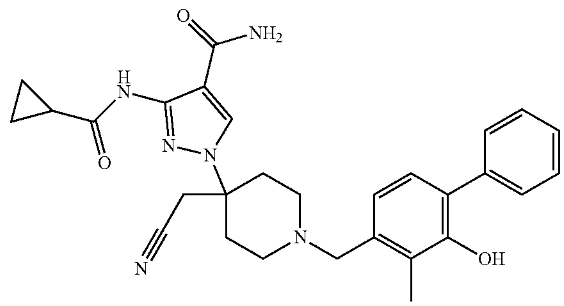 [SMILES: Cc1c(CN2CCC(CC#N)(n3cc(C(N)=O)c(NC(=O)C4CC4)n3)CC2)ccc(-c2ccccc2)c1O] | 1-[4-(cyanomethyl)-1-[(3-hydroxy-2-methyl-4-phenyl-phenyl)methyl]-4-piperidyl]-3-(cyclopropanecarbonylamino)pyrazole-4-carboxamide |
| 195 | 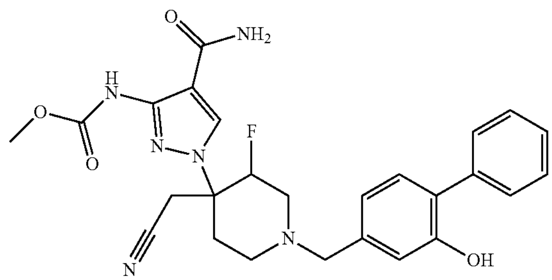 [SMILES: COC(=O)Nc1nn(C2(CC#N)CCN(Cc3ccc(-c4ccccc4)c(O)c3)CC2F)cc1C(N)=O] | methyl N-[4-carbamoyl-1-[4-(cyanomethyl)-3-fluoro-1-[(3-hydroxy-4-phenyl-phenyl)methyl]-4-piperidyl]pyrazol-3-yl]carbamate |
| 196 | 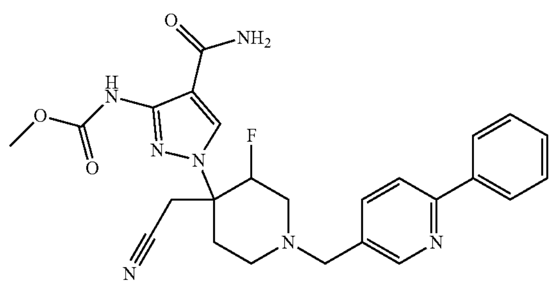 [SMILES: COC(=O)Nc1nn(C2(CC#N)CCN(Cc3ccc(-c4ccccc4)nc3)CC2F)cc1C(N)=O] | methyl N-[4-carbamoyl-1-[4-(cyanomethyl)-3-fluoro-1-[(6-phenyl-3-pyridyl)methyl]-4-piperidyl]pyrazol-3-yl]carbamate |
| 197 | 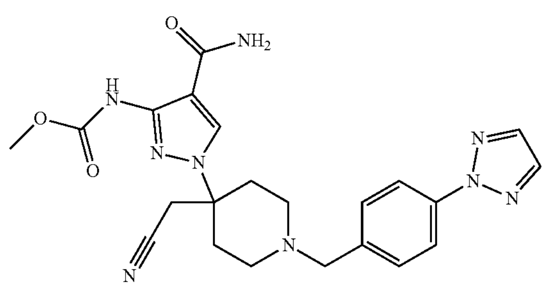 [SMILES: COC(=O)Nc1nn(C2(CC#N)CCN(Cc3ccc(-n4nccn4)cc3)CC2)cc1C(N)=O] | methyl N-[4-carbamoyl-1-[4-(cyanomethyl)-1-[[4-(triazol-2-yl)phenyl]methyl]-4-piperidyl]pyrazol-3-yl]carbamate |
| 198 | 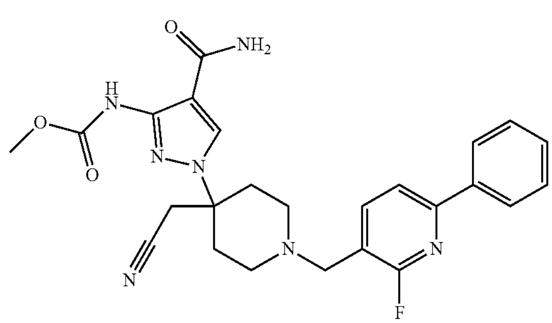 [SMILES: COC(=O)Nc1nn(C2(CC#N)CCN(Cc3ccc(-c4ccccc4)nc3F)CC2)cc1C(N)=O] | methyl N-[4-carbamoyl-1-[4-(cyanomethyl)-1-[(2-fluoro-6-phenyl-3-pyridyl)methyl]-4-piperidyl]pyrazol-3-yl]carbamate |

TABLE 1-continued

Exemplary Compounds of the Present Invention

| Ex. | Structure | Name |
|---|---|---|
| 199 | 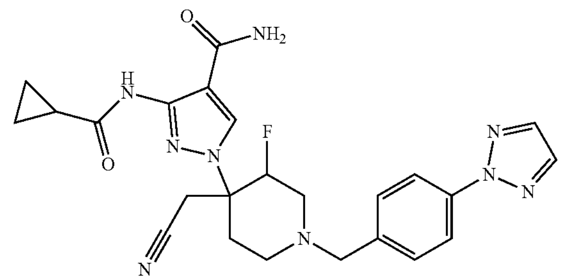 [SMILES: N#CCC1(n2cc(C(N)=O)c(NC(=O)C3CC3)n2)CCN(Cc2ccc(-n3nccn3)cc2)CC1F] | 1-[4-(cyanomethyl)-3-fluoro-1-[[4-(triazol-2-yl)phenyl]methyl]-4-piperidyl]-3-(cyclopropanecarbonylamino)pyrazole-4-carboxamide |
| 200 | 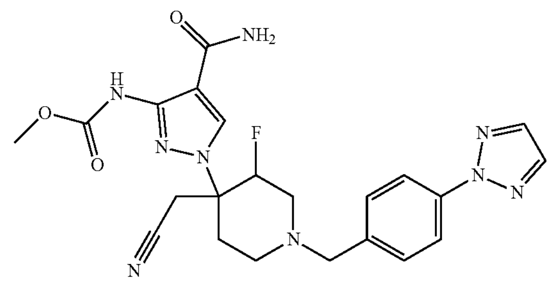 [SMILES: COC(=O)Nc1nn(C2(CC#N)CCN(Cc3ccc(-n4nccn4)cc3)CC2F)cc1C(N)=O] | methyl N-[4-carbamoyl-1-[4-(cyanomethyl)-3-fluoro-1-[[4-(triazol-2-yl)phenyl]methyl]-4-piperidyl]pyrazol-3-yl]carbamate |
| 201 | 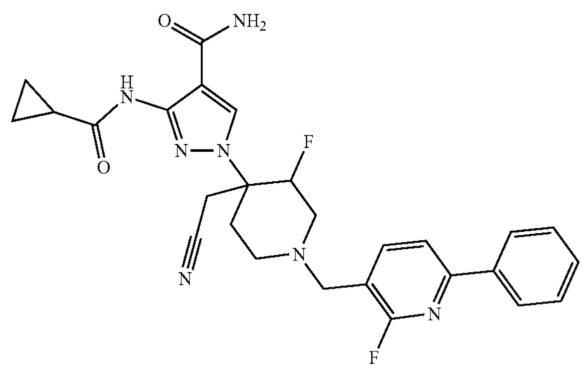 [SMILES: N#CCC1(n2cc(C(N)=O)c(NC(=O)C3CC3)n2)CCN(Cc2ccc(-c3ccccc3)nc2F)CC1F] | 1-[4-(cyanomethyl)-3-fluoro-1-[(2-fluoro-6-phenyl-3-pyridyl)methyl]-4-piperidyl]-3-(cyclopropanecarbonylamino)pyrazole-4-carboxamide |
| 202 | 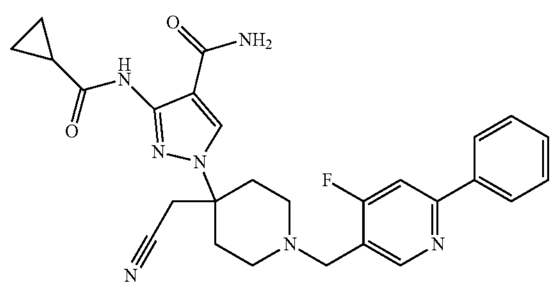 [SMILES: N#CCC1(n2cc(C(N)=O)c(NC(=O)C3CC3)n2)CCN(Cc2cnc(-c3ccccc3)cc2F)CC1] | 1-[4-(cyanomethyl)-1-[(4-fluoro-6-phenyl-3-pyridyl)methyl]-4-piperidyl]-3-(cyclopropanecarbonylamino)pyrazole-4-carboxamide |
| 203 | 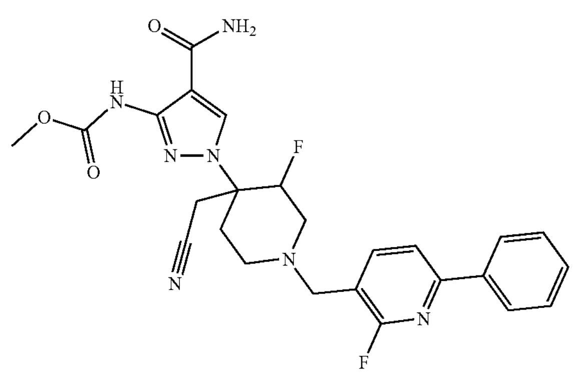 [SMILES: COC(=O)Nc1nn(C2(CC#N)CCN(Cc3ccc(-c4ccccc4)nc3F)CC2F)cc1C(N)=O] | methyl N-[4-carbamoyl-1-[4-(cyanomethyl)-3-fluoro-1-[(2-fluoro-6-phenyl-3-pyridyl)methyl]-4-piperidyl]pyrazol-3-yl]carbamate |

TABLE 1-continued

Exemplary Compounds of the Present Invention

| Ex. | Structure | Name |
|---|---|---|
| 204 | 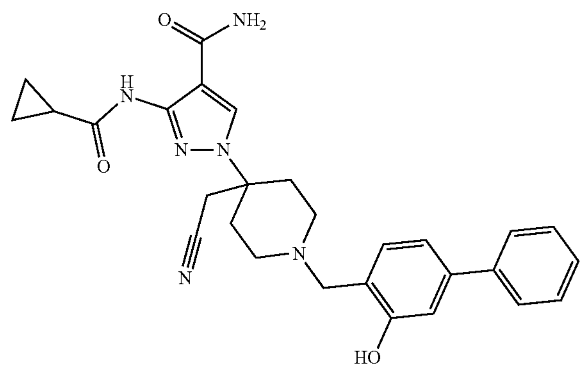 [SMILES: N#CCC1(n2cc(C(N)=O)c(NC(=O)C3CC3)n2)CCN(Cc2ccc(-c3ccccc3)cc2O)CC1] | 1-[4-(cyanomethyl)-1-[(2-hydroxy-4-phenyl-phenyl)methyl]-4-piperidyl]-3-(cyclopropanecarbonylamino)pyrazole-4-carboxamide |
| 205 | 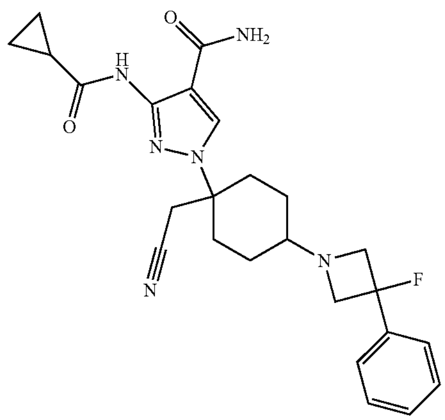 [SMILES: N#CCC1(n2cc(C(N)=O)c(NC(=O)C3CC3)n2)CCC(N2CC(F)(c3ccccc3)C2)CC1] | 1-[1-(cyanomethyl)-4-(3-fluoro-3-phenyl-azetidin-1-yl)cyclohexyl]-3-(cyclopropanecarbonylamino)pyrazole-4-carboxamide |
| 206 | 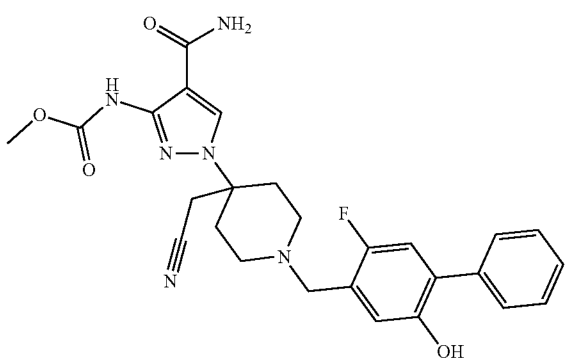 [SMILES: COC(=O)Nc1nn(C2(CC#N)CCN(Cc3cc(O)c(-c4ccccc4)cc3F)CC2)cc1C(N)=O] | methyl N-[4-carbamoyl-1-[4-(cyanomethyl)-1-[(2-fluoro-5-hydroxy-4-phenyl-phenyl)methyl]-4-piperidyl]pyrazol-3-yl]carbamate |
| 207 | 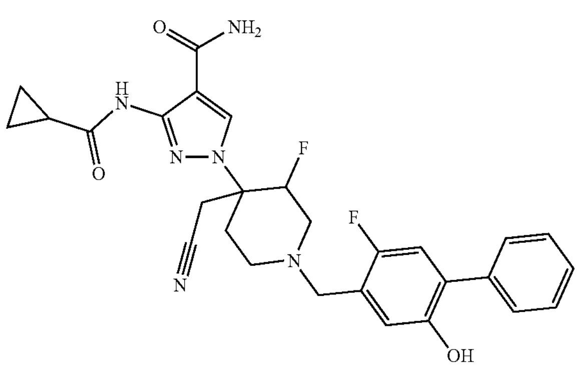 [SMILES: N#CCC1(n2cc(C(N)=O)c(NC(=O)C3CC3)n2)CCN(Cc2cc(O)c(-c3ccccc3)cc2F)CC1F] | 1-[4-(cyanomethyl)-3-fluoro-1-[(2-fluoro-5-hydroxy-4-phenyl-phenyl)methyl]-4-piperidyl]-3-(cyclopropanecarbonylamino)pyrazole-4-carboxamide |

TABLE 1-continued

Exemplary Compounds of the Present Invention

| Ex. | Structure | Name |
|---|---|---|
| 208 | 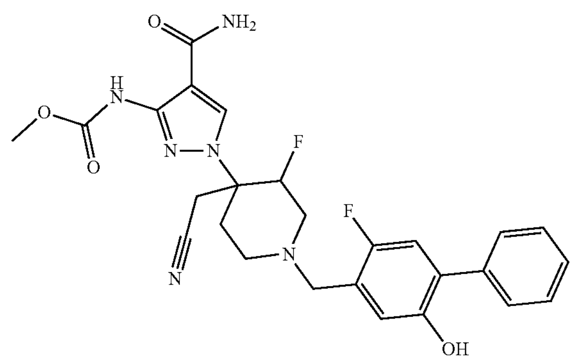 [SMILES: COC(=O)Nc1nn(C2(CC#N)CCN(Cc3cc(O)c(-c4ccccc4)cc3F)CC2F)cc1C(N)=O] | methyl N-[4-carbamoyl-1-[4-(cyanomethyl)-3-fluoro-1-[(2-fluoro-5-hydroxy-4-phenyl-phenyl)methyl]-4-piperidyl]pyrazol-3-yl]carbamate |
| 209 | 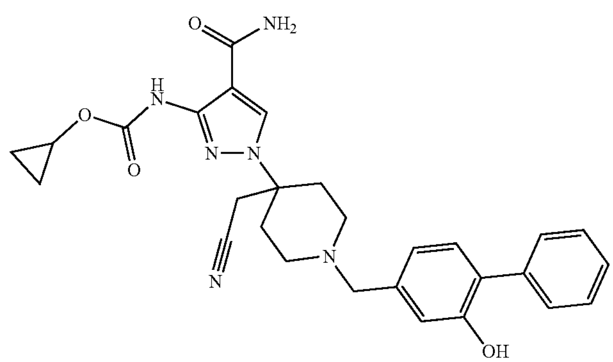 [SMILES: N#CCC1(n2cc(C(N)=O)c(NC(=O)OC3CC3)n2)CCN(Cc2ccc(-c3ccccc3)c(O)c2)CC1] | cyclopropyl N-[4-carbamoyl-1-[4-(cyanomethyl)-1-[(3-hydroxy-4-phenyl-phenyl)methyl]-4-piperidyl]pyrazol-3-yl]carbamate |
| 210 | 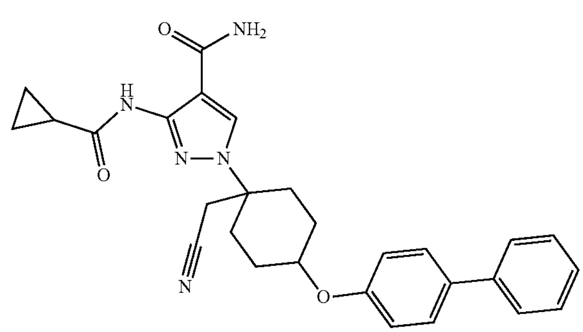 [SMILES: N#CCC1(n2cc(C(N)=O)c(NC(=O)C3CC3)n2)CCC(Oc2ccc(-c3ccccc3)cc2)CC1] | 1-[1-(cyanomethyl)-4-(4-phenylphenoxy)cyclohexyl]-3-(cyclopropanecarbonylamino)pyrazole-4-carboxamide |
| 211 | 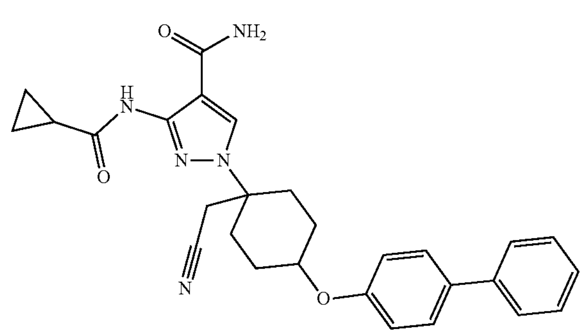 [SMILES: N#CCC1(n2cc(C(N)=O)c(NC(=O)C3CC3)n2)CCC(Oc2ccc(-c3ccccc3)cc2)CC1] | 1-[1-(cyanomethyl)-4-(4-phenylphenoxy)cyclohexyl]-3-(cyclopropanecarbonylamino)pyrazole-4-carboxamide |

TABLE 1-continued

Exemplary Compounds of the Present Invention

| Ex. | Structure | Name |
|---|---|---|
| 212 | 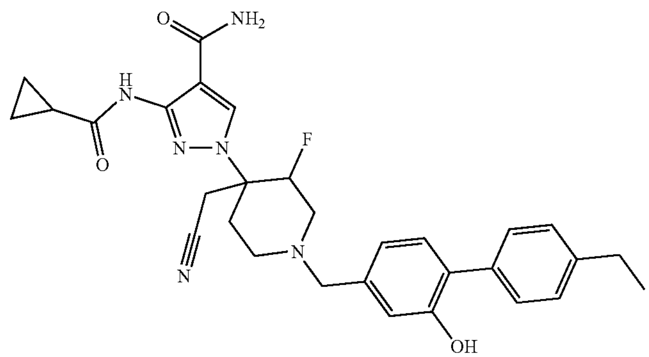 [SMILES: CCc1ccc(-c2ccc(CN3CCC(CC#N)(n4cc(C(N)=O)c(NC(=O)C5CC5)n4)C(F)C3)cc2O)cc1] | 1-[4-(cyanomethyl)-1-[[4-(4-ethylphenyl)-3-hydroxy-phenyl]methyl]-3-fluoro-4-piperidyl]-3-(cyclopropanecarbonylamino)pyrazole-4-carboxamide |
| 213 | 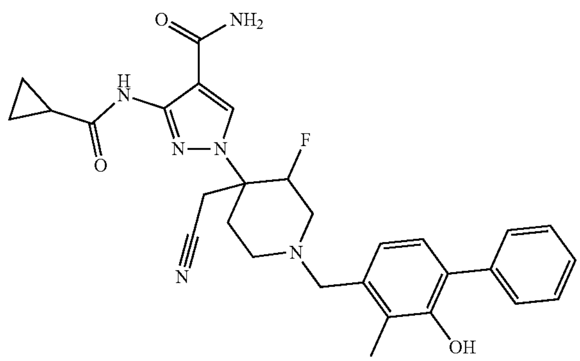 [SMILES: Cc1c(CN2CCC(CC#N)(n3cc(C(N)=O)c(NC(=O)C4CC4)n3)C(F)C2)ccc(-c2ccccc2)c1O] | 1-[4-(cyanomethyl)-3-fluoro-1-[(3-hydroxy-2-methyl-4-phenyl-phenyl)methyl]-4-piperidyl]-3-(cyclopropanecarbonylamino)pyrazole-4-carboxamide |
| 214 | 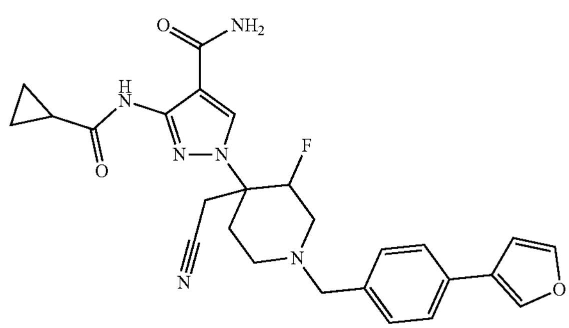 [SMILES: N#CCC1(n2cc(C(N)=O)c(NC(=O)C3CC3)n2)CCN(Cc2ccc(-c3ccoc3)cc2)CC1F] | 1-[4-(cyanomethyl)-3-fluoro-1-[[4-(3-furyl)phenyl]methyl]-4-piperidyl]-3-(cyclopropanecarbonylamino)pyrazole-4-carboxamide |
| 215 | 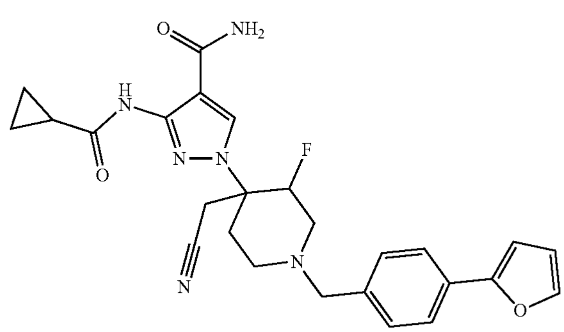 [SMILES: N#CCC1(n2cc(C(N)=O)c(NC(=O)C3CC3)n2)CCN(Cc2ccc(-c3ccco3)cc2)CC1F] | 1-[4-(cyanomethyl)-3-fluoro-1-[[4-(2-furyl)phenyl]methyl]-4-piperidyl]-3-(cyclopropanecarbonylamino)pyrazole-4-carboxamide |

TABLE 1-continued

Exemplary Compounds of the Present Invention

| Ex. | Structure | Name |
|---|---|---|
| 216 | 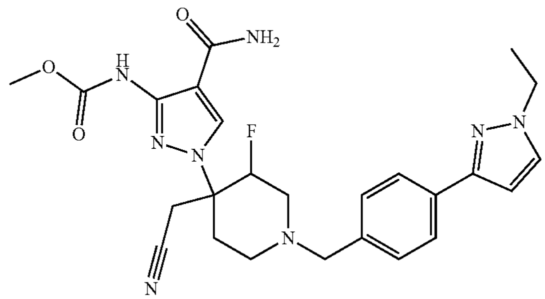 [SMILES: CCn1ccc(-c2ccc(CN3CCC(CC#N)(n4cc(C(N)=O)c(NC(=O)OC)n4)C(F)C3)cc2)n1] | methyl N-[4-carbamoyl-1-[4-(cyanomethyl)-1-[[4-(1-ethylpyrazol-3-yl)phenyl]methyl]-3-fluoro-4-piperidyl]pyrazol-3-yl]carbamate |
| 217 | 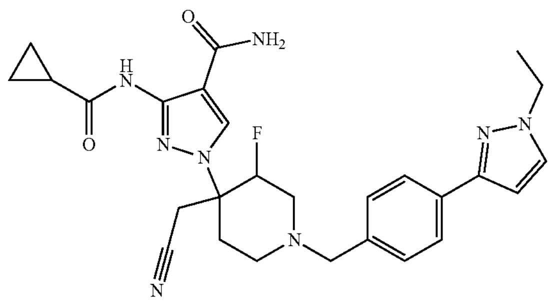 [SMILES: CCn1ccc(-c2ccc(CN3CCC(CC#N)(n4cc(C(N)=O)c(NC(=O)C5CC5)n4)C(F)C3)cc2)n1] | 1-[4-(cyanomethyl)-1-[[4-(1-ethylpyrazol-3-yl)phenyl]methyl]-3-fluoro-4-piperidyl]-3-(cyclopropanecarbonylamino)pyrazole-4-carboxamide |
| 218 | 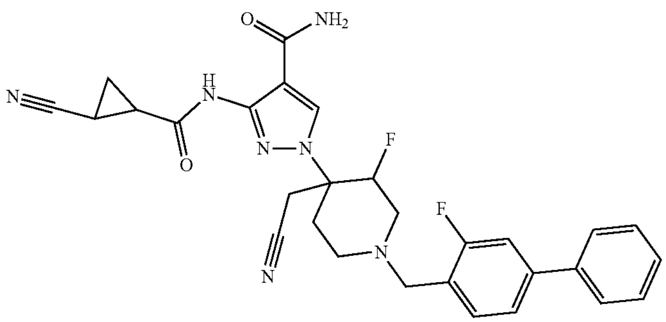 [SMILES: N#CCC1(n2cc(C(N)=O)c(NC(=O)C3CC3C#N)n2)CCN(Cc2ccc(-c3ccccc3)cc2F)CC1F] | 3-[(2-cyanocyclopropanecarbonyl)amino]-1-[4-(cyanomethyl)-3-fluoro-1-[(2-fluoro-4-phenyl-phenyl)methyl]-4-piperidyl]pyrazole-4-carboxamide |
| 219 | 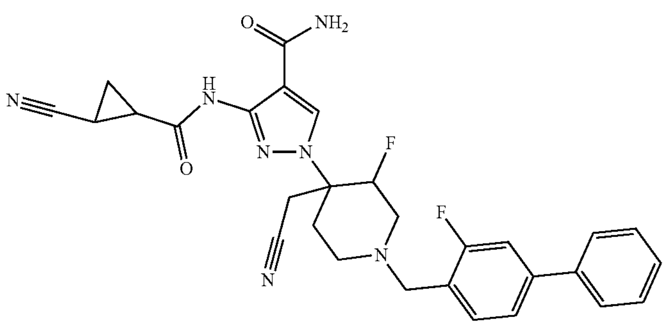 [SMILES: N#CCC1(n2cc(C(N)=O)c(NC(=O)C3CC3C#N)n2)CCN(Cc2ccc(-c3ccccc3)cc2F)CC1F] | 3-[(2-cyanocyclopropanecarbonyl)amino]-1-[4-(cyanomethyl)-3-fluoro-1-[(2-fluoro-4-phenyl-phenyl)methyl]-4-piperidyl]pyrazole-4-carboxamide |
| 220 | 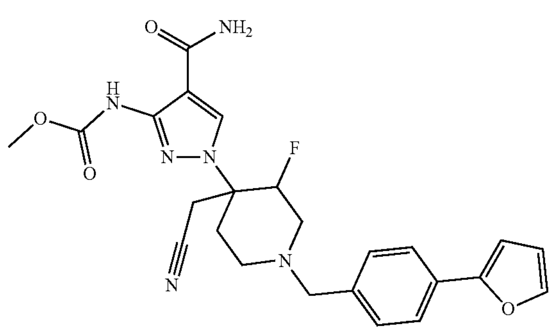 [SMILES: COC(=O)Nc1nn(C2(CC#N)CCN(Cc3ccc(-c4ccco4)cc3)CC2F)cc1C(N)=O] | methyl N-[4-carbamoyl-1-[4-(cyanomethyl)-3-fluoro-1-[[4-(2-furyl)phenyl]methyl]-4-piperidyl]pyrazol-3-yl]carbamate |

TABLE 1-continued

Exemplary Compounds of the Present Invention

| Ex. | Structure | Name |
|---|---|---|
| 221 | 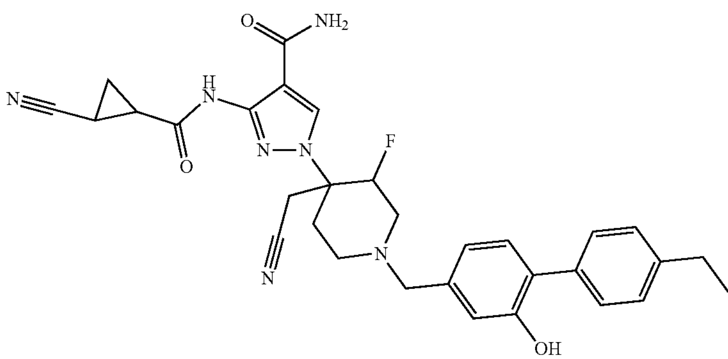 [SMILES: CCc1ccc(-c2ccc(CN3CCC(CC#N)(n4cc(C(N)=O)c(NC(=O)C5CC5C#N)n4)C(F)C3)cc2O)cc1] | 3-[(2-cyanocyclopropanecarbonyl)amino]-1-[4-(cyanomethyl)-1-[[4-(4-ethylphenyl)-3-hydroxy-phenyl]methyl]-3-fluoro-4-piperidyl]pyrazole-4-carboxamide |
| 222 | 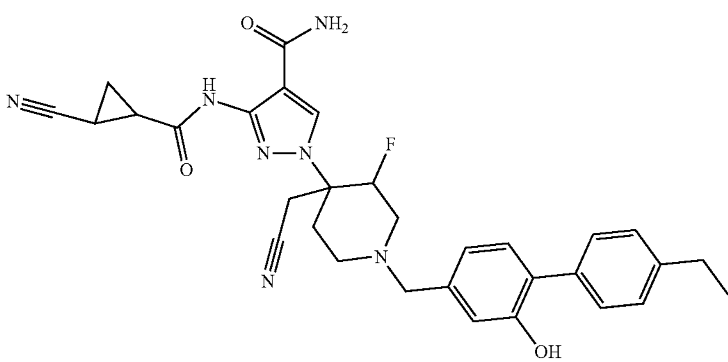 [SMILES: CCc1ccc(-c2ccc(CN3CCC(CC#N)(n4cc(C(N)=O)c(NC(=O)C5CC5C#N)n4)C(F)C3)cc2O)cc1] | 3-[(2-cyanocyclopropanecarbonyl)amino]-1-[4-(cyanomethyl)-1-[[4-(4-ethylphenyl)-3-hydroxy-phenyl]methyl]-3-fluoro-4-piperidyl]pyrazole-4-carboxamide |
| 223 | 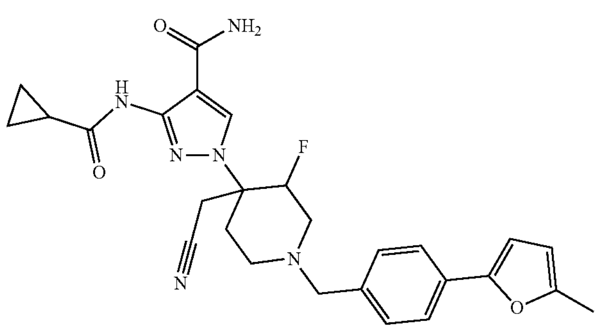 [SMILES: Cc1ccc(-c2ccc(CN3CCC(CC#N)(n4cc(C(N)=O)c(NC(=O)C5CC5)n4)C(F)C3)cc2)o1] | 1-[4-(cyanomethyl)-3-fluoro-1-[[4-(5-methyl-2-furyl)phenyl]methyl]-4-piperidyl]-3-(cyclopropanecarbonylamino)pyrazole-4-carboxamide |
| 224 | 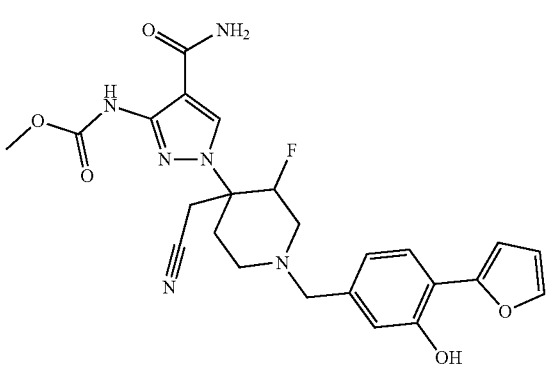 [SMILES: COC(=O)Nc1nn(C2(CC#N)CCN(Cc3ccc(-c4ccco4)c(O)c3)CC2F)cc1C(N)=O] | methyl N-[4-carbamoyl-1-[4-(cyanomethyl)-3-fluoro-1-[[4-(2-furyl)-3-hydroxy-phenyl]methyl]-4-piperidyl]pyrazol-3-yl]carbamate |

TABLE 1-continued

Exemplary Compounds of the Present Invention

| Ex. | Structure | Name |
|---|---|---|
| 225 | 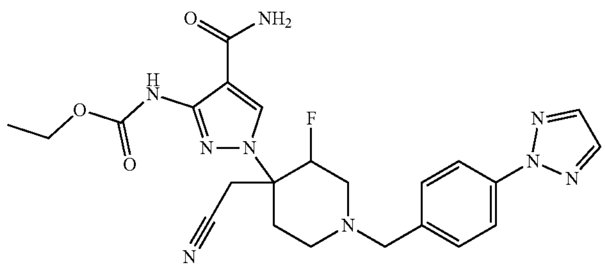 [SMILES: CCOC(=O)Nc1nn(C2(CC#N)CCN(Cc3ccc(-n4nccn4)cc3)CC2F)cc1C(N)=O] | ethyl N-[4-carbamoyl-1-[4-(cyanomethyl)-3-fluoro-1-[[4-(triazol-2-yl)phenyl]methyl]-4-piperidyl]pyrazol-3-yl]carbamate |
| 226 | 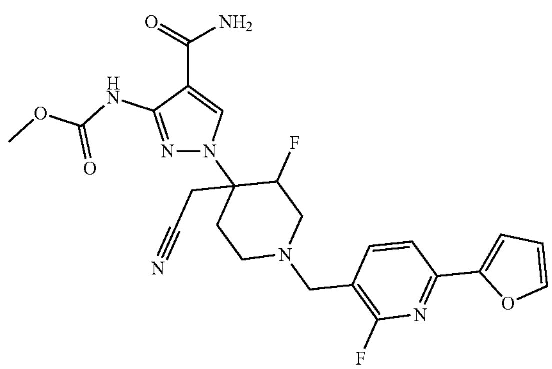 [SMILES: COC(=O)Nc1nn(C2(CC#N)CCN(Cc3ccc(-c4ccco4)nc3F)CC2F)cc1C(N)=O] | methyl N-[4-carbamoyl-1-[4-(cyanomethyl)-3-fluoro-1-[[2-fluoro-6-(2-furyl)-3-pyridyl]methyl]-4-piperidyl]pyrazol-3-yl]carbamate |
| 227 | 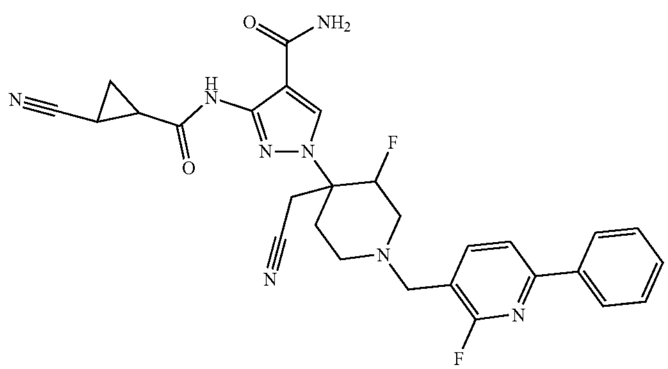 [SMILES: N#CCC1(n2cc(C(N)=O)c(NC(=O)C3CC3C#N)n2)CCN(Cc2ccc(-c3ccccc3)nc2F)CC1F] | 3-[(2-cyanocyclopropanecarbonyl)amino]-1-[4-(cyanomethyl)-3-fluoro-1-[(2-fluoro-6-phenyl-3-pyridyl)methyl]-4-piperidyl]pyrazole-4-carboxamide |
| 228 | 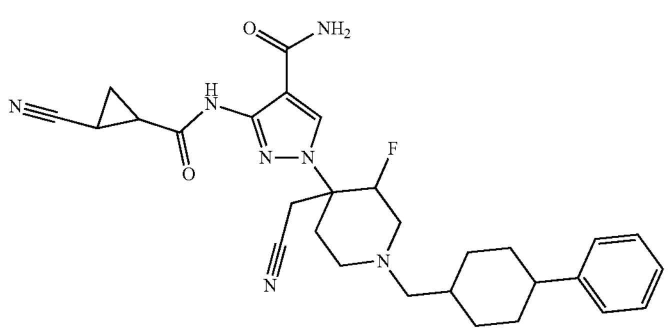 [SMILES: N#CCC1(n2cc(C(N)=O)c(NC(=O)C3CC3C#N)n2)CCN(CC2CCC(c3ccccc3)CC2)CC1F] | 3-[(2-cyanocyclopropanecarbonyl)amino]-1-[4-(cyanomethyl)-3-fluoro-1-[(4-phenylcyclohexyl)methyl]-4-piperidyl]pyrazole-4-carboxamide |

TABLE 1-continued

Exemplary Compounds of the Present Invention

| Ex. | Structure | Name |
|---|---|---|
| 229 | 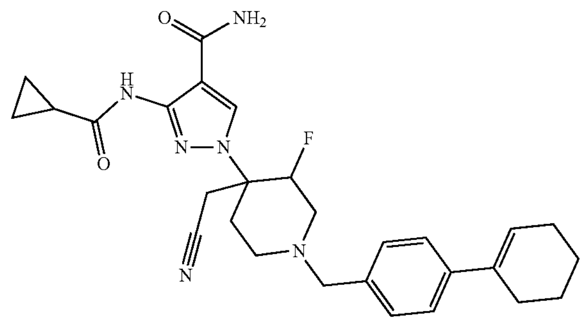 [SMILES: N#CCC1(n2cc(C(N)=O)c(NC(=O)C3CC3)n2)CCN(Cc2ccc(C3=CCCCC3)cc2)CC1F] | 1-[4-(cyanomethyl)-1-[[4-(cyclohexen-1-yl)phenyl]methyl]-3-fluoro-4-piperidyl]-3-(cyclopropanecarbonylamino)pyrazole-4-carboxamide |
| 230 | 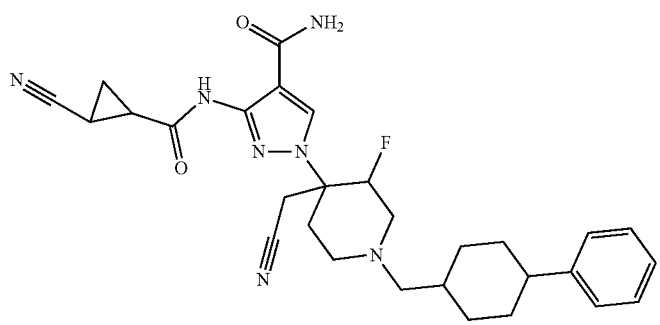 [SMILES: N#CCC1(n2cc(C(N)=O)c(NC(=O)C3CC3C#N)n2)CCN(CC2CCC(c3ccccc3)CC2)CC1F] | 3-[(2-cyanocyclopropanecarbonyl)amino]-1-[4-(cyanomethyl)-3-fluoro-1-[(4-phenylcyclohexyl)methyl]-4-piperidyl]pyrazole-4-carboxamide |
| 231 | 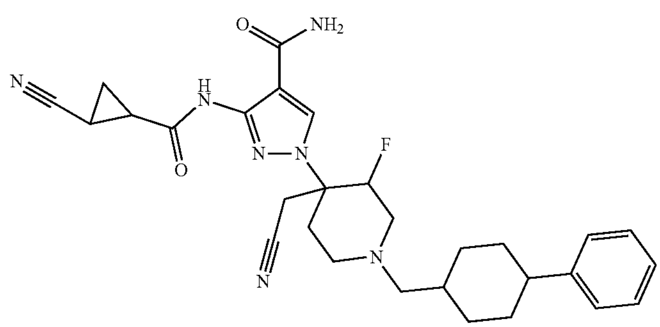 [SMILES: N#CCC1(n2cc(C(N)=O)c(NC(=O)C3CC3C#N)n2)CCN(CC2CCC(c3ccccc3)CC2)CC1F] | 3-[(2-cyanocyclopropanecarbonyl)amino]-1-[4-(cyanomethyl)-3-fluoro-1-[(4-phenylcyclohexyl)methyl]-4-piperidyl]pyrazole-4-carboxamide |
| 232 | 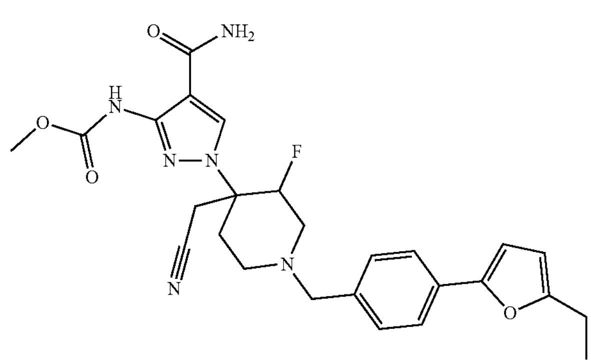 [SMILES: CCc1ccc(-c2ccc(CN3CCC(CC#N)(n4cc(C(N)=O)c(NC(=O)OC)n4)C(F)C3)cc2)o1] | methyl N-[4-carbamoyl-1-[4-(cyanomethyl)-1-[[4-(5-ethyl-2-furyl)phenyl]methyl]-3-fluoro-4-piperidyl]pyrazol-3-yl]carbamate |

TABLE 1-continued

Exemplary Compounds of the Present Invention

| Ex. | Structure | Name |
| --- | --- | --- |
| 233 | 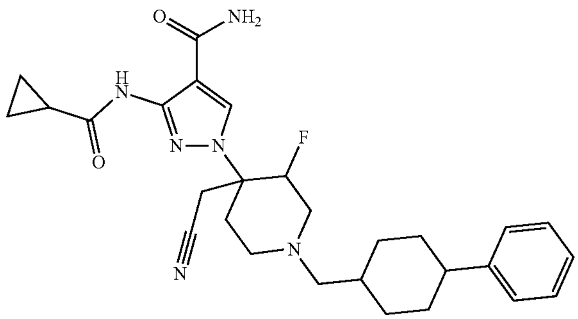 [SMILES: N#CCC1(n2cc(C(N)=O)c(NC(=O)C3CC3)n2)CCN(CC2CCC(c3ccccc3)CC2)CC1F] | 1-[4-(cyanomethyl)-3-fluoro-1-[(4-phenylcyclohexyl)methyl]-4-piperidyl]-3-(cyclopropanecarbonylamino)pyrazole-4-carboxamide |
| 234 | 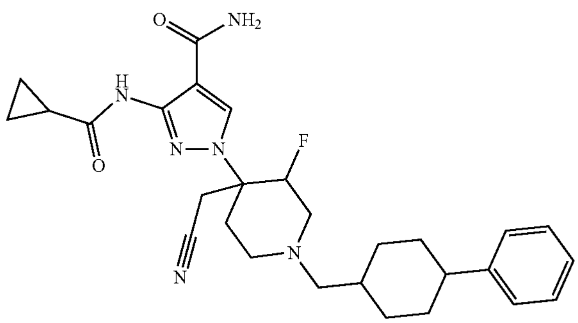 [SMILES: N#CCC1(n2cc(C(N)=O)c(NC(=O)C3CC3)n2)CCN(CC2CCC(c3ccccc3)CC2)CC1F] | 1-[4-(cyanomethyl)-3-fluoro-1-[(4-phenylcyclohexyl)methyl]-4-piperidyl]-3-(cyclopropanecarbonylamino)pyrazole-4-carboxamide |
| 235 | 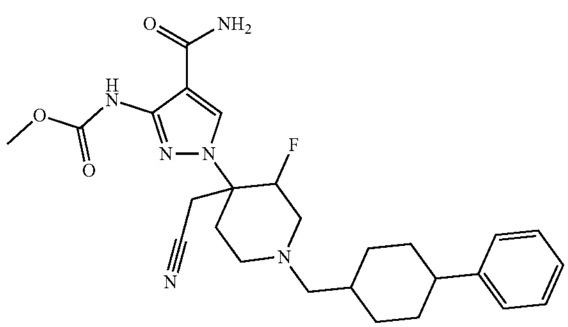 [SMILES: COC(=O)Nc1nn(C2(CC#N)CCN(CC3CCC(c4ccccc4)CC3)CC2F)cc1C(N)=O] | methyl N-[4-carbamoyl-1-[4-(cyanomethyl)-3-fluoro-1-[(4-phenylcyclohexyl)methyl]-4-piperidyl]pyrazol-3-yl]carbamate |
| 236 | 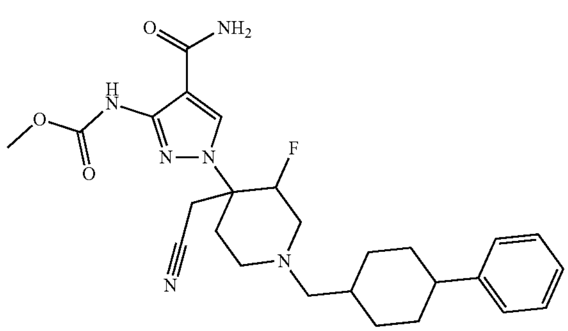 [SMILES: COC(=O)Nc1nn(C2(CC#N)CCN(CC3CCC(c4ccccc4)CC3)CC2F)cc1C(N)=O] | methyl N-[4-carbamoyl-1-[4-(cyanomethyl)-3-fluoro-1-[(4-phenylcyclohexyl)methyl]-4-piperidyl]pyrazol-3-yl]carbamate |

TABLE 1-continued

Exemplary Compounds of the Present Invention

| Ex. | Structure | Name |
|---|---|---|
| 237 | 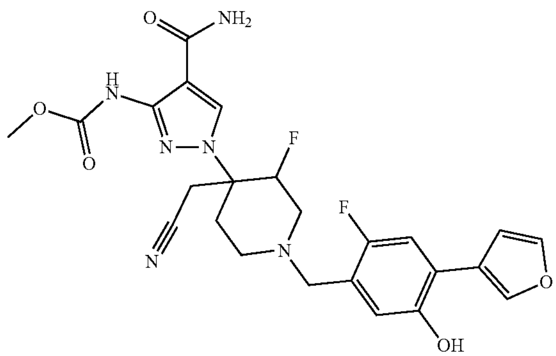 [SMILES: COC(=O)Nc1nn(C2(CC#N)CCN(Cc3cc(O)c(-c4ccoc4)cc3F)CC2F)cc1C(N)=O] | methyl N-[4-carbamoyl-1-[4-(cyanomethyl)-3-fluoro-1-[[2-fluoro-4-(3-furyl)-5-hydroxy-phenyl]methyl]-4-piperidyl]pyrazol-3-yl]carbamate |
| 238 | 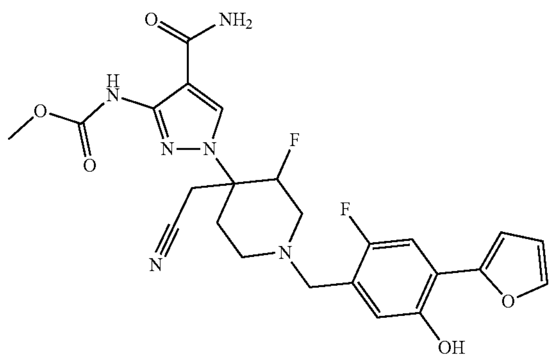 [SMILES: COC(=O)Nc1nn(C2(CC#N)CCN(Cc3cc(O)c(-c4ccco4)cc3F)CC2F)cc1C(N)=O] | methyl N-[4-carbamoyl-1-[4-(cyanomethyl)-3-fluoro-1-[[2-fluoro-4-(2-furyl)-5-hydroxy-phenyl]methyl]-4-piperidyl]pyrazol-3-yl]carbamate |
| 239 | 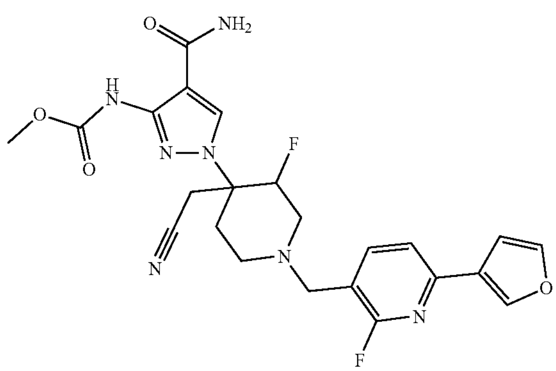 [SMILES: COC(=O)Nc1nn(C2(CC#N)CCN(Cc3ccc(-c4ccoc4)nc3F)CC2F)cc1C(N)=O] | methyl N-[4-carbamoyl-1-[4-(cyanomethyl)-3-fluoro-1-[[2-fluoro-6-(3-furyl)-3-pyridyl]methyl]-4-piperidyl]pyrazol-3-yl]carbamate |
| 240 | 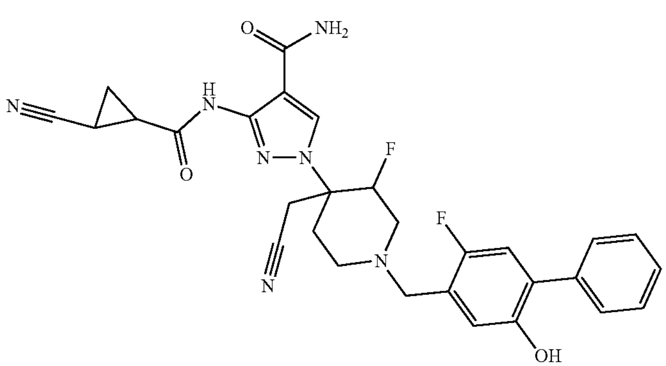 [SMILES: N#CCC1(n2cc(C(N)=O)c(NC(=O)C3CC3C#N)n2)CCN(Cc2cc(O)c(-c3ccccc3)cc2F)CC1F] | 3-[(2-cyanocyclopropanecarbonyl)amino]-1-[4-(cyanomethyl)-3-fluoro-1-[(2-fluoro-5-hydroxy-4-phenyl-phenyl)methyl]-4-piperidyl]pyrazole-4-carboxamide |

TABLE 1-continued

Exemplary Compounds of the Present Invention

| Ex. | Structure | Name |
|---|---|---|
| 241 | 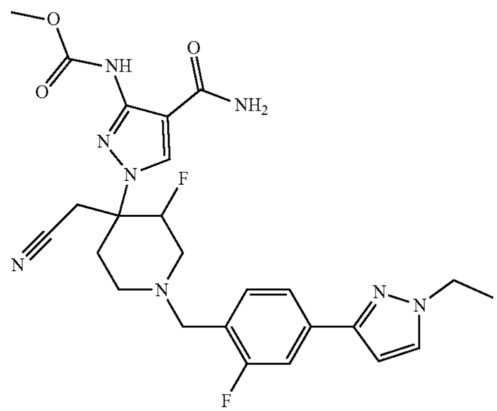 [SMILES: CCn1ccc(-c2ccc(CN3CCC(CC#N)(n4cc(C(N)=O)c(NC(=O)OC)n4)C(F)C3)c(F)c2)n1] | methyl N-[4-carbamoyl-1-[4-(cyanomethyl)-1-[[4-(1-ethylpyrazol-3-yl)-2-fluoro-phenyl]methyl]-3-fluoro-4-piperidyl]pyrazol-3-yl]carbamate |
| 242 | 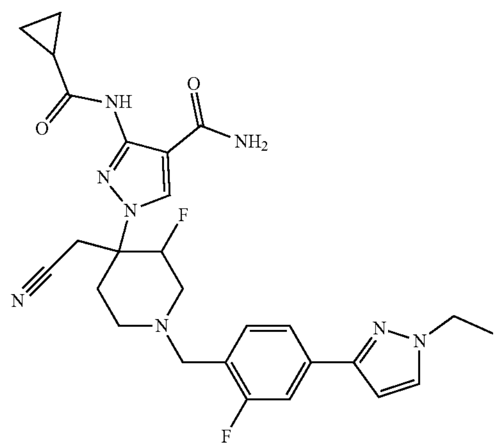 [SMILES: CCn1ccc(-c2ccc(CN3CCC(CC#N)(n4cc(C(N)=O)c(NC(=O)C5CC5)n4)C(F)C3)c(F)c2)n1] | 1-[4-(cyanomethyl)-1-[[4-(1-ethylpyrazol-3-yl)-2-fluoro-phenyl]methyl]-3-fluoro-4-piperidyl]-3-(cyclopropanecarbonylamino)pyrazole-4-carboxamide |
| 243 | 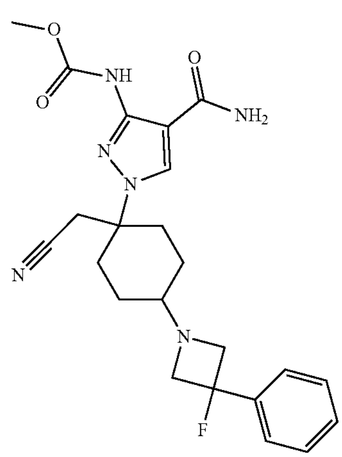 [SMILES: COC(=O)Nc1nn(C2(CC#N)CCC(N3CC(F)(c4ccccc4)C3)CC2)cc1C(N)=O] | methyl N-[4-carbamoyl-1-[1-(cyanomethyl)-4-(3-fluoro-3-phenyl-azetidin-1-yl)cyclohexyl]pyrazol-3-yl]carbamate |

TABLE 1-continued

Exemplary Compounds of the Present Invention

| Ex. | Structure | Name |
|---|---|---|
| 244 | 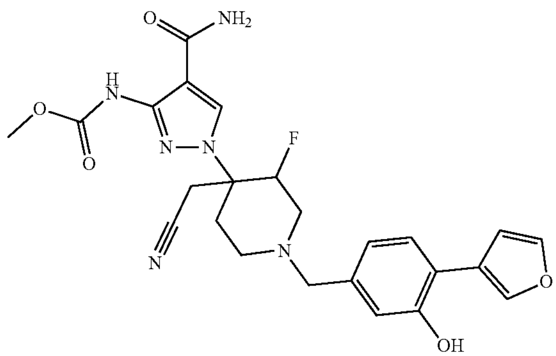 [SMILES: COC(=O)Nc1nn(C2(CC#N)CCN(Cc3ccc(-c4ccoc4)c(O)c3)CC2F)cc1C(N)=O] | methyl N-[4-carbamoyl-1-[4-(cyanomethyl)-3-fluoro-1-[[4-(3-furyl)-3-hydroxyphenyl]methyl]-4-piperidyl]pyrazol-3-yl]carbamate |
| 245 | 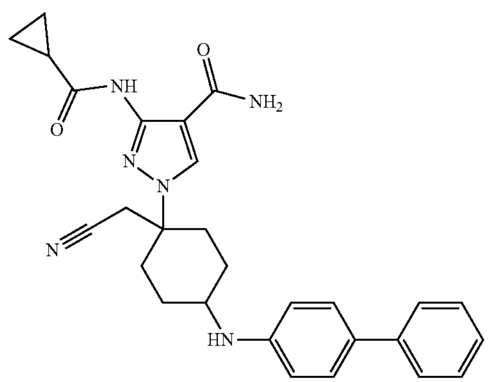 [SMILES: N#CCC1(n2cc(C(N)=O)c(NC(=O)C3CC3)n2)CCC(Nc2ccc(-c3ccccc3)cc2)CC1] | 1-[1-(cyanomethyl)-4-(4-phenylanilino)cyclohexyl]-3-(cyclopropanecarbonylamino)pyrazole-4-carboxamide |
| 246 | 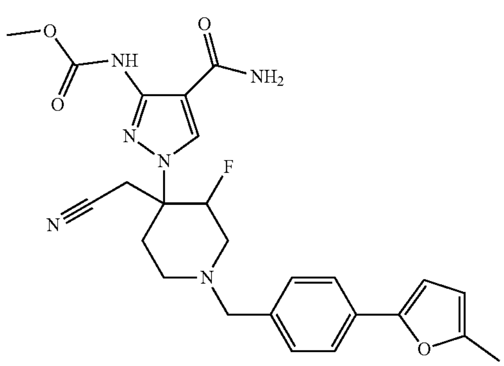 | methyl N-[4-carbamoyl-1-[4-(cyanomethyl)-3-fluoro-1-[[4-(5-methyl-2-furyl)phenyl]methyl]-4-piperidyl]pyrazol-3-yl]carbamate |
| 247 | 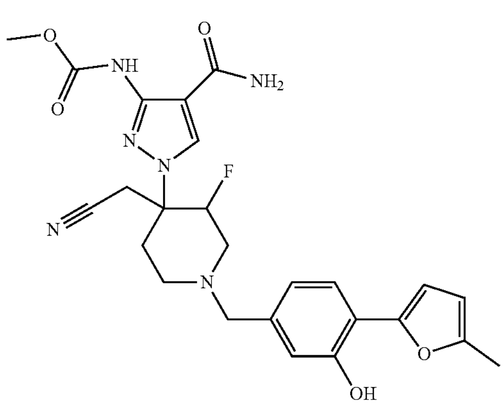 | methyl N-[4-carbamoyl-1-[4-(cyanomethyl)-3-fluoro-1-[[3-hydroxy-4-(5-methyl-2-furyl)phenyl]methyl]-4-piperidyl]pyrazol-3-yl]carbamate |

TABLE 1-continued

Exemplary Compounds of the Present Invention

| Ex. | Structure | Name |
|---|---|---|
| 248 | 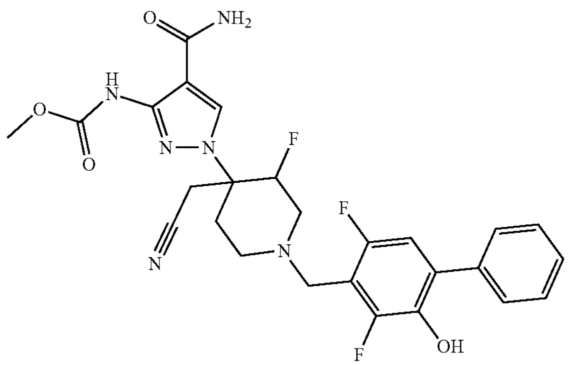 [SMILES: COC(=O)Nc1nn(C2(CC#N)CCN(Cc3c(F)cc(-c4ccccc4)c(O)c3F)CC2F)cc1C(N)=O] | methyl N-[4-carbamoyl-1-[4-(cyanomethyl)-1-[(2,6-difluoro-3-hydroxy-4-phenyl-phenyl)methyl]-3-fluoro-4-piperidyl]pyrazol-3-yl]carbamate |
| 249 | 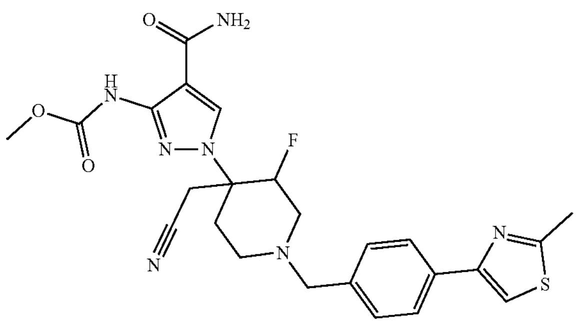 | methyl N-[4-carbamoyl-1-[4-(cyanomethyl)-3-fluoro-1-[[4-(2-methylthiazol-4-yl)phenyl]methyl]-4-piperidyl]pyrazol-3-yl]carbamate |
| 250 | 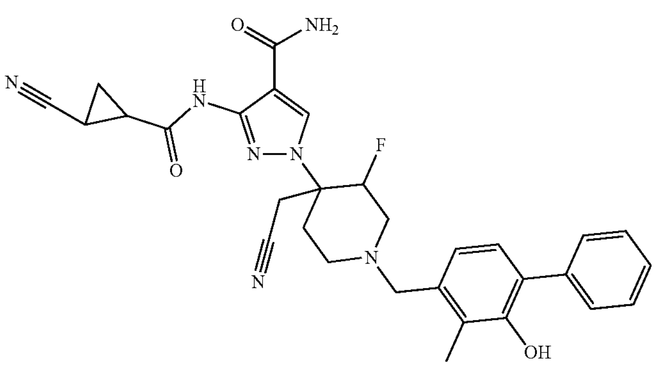 [SMILES: Cc1c(CN2CCC(CC#N)(n3cc(C(N)=O)c(NC(=O)C4CC4C#N)n3)C(F)C2)ccc(-c2ccccc2)c1O] | 3-[(2-cyanocyclopropanecarbonyl)amino]-1-[4-(cyanomethyl)-3-fluoro-1-[(3-hydroxy-2-methyl-4-phenyl-phenyl)methyl]-4-piperidyl]pyrazole-4-carboxamide; formic acid |
| 251 | 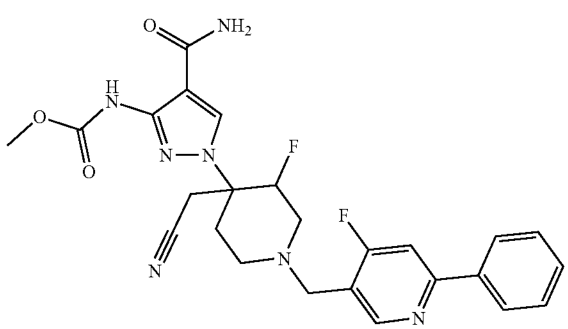 [SMILES: COC(=O)Nc1nn(C2(CC#N)CCN(Cc3cnc(-c4ccccc4)cc3F)CC2F)cc1C(N)=O] | methyl N-[4-carbamoyl-1-[4-(cyanomethyl)-3-fluoro-1-[(4-fluoro-6-phenyl-3-pyridyl)methyl]-4-piperidyl]pyrazol-3-yl]carbamate |

TABLE 1-continued

Exemplary Compounds of the Present Invention

| Ex. | Structure | Name |
|---|---|---|
| 252 | 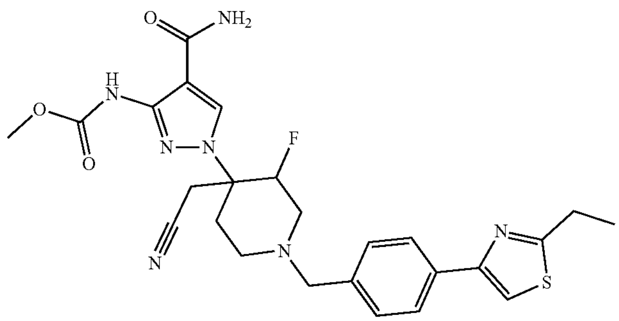 [SMILES: CCc1nc(-c2ccc(CN3CCC(CC#N)(n4cc(C(N)=O)c(NC(=O)OC)n4)C(F)C3)cc2)cs1] | methyl N-[4-carbamoyl-1-[4-(cyanomethyl)-1-[[4-(2-ethylthiazol-4-yl)phenyl]methyl]-3-fluoro-4-piperidyl]pyrazol-3-yl]carbamate |
| 253 | 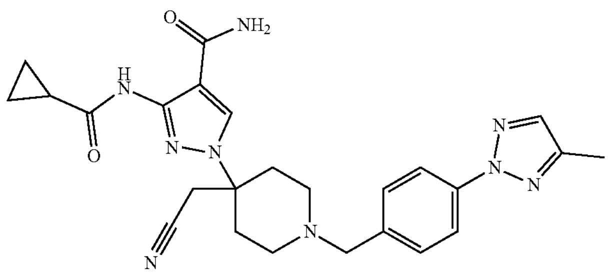 [SMILES: Cc1cnn(-c2ccc(CN3CCC(CC#N)(n4cc(C(N)=O)c(NC(=O)C5CC5)n4)CC3)cc2)n1] | 1-[4-(cyanomethyl)-1-[[4-(4-methyltriazol-2-yl)phenyl]methyl]-4-piperidyl]-3-(cyclopropanecarbonylamino)pyrazole-4-carboxamide |
| 254 | 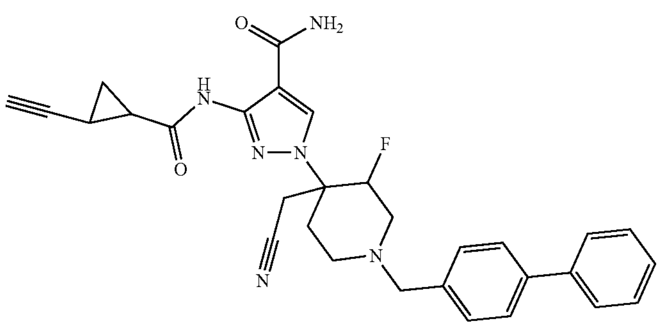 [SMILES: C#CC1CC1C(=O)Nc1nn(C2(CC#N)CCN(Cc3ccc(-c4ccccc4)cc3)CC2F)cc1C(N)=O] | 1-[4-(cyanomethyl)-3-fluoro-1-[(4-phenylphenyl)methyl]-4-piperidyl]-3-[(2-ethynylcyclopropanecarbonyl)amino]pyrazole-4-carboxamide |
| 255 | 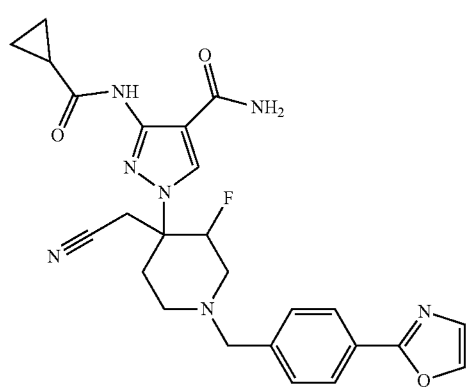 [SMILES: N#CCC1(n2cc(C(N)=O)c(NC(=O)C3CC3)n2)CCN(Cc2ccc(-c3ncco3)cc2)CC1F] | 1-[4-(cyanomethyl)-3-fluoro-1-[(4-oxazol-2-ylphenyl)methyl]-4-piperidyl]-3-(cyclopropanecarbonylamino)pyrazole-4-carboxamide |

TABLE 1-continued

Exemplary Compounds of the Present Invention

| Ex. | Structure | Name |
|---|---|---|
| 256 | 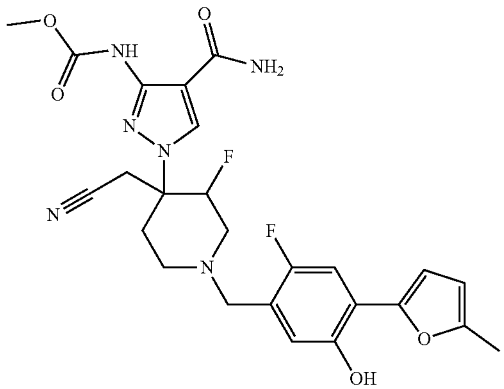 | methyl N-[4-carbamoyl-1-[4-(cyanomethyl)-3-fluoro-1-[[2-fluoro-5-hydroxy-4-(5-methyl-2-furyl)phenyl]methyl]-4-piperidyl]pyrazol-3-yl]carbamate |
| 257 | 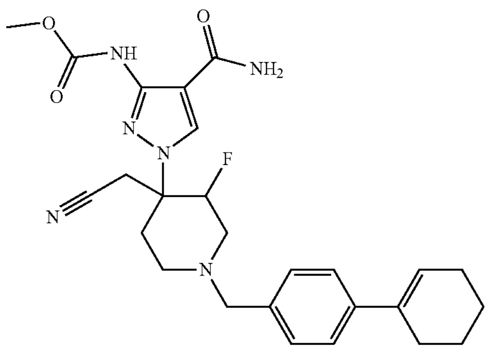 [SMILES: COC(=O)Nc1nn(C2(CC#N)CCN(Cc3ccc(C4=CCCCC4)cc3)CC2F)cc1C(N)=O] | methyl N-[4-carbamoyl-1-[4-(cyanomethyl)-1-[[4-(cyclohexen-1-yl)phenyl]methyl]-3-fluoro-4-piperidyl]pyrazol-3-yl]carbamate |
| 258 | 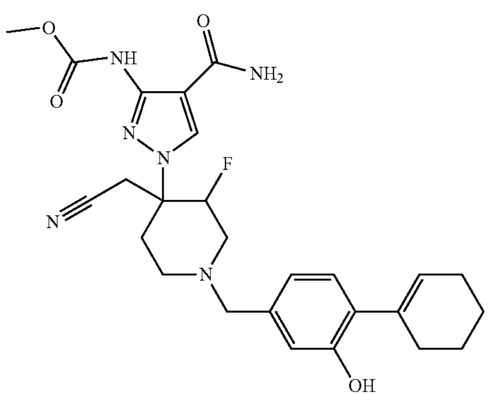 [SMILES: COC(=O)Nc1nn(C2(CC#N)CCN(Cc3ccc(C4=CCCCC4)c(O)c3)CC2F)cc1C(N)=O] | methyl N-[4-carbamoyl-1-[4-(cyanomethyl)-1-[[4-(cyclohexen-1-yl)-3-hydroxy-phenyl]methyl]-3-fluoro-4-piperidyl]pyrazol-3-yl]carbamate |
| 259 | 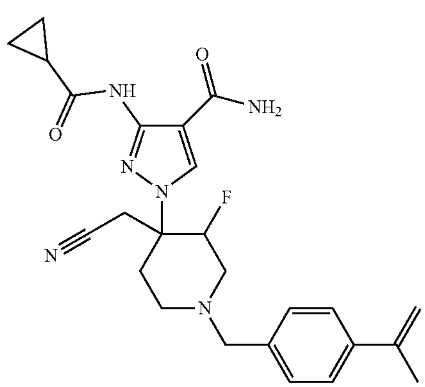 [SMILES: C=C(C)c1ccc(CN2CCC(CC#N)(n3cc(C(N)=O)c(NC(=O)C4CC4)n3)C(F)C2)cc1] | 1-[4-(cyanomethyl)-3-fluoro-1-[(4-isopropenylphenyl)methyl]-4-piperidyl]-3-(cyclopropanecarbonylamino)pyrazole-4-carboxamide |

TABLE 1-continued

Exemplary Compounds of the Present Invention

| Ex. | Structure | Name |
|---|---|---|
| 260 | 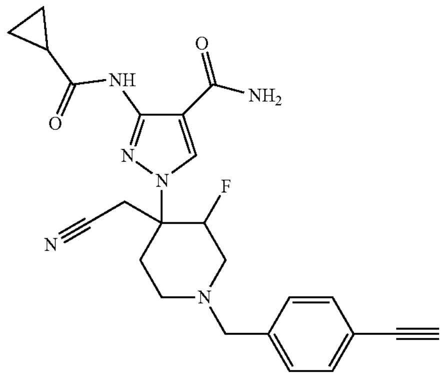 [SMILES: C#Cc1ccc(CN2CCC(CC#N)(n3cc(C(N)=O)c(NC(=O)C4CC4)n3)C(F)C2)cc1] | 1-[4-(cyanomethyl)-1-[(4-ethynylphenyl)methyl]-3-fluoro-4-piperidyl]-3-(cyclopropanecarbonylamino)pyrazole-4-carboxamide |
| 261 | 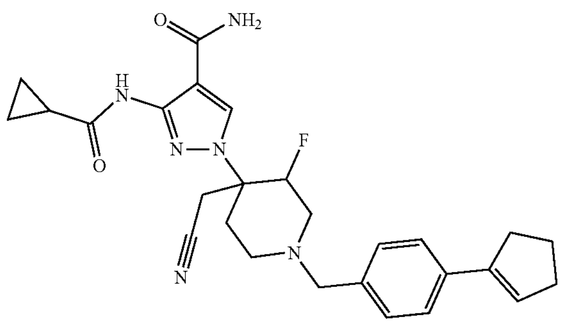 [SMILES: N#CCC1(n2cc(C(N)=O)c(NC(=O)C3CC3)n2)CCN(Cc2ccc(C3=CCCC3)cc2)CC1F] | 1-[4-(cyanomethyl)-1-[[4-(cyclopenten-1-yl)phenyl]methyl]-3-fluoro-4-piperidyl]-3-(cyclopropanecarbonylamino)pyrazole-4-carboxamide |
| 262 | 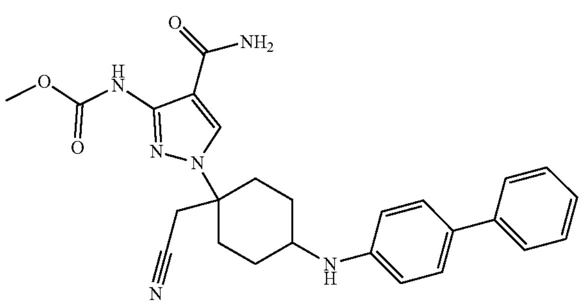 [SMILES: COC(=O)Nc1nn(C2(CC#N)CCC(Nc3ccc(-c4ccccc4)cc3)CC2)cc1C(N)=O] | methyl N-[4-carbamoyl-1-[1-(cyanomethyl)-4-(4-phenylanilino)cyclohexyl]pyrazol-3-yl]carbamate |
| 263 | 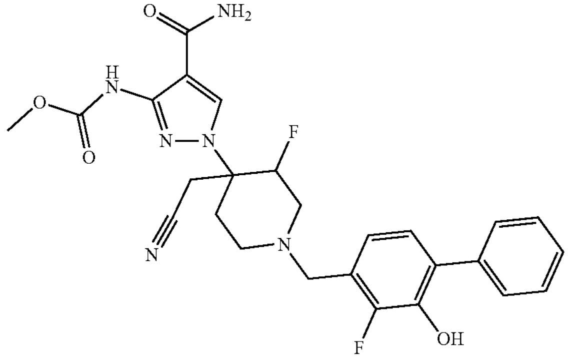 [SMILES: COC(=O)Nc1nn(C2(CC#N)CCN(Cc3ccc(-c4ccccc4)c(O)c3F)CC2F)cc1C(N)=O] | methyl N-[4-carbamoyl-1-[4-(cyanomethyl)-3-fluoro-1-[(2-fluoro-3-hydroxy-4-phenyl-phenyl)methyl]-4-piperidyl]pyrazol-3-yl]carbamate |

TABLE 1-continued

Exemplary Compounds of the Present Invention

| Ex. | Structure | Name |
|---|---|---|
| 264 | 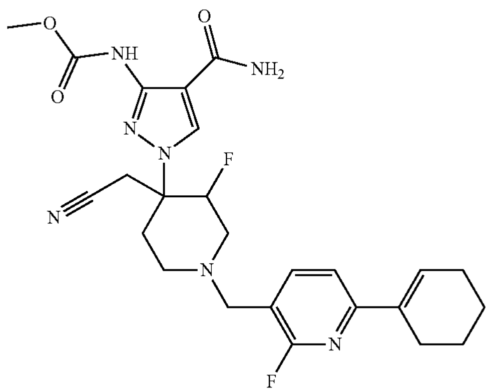 [SMILES: COC(=O)Nc1nn(C2(CC#N)CCN(Cc3ccc(C4=CCCCC4)nc3F)CC2F)cc1C(N)=O] | methyl N-[4-carbamoyl-1-[4-(cyanomethyl)-1-[[6-(cyclohexen-1-yl)-2-fluoro-3-pyridyl]methyl]-3-fluoro-4-piperidyl]pyrazol-3-yl]carbamate |
| 265 | 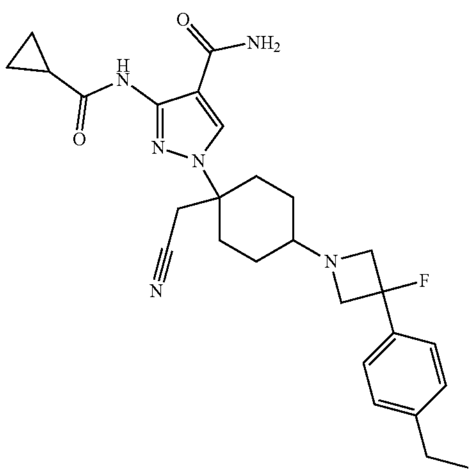 [SMILES: CCc1ccc(C2(F)CN(C3CCC(CC#N)(n4cc(C(N)=O)c(NC(=O)C5CC5)n4)CC3)C2)cc1] | 1-[1-(cyanomethyl)-4-[3-(4-ethylphenyl)-3-fluoro-azetidin-1-yl]cyclohexyl]-3-(cyclopropanecarbonylamino)pyrazole-4-carboxamide |
| 266 | 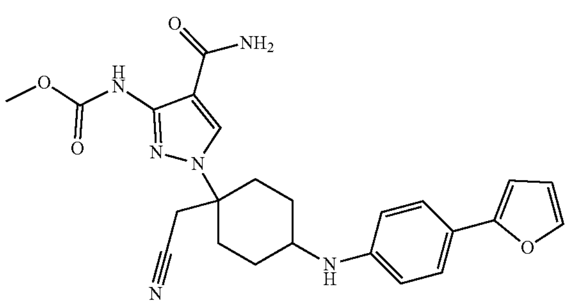 [SMILES: COC(=O)Nc1nn(C2(CC#N)CCC(Nc3ccc(-c4ccco4)cc3)CC2)cc1C(N)=O] | methyl N-[4-carbamoyl-1-[1-(cyanomethyl)-4-[4-(2-furyl)anilino]cyclohexyl]pyrazol-3-yl]carbamate |
| 267 | 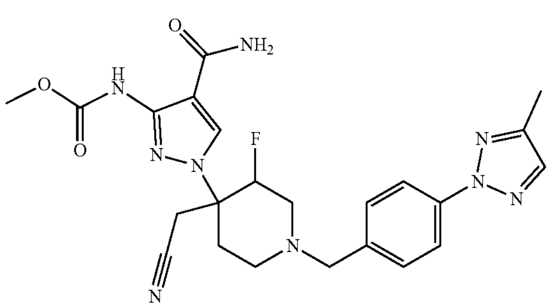 [SMILES: COC(=O)Nc1nn(C2(CC#N)CCN(Cc3ccc(-n4ncc(C)n4)cc3)CC2F)cc1C(N)=O] | methyl N-[4-carbamoyl-1-[4-(cyanomethyl)-3-fluoro-1-[[4-(4-methyltriazol-2-yl)phenyl]methyl]-4-piperidyl]pyrazol-3-yl]carbamate |

TABLE 1-continued

Exemplary Compounds of the Present Invention

| Ex. | Structure | Name |
|---|---|---|
| 268 | 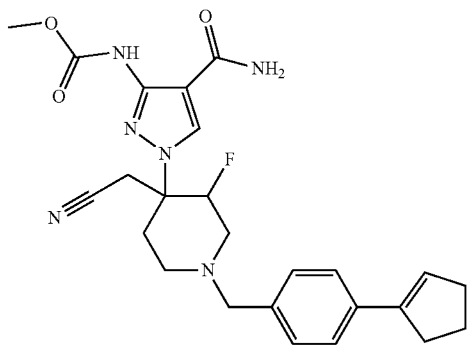 [SMILES: COC(=O)Nc1nn(C2(CC#N)CCN(Cc3ccc(C4=CCCC4)cc3)CC2F)cc1C(N)=O] | methyl N-[4-carbamoyl-1-[4-(cyanomethyl)-1-[[4-(cyclopenten-1-yl)phenyl]methyl]-3-fluoro-4-piperidyl]pyrazol-3-yl]carbamate |
| 269 | 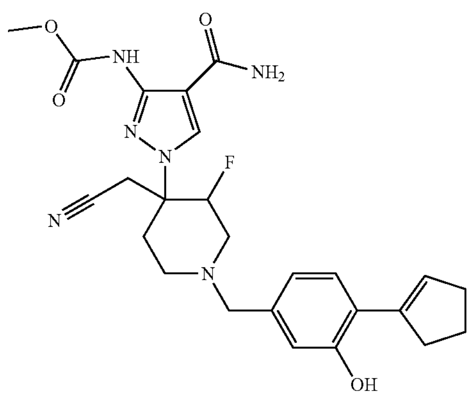 [SMILES: COC(=O)Nc1nn(C2(CC#N)CCN(Cc3ccc(C4=CCCC4)c(O)c3)CC2F)cc1C(N)=O] | methyl N-[4-carbamoyl-1-[4-(cyanomethyl)-1-[[4-(cyclopenten-1-yl)-3-hydroxy-phenyl]methyl]-3-fluoro-4-piperidyl]pyrazol-3-yl]carbamate |
| 270 | 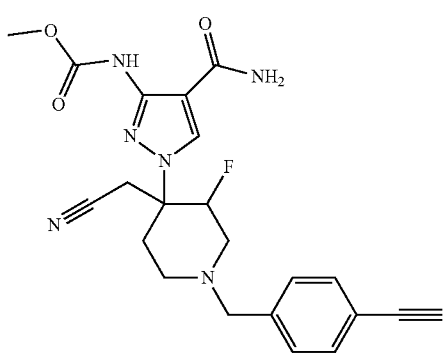 [SMILES: C#Cc1ccc(CN2CCC(CC#N)(n3cc(C(N)=O)c(NC(=O)OC)n3)C(F)C2)cc1] | methyl N-[4-carbamoyl-1-[4-(cyanomethyl)-1-[(4-ethynylphenyl)methyl]-3-fluoro-4-piperidyl]pyrazol-3-yl]carbamate |
| 271 | 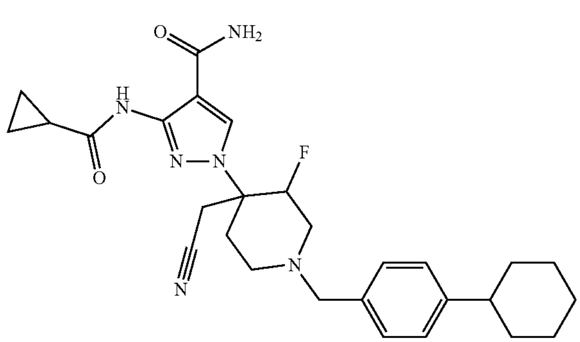 [SMILES: N#CCC1(n2cc(C(N)=O)c(NC(=O)C3CC3)n2)CCN(Cc2ccc(C3CCCCC3)cc2)CC1F] | 1-[4-(cyanomethyl)-1-[(4-cyclohexylphenyl)methyl]-3-fluoro-4-piperidyl]-3-(cyclopropanecarbonylamino)pyrazole-4-carboxamide |

TABLE 1-continued

Exemplary Compounds of the Present Invention

| Ex. | Structure | Name |
|---|---|---|
| 272 | 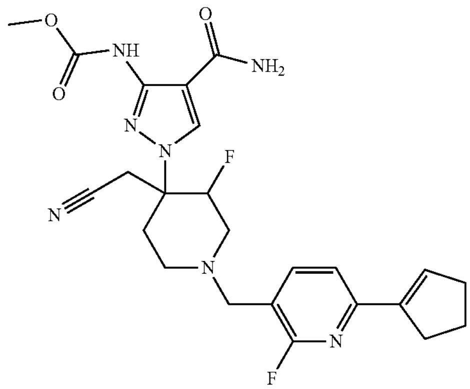 [SMILES: COC(=O)Nc1nn(C2(CC#N)CCN(Cc3ccc(C4=CCCC4)nc3F)CC2F)cc1C(N)=O] | methyl N-[4-carbamoyl-1-[4-(cyanomethyl)-1-[[6-(cyclopenten-1-yl)-2-fluoro-3-pyridyl]methyl]-3-fluoro-4-piperidyl]pyrazol-3-yl]carbamate |
| 273 | 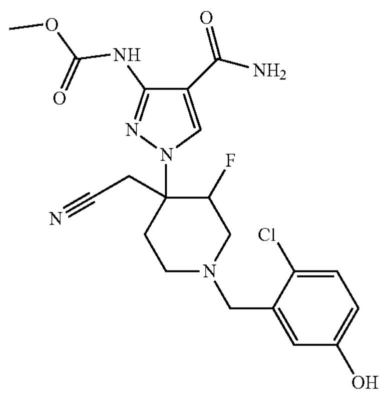 [SMILES: COC(=O)Nc1nn(C2(CC#N)CCN(Cc3cc(O)ccc3Cl)CC2F)cc1C(N)=O] | methyl N-[4-carbamoyl-1-[1-[(2-chloro-5-hydroxy-phenyl)methyl]-4-(cyanomethyl)-3-fluoro-4-piperidyl]pyrazol-3-yl]carbamate |
| 274 | 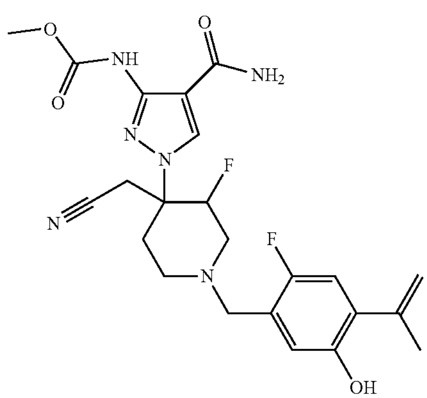 [SMILES: C=C(C)c1cc(F)c(CN2CCC(CC#N)(n3cc(C(N)=O)c(NC(=O)OC)n3)C(F)C2)cc1O] | methyl N-[4-carbamoyl-1-[4-(cyanomethyl)-3-fluoro-1-[(2-fluoro-5-hydroxy-4-isopropenyl-phenyl)methyl]-4-piperidyl]pyrazol-3-yl]carbamate |
| 275 | 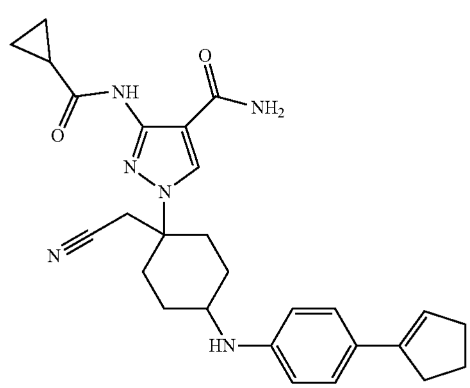 [SMILES: N#CCC1(n2cc(C(N)=O)c(NC(=O)C3CC3)n2)CCC(Nc2ccc(C3=CCCC3)cc2)CC1] | 1-[1-(cyanomethyl)-4-[4-(cyclopenten-1-yl)anilino]cyclohexyl]-3-(cyclopropanecarbonylamino)pyrazole-4-carboxamide |

TABLE 1-continued

Exemplary Compounds of the Present Invention

| Ex. | Structure | Name |
|---|---|---|
| 276 | 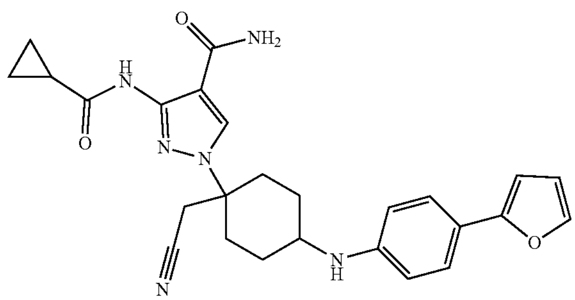 [SMILES: N#CCC1(n2cc(C(N)=O)c(NC(=O)C3CC3)n2)CCC(Nc2ccc(-c3ccco3)cc2)CC1] | 1-[1-(cyanomethyl)-4-[4-(2-furyl)anilino]cyclohexyl]-3-(cyclopropanecarbonylamino)pyrazole-4-carboxamide |
| 277 | 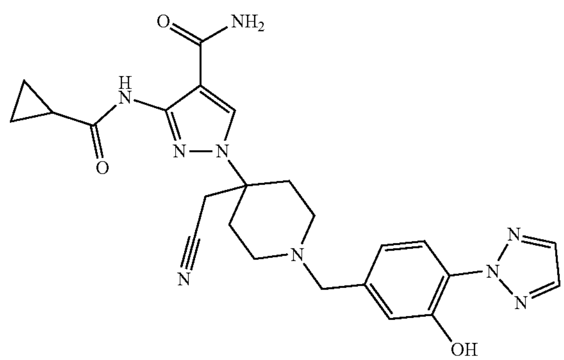 [SMILES: N#CCC1(n2cc(C(N)=O)c(NC(=O)C3CC3)n2)CCN(Cc2ccc(-n3nccn3)c(O)c2)CC1] | 1-[4-(cyanomethyl)-1-[[3-hydroxy-4-(triazol-2-yl)phenyl]methyl]-4-piperidyl]-3-(cyclopropanecarbonylamino)pyrazole-4-carboxamide |
| 278 | 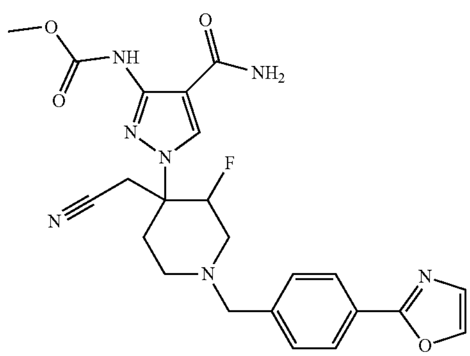 [SMILES: COC(=O)Nc1nn(C2(CC#N)CCN(Cc3ccc(-c4ncco4)cc3)CC2F)cc1C(N)=O] | methyl N-[4-carbamoyl-1-[4-(cyanomethyl)-3-fluoro-1-[(4-oxazol-2-ylphenyl)methyl]-4-piperidyl]pyrazol-3-yl]carbamate |
| 279 | 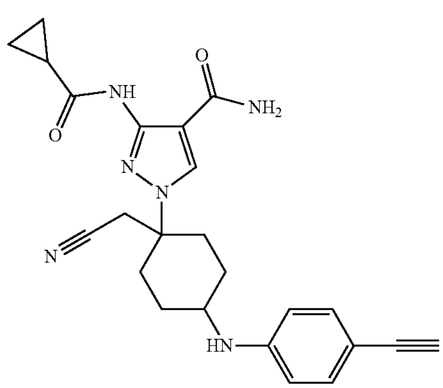 [SMILES: C#Cc1ccc(NC2CCC(CC#N)(n3cc(C(N)=O)c(NC(=O)C4CC4)n3)CC2)cc1] | 1-[1-(cyanomethyl)-4-(4-ethynylanilino)cyclohexyl]-3-(cyclopropanecarbonylamino)pyrazole-4-carboxamide |

TABLE 1-continued

Exemplary Compounds of the Present Invention

| Ex. | Structure | Name |
|---|---|---|
| 280 | 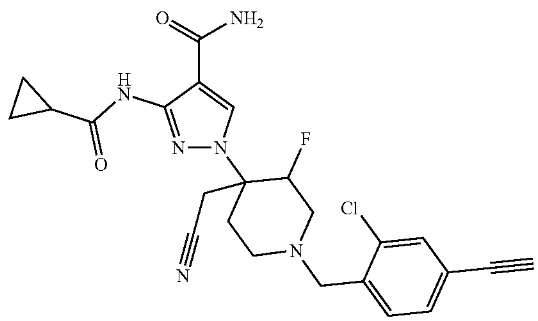 [SMILES: C#Cc1ccc(CN2CCC(CC#N)(n3cc(C(N)=O)c(NC(=O)C4CC4)n3)C(F)C2)c(Cl)c1] | 1-[1-[(2-chloro-4-ethynyl-phenyl)methyl]-4-(cyanomethyl)-3-fluoro-4-piperidyl]-3-(cyclopropanecarbonylamino)pyrazole-4-carboxamide |
| 281 | 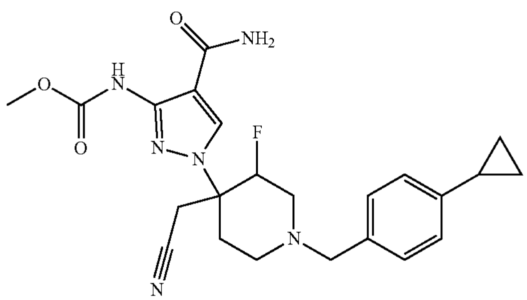 [SMILES: COC(=O)Nc1nn(C2(CC#N)CCN(Cc3ccc(C4CC4)cc3)CC2F)cc1C(N)=O] | methyl N-[4-carbamoyl-1-[4-(cyanomethyl)-1-[(4-cyclopropylphenyl)methyl]-3-fluoro-4-piperidyl]pyrazol-3-yl]carbamate |
| 282 | 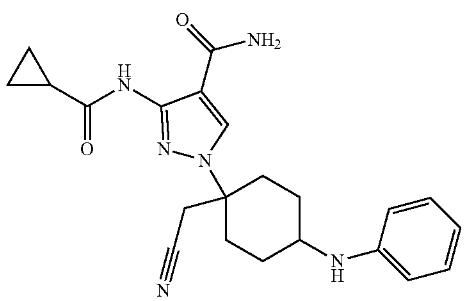 [SMILES: N#CCC1(n2cc(C(N)=O)c(NC(=O)C3CC3)n2)CCC(Nc2ccccc2)CC1] | 1-[4-anilino-1-(cyanomethyl)cyclohexyl]-3-(cyclopropanecarbonylamino)pyrazole-4-carboxamide |
| 283 | 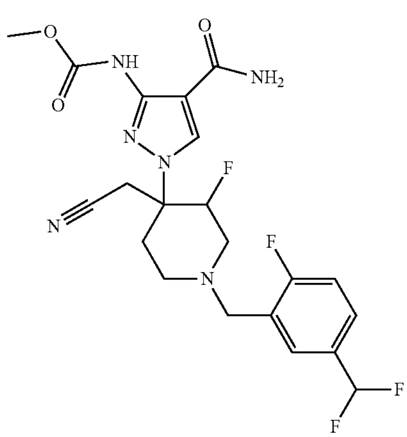 [SMILES: COC(=O)Nc1nn(C2(CC#N)CCN(Cc3cc(C(F)F)ccc3F)CC2F)cc1C(N)=O] | methyl N-[4-carbamoyl-1-[4-(cyanomethyl)-1-[[5-(difluoromethyl)-2-fluoro-phenyl]methyl]-3-fluoro-4-piperidyl]pyrazol-3-yl]carbamate |

TABLE 1-continued

Exemplary Compounds of the Present Invention

| Ex. | Structure | Name |
| --- | --- | --- |
| 284 | 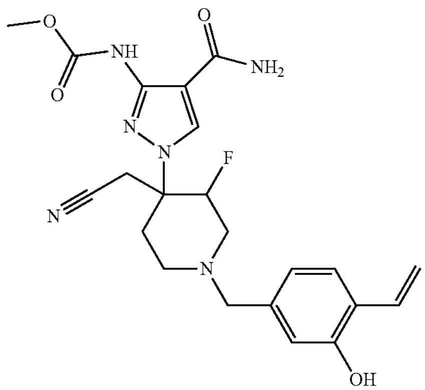 [SMILES: C=Cc1ccc(CN2CCC(CC#N)(n3cc(C(N)=O)c(NC(=O)OC)n3)C(F)C2)cc1O] | methyl N-[4-carbamoyl-1-[4-(cyanomethyl)-3-fluoro-1-[(3-hydroxy-4-vinyl-phenyl)methyl]-4-piperidyl]pyrazol-3-yl]carbamate |
| 285 | 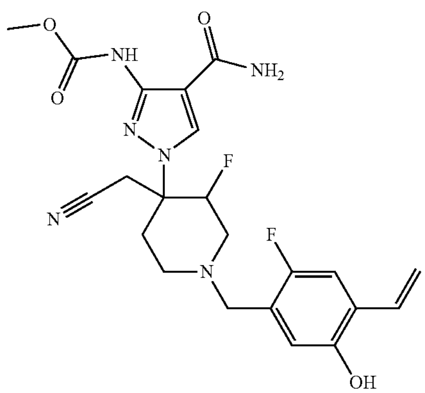 [SMILES: C=Cc1cc(F)c(CN2CCC(CC#N)(n3cc(C(N)=O)c(NC(=O)OC)n3)C(F)C2)cc1O] | methyl N-[4-carbamoyl-1-[4-(cyanomethyl)-3-fluoro-1-[(2-fluoro-5-hydroxy-4-vinyl-phenyl)methyl]-4-piperidyl]pyrazol-3-yl]carbamate |
| 286 | 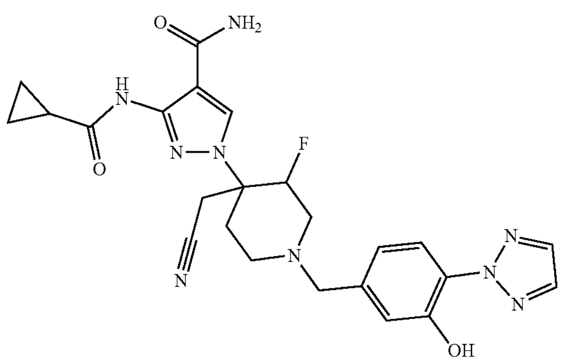 [SMILES: N#CCC1(n2cc(C(N)=O)c(NC(=O)C3CC3)n2)CCN(Cc2ccc(-n3nccn3)c(O)c2)CC1F] | 1-[4-(cyanomethyl)-3-fluoro-1-[[3-hydroxy-4-(triazol-2-yl)phenyl]methyl]-4-piperidyl]-3-(cyclopropanecarbonylamino)pyrazole-4-carboxamide |
| 287 | 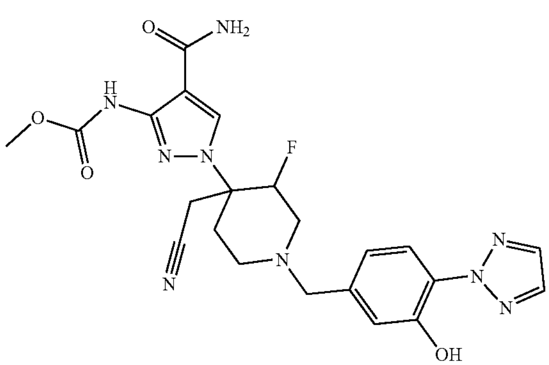 [SMILES: COC(=O)Nc1nn(C2(CC#N)CCN(Cc3ccc(-n4nccn4)c(O)c3)CC2F)cc1C(N)=O] | methyl N-[4-carbamoyl-1-[4-(cyanomethyl)-3-fluoro-1-[[3-hydroxy-4-(triazol-2-yl)phenyl]methyl]-4-piperidyl]pyrazol-3-yl]carbamate |

TABLE 1-continued

Exemplary Compounds of the Present Invention

| Ex. | Structure | Name |
|---|---|---|
| 288 | 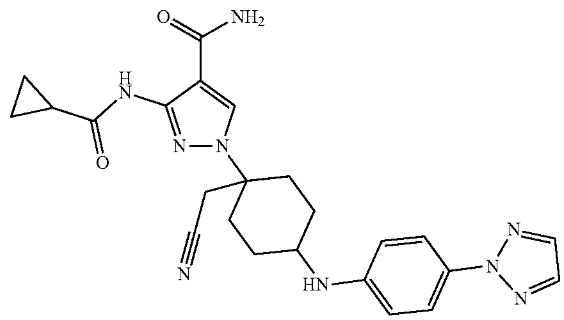 [SMILES: N#CCC1(n2cc(C(N)=O)c(NC(=O)C3CC3)n2)CCC(Nc2ccc(-n3nccn3)cc2)CC1] | 1-[1-(cyanomethyl)-4-[4-(triazol-2-yl)anilino]cyclohexyl]-3-(cyclopropanecarbonylamino)pyrazole-4-carboxamide |
| 289 | 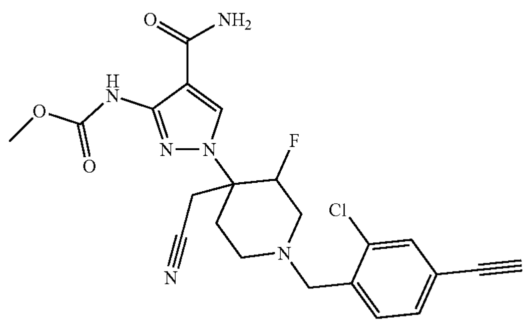 [SMILES: C#Cc1ccc(CN2CCC(CC#N)(n3cc(C(N)=O)c(NC(=O)OC)n3)C(F)C2)c(Cl)c1] | methyl N-[4-carbamoyl-1-[1-[(2-chloro-4-ethynyl-phenyl)methyl]-4-(cyanomethyl)-3-fluoro-4-piperidyl]pyrazol-3-yl]carbamate |
| 290 | 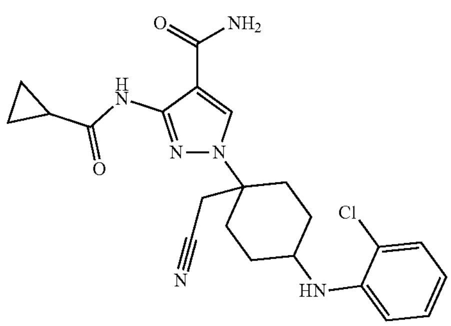 [SMILES: N#CCC1(n2cc(C(N)=O)c(NC(=O)C3CC3)n2)CCC(Nc2ccccc2Cl)CC1] | 1-[4-(2-chloroanilino)-1-(cyanomethyl)cyclohexyl]-3-(cyclopropanecarbonylamino)pyrazole-4-carboxamide |
| 291 | 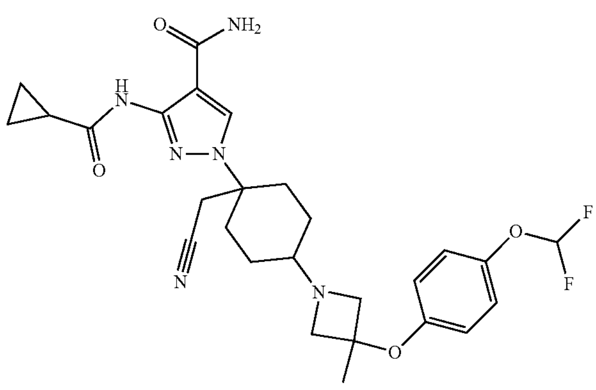 [SMILES: CC1(Oc2ccc(OC(F)F)cc2)CN(C2CCC(CC#N)(n3cc(C(N)=O)c(NC(=O)C4CC4)n3)CC2)C1] | 1-[1-(cyanomethyl)-4-[3-[4-(difluoromethoxy)phenoxy]-3-methyl-azetidin-1-yl]cyclohexyl]-3-(cyclopropanecarbonylamino)pyrazole-4-carboxamide |

TABLE 1-continued

Exemplary Compounds of the Present Invention

| Ex. | Structure | Name |
|---|---|---|
| 292 | 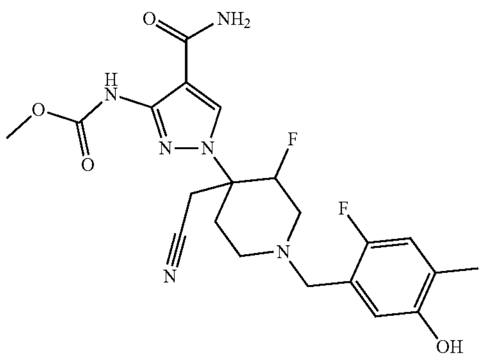 | methyl N-[4-carbamoyl-1-[4-(cyanomethyl)-3-fluoro-1-[(2-fluoro-5-hydroxy-4-methyl-phenyl)methyl]-4-piperidyl]pyrazol-3-yl]carbamate |
| 293 | 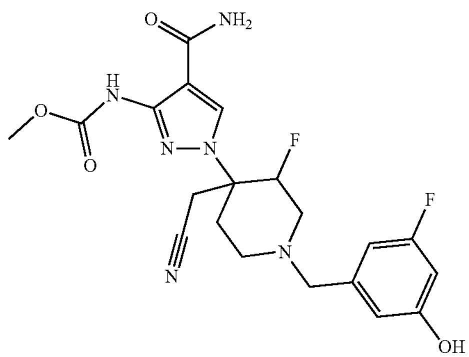 [SMILES: COC(=O)Nc1nn(C2(CC#N)CCN(Cc3cc(O)cc(F)c3)CC2F)cc1C(N)=O] | methyl N-[4-carbamoyl-1-[4-(cyanomethyl)-3-fluoro-1-[(3-fluoro-5-hydroxy-phenyl)methyl]-4-piperidyl]pyrazol-3-yl]carbamate |
| 294 | 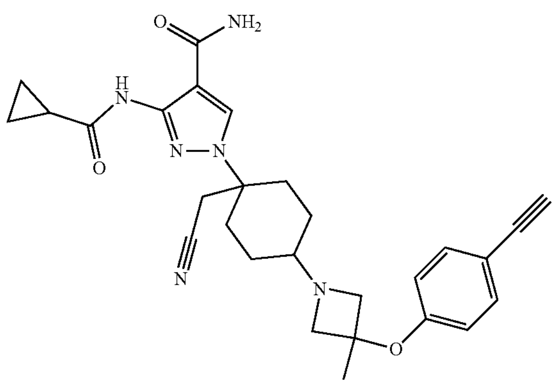 [SMILES: C#Cc1ccc(OC2(C)CN(C3CCC(CC#N)(n4cc(C(N)=O)c(NC(=O)C5CC5)n4)CC3)C2)cc1] | 1-[1-(cyanomethyl)-4-[3-(4-ethynylphenoxy)-3-methyl-azetidin-1-yl]cyclohexyl]-3-(cyclopropanecarbonylamino)pyrazole-4-carboxamide |
| 295 | 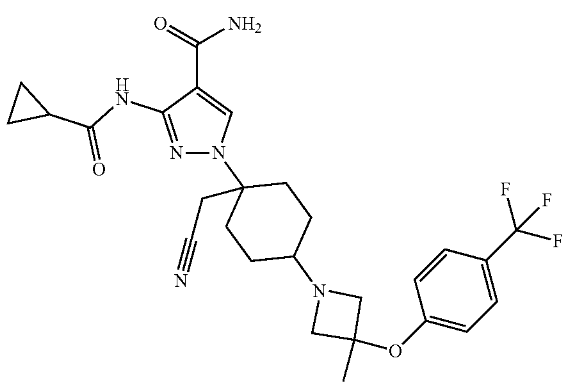 [SMILES: CC1(Oc2ccc(C(F)(F)F)cc2)CN(C2CCC(CC#N)(n3cc(C(N)=O)c(NC(=O)C4CC4)n3)CC2)C1] | 1-[1-(cyanomethyl)-4-[3-methyl-3-[4-(trifluoromethyl)phenoxy]azetidin-1-yl]cyclohexyl]-3-(cyclopropanecarbonylamino)pyrazole-4-carboxamide |

TABLE 1-continued

Exemplary Compounds of the Present Invention

| Ex. | Structure | Name |
|---|---|---|
| 296 | 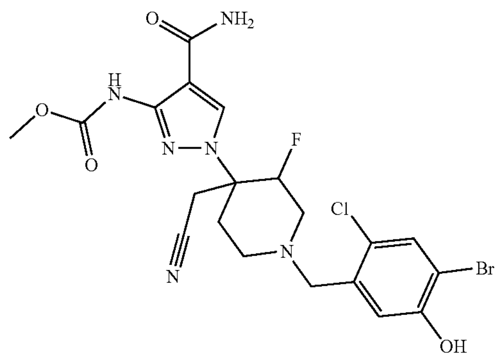 [SMILES: COC(=O)Nc1nn(C2(CC#N)CCN(Cc3cc(O)c(Br)cc3Cl)CC2F)cc1C(N)=O] | methyl N-[1-[1-[(4-bromo-2-chloro-5-hydroxy-phenyl)methyl]-4-(cyanomethyl)-3-fluoro-4-piperidyl]-4-carbamoyl-pyrazol-3-yl]carbamate |
| 297 | 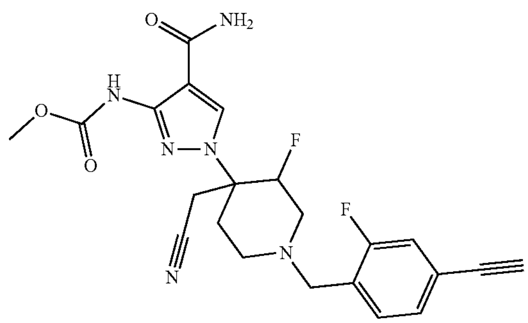 [SMILES: C#Cc1ccc(CN2CCC(CC#N)(n3cc(C(N)=O)c(NC(=O)OC)n3)C(F)C2)c(F)c1] | methyl N-[4-carbamoyl-1-[4-(cyanomethyl)-1-[(4-ethynyl-2-fluoro-phenyl)methyl]-3-fluoro-4-piperidyl]pyrazol-3-yl]carbamate |
| 298 | 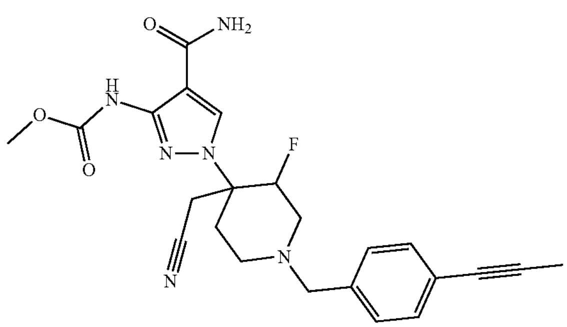 [SMILES: CC#Cc1ccc(CN2CCC(CC#N)(n3cc(C(N)=O)c(NC(=O)OC)n3)C(F)C2)cc1] | methyl N-[4-carbamoyl-1-[4-(cyanomethyl)-3-fluoro-1-[(4-prop-1-ynylphenyl)methyl]-4-piperidyl]pyrazol-3-yl]carbamate |
| 299 | 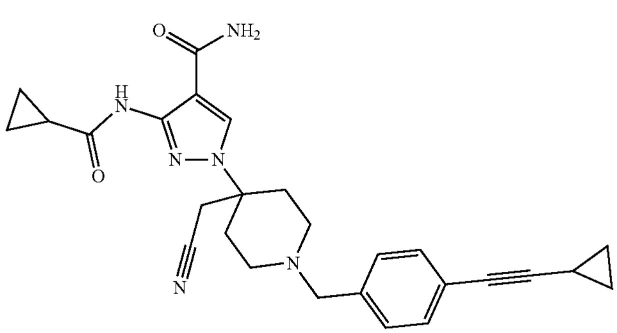 [SMILES: N#CCC1(n2cc(C(N)=O)c(NC(=O)C3CC3)n2)CCN(Cc2ccc(C#CC3CC3)cc2)CC1] | 1-[4-(cyanomethyl)-1-[[4-(2-cyclopropylethynyl)phenyl]methyl]-4-piperidyl]-3-(cyclopropanecarbonylamino)pyrazole-4-carboxamide |

TABLE 1-continued

Exemplary Compounds of the Present Invention

| Ex. | Structure | Name |
|---|---|---|
| 300 | 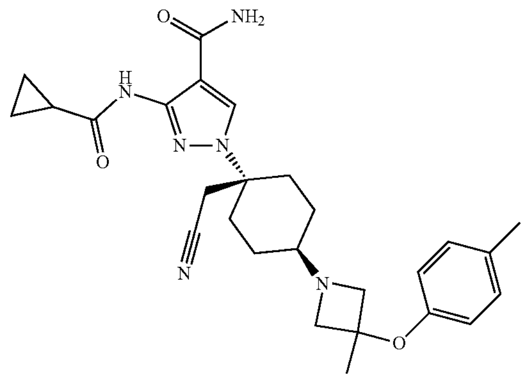 [SMILES: Cc1ccc(OC2(C)CN([C@H]3CC[C@](CC#N)(n4cc(C(N)=O)c(NC(=O)C5CC5)n4)CC3)C2)cc1] | 1-[1-(cyanomethyl)-4-[3-methyl-3-(4-methylphenoxy)azetidin-1-yl]cyclohexyl]-3-(cyclopropanecarbonylamino)pyrazole-4-carboxamide |
| 301 | 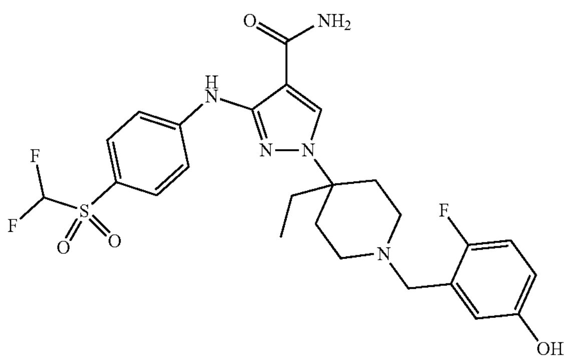 [SMILES: CCC1(n2cc(C(N)=O)c(Nc3ccc(S(=O)(=O)C(F)F)cc3)n2)CCN(Cc2cc(O)ccc2F)CC1] | 3-[4-(difluoromethylsulfonyl)anilino]-1-[4-ethyl-1-[(2-fluoro-5-hydroxyphenyl)methyl]-4-piperidyl]pyrazole-4-carboxamide |
| 302 | 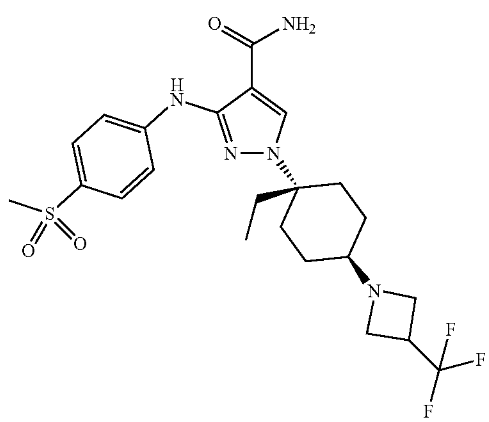 [SMILES: CC[C@]1(n2cc(C(N)=O)c(Nc3ccc(S(C)(=O)=O)cc3)n2)CC[C@H](N2CC(C(F)(F)F)C2)CC1] | 1-[1-ethyl-4-[3-(trifluoromethyl)azetidin-1-yl]cyclohexyl]-3-(4-methylsulfonylanilino)pyrazole-4-carboxamide |
| 303 | 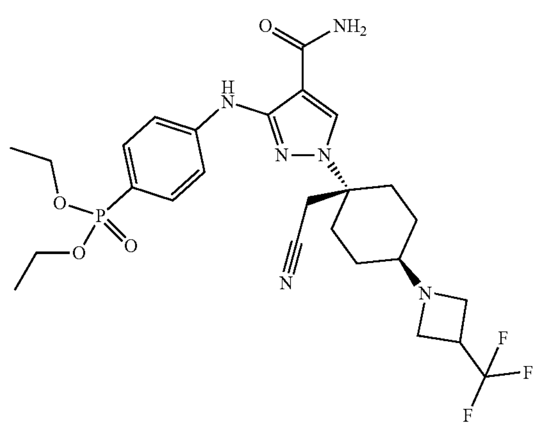 [SMILES: CCOP(=O)(OCC)c1ccc(Nc2nn([C@]3(CC#N)CC[C@@H](N4CC(C(F)(F)F)C4)CC3)cc2C(N)=O)cc1] | 1-[1-(cyanomethyl)-4-[3-(trifluoromethyl)azetidin-1-yl]cyclohexyl]-3-(4-diethoxyphosphorylanilino)pyrazole-4-carboxamide |

TABLE 1-continued

Exemplary Compounds of the Present Invention

| Ex. | Structure | Name |
| --- | --- | --- |
| 304 | 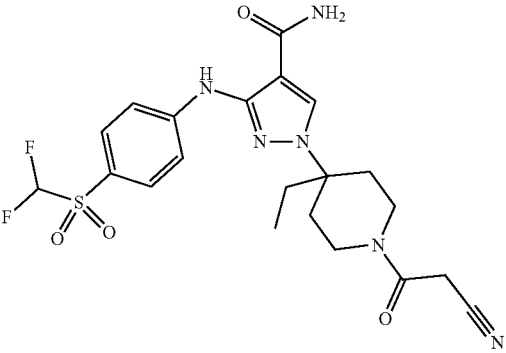 [SMILES: CCC1(n2cc(C(N)=O)c(Nc3ccc(S(=O)(=O)C(F)F)cc3)n2)CCN(C(=O)CC#N)CC1] | 1-[1-(2-cyanoacetyl)-4-ethyl-4-piperidyl]-3-[4-(difluoromethylsulfonyl)anilino]pyrazole-4-carboxamide |

In one embodiment the disease or condition is cancer, polycythemia vera, essential thrombocytosis, myelofibrosis, chronic myelogenous leukemia (CML), rheumatoid arthritis, inflammatory bowel syndrome, Crohn's disease, psoriasis, contact dermatitis or delayed hypersensitivity reactions.

In one embodiment the use of a compound of Formula (I) or a salt thereof, for the treatment of cancer, polycythemia vera, essential thrombocytosis, myelofibrosis, chronic myelogenous leukemia (CML), rheumatoid arthritis, inflammatory bowel syndrome, Crohn's disease, psoriasis, contact dermatitis or delayed hypersensitivity reactions is provided.

In one embodiment a composition that is formulated for administration by inhalation is provided.

In one embodiment a metered dose inhaler that comprises a compound of Formula (I) or a salt thereof is provided.

In one embodiment the compound of Formula (I) or a salt thereof is at least five-times more potent as an inhibitor of JAK1 than as an inhibitor of JAK2.

In one embodiment the compound of Formula (I) or a salt thereof is at least ten-times more potent as an inhibitor of JAK1 than as an inhibitor of JAK2.

In one embodiment the compound of Formula (I) or a salt thereof is at least five-times more potent as an inhibitor of JAK1 than as an inhibitor of JAK3.

In one embodiment the compound of Formula (I) or a salt thereof is at least ten-times more potent as an inhibitor of JAK1 than as an inhibitor of JAK3.

In one embodiment a method for treating hair loss in a mammal comprising administering a compound of Formula (I) or a salt thereof to the mammal is provided.

In one embodiment the use of a compound of Formula (I) or a salt thereof for the treatment of hair loss is provided.

In one embodiment the use of a compound of Formula (I) or a salt thereof to prepare a medicament for treating hair loss in a mammal is provided.

Synthesis of Janus Kinase Inhibitor Compounds

Compounds of the invention may be synthesized by synthetic routes described herein. In certain embodiments, processes well-known in the chemical arts can be used, in addition to, or in light of, the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-19, Wiley, N.Y. (1967-1999 ed.), Beilsteins Handbuch der organischen Chemie, 4, Aufl. ed. Springer-Verlag, Berlin, including supplements (also available via the Beilstein online database)), or Comprehensive Heterocyclic Chemistry, Editors Katrizky and Rees, Pergamon Press, 1984.

Compounds may be prepared singly or as compound libraries comprising at least 2, for example 5 to 1,000 compounds, or 10 to 100 compounds. Libraries of compounds may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds of the invention, such as a compound of Formula (I).

For illustrative purposes, reaction Schemes below provide routes for synthesizing the compounds of the invention as well as key intermediates. For a more detailed description of the individual reaction steps, see the Examples section below. Those skilled in the art will appreciate that other synthetic routes may be used. Although some specific starting materials and reagents are depicted in the Schemes and discussed below, other starting materials and reagents can be substituted to provide a variety of derivatives or reaction conditions. In addition, many of the compounds prepared by the methods described below can be further modified in light of this disclosure using conventional chemistry well known to those skilled in the art.

In the preparation of compounds of the invention, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, benzyl, phenyl sulfonyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Other conversions commonly used in the synthesis of compounds of the invention, and which can be carried out using a variety of reagents and conditions, include the following:

(1) Reaction of a carboxylic acid with an amine to form an amide. Such a transformation can be achieved using various reagents known to those skilled in the art but a comprehensive review can be found in *Tetrahedron,* 2005, 61, 10827-10852.

(2) Reaction of a primary or secondary amine with an aryl halide or pseudo halide, e.g., a triflate, commonly known as a "Buchwald-Hartwig cross-coupling," can be achieved using a variety of catalysts, ligands and bases. A review of these methods is provided in *Comprehensive Organic Name Reactions and Reagents,* 2010, 575-581.

(3) A palladium cross-coupling reaction between an aryl halide and a vinyl boronic acid or boronate ester. This transformation is a type of "Suzuki-Miyaura cross-coupling," a class of reaction that has been thoroughly reviewed in *Chemical Reviews,* 1995, 95(7), 2457-2483.

(4) The hydrolysis of an ester to give the corresponding carboxylic acid is well known to those skilled in the art and conditions include: for methyl and ethyl esters, the use of a strong aqueous base such as lithium, sodium or potassium hydroxide or a strong aqueous mineral acid such as HCl; for a tert-butyl ester, hydrolysis would be carried out using acid, for example, HCl in dioxane or trifluoroacetic acid (TFA) in dichloromethane (DCM).

Scheme 1

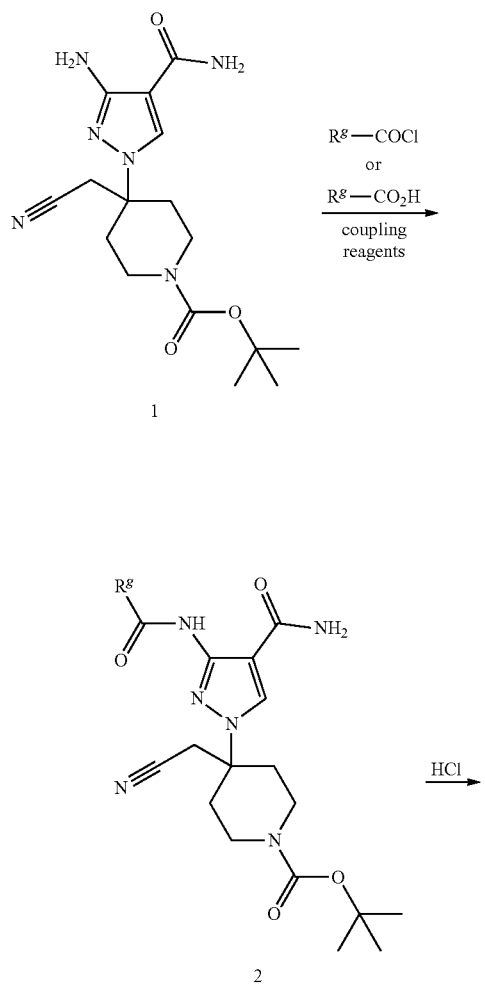

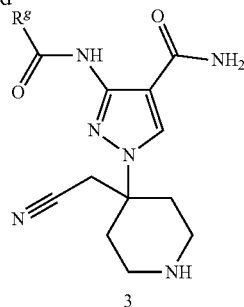

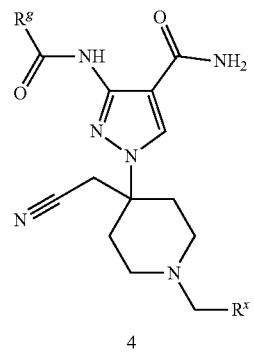

Compounds of formula 4 may be prepared by general synthetic methods as shown in Scheme 1.

Compounds of formula 2 can be synthesized by treatment of aniline 1 with various acid chlorides in a suitable organic solvent such as, but not limited to, dichloromethane (DCM) at a temperature ranging from 0° C. to room temperature and for a time varying from about 30 min to 48 hrs. Alternatively, compounds of formula 2 can be prepared by treatment of aniline 1 with various carboxylic acids in the presence of an amide coupling reagent such as, but not limited to, (1-[bis(dimethylamino)methylene]-1H-1,2,3-triazolo[4,5-b]pyridinium 3-oxidhexafluorophosphate) (HATU) in a suitable organic solvent such as, but not limited to, N,N-dimethylformamide (DMF) at a temperature ranging from room temperature to 65° C. for a time of about 12 hours. Deprotection of the N-tert-butoxycarbonyl (Boc) group of 2 using a protic acid such as, but not limited to, trifluoroacetic acid or hydrochloric acid at about room temperature readily affords compounds of formula 3. Compounds of formula 4 can be synthesized through reductive amination using compounds of formula 3 and the appropriate aldehyde or ketone in the presence of a reducing agent such as, but not limited to, sodium triacetoxyborohydride in a suitable organic solvent such as, but not limited to, dichloromethane at about room temperature and for a time varying from about 30 minutes to 48 hours. Alternatively, compounds of formula 4 can be synthesized through direct alkylation of the piperidine of 3 using an alkyl iodide/bromide/mesylate/triflate in the presence of a base such as, but not limited to, diisopropylethylamine (DIEA) or triethylamine (TEA) in a suitable organic solvent such as, but not limited to, DCM or DMF at a temperature ranging from about 0° C. to about room temperature. Treatment of 4 (wherein $R^g$ includes a suitable group such as for example Cl, Br, I, OTf, etc.) with aryl, heteroaryl or heterocyclic boronic acid or boronate ester under palladium catalyst conditions such as, but not limited to, [1,1'-bis(diphenylphosphino)ferrocene] dichloropalladium(II) in the presence of an inorganic base such as, but not limited to, potassium carbonate in an organic solvent such as, but not limited to, 1,4-dioxane at an elevated temperature affords the corresponding aryl, heteroaryl or heterocyclic substituted compound.

Scheme 2

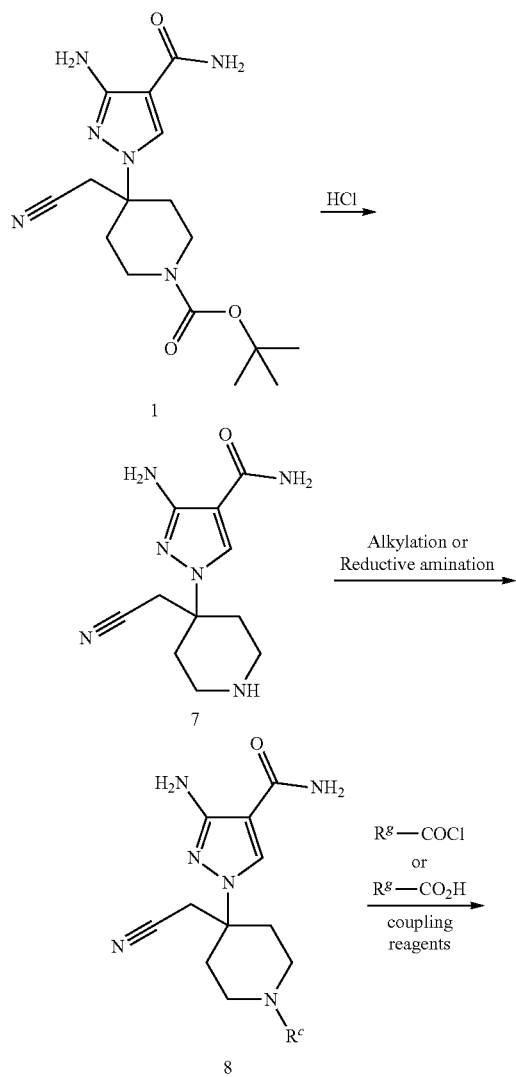

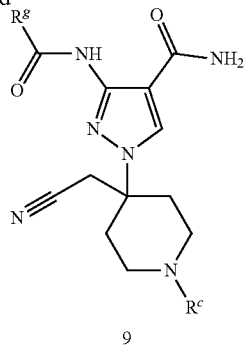

Compounds of formula 9 may be prepared by general synthetic methods as shown in Scheme 2.

Deprotection of the Boc group of 1 using a protic acid such as, but not limited to, trifluoroacetic acid or hydrochloric acid at about room temperature readily affords compound 7. Compounds of formula 8 can be synthesized through reductive amination by treatment of 7 and the appropriate aldehyde or ketone in the presence of a reducing agent such as, but not limited to, sodium triacetoxyborohydride in a suitable organic solvent such as, but not limited to, dichloromethane at about room temperature and for a time varying from about 6 hrs to 12 hrs. Alternatively, compounds of formula 8 can be synthesized through direct alkylation of the piperidine of 7 using an alkyl iodide/bromide/mesylate/triflate in the presence of a base such as, but not limited to, diisopropylethylamine or triethylamine in a suitable organic solvent such as, but not limited to, DCM or DMF at a temperature ranging from about 0° C. to about room temperature. Treatment of compounds of formula 8 with various acid chlorides in a suitable organic solvent such as, but not limited to, dichloromethane (DCM) at a temperature ranging from 0° C. to room temperature and for a time varying from about 30 min to 12 hours to afford compounds of formula 9. Alternatively, compounds of formula 9 can be prepared by treatment of aniline 8 with various carboxylic acids in the presence of an amide coupling reagent such as, but not limited to, HATU in a suitable organic solvent such as, but not limited to, DMF at a temperature ranging from room temperature to 65° C. for a time of about 12 hours.

Scheme 3

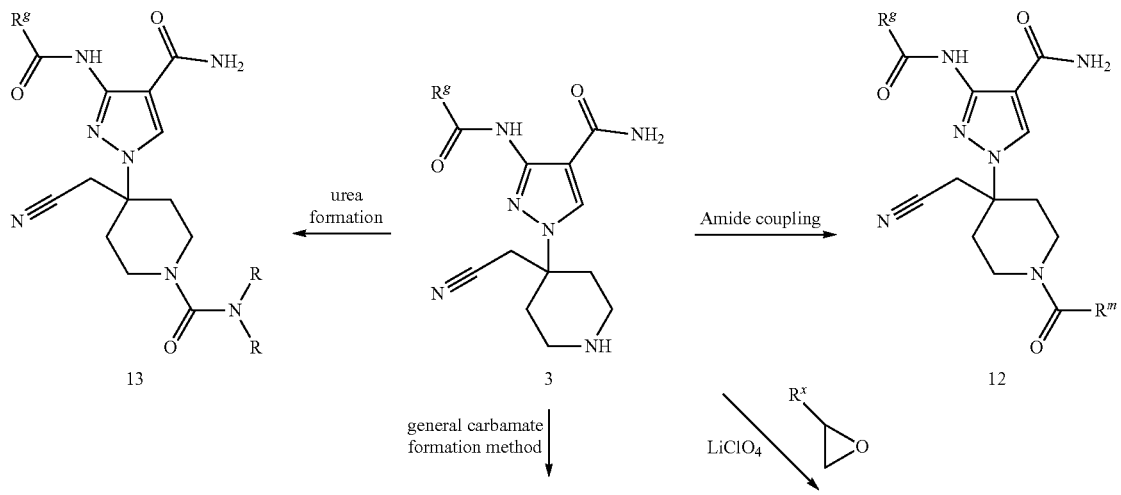

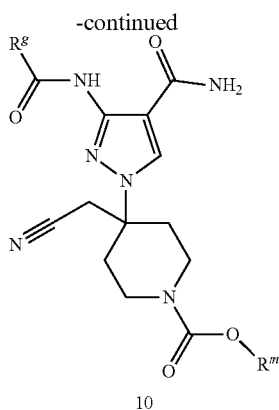

10

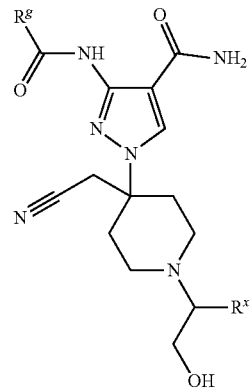

11

Compounds of formula 10, 11 and 12 may be prepared by general synthetic methods as shown in Scheme 3.

Compounds of formula 10 can be synthesized by treatment of 3 with various to substituted 4-nitro carbonates and an organic base such as, but not limited to, triethylamine in a suitable organic solvent such as, but not limited to, ethanol (EtOH) at about room temperature and for a time varying from about 30 minutes to 12 hours. Likewise, other carbamate formation methods can be employed such as, but not limited to, treatment of compound 3 with alkyl or aryl chloroformates. Treatment of compounds of formula 3 with an appropriately substituted oxirane, lithium perchlorate and an organic base such as, but not limited to, DIEA in a suitable organic solvent such as, but not limited to, acetonitrile at about room temperature and for a time varying from about 6 hours to 16 hours afforded compounds of formula 11. Compounds of formula 12 can be prepared by treatment of piperidine 3 with various carboxylic acids in the presence of an amide coupling reagent such as, but not limited to, HATU in a suitable organic solvent such as, but not limited to, DMF at a temperature ranging from room temperature to 65° C. for a time of about 12 hours. From compound 3, compounds of formula 13 can be formed by treatment of compound 3 with carbonyldiimidazole, an organic base such as, but not limited to, DIEA in an organic solvent such as, but not limited to, 1-methyl-2-pyrrolidinone for a time ranging from 1 hr to 24 hrs at a temperature of about 80° C. Alternatively other methods can be used to form compounds of formula 13 such as, but not limited to, treatment of compound 3 with various substituted isocyanates.

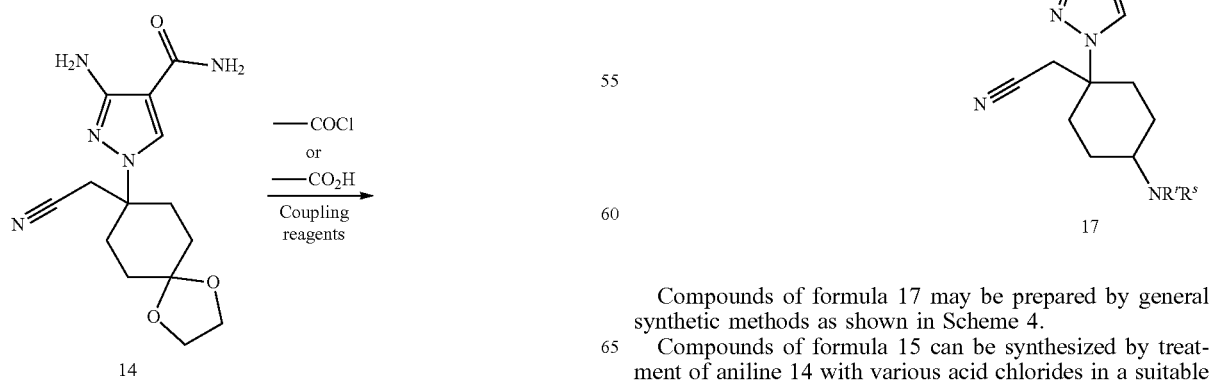

Compounds of formula 17 may be prepared by general synthetic methods as shown in Scheme 4.

Compounds of formula 15 can be synthesized by treatment of aniline 14 with various acid chlorides in a suitable organic solvent such as, but not limited to, dichloromethane (DCM) at a temperature ranging from 0° C. to room temperature and for a time varying from about 30 minutes to 48 hours. Alternatively, compounds of formula 15 can be prepared by treatment of aniline 14 with various carboxylic acids in the presence of an amide coupling reagent such as, but not limited to, HATU in a suitable organic solvent such as, but not limited to, DMF at a temperature ranging from room temperature to 65° C. for a time of about 12 hours. Deprotection of the acetal group of 15 using a protic acid such as, but not limited to, trifluoroacetic acid or hydrochloric acid at about room temperature readily affords ketone 16. Compounds of formula 17 can be synthesized through reductive amination using compounds of formula 16 and the appropriately substituted amine in the presence of a reducing agent such as, but not limited to, sodium triacetoxyborohydride in a suitable organic solvent such as, but not limited to, dichloromethane at about room temperature and for a time varying from about 6 hours to 12 hours.

Compounds of formula 1 may be prepared by general synthetic methods as shown in Scheme 5.

Treatment of 18 with diethyl (cyanomethyl)phosphonate in tetrahydrofuran with sodium hydride at a temperature ranging from 0° C. to about room temperature afforded compound 19. Compound 20 can be formed from the 1,4-conjugate addition of 3-amino-1H-pyrazole-4-carboxamide and compound 19 in acetonitrile in presence of an organic base such as, but not limited to, 1,8-diazabicyclo [5.4.0]undec-7-ene (DBU) at about room temperature for about 48 hrs.

Scheme 6

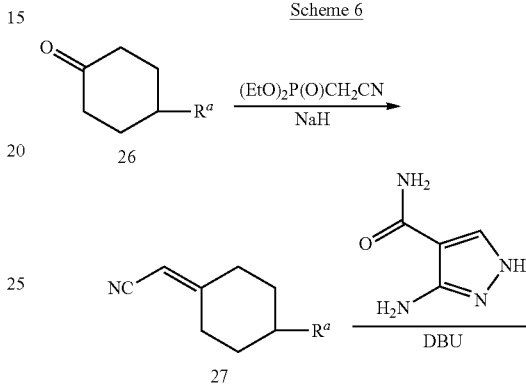

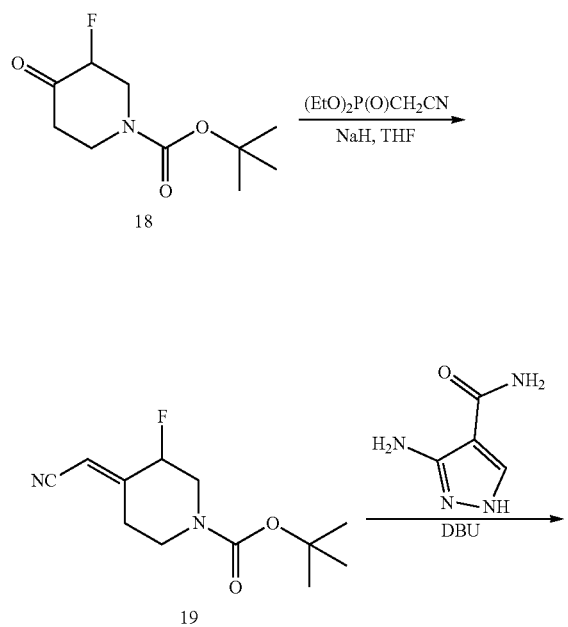

Scheme 5

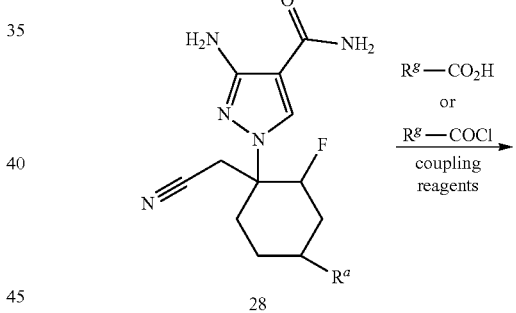

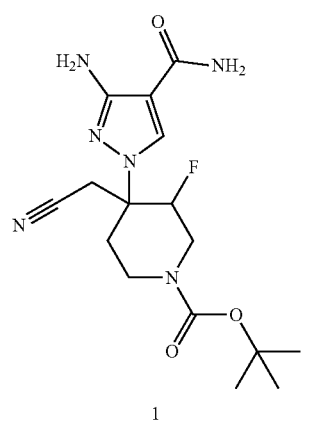

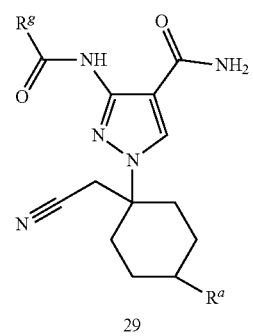

Compounds of formula 29 may be prepared by general synthetic methods as shown in Scheme 6.

Compounds of formula 29 can be prepared using similar general methods outlined in Scheme 1 and Scheme 5.

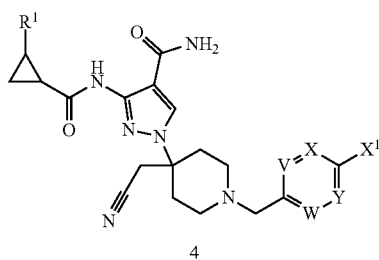
4

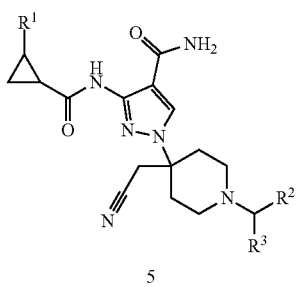
5

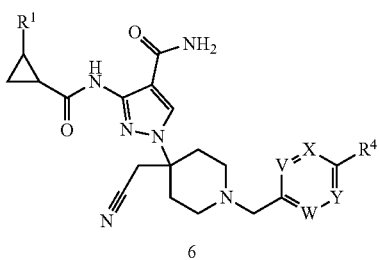
6

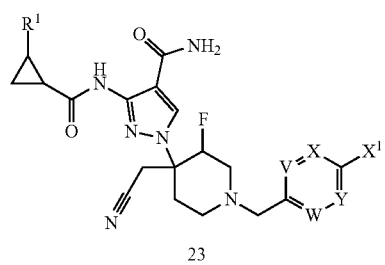
23

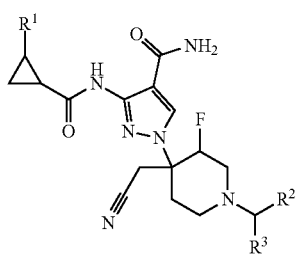
24

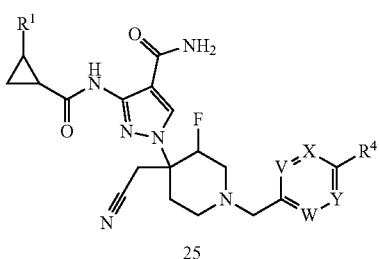
25

1) reduction
2) conversion to dithiane
3) reduction

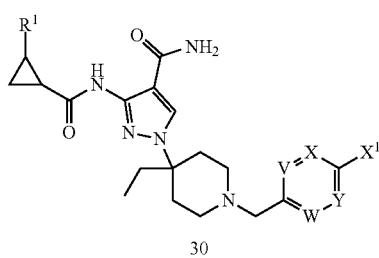
30

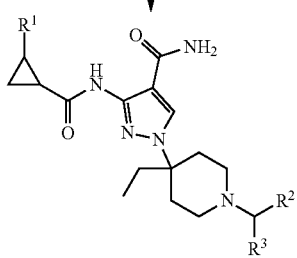
31

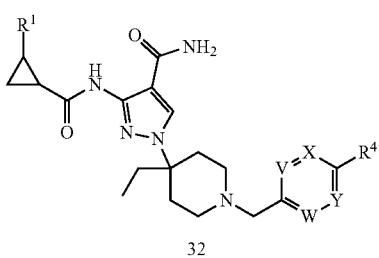
32

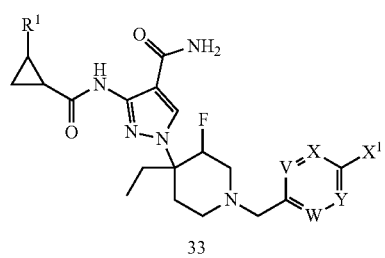
33

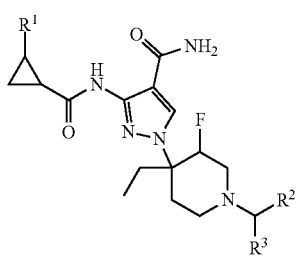
34

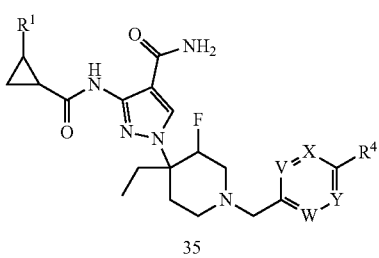
35

Compounds of formula 30, 31, 32, 33, 34 and 35 may be prepared by general synthetic methods as shown in Scheme 7.

Compounds of formula 30-35 can be synthesized directly from their corresponding acetonitrile analogues 4-6 and 23-25. Treatment of the 4-6 and 23-25 individually with diisobutyl aluminum hydride in a suitable organic solvent such as, but not limited to, DCM at a temperature of -78° C. and for a time varying from about 2 to 4 hrs afforded the corresponding aldehydes. Treatment of these aldehydes with ethane-1,2-dithiol and an acid such as, but not limited to, 4-methylbenzenesulfonic acid in a suitable organic solvent such as, but not limited to, DCM at a temperature ranging from room temperature to 60° C. and for a time varying from about 2 to 6 hrs produced the corresponding dithianes. The dithianes can be treated with Raney Ni under a hydrogen atmosphere in a suitable organic solvent such as, but not limited to, THF at a temperature of room temperature for a time varying from about 8 to 24 hrs to yield the individual corresponding ethyl analogues 30-35. See, e.g., WO 2016/061751 and WO 2016/064935 for further examples.

It will be appreciated that where appropriate functional groups exist, compounds of various formulae or any intermediates used in their preparation may be further derivatized by one or more standard synthetic methods employing condensation, substitution, oxidation, reduction, or cleavage reactions. Particular substitution approaches include conventional alkylation, arylation, heteroarylation, acylation, sulfonylation, halogenation, nitration, formylation and coupling procedures.

In a further example, primary amine or secondary amine groups may be converted into amide groups (—NHCOR' or —NRCOR') by acylation. Acylation may be achieved by reaction with an appropriate acid chloride in the presence of a base, such as triethylamine, in a suitable solvent, such as dichloromethane, or by reaction with an appropriate carboxylic acid in the presence of a suitable coupling agent such HATU (O—(7-azabenzotriazol-1-yl)-N,N,N',N'-tetramethyluronium hexafluorophosphate) in a suitable solvent such as dichloromethane. Similarly, amine groups may be converted into sulphonamide groups (—NHSO$_2$R' or —NR"SO$_2$R') groups by reaction with an appropriate sulphonyl chloride in the presence of a suitable base, such as triethylamine, in a suitable solvent such as dichloromethane. Primary or secondary amine groups can be converted into urea groups (—NHCONR'R" or —NRCONR'R") by reaction with an appropriate isocyanate in the presence of a suitable base such as triethylamine, in a suitable solvent, such as dichloromethane.

An amine (—NH$_2$) may be obtained by reduction of a nitro (—NO$_2$) group, for example by catalytic hydrogenation, using for example hydrogen in the presence of a metal catalyst, for example palladium on a support such as carbon in a solvent such as ethyl acetate or an alcohol e.g., methanol. Alternatively, the transformation may be carried out by chemical reduction using for example a metal, e.g., tin or iron, in the presence of an acid such as hydrochloric acid.

In a further example, amine (—CH$_2$NH$_2$) groups may be obtained by reduction of nitriles (—CN), for example by catalytic hydrogenation using for example hydrogen in the presence of a metal catalyst, for example palladium on a support such as carbon, or Raney nickel, in a solvent such as an ether e.g., a cyclic ether such as tetrahydrofuran, at an appropriate temperature, for example from about −78° C. to the reflux temperature of the solvent.

In a further example, amine (—NH$_2$) groups may be obtained from carboxylic acid groups (—CO$_2$H) by conversion to the corresponding acyl azide (—CON$_3$), Curtius rearrangement and hydrolysis of the resultant isocyanate (—N=C=O).

Aldehyde groups (—CHO) may be converted to amine groups (—CH$_2$NR'R")) by reductive amination employing an amine and a borohydride, for example sodium triacetoxyborohydride or sodium cyanoborohydride, in a solvent such as a halogenated hydrocarbon, for example dichloromethane, or an alcohol such as ethanol, where necessary in the presence of an acid such as acetic acid at around ambient temperature.

In a further example, aldehyde groups may be converted into alkenyl groups (—CH=CHR') by the use of a Wittig or Wadsworth-Emmons reaction using an appropriate phosphorane or phosphonate under standard conditions known to those skilled in the art.

Aldehyde groups may be obtained by reduction of ester groups (such as —CO$_2$Et) or nitriles (—CN) using diisobutylaluminum hydride in a suitable solvent such as toluene. Alternatively, aldehyde groups may be obtained by the oxidation of alcohol groups using any suitable oxidizing agent known to those skilled in the art.

Ester groups (—CO$_2$R') may be converted into the corresponding acid group (—CO$_2$H) by acid- or base-catalyzed hydrolysis, depending on the nature of R. If R is t-butyl, acid-catalyzed hydrolysis can be achieved for example by treatment with an organic acid such as trifluoroacetic acid in an aqueous solvent, or by treatment with an inorganic acid such as hydrochloric acid in an aqueous solvent.

Carboxylic acid groups (—CO$_2$H) may be converted into amides (CONHR' or —CONR'R") by reaction with an appropriate amine in the presence of a suitable coupling agent, such as HATU, in a suitable solvent such as dichloromethane.

In a further example, carboxylic acids may be homologated by one carbon (i.e —CO$_2$H to —CH$_2$CO$_2$H) by conversion to the corresponding acid chloride (—COCl) followed by Arndt-Eistert synthesis.

In a further example, —OH groups may be generated from the corresponding ester (e.g., —CO$_2$R'), or aldehyde (—CHO) by reduction, using for example a complex metal hydride such as lithium aluminum hydride in diethyl ether or tetrahydrofuran, or sodium borohydride in a solvent such as methanol. Alternatively, an alcohol may be prepared by reduction of the corresponding acid (—CO$_2$H), using for example lithium aluminum hydride in a solvent such as tetrahydrofuran, or by using borane in a solvent such as tetrahydrofuran.

Alcohol groups may be converted into leaving groups, such as halogen atoms or sulfonyloxy groups such as an alkylsulfonyloxy, e.g., trifluoromethylsulfonyloxy or arylsulfonyloxy, e.g., p-toluenesulfonyloxy group using conditions known to those skilled in the art. For example, an alcohol may be reacted with thioyl chloride in a halogenated hydrocarbon (e.g., dichloromethane) to yield the corresponding chloride. A base (e.g., triethylamine) may also be used in the reaction.

In another example, alcohol, phenol or amide groups may be alkylated by coupling a phenol or amide with an alcohol in a solvent such as tetrahydrofuran in the presence of a phosphine, e.g., triphenylphosphine and an activator such as diethyl-, diisopropyl, or dimethylazodicarboxylate. Alternatively alkylation may be achieved by deprotonation using a suitable base e.g., sodium hydride followed by subsequent addition of an alkylating agent, such as an alkyl halide.

Aromatic halogen substituents in the compounds may be subjected to halogen-metal exchange by treatment with a base, for example a lithium base such as n-butyl or t-butyl lithium, optionally at a low temperature, e.g., around −78° C., in a solvent such as tetrahydrofuran, and then quenched with an electrophile to introduce a desired substituent. Thus, for example, a formyl group may be introduced by using N,N-dimethylformamide as the electrophile. Aromatic halogen substituents may alternatively be subjected to metal (e.g., palladium or copper) catalyzed reactions, to introduce, for example, acid, ester, cyano, amide, aryl, heteroaryl, alkenyl, alkynyl, thio- or amino substituents. Suitable procedures which may be employed include those described by Heck, Suzuki, Stille, Buchwald or Hartwig.

Aromatic halogen substituents may also undergo nucleophilic displacement following reaction with an appropriate nucleophile such as an amine or an alcohol. Advantageously, such a reaction may be carried out at elevated temperature in the presence of microwave irradiation.

Methods Of Separation

In each of the exemplary Schemes it may be advantageous to separate reaction products from one another or from starting materials. The desired products of each step or series of steps is separated or purified (hereinafter separated) to the desired degree of homogeneity by the techniques common in the art. Typically such separations involve multiphase extraction, crystallization or trituration from a solvent or solvent mixture, distillation, sublimation, or chromatography. Chromatography can involve any number of methods including, for example: reverse-phase and normal phase; size exclusion; ion exchange; supercritical fluid; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. Example separation methods include boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereoisomers on the basis of their physical chemical differences by methods well known to those skilled in the art, such as by chromatography or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column or supercritical fluid chromatography.

A single stereoisomer, e.g., an enantiomer, substantially free of its stereoisomer may be obtained by resolution of the racemic mixture using a method such as formation of diastereomers using optically active resolving agents (Eliel, E. and Wilen, S., Stereochemistry of Organic Compounds, John Wiley & Sons, Inc., New York, 1994; Lochmuller, C. H., J. Chromatogr., 113 (3):283-302 (1975)). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Drug Stereochemistry, Analytical Methods and Pharmacology, Irving W. Wainer, Ed., Marcel Dekker, Inc., New York (1993).

Diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, the substrate to be resolved is reacted with one enantiomer of a chiral compound to form a diastereomeric pair (Eliel, E. and Wilen, S., Stereochemistry of Organic Compounds, John Wiley & Sons, Inc., New York, 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob, J. Org. Chem. 47:4165 (1982)), of the racemic mixture, and analyzing the NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111, incorporated herein by reference). By method ($_3$), a racemic mixture of two enantiomers can be separated by chromatography using a chiral stationary phase (Chiral Liquid Chromatography W. J. Lough, Ed., Chapman and Hall, New York, (1989); Okamoto, J. of Chromatogr. 513: 375-378 (1990)). Enriched or purified enantiomers can be distinguished by methods used to distinguish other chiral molecules with asymmetric carbon atoms, such as optical rotation and circular dichroism. The absolute stereochemistry of chiral centers and enantiomers can be determined by x-ray crystallography.

Positional isomers, for example E and Z forms, of compounds of Formula (I) and intermediates for their synthesis, may be observed by characterization methods such as NMR and analytical HPLC. For certain compounds where the energy barrier for interconversion is sufficiently high, the E and Z isomers may be separated, for example by preparatory HPLC.

Pharmaceutical Compositions And Administration

The compounds with which the invention is concerned are JAK kinase inhibitors, such as JAK1 inhibitors, and are useful in the treatment of several diseases, for example, inflammatory diseases, such as asthma.

Accordingly, another embodiment provides pharmaceutical compositions or medicaments containing a compound of the invention, such as a compound of Formula (I), or a salt thereof (e.g., a pharmaceutically acceptable salt), and a pharmaceutically acceptable carrier, diluent or excipient, as well as methods of using the compounds of the invention to prepare such compositions and medicaments.

In one example, a compound of Formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but typically ranges anywhere from about 3 to about 8. In one example, a compound of Formula (I) is formulated in an acetate buffer, at pH 5. In another embodiment, the compounds of the present invention, such as a compound of Formula (I) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial, as is required in the pharmaceutical art. In general, the daily dose range for oral administration will lie within the range of from about 0.001 mg to about 100 mg per kg body weight of a human, often 0.01 mg to about 50 mg per kg, for example 0.1 to 10 mg per kg, in single or divided doses. In general, the daily dose range for inhaled administration will lie within the range of from about 0.1 µg to about 1 mg per kg body weight of a human, preferably 0.1 µg to 50 µg per kg, in single or divided doses. On the other hand, it may be necessary to use dosages outside these limits in some cases.

The compounds of the invention, such as a compound of Formula (I), may be administered by any suitable means, including oral, topical (including buccal and sublingual), rectal, vaginal, transdermal, parenteral, subcutaneous, intraperitoneal, intrapulmonary, intradermal, intrathecal, inhaled and epidural and intranasal, and, if desired for local treatment, intralesional administration. Parenteral infusions include intramuscular, intravenous, intraarterial, intraperitoneal, or subcutaneous administration. In some embodiments, inhaled administration is employed.

The compounds of the present invention, such as a compound of Formula (I), may be administered in any convenient administrative form, e.g., tablets, powders, capsules, lozenges, granules, solutions, dispersions, suspensions, syrups, sprays, vapors, suppositories, gels, emulsions, patches, etc. Such compositions may contain components conventional in pharmaceutical preparations, e.g., diluents (e.g., glucose, lactose or mannitol), carriers, pH modifiers, buffers, sweeteners, bulking agents, stabilizing agents, surfactants, wetting agents, lubricating agents, emulsifiers, suspending agents, preservatives, antioxidants, opaquing agents, glidants, processing aids, colorants, perfuming agents, flavoring agents, other known additives as well as further active agents.

Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. For example, carriers include solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, pp 1289-1329, 1990). Except insofar as any conventional carrier is incompatible with the active ingredient, its use in the therapeutic or pharmaceutical compositions is contemplated. Exemplary excipients include dicalcium phosphate, mannitol, lactose, starch, magnesium stearate, sodium saccharine, cellulose, magnesium carbonate or combinations thereof. A pharmaceutical composition may comprise different types of carriers or excipients depending on whether it is to be administered in solid, liquid or aerosol form, and whether it need to be sterile for such routes of administration.

For example, tablets and capsules for oral administration may be in unit dose presentation form, and may contain conventional excipients such as binding agents, for example syrup, acacia, gelatin, sorbitol, tragacanth, or polyvinylpyrrolidone; fillers, for example, lactose, sugar, maize-starch, calcium phosphate, sorbitol or glycine; tabletting lubricant, for example, magnesium stearate, talc, polyethylene glycol or silica; disintegrants, for example, potato starch, or acceptable wetting agents such as sodium lauryl sulfate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example, sorbitol, syrup, methyl cellulose, glucose syrup, gelatin hydrogenated edible fats; emulsifying agents, for example, lecithin, sorbitan monooleate, or acacia; non-aqueous vehicles (which may include edible oils), for example, almond oil, fractionated coconut oil, oily esters such as glycerine, propylene glycol, or ethyl alcohol; preservatives, for example, methyl or propyl p-hydroxybenzoate or sorbic acid, and if desired conventional flavoring or coloring agents.

For topical application to the skin, a compound may be made up into a cream, lotion or ointment. Cream or ointment formulations which may be used for the drug are conventional formulations well known in the art, for example as described in standard textbooks of pharmaceutics such as the British Pharmacopoeia.

Compounds of the invention, such as a compound of Formula (I), may also be formulated for inhalation, for example, as a nasal spray, or dry powder or aerosol inhalers. For delivery by inhalation, the compound is typically in the form of microparticles, which can be prepared by a variety of techniques, including spray-drying, freeze-drying and micronisation. Aerosol generation can be carried out using, for example, pressure-driven jet atomizers or ultrasonic atomizers, such as by using propellant-driven metered aerosols or propellant-free administration of micronized compounds from, for example, inhalation capsules or other "dry powder" delivery systems.

By way of example, a composition of the invention may be prepared as a suspension for delivery from a nebulizer or as an aerosol in a liquid propellant, for example, for use in a pressurized metered dose inhaler (PMDI). Propellants suitable for use in a PMDI are known to the skilled person, and include CFC-12, HFA-134a, HFA-227, HCFC-22 ($CCl_2F_2$) and HFA-152 ($CH_4F_2$ and isobutane).

In some embodiments, a composition of the invention is in dry powder form, for delivery using a dry powder inhaler (DPI). Many types of DPI are known.

Microparticles for delivery by administration may be formulated with excipients that aid delivery and release. For example, in a dry powder formulation, microparticles may be formulated with large carrier particles that aid flow from the DPI into the lung. Suitable carrier particles are known, and include lactose particles; they may have a mass median aerodynamic diameter of, for example, greater than 90 µm.

In the case of an aerosol-based formulation, an example is:

Compound of the invention* 24 mg/canister
Lecithin, NF Liq. Conc. 1.2 mg/canister
Trichlorofluoromethane, NF 4.025 g/canister
Dichlorodifluoromethane, NF 12.15 g/canister.
*Such as a compound of Formula (I).

A compound, such as a compound of Formula (I), may be dosed as described depending on the inhaler system used. In addition to the compound, the administration forms may additionally contain excipients as described above, or, for example, propellants (e.g., Frigen in the case of metered aerosols), surface-active substances, emulsifiers, stabilizers, preservatives, flavorings, fillers (e.g., lactose in the case of powder inhalers) or, if appropriate, further active compounds.

For the purposes of inhalation, a large number of systems are available with which aerosols of optimum particle size can be generated and administered, using an inhalation technique which is appropriate for the patient. In addition to the use of adaptors (spacers, expanders) and pear-shaped containers (e.g., Nebulator®, Volumatic®), and automatic devices emitting a puffer spray (Autohaler®), for metered aerosols, in the case of powder inhalers in particular, a number of technical solutions are available (e.g., Diskhaler®, Rotadisk®, Turbohaler® or the inhalers, for example, as described in U.S. Pat. No. 5,263,475, incorporated herein by reference). Additionally, compounds of the invention, such as a compound of Formula (I), may be delivered in multi-chamber devices thus allowing for delivery of combination agents.

The compound, such as a compound of Formula (I), may also be administered parenterally in a sterile medium. Depending on the vehicle and concentration used, the compound can either be suspended or dissolved in the vehicle. Advantageously, adjuvants such as a local anaesthetic, preservative or buffering agents can be dissolved in the vehicle.

Targeted Inhaled Drug Delivery

Optimisation of drugs for delivery to the lung by topical (inhaled) administration has been recently reviewed (Cooper, A. E. et al. Curr. Drug Metab. 2012, 13, 457-473). Due to limitations in the delivery device, the dose of an inhaled drug is likely to be low (approximately <1mg/day) in humans which necessitates highly potent molecules. For compounds destined to be delivered via dry powder inhalation there is also a requirement to be able to generate crystalline forms of the compound that can be micronized to 1-5 µm in size. Additionally, the compound needs to maintain a sufficient concentration in the lung over a given time period so as to be able to exert a pharmacological effect of the desired duration, and for pharmacological targets where systemic inhibition of said target is undesired, to have a low systemic exposure. The lung has an inherently high permeability to both large molecules (proteins, peptides) as well as small molecules with concomitant short lung half-lives, thus it is necessary to attenuate the lung absorption rate through modification of one or more features of the compounds: minimizing membrane permeability, reducing dissolution rate, or introducing a degree of basicity into the compound to enhance binding to the phospholipid-rich lung tissue or through trapping in acidic sub-cellular compartments such as lysosomes (pH 5). Accordingly, in some embodiments, compounds of the present invention exhibit one or more of these features.

Methods of Treatment With and Uses of Janus Kinase Inhibitors

The compounds of the present invention, such as a compound of Formula (I), inhibit the activity of a Janus kinase, such as JAK1 kinase. For example, a compound of the present invention, such as a compound of Formula (I), inhibits the phosphorylation of signal transducers and activators of transcription (STATs) by JAK1 kinase as well as STAT mediated cytokine production. Compounds of the present invention, such as a compound of Formula (I), are useful for inhibiting JAK1 kinase activity in cells through cytokine pathways, such as IL-6, IL-15, IL-7, IL-2, IL-4, IL-9, IL-10, IL-13, IL-21, G-CSF, IFNalpha, IFNbeta or IFNgamma pathways. Accordingly, in one embodiment is provided a method of contacting a cell with a compound of the present invention, such as a compound of Formula (I), to inhibit a Janus kinase activity in the cell (e.g., JAK1 activity).

The compounds of the present invention, such as compounds of Formula (I), can be used for the treatment of immunological disorders driven by aberrant IL-6, IL-15, IL-7, IL-2, IL-4, IL9, IL-10, IL-13, IL-21, G-CSF, IFNalpha, IFNbeta or IFNgamma cytokine signaling.

Accordingly, one embodiment includes compounds of the present invention, such as a compound of Formula (I), for use in therapy.

In some embodiments, there is provided use a compound of the present invention, such as a compound of Formula (I), in the treatment of an inflammatory disease. Further provided is use of a compound of the present invention, such as a compound of Formula (I), for the preparation of a medicament for the treatment of an inflammatory disease, such as asthma. Also provided is a compound of the present invention, such as a compound of Formula (I), for use in the treatment of an inflammatory disease, such as asthma.

Another embodiment includes a method of preventing, treating or lessening the severity of a disease or condition, such as asthma, responsive to the inhibition of a Janus kinase activity, such as JAK1 kinase activity, in a patient. The method can include the step of administering to a patient a therapeutically effective amount of a compound of the present invention, such as a compound of Formula (I). In one embodiment, the disease or condition responsive to the inhibition of a Janus kinase, such as JAK1 kinase, is asthma.

In one embodiment, the disease or condition is cancer, stroke, diabetes, hepatomegaly, cardiovascular disease, multiple sclerosis, Alzheimer's disease, cystic fibrosis, viral disease, autoimmune diseases, atherosclerosis, restenosis, psoriasis, rheumatoid arthritis, inflammatory bowel disease, asthma, allergic disorders, inflammation, neurological disorders, a hormone-related disease, conditions associated with organ transplantation (e.g., transplant rejection), immunodeficiency disorders, destructive bone disorders, proliferative disorders, infectious diseases, conditions associated with cell death, thrombin-induced platelet aggregation, liver disease, pathologic immune conditions involving T cell activation, CNS disorders or a myeloproliferative disorder.

In one embodiment, the inflammatory disease is rheumatoid arthritis, psoriasis, asthma, inflammatory bowel disease, contact dermatitis or delayed hypersensitivity reactions. In one embodiment, the autoimmune disease is rheumatoid arthritis, lupus or multiple sclerosis.

In one embodiment, the cancer is breast, ovary, cervix, prostate, testis, penile, genitourinary tract, seminoma, esophagus, larynx, gastric, stomach, gastrointestinal, skin, keratoacanthoma, follicular carcinoma, melanoma, lung, small cell lung carcinoma, non-small cell lung carcinoma (NSCLC), lung adenocarcinoma, squamous carcinoma of the lung, colon, pancreas, thyroid, papillary, bladder, liver, biliary passage, kidney, bone, myeloid disorders, lymphoid disorders, hairy cells, buccal cavity and pharynx (oral), lip, tongue, mouth, salivary gland, pharynx, small intestine, colon, rectum, anal, renal, prostate, vulval, thyroid, large intestine, endometrial, uterine, brain, central nervous system, cancer of the peritoneum, hepatocellular cancer, head cancer, neck cancer, Hodgkin's or leukemia.

In one embodiment, the disease is a myeloproliferative disorder. In one embodiment, the myeloproliferative disorder is polycythemia vera, essential thrombocytosis, myelofibrosis or chronic myelogenous leukemia (CML).

Another embodiment includes the use of a compound of the present invention, such as a compound of Formula (I), for the manufacture of a medicament for the treatment of a disease described herein (e.g., an inflammatory disorder, an immunological disorder or cancer). In one embodiment, the invention provides a method of treating a disease or condition as described herein e.g., an inflammatory disorder, an immunological disorder or cancer) by targeting inhibition of a JAK kinase, such as JAK1.

Combination Therapy

The compounds of the present invention, such as a compound of Formula (I), may be employed alone or in combination with other agents for treatment. The second compound of a pharmaceutical composition or dosing regimen typically has complementary activities to the compound of this invention such that they do not adversely affect each other. Such agents are suitably present in combination in amounts that are effective for the purpose intended. The compounds may be administered together in a unitary pharmaceutical composition or separately and, when administered separately this may occur simultaneously or sequentially. Such sequential administration may be close or remote in time.

For example, other compounds may be combined with compounds with which the invention is concerned for the prevention or treatment of inflammatory diseases, such as asthma. Thus the present invention is also concerned with pharmaceutical compositions comprising a therapeutically effective amount of a compound of the invention and one or more other therapeutic agents. Suitable therapeutic agents for a combination therapy with compounds of the invention include, but are not limited to: an adenosine A2A receptor antagonist; an anti-infective; a non-steroidal Glucocorticoid Receptor (GR Receptor) agonist; an antioxidant; a β2 adrenoceptor agonist; a CCR1 antagonist; a chemokine antagonist (not CCR1); a corticosteroid; a CRTh2 antagonist; a DP1 antagonist; a formyl peptide receptor antagonist; a histone deacetylase activator; a chloride channel hCLCA1 blocker; an epithelial sodium channel blocker (ENAC blocker; an inter-cellular adhesion molecule 1 blocker (ICAM blocker); an IKK2 inhibitor; a JNK inhibitor; a cyclooxygenase inhibitor (COX inhibitor); a lipoxygenase inhibitor; a leukotriene receptor antagonist; a dual β2 adrenoceptor agonist/M3 receptor antagonist (MABA compound); a MEK-1 inhibitor; a myeloperoxidase inhibitor (MPO inhibitor); a muscarinic antagonist; a p38 MAPK inhibitor; a phosphodiesterase PDE4 inhibitor; a phosphatidylinositol 3-kinase δ inhibitor (PI3-kinase δ inhibitor); a phosphatidylinositol 3-kinase γ inhibitor (PI3-kinase γ inhibitor); a peroxisome proliferator activated receptor agonist (PPARγ agonist); a protease inhibitor; a retinoic acid receptor modulator (RAR γ modulator); a statin; a thromboxane antagonist; a TLR7 receptor agonist; or a vasodilator.

In addition, compounds of the invention, such as a compound of Formula (I), may be combined with: (1) corticosteroids, such as alclometasone dipropionate, amelometasone, beclomethasone dipropionate, budesonide, butixocort propionate, biclesonide, blobetasol propionate, desisobutyrylciclesonide, dexamethasone, dtiprednol dicloacetate, fluocinolone acetonide, fluticasone furoate, fluticasone propionate, loteprednol etabonate (topical) or mometasone furoate; (2) β2-adrenoreceptor agonists such as salbutamol, albuterol, terbutaline, fenoterol, bitolterol, carbuterol, clenbuterol, pirbuterol, rimoterol, terbutaline, tretoquinol, tulobuterol and long acting β2-adrenoreceptor agonists such as metaproterenol, isoproterenol, isoprenaline, salmeterol, indacaterol, formoterol (including formoterol fumarate), arformoterol, carmoterol, abediterol, vilanterol trifenate, olodaterol; (3) corticosteroid/long acting β2 agonist combination products such as salmeterol/fluticasone propionate (Advair®, also sold as Seretide®), formoterol/budesonide (Symbicort®), formoterol/fluticasone propionate (Flutiform®), formoterol/ciclesonide, formoterol/mometasone furoate, indacaterol/mometasone furoate, vilanterol trifenate/fluticasone furoate, or arformoterol/ciclesonide; (4) anticholinergic agents, for example, muscarinic-3 (M3) receptor antagonists such as ipratropium bromide, tiotropium bromide, aclidinium (LAS-34273), glycopyrronium bromide, umeclidinium bromide; (5) M3-anticholinergic/β2-adrenoreceptor agonist combination products such as vilanterol/umeclidinium (Anoro® Ellipta®), olodaterol/tiotropium bromide, glycopyrronium bromide/indacaterol (Ultibro®, also sold as Xoterna®), fenoterol hydrobromide/ipratropium bromide (Berodual®), albuterol sulfate/ipratropium bromide (Combivent®), formoterol fumarate/glycopyrrolate, or aclidinium bromide/formoterol (6) dual pharmacology M3-anticholinergic/β2-adrenoreceptor agonists such as batefenterol succinate, AZD-2115 or LAS-190792; (7) leukotriene modulators, for example, leukotriene antagonists such as montelukast, zafirulast or pranlukast or leukotriene biosynthesis inhibitors such as zileuton, or LTB4 antagonists such as amelubant, or FLAP inhibitors such as fiboflapon, GSK-2190915; (8) phosphodiesterase-IV (PDE-IV) inhibitors (oral or inhaled), such as roflumilast, cilomilast, oglemilast, rolipram , tetomilast, AVE-8112, revamilast, CHF 6001; (9) antihistamines, for example, selective histamine-1 (H1) receptor antagonists such as fexofenadine, citirizine, loratidine or astemizole or dual H1/H3 receptor antagonists such as GSK 835726, or GSK 1004723; (10) antitussive agents, such as codeine or dextramorphan; (11) a mucolytic, for example, N-acetyl cysteine or fudostein; (12) a expectorant/mucokinetic modulator, for example, ambroxol, hypertonic solutions (e.g., saline or mannitol) or surfactant; (13) a peptide mucolytic, for example, recombinant human deoxyribonuclease I (dornase-alpha and rhDNase) or helicidin; (14) antibiotics, for example azithromycin, tobramycin or aztreonam; (15) non-selective COX-1/COX-2 inhibitors, such as ibuprofen or ketoprofen; (16) COX-2 inhibitors, such as celecoxib and rofecoxib; (17) VLA-4 antagonists, such as those described in WO97/03094 and WO97/02289, each incorporated herein by reference; (18) TACE inhibitors and TNF-α inhibitors, for example anti-TNF monoclonal antibodies, such as Remicade® and CDP-870 and TNF receptor immunoglobulin molecules, such as Enbrel®; (19) inhibitors of matrix metalloprotease, for example MMP-12; (20) human neutrophil elastase inhibitors, such as BAY-85-8501 or those described in WO2005/026124, WO2003/053930 and WO06/082412, each incorporated herein by reference; (21) A2b antagonists such as those described in WO2002/42298, incorporated herein by reference; (22) modulators of chemokine receptor function, for example antagonists of CCR3 and CCR8; (23) compounds which modulate the action of other prostanoid receptors, for example, a thromboxane $A_2$ antagonist; DP1 antagonists such as laropiprant or asapiprant CRTH2 antagonists such as OC000459, fevipiprant, ADC 3680 or ARRY 502; (24) PPAR agonists including PPAR alpha agonists (such as fenofibrate), PPAR delta agonists, PPAR gamma agonists such as pioglitazone, rosiglitazone and balaglitazone; (25) methylxanthines such as theophylline or aminophylline and methylxanthine/corticosteroid combinations such as theophylline/budesonide, theophylline/fluticasone propionate, theophylline/ciclesonide, theophylline/mometasone furoate and theophylline/beclometasone dipropionate; (26) A2a agonists such as those described in EP1052264 and EP1241176; (27) CXCR2 or IL-8 antagonists such as AZD-5069, AZD-4721, danirixin; (28) IL-R signalling modulators such as kineret and ACZ 885; (29) MCP-1 antagonists such as ABN-912; (30) a p38 MAPK inhibitor such as BCT197, JNJ49095397, losmapimod or PH-797804; (31) TLR7 receptor agonists such as AZD 8848; (32) PI3-kinase inhibitors such as RV1729 or GSK2269557.

In some embodiments, the compounds of the present invention, such as a compound of Formula (I), can be used in combination with one or more additional drugs, for example anti-hyperproliferative, anti-cancer, cytostatic, cytotoxic, anti-inflammatory or chemotherapeutic agents, such as those agents disclosed in U.S. Publ. Appl. No. 2010/0048557, incorporated herein by reference. A compound of the present invention, such as a compound of Formula (I), can be also used in combination with radiation therapy or surgery, as is known in the art.

Articles of Manufacture

Another embodiment includes an article of manufacture (e.g., a kit) for treating a disease or disorder responsive to the inhibition of a Janus kinase, such as a JAK1 kinase. The kit can comprise:

(a) a first pharmaceutical composition comprising a compound of the present invention, such as a compound of Formula (I); and (b) instructions for use.

In another embodiment, the kit further comprises:

(c) a second pharmaceutical composition, such as a pharmaceutical composition comprising an agent for treatment as described above, such as an agent for treatment of an inflammatory disorder, or a chemotherapeutic agent.

In one embodiment, the instructions describe the simultaneous, sequential or separate administration of said first and second pharmaceutical compositions to a patient in need thereof.

In one embodiment, the first and second compositions are contained in separate containers. In another embodiment, the first and second compositions are contained in the same container.

Containers for use include, for example, bottles, vials, syringes, blister pack, etc. The containers may be formed from a variety of materials such as glass or plastic. The container includes a compound of the present invention, such as a compound of Formula (I), or composition thereof, which is effective for treating the condition and may have a sterile access port (for example the container may be an intravenous solution bag or a vial having a stopper pierceable by a hypodermic injection needle). The label or package insert indicates that the compound or composition is used for treating the condition of choice, such as asthma or cancer. In one embodiment, the label or package inserts indicates that the compound or composition can be used to treat a disorder. In addition, the label or package insert may indicate that the patient to be treated is one having a disorder characterized by overactive or irregular Janus kinase activity, such as overactive or irregular JAK1 activity. The label or package insert may also indicate that the compound or composition can be used to treat other disorders.

Alternatively, or additionally, the kit may further comprise a second (or third) container comprising a pharmaceutically acceptable buffer, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare other compounds of the present invention, and alternative methods for preparing the compounds are within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, or by making routine modifications of reaction conditions. Alternatively, other reactions disclosed herein or known in the art will be recognized as having applicability for preparing other compounds of the invention.

EXAMPLES

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as defined by the claims.

377

Examples 1 & 2

(General Procedure A)

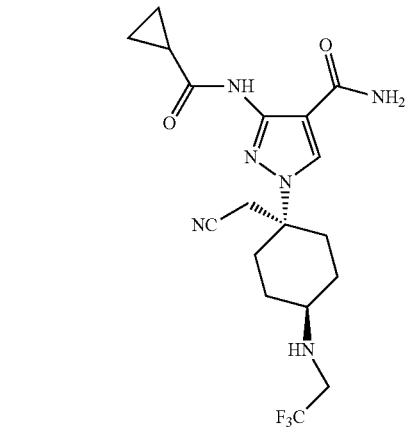

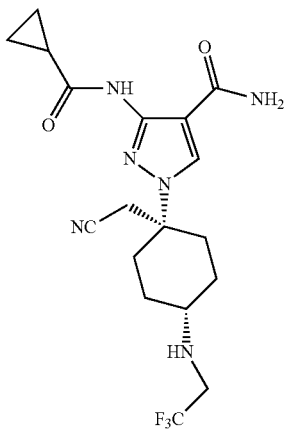

1-(((1S,4S)-1-(Cyanomethyl)-4-((2,2,2-trifluoroethyl) amino)cyclohexyl)-3-(cyclopropanecarboxamido)-1H-pyrazole-4-carboxamide & 1-((1R,4R)-1-(cyanomethyl)-4-((2,2,2-trifluoroethyl) amino)cyclohexyl)-3-(cyclopropanecarboxamido)-1H-pyrazole-4-carboxamide

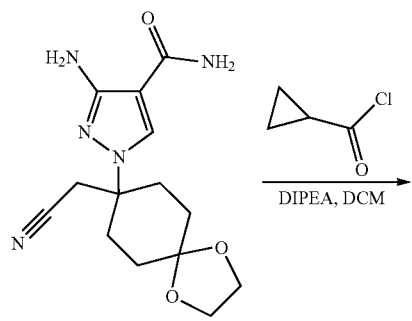

378

-continued

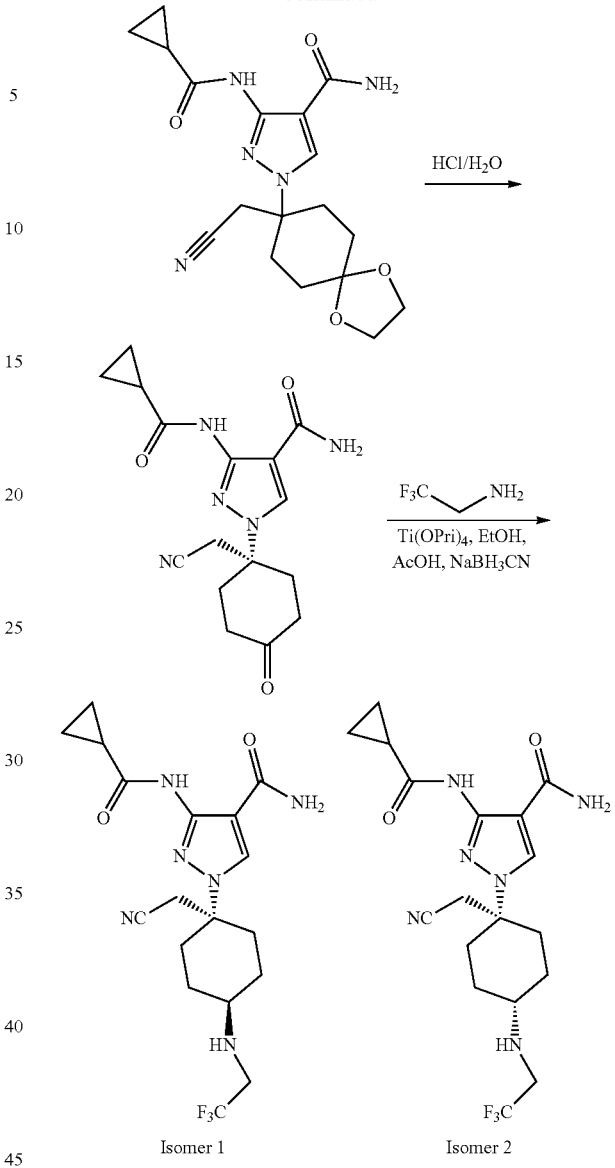

Cyclopropanecarbonyl chloride (750 mg, 7.18 mmol) was added dropwise to a solution of 3-amino-1-[8-(cyanomethyl)-1,4-dioxaspiro[4.5]decan-8-yl]-1H-pyrazole-4-carboxamide (2.00 g, 6.55 mmol) and DIPEA (1.69 g, 13.1 mmol) in dichloromethane (50 mL) at 0° C. The resulting solution was stirred for 5 h at 20° C. and concentrated under reduced pressure. The residue was purified by flash chromatography on silica gel eluting with dichloromethane/ methanol (10/1). The appropriate fractions were combined and concentrated under reduced pressure to give 1.60 g (65%) of 1-(8-(cyanomethyl)-1,4-dioxaspiro[4.5]decan-8-yl)-3-(cyclopropanecarboxamido)-1H-pyrazole-4-carboxamide as a yellow solid. TLC: $R_f$=0.6; DCM/MeOH=10/1.

A solution of 1-(8-(cyanomethyl)-1,4-dioxaspiro[4.5]decan-8-yl)-3-(cyclopropanecarboxamido)-1H-pyrazole-4-carboxamide (1.50 g, 4.02 mmol) in tetrahydrofuran (10 mL) and 4N HCl aqueous solution (20 mL) was stirred at 20° C. overnight. $K_2CO_3$ was added carefully until the pH reached ~8. The mixture was extracted with ethyl acetate (5×). The organic layers were combined, dried over anhydrous sodium sulfate and concentrated under reduced pressure. The residue was purified by flash chromatography on silica gel eluting with dichloromethane/methanol (5/1). The appropriate fractions were combined and concentrated under reduced pressure to afford 0.801 g (56%) of 1-(1-(cyanomethyl)-4-oxocyclohexyl)-3-(cyclopropane-carboxamido)-1H-pyrazole-4-carboxamide as a yellow solid. TLC: $R_f$=0.5; DCM/MeOH=10/1.

To a solution 1-(1-(cyanomethyl)-4-oxocyclohexyl)-3-cyclopropane-carboxamido)-1H-pyrazole-4-carboxamide (150 mg, 0.455 mmol) in ethanol (8.0 mL) was added 2,2,2-trifluoroethan-1-amine (68.0 mg, 0.686 mmol) and tetrakis(propan-2-yloxy)titanium (263 mg, 0.925 mmol) under nitrogen. The reaction mixture was stirred for 2 h at 60° C. AcOH (0.1 mL) and NaBH$_3$CN (29.0 mg, 0.461 mmol) were added. The resulting solution was stirred at 60° C. overnight, and concentrated under reduced pressure. The residue was passed through a short pad of silica gel eluting with dichloromethane/methanol (3/1). The appropriate fractions were combined and concentrated. The residue (150 mg) was further purified by Prep-HPLC with the following conditions: Column, XBridge Shield RP18 OBD Column, 19*150 mm, 5 um; mobile phase, 10 mM NH$_4$HCO$_3$ in water and CH$_3$CN (10.0% CH$_3$CN up to 28.0% in 8 min); Detector, UV 254 nm to give two fractions. Absolute configuration was arbitrarily assigned to each diastereomer:

Example 1: The first fraction, 28.4 mg as a white solid, LC/MS (Method A, ESI): [M+H]$^+$=413, $R_T$=1.04 min; $^1$H NMR (300 MHz, CD$_3$OD): δ (ppm) 8.35 (s, 1H), 3.21-3.06 (m, 3H), 2.91 (s, 2H), 2.79-2.53 (m, 3H), 1.84-1.65 (m, 4H), 1.11-0.93 (m, 2H), 0.90-0.85 (m, 4H).

Example 2: The second fraction, 5.6 mg as a white solid, LC/MS (Method B, ESI): [M+H]$^+$=413.1, $R_T$=1.42 min; $^1$H NMR (300 MHz, CD$_3$OD): δ (ppm) 8.41 (s, 1H), 3.29-3.10 (m, 4H), 2.78-2.76 (m, 1H), 2.39-2.36 (m, 2H), 2.19-2.11 (m, 2H), 1.96-1.85 (m, 3H), 1.68-1.51 (m, 2H), 1.05-0.86 (m, 4H).

Example 3

(General Procedure B)

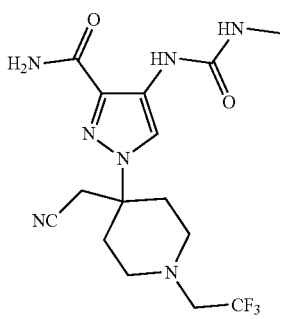 [SMILES: CNC(=O)Nc1cn(C2(CC#N)CCN(CC(F)(F)F)CC2)nc1C(N)=O]

1-(4-(Cyanomethyl)-1-(2,2,2-trifluoroethyl)piperidin-4-yl)-4-(3-methylureido)-1H-pyrazole-3-carboxamide

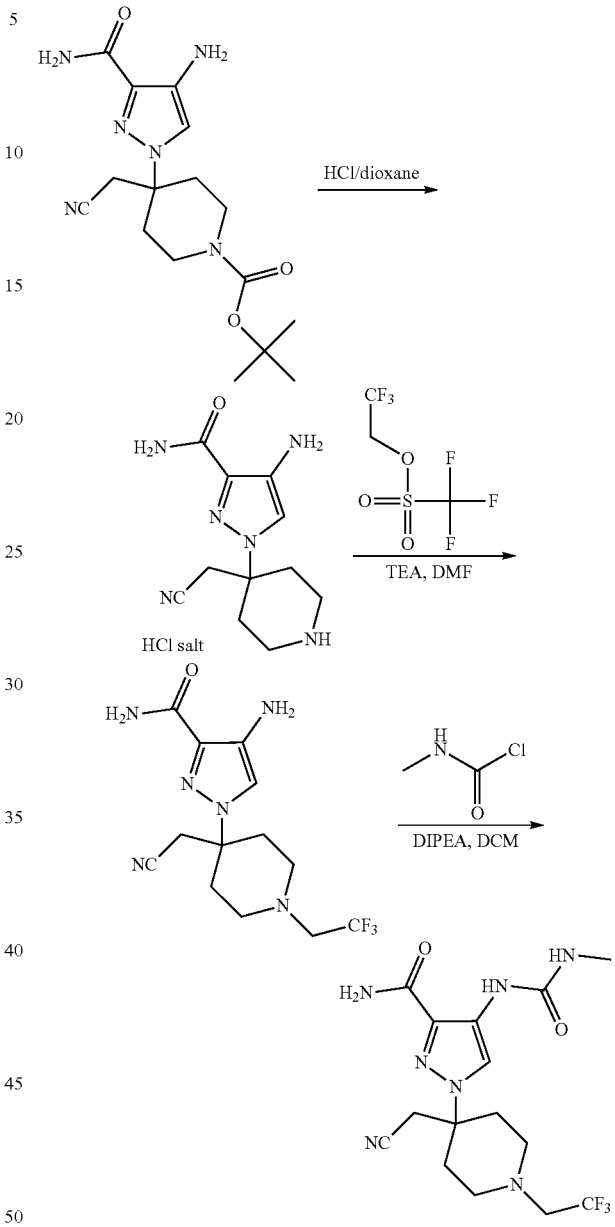

Tert-butyl 4-(3-amino-4-carbamoyl-1H-pyrazol-1-yl)-4-(cyanomethyl) piperidine-1-carboxylate (5.00 g, 14.4 mmol) was added to 4N HCl in dioxane (50 mL). The reaction mixture was stirred at room temperature for 6 h. The precipitates were collected by filtration and dried under reduced pressure to afford 5.30 g of 3-amino-1-[4-(cyanomethyl) piperidin-4-yl]-1H-pyrazole-4-carboxamide hydrochloride as an off-white solid, which was used directly without further purification. LC/MS (Method G, ESI): [M+H]$^+$=249, $R_T$=0.16 min.

To a solution of 3-amino-1-[4-(cyanomethyl)piperidin-4-yl]-1H-pyrazole-4-carboxamide hydrochloride (1.00 g, crude from last step) in N,N-dimethylformamide (30 mL) was added triethylamine (710 mg, 7.02 mmol) and 2,2,2-trifluoroethyl trifluoromethanesulfonate (980 mg, 4.22 mmol) at room temperature. The reaction mixture was stirred at room temperature overnight. The reaction was then quenched by the addition of 40% aqueous methylamine solution, and concentrated under reduced pressure. The residue was partitioned between water and dichloromethane. The aqueous phase was extracted with dichloromethane (2×). The combined organic phases were washed with water and brine, dried over sodium sulfate and concentrated under reduced pressure. The residue was purified by flash chromatography on silica gel eluting with dichloromethane/methanol (95/5). The appropriate fractions were combined and concentrated under reduced pressure to afford 1.10 g (95%) of 3-amino-1-[4-(cyanomethyl)-1-(2,2,2-trifluoroethyl) piperidin-4-yl]-1H-pyrazole-4-carboxamide as a yellow solid. LC/MS (Method G, ESI): [M+H]$^+$=331, R$_T$=0.54 min.

To a solution of 3-amino-1-[4-(cyanomethyl)-1-(2,2,2-trifluoroethyl)piperidin-4-y1]-1H-pyrazole-4-carboxamide (100 mg, 0.303 mmol) and DIPEA (78.3 mg, 0.606 mmol) in dichloromethane (30 mL) was added methylcarbamic chloride (34.3 mg, 0.363 mmol) at 0° C. under nitrogen. The reaction mixture was stirred at room temperature for 4 h. Water (20 mL) was added and the phases were separated. The aqueous phase was extracted with dichloromethane (2×). The combined organic phases were washed with brine, dried over anhydrous sodium sulfate and concentrated under reduced pressure. The residue was passed through a short pad of silica gel eluting with dichloromethane/methanol (95:5). The appropriate fractions were combined and concentrated under reduced pressure. The crude product was further purified by Prep-HPLC with the following conditions: Column, XBridge Shield RP18 OBD Column, 19*150 mm, 5 um; mobile phase: Water (0.05% NH$_4$OH) and CH$_3$CN (18% CH$_3$CN up to 50% in 6 min); Detector, UV 254/220 nm to afford 11.1 mg (9%) of 1-[4-(cyanomethyl)-1-(2,2,2-trifluoroethyl) piperidin-4-yl]-3-[(methylcarbamoyl) amino]-1H-pyrazole-4-carboxamide as a white solid. LC/MS (Method D, ESI): [M+H]$^+$=388, R$_T$=1.89 min; $^1$H NMR (400 MHz, CD$_3$OD): δ (ppm) 8.46 (s, 1H), 3.16-3.05 (m, 4H), 2.93-2.90 (m, 5H), 2.59-2.54 (m, 4H), 2.24-2.17 (m, 2H).

Example 4

(General Procedure C)

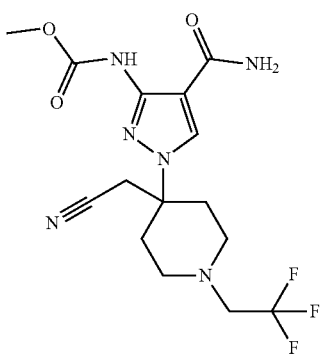 [SMILES: COC(=O)Nc1nn(C2(CC#N)CCN(CC(F)(F)F)CC2)cc1C(N)=O]

Methyl (4-carbamoyl-1-(4-(cyanomethyl)-1-(2,2,2-trifluoroethyl)piperidin-4-yl)-1H-pyrazol-3-yl)carbamate

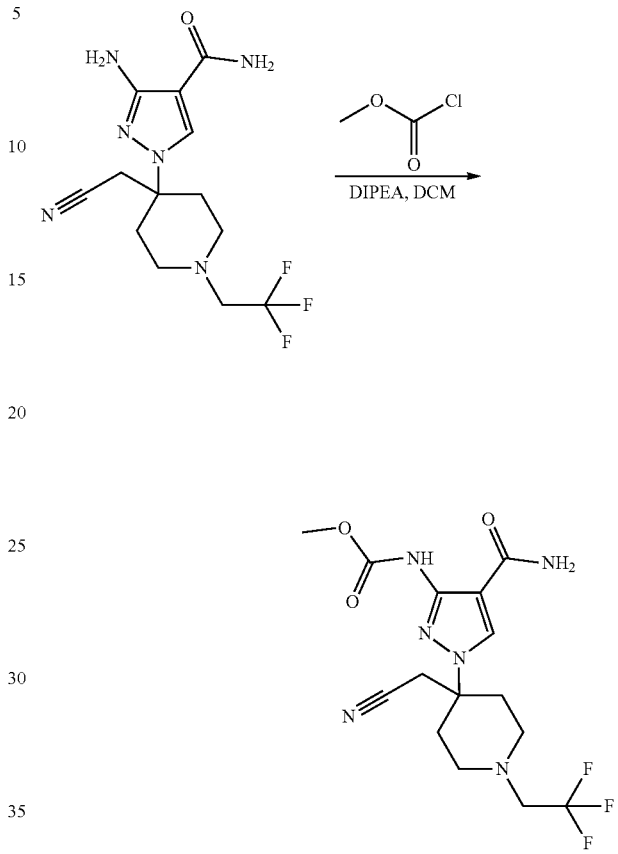

To a solution of 3-amino-1-[4-(cyanomethyl)-1-(2,2,2-trifluoroethyl)piperidin-4-yl]-1H-pyrazole-4-carboxamide (100 mg, 0.303 mmol) in dichloromethane (15 mL) and DIPEA (78.3 mg, 0.606 mmol) was added methyl chloroformate (42.9 mg, 0.454 mmol) at room temperature. The reaction mixture was stirred at room temperature for 12 h. The resulting mixture was partitioned between dichloromethane and water. The organic phase was washed with brine, dried over anhydrous sodium sulfate and concentrated under reduced pressure. The residue was passed through a short pad of silica gel eluting with dichloromethane/methanol (95/5). The crude product was further purified by Prep-HPLC with the following conditions: Column, XBridge Shield RP18 OBD Column, 19*150 mm, 5 um; mobile phase, Water (0.05% NH$_4$OH) and CH$_3$CN (35% CH$_3$CN up to 38% in 9 min); Detector, UV 254/220 nm to give 52.7 mg (45%) of methyl N-[4-carbamoyl-1-[4-(cyanomethyl)-1-(2,2,2-trifluoroethyl)-piperidin-4-yl]-1H-pyrazol-3-yl]carbamate as a white solid. LC/MS (Method E, ESI): [M+H]$^+$=389, R$_T$=1.27 min; $^1$H NMR (300 MHz, CD$_3$OD): δ (ppm) 8.43 (s, 1H), 3.79 (s, 3H), 3.13 (s, 2H), 3.06 (q, J=9.9 Hz, 2H), 2.90-2.84 (m, 2H), 2.62-2.48 (m, 4H), 2.21-2.13 (m, 2H).

Example 5

(General Procedure D)

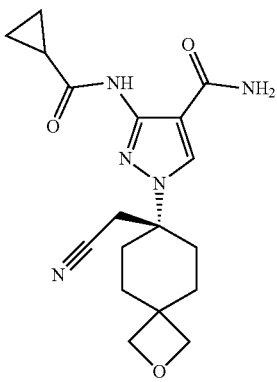

1-(7-(Cyanomethyl)-2-oxaspiro[3.5]nonan-7-yl)-3-(cyclopropanecarboxamido)-1H-pyrazole-4-carboxamide

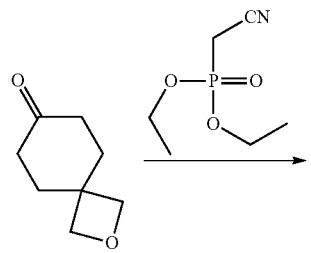

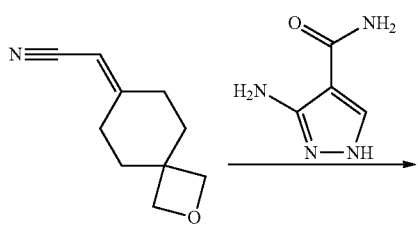

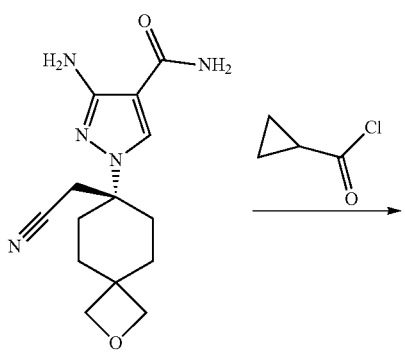

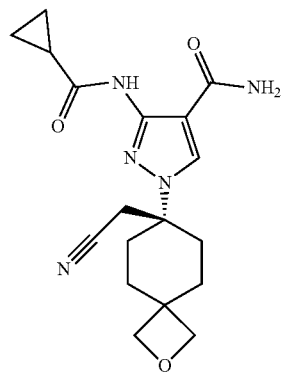

To a solution of diethyl (cyanomethyl)phosphonate (303 mg, 1.71 mmol) in tetrahydrofuran (7.0 mL) was added sodium hydride (40.0 mg, 60% dispersion in mineral oil, 1.00 mmol) under nitrogen at room temperature. The reaction mixture was stirred for 2 h at room temperature. Then 2-oxaspiro[3.5]nonan-7-one (200 mg, 1.43 mmol) was added. The resulting solution was stirred for 12 h at 25° C., and quenched with water. The resulting solution was extracted with dichloromethane (3×) and the organic layers combined and concentrated under reduced pressure. The residue was purified by flash chromatography on silica gel eluting with dichloromethane/methanol (100/3) to 190 mg of 2-[2-oxaspiro[3.5]nonan-7-ylidene]acetonitrile as a white solid. TLC: $R_f$=0.4; ethyl acetate/hexane =1/4.

To a solution of 2-[2-oxaspiro[3.5]nonan-7-ylidene]acetonitrile (190 mg, 1.16 mmol,) in $CH_3CN$ (4.0 mL) was added DBU (354 mg, 2.33 mmol) and 3-amino-1H-pyrazole-4-carboxamide (150 mg, 1.19 mmol). The reaction mixture was stirred for 12 h at 50° C., and concentrated under reduced pressure. The residue was purified by flash chromatography on silica gel eluting with dichloromethane/methanol (10/1) to afford 160 mg (50%) of 3-amino-1-[7-(cyanomethyl)-2-oxaspiro[3.5]nonan-7-yl]-1H-pyrazole-4-carboxamide as a white solid. TLC: $R_f$=0.5; DCM/MeOH=10/1.

To a solution of 3-amino-1-[7-(cyanomethyl)-2-oxaspiro[3.5]nonan-7-yl]-1H-pyrazole-4-carboxamide (160 mg, 0.553 mmol) and DIPEA (143 mg, 1.11 mmol) in dichloromethane (5.0 mL) was added dropwise cyclopropanecarbonyl chloride (64.0 mg, 0.612 mmol) at 0° C. The resulting solution was stirred for 12 h at 25° C., and concentrated under reduced pressure. The residue was passed through a short pad of silica gel eluting with dichloromethane/methanol (10/1). The appropriate fractions were combined and concentrated under reduced pressure. The crude product (160 mg) was further purified by Prep-HPLC with the following conditions: Column, Xbridge Phenyl OBD Column, 19*150 mm, 5um; mobile phase, Water (0.05% $NH_4OH$) and $CH_3CN$ (5% $CH_3CN$ up to 35% in 8 min); Detector, UV 220 nm to afford 98.2 mg of 1-(7-(cyanomethyl)-2-oxaspiro[3.5]nonan-7-yl)-3-(cyclopropanecarboxamido)-1H-pyrazole-4-carboxamide as a white solid. LC/MS (Method A, ESI): [M+H]$^+$=358, $R_T$=1.20 min; $^1$H NMR (300 MHz, DMSO-d$_6$): δ (ppm) 10.13 (s, 1H), 8.45 (s, 1H), 7.50 (s, 1H), 7.21 (s, 1H), 4.33 (s, 2H), 4.18 (s, 2H), 3.02 (s, 2H), 2.32-2.28 (m, 2H), 1.96-1.78 (m, 5H), 1.52-1.45 (m, 2H), 0.81-0.79 (m, 4H).

Example 6

(General Procedure E)

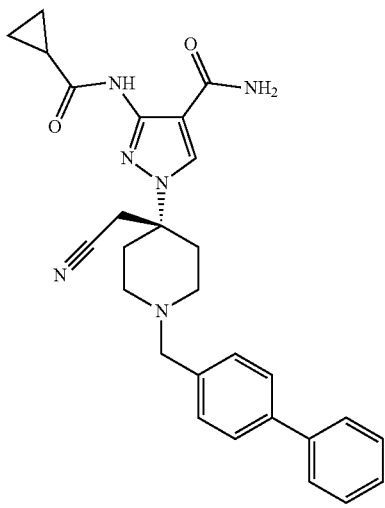

1-(1-([1,1'-Biphenyl]-4-ylmethyl)-4-(cyanomethyl)piperidin-4-yl)-3-(cyclopropanecarboxamido)-1H-pyrazole-4-carboxamide

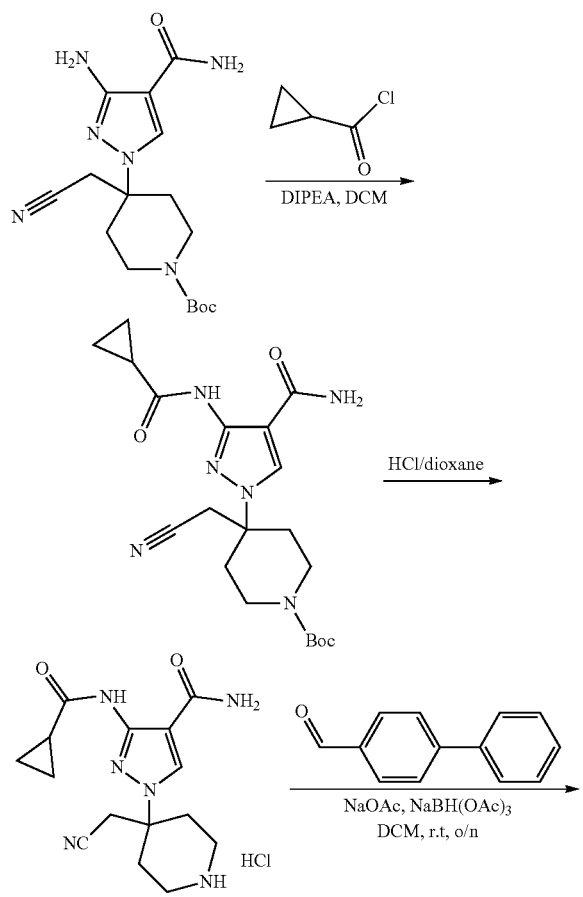

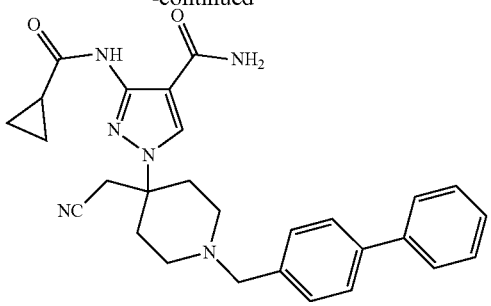

To a solution of 3-amino-1-[4-(cyanomethyl)piperidin-4-yl]-1H-pyrazole-4-carboxamide (10.0 g, 40.3 mmol) and DIPEA (7.41 g, 57.4 mmol) in dichloromethane (200 mL) at 0° C. was added dropwise cyclopropanecarbonyl chloride (4.48 g, 42.9 mmol). The resulting solution was stirred for 2 days at room temperature, and concentrated under reduced pressure. The residue was purified by flash chromatography on silica gel eluting with dichloromethane/methanol (10/1)) to afford 12.4 g (74%) of tert-butyl 4-(4-carbamoyl-3-(cyclopropanecarboxamido)-1H-pyrazol-1-yl)-4-(cyanomethyl) piperidine-1-carboxylate as a yellow solid. TLC: $R_f$=0.6; DCM/MeOH=10/1.

To a solution of tert-butyl 4-(4-carbamoyl-3-(cyclopropanecarboxamido)-1H-pyrazol-1-yl)-4-(cyanomethyl) piperidine-1-carboxylate (12.1 g, 29.1 mmol) in dioxane (150 mL) was added 4N HCl in dioxane solution (40 mL). The resulting solution was stirred for 6 h at room temperature. The precipitates were collected by filtration. The filtrate was concentrated under reduced pressure to afford an additional crop of product. The solids were combined and dried under reduced pressure to afford 11.4 g of 1-(4-(cyanomethyl) piperidin-4-yl)-3-(cyclopropanecarboxamido)-1H-pyrazole-4-carboxamide hydrochloride as a white solid. LC/MS (Method G, ESI): [M+H]$^+$=317, $R_T$=0.52 min.

To a mixture of 1-(4-(cyanomethyl)piperidin-4-yl)-3-(cyclopropanecarboxamido)-1H-pyrazole-4-carboxamide hydrochloride salt (100 mg, 0.283 mmol) in dichloromethane (3.0 mL) was added 4-phenylbenzaldehyde (103 mg, 0.565 mmol) and NaOAc (23.0 mg, 0.280 mmol). The mixture was stirred at room temperature for 1 h, and then NaBH(OAc)$_3$ (120 mg, 0.566 mmol) was added. The resulting solution was stirred overnight at room temperature, and concentrated under reduced pressure. The residue was passed through a short pad of silica gel eluting with EtOAc/THF (85/15). The appropriate fractions were combined and concentrated under reduced pressure. The crude product (50 mg) was further purified by Prep-HPLC with the following conditions: Column, XBridge Shield RP18 OBD Column, 19*150 mm, 5um; mobile phase, 10 mM NH$_4$HCO$_3$ solution and CH$_3$CN (23% CH$_3$CN up to 45% in 8 min); Detector, UV 254 nm to afford 10.5 mg of 1-(1-([1,1'-biphenyl]-4-ylmethyl)-4-(cyanomethyl)piperidin-4-yl)-3-(cyclopropanecarboxamido)-1H-pyrazole-4-carboxamide as a white solid. LC/MS (Method E, ESI): [M+H]$^+$=483, $R_T$=1.66 min. $^1$H NMR (400 MHz, CD$_3$OD): δ (ppm) 8.46 (s, 1H), 7.65-7.55 (m, 4H), 7.46-7.41 (m, 4H), 7.34 (m, 1H), 3.55 (s, 2H), 3.14 (s, 2H), 2.78-2.75 (m, 2H), 2.63-2.60 (m, 2H), 2.29-2.20 (m, 2H), 2.17-2.14 (m, 2H), 1.90-1.70 (m, 1H), 1.04-1.00 (m, 2H), 0.98-0.94 (m, 2H).

Examples 7 & 8

(General Procedure F)

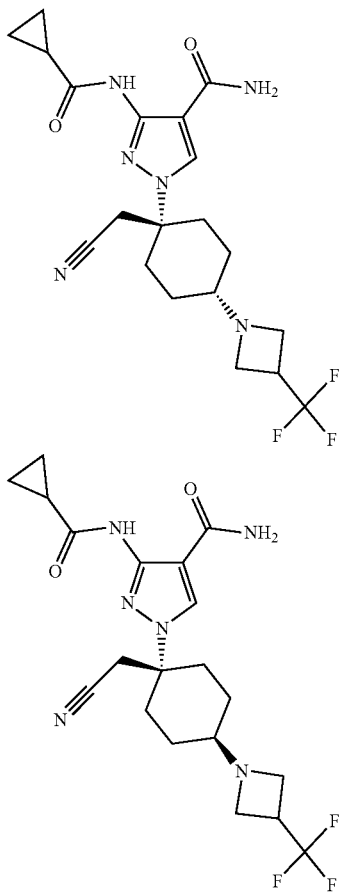

1-((1S,4S)-1-(Cyanomethyl)-4-(3-(trifluoromethyl)azetidin-1-yl)cyclohexyl)-3-(cyclopropanecarboxamido)-1H-pyrazole-4-carboxamide & 1-((1R,4R)-1-(cyanomethyl)-4-(3-(trifluoromethyl) azetidin-1-yl)cyclohexyl)-3-(cyclopropanecarboxamido)-1H-pyrazole-4-carboxamide

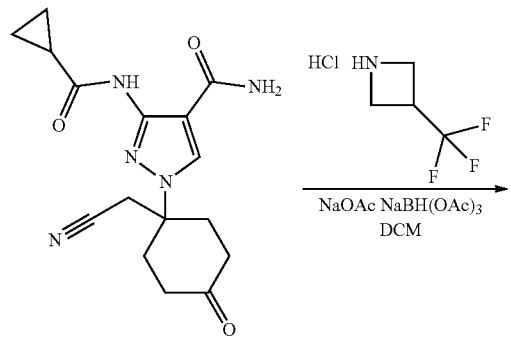

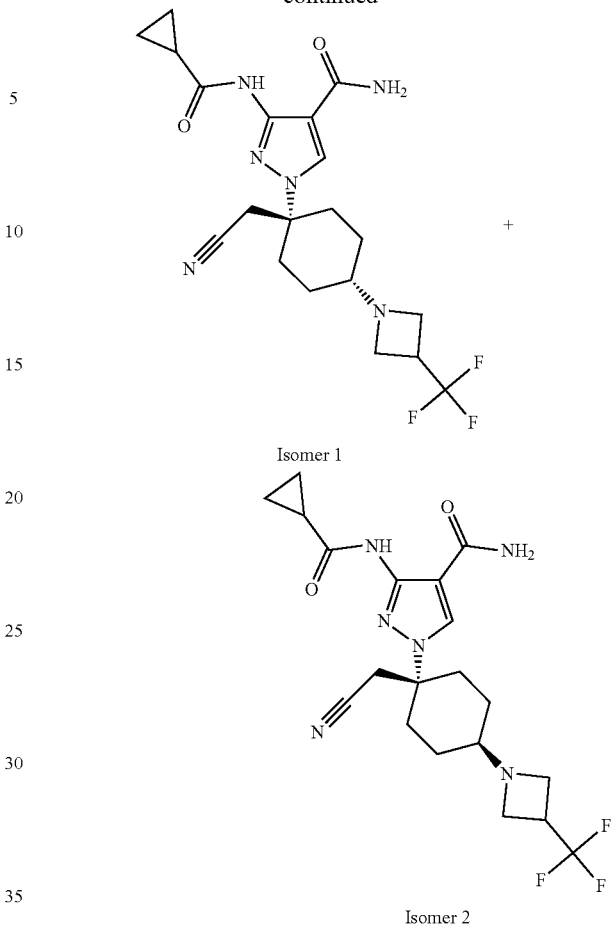

Isomer 1

Isomer 2

To a solution of 1-(1-(cyanomethyl)-4-oxocyclohexyl)-3-(cyclopropane-carboxamido)-1H-pyrazole-4-carboxamide (200 mg, 0.607 mmol) in dichloromethane (10 mL) was added 3-(trifluoromethyl)azetidine hydrochloride (118 mg, 0.730 mmol) and NaOAc (49.8 mg, 0.607 mmol). The mixture was stirred at room temperature for 1 h, and then NaBH(OAc)$_3$ (258 mg, 1.22 mmol) was added. The resulting solution was stirred for 4 h at room temperature and water was added. The resulting solution was extracted with ethyl acetate (3×) and the organic layers combined. The organic phases were washed with of water and brine, dried over anhydrous sodium sulfate and concentrated under reduced pressure. The residue was passed through a short pad of silica gel eluting with dichloromethane/methanol (95/5). The crude product (120 mg) was purified by Prep-HPLC with the following conditions: Column, XBridge Shield RP18 OBD Column, 19*150 mm, 5um; mobile phase: 10 mM NH$_4$HCO$_3$ solution and CH$_3$CN (22% CH$_3$CN up to 46% in 9 min); Detector, UV 254 nm to give two fractions. Absolute configuration was arbitrarily assigned to each diastereomer:

Example 7: the first fraction, 36.7 mg as an off-white solid, LC/MS (Method E, ESI): [M+H]$^+$=439, R$_T$=1.31 min, $^1$H NMR (400 MHz, CD$_3$OD): δ (ppm) 8.45 (s, 1H), 3.59-3.46 (m, 2H), 3.29-3.15 (m, 3H), 3.04 (s, 2H), 2.75 (m, 2H), 2.35-2.30 (m, 1H), 1.96-1.78 (m, 5H), 1.15-0.98 (m, 4H), 0.96-0.92 (m, 2H).

Example 8: the second fraction, 19.3 mg as a white solid, LC/MS (Method D, ESI): [M+H]$^+$=439, R$_T$=2.16 min, $^1$H NMR (400 MHz, CD₃OD): δ (ppm) 8.40 (s, 1H), 3.56-3.50 (m, 2H), 3.30-3.24 (m, 3H), 3.16 (s, 2H), 2.33-2.28 (m, 3H), 2.20-2.14 (m, 2H), 1.90-1.70 (m, 1H), 1.69-1.64 (m, 2H), 1.47-1.41 (m, 2H), 1.04-1.00 (m, 2H), 0.98-0.92 (m, 2H).

Examples 9 & 10

(General Procedure G)

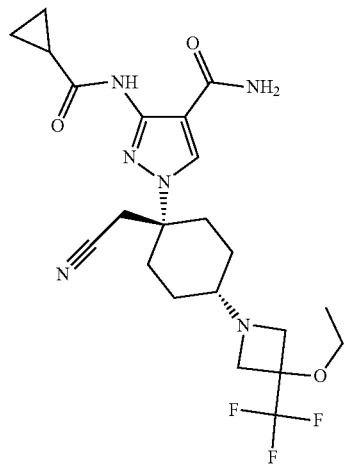

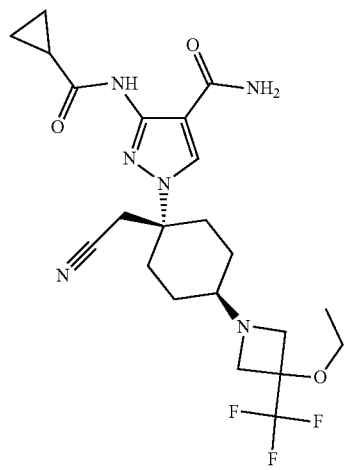

1-((1S,4S)-1-(Cyanomethyl)-4-(3-ethoxy-3-(trifluoromethyl)azetidin-1-yl)cyclohexyl)-3-(cyclopropanecarboxamido)-1H-pyrazole-4-carboxamide & 1-((1R,4R)-1-(cyanomethyl)-4-(3-ethoxy-3-(trifluoromethyl) azetidin-1-yl) cyclohexyl)-3-(cyclopropanecarboxamido)-1H-pyrazole-4-carboxamide

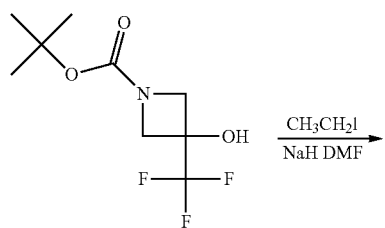

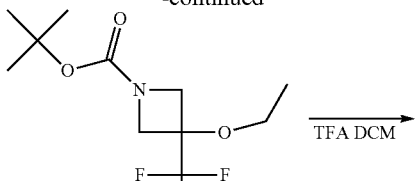

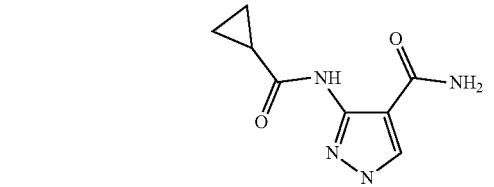

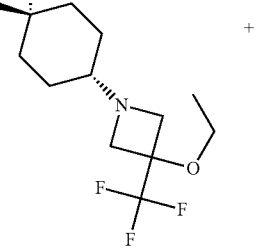

Isomer 1

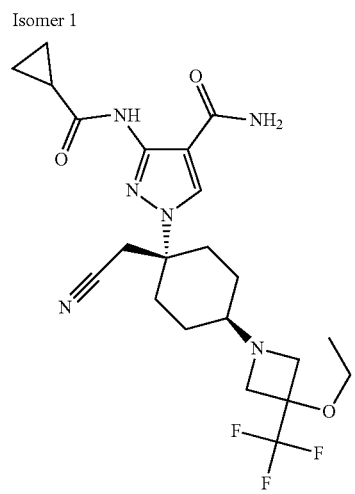

Isomer 2

To a solution of tert-butyl 3-hydroxy-3-(trifluoromethyl) azetidine-1-carboxylate (250 mg, 1.04 mmol) in N,N-dimethylformamide (10 mL) was added sodium hydride (104 mg, 60% dispersion in mineral oil, 2.59 mmol). The resulting solution was stirred for 20 min at 0° C., and then iodoethane (809 mg, 5.19 mmol) was added dropwise under nitrogen. The resulting solution was stirred for 3 h at room temperature, and poured into water (20 mL), extracted with ethyl acetate (3×). The organic extracts were combined and washed successively with water and brine, dried over anhydrous sodium sulfate and concentrated under reduced pressure to afford 183 mg (66%) of tert-butyl 3-ethoxy-3-(trifluoromethyl) azetidine-1-carboxylate as a yellow solid.

To a solution of tert-butyl 3-ethoxy-3-(trifluoromethyl) azetidine-1-carboxylate (180 mg, 0.668 mmol) in dichloromethane (5.0 mL) was added trifluoroacetic acid (8.0 mL). The resulting solution was stirred for 4 h at room temperature and concentrated under reduced pressure. This resulted in 169 mg (crude) of 3-ethoxy-3-(trifluoromethyl) azetidine TFA salt as a light yellow solid, which was used without further purification.

To a solution of 1-(1-(cyanomethyl)-4-oxocyclohexyl)-3-(cyclopropane-carboxamido)-1H-pyrazole-4-carboxamide (160 mg, 0.486 mmol) in dichloromethane (8.0 mL) was added 3-ethoxy-3-(trifluoromethyl)azetidine TFA salt (98.6 mg) and NaOAc (39.9 mg, 0.486 mmol). The solution was stirred for 2 h at room temperature, and then NaBH(OAc)$_3$ (206 mg, 0.973 mmol) was added. The reaction mixture was stirred overnight at room temperature, and then partitioned between water and ethyl acetate. Phases were separated. The aqueous phase was extracted with ethyl acetate (2×). The organic phases were combined and washed successively with water and brine, dried over anhydrous sodium sulfate and concentrated under reduced pressure. The residue was passed through a short pad of silica gel eluting with dichloro-methane/methanol (95/5). The crude product (120 mg) was further purified by Prep-HPLC with the following conditions: Column, XBridge Shield RP18 OBD Column, 19*150 mm, 5 um; mobile phase: Water (0.05% NH$_4$OH) and CH$_3$CN (40% CH$_3$CN up to 90% in 9 min); Detector, UV 220 nm to afford two fractions. Absolute configuration was arbitrarily assigned to each diastereomer:

Example 9: the first fraction, 19.6 mg as a white solid, LC/MS (Method F, ESI): [M+H]$^+$=483, R$_T$=1.19 min, $^1$H NMR (400 MHz, CD$_3$OD): δ (ppm) 8.44 (s, 1H), 3.67 (q, J=6.8 Hz, 2H), 3.52 (d, J=9.8 Hz, 2H, AB), 3.40 (d, J=9.8 Hz, 2H, AB), 3.04 (s, 2H), 2.75 (m, 2H), 2.38-2.32 (m, 1H), 1.90-1.78 (m, 5H), 1.23 (t, J=6.8 Hz, 3H), 1.14-1.01 (m, 2H), 1.00-0.98 (m, 2H), 0.96-0.91 (m, 2H).

Example 10: the second fraction, 20.6 mg as a white solid, LC/MS (Method F, ESI): [M+H]$^+$=483, R$_T$=1.22 min; $^1$H NMR (400 MHz, CD$_3$OD): δ (ppm) 8.40 (s, 1H), 3.72 (q, J=6.8 Hz, 2H), 3.55 (d, J=9.4 Hz, 2H, AB), 3.40 (d, J=9.4 Hz, 2H, AB), 3.15 (s, 2H), 2.39-2.29 (m, 3H), 2.19-2.17 (m, 2H), 1.94-1.60 (m, 3H), 1.49-1.47 (m, 2H), 1.25 (t, J=6.8 Hz, 3H), 1.04-0.93 (m, 4H).

Example 11

(General Procedure H)

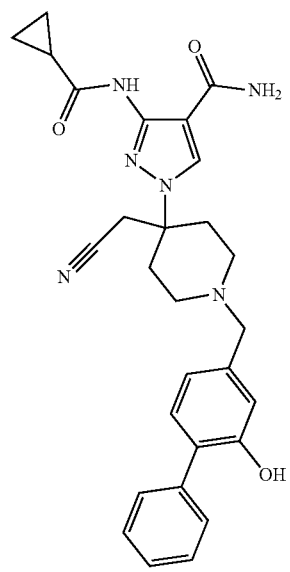 [SMILES: N#CCC1(n2cc(C(N)=O)c(NC(=O)C3CC3)n2)CCN(Cc2ccc(-c3ccccc3)c(O)c2)CC1]

1-(4-(Cyanomethyl)-1-((2-hydroxy-[1,1'-biphenyl]-4-yl)methyl)piperidin-4-yl)-3-(cyclopropanecarboxamido)-1H-pyrazole-4-carboxamide

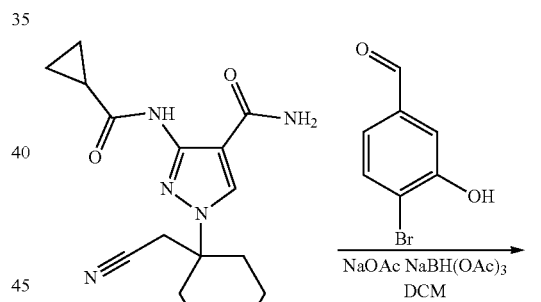

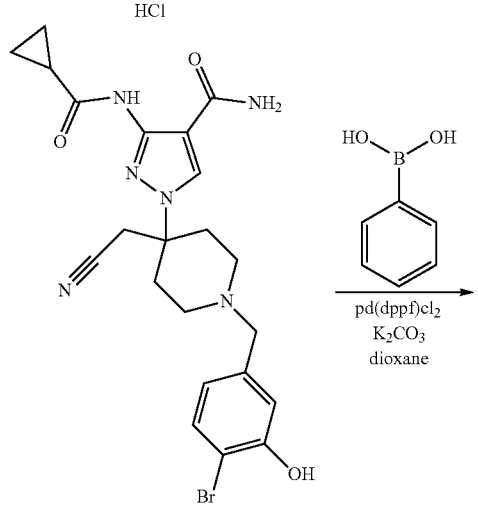

-continued

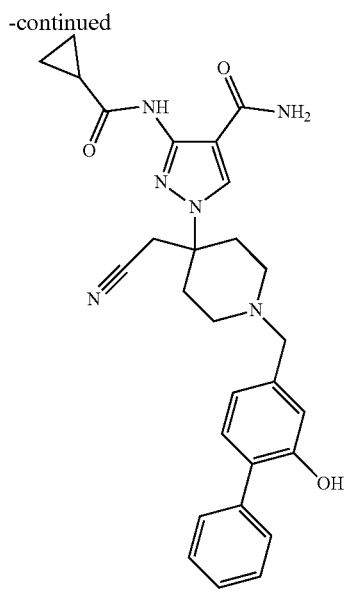

To a mixture of 1-(4-(cyanomethyl)piperidin-4-yl)-3-(cyclopropanecarbox-amido)-1H-pyrazole-4-carboxamide hydrochloride (300 mg, 0.850 mmol) in dichloromethane (8.0 mL) was added 4-bromo-3-hydroxybenzaldehyde (341 mg, 1.70 mmol) and NaOAc (69.9 mg, 0.852 mmol). The mixture was stirred for 2h, then NaBH(OAc)$_3$ (361 mg, 1.71 mmol) was added. The resulting solution was stirred overnight at room temperature, and partitioned between ethyl acetate and water. The aqueous phase was extracted with ethyl acetate (2×). The combined organic phases were washed with water and brine successively, dried over anhydrous sodium sulfate and concentrated under reduced pressure. The residue was purified by flash chromatography on silica gel eluting with dichloromethane/methanol (95/5). The appropriate fractions were combined and concentrated under reduced pressure to afford 310 mg (73%) of 1-(1-(4-bromo-3-hydroxybenzyl)-4-(cyanomethyl) piperidin-4-yl)-3-(cyclopropane-carboxamido)-1H-pyrazole-4-carboxamide as a white solid.

To a solution of 1-(1-(4-bromo-3-hydroxybenzyl)-4-(cyanomethyl)piperidin-4-yl)-3-(cyclopropanecarboxamido)-1H-pyrazole-4-carboxamide (100 mg, 0.199 mmol) in dioxane (5.0 mL) was added phenylboronic acid (36.6 mg, 0.300 mmol), Pd(dppf)Cl$_2$ (14.6 mg, 0.0200 mmol), potassium carbonate (55.2 mg, 0.399 mmol) and water (0.50 mL) under nitrogen. The reaction mixture was stirred for 2 h at 80° C., allowed to cool to room temperature and poured into water (10 mL). The resulting solution was extracted with ethyl acetate (3×). The combined organic phases were washed with water and brine, dried over anhydrous sodium sulfate and concentrated under reduced pressure. The residue was passed through a short pad of silica gel eluting with dichloromethane/methanol (95/5). The crude product was purified by Prep-HPLC with the following conditions: Column, XBridge Shield RP18 OBD Column, 19*150 mm, 5 um; mobile phase: Water (0.05% NH$_4$OH) and CH$_3$CN (20% CH$_3$CN up to 50% in 6 min); Detector, UV 220 nm to afford 10.2 mg (10%) of 1-(4-(cyanomethyl)-1-((2-hydroxy-[1,1'-biphenyl]-4-yl) methyl)piperidin-4-yl)-3-(cyclopropanecarboxamido)-1H-pyrazole-4-carboxamide as a white solid. LC/MS (Method C, ESI): [M+H]$^+$=499, R$_t$=1.49 min; $^1$H NMR (300 MHz, CD$_3$OD): δ (ppm) 8.45 (s, 1H), 7.54-7.51 (m, 2H), 7.39-7.34 (m, 2H), 7.29-7.21 (m, 1H), 7.19 (d, J=7.8 Hz, 1H), 6.87-6.84 (m, 2H), 3.45 (s, 2H), 3.12 (s, 2H), 2.76-2.73 (m, 2H), 2.62-2.58 (m, 2H), 2.26-2.12 (m, 4H), 1.90-1.65 (m, 1H), 1.03-0.91 (m, 4H).

Examples 12, 13, 14 & 15

(General Procedure I)

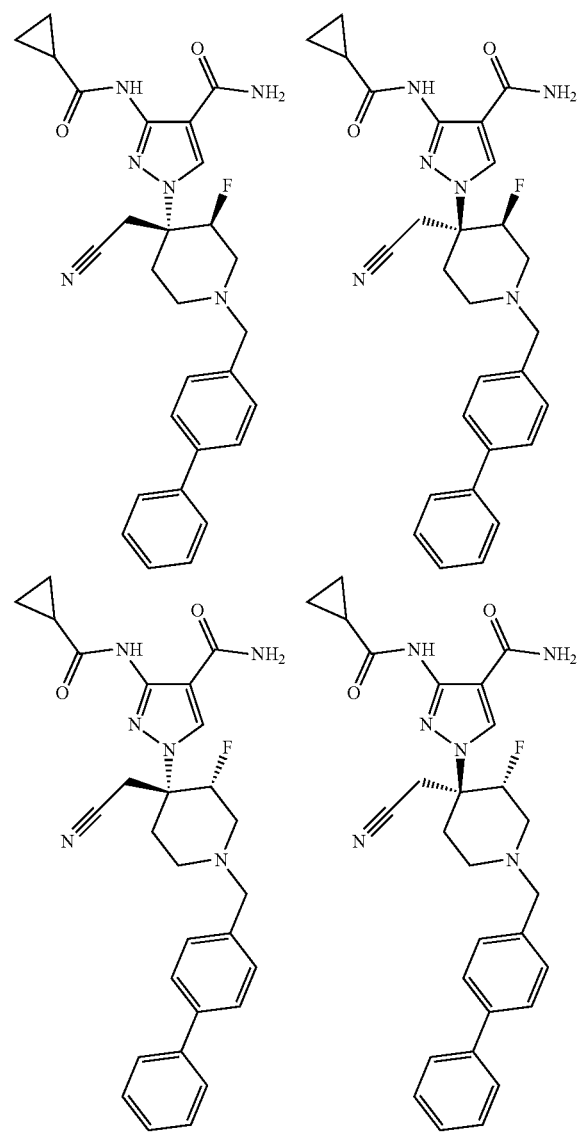

1-((3S,4R)-1-([1,1'-biphenyl]-4-ylmethyl)-4-(cyanomethyl)-3-fluoropiperidin-4-yl)-3-(cyclopropanecarboxamido)-1H-pyrazole-4-carboxamide; 1-((3S,4S)-1-([1,1'-biphenyl]-4-ylmethyl)-4-(cyanomethyl)-3-fluoropiperidin-4-yl)-3- (cyclopropanecarboxamido)-1H-pyrazole-4-carboxamide; 1-((3R,4R)-1-([1,1'-biphenyl]-4-ylmethyl)-4-(cyanomethyl)-3-fluoropiperidin-4-yl)-3-(cyclopropanecarboxamido)-1H-pyrazole- 4-carboxamide & 1-((3R,4S)-1-([1,1'-biphenyl]-4-ylmethyl)-4-(cyanomethyl)-3-fluoropiperidin-4-yl)-3- (cyclopropanecarboxamido)-1H-pyrazole-4-carb oxamide

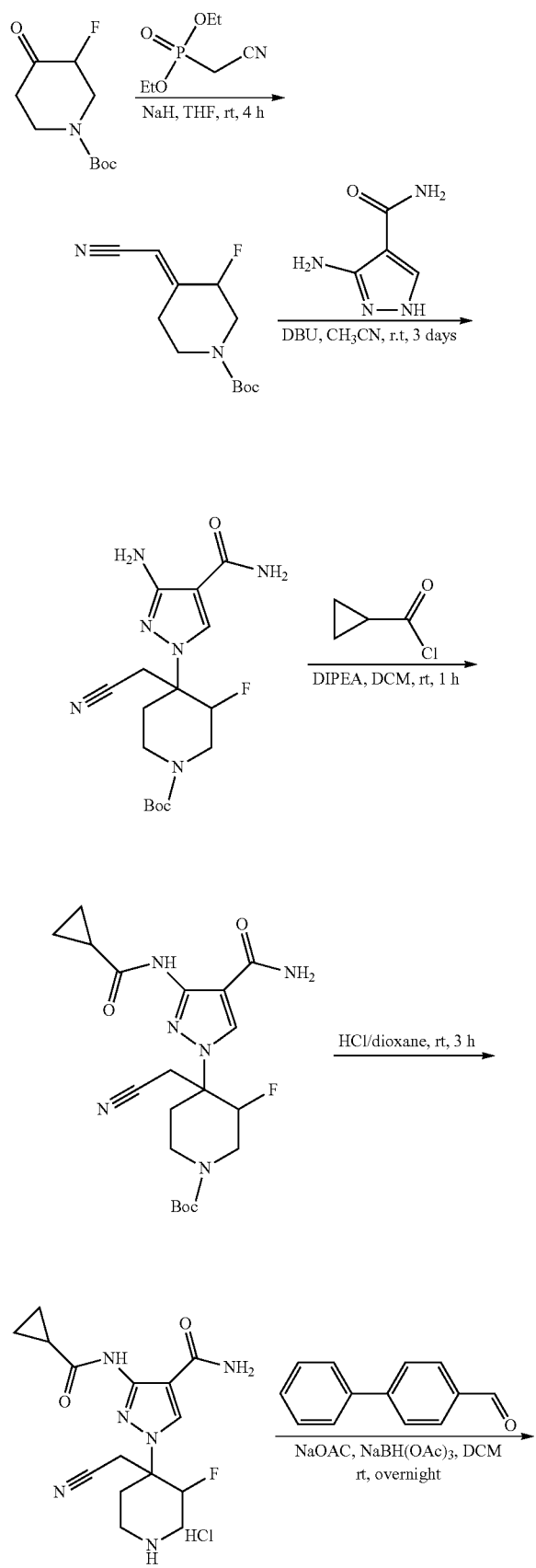
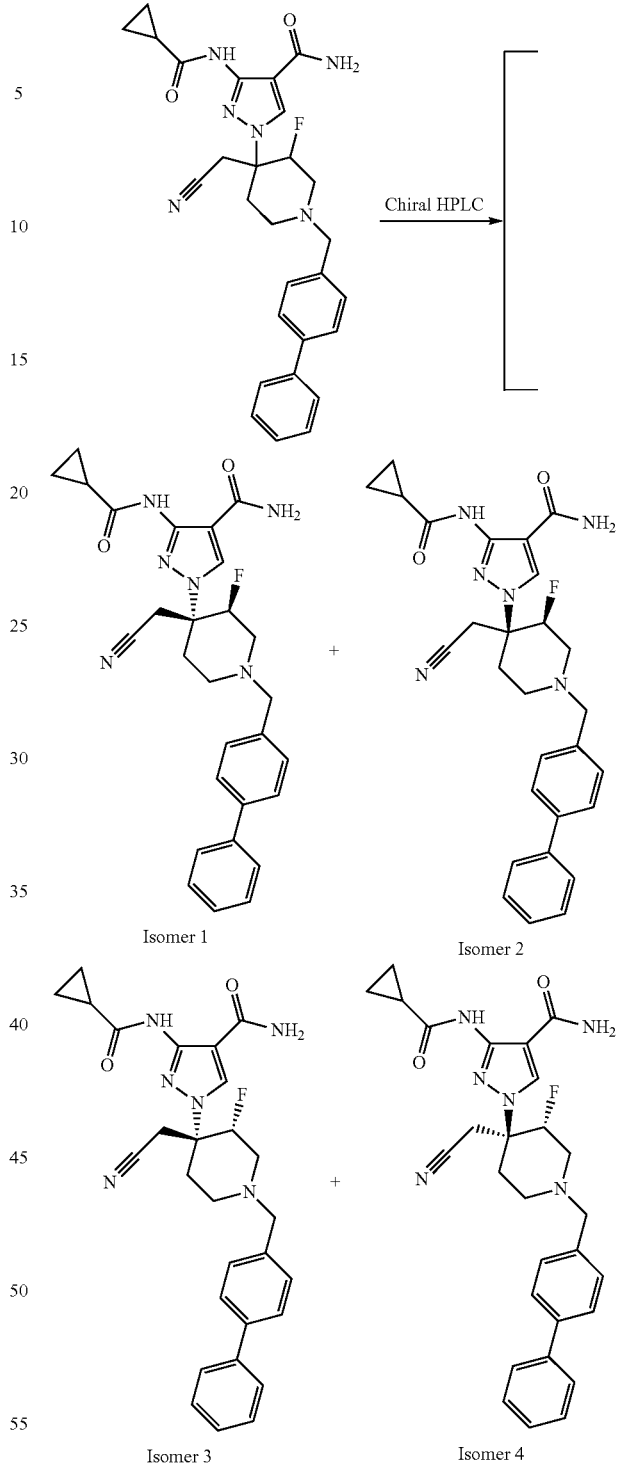

Isomer 1     Isomer 2

Isomer 3     Isomer 4

To a solution of diethyl (cyanomethyl)phosphonate (44.9 g, 253 mmol) in tetrahydrofuran (500 mL) was added sodium hydride (18.3 g, 60% dispersion in mineral oil, 275 mmol) in several batches at 0-10° C. The resulting solution was stirred for 1 h at room temperature and then tert-butyl 3-fluoro-4-oxopiperidine-1-carboxylate (50.0 g, 230 mmol) was added. The resulting solution was stirred for 1 h at room temperature. Water (300 mL) was added. The resulting solution was extracted with ethyl acetate (3×) and the organic layers combined. The organic phases were washed with brine (200 mL), dried over anhydrous sodium sulfate and concentrated under reduced pressure. The residue was triturated in hexane, and the solid was collected by filtration and dried under reduced pressure to afford 44.0 g (80%) of tert-butyl (4Z)-4-(cyanomethylidene)-3-fluoropiperidine-1-carboxylate as a yellow solid. LC/MS (Method G, ESI): [M+H]$^+$=241, R$_T$=0.87 min & 0.94 min.

To a solution of tert-butyl (4Z)-4-(cyanomethylidene)-3-fluoropiperidine-1-carboxylate (22.9 g, 95.1 mmol) in CH$_3$CN (100 mL) was added 3-amino-1H-pyrazole-4-carboxamide (10.0 g, 79.3 mmol) and DBU (24.1 g, 159 mmol). The reaction mixture was stirred for 3 days at room temperature and concentrated under reduced pressure. The residue was purified by flash chromatography on silica gel eluting with dichloromethane/ethyl acetate (100/70). The appropriate fractions were combined and concentrated under reduced pressure to afford 7.01 g (24%) of tert-butyl 4-(3-amino-4-carbamoyl-1H-pyrazol-1-yl)-4-(cyanomethyl)-3-fluoropiperidine-1-carboxylate as a yellow solid. LC/MS (Method F, ESI): [M+H]$^+$=367, R$_T$=1.12 min & 1.19 min.

Cyclopropanecarbonyl chloride (500 mg, 4.78 mmol) was added dropwise to a solution of tert-butyl 4-(3-amino-4-carbamoyl-1H-pyrazol-1-yl)-4-(cyanomethyl)-3-fluoropiperidine-1-carboxylate (500 mg, 1.37 mmol) and DIPEA (800 mg, 6.19 mmol) in dichloromethane (50 mL) at 0-10° C. The resulting solution was stirred for 2 h at room temperature and then quenched by the addition of 20 mL of water. Phases were separated. The aqueous phase was extracted with dichloromethane (3×). The combined organic layers were washed with water and brine successively, dried over anhydrous sodium sulfate and concentrated under reduced pressure. The residue was purified by flash chromatography on silica gel eluting with dichloromethane/methanol (100/5). The appropriate fractions were combined and concentrated under reduced pressure to 500 mg (84%) of tert-butyl 4-(4-carbamoyl-3-cyclopropaneamido-1H-pyrazol-1-yl)-4-(cyanomethyl)-3-fluoropiperidine-1-carboxylate as a yellow solid. LC/MS (Method F, ESI): [M+H]$^+$=435, R$_T$=1.25 min & 1.30 min.

A solution of tert-butyl 4-(4-carbamoyl-3-cyclopropaneamido-1H-pyrazol-1-yl)-4-(cyanomethyl)-3-fluoropiperidine-1-carboxylate (200 mg, 0.460 mmol) in 4N HCl in dioxane (10 mL) was stirred for 3 h at room temperature. The reaction mixture was then concentrated under reduced pressure to afford 200 mg of 1-(4-(cyanomethyl)-3-fluoropiperidin-4-yl)-3-(cyclopropanecarboxamido)-1H-pyrazole-4-carboxamide hydrochloride as a yellow solid. LC/MS (Method I, ESI): [M+H]$^+$=335, R$_T$=0.87 min.

To a mixture of above crude 1-(4-(cyanomethyl)-3-fluoropiperidin-4-yl)-3-(cyclopropanecarboxamido)-1H-pyrazole-4-carboxamide hydrochloride (200 mg) in dichloromethane (20 mL) was added 4-phenylbenzaldehyde (125 mg, 0.688 mmol) and NaOAc (112 mg, 1.38 mmol). The mixture was stirred for 4 h at 30° C., allowed to cool to room temperature and NaBH(OAc)$_3$ (292 mg, 1.38 mmol) was added. The resulting solution was stirred overnight at room temperature, and then quenched by the addition of 100 ml of saturated sodium bicarbonate solution. The resulting solution was extracted with ethyl acetate (3×). The organic layers were combined, washed with brine, dried over sodium sulfate and concentrated under reduced pressure. The residue was purified by flash chromatography on silica gel eluting with tetrahydrofuran/ethyl acetate (1:3). The appropriate fractions were combined and concentrated under reduced pressure. The racemic mixtures were separated by chiral-HPLC with following condition: Column: CHIRAL ART Cellulose-SB, 250*20 mm; Mobile Phase A: Hexane, Mobile Phase B: EtOH; Flow rate: 20 mL/min; Gradient: 20% B in 25 min; 254/220 nm to afford 4 isomers. Absolute configuration was arbitrarily assigned to each stereoisomer:

Example 12: RT$_1$: 16.76 min; the first fraction, 12.9 mg as a white solid, LC/MS (Method A, ESI): [M+H]$^+$=501, R$_T$=1.49 min; $^1$H NMR (400 MHz, CD$_3$OD): δ (ppm) 8.40 (s, 1H), 7.51-7.46 (m, 4H), 7.34-7.29 (m, 4H), 7.22 (t, J=7.4 Hz, 1H), 5.39-5.28 (m, 1H), 3.50 (d, J=13.2 Hz, 1H, AB), 3.45 (d, J=13.2 Hz, 1H, AB), 3.25 (d, J=17.2 Hz, 1H, AB), 3.08 (d, J=17.2 Hz, 1H, AB), 2.95-2.75 (m, 1H), 2.72-2.70 (m, 1H), 2.49-2.46 (m, 1H), 2.33-2.15 (m, 3H), 1.77-1.64 (m, 1H), 0.92-0.78 (m, 4H).

Example 13: RT$_2$: 18.54 min, the second fraction, 7.9 mg as a white solid. LC/MS (Method A, ESI): [M+H]$^+$=501, R$_T$=1.49 min; $^1$H NMR (400 MHz, CD$_3$OD): δ (ppm) 8.30 (s, 1H), 7.50 (m, 4H), 7.34-7.31 (m, 4H), 7.22 (t, J=7.2 Hz, 1H), 5.24-4.92 (m, 1H), 3.59 (d, J=12.8 Hz, 1H, AB), 3.54 (d, J=12.8 Hz, 1H, AB), 3.49-3.43 (m, 1H), 3.21-3.10 (m, 1H), 2.95-2.91 (m, 1H), 2.76-2.47 (m, 4H), 2.11-2.08 (m, 1H), 1.93-1.68 (m, 1H), 0.91-0.82 (m, 4H).

Example 14: RT$_3$: 20.7 min; the third fraction, 8.8 mg as a white solid. LC/MS (Method A, ESI): [M+H]$^+$=501, R$_T$=1.49 min; $^1$H NMR (400 MHz, CD$_3$OD): δ (ppm) 8.30 (s, 1H), 7.50 (m, 4H), 7.39-7.31 (m, 4H), 7.22 (t, J=7.2 Hz, 1H), 5.03-4.92 (m, 1H), 3.60 (d, J=13.2 Hz, 1H, AB), 3.55 (d, J=13.2 Hz, 1H, AB), 3.49 (d, J=16.8 Hz, 1H, AB), 3.19 (d, J=16.8 Hz, 1H, AB), 2.95-2.92 (m, 1H), 2.77-2.48 (m, 4H), 2.12-2.09 (m, 1H), 1.93-1.51 (m, 1H), 0.91-0.78 (m, 4H).

Example 15: RT$_4$: 23.36 min, the fourth fraction, 15 mg as a white solid. LC/MS (Method A, ESI): [M+H]$^+$=501, R$_T$=1.49 min; $^1$H NMR (400 MHz, CD$_3$OD): δ (ppm) 8.40 (s, 1H), 7.49 (m, 4H), 7.34-7.29 (m, 4H), 7.22 (t, J=7.4 Hz, 1H), 5.40-5.28 (m, 1H), 3.51 (d, J=12.8 Hz, 1H, AB), 3.46 (d, J=12.8 Hz, 1H, AB), 3.25 (d, J=17.2 Hz, 1H, AB), 3.08 (d, J=17.2 Hz, 1H, AB), 2.95-2.88 (m, 1H), 2.72-2.71 (m, 1H), 2.49-2.46 (m, 1H), 2.34-2.24 (m, 3H), 1.93-1.70 (m, 1H), 0.92-0.91 (m, 2H), 0.90-0.78 (m, 2H).

Example 16

(General Procedure J)

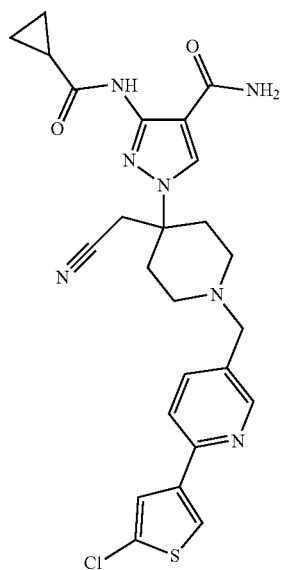 [SMILES: N#CCC1(n2cc(C(N)=O)c(NC(=O)C3CC3)n2)CCN(Cc2ccc(-c3csc(Cl)c3)nc2)CC1]

1-(1-((6-(5-Chlorothiophen-3-yl)pyridin-3-yl)methyl)-4-(cyanomethyl)piperidin-4-yl)-3-(cyclopropanecarboxamido)-1H-pyrazole-4- carboxamide

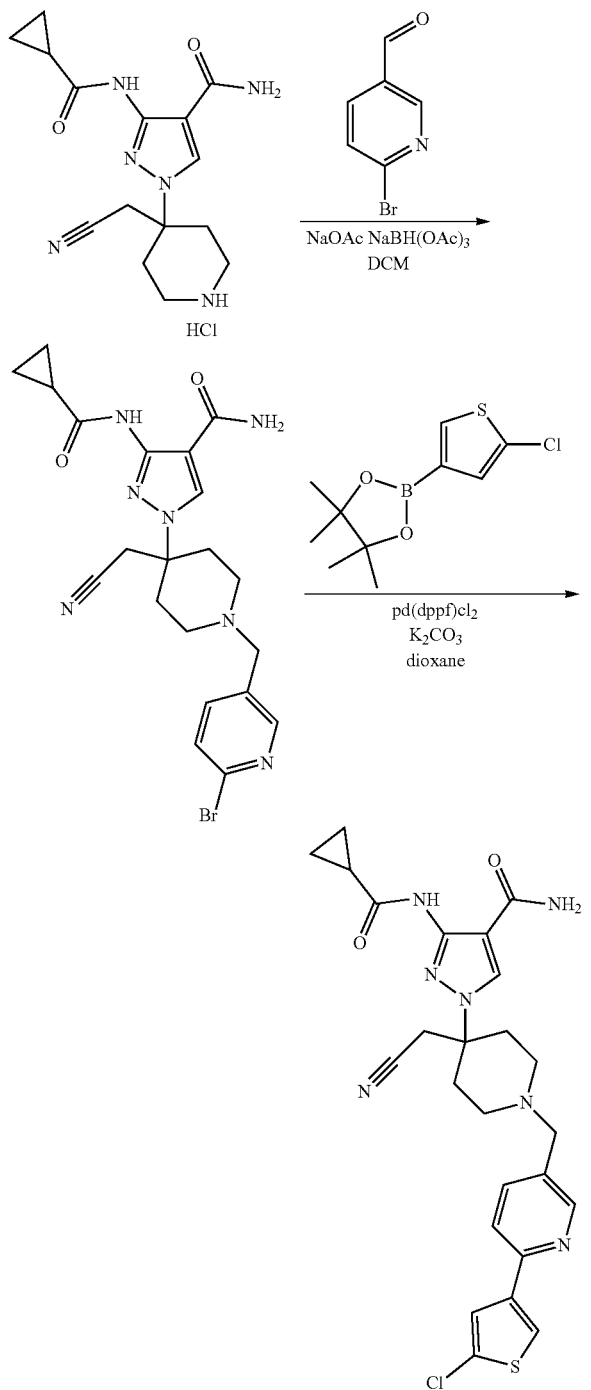

To a mixture of 1-(4-(cyanomethyl)piperidin-4-yl)-3-(cyclopropane-carboxamido)-1H-pyrazole-4-carboxamide hydrochloride (217 mg, 0.615 mmol) in dichloromethane (8.0 ml) was added 6-bromopyridine-3-carbaldehyde (200 mg, 1.08 mmol) and NaOAc (46.6 mg, 0.568 mmol). The reaction mixture was stirred for 1 h at room temperature and then NaBH(OAc)₃ (241 mg, 1.14 mmol) was added. The resulting reaction mixture was stirred overnight at room temperature. Water (10 mL) was added. Phases were separated. The aqueous phase was extracted with ethyl acetate (2×). The organic layers were combined, water and brine successively, dried over anhydrous sodium sulfate and concentrated under reduced pressure. The residue purified by flash chromatography on silica gel eluting with dichloromethane/methanol (85/15). The appropriate fractions were combined and concentrated under reduced pressure to afford 182 mg (61%) of 1-(1-((6-bromopyridin-3-yl)methyl)-4-(cyanomethyl)piperidin-4-yl)-3-(cyclopropanecarboxamido)-1H-pyrazole-4- carboxamide as a white solid.

To a solution of 1-(1-((6-bromopyridin-3-yl)methyl)-4-(cyanomethyl)piperidin-4-yl)-3-(cyclopropanecarboxamido)-1H-pyrazole-4-carboxamide (100 mg, 0.173 mmol) in dioxane (8.0 mL) was added 2-(5-chlorothiophen-3-yl)-4,4,5,5-tetramethyl-1,3,2-dioxaborolane (151 mg, 0.617 mmol), Pd(dppf)Cl₂ (15.1 mg, 0.0206 mmol), potassium carbonate (56.9 mg, 0.412 mmol) and water (0.30 mL) under nitrogen. The reaction mixture was stirred overnight at 80° C., and allowed to cool to room temperature. Water (10 mL) was added. The resulting solution was extracted ethyl acetate (3×). The organic layers were combined, washed with water and brine successively, dried over anhydrous sodium sulfate and concentrated under reduced pressure. The residue was purified by flash chromatography on silica gel eluting with dichloromethane/methanol (90/10). The appropriate fractions were combined and concentrated under reduced pressure to afford 42.2 mg (46%) of 1-(1-((6-(5-chlorothiophen-3-yl)pyridin-3-yl)methyl)-4-(cyanomethyl) piperidin-4-yl)-3-(cyclopropanecarboxamido)-1H-pyrazole-4-carboxamide as a white solid. LC/MS (Method F, ESI): [M+H]⁺=524, $R_T$=1.47 min; ¹H NMR (400 MHz, CD₃OD): δ (ppm) 8.49 (s, 1H), 8.45 (s, 1H), 7.86-7.82 (m, 2H), 7.76 (d, J=8.0 Hz, 1H), 7.60 (d, J=1.6 Hz, 1H), 3.57 (s, 2H), 3.14 (s, 2H), 2.76 (m, 2H), 2.62 (m, 2H), 2.29-2.20 (m, 2H), 2.19-2.05 (m, 2H), 1.90-1.70 (m, 1H), 1.04-0.98 (m, 2H), 0.97-0.92 (m, 2H).

Example 17

(General Procedure K)

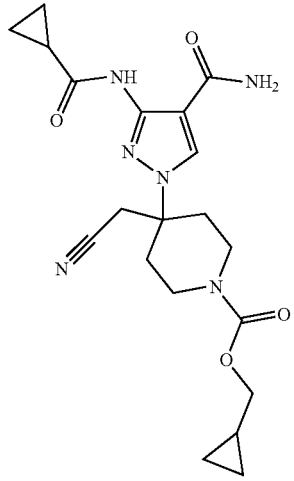 [SMILES: N#CCC1(n2cc(C(N)=O)c(NC(=O)C3CC3)n2)CCN(C(=O)OCC2CC2)CC1]

Cyclopropylmethyl 4-(4-carbamoyl-3-(cyclopropanecarboxamido)-1H-pyrazol-1-yl)4-(cyanomethyl) piperidine-1-carboxylate

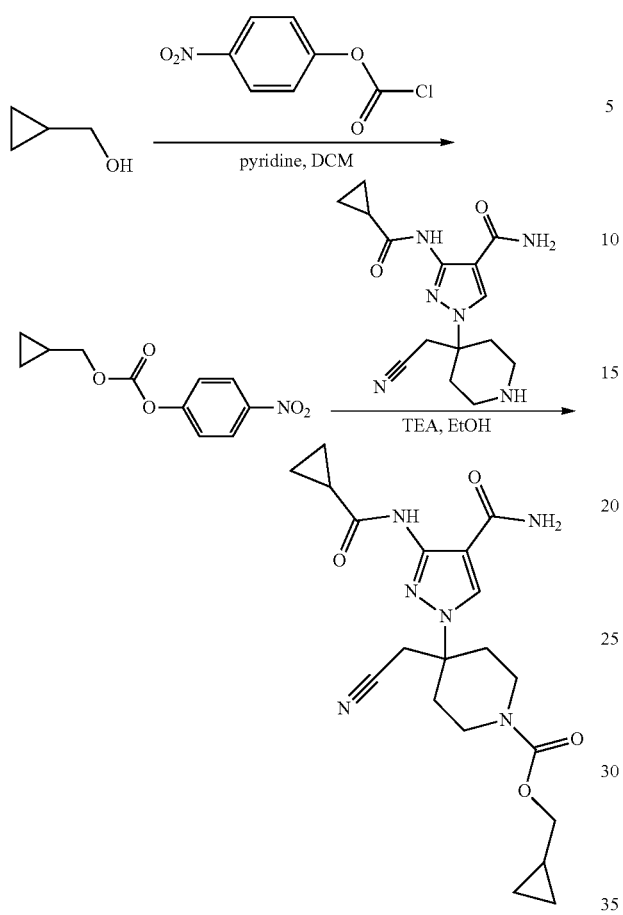

To a solution of cyclopropylmethanol (1.00 g, 13.8 mmol) and pyridine (1.32 g, 16.6 mmol) in dichloromethane (30 mL) was added dropwise 4-nitrophenyl chloroformate (1.68 g, 8.33 mmol) at 0° C. under nitrogen. The resulting solution was stirred overnight at room temperature. Water (10 mL) was added. The resulting mixture was then washed with 10 ml of brine. The organic mixture was dried over anhydrous sodium sulfate and the solid was filtered out. The organic mixture was concentrated under reduced pressure. The crude product was purified by re-crystallization from n-hexane. This resulted in 1.20 g (36%) of cyclopropylmethyl 4-nitrophenyl carbonate as a white solid. TLC: $R_f$=0.5; Hex/EA=4/1.

To solution of 1-(4-(cyanomethyl)piperidin-4-yl)-3-(cyclopropanecarboxamido)-1H-pyrazole-4-carboxamide (100 mg, 0.316 mmol) and triethylamine (95.9 mg, 0.948 mmol) in ethanol (30 mL) was added cyclopropylmethyl 4-nitrophenyl carbonate (74.9 mg, 0.316 mmol). The resulting solution was stirred for 12 h at room temperature, and concentrated under reduced pressure. The residue was partitioned between dichloromethane and water. Phases were separated. The organic phase was washed with brine, dried over anhydrous sodium sulfate and concentrated under reduced pressure. The residue was passed through a short pad of silica gel eluting with dichloromethane/methanol (93:7). The appropriate fractions were collected and concentrated. The crude product was purified by Prep-HPLC with the following conditions: XBridge Shield RP18 OBD Column, 19*150 mm, 5um; mobile phase: Water (0.05% NH₄OH) and CH₃CN (18% CH₃CN to 50.0% in 6 min); Detector, UV 254/220 nm to afford 48.5 mg (37%) of cyclopropylmethyl 4-(4-carbamoyl-3-(cyclopropanecarboxamido)-1H-pyrazol-1-yl)-4-(cyanomethyl) piperidine-1-carboxylate as a white solid. LC/MS (Method E, ESI): [M+H]⁺=415, $R_T$=1.31 min; ¹H NMR (300 MHz, CD₃OD): δ (ppm) 8.47 (s, 1 H), 3.94-3.90 (m, 4 H), 3.15-3.08 (m, 4 H), 2.63-2.58 (m, 2 H), 2.10-2.01 (m, 2 H), 1.94-1.80 (m, 1 H), 1.19-1.11 (m, 1 H), 1.04-0.98 (m, 2 H), 0.97-0.90 (m, 2 H), 0.59-0.53 (m, 2 H), 0.32-0.27 (m, 2 H).

Example 18

(General Procedure L)

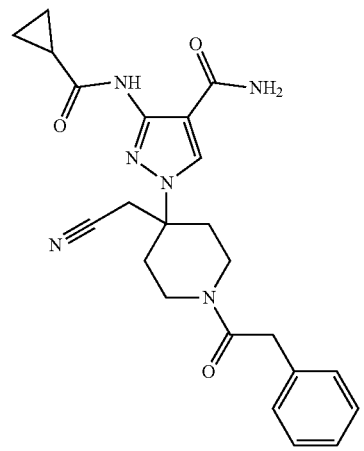 [SMILES: N#CCC1(n2cc(C(N)=O)c(NC(=O)C3CC3)n2)CCN(C(=O)Cc2ccccc2)CC1]

1-(4-(Cyanomethyl)-1-(2-phenylacetyl)piperidin-4-yl)-3-(cyclopropanecarboxamido)-1H-pyrazole-4-carboxamide

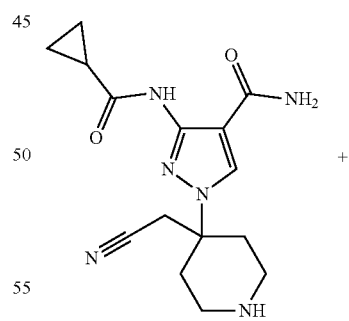

+

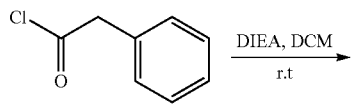

403

-continued

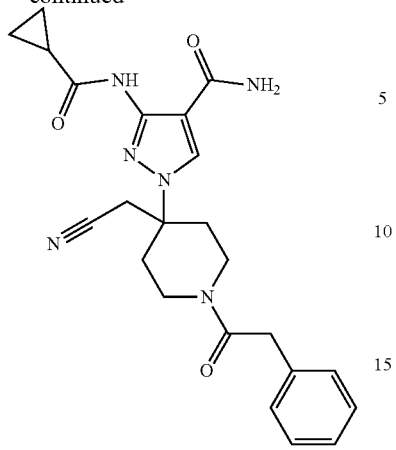

404

-continued

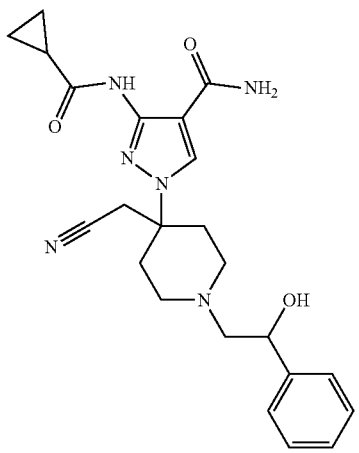

To a solution of 1-(4-(cyanomethyl)piperidin-4-yl)-3-(cyclopropanecarboxamido)-1H-pyrazole-4-carboxamide (100 mg, 0.316 mmol) and diisopropylethylamine (109 mg, 0.843 mmol) in dichloromethane (5 mL) was added dropwise 2-phenylacetyl chloride (79.0 mg, 0.511 mmol) at 0° C. The resulting solution was allowed to warm to room temperature and stirred for 6 h. The resulting mixture was concentrated under reduced pressure. The residue was passed through a short pad of silica gel eluting with ethyl acetate:THF (85: 15).The appropriate fractions were combined and concentrated under reduced pressure. The residue was further purified by Prep-HPLC with the following conditions: XBridge Shield RP18 OBD Column, 19*150 mm, 5um; mobile phase, 10 mM $NH_4HCO_3$ aqueous solution and $CH_3CN$ (23% $CH_3CN$ up to 45% in 12 min); Detector, UV 254 nm to afford 4.70 mg of 1-(4-(cyanomethyl)-1-(2-phenylacetyl)piperidin-4-yl)-3-(cyclopropanecarboxamido)-1H-pyrazole-4- carboxamide as a white solid. LC/MS (Method E, ESI): [M+H]$^+$=435, $R_T$=1.22 min. $^1$H NMR (400 MHz, $CD_3OD$): δ (ppm) 8.31 (s, 1H), 7.24-7.21 (m, $_2$H), 7.16-7.14 (m, 3H), 4.16 (d, J=13.6 Hz, 1H), 3.74 (d, J=15.2 Hz, 1H), 3.71 (s, 2H), 3.22-2.90 (m, 4H), 2.52-2.40 (m, 2H), 1.95-1.85 (m, 1H), 1.73-1.67 (m, 2 H), 0.92-0.88 (m, 2H), 0.85-0.81 (m, $_2$H).

Examples 19 & 20

(General Procedure M)

1-(4-(Cyanomethyl)-1-(2-hydroxy-1-phenylethyl)piperidin-4-yl)-3-(cyclopropanecarboxamido)-1H-pyrazole-4-carboxamide & 1-(4-(cyanomethyl)-1-(2-hydroxy-2-phenylethyl) piperidin-4-yl)-3-(cyclopropanecarboxamido)-1H-pyrazole-4-carboxamide

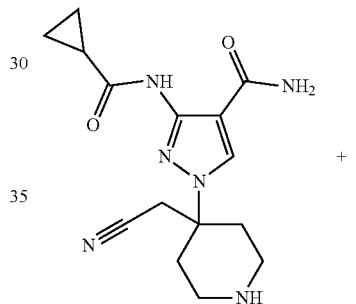

+

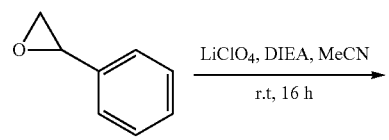

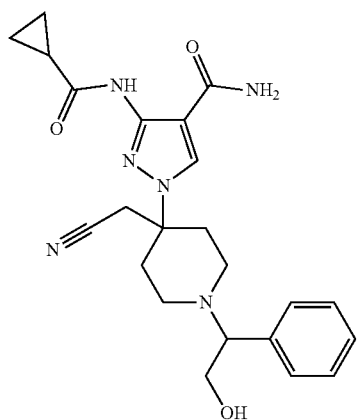

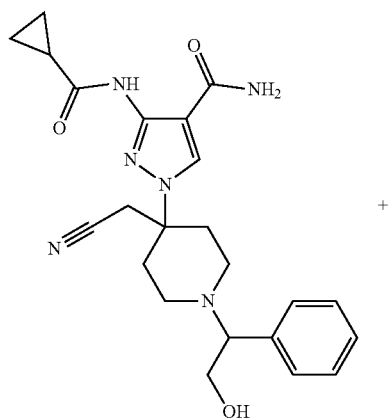

+

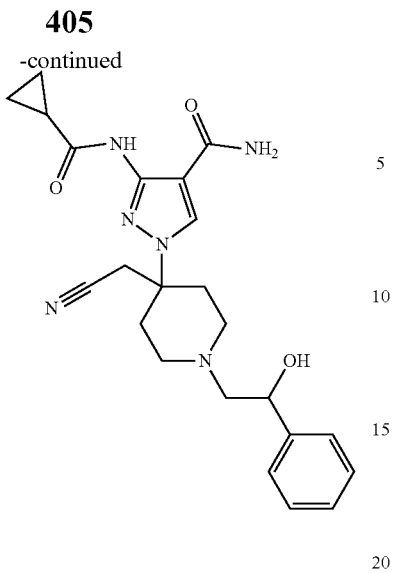

To a solution of 1-(4-(cyanomethyl)piperidin-4-yl)-3-(cyclopropanecarbox-amido)-1H-pyrazole-4-carboxamide (100 mg, 0.316 mmol) in acetonitrile (15 mL) was added 2-phenyloxirane (34.0 mg, 0.283 mmol), lithium perchlorate (30.0 mg, 0.282 mmol) and DIPEA (36.0 mg, 0.279 mmol). The reaction mixture was stirred for 16 h at room temperature and concentrated under reduced pressure. The residue was passed through a short pad of silica gel eluting with ethyl acetate:THF (85:15). The appropriate fractions were combined and concentrated under reduced pressure. The residue was further purified by Prep-HPLC with the following conditions: XBridge Prep C18 OBD Column, 19*150 mm, 5um; mobile phase, 10 mM NH$_4$HCO$_3$ aqueous solution and CH$_3$CN (7% CH$_3$CN up to 39% in 7 min); Detector, UV 254 nm to afford two fractions:

Example 19: The first fraction (8.3 mg) as a white solid, LC/MS (Method E, ESI): [M+H]$^+$=437, R$_T$=1.16 min. $^1$H NMR (400 MHz, CD$_3$OD): δ (ppm) 8.39 (s, 1 H), 7.35-7.27 (m, 5 H), 3.97-3.92 (m, 1 H), 3.82-3.78 (m, 1 H), 3.47-3.44 (m, 1 H), 3.07 (s, 2 H), 2.90-2.80 (m, 1 H), 2.68-2.66 (m, 1 H), 2.60-2.52 (m, 2 H), 2.40-2.30 (m, 1 H), 2.25-2.05 (m, 3 H), 1.85-1.75 (m, 1 H), 1.03-0.99 (m, 2 H), 0.96-0.91 (m, 2 H).

Example 20: The second fraction (10.5 mg) as a white solid. LC/MS (Method D, ESI): [M+H]$^+$=437, R$_T$=1.91 min. $^1$H NMR (400 MHz, CD$_3$OD): δ (ppm) 8.47 (s, 1 H), 7.39-7.31 (m, 4 H), 7.28-7.24 (m, 1 H), 4.82 (dd, J=9.2, 3.6 Hz, 1 H), 3.15 (s, 2 H), 2.91-2.89 (m, 1 H), 2.83-2.80 (m, 1 H), 2.66-2.60 (m, 3 H), 2.50-2.43 (m, 2 H), 2.34-2.25 (m, 1 H), 2.23-2.17 (m, 2 H), 1.85-1.70 (m, 1 H), 1.04-1.00 (m, 2 H), 0.97-0.92 (m, 2 H).

Example 21

(General Procedure N)

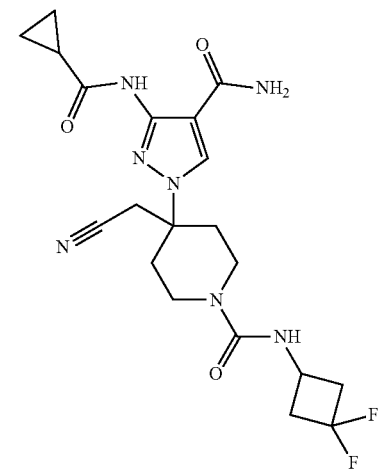 [SMILES: N#CCC1(n2cc(C(N)=O)c(NC(=O)C3CC3)n2)CCN(C(=O)NC2CC(F)(F)C2)CC1]

4-(4-Carbamoyl-3-(cyclopropanecarboxamido)-1H-pyrazol-1-yl)-4-(cyanomethyl)-N-(3,3-difluorocyclobutyl) piperidine-1-carboxamide

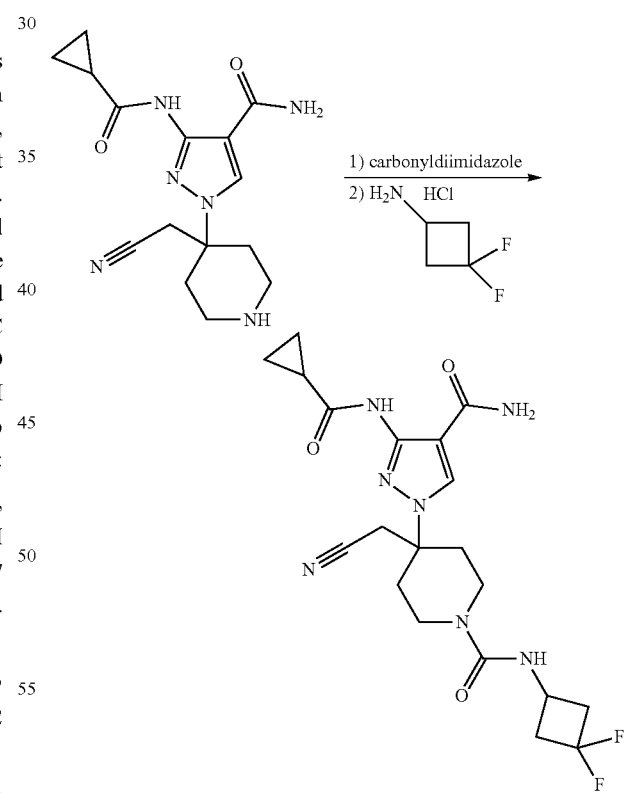

A solution of 1-[4-(cyanomethyl)-4-piperidyl]-3-(cyclopropanecarbonylamino)-pyrazole-4-carboxamide (25.0 mg, 0.0790 mmol), carbonyldiimidazole (14.1 mg, 0.0869 mmol), 1-methyl-2-pyrrolidinone (0.395 mL), and N,N-diisopropylethylamine (0.206 mL, 1.19 mmol) was stirred for 1 hr at room temperature. 3,3-difluorocyclobutanamine hydrochloride (113 mg, 0.790 mmol) was added, and the reaction was stirred at 80° C. for 16 hours. The mixture was purified directly and was purified by reverse phase chromatography ((20-60% acetonitrile: 0.10% aqueous NH₄OH solution in 15 min), yielding 4-[4-carbamoyl-3-(cyclopropanecarbonyl-amino)pyrazol-1-yl]-4-(cyanomethyl)-N-(3,3-difluorocyclobutyl) piperidine-1-carboxamide (3.8 mg, 11%) as a white solid. LC/MS (Method J, ESI): [M+H]⁺=450, R$_T$=3.25 min. ¹H NMR (400 MHz, DMSO-d₆): δ 10.15 (s, 1H), 8.48 (s, 1H), 7.47 (s, 1H), 7.23 (s, 1H), 6.91 (d, J=6.5 Hz, 1H), 4.03-3.86 (m, 1H), 3.75-3.58 (m, 2H), 3.13 (s, 2H), 3.01-2.87 (m, 2H), 2.87-2.73 (m, ₂H), 2.69-2.38 (m, 2H), 2.40-2.26 (m, 2H), 1.99-1.82 (m, 2H), 0.94 (d, J=6.9, 5.7 Hz, 1H), 0.80 (d, J=6.4 Hz, 4H).

Example 186

(General Procedure O)

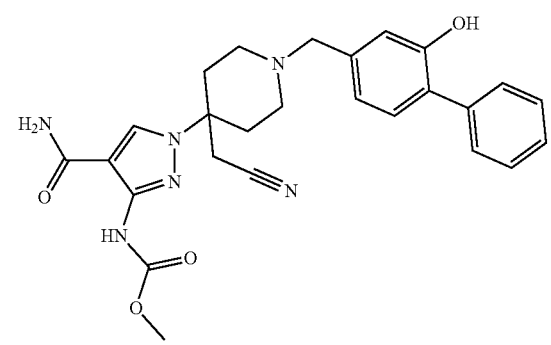 [SMILES: COC(=O)Nc1nn(C2(CC#N)CCN(Cc3ccc(-c4ccccc4)c(O)c3)CC2)cc1C(N)=O]

Methyl (4-carbamoyl-1-(4-(cyanomethyl)-1-((2-hydroxy-[1,1'-biphenyl]-4-yl) Methyl)piperidin-4-yl)-1H-pyrazol-3-yl)carbamate

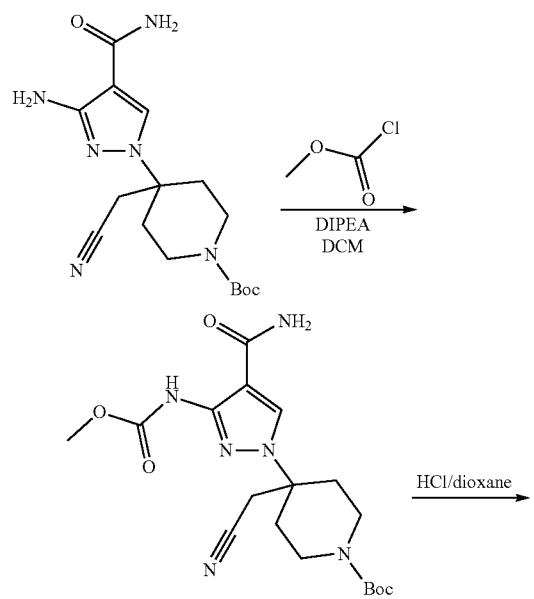

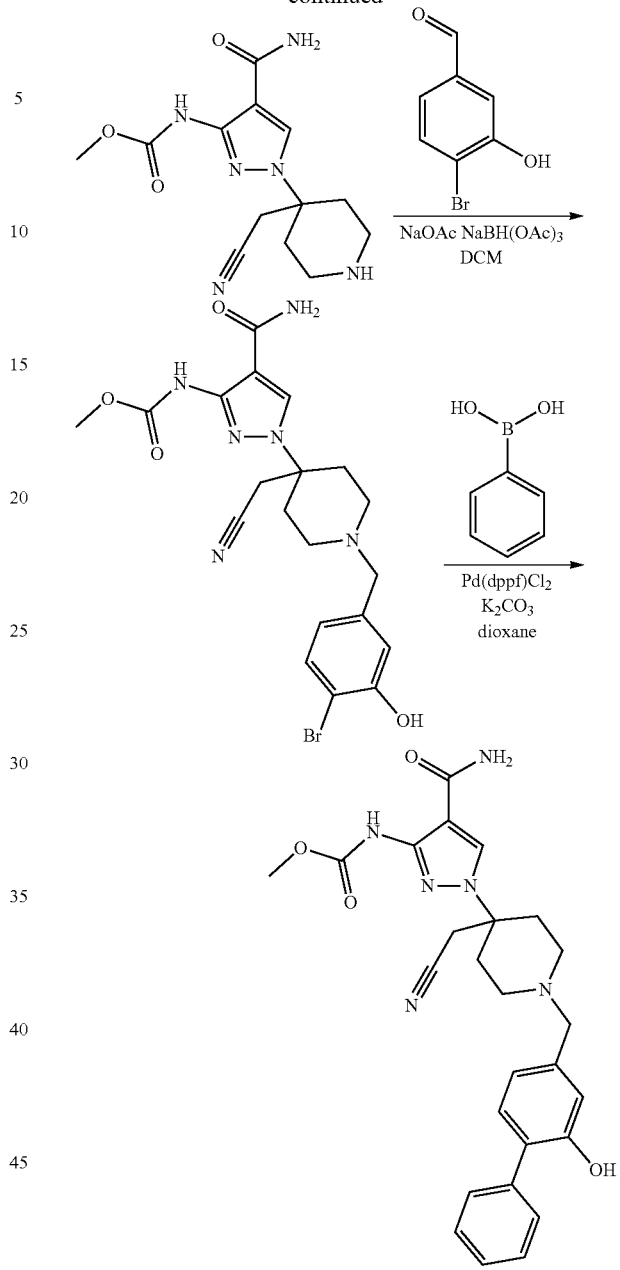

A solution of tert-butyl 4-(3-amino-4-carbamoyl-1H-pyrazol-1-yl)-4-(cyanomethyl) piperidine-1-carboxylate (300 mg, 0.861 mmol), DIPEA (222 mg, 1.72 mmol) in dichloromethane (8.00 mL) was stirred for 30 min at 0° C. Methyl chloroformate (121 mg, 1.28 mmol) was added dropwise to the resulting mixture. The reaction mixture was allowed to warm to room temperature and stirred for 3 days. Water was added and the resulting solution was extracted with ethyl acetate (3×). The combined organic phase was washed with water and brine, dried over anhydrous sodium sulfate and concentrated under reduced pressure. The residue was purified by flash chromatography on silica gel eluting with dichloromethane/methanol (90:10). The appropriate fractions were combined and concentrated under reduced pressure to afford 164 mg (47%) of tert-butyl 4-[4-carbamoyl-3-[(methoxycarbonyl)amino]-1H-pyrazol- 1-yl]-4-(cyanomethyl) piperidine-1-carboxylate as a white solid. TLC: Rf=0.4; PE/EA=1/1.

A mixture of tert-butyl 4-[4-carbamoyl-3-[(methoxycarbonyl)amino]-1H-pyrazol-1-yl]-4-(cyanomethyl) piperidine-1-carboxylate (164 mg, 0.404 mmol) and HCl/dioxane (4 M, 10 ml) was stirred for 3 h at room temperature. The resulting mixture was concentrated under reduced pressure to afford the HCl salt of methyl N-[4-carbamoyl-1-[4-(cyanomethyl) piperidin-4-yl]-1H-pyrazol-3-yl]carbamate (176 mg) as a white solid.

A mixture of methyl N-[4-carbamoyl-1-[4-(cyanomethyl) piperidin-4-yl]-1H-pyrazol-3-yl]carbamate HCl salt (176 mg), 4-bromo-3-hydroxybenzaldehyde (230 mg, 1.14 mmol), NaOAc (47.2 mg, 0.575 mmol), NaBH(OAc)$_3$ (243 mg, 1.15 mmol) in dichlromethane (8 mL) was stirred overnight at room temperature. Water and ethyl acetate were added and phases were separated. The organic layer was washed with water and brine, dried over anhydrous sodium sulfate, filtered and concentrated under reduced pressure. The resultant residue was purified by flash chromatography on silica gel eluting with dichloromethane/methanol (90:10). The appropriate fractions were combined and concentrated under reduced pressure to afford 169 mg (60%) of methyl N-(1-[1-[(4-bromo-3-hydroxyphenyl)methyl]-4-(cyanomethyl)piperidin-4-yl]-4-carbamoyl-1H-pyrazol-3-yl) carbamate as a white solid. TLC: Rf=0.4; MeOH/DCM=1/10.

To a 35 mL microwave reaction vessel was placed ethyl N-(1-[1-[(4-bromo-3-hydroxyphenyl) methyl]-4-(cyanomethyl)piperidin-4-yl]-4-carbamoyl-1H-pyrazol-3-yl) carbamate (169 mg, 0.334 mmol), phenylboronic acid (63.1 mg, 0.518 mmol), Pd(dppf)Cl$_2$ (28.1 mg, 0.0380 mmol,), potassium carbonate (95.2 mg, 0.689 mmol), water (1.50 mL) and dioxane (7.00 mL). The reaction vessel was then degassed and charged with nitrogen 3 times. The resulting mixture was heated for 2 h at 80° C. in an oil bath and allowed to cool to room temperature. The resulting mixture was diluted with water and extracted with ethyl acetate (×2). The combined organic phase was washed with water and brine, dried over sodium sulfate, filtered and concentrated under reduced pressure. The residue was purified by flash chromatography on silica gel eluting with dichloromethane/methanol (90:10). The appropriate fractions were combined and concentrated under reduced pressure. The crude product was further purified by Prep-HPLC with the following conditions Column: XBridge Prep C18 OBD Column, 5 um,19*150 mm; mobile phase, Water (0.05% NH$_3$H$_2$O) and ACN (25% ACN up to 40% in 11 min); Detector, UV 220, 254 nm to afford 27.5 mg (17%) of methyl N-[4-carbamoyl-1-[4-(cyanomethyl)-1-[(3-hydroxy-4-phenylphenyl) methyl]piperidin-4-yl]-1H-pyrazol-3-yl]carbamate as a white solid. LC/MS (Method F, ESI): [M+H]$^+$=489.2, R$_T$=1.35. $^1$H NMR (400 MHz, CD$_3$OD): δ (ppm) 8.45 (s, 1H), 7.55 (dd, J=8.4, 1.2 Hz, 2H), 7.39 (dd, J=8.4, 7.6 Hz, 2H), 7.31-7.26 (m, 1H), 7.22 (d, J=7.6 Hz, 1H), 6.90 (d, J=1.6 Hz, 1H), 6.89 (dd, J=7.6, 1.6 Hz, 1H), 3.80 (s, 3H), 3.48 (s, 2H), 3.15 (s, 2H), 2.79-2.76 (m, 2H), 2.63-2.60 (m, 2H), 2.29-2.21 (m, 2H), 2.18-2.15 (m, 2H).

Example 210 & 211

(General Method P)

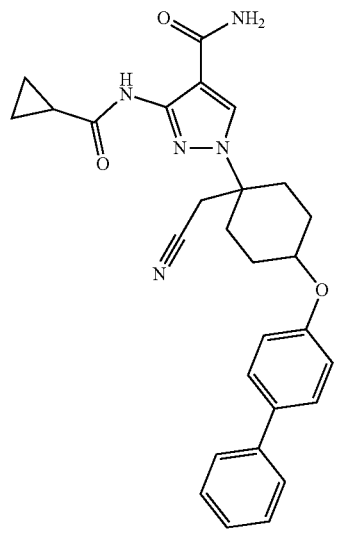

Isomer 1

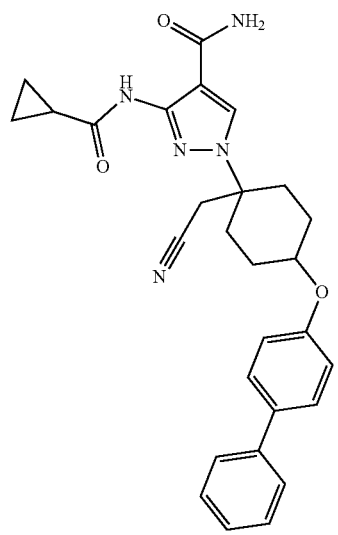

Isomer 2

1-(4-([1,1'-Biphenyl]-4-yloxy)-1-(cyanomethyl)cyclohexyl)-3-(cyclopropanecarboxamido)-1H-pyrazole-4-carboxamide

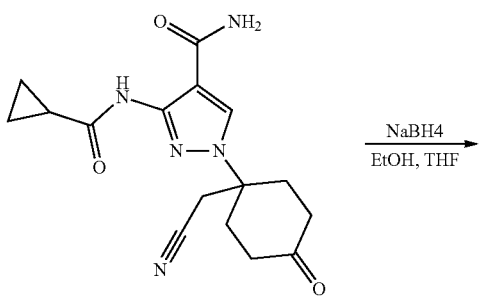

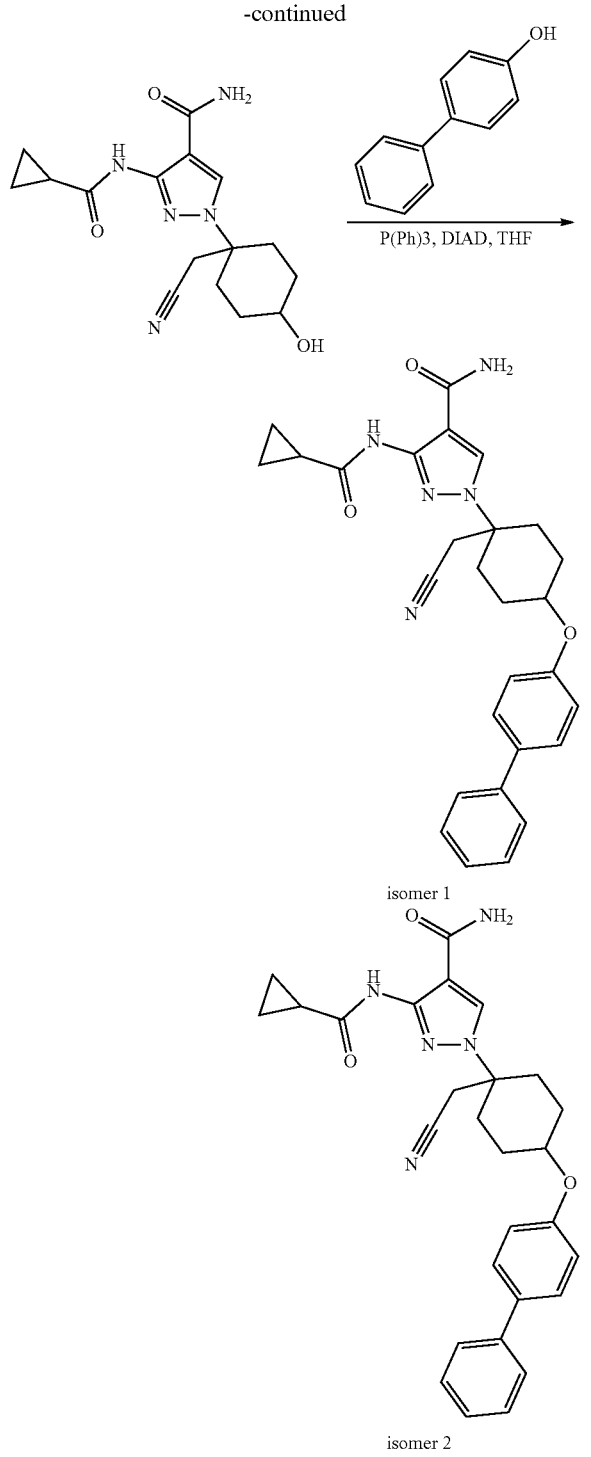

isomer 1 isomer 2

To a solution of 1-(1-(cyanomethyl)-4-oxocyclohexyl)-3-(cyclopropanecarbox-amido)-1H-pyrazole-4-carboxamide (500 mg, 1.51 mmol) in tetrahydrofuran (9.0 mL) and ethanol (3.0 mL) was added NaBH₄ (115 mg, 3.04 mmol). The resulting solution was stirred for 4 h at room temperature. The reaction was then quenched by the addition of water (1.0 mL) and concentrated under reduced pressure. The residue was partitioned between water and EtOAc. The organic layer was washed with brine, dried over sodium sulfate, concentrated under reduced pressure. The residue was purified by flash chromatography on silica gel eluting with dichloromethane/methanol (90/10). The appropriate fractions were combined and concentrated under reduced pressure to afford 475 mg (94%) of 1-(1-(cyanomethyl)-4-hydroxycyclohexyl)-3-(cyclopropanecarboxamido)-1H-pyrazole-4-carboxamide as a yellow solid. TLC: R$_f$=0.3; PE/EA=1/1.

To a solution of 1-(1-(cyanomethyl)-4-hydroxycyclohexyl)-3-(cyclopropane-carboxamido)-1H-pyrazole-4-carboxamide (400 mg, 1.20 mmol) in tetrahydrofuran (20.0 mL) was added 4-phenylphenol (308 mg, 1.81 mmol), PPh₃ (475 mg, 1.81 mmol) and DIAD (366 mg, 1.81 mmol). The resulting solution was stirred overnight at room temperature then concentrated under reduced pressure. The residue was purified by flash chromatography on silica gel eluting with dichloromethane/methanol (97/3). The appropriate fractions were combined and concentrated under reduced pressure to obtain two fractions with the same mass ion:

Undesired isomer: 4.60 mg (1%) of 1-(4-([1,1'-biphenyl]-4-yloxy)-1-(cyanomethyl) cyclohexyl)-3-(cyclopropanecarboxamido)-1H-pyrazole-4-carboxamide (isomer 1) as a white solid., LC/MS (Method J, ESI): [M+H]⁺=484.4, R$_T$=3.31 min; ¹H NMR (400 MHz, CD₃OD): δ (ppm) 8.52 (s, 1H), 7.56 (dd, J=7.6, 1.6 Hz, 2H), 7.54 (d, J=8.8 Hz, 2H), 7.41 (dd, J=8.0, 7.6 Hz, 2H), 7.31-7.27 (m, 1H), 7.02 (d, J=8.8 Hz, 2H), 4.60-4.50 (m, 1H), 3.17 (s, 2H), 2.80-2.65 (m, 2H), 2.13-2.05 (m, 4H), 1.95-1.75 (m, 1H), 1.68-1.63 (m, 2H), 1.05-1.01 (m, 2H), 0.97-0.93 (m, 2H).

Desired isomer: 10.8 mg (2%) of 1-(4-([1,1'-biphenyl]-4-yloxy)-1-(cyanomethyl) cyclohexyl)-3-(cyclopropanecarboxamido)-1H-pyrazole-4-carboxamide (isomer 2) as a white solid. LC/MS (Method K, ESI): [M+H]⁺=484.3, R$_T$=1.90 min; ¹H NMR (400 MHz, CD₃OD): δ (ppm) 8.50 (s, 1H), 7.57 (d, J=8.8 Hz, 2H), 7.59-7.55 (dd, J=8.4, 1.6 Hz, 2H), 7.42 (dd, J=8.4, 7.6 Hz, 2H), 7.31-7.27 (m, 1H), 7.07 (d, J=8.8 Hz, ₂H), 4.68-4.58 (m, 1H), 3.14 (s, 2H), 2.56-2.52 (m, 2H), 2.35-2.29 (m, 2H), 2.04-2.00 (m, 2H), 1.95-1.85 (m, 3H), 1.05-0.1.01 (m, 2H), 0.98-0.92 (m, 2H).

Example 248

(General Procedure R)

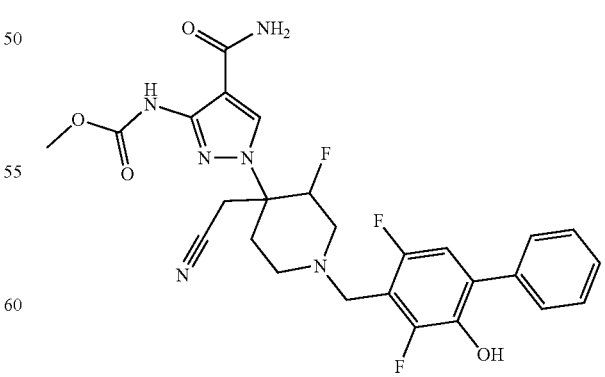

Methyl N-[4-carbamoyl-1-[4-(cyanomethyl)-1-[(2,6-difluoro-3-hydroxy-4-phenylphenyl) methyl]-3-fluoropiperidin-4-yl]-1H-pyrazol-3-yl]carbamate

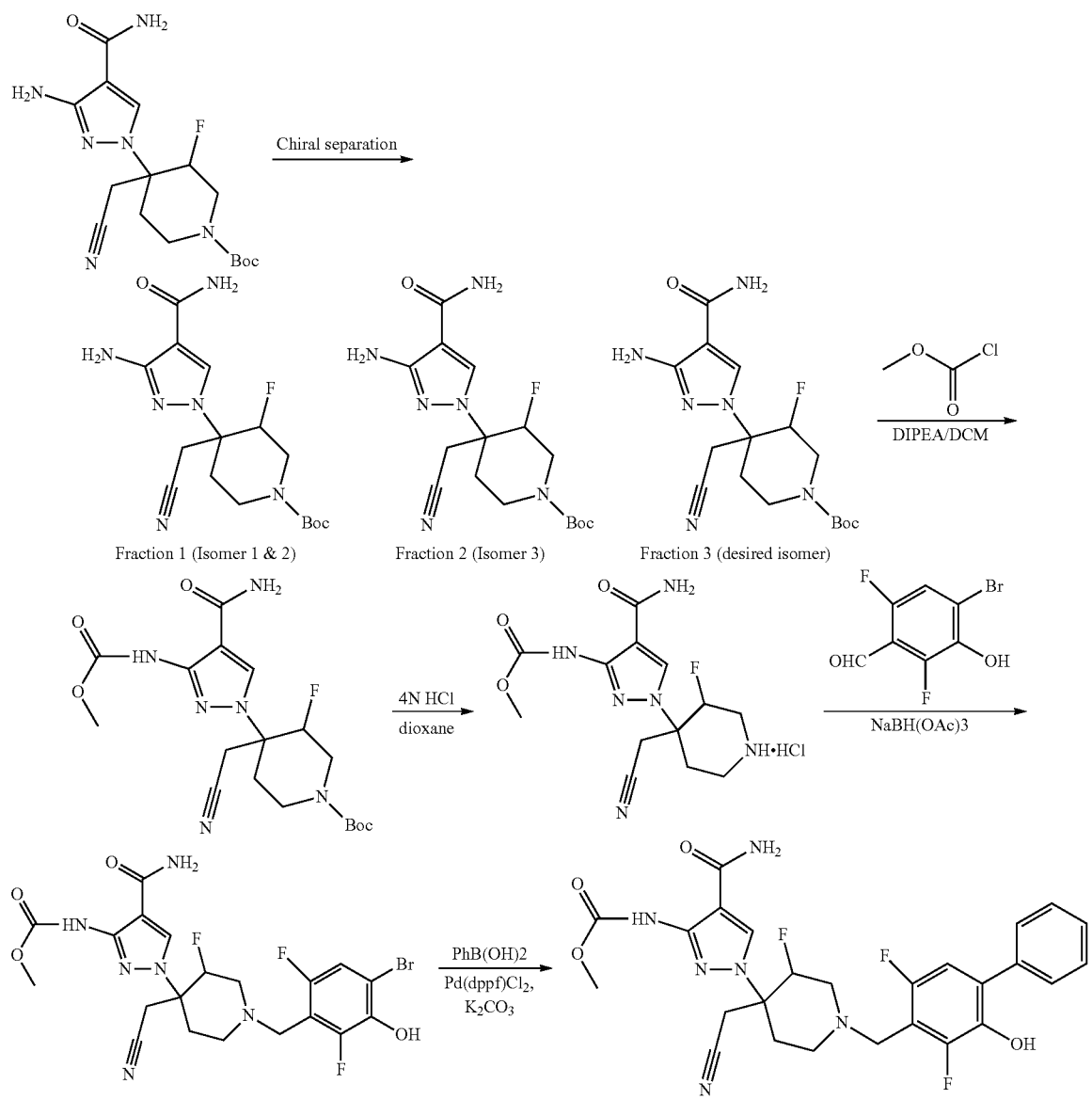

Racemic tert-butyl 4-(3-amino-4-carbamoyl-1H-pyrazol-1-yl)-4-(cyanomethyl)-3-fluoropiperidine-1-carboxylate (280g, mixture of 4 isomers) was separated by chiral SFC using the following conditions: Column: CHIRALPAK IA-SFC-02, 5 um, 5 cm*25 cm; Mobile Phase A: $CO_2$: 60, Mobile Phase B: ethanol: 40; Flow rate: 160 mL/min; Detector: 220 nm; $R_{T1}$=3.74 min (containing two peaks); $R_{T2}$=4.91 min; $R_{T3}$=6.65 min. Fractions from the third peak were collected and evaporated to afford 25.76 g (5.5%) of tert-butyl 4-(3-amino-4-carbamoyl-1H-pyrazol-1-yl)-4-(cyanomethyl)-3-fluoropiperidine-1-carboxylate as an off-white solid. LC/MS (Method N, ESI): [M+H]$^+$=367.2, $R_T$=1.07 min. $^1$H NMR (300 MHz, CD$_3$OD): δ (ppm) 8.17 (s, 1H), 5.08-5.01 (m, 1H), 4.28-4.20 (m, 2H), 3.42-3.36 (m, 3H), 3.32-3.17 (m, 1H), 2.46-2.42 (m, 1H), 2.15-2.10 (m, 1H), 1.46 (s, 9H).

To a solution of single desired isomer tert-butyl 4-(3-amino-4-carbamoyl-1H-pyrazol-1-yl)-4-(cyanomethyl)-3-fluoropiperidine-1-carboxylate (4.00 g, 10.9 mmol) in dichloromethane (35.0 mL) was added DIPEA (8.40 g, 65.0 mmol). The resulting solution was cooled to 0° C. in a water/ice bath before dropwise addition of methyl chloroformate (7.60 g, 80.4 mmol). The resulting solution was stirred overnight at room temperature. Water (30 mL) was added and the mixture extracted with ethyl acetate (3×20 mL). The combined organic layer was washed with water and brine, dried over anhydrous sodium sulfate and concentrated under reduced pressure. The residue was purified by silica gel column chromatography eluting with ethyl acetate/petroleum ether (70/30). Appropriate fractions were combined and evaporated to afford 3.9 g (84%) of tert-butyl 4-[4-carbamoyl-3-[(methoxycarbonyl)amino]-1H-pyrazol-1-yl]-4-(cyanomethyl)-3-fluoropiperidine-1-carboxylate as a light yellow solid. LC/MS (Method N, ESI): [M+H]$^+$=425.2, $R_T$=1.08 min.

A solution of tert-butyl 4-[4-carbamoyl-3-[(methoxycarbonyl)amino]-1H-pyrazol-1-yl]-4-(cyanomethyl)-3-fluoropiperidine-1-carboxylate (5.00 g, 11.78 mmol,) in HCl/dioxane (4.0 M, 30 ml) was stirred for 4 h at room temperature. The mixture was concentrated under reduced pressure and the resultant residue triturated with ethyl acetate. The precipitated solid was collected by filtration to afford 4.30 g of the hydrochloride salt of methyl N-[4-carbamoyl-1-[4-(cyanomethyl)-3-fluoropiperidin-4-yl]-1H-pyrazol-3-yl]carbamate as a light yellow solid. LC/MS (Method N, ESI): [M+H]$^+$=325.1, R$_T$=0.66 min.

To a solution of methyl N-4-carbamoyl-1-[4-(cyanomethyl)-3-fluoropiperidin-4-yl]-1H-pyrazol-3-ylcarbamate (320 mg, 0.987 mmol) in dichloromethane (25 mL) was added 4-bromo-2,6-difluoro-3-hydroxybenzaldehyde (300 mg, 1.26 mmol), DIPEA (150 mg, 1.16 mmol) and NaBH(OAc)$_3$ (600 mg, 2.83 mmol). The resulting solution was stirred overnight at room temperature and concentrated under reduced pressure. The residue was purified by silica gel column chromatography eluting with petroleum ether/ethyl acetate (50/50). The appropriate fractions were combined and concentrated under reduced pressure to afford 40 mg (6%) of methyl N-(1-[1-[(4-bromo-2,6- difluoro-3-hydroxyphenyl)methyl]-4-(cyanomethyl)-3-fluoropiperidin-4-yl]-4-carbamoyl-1H-pyrazol-3-yl) carbamate as a white solid. LC/MS (Method N, ESI): [M+H]$^+$=545.2, R$_T$=0.93 min.

A degassed mixture of methyl N-(1-[1-[(4-bromo-2,6-difluoro-3-hydroxyphenyl) methyl]-4-(cyanomethyl)-3-fluoropiperidin-4-yl]-4-carbamoyl-1H-pyrazol-3-yl) carbamate (20.0 mg, 0.037 mmol), phenylboronic acid (10.0 mg, 0.0820 mmol), Pd(dppf)Cl$_2$ (3 mg, 0.00367 mmol) and Cs$_2$CO$_3$ (24.0 mg, 0.0740 mmol) in dioxane (5.0 mL) and water (1.0 mL) was heated for 6 h at 60° C. then concentrated under reduced pressure. The residue was purified by flash chromatography on silica gel eluting with dichloromethane/methanol (95/5). The appropriate fractions were combined and concentrated under reduced pressure. The crude product was purified by Prep-HPLC with the following conditions: Column, XBridge Prep C18 OBD Column, 5 um,19*150 mm; mobile phase, Water (0.05% NH$_3$H$_2$O) and ACN (25% ACN up to 50% in 10 min); Detector, UV 220, 254 nm. Appropriate fractions were combined and evaporated to afford 3.90 mg (20%) of methyl N-[4-carbamoyl-1-[4-(cyanomethyl)-1-[(2,6-difluoro-3-hydroxy-4-phenylphenyl) methyl]-3-fluoropiperidin-4-yl]-1H-pyrazol-3-yl]carbamate as an off-white solid. LC/MS (Method K, ESI): [M+H]$^+$=543.3, R$_T$=1.36 min; $^1$H NMR (400 MHz, DMSO-d$_6$): δ (ppm) 9.54 (s, 1H), 9.49 (s, 1H), 8.44 (s, 1H), 7.63 (s, 1H), 7.60 (dd, J=6.8, 1.6 Hz, 2H), 7.44 (dd, J=8.4, 6.8, 2H), 7.39-7.34 (m, 1H), 7.30 (s, 1H), 7.04 (dd, J=10.4, 2.0 Hz, 1H), 5.00-4.88 (m, 1H), 3.69 (s, 2H), 3.64 (s, 3H), 3.36-3.33 (m, 1H), 3.22 (s, 2H), 2.95-2.80 (m, 2H), 2.75-2.60 (m, 2H), 2.06-2.03 (m, 1H).

Example 262

(General Method Q)

Isomer 2

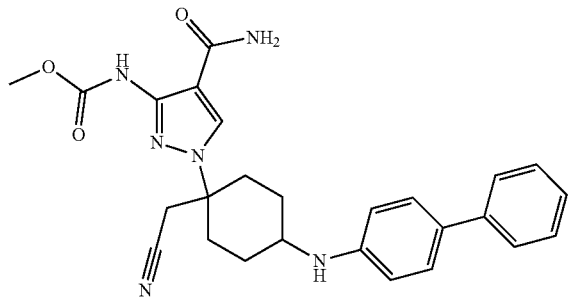

Methyl N-[4-carbamoyl-1-[1-(cyanomethyl)-4-[(2-phenylphenyl) amino]cyclohexyl]-1H-pyrazol-3-yl]carbamate

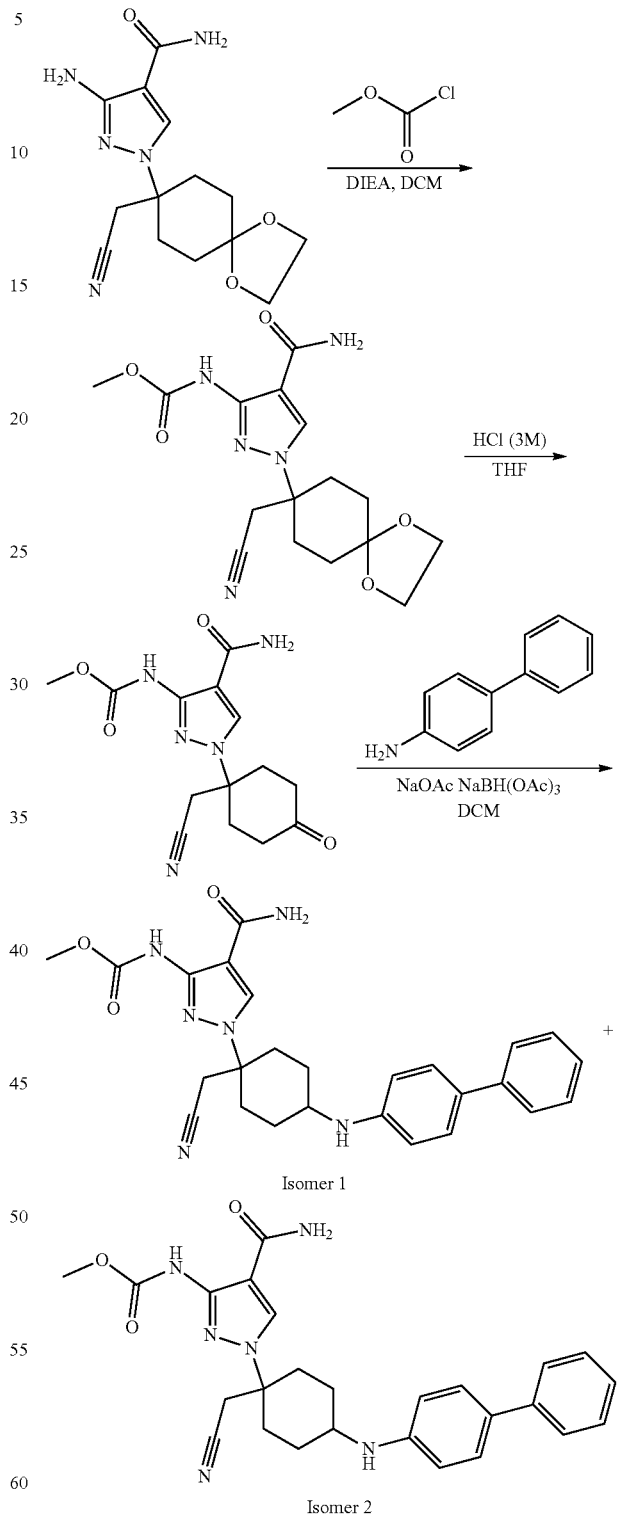

To a solution of 3-amino-1-[8-(cyanomethyl)-1,4-dioxaspiro[4.5]decan-8-yl]-1H-pyrazole-4-carboxamide (1.00 g, 3.27 mmol) and DIPEA (1.70 g, 13.1 mmol) in dichloromethane (10 mL) was added methyl chloroformate (2.45g, 22.5 mmol) at 0° C. The resulting solution was stirred for 15 min at 0° C. in a water/ice bath then allowed to warm to room temperature and stirred for 3 h. The reaction mixture was diluted with water and extracted with dichloromethane (3×). The combined organic phase was washed with brine, dried over sodium sulfate, concentrated under reduced pressure. The residue was purified by flash chromatography on silica gel eluting with dichloromethane/methanol (10/1). The appropriate fractions were combined and concentrated under reduced pressure to afford 1.82 g of methyl N-[4-carbamoyl-1-[8-(cyanomethyl)-1,4-dioxaspiro[4.5]decan-8-yl]-1H-pyrazol-3-yl]carbamate as a white solid. TLC: R =0.4; PE/EA=2/1.

A solution of methyl N-[4-carbamoyl-1-[8-(cyanomethyl)-1,4-dioxaspiro-[4.5]decan-8-yl]-1H-pyrazol-3-yl] carbamate (500 mg, 1.38 mmol) in tetrahydrofuran (5mL) and 3N HCl aqueous solution (5 mL) was stirred for 3 h at room temperature. The resulting mixture was concentrated under reduced pressure. The residue was partitioned between ethyl acetate and saturated sodium bicarbonate solution. The aqueous phase was extracted with ethyl acetate (3×). The combined organic layer was washed with brine, dried over sodium sulfate and concentrated under reduced pressure. The residue was purified by flash chromatography on silica gel eluting with dichloromethane/methanol (10/1). The appropriate fractions were combined and concentrated under reduced pressure to afford 150 mg (34%) of methyl N-[4-carbamoyl-1-[1-(cyanomethyl)-4-oxocyclohexyl]-1H-pyrazol-3-yl]carbamate as a yellow solid. TLC: $R_f$=0.3; PE/EA=2/1.

To a solution of methyl N-[4-carbamoyl-1-[1-(cyanomethyl)-4-oxocyclohexyl]-1H-pyrazol-3-yl]carbamate (300 mg, 0.940 mmol) in dichloromethane (10 mL) was added 4-phenylaniline (238 mg, 1.40 mmol), NaOAc (77.1 mg, 0.940 mmol) and NaBH(OAc)$_3$ (399 mg, 1.88 mmol). The resulting solution was stirred for 12 h at room temperature then concentrated under reduced pressure. The residue was purified by flash chromatography on silica gel eluting with dichloromethane/methanol (95/5). The appropriate fractions were combined and concentrated under reduced pressure. The crude product was further purified by Prep-HPLC with the following conditions: Column, XBridge Prep C18 OBD Column, 5 um, 19*150 mm; mobile phase, Waters (0.05% NH$_3$H$_2$O) and ACN (25% ACN up to 50% in 10 min); Detector, VU 220, 254 nm to afford two fractions with correct mass ion:

Isomer 1: 14.0 mg (3%) of methyl N-[4-carbamoyl-1-[1-(cyanomethyl)-4-[(2-phenylphenyl) amino]cyclohexyl]-1H-pyrazol-3-yl]carbamate (isomer1) as a white solid, LC/MS (Method F, ESI): [M+H]$^+$=473.3, $R_T$=1.61 min; $^1$H NMR (400 MHz, CD$_3$OD): δ (ppm) 8.52 (s, 1H), 7.52 (dd, J=8.4, 1.2 Hz, 2H), 7.41 (dd, J=6.4, 2.0 Hz, 2H), 7.36 (dd, J=8.4, 7.6 Hz, 2H), 7.24-7.20 (m, 1H), 6.73 (dd, J=6.4, 2.0 Hz, 2H), 3.80 (s, 3H), 3.50-3.46 (m, 1H), 3.08 (s, 2H), 2.85-2.81 (m, 2H), 2.11-1.96 (m, 4H), 1.32-1.23 (m, 2H).

Isomer 2, 1.40 mg of methyl N-[4-carbamoyl-1-[1-(cyanomethyl)-4-[(2-phenylphenyl) amino]cyclohexyl]-1H-pyrazol-3-yl]carbamate (isomer2) as a white solid. LC/MS (Method L, ESI): [M+H]$^+$=473.3, $R_T$=2.95 min; $^1$H NMR (400 MHz, CD$_3$OD): δ (ppm) 8.44 (s, 1H), 7.54 (dd, J=7.2, 1.6 Hz, 2H), 7.43 (d, J=8.8 Hz, 2H), 7.37 (dd, J=7.6, 7.2 Hz, 2H), 7.24-7.20 (m, 1H), 6.77 (d, J=8.8 Hz, 2H), 3.81 (s, 3H), 3.60-3.50 (m, 1H), 3.30 (s, 2H), 2.45-2.35 (m, 2H), 2.30-2.20 (m, 2H), 2.05-1.95 (m, 2H), 1.70-1.60 (m, 2H).

Example 294

(General Procedure S)

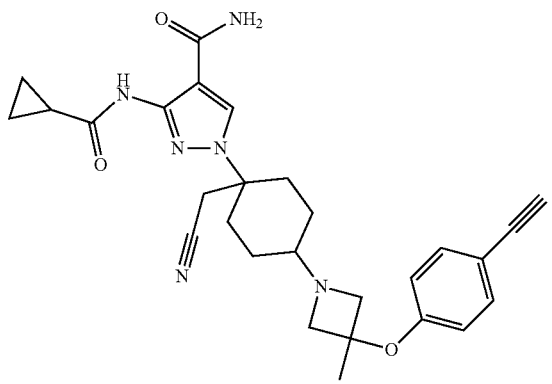 [SMILES: C#Cc1ccc(OC2(C)CN(C3CCC(CC#N)(n4cc(C(N)=O)c(NC(=O)C5CC5)n4)CC3)C2)cc1]

1-(1-(Cyanomethyl)-4-(3-(4-ethynylphenoxy)-3-methyl-azetidin-1-yl)cyclohexyl)-3-(cyclopropanecarboxamido)-1H-pyrazole-4-carboxamide

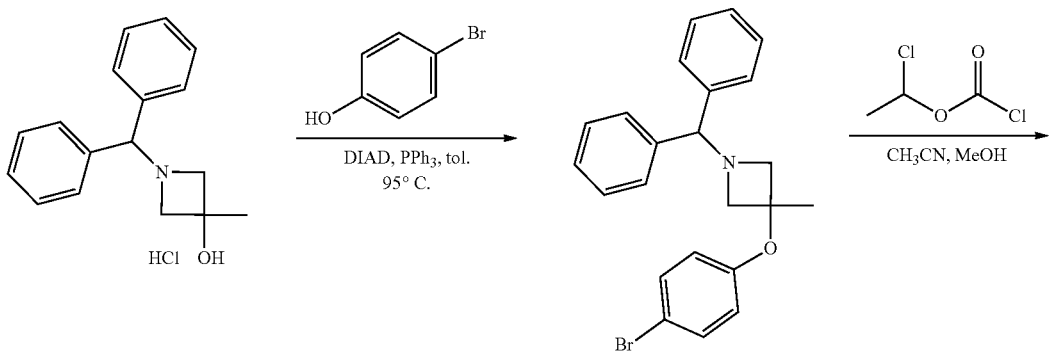

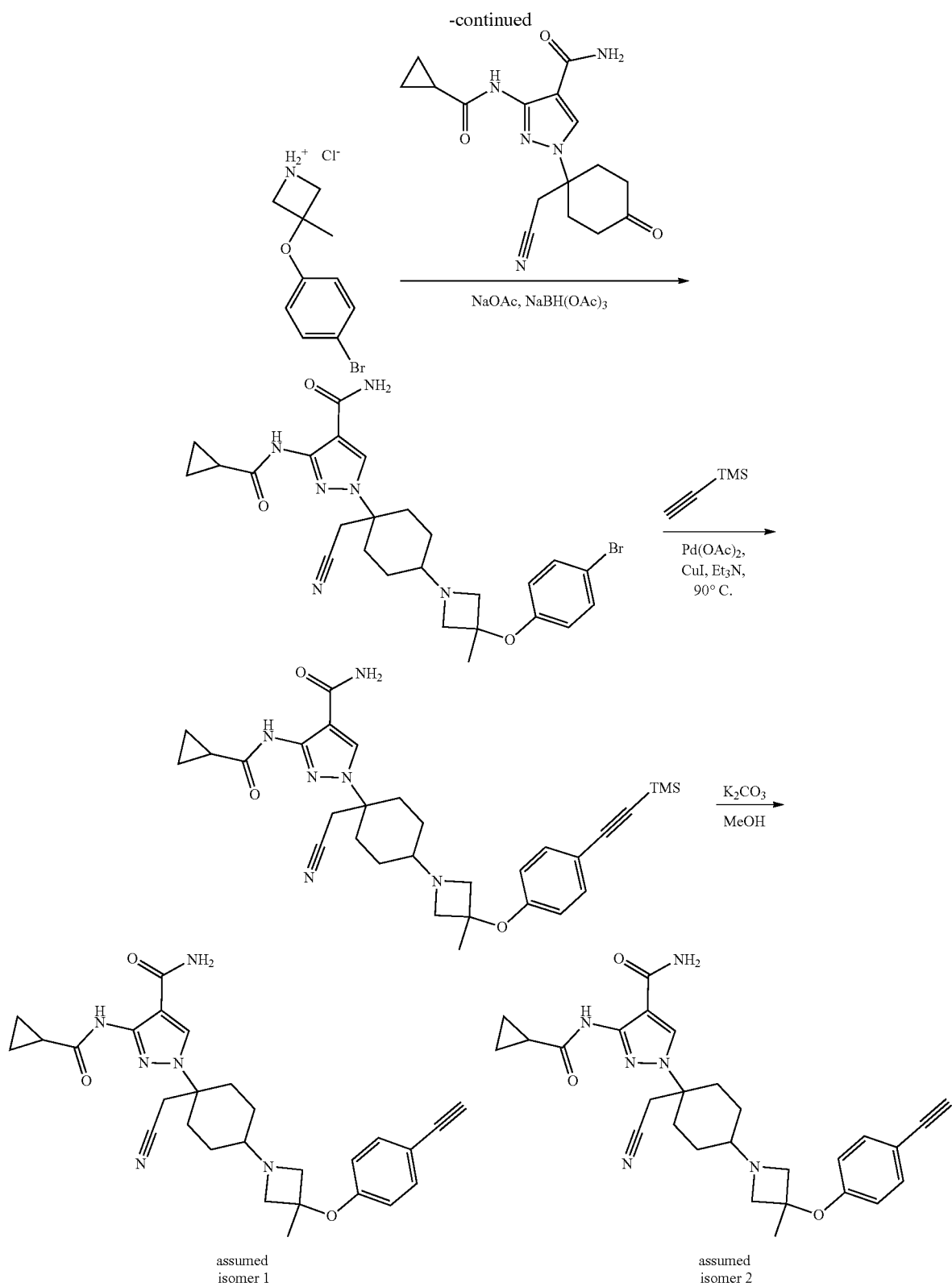

assumed isomer 1 assumed isomer 2

A mixture of 4-bromophenol (1.74 g, 10.0 mmol) and Ph$_3$P (2.33 g, 8.88 mmol) in toluene (15.0 mL) was heated for 10 min at 50° C. To the heated reaction mixture was added a solution of 1-(diphenylmethyl)-3-methylazetidin-3-ol (1.50 g, 5.92 mmol) and DIAD (1.80 g, 8.90 mmol) in toluene (15 mL). The resulting solution was heated overnight at 95° C., allowed to cool to room temperature and concentrated under reduced pressure. The residue was purified by flash chromatography on silica gel eluting with ethyl acetate/petroleum ether (1/20). The appropriate fractions were combined and concentrated under reduced pressure to afford 1.10 g (45%) of 3-(4-bromophenoxy)-1-(diphenylmethyl)-3-methylazetidine as an off-white solid. LC/MS (Method N, ESI): [M+H]$^+$=408.1; 410.1, R$_T$=1.18 min.

1-Chloroethyl chloroformate (4.25 g, 29.7 mmol) was added to a solution of 3-(4-bromophenoxy)-1-(diphenylmethyl)-3-methylazetidine (1.10 g, 2.694 mmol) in CH$_3$CN (20.0 mL). The resulting solution was stirred for 5 h at 50° C. Methanol (20.0 mL) was added and the mixture stirred for an additional 2 h at 50° C. The mixture was allowed to cool to ambient temperature and the solid removed by filtration. The filtrate was concentrated under reduced pressure to afford 760 mg of 3-(4-bromophenoxy)-3-methylazetidine hydrochloride as a yellow crude solid. LC/MS (Method N, ESI): [M+H]$^+$=242.1; 244.1, R$_T$=0.95 min.

A mixture of 1-(1-(cyanomethyl)-4-oxocyclohexyl)-3-(cyclopropane-carboxamido)-1H-pyrazole-4-carboxamide (500 mg, 1.51 mmol), 3-(4-bromophenoxy)-3-methylazetidine hydrochloride (509 mg, 1.82 mmol) and NaOAc (125 mg, 1.52 mmol) in dichloromethane (40.0 mL) was stirred overnight at room temperature before addition of NaBH(OAc)$_3$ (644 mg, 3.03 mmol). The resulting solution was stirred for an additional 4 h at room temperature then concentrated under reduced pressure. The residue was purified by flash chromatography on silica gel eluting with dichloromethane/methanol (15/1). The appropriate fractions were combined and concentrated under reduced pressure to afford 620 mg (74%) of 1-(4-(3-(4-bromo-phenoxy)-3-methylazetidin-1-yl)-1-(cyanomethyl) cyclohexyl)-3-(cyclopropane-carboxamido)-1H-pyrazole-4-carboxamide as a light yellow solid. LC/MS (Method N, ESI): [M+H]$^+$=555.2 & 557.2, R$_T$=1.02 min.

A degassed mixture of 1-(4-(3-(4-bromophenoxy)-3-methylazetidin-1-yl)-1-(cyanomethyl) cyclohexyl)-3-(cyclopropanecarboxamido)-1H-pyrazole-4-carboxamide (300 mg, 0.540 mmol), ethynyltrimethylsilane (529 mg, 5.38 mmol), Pd(OAc)$_2$ (24.0 mg, 0.107 mmol), P(t-Bu)$_3$.HBF$_4$ (63.0 mg, 0.217 mmol), CuI (21.0 mg, 0.110 mmol) and triethylamine (6.00 mL) in DMSO (2.00 mL) was heated for 6 h at 90° C. The reaction was allowed to cool to room temperature and quenched by the addition of water (50 mL). The resulting solution was extracted with ethyl acetate (3×) and the combined organic layer dried over anhydrous magnesium sulfate, filtered and concentrated under reduced pressure. The residue was purified by flash chromatography on silica gel eluting with dichloromethane/methanol (16/1). The appropriate fractions were combined and concentrated under reduced pressure to afford 200 mg (65%) of 1-(1-(cyanomethyl)-4-(3-methyl-3-(4-((trimethylsilyl) ethynyl) phenoxy)azetidin-1-yl)cyclohexyl)-3-(cyclopropanecarboxamido)-1H-pyrazole-4-carboxamide as a brown solid. LC/MS (Method N, ESI): [M+H]$^+$=573.4, R$_T$=1.17 min.

A mixture of 1-(1-(cyanomethyl)-4-(3-methyl-3-(4-((trimethylsilyl)-ethynyl) phenoxy)azetidin-1-yl)cyclohexyl)-3-(cyclopropanecarboxamido)-1H-pyrazole-4-carboxamide (200 mg, 0.349 mmol) and potassium carbonate (145 mg, 1.04 mmol) in methanol (10 mL) was stirred for 2 h at room temperature then concentrated under reduced pressure. The residue was purified by flash chromatography on silica gel eluting with dichloromethane/methanol (13/1). The appropriate fractions were combined and concentrated under reduced pressure. The mixture of isomers was separated by Prep-HPLC with the following conditions: Column, Kinetex EVO C18 Column, 5 um, 30*150 mm; mobile phase, Water (10 mmol/L NH$_4$HCO$_3$) and ACN (30% ACN up to 40% in 10 min); Detector, UV 254 nm to afford two fractions:

Isomer 1 (first fraction): 24.8 mg (14%) of 1-[1-(cyanomethyl)-4-[3-(4-ethynylphenoxy)-3-methylazetidin-1-yl]cyclohexyl]-3-cyclopropane-1H-pyrazole-3,4-diamido as a white solid. Isomer 1: LC/MS (Method M, ESI): [M+H]$^+$=501.3, R$_T$=2.15 min. $^1$H NMR (400 MHz, DMSO-d$_6$): δ (ppm) 10.18 (s, 1H), 8.43 (s, 1H), 7.53 (s, 1H), 7.37 (d, J=8.8 Hz, 2H), 7.23 (s, 1H), 6.71 (d, J=8.8 Hz, 2H), 4.03 (s, 1H), 3.45 (d, J=7.6 Hz, 2H), 3.07 (d, J=7.2 Hz, 2H), 3.01 (s, 2H), 2.50-2.45 (m, 3H), 2.15-2.05 (m, 1H), 1.80-1.65 (m, 4H), 1.53 (s, 3H), 0.95-0.85 (m, 2H), 0.85-0.75 (m, 4H).

Isomer, 21.4 mg (12%) of 1-[1-(cyanomethyl)-4-[3-(4-ethynylphenoxy)-3-methylazetidin-1-yl]cyclohexyl]-$_3$-cyclopropane-1H-pyrazole-3,4-diamido as a white solid. LC/MS (Method M, ESI): [M+H]$^+$=501.3, R$_T$=2.15 min. $^1$H NMR (400 MHz, DMSO-d$_6$): δ (ppm) 10.18 (s, 1H), 8.43 (s, 1H), 7.52 (s, 1H), 7.38 (d, J=8.4 Hz, 2H), 7.22 (s, 1H), 6.74 (d, J=8.8 Hz, 2H), 4.04 (s, 1H), 3.52 (d, J=7.6 Hz, 2H), 3.10 (d, J=7.2 Hz, 2H), 3.09 (s, 2H), 2.51-2.50 (m, 1H), 2.25-2.20 (m, 1H), 2.18-2.00 (m, 4H), 1.61 (s, $_3$H), 1.50-1.35 (m, 4H), 1.85-1.75 (m, 4H).

Example 298

(General Procedure T)

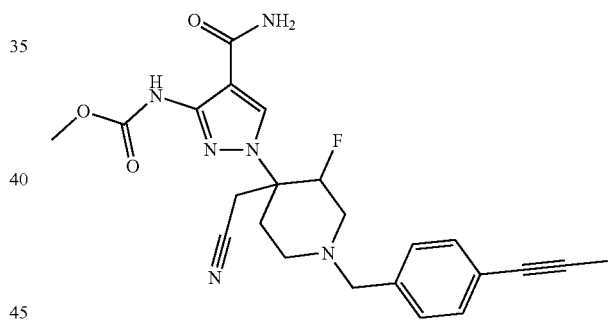

Methyl (4-carbamoyl-1-(4-(cyanomethyl)-3-fluoro-1-(4-(prop-1-yn-1-yl) benzyl)piperidin-4-yl)-1H-pyrazol-3-yl) carbamate

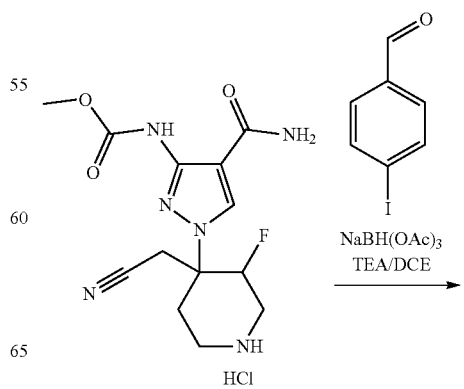

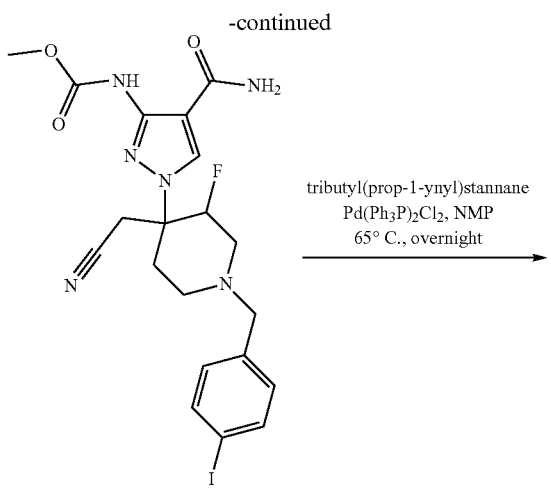

To a mixture of methyl (4-carbamoyl-1-(4-(cyanomethyl)-3-fluoropiperidin-4-yl)-1H-pyrazol-3-yl) carbamate hydrochloride (180 mg, 0.50 mmol) in 1,2-dichloroethane (3.0 ml) was added trimethylamine (0.21 mL, 1.50 mmol) and 4-iodobenzaldehyde (174 mg, 0.75 mmol). The reaction mixture was stirred for 10 mins at room temperature, and then NaBH(OAc)$_3$ (423 mg, 1.99 mmol) was added. The resulting reaction mixture was stirred overnight at room temperature. Water (20 mL) was added and the phases were separated. The aqueous phase was extracted with dichloromethane (2×). The combined organic layer was washed with water and brine, dried over anhydrous sodium sulfate and concentrated under reduced pressure. The residue purified by flash chromatography on silica gel eluting with dichloromethane/methanol (85/15). The appropriate fractions were combined and concentrated under reduced pressure to afford 105 mg (39%) of methyl (4-carbamoyl-1-(4-(cyanomethyl)-3-fluoro-1-(4-iodobenzyl) piperidin-4-yl)-1H-pyrazol-3-yl) carbamate as a white solid. LC/MS (Method P, ESI): [M+H]$^+$=541.2, R$_T$=1.14 min.

A degassed solution of methyl (4-carbamoyl-1-(4-(cyanomethyl)-3-fluoro-1-(4-iodobenzyl) piperidin-4-yl)-1H-pyrazol-3-yl)carbamate (105 mg, 0.194 mmol), bis(triphenylphosphine)palladium chloride (14 mg, 0.019 mmol), tributyl(prop-1-ynyl) stannane (99 mg, 0.292 mmol) in N-methyl-2-pyrrolidone (1 mL) was stirred at 65° C. for 18 h. The mixture was allowed to cool to room temperature; ethyl acetate was added the precipitated solid was removed by filtration through celite. The filtrate was washed with water and saturated aqueous sodium chloride solution. The organic phase was dried over magnesium sulfate, filtered, and concentrated. The residue was purified by silica gel chromatography eluting with 0 to 15% methanol in dichloromethane.

Appropriate fractions were combined and evaporated to afford methyl (4-carbamoyl-1- (4-(cyanomethyl)-3-fluoro-1-(4-(prop-1-yn-1-yl)benzyl)piperidin-4-yl)-1H-pyrazol-3-yl)carbamate (22 mg, 25%) as an orange solid. LC/MS (Method P, ESI): [M+H]$^+$=453.3, R$_T$=1.14 min; $^1$H NMR (400 MHz, DMSO-d$_6$) δ (ppm) 9.48 (s, 1H), 8.46 (s, 1H), 7.61 (s, 1H), 7.48 (s, 1H), 7.40-7.32 (m, 2H), 7.31-7.19 (m, 2H), 5.05-4.75 (m, 1H), 3.64 (s, 3H), 3.57 (s, 2H), 3.48-3.38 (m, 1H), 3.38-3.31 (m, 1H), 2.87-2.82 (m, 1H), 2.75-2.67 (m, 2H), 2.66-2.49 (m, 2H), 2.07-2.00 (m, 1H), 2.03 (s, 3H).

Example 299

(General Procedure U)

1-(4-(Cyanomethyl)-1-(4-(cyclopropylethynyl)benzyl)piperidin-4-yl)-3-(cyclopropanecarboxamido)-1H-pyrazole-4-carboxamide

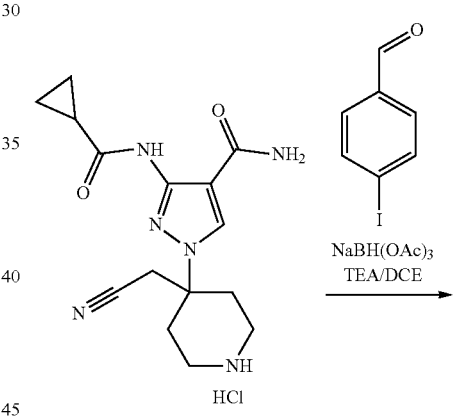

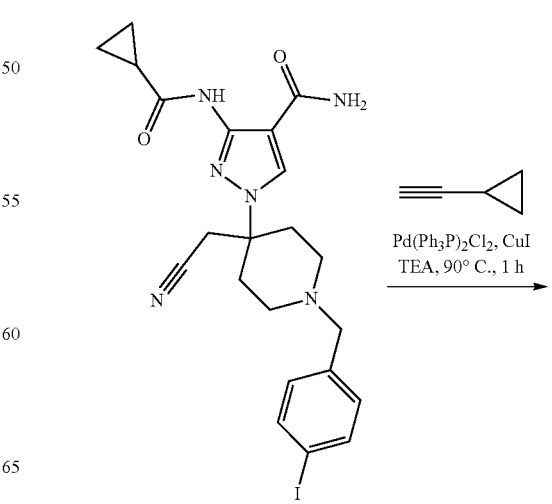

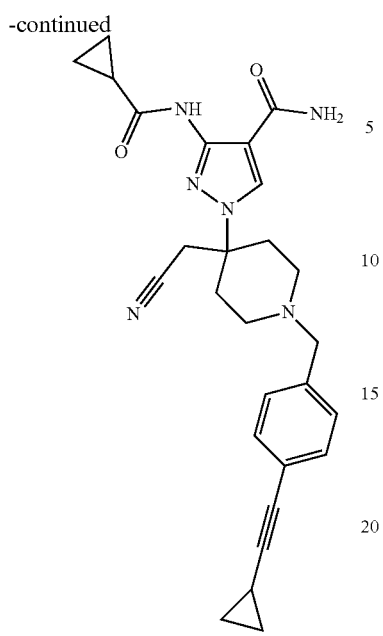

A mixture of 1-(4-(cyanomethyl)piperidin-4-yl)-3-(cyclopropanecarboxamido)-1H-pyrazole-4-carboxamide hydrochloride (1.00 g, 2.83 mmol), trimethylamine (1.19 mL, 8.5 mmol) and 4-iodobenzaldehyde (986 mg, 4.25 mmol) in 1,2-dichloroethane (15.0 ml) was stirred for 10 mins at room temperature before addition of NaBH(OAc)$_3$ (2.40 g, 11.34 mmol). The resulting reaction mixture was stirred overnight at room temperature. Water (50 mL) was added and the mixture was extracted with dichloromethane (3×). The combined organic layer was washed with water and brine, dried over anhydrous magnesium sulfate and concentrated under reduced pressure. The residue purified by flash chromatography on silica gel eluting with dichloromethane/methanol (85/15). The appropriate fractions were combined and concentrated under reduced pressure to afford 570 mg (38%) of 1-(4-(cyanomethyl)-1-(4-iodobenzyl)-piperidin-4-yl)-3-(cyclopropanecarboxamido)-1H-pyrazole-4-carboxamide as a white solid. LC/MS (Method P, ESI): [M+H]$^+$=533.1, R$_T$=0.94 min.

A degassed solution of 1-(4-(cyanomethyl)-1-(4-iodobenzyl)piperidin-4-yl)-3-(cyclopropanecarboxamido)-1H-pyrazole-4-carboxamide (50 mg, 0.094 mmol), bis(triphenylphosphine)palladium chloride (7 mg, 0.0094 mmol), copper(I) iodide (2 mg, 0.0094 mmol), ethynylcyclopropane (10 mg, 0.14 mmol) and trimethylamine (0.2 mL, 1.43 mmol) in N-methyl-2-pyrrolidone (0.4 mL) was stirred at 90° C. for 1 h. The mixture was allowed to cool to room temperature, ethyl acetate was added and the precipitated solid removed by filtration through celite. The filtrate was washed with water and saturated aqueous sodium chloride solution, dried over magnesium sulfate, filtered, and concentrated. The residue was purified by silica gel column chromatography eluting with 0 to 15% methanol in dichloromethane. Appropriate fractions were combined and evaporated to afford 30 mg (67%) of 1-(4-(cyanomethyl)-1-(4-(cyclopropyl-ethynyl) benzyl)-piperidin-4-yl)-3-(cyclopropanecarboxamido)-1H-pyrazole-4-carboxamide as a white solid. LC/MS (Method P, ESI): [M+H]$^+$=471.2, R$_T$=1.13 min; $^1$H NMR (400 MHz, DMSO-d$_6$) δ (ppm) 10.13 (s, 1H), 8.47 (s, 1H), 7.48 (s, 1H), 7.29 (d, J=8.2 Hz, 2H), 7.23 (d, J=8.1 Hz, 2H), 3.40 (s, 2H), 3.17 (d, J=5.3 Hz, 0H), 3.06 (s, 2H), 2.60 (d, J=8.8 Hz, 2H), 2.45-2.36 (m, 2H), 2.06-1.93 (m, 3H), 1.52 (tt, J=8.3, 5.0 Hz, 1H), 0.92-0.82 (m, 2H), 0.86-0.76 (m, 4H), 0.77-0.66 (m, 2H).

Example 301

(General Procedure V)

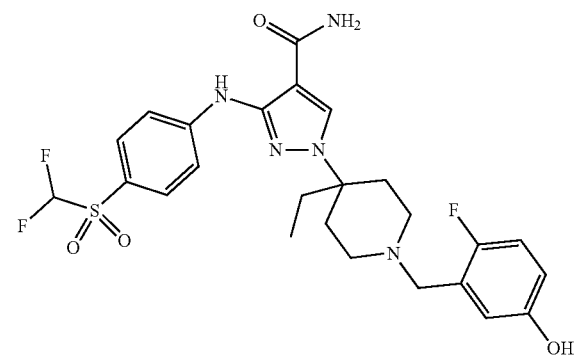 [SMILES: CCC1(n2cc(C(N)=O)c(Nc3ccc(S(=O)(=O)C(F)F)cc3)n2)CCN(Cc2cc(O)ccc2F)CC1]

3-((4-((Difluoromethyl)sulfonyl)phenyl)amino)-1-(4-ethyl-1-(2-fluoro-5-hydroxybenzyl) piperidin-4-yl)-1H-pyrazole-4-carboxamide

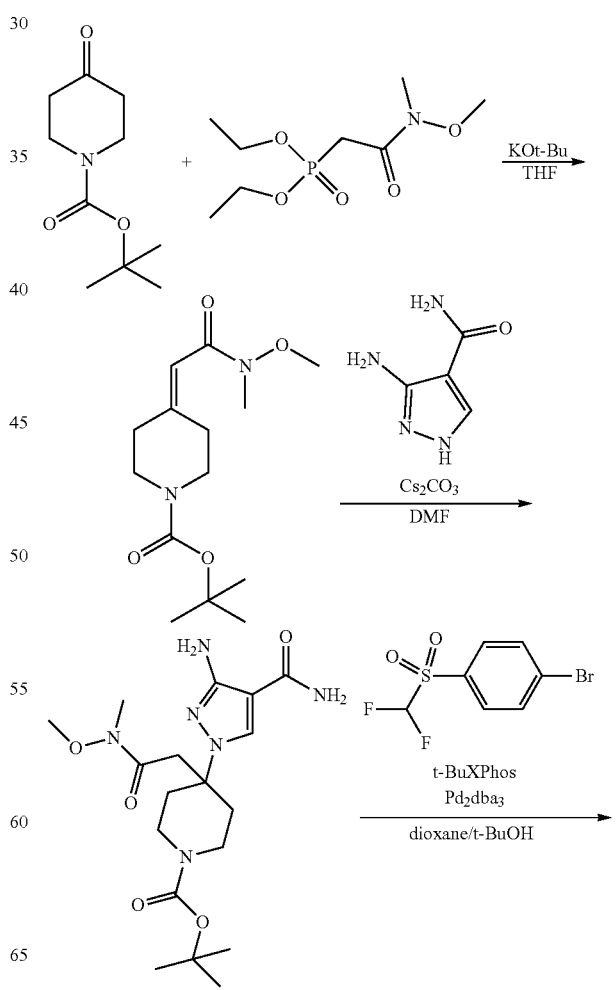

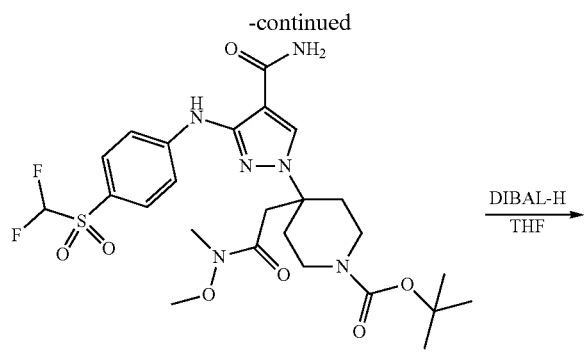
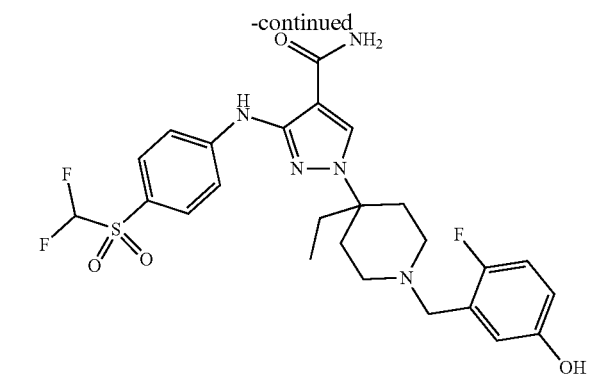
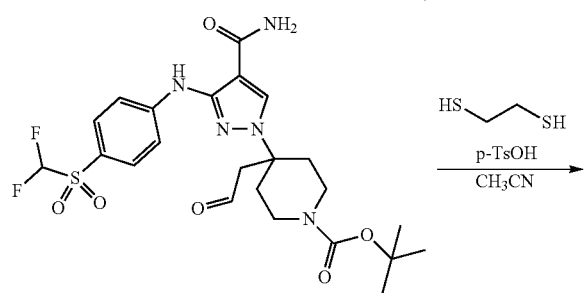
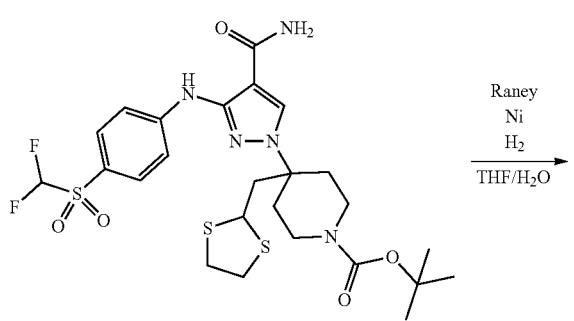
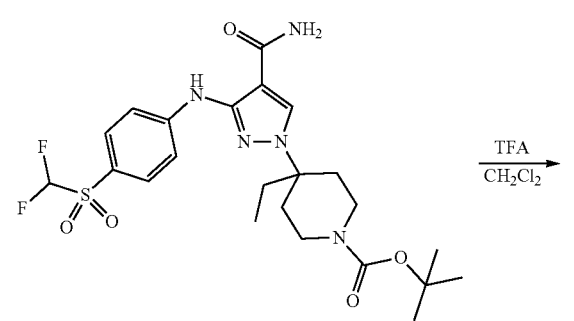
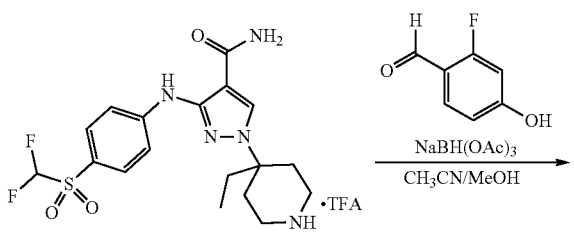

To a cooled (0° C.) solution of potassium tert-butoxide (3.55 g, 31.6 mmol, 1.05 equiv) in tetrahydrofuran (50 mL) was added 2-diethoxyphosphoryl-N-methoxy-N-methyl-acetamide (7.92 g, 33.1 mmol). The reaction mixture was allowed to warm to room temperture over 30 mins then stirred for an additional 1 h at room temperature. The mixture was cooled to −78° C. and a solution of tert-butyl 4-oxopiperidine-1-carboxylate (6 g, 30.1 mmol) in tetrahydrofuran (50 mL) was added. The mixture was allowed to slowly warm to room temperature and allowed to stir for 16 h. Water (250 mL) was added and the mixture extracted with isopropyl acetate (3×100 mL). The combined organic layer was washed with water and brine, dried over sodium sulfate and concentrated under reduced pressure to afford tert-butyl 4-[2-[methoxy(methyl)amino]-2-oxo-ethylidene]piperidine-1-carboxylate as a white solid that was used in the next step without further purification.

A suspension of 5-amino-1H-pyrazole-4-carboxamide hemisulfate (6.31 g, 36 mmol) and tert-butyl 4-[2-[methoxy(methyl)amino]-2-oxo-ethylidene]piperidine-1-carboxylate (8.53 g, 30 mmol) in N,N-dimethylformamide (100 mL) was treated with cesium carbonate (21.5 g, 66 mmol) then stirred 16 h at room temperature. The precipitated solid was removed by filtration through Celite and the filtrate concentrated under reduced pressure. The residue was purified by flash chromatography on silica gel eluting with a gradient of 0 to 10% methanol in dichloromethane. The appropriate fractions were combined and concentrated under reduced pressure to afford 600 mg (5%) of tert-butyl 4-(3-amino-4-carbamoyl-pyrazol-1-yl)-4-[2-[methoxy(methyl)amino]-2-oxo-ethyl]piperidine-1-carboxylate as a white solid.

A degassed mixture of tert-butyl 4-(3-amino-4-carbamoyl-pyrazol-1-yl)-4-[2-[methoxy (methyl)amino]-2-oxo-ethyl]piperidine-1-carboxylate (600 mg, 1.46 mmol), 1-bromo-4-(difluoromethylsulfonyl) benzene (594 mg, 2.19 mmol), potassium phosphate tribasic (640 mg, 2.92 mmol), 2-di-tert-butylphosphino-2',4',6'-triisopropylbiphenyl (32 mg, 0.073 mmol, 0.05 equiv) and tris(dibenzylideneacetone) dipalladium(0) (17 mg, 0.018 mmol, 0.0125 equiv) in 1,4-dioxane (20 mL) and tert-butyl alcohol (5 mL) was heated for 16 h at 80° C. The mixture was allowed to cool to room temperature and the precipitated solid removed by filtration through Celite. The filtrate was concentrated under reduced pressure and the residue was purified by flash chromatography on silica gel eluting with a gradient of 0 to 5% methanol in dichloromethane. The appropriate fractions were combined and concentrated under reduced pressure to afford 600 mg (68%) of tert-butyl 4-[4-carbamoyl-3-[4-(difluoromethylsulfonyl)anilino]pyrazol-1-yl]-4-[2-[methoxy (methyl)amino]-2-oxo-ethyl]piperidine-1-carboxylate as a white solid.

Diisobutylaluminum hydride (1M in heptane, 10 mL, 10 mmol) was added to a cooled (−78° C.) solution of tert-butyl 4-[4-carbamoyl-3-[4-(difluoromethyl-sulfonyl) anilino] pyrazol-1-yl]-4-[2-[methoxy(methyl)amino]-2-oxo-ethyl] piperidine-1-carboxylate (600 mg, 1.0 mmol) in tetrahydrofuran (10 mL). The mixture was allowed to stir for 30 mins at −78° C. then quenched with 5% aqueous citric acid (50 mL) and saturated sodium sulfate (50 mL). iPrOAc (100 mL) was added and the precipitated solid was removed by filtration through Celite. The layers of the filtrate were separated, the organic extract was washed with brine; the aqueous layer was extracted with dichloromethane (100 mL). The combined organic layer was dried over sodium sulfate, filtered, and concentrated under reduced pressure to afford 620 mg of tert-butyl 4-[4-carbamoyl-3-[4-(difluoromethylsulfonyl) anilino]pyrazol-1-yl]-4-(2-oxoethyl)piperidine-1-carboxylate as a white solid which was used without further purification.

To a solution of tert-butyl 4-[4-carbamoyl-3-[4-(difluoromethylsulfonyl)-anilino]pyrazol-1-yl]-4-(2-oxoethyl)piperidine-1-carboxylate (270 mg, 0.50 mmol) in acetonitrile (3 mL) was added 1,2-ethanedithiol (0.41 mL, 470 mg, 5.0 mmol) followed by p-toluenesulfonic acid monohydrate (10 mg, 0.05 mmol). The mixture was stirred at room temperature for 16 h then concentrated under reduced pressure. The residue was purified by flash chromatography on silica gel eluting with a gradient of 0 to 5% methanol in dichloromethane. The appropriate fractions were combined and concentrated under reduced pressure to afford 220 mg (71%) of tert-butyl 4-[4-carbamoyl-3-[4-(difluoromethylsulfonyl) anilino]-pyrazol-1-yl]-4-(1,3-dithiolan-2-ylmethyl)piperidine-1-carboxylate as a white solid.

To a solution of tert-butyl 4-[4-carbamoyl-3-[4-(difluoromethylsulfonyl)anilino]-pyrazol-1-yl]-4-(1,3-dithiolan-2-ylmethyl) piperidine-1-carboxylate (220 mg, 0.36 mmol) in tetrahydrofuran (4 mL) was added a slurry of Raney nickel (Raney 2800, approx. 50% (w/v) in water, 1 mL). The mixture was stirred under a blloon of hydrogen at RT for 1 h. The solid was removed by filtration through Celite and the filtrate concentrated under reduced pressure. The residue was purified by flash chromatography on silica gel eluting with a gradient of 0 to 5% methanol in dichloromethane. The appropriate fractions were combined and concentrated under reduced pressure to afford 73 mg (39%) of tert-butyl 4-[4-carbamoyl-3-[4-(difluoromethylsulfonyl) anilino]pyrazol-1-yl]-4-ethyl-piperidine-1-carboxylate as a white solid.

Trifluoroacetic acid (1 mL) was added to a solution of tert-butyl 4-[4-carbamoyl-3-[4-(difluoromethylsulfonyl) anilino]pyrazol-1-yl]-4-ethyl-piperidine-1-carboxylate (73 mg, 0.14 mmol) in dichloromethane (3 mL) and the mixture was stirred 1 h at room temperature. Toluene (5 mL) was added, and the mixture was concentrated under reduced pressure. The residue was co-evaporated two more times with toluene (2×5 mL) to afford 3-[4-(difluoromethylsulfonyl)anilino]-1-(4-ethyl-4-piperidyl)pyrazole-4-carboxamide trifluoroacetate salt, the entirety of which was used in the next step without purification.

A mixture of 3-[4-(difluoromethylsulfonyl)anilino]-1-(4-ethyl-4-piperidyl)-pyrazole-4-carboxamide trifluoroacetate salt (all of the crude material from the previous step), 3-hydroxy-6-fluorobenzaldehyde (29 mg, 0.21 mmol, 1.5 equiv) and sodium triacetoxyborohydride (59 mg, 0.28 mmol, 2.0 equiv) in acetonitrile (2 mL) was stirred for 16 h at room temperature. Incomplete conversion was noted, methanol (1 mL), 3-hydroxy-6-fluorobenzaldehyde (29 mg, 0.21 mmol), and sodium triacetoxyborohydride (59 mg, 0.28 mmol) were added and stirring continued for 2 h at room temperature. The reaction mixture was directly loaded for purification by flash chromatography on silica gel eluting with a gradient of 0 to 20% methanol in dichloromethane. The appropriate fractions were combined and concentrated under reduced pressure to afford 36 mg (47%) of 3-[4-(difluoromethylsulfonyl)anilino]-1-[4-ethyl-1-[(2-fluoro-5-hydroxy-phenyl) methyl]-4-piperidyl]pyrazole-4-carboxamide as a white solid. LC/MS (Method J, ESI): [M+H]$^+$=552.1, R$_T$=3.58 min; $^1$H NMR (400 MHz, DMSO-d$_6$): δ (ppm) 11.94 (s, 2H), 9.76 (s, 1H), 9.26 (s, 1H), 8.45 (s, 1H), 7.86-7.75 (m, 4H), 7.62 (s, 1H), 7.40-6.57 (m, 4H), 3.44-3.32 (m, 2H), 2.68-2.61 (m, 2H), 2.41-2.33 (m, 2H), 2.14-2.09 (m, 3H), 1.91 (s, 2H), 1.81-1.72 (m, 2H), 0.54 (t, J=7.1 Hz, 4H).

Example 302

(General Procedure X)

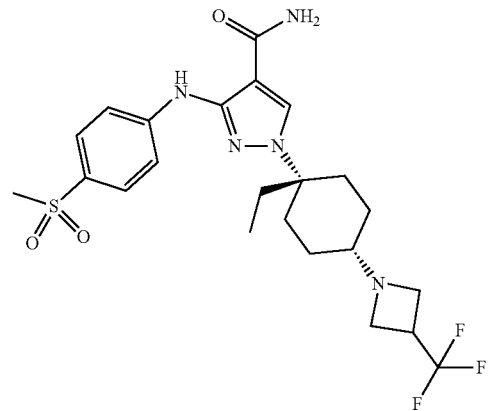

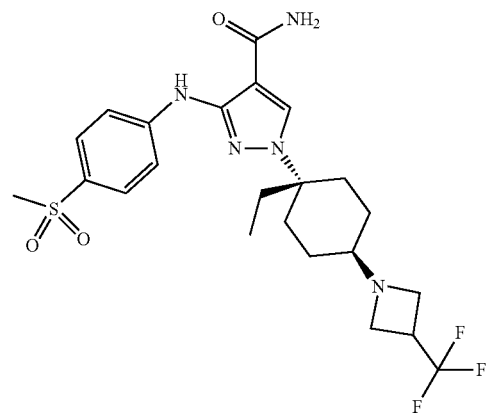

1-((1S,4S)-1-ethyl-4-(3-(trifluoromethyl)azetidin-1-yl) cyclohexyl)-3-((4-(methylsulfonyl) phenyl)amino)-1H-pyrazole-4-carboxamide & 1-((1R,4R)-1-ethyl-4-(3-(trifluoromethyl) azetidin-1-yl)cyclohexyl)-3-((4-(methylsulfonyl)phenyl)amino)-1H-pyrazole-4-carboxamide 431
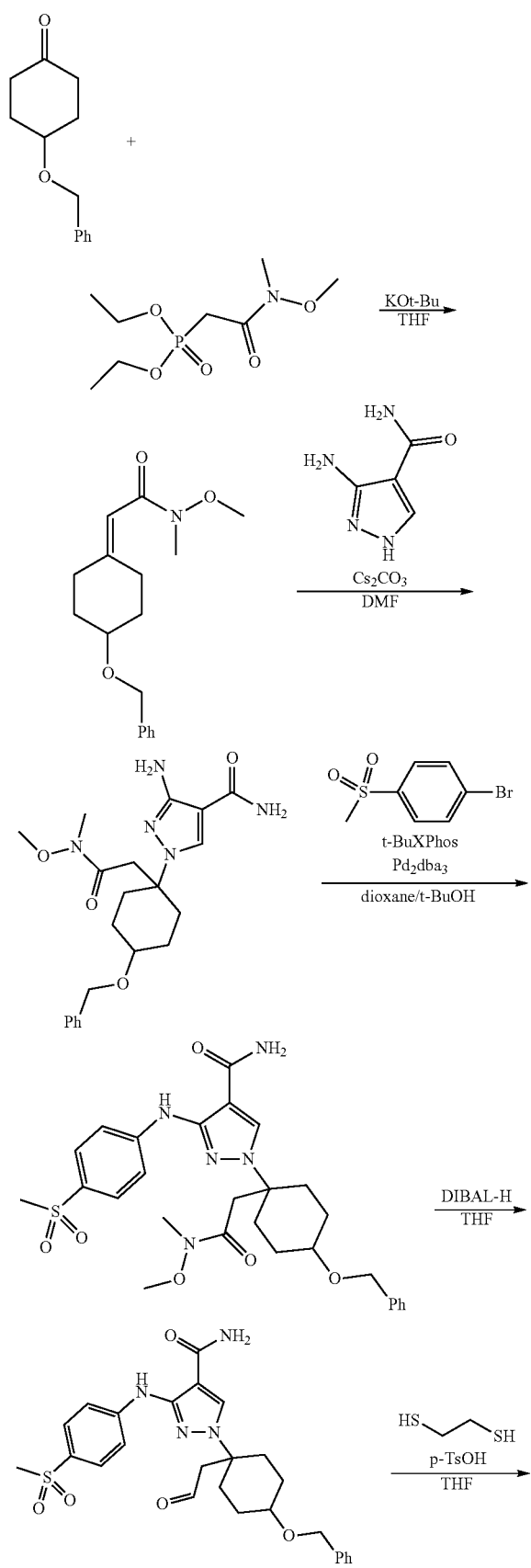
432
-continued
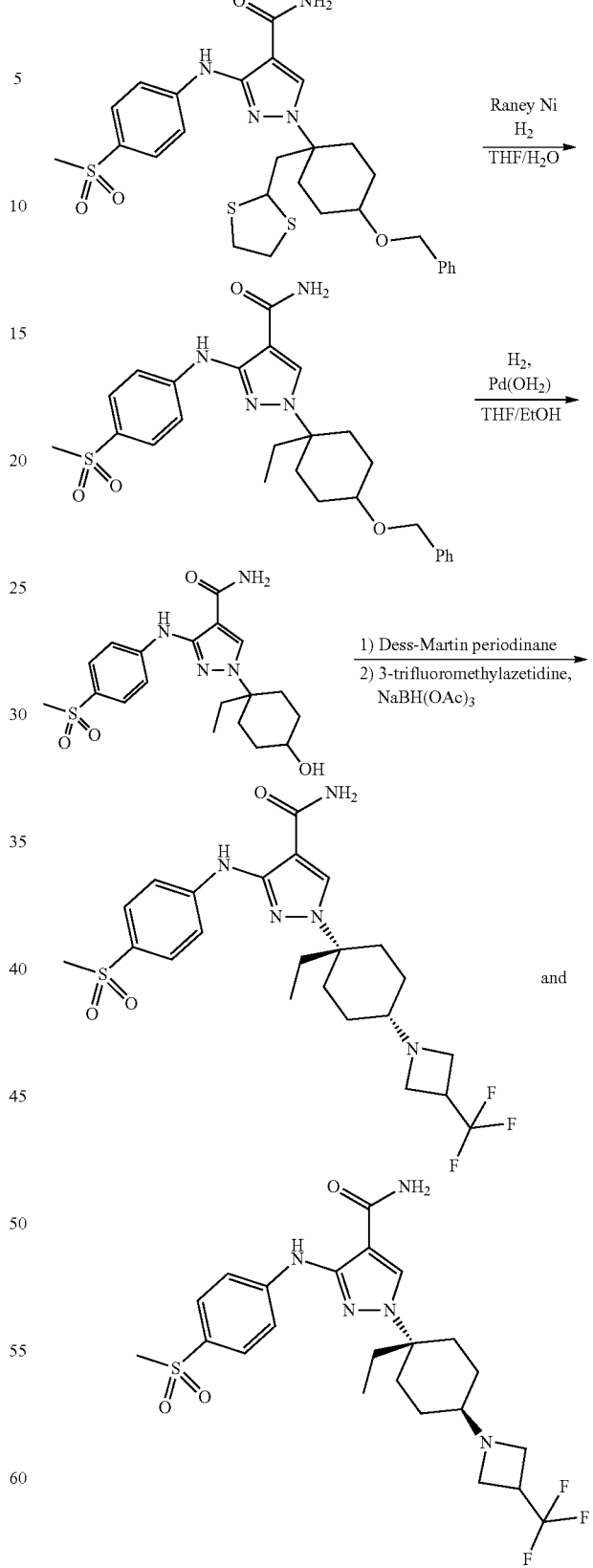
and
To a cooled (0° C.) solution of potassium tert-butoxide (4.6 g, 41 mmol) in tetrahydrofuran (50 mL) was added 2-diethoxyphosphoryl-N-methoxy-N-methyl-acetamide (10 g, 43 mmol). The mixture was allowed to warm to room temperature over 30 mins and stirred for an additional 1 h. The mixture was cooled to −78° C., and a solution of 4-benzyloxycyclohexanone (7.9 g, 39 mmol, 1.0 equiv) tetrahydrofuran (50 mL) was added. The mixture was allowed to slowly warm to room temperature and was stirred for 16 h. The mixture was diluted with water (250 mL) and extracted with isopropyl acetate (3×100 mL). The combined organic layer was washed with water and brine, dried over sodium sulfate and concentrated under reduced pressure. The residue was purified by flash chromatography on silica gel eluting with a gradient of 0 to 70% isopropyl acetate in heptane. The appropriate fractions were combined and concentrated under reduced pressure to afford 10 g (89%) of 2-(4-benzyloxycyclohexylidene)-N-methoxy-N-methyl-acetamide as a colorless oil.

To a solution of 3-amino-1H-pyrazole-4-carboxamide (5 g, 39.6 mmol) and 2-(4-benzyloxycyclohexylidene)-N-methoxy-N-methyl-acetamide (10.0 g, 34.6 mmol) in N,N-dimethylformamide (50 mL) was added cesium carbonate (12.4 g, 38.0 mmol). The mixture was stirred for 16 h at room temperature. Low conversion was noted, so to the mixture was added 1,8-diazabicyclo[5.4.0]undec-7-ene (5.2 mL, 34.6 mmol) and the mixture was heated to 60° C. for 3 h. After this time the reaction was quenched with 5% aq. Citric acid (150 mL) and extracted with isopropyl acetate (3×100 mL). The combined organic layer was washed with water and brine, dried over sodium sulfate and concentrated under reduced pressure. The residue was purified by flash chromatography on silica gel eluting with a gradient of 0 to 8% methanol in dichloromethane. The appropriate fractions were combined and concentrated under reduced pressure to afford 3.3 g (23%) of 3-amino-1-[4-benzyloxy-1-[2-[methoxy(methyl)amino]-2-oxo-ethyl]cyclohexyl]pyrazole-4-carboxamide as a white solid.

A degassed solution of 3-amino-1-[4-benzyloxy-1-[2-[methoxy(methyl)amino]-2-oxo-ethyl]cyclohexyl]pyrazole-4-carboxamide (1.0 g, 2.4 mmol), 1-bromo-4-methylsulfonyl-benzene (622 mg, 2.65 mmol), potassium phosphate tribasic (1.05 g, 4.8 mmol), 2-di-tert-butylphosphino-2',4',6'-triisopropylbiphenyl (53 mg, 0.12 mmol) and tris(dibenzylideneacetone)dipalladium(0) (28 mg, 0.03 mmol) in 1,4-dioxane (20 mL) and tert-butyl alcohol (5 mL) was heated for 16 h at 80° C. The mixture was allowed to cool to room temperature and the solid removed by filtration through Celite and the filtrate concentrated under reduced pressure. The residue was purified by flash chromatography on silica gel eluting with a gradient of 0 to 7% methanol in dichloromethane. The appropriate fractions were combined and concentrated under reduced pressure to afford 1.36 g (99%) of 1-[4-benzyloxy-1-[2-[methoxy (methyl)amino]-2-oxo-ethyl]cyclohexyl]-3-(4-methylsulfonylanilino)pyrazole-4-carboxamide as a white solid.

Diisobutylaluminum hydride (1 M in heptane, 24 mL, 24 mmol) was added to a cooled (−78° C.) solution of 1-[4-benzyloxy-1-[2-[methoxy(methyl)amino]-2-oxo-ethyl]cyclohexyl]-3-(4-methylsulfonylanilino)pyrazole-4-carboxamide (1.36 g, 2.4 mmol) in tetrahydrofuran (20 mL). The mixture was stirred 30 mins at −78° C. then quenched with saturated sodium sulfate (25 mL) and stirred 10 mins. Solid anhydrous sodium sulfate was added and the mixture stirred for an additional 30 mins. The solid was removed by filtration through Celite and the pad was washed thoroughly with tetrahydrofuran. The filtrate was concentrated under reduced pressure and purified by flash chromatography on silica gel eluting with a gradient of 0 to 10% methanol in dichloromethane. The appropriate fractions were combined and concentrated under reduced pressure to afford 800 mg (66%) of 1-[4-benzyloxy-1-(2-oxoethyl)cyclohexyl]-3-(4-methylsulfonylanilino) pyrazole-4-carboxamide as a white solid.

To a solution of 1-[4-benzyloxy-1-(2-oxoethyl)cyclohexyl]-3-(4-methylsulfonylanilino) pyrazole-4-carboxamide (800 mg, 1.6 mmol) in tetrahydrofuran (10 mL) was added 1,2-ethanedithiol (1.29 mL, 15.7 mmol) and p-toluenesulfonic acid monohydrate (30 mg, 0.16 mmol). The mixture was stirred at room temperature for 16 h then concentrated under reduced pressure. The residue was purified by flash chromatography on silica gel eluting with a gradient of 0 to 5% methanol in dichloromethane. The appropriate fractions were combined and concentrated under reduced pressure to afford 530 mg (58%) of 1-[4-benzyloxy-1-(1,3-dithiolan-2-ylmethyl) cyclohexyl]-3-(4-methylsulfonylanilino)pyrazole-4-carboxamide as a white solid.

A mixture of 1-[4-benzyloxy-1-(1,3-dithiolan-2-ylmethyl)cyclohexyl]-3-(4-methylsulfonylanilino) pyrazole-4-carboxamide (530 mg, 0.9 mmol) and a slurry of Raney nickel (Raney 2800, approx. 50% (w/v) in water, 2 mL) in tetrahydrofuran (4 mL) was stirred at room temperature for 16 h under a balloon of hydrogen. The solid was removed by filtration through Celite and the filtrate concentrated under reduced pressure. The residue was purified by flash chromatography on silica gel eluting with a gradient of 0 to 5% methanol in dichloromethane. The appropriate fractions were combined and concentrated under reduced pressure to afford 100 mg (22%) of 1-(4-benzyloxy-1-ethyl-cyclohexyl)-3-(4-methylsulfonylanilino) pyrazole-4-carboxamide as a white solid.

To a solution of 1-(4-benzyloxy-1-ethyl-cyclohexyl)-3-(4-methylsulfonylanilino) pyrazole-4-carboxamide (100 mg, 0.20 mmol) in ethanol (2 mL) and tetrahydrofuran (2 mL) was added 10% palladium on carbon (43 mg, 0.04 mmol). The mixture was stirred for 16 h at room temperature under a balloon of hydrogen. Low conversion was noted, so to the mixture was added 10% palladium hydroxide (57 mg, 0.04 mmol) and the mixture stirred for 72 h at 50° C. under a balloon of hydrogen. The solid was removed by filtration through Celite and concentrated under reduced pressure. The residue was purified by flash chromatography on silica gel eluting with a gradient of 0 to 10% methanol in dichloromethane. The appropriate fractions were combined and concentrated under reduced pressure to afford 10 mg (12%) of 1-(1-ethyl-4-hydroxy-cyclohexyl)-3-(4-methylsulfonylanilino) pyrazole-4-carboxamide as a white solid.

Dess-Martin periodinane (21 mg, 0.05 mmol) was added to a solution of 1-(1-ethyl-4-hydroxy-cyclohexyl)-3-(4-methylsulfonylanilino) pyrazole-4-carboxamide (10 mg, 0.02 mmol) in dichloromethane (2 mL) and the mixture was stirred 1 h at room temperature. Incomplete conversion was noted, so to the mixture was added more Dess-Martin periodinane (21 mg, 0.05 mmol) and stirring continued for 1 h at room temperature. A further portion was added of Dess-Martin periodinane (21 mg, 0.05 mmol) was added and the mixture stirred at room temperature for 1 h. Acetonitrile (2 mL), 3-(trifluoromethyl)azetidine hydrochloride (32 mg, 0.20 mmol), and sodium triacetoxyborohydride (42 mg, 0.20 mmol,) were added and the mixture was stirred 1 h at room temperature. The reaction mixture was loaded directly on to the column for purification by flash chromatography on silica gel eluting with a gradient of 0 to 25% methanol in dichloromethane. The appropriate fractions were combined and concentrated under reduced pressure to afford 15 mg of 1-[1-ethyl-4-[3-(trifluoromethyl)azetidin-1-yl]cyclohexyl]-

3-(4-methylsulfonylanilino)pyrazole-4-carboxamide as a mixture of diastereomers. The diastereomers were resolved using chiral SFC with the following conditions: Column: Chiralpak IA 150×21.2 mm I.D., 5 μm Mobile phase: A: CO₂ B:Methanol (0.1% NH₄OH) Isocratic: 25% B in 6 min Flow rate: 70 mL/min Column temperature: 40° C., BPR: 100 bar, Detector, UV 254 nm to give two fractions. Relative configuration was arbitrarily assigned to each diastereomer:

First eluted fraction, 2.1 mg (17%) as a white solid, LC/MS (Method J, ESI): [M+H]$^+$=514.2, $R_T$=3.21 min Second eluted fraction, 1.9 mg (15%) as a white solid, LC/MS (Method J, ESI): [M+H]$^+$=514.2, $R_T$=3.00 min

Example 303

(General Procedure Y)

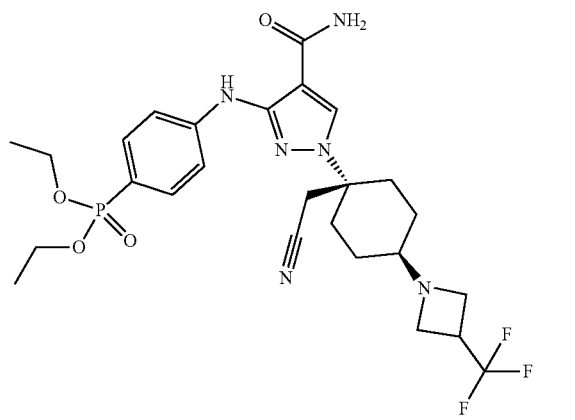 [SMILES: CCOP(=O)(OCC)c1ccc(Nc2nn([C@]3(CC#N)CC[C@@H](N4CC(C(F)(F)F)C4)CC3)cc2C(N)=O)cc1]

Diethyl (4-((4-carbamoyl-1-((1R,4R)-1-(cyanomethyl)-4-(3-(trifluoromethyl)azetidin-1-yl) cyclohexyl)-1H-pyrazol-3-yl)amino)phenyl)phosphonate

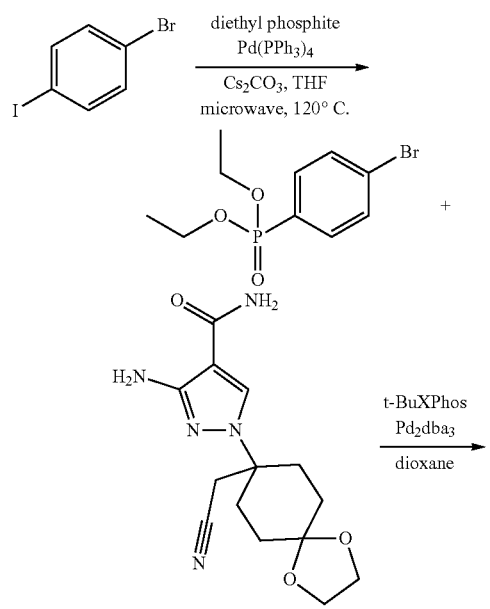

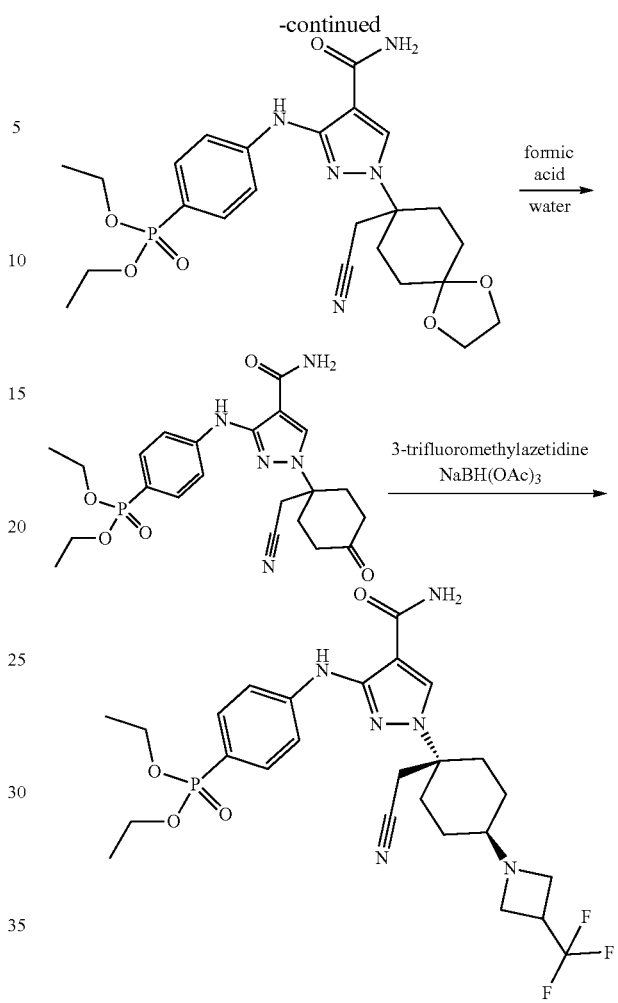

A degassed suspension of 1-bromo-4-iodo-benzene (2.42 g, 8.54 mmol), cesium carbonate (3.8 g, 11.6 mmol), tetrakis (triphenylphosphine)palladium(0) (449 mg, 0.38 mmol) and diethyl phosphite (1 mL, 1.1 g, 7.82 mmol) in tetrahydrofuran (10 mL) was heated under microwave irradiation at 120° C. for 30 mins. The mixture was allowed to cool to room temperature, the solid removed by filtration through Celite and the filtrate concentrated under reduced pressure. The residue was purified by flash chromatography on silica gel eluting with a gradient of 0 to 5% methanol in dichloromethane. The appropriate fractions were combined and concentrated under reduced pressure to afford 430 mg (19%) of 1-bromo-4-diethoxyphosphoryl-benzene as a pale yellow oil.

A degassed mixture of 3-amino-1-[8-(cyanomethyl)-1,4-dioxaspiro[4.5]decan-8-yl]-1H-pyrazole-4-carboxamide (400 mg, 1.3 mmol), 1-bromo-4-dimethylphosphoryl-benzene (430 mg, 1.5 mmol), potassium phosphate tribasic (573 mg, 2.6 mmol), 2-di-tert-butylphosphino-2', 4',6 '-triisopropylbiphenyl (29 mg, 0.065 mmol) and tris(dibenzylideneacetone)dipalladium(0) (15 mg, 0.016 mmol) in 1,4-dioxane (8 mL) was heated for 16 h at 100° C. The mixture was allowed to cool to room temperature, the solid removed by filtration through Celite and the filtrate concentrated under reduced pressure. The residue was purified by flash chromatography on silica gel eluting with a gradient of 0 to 10% methanol in isopropyl acetate. The appropriate fractions were combined and concentrated under reduced pressure to afford 160 mg (24%) of 1-[8-(cyanomethyl)-1,4-dioxaspiro[4.5]decan-8-yl]-3-(4-diethoxyphosphorylanilino)pyrazole-4-carboxamide as a white solid.

Formic acid (4 mL) was added to a suspension of 1-[8-(cyanomethyl)-1,4-dioxaspiro[4.5]decan-8-yl]-3-(4-dimethylphosphorylanilino)pyrazole-4-carboxamide (160 mg, 0.31 mmol) in water (0.2 mL) and the mixture was stirred at room temperature for 16 h. The mixture was concentrated under reduced pressure to afford 146 mg (100%) of 1-[1-(cyanomethyl)-4-oxo-cyclohexyl]-3-(4-diethoxyphosphorylanilino)pyrazole-4-carboxamide as a white solid which was used without further purification.

To a mixture of 3-(trifluoromethyl)azetidine hydrochloride (75 mg, 0.46 mmol), 1-[1-(cyanomethyl)-4-oxo-cyclohexyl]-3-(4-dimethylphosphorylanilino)pyrazole-4-carboxamide (146 mg, 0.31 mmol) in acetonitrile (2 mL) was added sodium triacetoxyborohydride (131 mg, 0.62 mmol) and the mixture was stirred for 2 h at room temperature. The mixture was loaded directly for purification by flash chromatography on silica gel eluting with a gradient of 0 to 20% methanol in dichloromethane. The appropriate fractions were combined and concentrated under reduced pressure to afford 50 mg (28%) of diethyl (4-((4-carbamoyl-1-((1R,4R)-1-(cyanomethyl)-4-(3-(trifluoromethyl) azetidin-1-yl)cyclohexyl)-1H-pyrazol -3-yl)amino)phenyl)phosphonate as a white solid. LC/MS (Method J, ESI): [M+H]$^+$=583.3, R$_T$=3.20 min; $^1$H NMR (400 MHz, DMSO-d$_6$) (ppm) δ 9.42 (s, 1H), 8.50 (s, 1H), 7.70-7.62 (m, 3H), 7.62-7.52 (m, 2H), 7.22 (s, 1H), 4.05-3.89 (m, 4H), 3.47-3.18 (m, 3H), 3.15-3.07 (m, 4H), 2.28-2.19 (m, 1H), 2.16-2.08 (m, 4H), 1.50-1.36 (m, 4H), 1.22 (t, J=7.0 Hz, 6H).

Example 304

(General Procedure W)

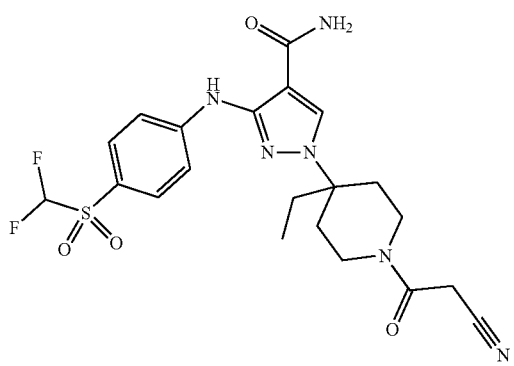 [SMILES: CCC1(n2cc(C(N)=O)c(Nc3ccc(S(=O)(=O)C(F)F)cc3)n2)CCN(C(=O)CC#N)CC1]

1-(1-(2-Cyanoacetyl)-4-ethylpiperidin-4-yl)-3-4-((difluoromethyl) sulfonyl)phenyl)amino)-1H-pyrazole-4-carboxamide

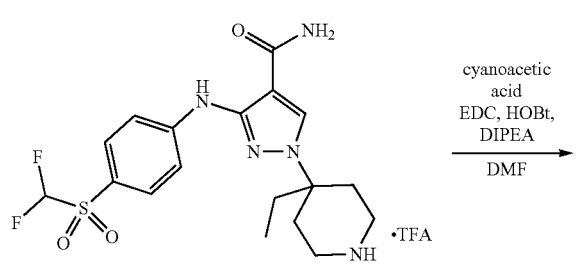

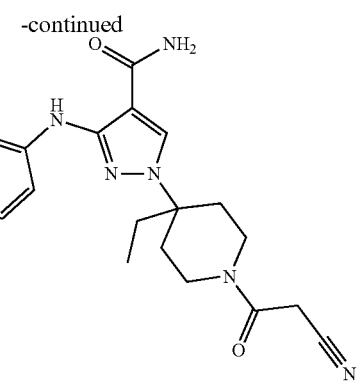

To a solution of 1-[4-(cyanomethyl)-4-piperidyl]-3-(cyclopropane-carbonyl-amino) pyrazole-4-carboxamide (88 mg, 0.16 mmol) in N,N-dimethylformamide (2 mL) was added sequentially cyanoacetic acid (17 mg, 0.19 mmol), N,N-diisopropyl-ethylamine (0.11 mL, 84 mg, 0.65 mmol), 1-hydroxybenzotriazole (27 mg, 0.19 mmol) and 1-(3-dimethylaminopropyl)-3-ethylcarbodiimide hydrochloride (40 mg, 0.21 mmol). The mixture was stirred for 16 h at room temperature. The reaction mixture was loaded directly for purification by reverse phase HPLC (Conditions: Column, Gemini-NX C18 5 µm, 50×30 mm; mobile phase: Water (0.1% formic acid) and CH$_3$CN (20% CH$_3$CN up to 60% in 10 min); Flow rate 60 ml/min). Appropriate fractions were combined and evaporated to afford 30 mg (36%) of 1-(1-(2-cyanoacetyl)-4-ethylpiperidin-4-yl)-3-((4-((difluoromethyl) sulfonyl)phenyl)amino)-1H-pyrazole-4-carboxamide as a white solid. LC/MS (Method J, ESI): [M+H]$^+$=495.1, R$_T$=4.50 min; $^1$H NMR (400 MHz, DMSO-d$_6$) δ (ppm) 9.74 (s, 1H), 8.48 (s, 1H), 7.88-7.74 (m, 4H), 7.61 (s, 1H), 7.36-6.97 (m, 2H), 4.16-3.96 (m, 3H), 3.65-3.52 (m, 1H), 3.17-3.04 (m, 1H), 3.00-2.87 (m, 1H), 2.45-2.30 (m, 2H), 2.03-1.90 (m, 1H), 1.90-1.70 (m, 3H), 0.57 (t, J=7.4 Hz, 3H).

Description of LCMS Methods Referenced Above

Method A

Experiments were performed on a SHIMADZU LCMS-2020 with a C18-reverse-phase column (50×3 mm Shimpack XR-ODS, 2.2 µm particle size), elution with solvent A: water+0.05% trifluoroacetic acid; solvent B: acetonitrile+0.05% trifluoroacetic acid.

Gradient:

| Gradient-Time | flow ml/min | % A | % B |
| --- | --- | --- | --- |
| 0.00 | 1.0 | 95 | 5 |
| 2.20 | 1.0 | 0 | 100 |
| 3.20 | 1.0 | 0 | 100 |
| 3.30 | 1.0 | 95 | 5 |

Detection—UV (220 and 254 nm) and ELSD

Method B

Experiments were performed on a SHIMADZU LCMS-2020 with a C18-reverse-phase column (50×3 mm Shimpack XR-ODS, 2.2 µm particle size), elution with solvent A: water+0.05% trifluoroacetic acid; solvent B: acetonitrile+0.05% trifluoroacetic acid.

Gradient:

| Gradient-Time | flow ml/min | % A | % B |
|---|---|---|---|
| 0.00 | 1.0 | 95 | 5 |
| 3.20 | 1.0 | 40 | 60 |
| 3.80 | 1.0 | 0 | 100 |
| 4.70 | 1.0 | 0 | 100 |
| 4.80 | 1.0 | 95 | 5 |

Detection—UV (220 and 254 nm) and ELSD

Method C

Experiments were performed on a SHIMADZU LCMS-2020 with a Shim-pack XR-ODS column (50×3 mm Shim-pack XR-ODS, 2.2 μm particle size), elution with solvent A: water+0.05% TFA; solvent B: acetonitrile+0.05% TFA.

Gradient:

| Gradient-Time | flow ml/min | % A | % B |
|---|---|---|---|
| 0.01 | 1.0 | 95 | 5 |
| 2.20 | 1.0 | 5 | 95 |
| 3.20 | 1.0 | 5 | 95 |
| 3.30 | 1.0 | 95 | 5 |

Detection—UV (220 and 254 nm) and ELSD

Method D

Experiments were performed on a SHIMADZU LCMS-2020 with a C18-reverse-phase column (50×3 mm Gemini-NX C18 110 A, 3.0 μm particle size), elution with solvent A: water 5mM $NH_4HCO_3$; solvent B: acetonitrile.

Gradient:

| Gradient-Time | flow ml/min | % A | % B |
|---|---|---|---|
| 0.00 | 1.2 | 90 | 10 |
| 3.20 | 1.2 | 40 | 60 |
| 4.00 | 1.2 | 5 | 95 |
| 4.40 | 1.2 | 5 | 95 |
| 4.50 | 1.2 | 90 | 10 |

Detection—UV (220 and 254 nm) and ELSD

Method E

Experiments were performed on a SHIMADZU LCMS-2020 with a C18-reverse-phase column (50×3 mm Gemini-NX C18 110 A, 3.0 μm particle size), elution with solvent A: water 5m $NH_4HCO_3$; solvent B: acetonitrile.

Gradient:

| Gradient-Time | flow ml/min | % A | % B |
|---|---|---|---|
| 0.00 | 1.2 | 90 | 10 |
| 2.00 | 1.2 | 5 | 95 |
| 3.20 | 1.2 | 5 | 95 |
| 3.30 | 1.2 | 90 | 10 |

Detection—UV (220 and 254 nm) and ELSD

Method F

Experiments were performed on a SHIMADZU LCMS-2020 with a C18-reverse-phase column (50×3 mm Gemini-NX C18 110 A, 3.0 μm particle size), elution with solvent A: water 5mM $NH_4HCO_3$; solvent B: acetonitrile.

Gradient:

| Gradient-Time | flow ml/min | % A | % B |
|---|---|---|---|
| 0.00 | 1.2 | 90 | 10 |
| 2.00 | 1.2 | 5 | 95 |
| 2.70 | 1.2 | 5 | 95 |
| 2.80 | 1.2 | 90 | 10 |

Detection—UV (220 and 254 nm) and ELSD

Method G

Experiments were performed on a SHIMADZU LCMS-2020 with a C18-reverse-phase column (50×2.1 mm Ascentis Express C18, 2.7 μm particle size), elution with solvent A: water+0.05% trifluoroacetic acid; solvent B: acetonitrile+0.05% trifluoroacetic acid.

Gradient:

| Gradient-Time | flow ml/min | % A | % B |
|---|---|---|---|
| 0.01 | 1.0 | 95 | 5 |
| 2.00 | 1.0 | 5 | 95 |
| 2.70 | 1.0 | 5 | 95 |

Detection—UV (220 and 254 nm) and ELSD

Method H

Experiments were performed on a SHIMADZU LCMS-2020 with an Ascentis Express C18 column (50×2.1 mm, 2.7 μm particle size), elution with solvent A: water+0.05% TFA; solvent B: acetonitrile+0.05% TFA.

Gradient:

| Gradient-Time | flow ml/min | % A | % B |
|---|---|---|---|
| 0.01 | 1.0 | 95 | 5 |
| 4.20 | 1.0 | 30 | 70 |
| 4.50 | 1.0 | 5 | 95 |
| 5.00 | 1.0 | 5 | 95 |

Detection—UV (220 and 254 nm) and ELSD

Method I

Experiments were performed on a SHIMADZU LCMS-2020 with an Ascentis Express C18 column (50×2.1 mm, 2.7 μm particle size), elution with solvent A: water+0.05% TFA; solvent B: acetonitrile+0.05% TFA.

Gradient:

| Gradient-Time | flow ml/min | % A | % B |
|---|---|---|---|
| 0.01 | 1.0 | 95 | 5 |
| 2.00 | 1.0 | 0 | 100 |
| 2.70 | 1.0 | 0 | 100 |

Detection—UV (220 and 254 nm) and ELSD

Method J

Experiments were performed on a SHIMADZU LCMS-2020 with a C18-reverse-phase column (50×3 mm Shimpack XR-ODS, 2.2 µm particle size), elution with solvent A: water+0.05% trifluoroacetic acid; solvent B: acetonitrile+0.05% trifluoroacetic acid. Gradient:

| Gradient-Time | flow ml/min | % A | % B |
|---|---|---|---|
| 0.00 | 1.2 | 95 | 5 |
| 3.50 | 1.2 | 30 | 70 |
| 3.70 | 1.2 | 0 | 100 |
| 4.70 | 1.2 | 0 | 100 |
| 4.75 | 1.2 | 95 | 5 |

Detection—UV (220 and 254 nm) and ELSD

Method K (LCMS15)

Experiments were performed on a SHIMADZU LCMS-2020 with a C18-reverse-phase column (50×3 mm Shimpack XR-ODS, 2.2 µm particle size), elution with solvent A: water+0.05% trifluoroacetic acid; solvent B: acetonitrile+0.05% trifluoroacetic acid.

Gradient:

| Gradient-Time | flow ml/min | % A | % B |
|---|---|---|---|
| 0.00 | 1.2 | 95 | 5 |
| 2.00 | 1.2 | 5 | 95 |
| 2.70 | 1.2 | 5 | 95 |
| 2.75 | 1.2 | 95 | 5 |

Detection—UV (220 and 254 nm) and ELSD

Method L (LCMS34)

Experiments were performed on a SHIMADZU LCMS-2020 with a C18-reverse-phase column (50×3 mm Gemini-NX C18 110 A, 3.0 µm particle size), elution with solvent A: water 5mNH$_4$HCO$_3$; solvent B: acetonitrile. Gradient:

| Gradient-Time | flow ml/min | % A | % B |
|---|---|---|---|
| 0.00 | 1.2 | 80 | 20 |
| 3.50 | 1.2 | 40 | 60 |
| 4.00 | 1.2 | 5 | 95 |
| 4.70 | 1.2 | 5 | 95 |
| 4.80 | 1.2 | 90 | 10 |

Detection—UV (220 and 254 nm) and ELSD

Method M (LCMS53)

Experiments were performed on a SHIMADZU LCMS-2020 with a C18-reverse-phase column (50×3 mm Shimpack XR-ODS, 2.2 µm particle size), elution with solvent A: water+0.05% trifluoroacetic acid; solvent B: acetonitrile+0.05% trifluoroacetic acid.

Gradient:

| Gradient-Time | flow ml/min | % A | % B |
|---|---|---|---|
| 0.00 | 1.2 | 95 | 5 |
| 3.50 | 1.2 | 40 | 60 |
| 3.70 | 1.2 | 0 | 100 |
| 4.70 | 1.2 | 0 | 100 |
| 4.75 | 1.2 | 95 | 5 |

Detection—UV (220 and 254 nm) and ELSD

Method N (LCMS53)

Experiments were performed on a SHIMADZU LCMS-2020 with a C18-reverse-phase column (50×3 mm Shimpack XR-ODS, 2.2 µm particle size), elution with solvent A: water+0.05% trifluoroacetic acid; solvent B: acetonitrile+0.05% trifluoroacetic acid.

Gradient:

| Gradient-Time | flow ml/min | % A | % B |
|---|---|---|---|
| 0.00 | 1.2 | 95 | 5 |
| 1.10 | 1.2 | 0 | 100 |
| 1.70 | 1.2 | 0 | 100 |
| 1.75 | 1.2 | 95 | 5 |

Detection—UV (220 and 254 nm) and ELSD

Method O

Experiments performed on an Agilent 1290 UHPLC coupled with Agilent MSD (6140) mass spectrometer using ESI as ionization source. The LC separation was using a Phenomenex XB-C18, 1.7 µm, 50×2.1 mm column with a 0.4 ml/minute flow rate. Solvent A is water with 0.1% formic acid and solvent B is acetonitrile with 0.1% formic acid. The gradient consisted with 2-98% solvent B over 7 min and hold 98% B for 1.5 min following equilibration for 1.5 min. LC column temperature is 40° C. UV absorbance was collected at 220 nm and 254 nm and mass spec full scan was applied to all experiments.

Method P

Experiments were performed on a SHIMADZU LCMS-2020 with a C18-reverse-phase column (Waters BEH 30×2.1mm, 1.7 µm particle size), elution with solvent A: water+0.1% formic acid; solvent B: acetonitrile+0.1% formic acid. Gradient:

| Gradient-Time (min) | flow ml/min | % A | % B |
|---|---|---|---|
| 0 | 0.7 | 98 | 2 |
| 2 | 0.7 | 2 | 98 |
| 2.19 | 0.7 | 2 | 98 |
| 2.2 | 0.7 | 98 | 2 |
| 2.5 | 0.7 | 98 | 2 |

Detection—UV (254 nm)

The examples in the following table were prepared using similar methods as described above. Absolute configuration was arbitrarily assigned to each stereoisomer.

TABLE 2

| | LCMS Procedures. | | |
|---|---|---|---|
| Example | General Procedure | Structure | m/z |
| 22 | B | | 421 |
| 23 | C | | 399 |
| 24 | C | | 373 |
| 25 | C | | 425 |

TABLE 2-continued

LCMS Procedures.

| Example | General Procedure | Structure | m/z |
|---|---|---|---|
| 26 | C | 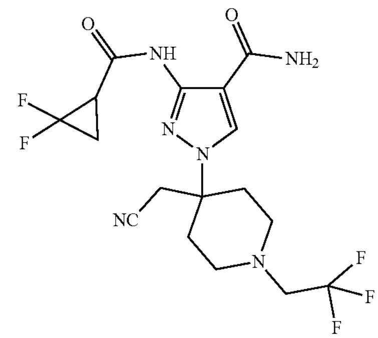 [SMILES: N#CCC1(n2cc(C(N)=O)c(NC(=O)C3CC3(F)F)n2)CCN(CC(F)(F)F)CC1] | 435 |
| 27 | C | 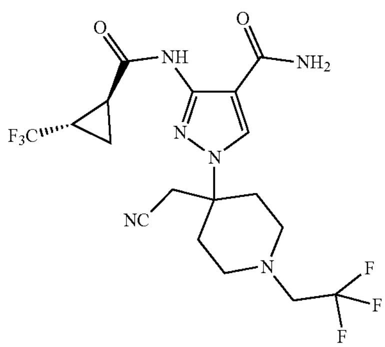 [SMILES: N#CCC1(n2cc(C(N)=O)c(NC(=O)[C@H]3C[C@@H]3C(F)(F)F)n2)CCN(CC(F)(F)F)CC1] | 467 |
| 28 | C | 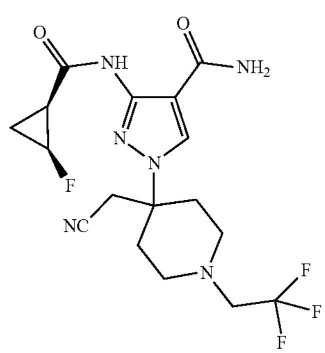 [SMILES: N#CCC1(n2cc(C(N)=O)c(NC(=O)[C@@H]3C[C@@H]3F)n2)CCN(CC(F)(F)F)CC1] | 417 |
| 29 | C | 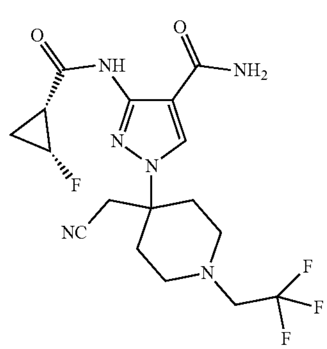 [SMILES: N#CCC1(n2cc(C(N)=O)c(NC(=O)[C@H]3C[C@H]3F)n2)CCN(CC(F)(F)F)CC1] | 417 |

TABLE 2-continued

| | | LCMS Procedures. | |
|---|---|---|---|
| Example | General Procedure | Structure | m/z |
| 30 | C | | 417 |
| 31 | C | | 439 |
| 32 | C | | 413 |
| 33 | D | | 316 |

TABLE 2-continued

LCMS Procedures.

| Example | General Procedure | Structure | m/z |
|---------|-------------------|-----------|-----|
| 34 | D | 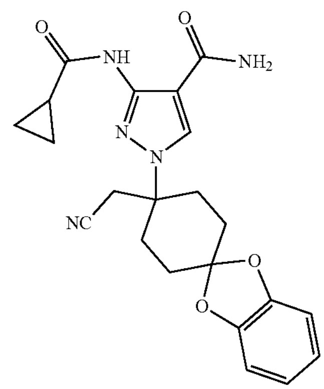 [SMILES: N#CCC1(n2cc(C(N)=O)c(NC(=O)C3CC3)n2)CCC2(CC1)Oc1ccccc1O2] | 422 |
| 35 | D | 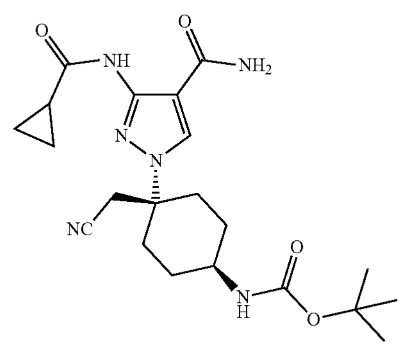 | 431 |
| 36 | D | 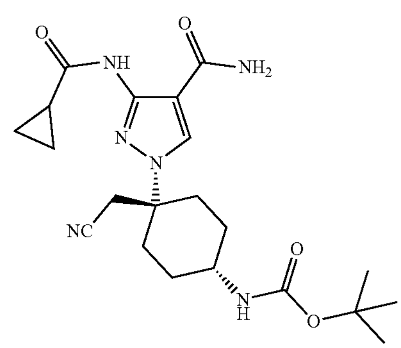 | 431 |
| 37 | E | 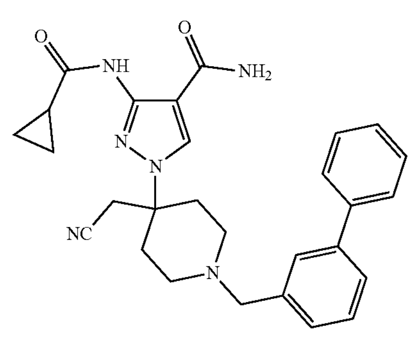 [SMILES: N#CCC1(n2cc(C(N)=O)c(NC(=O)C3CC3)n2)CCN(Cc2cccc(-c3ccccc3)c2)CC1] | 483 |

TABLE 2-continued
LCMS Procedures.
| Example | General Procedure | Structure | m/z |
|---|---|---|---|
| 38 | E | 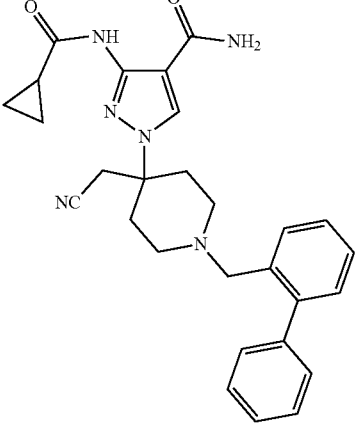 | 483 |
| 39 | E | 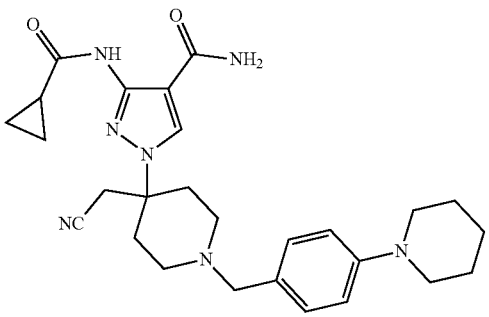 [SMILES: N#CCC1(n2cc(C(N)=O)c(NC(=O)C3CC3)n2)CCN(Cc2ccc(N3CCCCC3)cc2)CC1] | 490 |
| 40 | E | 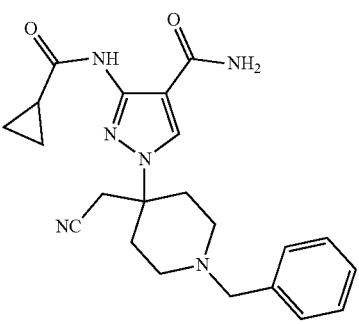 [SMILES: N#CCC1(n2cc(C(N)=O)c(NC(=O)C3CC3)n2)CCN(Cc2ccccc2)CC1] | 407 |
| 41 | E | 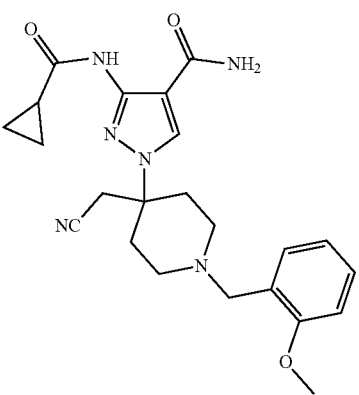 [SMILES: COc1ccccc1CN1CCC(CC#N)(n2cc(C(N)=O)c(NC(=O)C3CC3)n2)CC1] | 437 |

TABLE 2-continued
LCMS Procedures.
| Example | General Procedure | Structure | m/z |
|---|---|---|---|
| 42 | E | 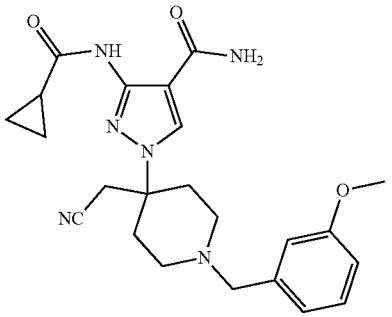 [SMILES: COc1cccc(CN2CCC(CC#N)(n3cc(C(N)=O)c(NC(=O)C4CC4)n3)CC2)c1] | 437 |
| 43 | E | 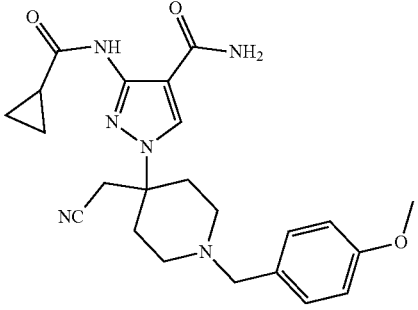 [SMILES: COc1ccc(CN2CCC(CC#N)(n3cc(C(N)=O)c(NC(=O)C4CC4)n3)CC2)cc1] | 437 |
| 44 | E | 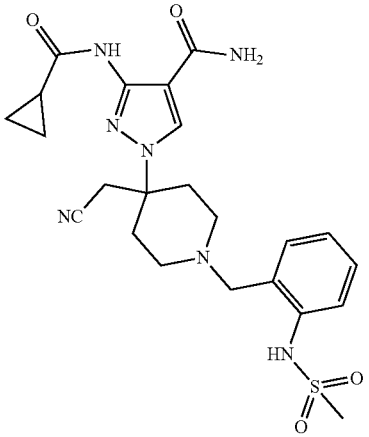 [SMILES: CS(=O)(=O)Nc1ccccc1CN1CCC(CC#N)(n2cc(C(N)=O)c(NC(=O)C3CC3)n2)CC1] | 500 |
| 45 | E | 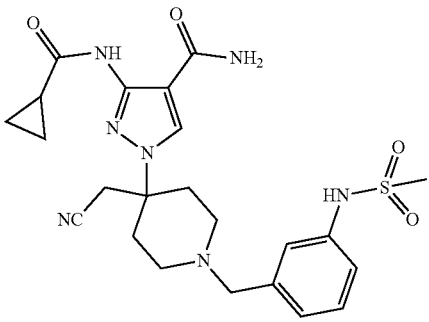 [SMILES: CS(=O)(=O)Nc1cccc(CN2CCC(CC#N)(n3cc(C(N)=O)c(NC(=O)C4CC4)n3)CC2)c1] | 500 |

TABLE 2-continued
LCMS Procedures.
| Example | General Procedure | Structure | m/z |
|---|---|---|---|
| 46 | E | 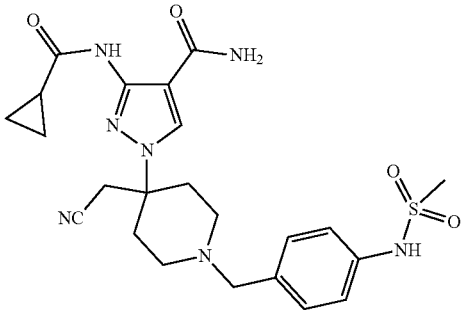 [SMILES: CS(=O)(=O)Nc1ccc(CN2CCC(CC#N)(n3cc(C(N)=O)c(NC(=O)C4CC4)n3)CC2)cc1] | 500 |
| 47 | E | 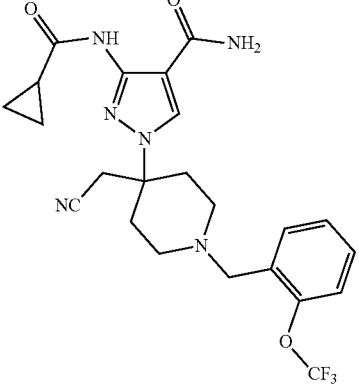 | 491 |
| 48 | E | 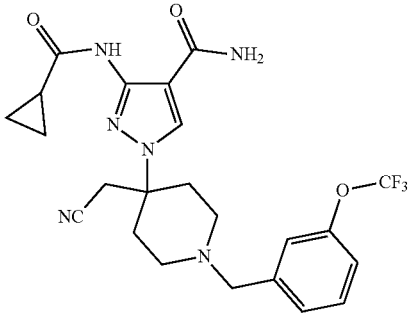 [SMILES: N#CCC1(n2cc(C(N)=O)c(NC(=O)C3CC3)n2)CCN(Cc2cccc(OC(F)(F)F)c2)CC1] | 491 |
| 49 | E | 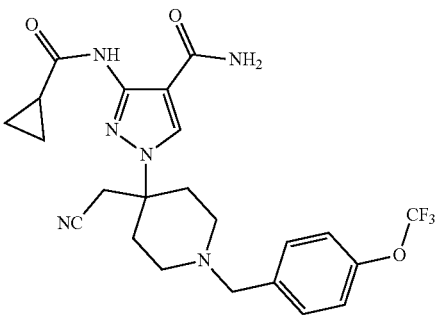 [SMILES: N#CCC1(n2cc(C(N)=O)c(NC(=O)C3CC3)n2)CCN(Cc2ccc(OC(F)(F)F)cc2)CC1] | 491 |

TABLE 2-continued
LCMS Procedures.
| Example | General Procedure | Structure | m/z |
|---|---|---|---|
| 50 | E | 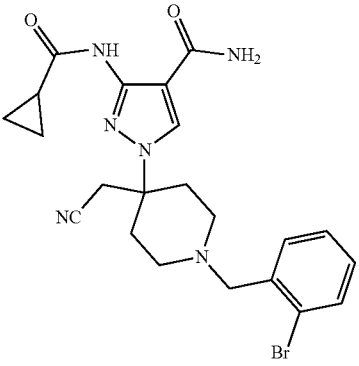 [SMILES: N#CCC1(n2cc(C(N)=O)c(NC(=O)C3CC3)n2)CCN(Cc2ccccc2Br)CC1] | 485 |
| 51 | E | 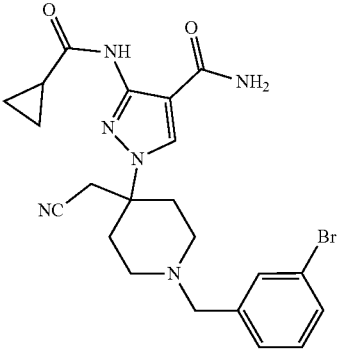 [SMILES: N#CCC1(n2cc(C(N)=O)c(NC(=O)C3CC3)n2)CCN(Cc2cccc(Br)c2)CC1] | 485 |
| 52 | E | 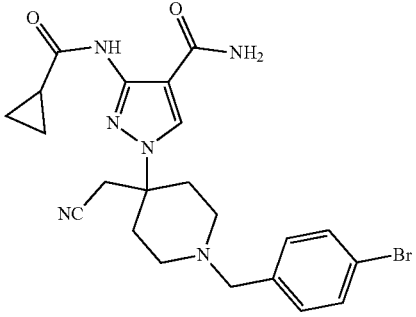 [SMILES: N#CCC1(n2cc(C(N)=O)c(NC(=O)C3CC3)n2)CCN(Cc2ccc(Br)cc2)CC1] | 485 |
| 53 | E | 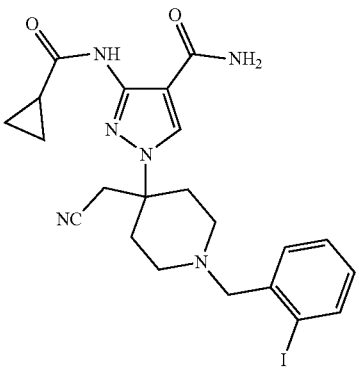 [SMILES: N#CCC1(n2cc(C(N)=O)c(NC(=O)C3CC3)n2)CCN(Cc2ccccc2I)CC1] | 533 |

TABLE 2-continued
LCMS Procedures.
| Example | General Procedure | Structure | m/z |
|---|---|---|---|
| 54 | E | 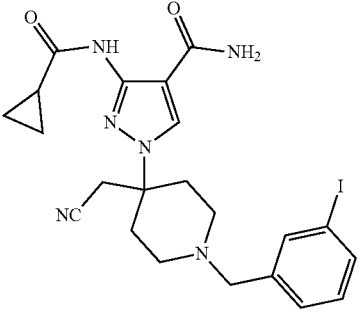 [SMILES: N#CCC1(n2cc(C(N)=O)c(NC(=O)C3CC3)n2)CCN(Cc2cccc(I)c2)CC1] | 533 |
| 55 | E | 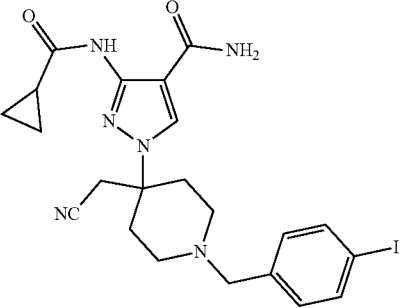 [SMILES: N#CCC1(n2cc(C(N)=O)c(NC(=O)C3CC3)n2)CCN(Cc2ccc(I)cc2)CC1] | 533 |
| 56 | E | 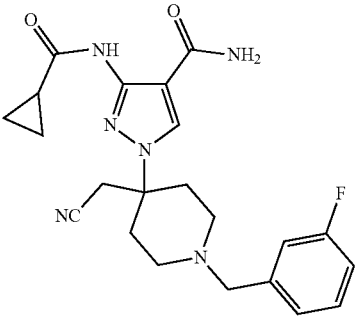 [SMILES: N#CCC1(n2cc(C(N)=O)c(NC(=O)C3CC3)n2)CCN(Cc2cccc(F)c2)CC1] | 425 |
| 57 | E | 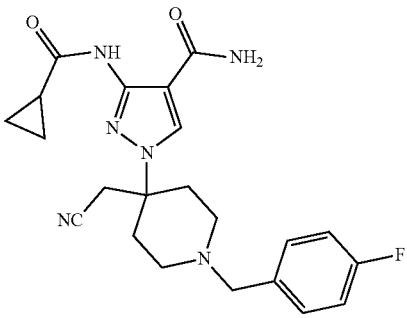 [SMILES: N#CCC1(n2cc(C(N)=O)c(NC(=O)C3CC3)n2)CCN(Cc2ccc(F)cc2)CC1] | 425 |

TABLE 2-continued

LCMS Procedures.

| Example | General Procedure | Structure | m/z |
|---|---|---|---|
| 58 | E | (cyclopropanecarboxamido-pyrazole-4-carboxamide, 1-[4-(cyanomethyl)-1-(2-chlorobenzyl)piperidin-4-yl]) | 441 |
| 59 | E | (cyclopropanecarboxamido-pyrazole-4-carboxamide, 1-[4-(cyanomethyl)-1-(3-chlorobenzyl)piperidin-4-yl]) | 441 |
| 60 | E | (cyclopropanecarboxamido-pyrazole-4-carboxamide, 1-[4-(cyanomethyl)-1-(4-chlorobenzyl)piperidin-4-yl]) | 441 |
| 61 | E | (cyclopropanecarboxamido-pyrazole-4-carboxamide, 1-[4-(cyanomethyl)-1-(2-trifluoromethylbenzyl)piperidin-4-yl]) | 475 |

TABLE 2-continued
LCMS Procedures.
| Example | General Procedure | Structure | m/z |
|---|---|---|---|
| 62 | E | 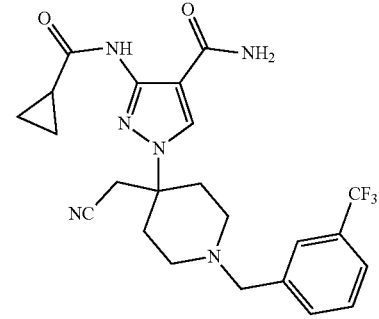 [SMILES: N#CCC1(n2cc(C(N)=O)c(NC(=O)C3CC3)n2)CCN(Cc2cccc(C(F)(F)F)c2)CC1] | 475 |
| 63 | E | 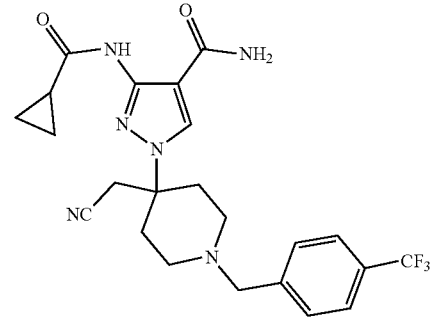 [SMILES: N#CCC1(n2cc(C(N)=O)c(NC(=O)C3CC3)n2)CCN(Cc2ccc(C(F)(F)F)cc2)CC1] | 475 |
| 64 | E | 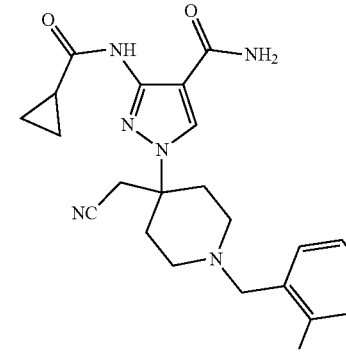 | 432 |
| 65 | E | 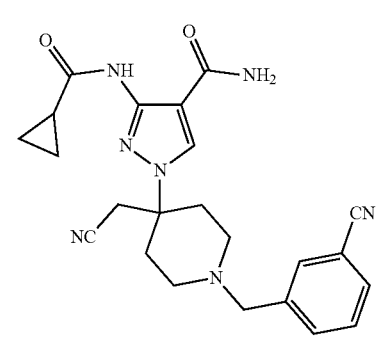 [SMILES: N#CCC1(n2cc(C(N)=O)c(NC(=O)C3CC3)n2)CCN(Cc2cccc(C#N)c2)CC1] | 432 |

TABLE 2-continued
LCMS Procedures.
| Example | General Procedure | Structure | m/z |
|---|---|---|---|
| 66 | E | 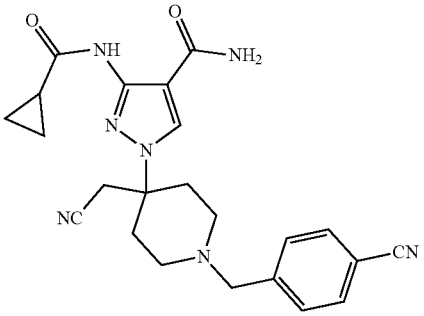 [SMILES: N#CCC1(n2cc(C(N)=O)c(NC(=O)C3CC3)n2)CCN(Cc2ccc(C#N)cc2)CC1] | 432 |
| 67 | E | 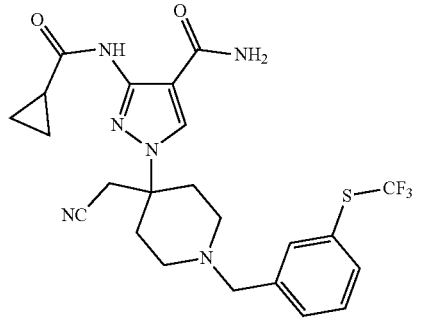 [SMILES: N#CCC1(n2cc(C(N)=O)c(NC(=O)C3CC3)n2)CCN(Cc2cccc(SC(F)(F)F)c2)CC1] | 507 |
| 68 | E | 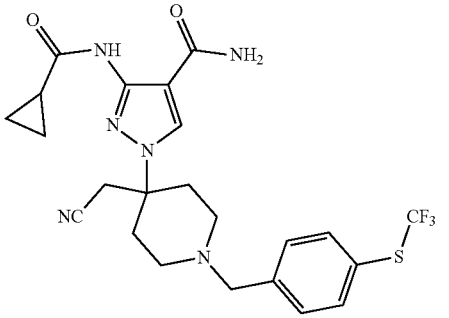 [SMILES: N#CCC1(n2cc(C(N)=O)c(NC(=O)C3CC3)n2)CCN(Cc2ccc(SC(F)(F)F)cc2)CC1] | 507 |
| 69 | E | 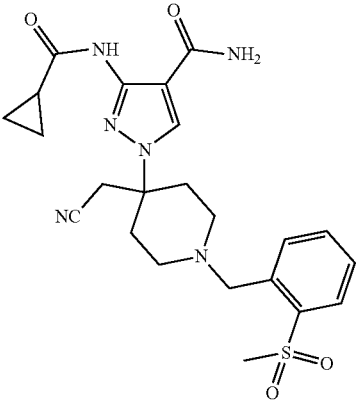 [SMILES: CS(=O)(=O)c1ccccc1CN1CCC(CC#N)(n2cc(C(N)=O)c(NC(=O)C3CC3)n2)CC1] | 485 |

TABLE 2-continued
LCMS Procedures.
| Example | General Procedure | Structure | m/z |
|---|---|---|---|
| 70 | E | 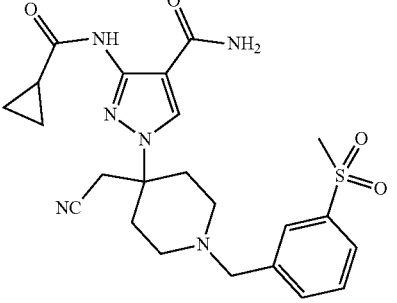 | 485 |
| 71 | E | 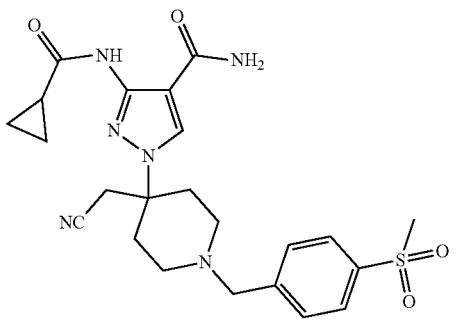 [SMILES: CS(=O)(=O)c1ccc(CN2CCC(CC#N)(n3cc(C(N)=O)c(NC(=O)C4CC4)n3)CC2)cc1] | 485 |
| 72 | E | 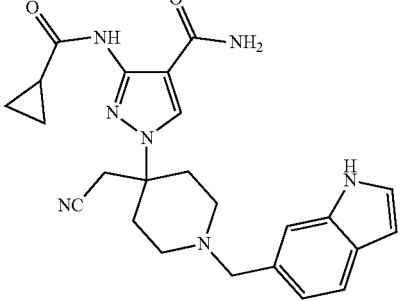 | 446 |
| 73 | E | 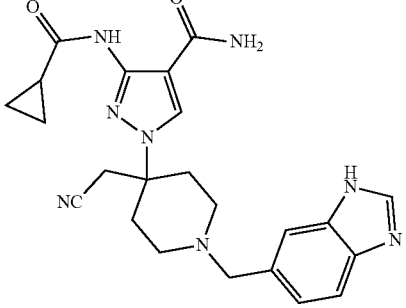 | 447 |

TABLE 2-continued
LCMS Procedures.
| Example | General Procedure | Structure | m/z |
|---|---|---|---|
| 74 | E | 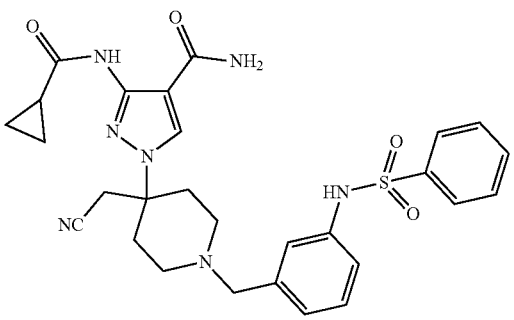 [SMILES: N#CCC1(n2cc(C(N)=O)c(NC(=O)C3CC3)n2)CCN(Cc2cccc(NS(=O)(=O)c3ccccc3)c2)CC1] | 562 |
| 75 | E | 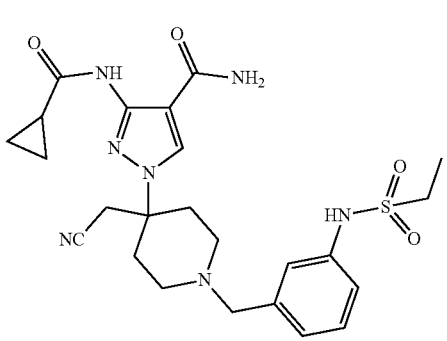 [SMILES: CCS(=O)(=O)Nc1cccc(CN2CCC(CC#N)(n3cc(C(N)=O)c(NC(=O)C4CC4)n3)CC2)c1] | 514 |
| 76 | E | 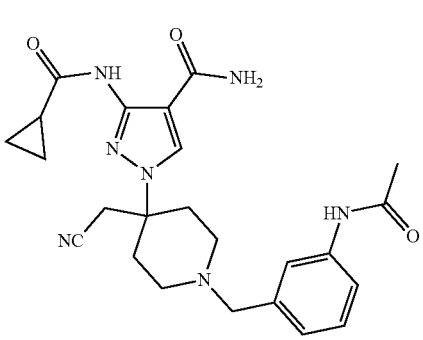 [SMILES: CC(=O)Nc1cccc(CN2CCC(CC#N)(n3cc(C(N)=O)c(NC(=O)C4CC4)n3)CC2)c1] | 464 |
| 77 | E | 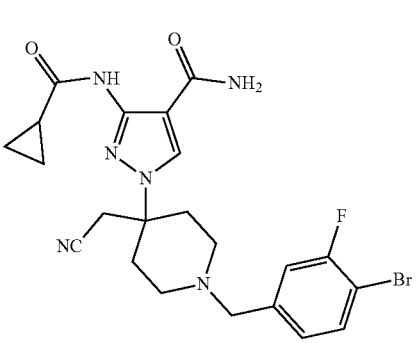 [SMILES: N#CCC1(n2cc(C(N)=O)c(NC(=O)C3CC3)n2)CCN(Cc2ccc(Br)c(F)c2)CC1] | 503 |

TABLE 2-continued
LCMS Procedures.
| Example | General Procedure | Structure | m/z |
|---|---|---|---|
| 78 | E | 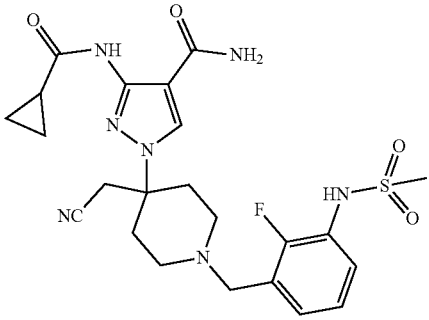 [SMILES: CS(=O)(=O)Nc1cccc(CN2CCC(CC#N)(n3cc(C(N)=O)c(NC(=O)C4CC4)n3)CC2)c1F] | 518 |
| 79 | E | 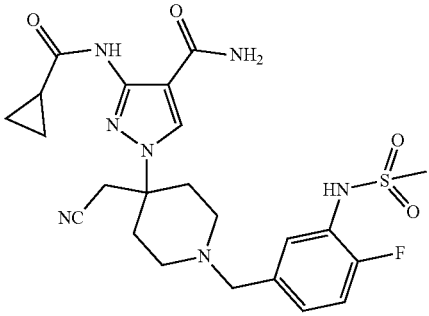 [SMILES: CS(=O)(=O)Nc1cc(CN2CCC(CC#N)(n3cc(C(N)=O)c(NC(=O)C4CC4)n3)CC2)ccc1F] | 518 |
| 80 | E | 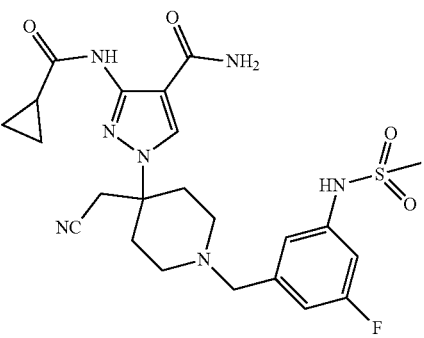 [SMILES: CS(=O)(=O)Nc1cc(F)cc(CN2CCC(CC#N)(n3cc(C(N)=O)c(NC(=O)C4CC4)n3)CC2)c1] | 518 |
| 81 | E | 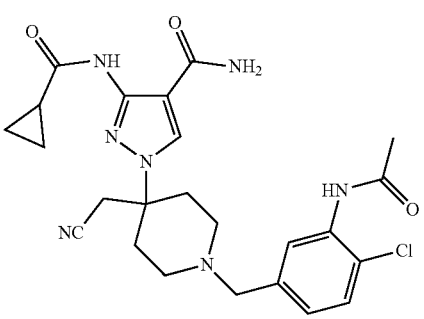 [SMILES: CC(=O)Nc1cc(CN2CCC(CC#N)(n3cc(C(N)=O)c(NC(=O)C4CC4)n3)CC2)ccc1Cl] | 498 |

TABLE 2-continued
LCMS Procedures.
| Example | General Procedure | Structure | m/z |
|---|---|---|---|
| 82 | E | 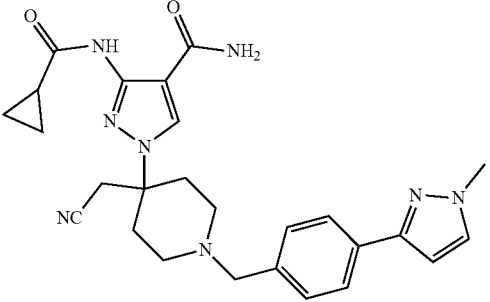 [SMILES: Cn1ccc(-c2ccc(CN3CCC(CC#N)(n4cc(C(N)=O)c(NC(=O)C5CC5)n4)CC3)cc2)n1] | 487 |
| 83 | E | 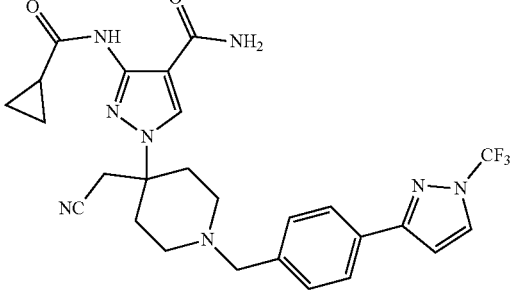 | 541 |
| 84 | E | 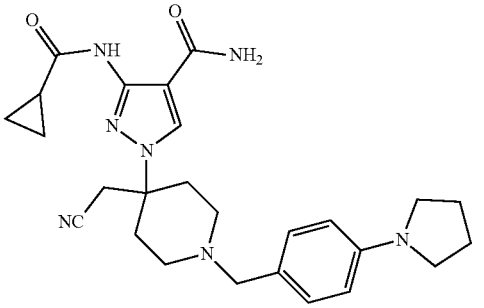 [SMILES: N#CCC1(n2cc(C(N)=O)c(NC(=O)C3CC3)n2)CCN(Cc2ccc(N3CCCC3)cc2)CC1] | 476 |
| 85 | E | 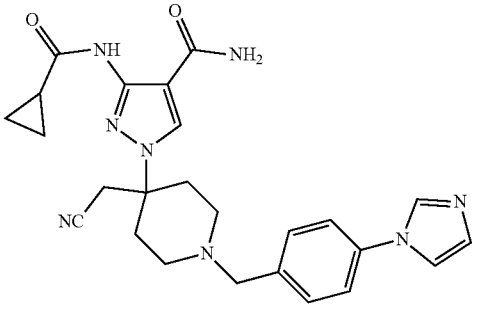 [SMILES: N#CCC1(n2cc(C(N)=O)c(NC(=O)C3CC3)n2)CCN(Cc2ccc(-n3ccnc3)cc2)CC1] | 473 |

TABLE 2-continued

LCMS Procedures.

| Example | General Procedure | Structure | m/z |
|---|---|---|---|
| 86 | E | (cyclopropanecarboxamido-pyrazole-4-carboxamide with 4-(cyanomethyl)piperidine N-benzyl-4-(1,2,4-triazol-1-yl)phenyl) | 474 |
| 87 | E | (cyclopropanecarboxamido-pyrazole-4-carboxamide with 4-(cyanomethyl)piperidine N-benzyl-4-(pyrazol-1-yl)phenyl) | 473 |
| 88 | E | (cyclopropanecarboxamido-pyrazole-4-carboxamide with 4-(cyanomethyl)piperidine N-benzyl-4-(benzimidazol-1-yl)phenyl) | 523 |
| 89 | E | (cyclopropanecarboxamido-pyrazole-4-carboxamide with 4-(cyanomethyl)piperidine N-benzyl-4-(2H-1,2,3-triazol-2-yl)phenyl) | 474 |

TABLE 2-continued
LCMS Procedures.
| Example | General Procedure | Structure | m/z |
|---|---|---|---|
| 90 | E | 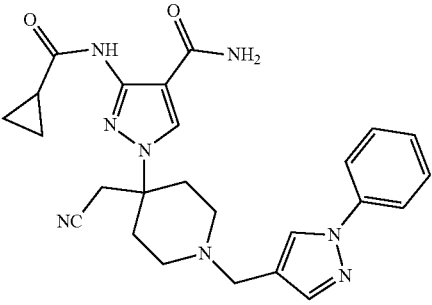 [SMILES: N#CCC1(n2cc(C(N)=O)c(NC(=O)C3CC3)n2)CCN(Cc2cnn(-c3ccccc3)c2)CC1] | 473 |
| 91 | E | 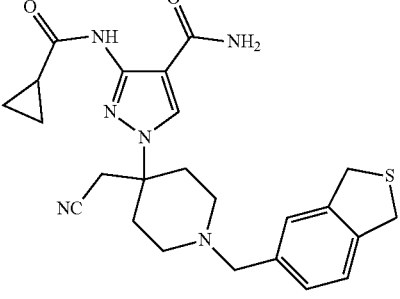 | 465 |
| 92 | E | 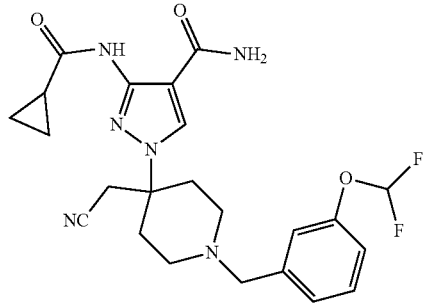 [SMILES: N#CCC1(n2cc(C(N)=O)c(NC(=O)C3CC3)n2)CCN(Cc2cccc(OC(F)F)c2)CC1] | 473 |
| 93 | E | 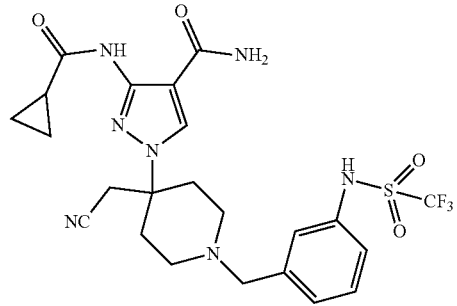 [SMILES: N#CCC1(n2cc(C(N)=O)c(NC(=O)C3CC3)n2)CCN(Cc2cccc(NS(=O)(=O)C(F)(F)F)c2)CC1] | 554 |

TABLE 2-continued
LCMS Procedures.
| Example | General Procedure | Structure | m/z |
|---|---|---|---|
| 94 | E | 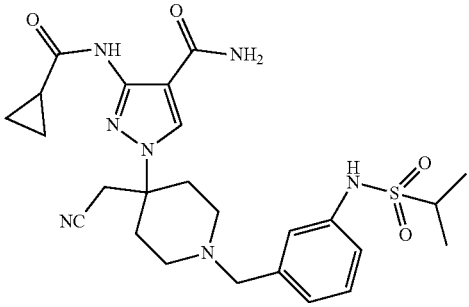 [SMILES: CC(C)S(=O)(=O)Nc1cccc(CN2CCC(CC#N)(n3cc(C(N)=O)c(NC(=O)C4CC4)n3)CC2)c1] | 528 |
| 95 | E | 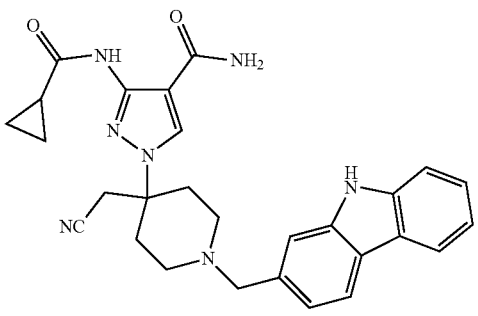 [SMILES: N#CCC1(n2cc(C(N)=O)c(NC(=O)C3CC3)n2)CCN(Cc2ccc3c(c2)[nH]c2ccccc23)CC1] | 496 |
| 96 | E | 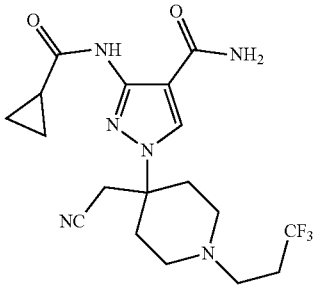 [SMILES: N#CCC1(n2cc(C(N)=O)c(NC(=O)C3CC3)n2)CCN(CCC(F)(F)F)CC1] | 413 |
| 97 | E | 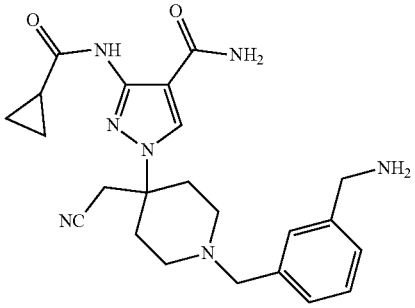 [SMILES: N#CCC1(n2cc(C(N)=O)c(NC(=O)C3CC3)n2)CCN(Cc2cccc(CN)c2)CC1] | 436 |

TABLE 2-continued
LCMS Procedures.
| Example | General Procedure | Structure | m/z |
|---|---|---|---|
| 98 | E | 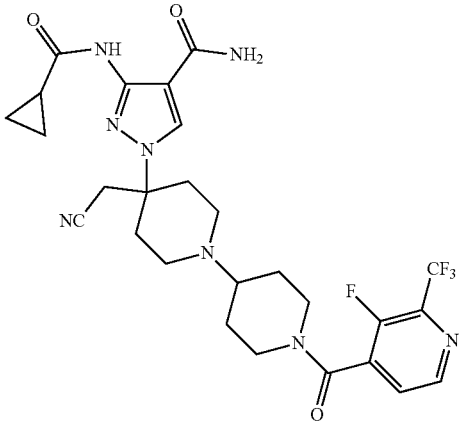 [SMILES: N#CCC1(n2cc(C(N)=O)c(NC(=O)C3CC3)n2)CCN(C2CCN(C(=O)c3ccnc(C(F)(F)F)c3F)CC2)CC1] | 591 |
| 99 | F | 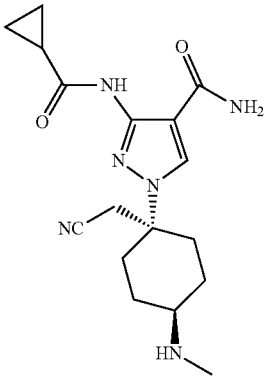 [SMILES: CN[C@H]1CC[C@](CC#N)(n2cc(C(N)=O)c(NC(=O)C3CC3)n2)CC1] | 345 |
| 100 | F | 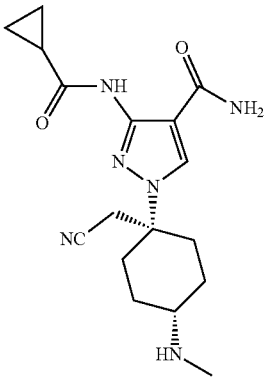 [SMILES: CN[C@H]1CC[C@@](CC#N)(n2cc(C(N)=O)c(NC(=O)C3CC3)n2)CC1] | 345 |

TABLE 2-continued
LCMS Procedures.
| Example | General Procedure | Structure | m/z |
|---|---|---|---|
| 101 | F | 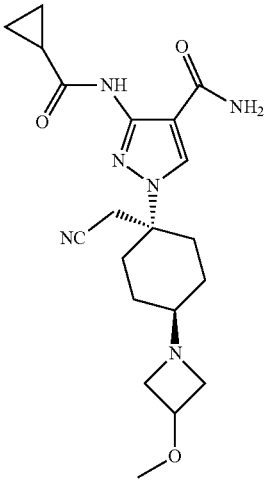 [SMILES: COC1CN([C@H]2CC[C@](CC#N)(n3cc(C(N)=O)c(NC(=O)C4CC4)n3)CC2)C1] | 401 |
| 102 | F | 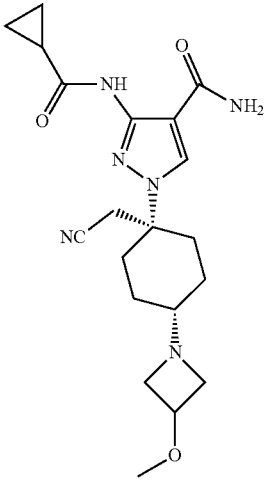 [SMILES: COC1CN([C@H]2CC[C@@](CC#N)(n3cc(C(N)=O)c(NC(=O)C4CC4)n3)CC2)C1] | 401 |
| 103 | F | 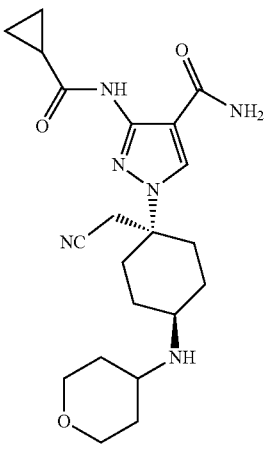 [SMILES: N#CC[C@]1(n2cc(C(N)=O)c(NC(=O)C3CC3)n2)CC[C@H](NC2CCOCC2)CC1] | 415 |

TABLE 2-continued
LCMS Procedures.
| Example | General Procedure | Structure | m/z |
|---|---|---|---|
| 104 | F | 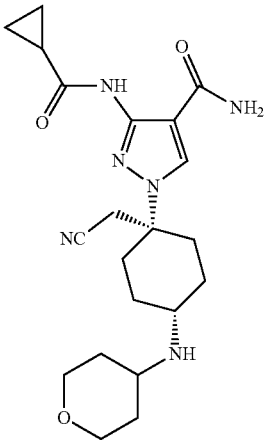 [SMILES: N#CC[C@]1(n2cc(C(N)=O)c(NC(=O)C3CC3)n2)CC[C@@H](NC2CCOCC2)CC1] | 415 |
| 105 | F | 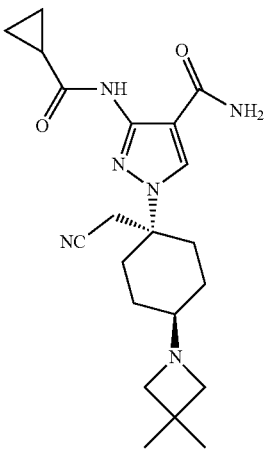 [SMILES: CC1(C)CN([C@H]2CC[C@](CC#N)(n3cc(C(N)=O)c(NC(=O)C4CC4)n3)CC2)C1] | 399 |
| 106 | F | 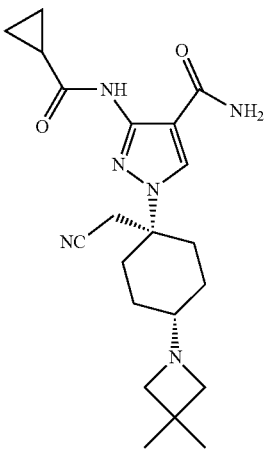 [SMILES: CC1(C)CN([C@H]2CC[C@@](CC#N)(n3cc(C(N)=O)c(NC(=O)C4CC4)n3)CC2)C1] | 399 |

TABLE 2-continued

LCMS Procedures.

| Example | General Procedure | Structure | m/z |
|---|---|---|---|
| 107 | F | 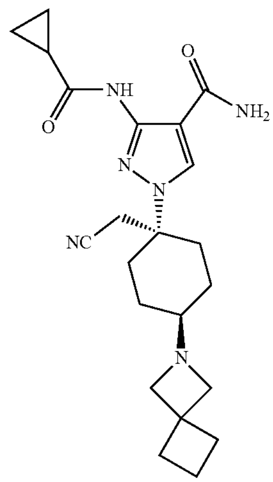 [SMILES: N#CC[C@]1(n2cc(C(N)=O)c(NC(=O)C3CC3)n2)CC[C@H](N2CC3(CCC3)C2)CC1] | 411 |
| 108 | F | 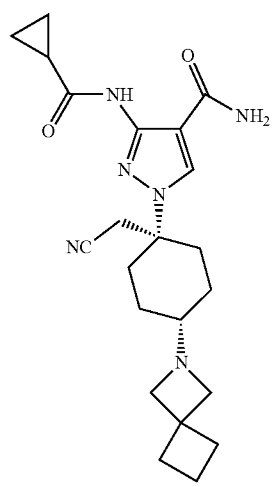 [SMILES: N#CC[C@]1(n2cc(C(N)=O)c(NC(=O)C3CC3)n2)CC[C@@H](N2CC3(CCC3)C2)CC1] | 411 |
| 109 | F | 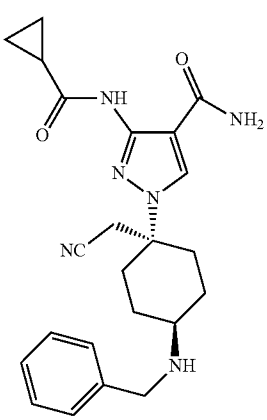 [SMILES: N#CC[C@]1(n2cc(C(N)=O)c(NC(=O)C3CC3)n2)CC[C@H](NCc2ccccc2)CC1] | 421 |

TABLE 2-continued

LCMS Procedures.

| Example | General Procedure | Structure | m/z |
|---------|-------------------|-----------|-----|
| 110 | F | 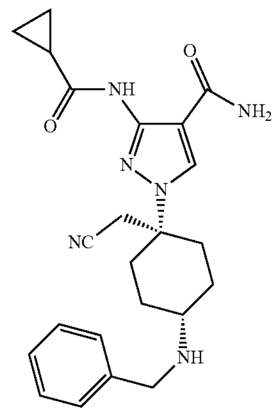 [SMILES: N#CC[C@]1(n2cc(C(N)=O)c(NC(=O)C3CC3)n2)CC[C@@H](NCc2ccccc2)CC1] | 421 |
| 111 | F | 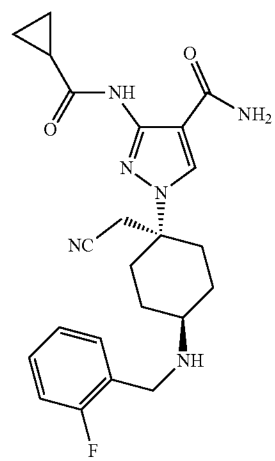 | 439 |
| 112 | F | 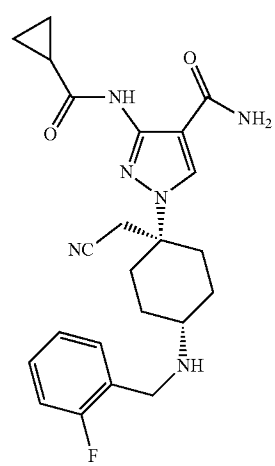 | 439 |

TABLE 2-continued

LCMS Procedures.

| Example | General Procedure | Structure | m/z |
|---|---|---|---|
| 113 | F | 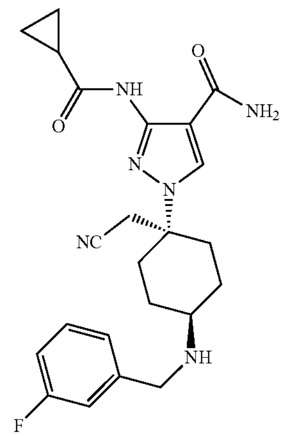 [SMILES: N#CC[C@]1(n2cc(C(N)=O)c(NC(=O)C3CC3)n2)CC[C@H](NCc2cccc(F)c2)CC1] | 439 |
| 114 | F | 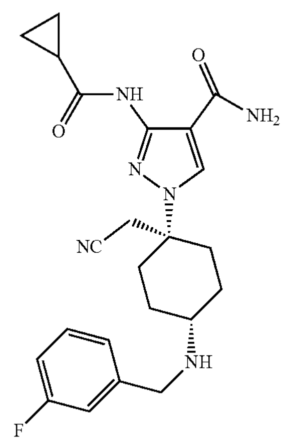 [SMILES: N#CC[C@]1(n2cc(C(N)=O)c(NC(=O)C3CC3)n2)CC[C@@H](NCc2cccc(F)c2)CC1] | 439 |
| 115 | F | 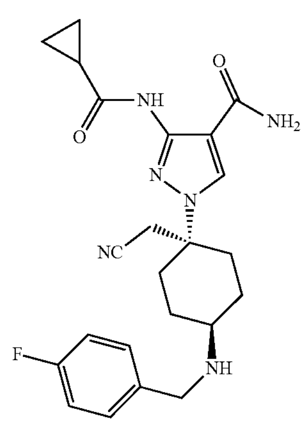 [SMILES: N#CC[C@]1(n2cc(C(N)=O)c(NC(=O)C3CC3)n2)CC[C@H](NCc2ccc(F)cc2)CC1] | 439 |

TABLE 2-continued
LCMS Procedures.
| Example | General Procedure | Structure | m/z |
|---|---|---|---|
| 116 | F | 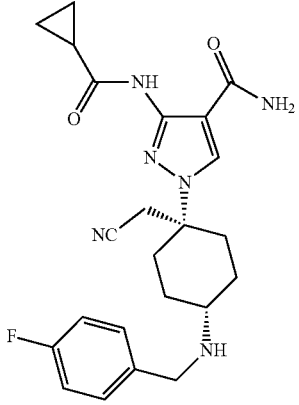 [SMILES: N#CC[C@]1(n2cc(C(N)=O)c(NC(=O)C3CC3)n2)CC[C@@H](NCc2ccc(F)cc2)CC1] | 439 |
| 117 | F | 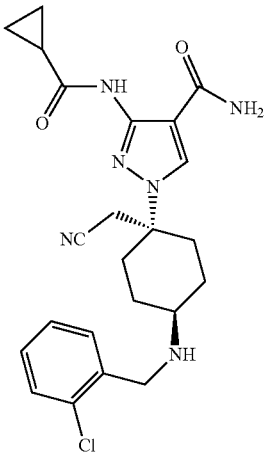 [SMILES: N#CC[C@]1(n2cc(C(N)=O)c(NC(=O)C3CC3)n2)CC[C@H](NCc2ccccc2Cl)CC1] | 455 |
| 118 | F | 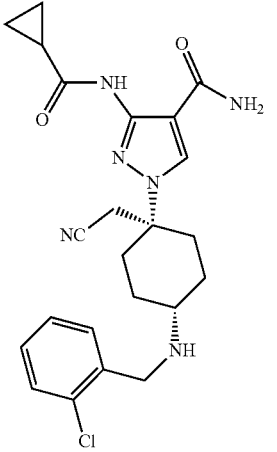 [SMILES: N#CC[C@]1(n2cc(C(N)=O)c(NC(=O)C3CC3)n2)CC[C@@H](NCc2ccccc2Cl)CC1] | 455 |

TABLE 2-continued

LCMS Procedures.

| Example | General Procedure | Structure | m/z |
|---|---|---|---|
| 119 | F | 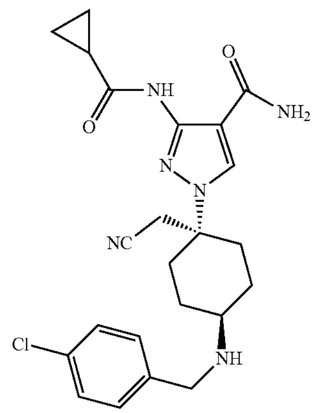 [SMILES: N#CC[C@]1(n2cc(C(N)=O)c(NC(=O)C3CC3)n2)CC[C@H](NCc2ccc(Cl)cc2)CC1] | 455 |
| 120 | F | 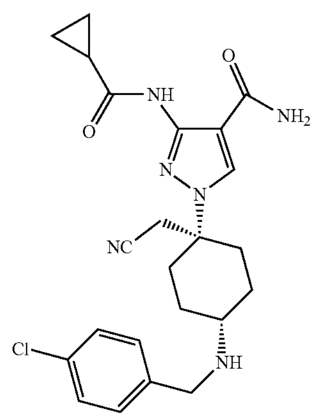 [SMILES: N#CC[C@]1(n2cc(C(N)=O)c(NC(=O)C3CC3)n2)CC[C@@H](NCc2ccc(Cl)cc2)CC1] | 455 |
| 121 | F | 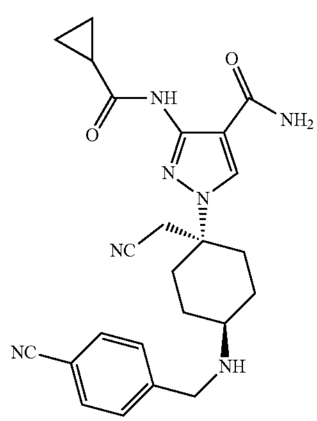 [SMILES: N#CC[C@]1(n2cc(C(N)=O)c(NC(=O)C3CC3)n2)CC[C@H](NCc2ccc(C#N)cc2)CC1] | 446 |

TABLE 2-continued
LCMS Procedures.
| Example | General Procedure | Structure | m/z |
|---|---|---|---|
| 122 | F | 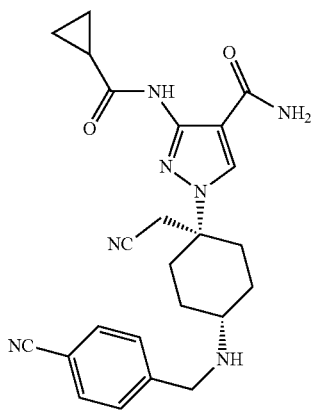 [SMILES: N#CC[C@]1(n2cc(C(N)=O)c(NC(=O)C3CC3)n2)CC[C@@H](NCc2ccc(C#N)cc2)CC1] | 446 |
| 123 | F | 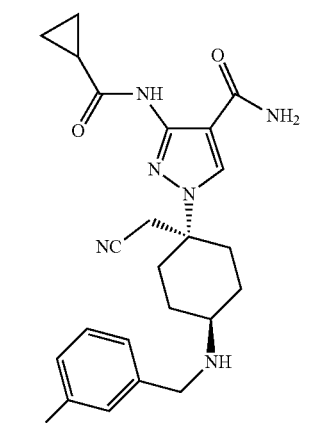 | 446 |
| 124 | F | 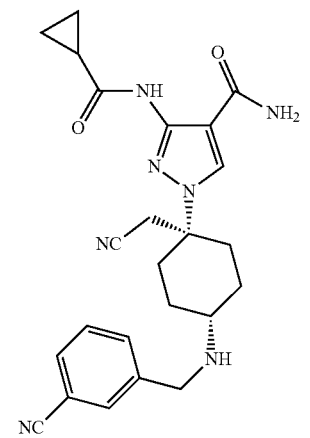 [SMILES: N#CC[C@]1(n2cc(C(N)=O)c(NC(=O)C3CC3)n2)CC[C@@H](NCc2cccc(C#N)c2)CC1] | 446 |

TABLE 2-continued

LCMS Procedures.

| Example | General Procedure | Structure | m/z |
|---|---|---|---|
| 125 | F | 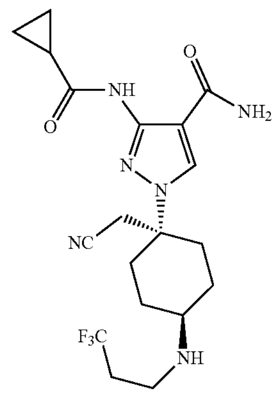 [SMILES: N#CC[C@]1(n2cc(C(N)=O)c(NC(=O)C3CC3)n2)CC[C@H](NCCC(F)(F)F)CC1] | 427 |
| 126 | F | 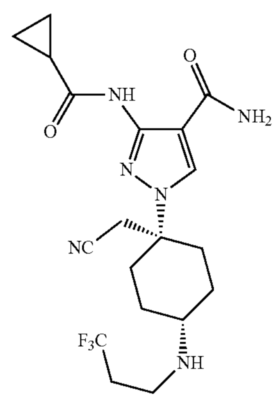 [SMILES: N#CC[C@]1(n2cc(C(N)=O)c(NC(=O)C3CC3)n2)CC[C@@H](NCCC(F)(F)F)CC1] | 427 |
| 127 | F | 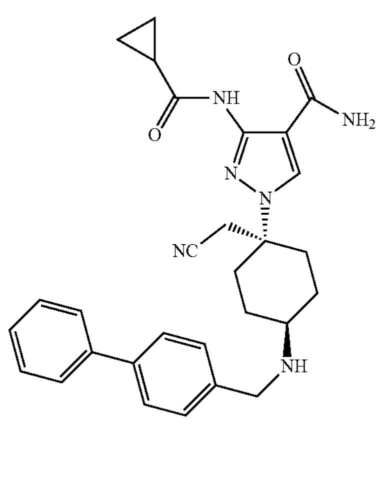 [SMILES: N#CC[C@]1(n2cc(C(N)=O)c(NC(=O)C3CC3)n2)CC[C@H](NCc2ccc(-c3ccccc3)cc2)CC1] | 497 |

TABLE 2-continued

LCMS Procedures.

| Example | General Procedure | Structure | m/z |
|---|---|---|---|
| 128 | F | 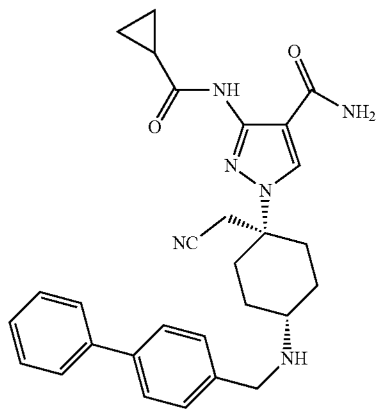 [SMILES: N#CC[C@]1(n2cc(C(N)=O)c(NC(=O)C3CC3)n2)CC[C@@H](NCc2ccc(-c3ccccc3)cc2)CC1] | 497 |
| 129 | F | 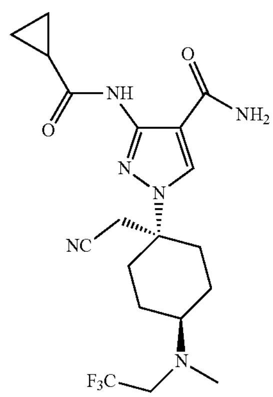 [SMILES: CN(CC(F)(F)F)[C@H]1CC[C@](CC#N)(n2cc(C(N)=O)c(NC(=O)C3CC3)n2)CC1] | 427 |
| 130 | F | 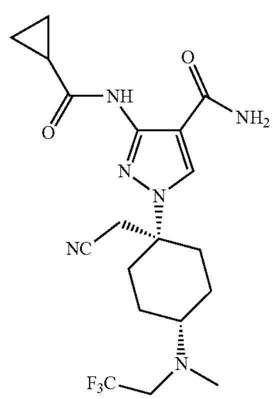 [SMILES: CN(CC(F)(F)F)[C@H]1CC[C@@](CC#N)(n2cc(C(N)=O)c(NC(=O)C3CC3)n2)CC1] | 427 |

TABLE 2-continued

LCMS Procedures.

| Example | General Procedure | Structure | m/z |
|---------|-------------------|-----------|-----|
| 131 | G | 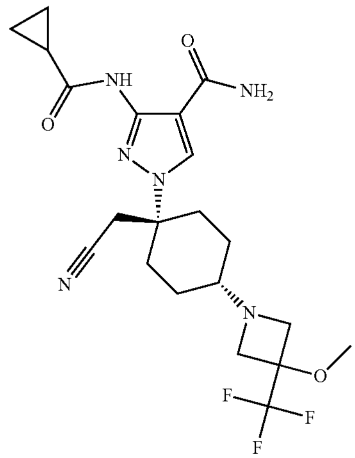 [SMILES: COC1(C(F)(F)F)CN([C@H]2CC[C@@](CC#N)(n3cc(C(N)=O)c(NC(=O)C4CC4)n3)CC2)C1] | 469 |
| 132 | G | 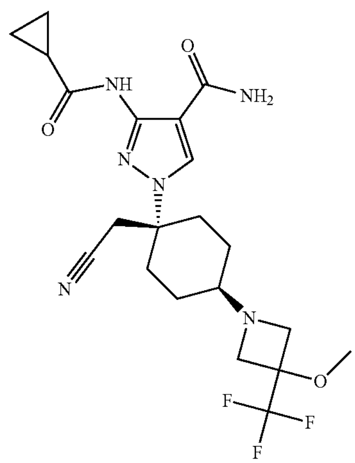 [SMILES: COC1(C(F)(F)F)CN([C@H]2CC[C@](CC#N)(n3cc(C(N)=O)c(NC(=O)C4CC4)n3)CC2)C1] | 469 |
| 133 | G | 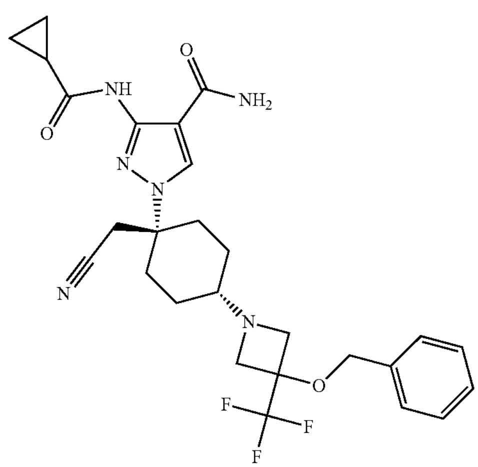 [SMILES: N#CC[C@]1(n2cc(C(N)=O)c(NC(=O)C3CC3)n2)CC[C@@H](N2CC(OCc3ccccc3)(C(F)(F)F)C2)CC1] | 545 |

TABLE 2-continued
LCMS Procedures.
| Example | General Procedure | Structure | m/z |
|---|---|---|---|
| 134 | G | 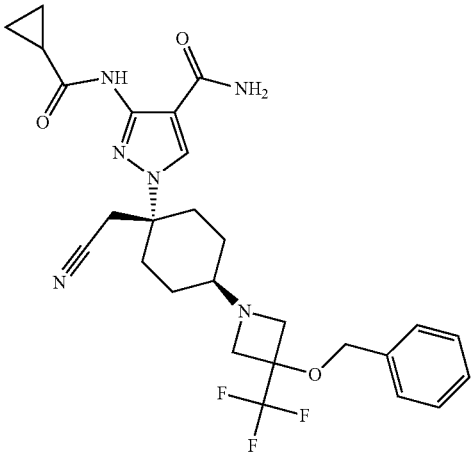 [SMILES: N#CC[C@]1(n2cc(C(N)=O)c(NC(=O)C3CC3)n2)CC[C@H](N2CC(OCc3ccccc3)(C(F)(F)F)C2)CC1] | 545 |
| 135 | G | 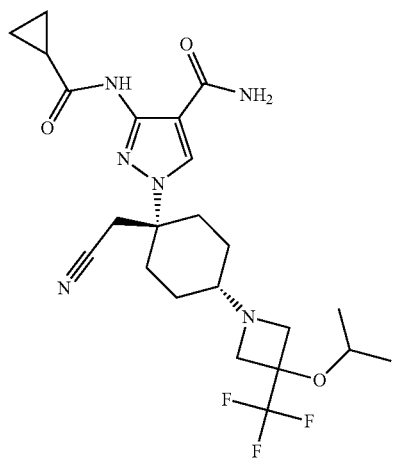 [SMILES: CC(C)OC1(C(F)(F)F)CN([C@H]2CC[C@@](CC#N)(n3cc(C(N)=O)c(NC(=O)C4CC4)n3)CC2)C1] | 497 |
| 136 | G | 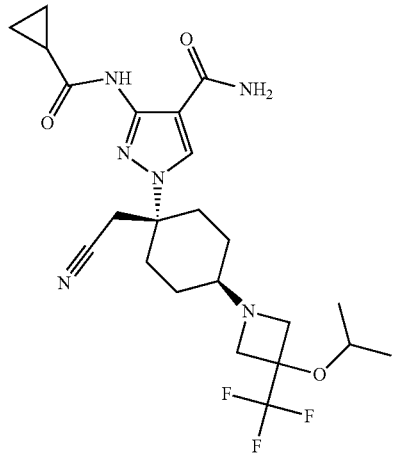 [SMILES: CC(C)OC1(C(F)(F)F)CN([C@H]2CC[C@](CC#N)(n3cc(C(N)=O)c(NC(=O)C4CC4)n3)CC2)C1] | 497 |

TABLE 2-continued
LCMS Procedures.
| Example | General Procedure | Structure | m/z |
|---|---|---|---|
| 137 | G | 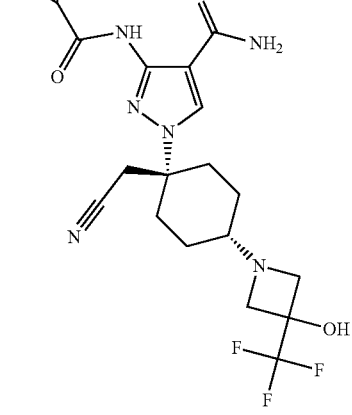 | 455 |
| 138 | G | 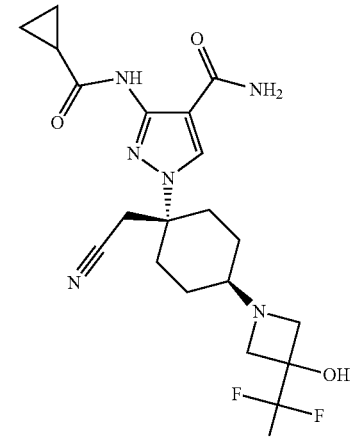 | 455 |
| 139 | H | 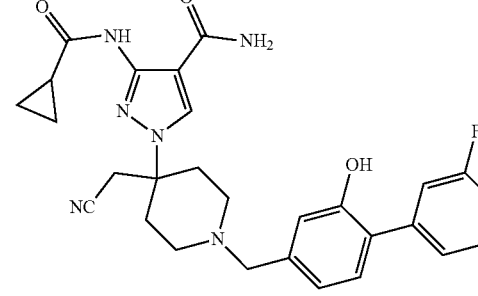 | 517 |
| 140 | H | 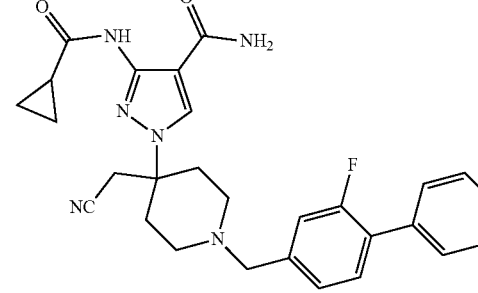 | 501 |

TABLE 2-continued
LCMS Procedures.
| Example | General Procedure | Structure | m/z |
|---|---|---|---|
| 141 | H | 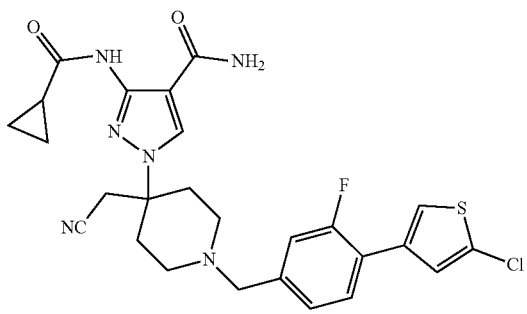 [SMILES: N#CCC1(n2cc(C(N)=O)c(NC(=O)C3CC3)n2)CCN(Cc2ccc(-c3csc(Cl)c3)c(F)c2)CC1] | 541 |
| 142 | H | 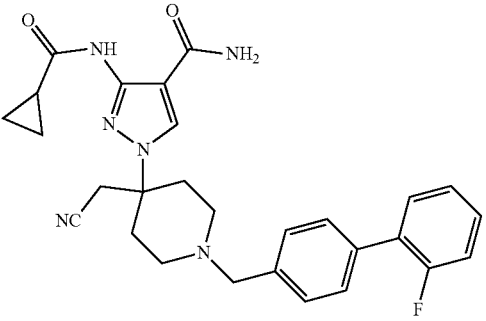 [SMILES: N#CCC1(n2cc(C(N)=O)c(NC(=O)C3CC3)n2)CCN(Cc2ccc(-c3ccccc3F)cc2)CC1] | 501 |
| 143 | H | 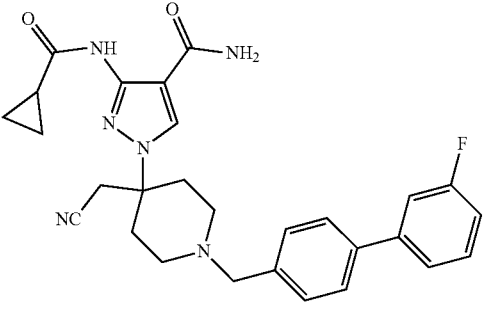 [SMILES: N#CCC1(n2cc(C(N)=O)c(NC(=O)C3CC3)n2)CCN(Cc2ccc(-c3cccc(F)c3)cc2)CC1] | 501 |
| 144 | H | 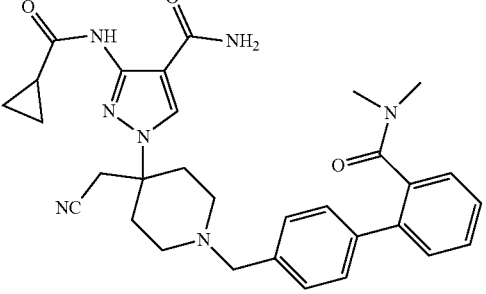 | 554 |

TABLE 2-continued

LCMS Procedures.

| Example | General Procedure | Structure | m/z |
|---|---|---|---|
| 145 | H | 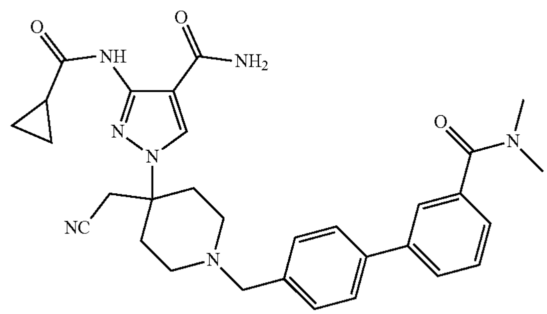 [SMILES: CN(C)C(=O)c1cccc(-c2ccc(CN3CCC(CC#N)(n4cc(C(N)=O)c(NC(=O)C5CC5)n4)CC3)cc2)c1] | 554 |
| 146 | H | 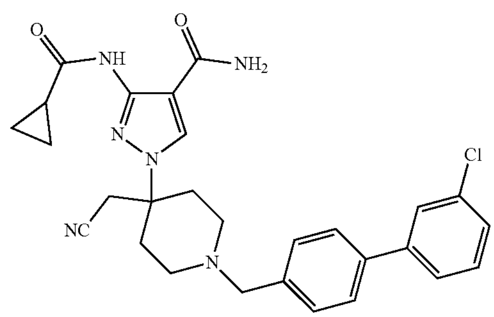 | 517 |
| 147 | H | 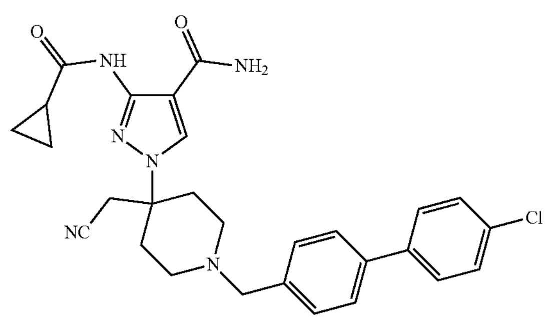 [SMILES: N#CCC1(n2cc(C(N)=O)c(NC(=O)C3CC3)n2)CCN(Cc2ccc(-c3ccc(Cl)cc3)cc2)CC1] | 517 |
| 148 | H | 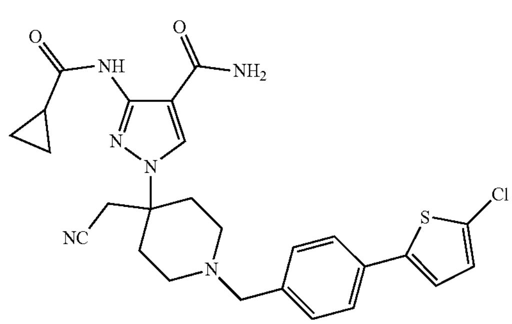 [SMILES: N#CCC1(n2cc(C(N)=O)c(NC(=O)C3CC3)n2)CCN(Cc2ccc(-c3ccc(Cl)s3)cc2)CC1] | 523 |

TABLE 2-continued
LCMS Procedures.
| Example | General Procedure | Structure | m/z |
|---|---|---|---|
| 149 | H | 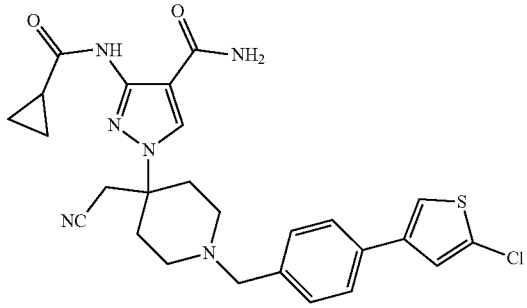 [SMILES: N#CCC1(n2cc(C(N)=O)c(NC(=O)C3CC3)n2)CCN(Cc2ccc(-c3csc(Cl)c3)cc2)CC1] | 523 |
| 150 | H | 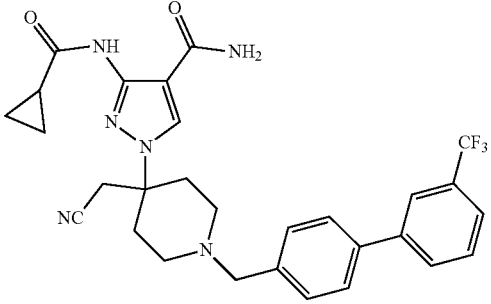 [SMILES: N#CCC1(n2cc(C(N)=O)c(NC(=O)C3CC3)n2)CCN(Cc2ccc(-c3cccc(C(F)(F)F)c3)cc2)CC1] | 551 |
| 151 | H | 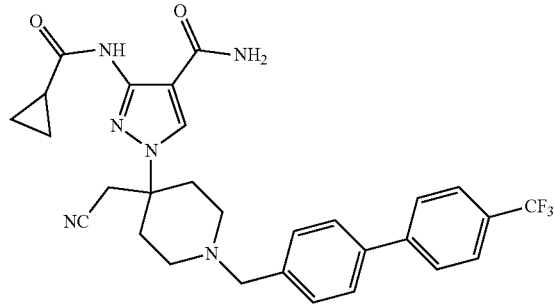 [SMILES: N#CCC1(n2cc(C(N)=O)c(NC(=O)C3CC3)n2)CCN(Cc2ccc(-c3ccc(C(F)(F)F)cc3)cc2)CC1] | 551 |
| 152 | H | 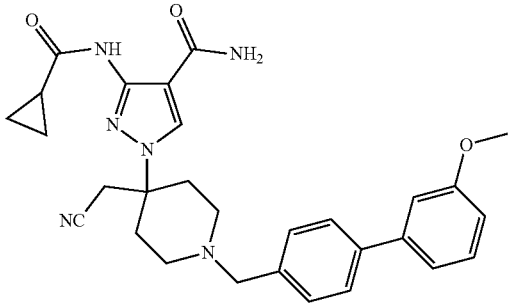 [SMILES: COc1cccc(-c2ccc(CN3CCC(CC#N)(n4cc(C(N)=O)c(NC(=O)C5CC5)n4)CC3)cc2)c1] | 513 |

TABLE 2-continued
LCMS Procedures.
| Example | General Procedure | Structure | m/z |
|---|---|---|---|
| 153 | H | 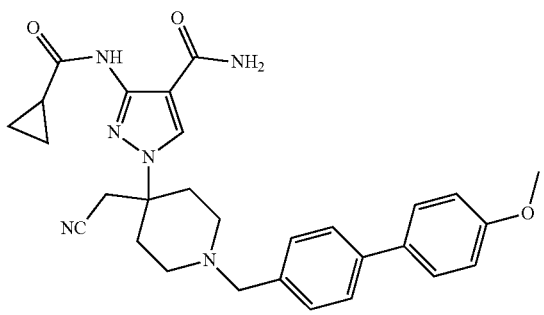 [SMILES: COc1ccc(-c2ccc(CN3CCC(CC#N)(n4cc(C(N)=O)c(NC(=O)C5CC5)n4)CC3)cc2)cc1] | 513 |
| 154 | H | 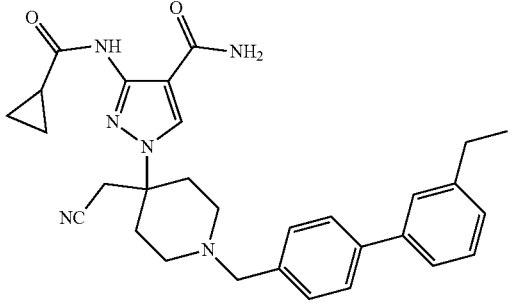 [SMILES: CCc1cccc(-c2ccc(CN3CCC(CC#N)(n4cc(C(N)=O)c(NC(=O)C5CC5)n4)CC3)cc2)c1] | 511 |
| 155 | H | 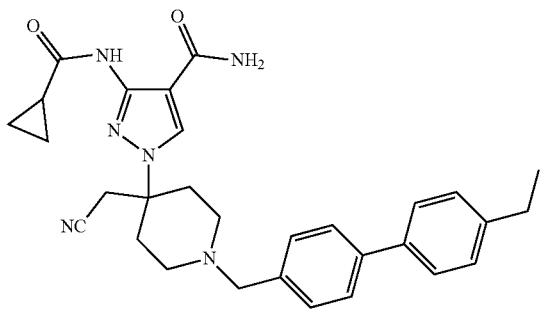 | 511 |
| 156 | H | 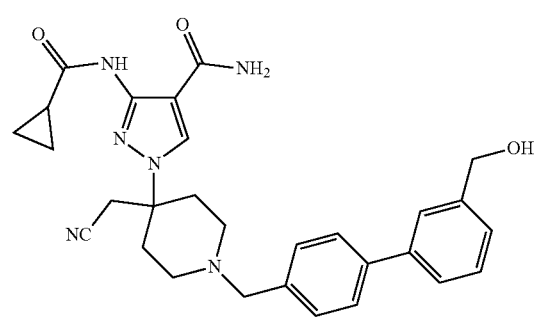 [SMILES: N#CCC1(n2cc(C(N)=O)c(NC(=O)C3CC3)n2)CCN(Cc2ccc(-c3cccc(CO)c3)cc2)CC1] | 513 |

TABLE 2-continued
LCMS Procedures.
| Example | General Procedure | Structure | m/z |
|---|---|---|---|
| 157 | H | 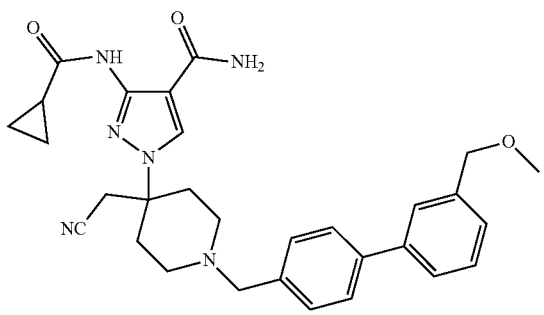 [SMILES: COCc1cccc(-c2ccc(CN3CCC(CC#N)(n4cc(C(N)=O)c(NC(=O)C5CC5)n4)CC3)cc2)c1] | 527 |
| 158 | H | 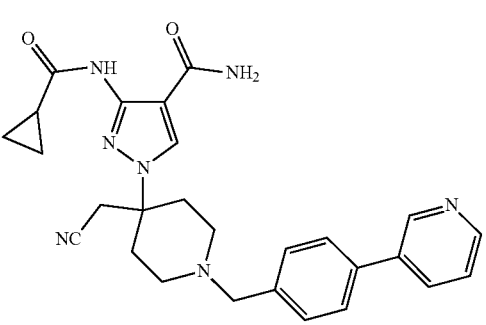 [SMILES: N#CCC1(n2cc(C(N)=O)c(NC(=O)C3CC3)n2)CCN(Cc2ccc(-c3cccnc3)cc2)CC1] | 484 |
| 159 | H | 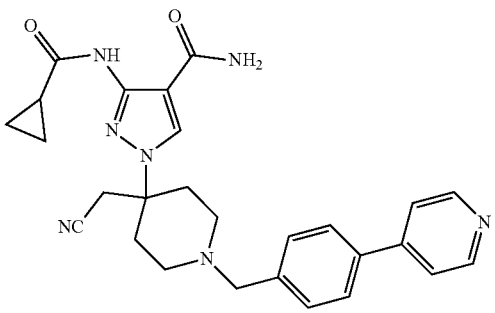 [SMILES: N#CCC1(n2cc(C(N)=O)c(NC(=O)C3CC3)n2)CCN(Cc2ccc(-c3ccncc3)cc2)CC1] | 484 |
| 160 | H | 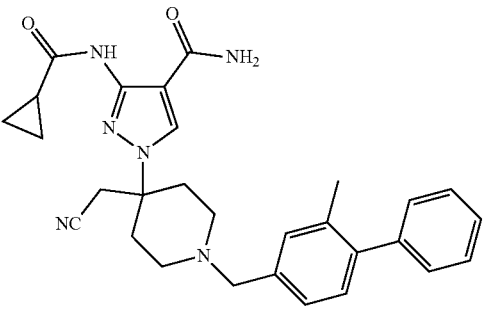 | 497 |

TABLE 2-continued
LCMS Procedures.
| Example | General Procedure | Structure | m/z |
|---|---|---|---|
| 161 | H | 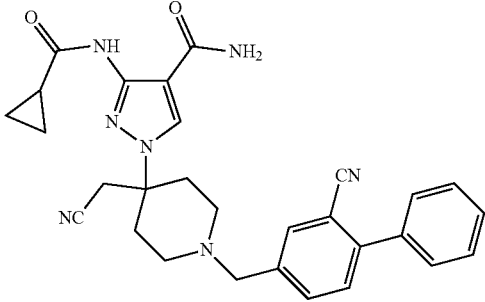 | 508 |
| 162 | H | 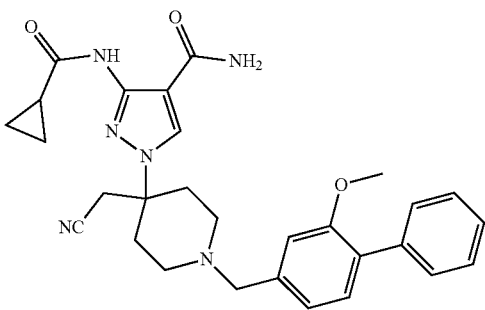 [SMILES: COc1cc(CN2CCC(CC#N)(n3cc(C(N)=O)c(NC(=O)C4CC4)n3)CC2)ccc1-c1ccccc1] | 513 |
| 163 | H | 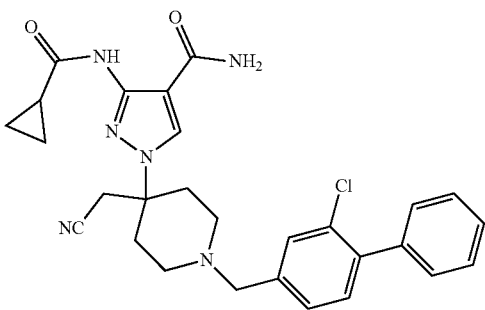 [SMILES: N#CCC1(n2cc(C(N)=O)c(NC(=O)C3CC3)n2)CCN(Cc2ccc(-c3ccccc3)c(Cl)c2)CC1] | 517 |
| 164 | I | 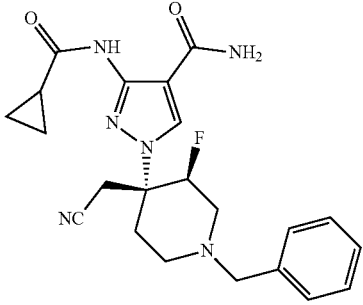 [SMILES: N#CC[C@]1(n2cc(C(N)=O)c(NC(=O)C3CC3)n2)CCN(Cc2ccccc2)C[C@@H]1F] | 425 |

TABLE 2-continued
LCMS Procedures.
| Example | General Procedure | Structure | m/z |
|---|---|---|---|
| 165 | I | 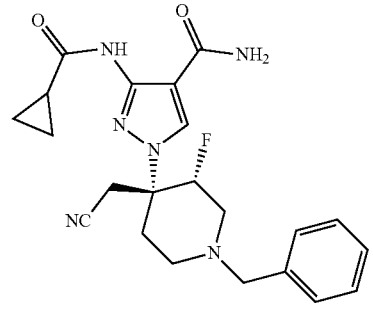 [SMILES: N#CC[C@]1(n2cc(C(N)=O)c(NC(=O)C3CC3)n2)CCN(Cc2ccccc2)C[C@H]1F] | 425 |
| 166 | J | 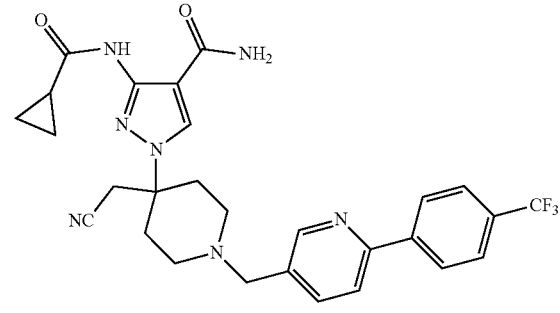 [SMILES: N#CCC1(n2cc(C(N)=O)c(NC(=O)C3CC3)n2)CCN(Cc2ccc(-c3ccc(C(F)(F)F)cc3)nc2)CC1] | 552 |
| 167 | K | 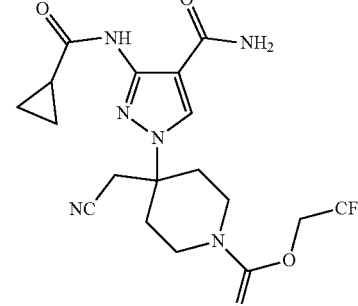 | 443 |
| 168 | L | 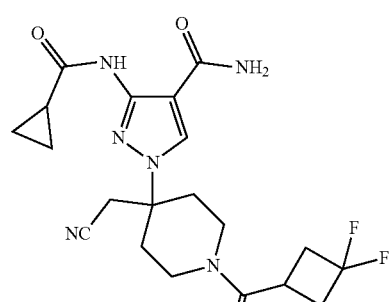 | 435 |

TABLE 2-continued

LCMS Procedures.

| Example | General Procedure | Structure | m/z |
|---|---|---|---|
| 169 | L | 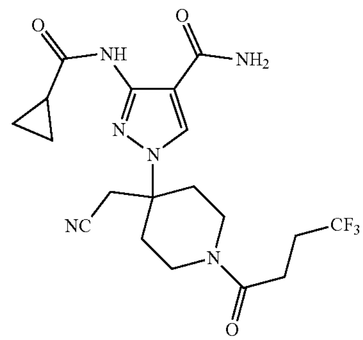 [SMILES: N#CCC1(n2cc(C(N)=O)c(NC(=O)C3CC3)n2)CCN(C(=O)CCC(F)(F)F)CC1] | 441 |
| 170 | L | 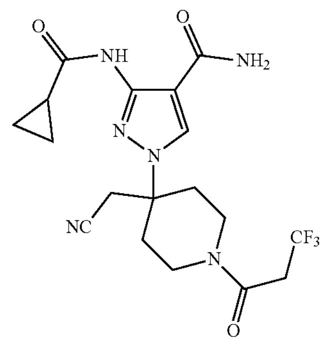 [SMILES: N#CCC1(n2cc(C(N)=O)c(NC(=O)C3CC3)n2)CCN(C(=O)CC(F)(F)F)CC1] | 427 |
| 171 | L | 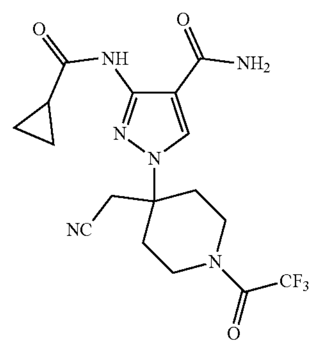 [SMILES: N#CCC1(n2cc(C(N)=O)c(NC(=O)C3CC3)n2)CCN(C(=O)C(F)(F)F)CC1] | 409 |
| 172 | F | 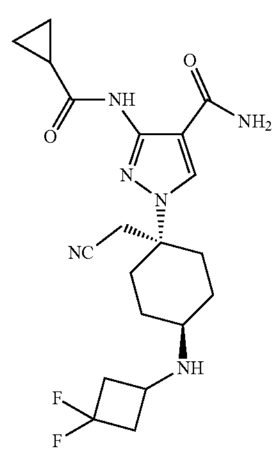 [SMILES: N#CC[C@]1(n2cc(C(N)=O)c(NC(=O)C3CC3)n2)CC[C@H](NC2CC(F)(F)C2)CC1] | 421 |

TABLE 2-continued

LCMS Procedures.

| Example | General Procedure | Structure | m/z |
|---|---|---|---|
| 173 | F | 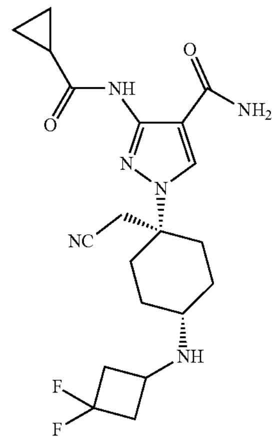 [SMILES: N#CC[C@]1(n2cc(C(N)=O)c(NC(=O)C3CC3)n2)CC[C@@H](NC2CC(F)(F)C2)CC1] | 421 |
| 174 | F | 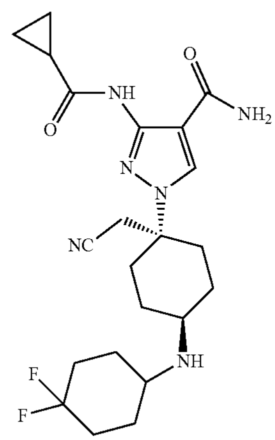 [SMILES: N#CC[C@]1(n2cc(C(N)=O)c(NC(=O)C3CC3)n2)CC[C@H](NC2CCC(F)(F)CC2)CC1] | 449 |
| 175 | F | 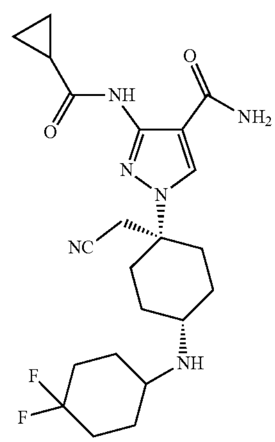 [SMILES: N#CC[C@]1(n2cc(C(N)=O)c(NC(=O)C3CC3)n2)CC[C@@H](NC2CCC(F)(F)CC2)CC1] | 449 |

TABLE 2-continued

LCMS Procedures.

| Example | General Procedure | Structure | m/z |
|---|---|---|---|
| 176 | C | 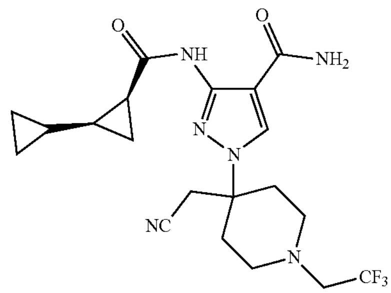 [SMILES: N#CCC1(n2cc(C(N)=O)c(NC(=O)[C@H]3C[C@H]3C3CC3)n2)CCN(CC(F)(F)F)CC1] | 439 |
| 177 | C | 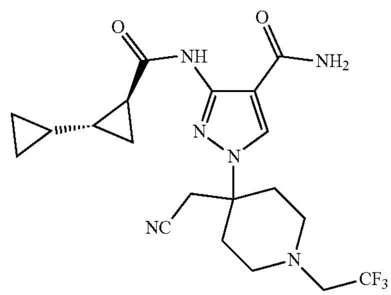 [SMILES: N#CCC1(n2cc(C(N)=O)c(NC(=O)[C@H]3C[C@@H]3C3CC3)n2)CCN(CC(F)(F)F)CC1] | 439 |
| 178 | F | 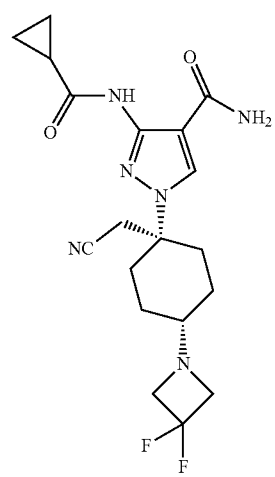 [SMILES: N#CC[C@]1(n2cc(C(N)=O)c(NC(=O)C3CC3)n2)CC[C@@H](N2CC(F)(F)C2)CC1] | 407 |
| 179 | F | 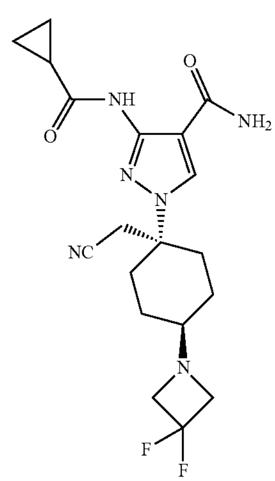 [SMILES: N#CC[C@]1(n2cc(C(N)=O)c(NC(=O)C3CC3)n2)CC[C@H](N2CC(F)(F)C2)CC1] | 407 |

TABLE 2-continued

LCMS Procedures.

| Example | General Procedure | Structure | m/z |
|---|---|---|---|
| 180 | F | 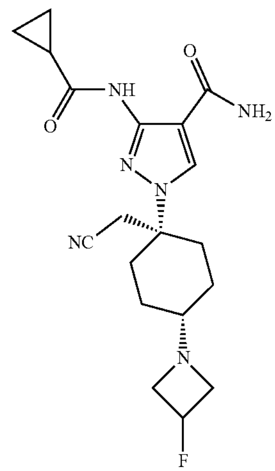 [SMILES: N#CC[C@]1(n2cc(C(N)=O)c(NC(=O)C3CC3)n2)CC[C@@H](N2CC(F)C2)CC1] | 389 |
| 181 | F | 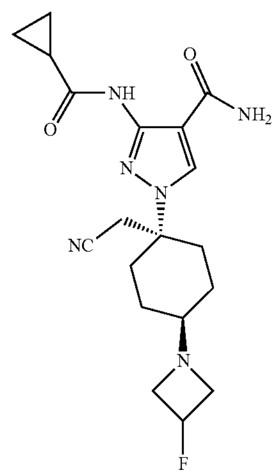 [SMILES: N#CC[C@]1(n2cc(C(N)=O)c(NC(=O)C3CC3)n2)CC[C@H](N2CC(F)C2)CC1] | 389 |
| 182 | K | 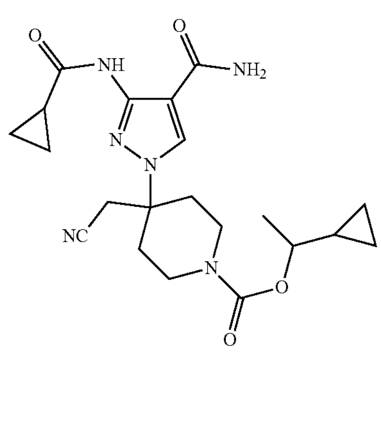 [SMILES: CC(OC(=O)N1CCC(CC#N)(n2cc(C(N)=O)c(NC(=O)C3CC3)n2)CC1)C1CC1] | 429 |

TABLE 2-continued

LCMS Procedures.

| Example | General Procedure | Structure | m/z |
|---------|-------------------|-----------|-----|
| 183 | E | 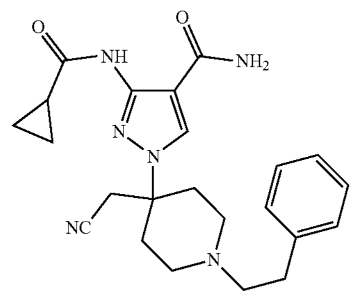 [SMILES: N#CCC1(n2cc(C(N)=O)c(NC(=O)C3CC3)n2)CCN(CCc2ccccc2)CC1] | 421 |
| 184 | E | 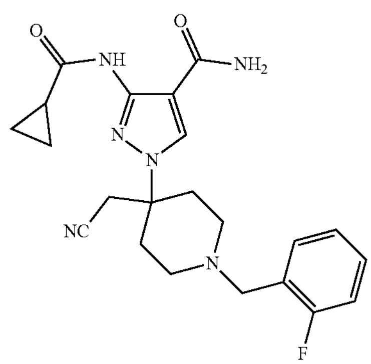 | 425 |
| 185 | H | 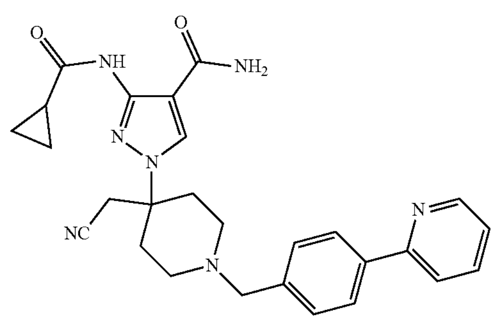 [SMILES: N#CCC1(n2cc(C(N)=O)c(NC(=O)C3CC3)n2)CCN(Cc2ccc(-c3ccccn3)cc2)CC1] | 484 |
| 186 | O | 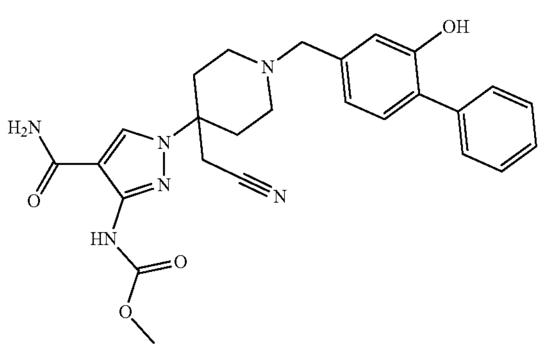 [SMILES: COC(=O)Nc1nn(C2(CC#N)CCN(Cc3ccc(-c4ccccc4)c(O)c3)CC2)cc1C(N)=O] | 489 |

TABLE 2-continued
LCMS Procedures.
| Example | General Procedure | Structure | m/z |
|---|---|---|---|
| 187 | O | 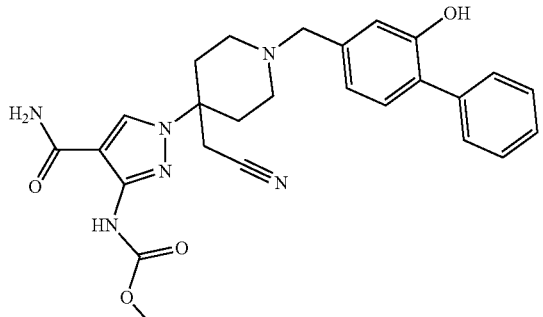 | 503 |
| 188 | H | 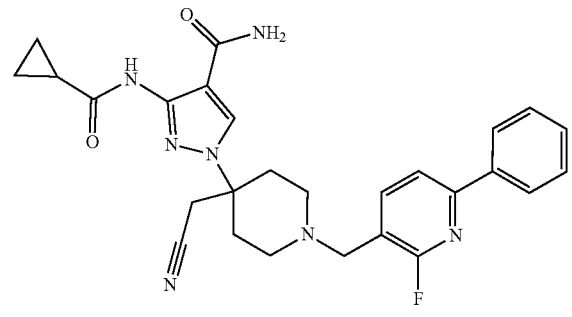 [SMILES: N#CCC1(n2cc(C(N)=O)c(NC(=O)C3CC3)n2)CCN(Cc2ccc(-c3ccccc3)nc2F)CC1] | 502 |
| 189 | H | 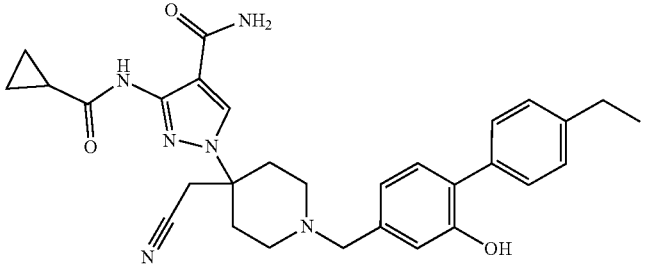 [SMILES: CCc1ccc(-c2ccc(CN3CCC(CC#N)(n4cc(C(N)=O)c(NC(=O)C5CC5)n4)CC3)cc2O)cc1] | 527 |
| 190 | H | 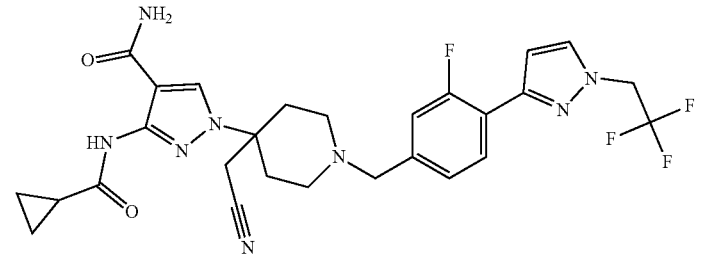 [SMILES: N#CCC1(n2cc(C(N)=O)c(NC(=O)C3CC3)n2)CCN(Cc2ccc(-c3ccn(CC(F)(F)F)n3)c(F)c2)CC1] | 573 |
| 191 | H | 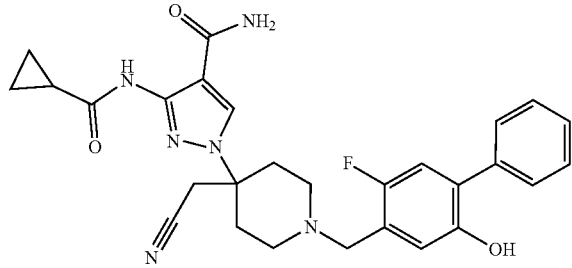 [SMILES: N#CCC1(n2cc(C(N)=O)c(NC(=O)C3CC3)n2)CCN(Cc2cc(O)c(-c3ccccc3)cc2F)CC1] | 517 |

TABLE 2-continued
LCMS Procedures.
| Example | General Procedure | Structure | m/z |
|---|---|---|---|
| 192 | I | 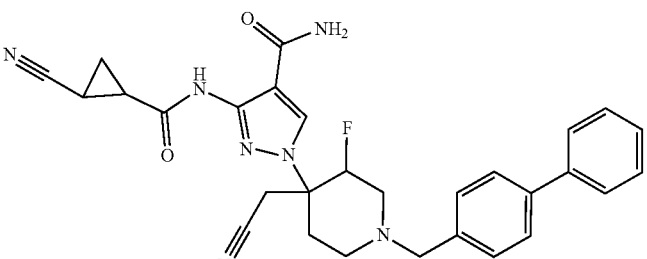 | 526 |
| 193 | I | 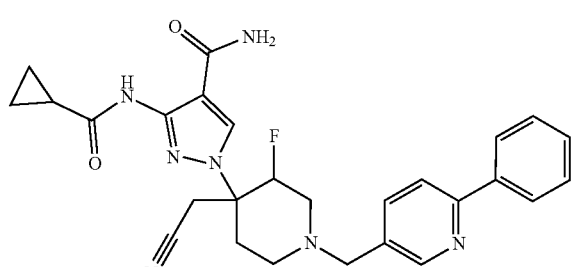 | 502 |
| 194 | H | 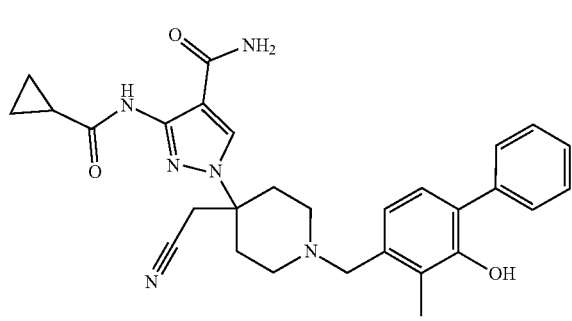 [SMILES: Cc1c(CN2CCC(CC#N)(n3cc(C(N)=O)c(NC(=O)C4CC4)n3)CC2)ccc(-c2ccccc2)c1O] | 513 |
| 195 | R | 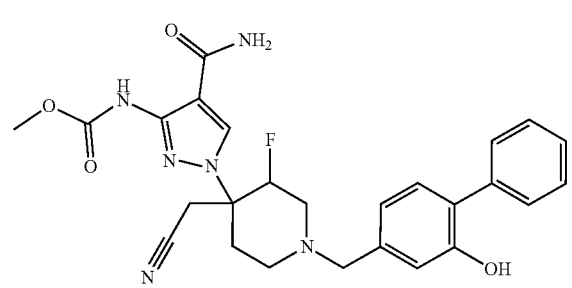 [SMILES: COC(=O)Nc1nn(C2(CC#N)CCN(Cc3ccc(-c4ccccc4)c(O)c3)CC2F)cc1C(N)=O] | 507 |
| 196 | R | 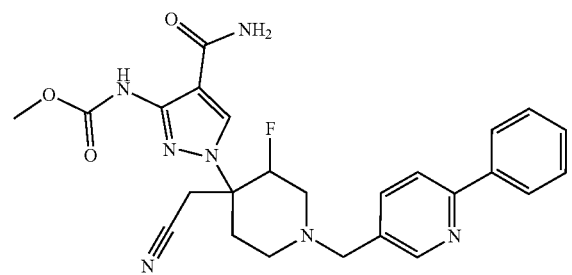 [SMILES: COC(=O)Nc1nn(C2(CC#N)CCN(Cc3ccc(-c4ccccc4)nc3)CC2F)cc1C(N)=O] | 492 |

TABLE 2-continued
LCMS Procedures.
| Example | General Procedure | Structure | m/z |
|---|---|---|---|
| 197 | O | 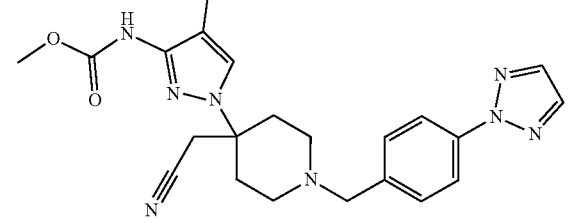 | 464 |
| 198 | O | 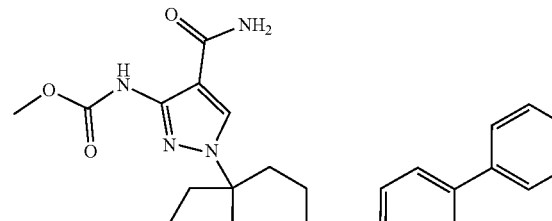 | 492 |
| 199 | I | 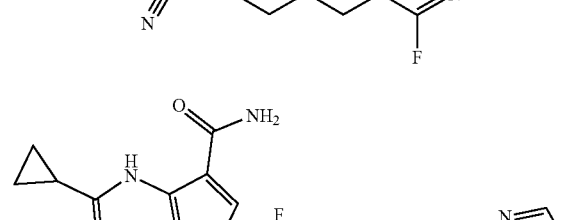 | 492 |
| 200 | R | 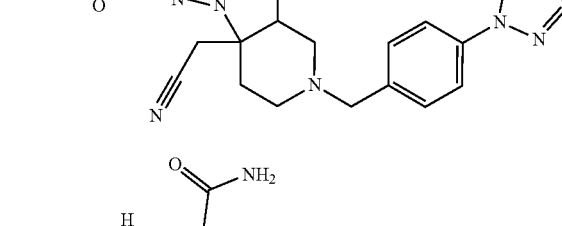 | 482 |
| 201 | I | 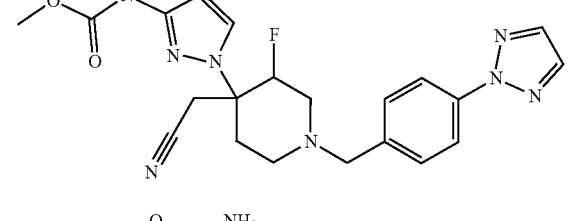 | 520 |

TABLE 2-continued
LCMS Procedures.
| Example | General Procedure | Structure | m/z |
|---|---|---|---|
| 202 | H | 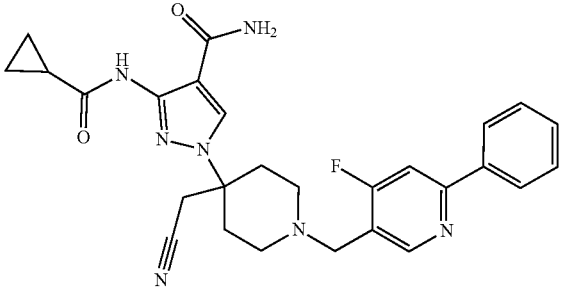 [SMILES: N#CCC1(n2cc(C(N)=O)c(NC(=O)C3CC3)n2)CCN(Cc2cnc(-c3ccccc3)cc2F)CC1] | 502 |
| 203 | R | 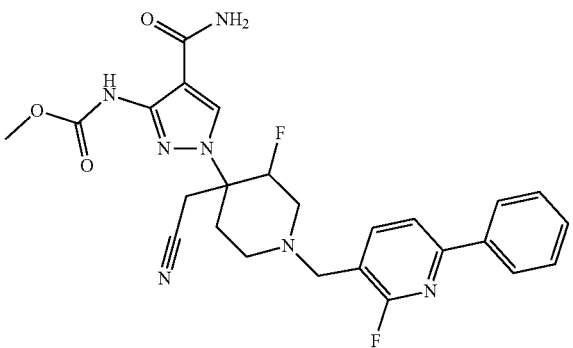 [SMILES: COC(=O)Nc1nn(C2(CC#N)CCN(Cc3ccc(-c4ccccc4)nc3F)CC2F)cc1C(N)=O] | 510 |
| 204 | H | 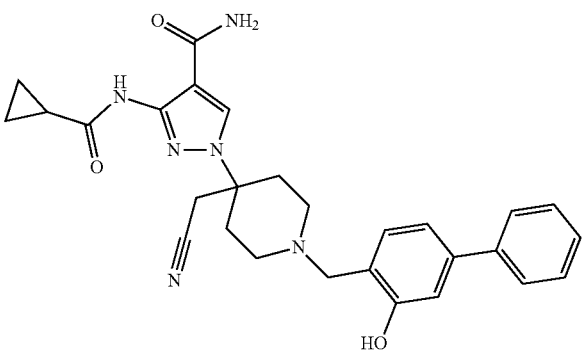 [SMILES: N#CCC1(n2cc(C(N)=O)c(NC(=O)C3CC3)n2)CCN(Cc2ccc(-c3ccccc3)cc2O)CC1] | 499 |
| 205 | F | 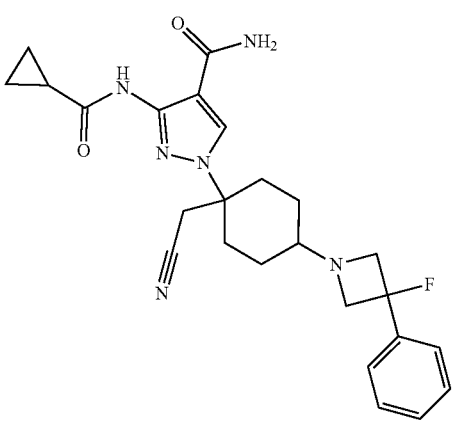 [SMILES: N#CCC1(n2cc(C(N)=O)c(NC(=O)C3CC3)n2)CCC(N2CC(F)(c3ccccc3)C2)CC1] | 465 |

TABLE 2-continued
LCMS Procedures.
| Example | General Procedure | Structure | m/z |
|---|---|---|---|
| 206 | O | 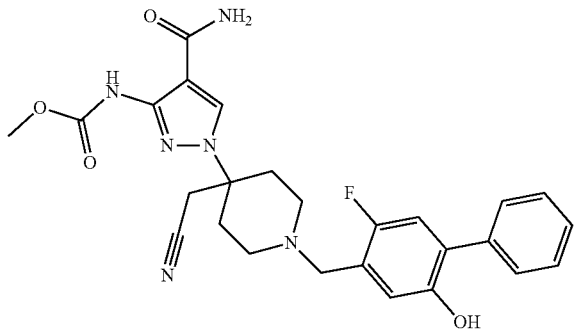 [SMILES: COC(=O)Nc1nn(C2(CC#N)CCN(Cc3cc(O)c(-c4ccccc4)cc3F)CC2)cc1C(N)=O] | 507 |
| 207 | I | 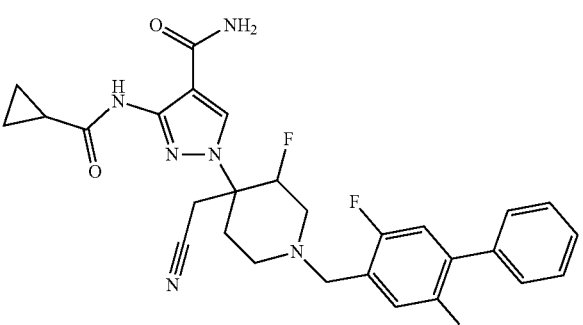 | 535 |
| 208 | R | 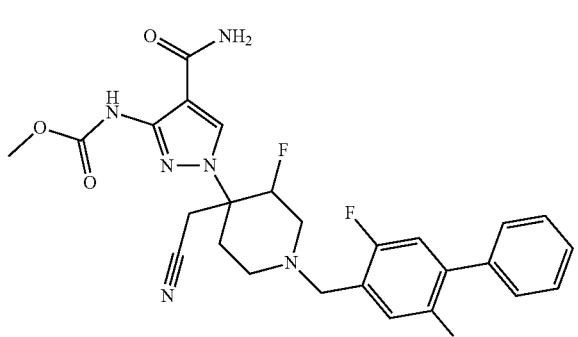 | 525 |
| 209 | E | 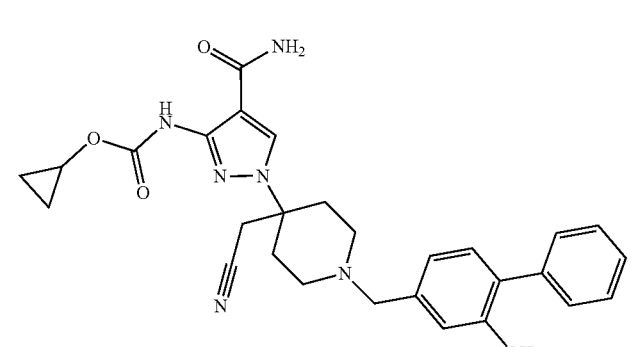 | 515 |

TABLE 2-continued
LCMS Procedures.
| Example | General Procedure | Structure | m/z |
|---|---|---|---|
| 210 | P | 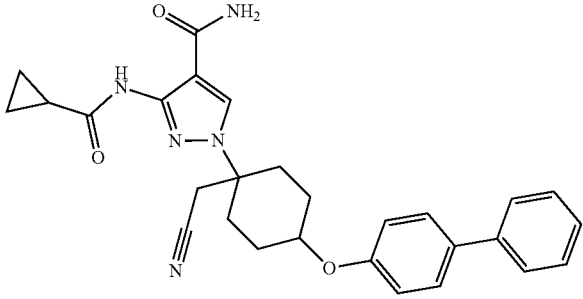 [SMILES: N#CCC1(n2cc(C(N)=O)c(NC(=O)C3CC3)n2)CCC(Oc2ccc(-c3ccccc3)cc2)CC1] | 484 |
| 211 | P | 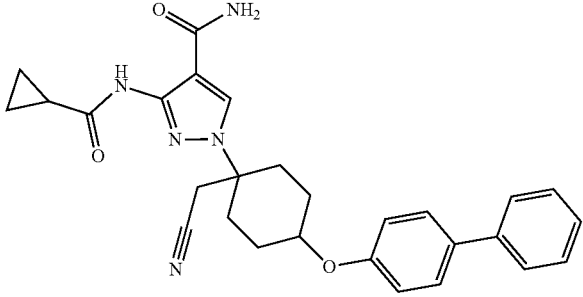 [SMILES: N#CCC1(n2cc(C(N)=O)c(NC(=O)C3CC3)n2)CCC(Oc2ccc(-c3ccccc3)cc2)CC1] | 484 |
| 212 | I | 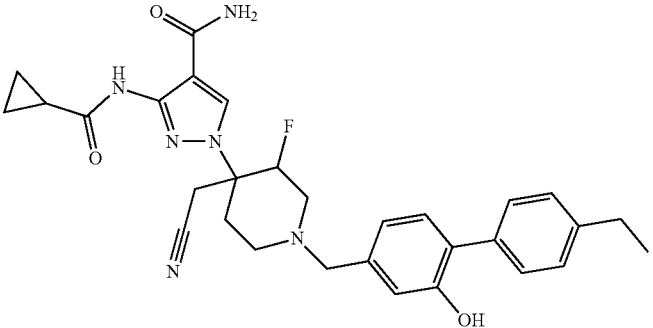 [SMILES: CCc1ccc(-c2ccc(CN3CCC(CC#N)(n4cc(C(N)=O)c(NC(=O)C5CC5)n4)C(F)C3)cc2O)cc1] | 545 |
| 213 | I | 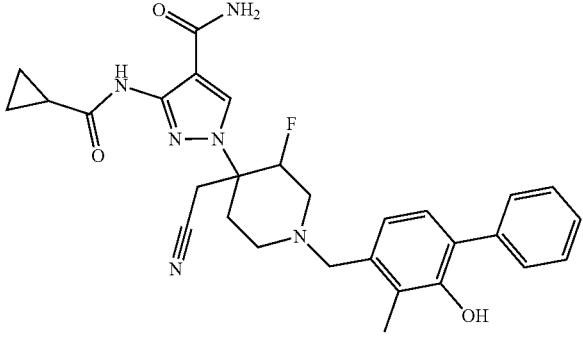 [SMILES: Cc1c(CN2CCC(CC#N)(n3cc(C(N)=O)c(NC(=O)C4CC4)n3)C(F)C2)ccc(-c2ccccc2)c1O] | 531 |

TABLE 2-continued

LCMS Procedures.

| Example | General Procedure | Structure | m/z |
|---------|-------------------|-----------|-----|
| 214 | I | 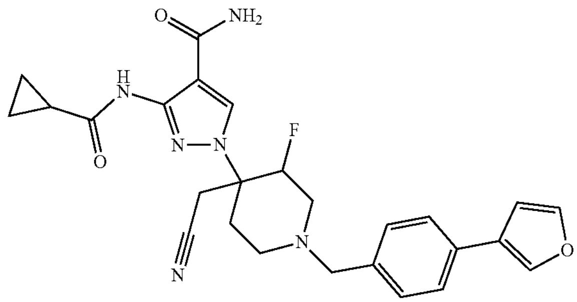 [SMILES: N#CCC1(n2cc(C(N)=O)c(NC(=O)C3CC3)n2)CCN(Cc2ccc(-c3ccoc3)cc2)CC1F] | 491 |
| 215 | I | 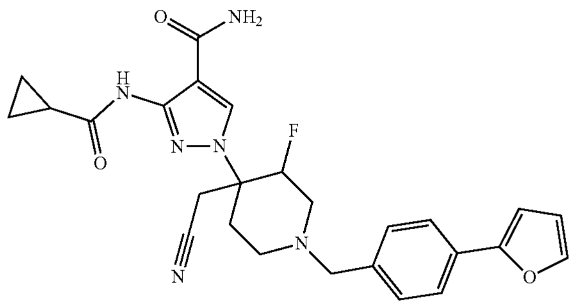 [SMILES: N#CCC1(n2cc(C(N)=O)c(NC(=O)C3CC3)n2)CCN(Cc2ccc(-c3ccco3)cc2)CC1F] | 491 |
| 216 | R | 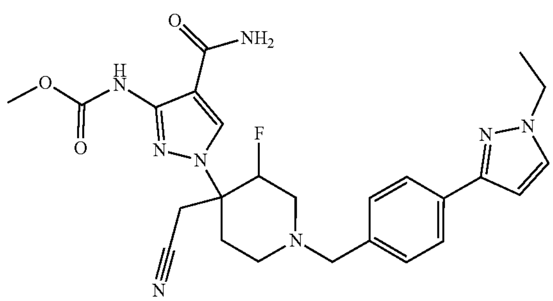 [SMILES: CCn1ccc(-c2ccc(CN3CCC(CC#N)(n4cc(C(N)=O)c(NC(=O)OC)n4)C(F)C3)cc2)n1] | 509 |
| 217 | I | 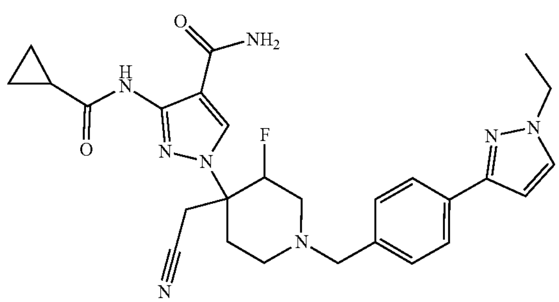 [SMILES: CCn1ccc(-c2ccc(CN3CCC(CC#N)(n4cc(C(N)=O)c(NC(=O)C5CC5)n4)C(F)C3)cc2)n1] | 519 |
| 218 | I | 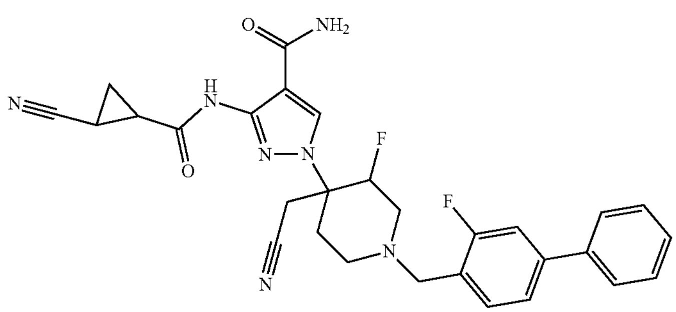 [SMILES: N#CCC1(n2cc(C(N)=O)c(NC(=O)C3CC3C#N)n2)CCN(Cc2ccc(-c3ccccc3)cc2F)CC1F] | 544 |

TABLE 2-continued

LCMS Procedures.

| Example | General Procedure | Structure | m/z |
|---|---|---|---|
| 219 | I | 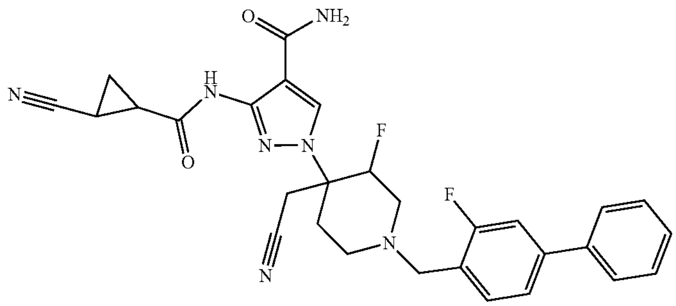 [SMILES: N#CCC1(n2cc(C(N)=O)c(NC(=O)C3CC3C#N)n2)CCN(Cc2ccc(-c3ccccc3)cc2F)CC1F] | 544 |
| 220 | R | 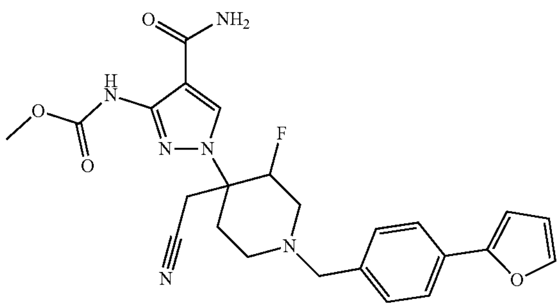 [SMILES: COC(=O)Nc1nn(C2(CC#N)CCN(Cc3ccc(-c4ccco4)cc3)CC2F)cc1C(N)=O] | 481 |
| 221 | I | 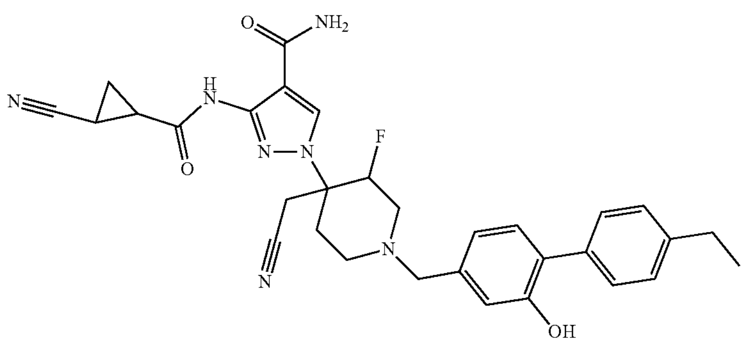 [SMILES: CCc1ccc(-c2ccc(CN3CCC(CC#N)(n4cc(C(N)=O)c(NC(=O)C5CC5C#N)n4)C(F)C3)cc2O)cc1] | 570 |
| 222 | I | 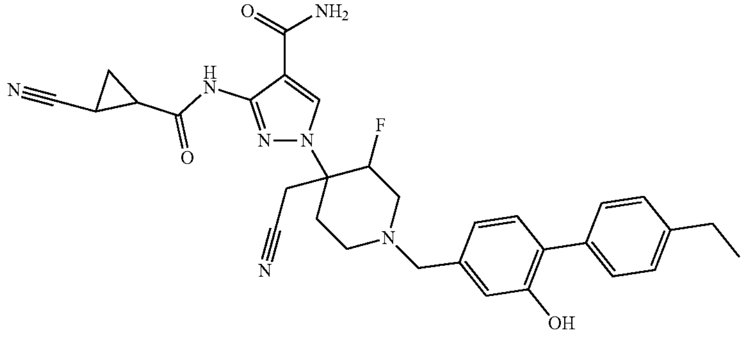 [SMILES: CCc1ccc(-c2ccc(CN3CCC(CC#N)(n4cc(C(N)=O)c(NC(=O)C5CC5C#N)n4)C(F)C3)cc2O)cc1] | 570 |

TABLE 2-continued
LCMS Procedures.
| Example | General Procedure | Structure | m/z |
|---|---|---|---|
| 223 | I | 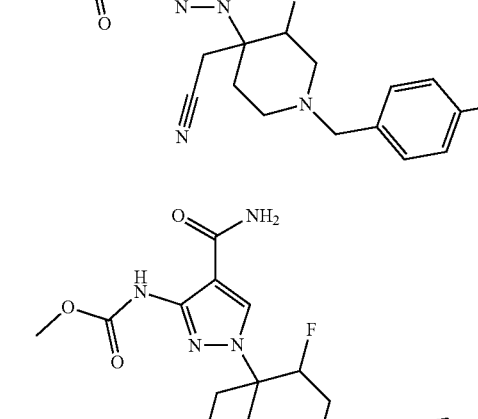 | 505 |
| 224 | R | 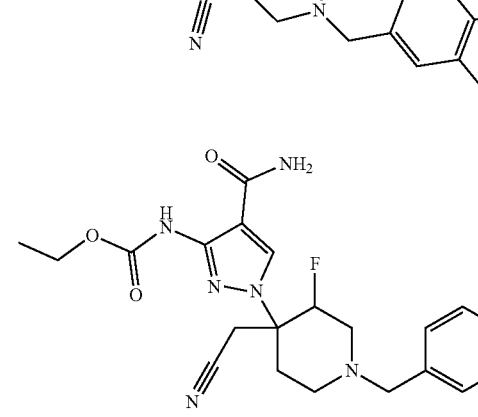 | 497 |
| 225 | R | 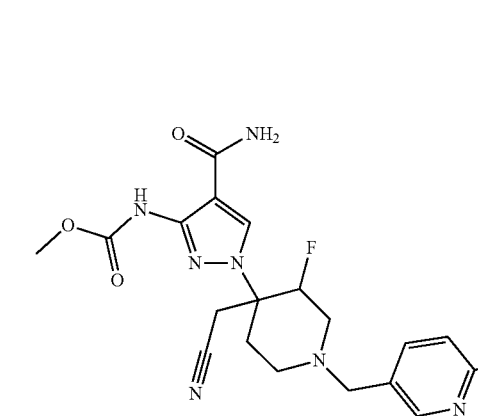 | 496 |
| 226 | R | 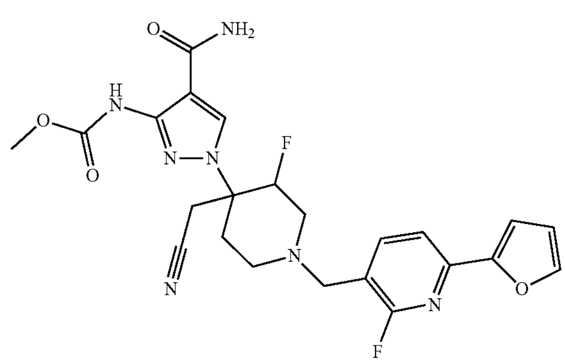 [SMILES: COC(=O)Nc1nn(C2(CC#N)CCN(Cc3ccc(-c4ccco4)nc3F)CC2F)cc1C(N)=O] | 500 |

TABLE 2-continued
LCMS Procedures.
| Example | General Procedure | Structure | m/z |
|---|---|---|---|
| 227 | I | 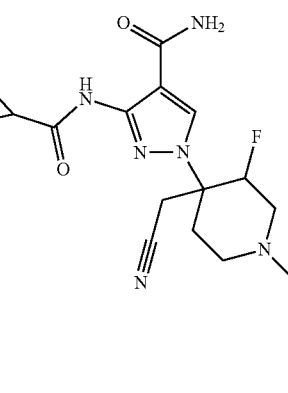 | 545 |
| 228 | I | 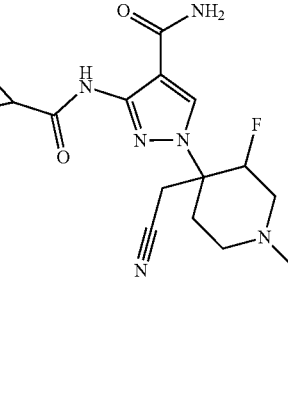 | 532 |
| 229 | I | 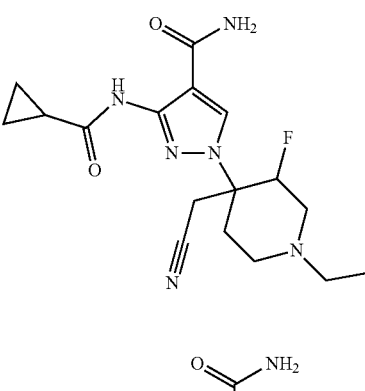 | 505 |
| 230 | I | 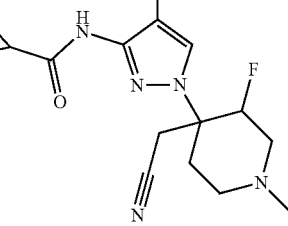 | 532 |

TABLE 2-continued

LCMS Procedures.

| Example | General Procedure | Structure | m/z |
|---------|-------------------|-----------|-----|
| 231 | I | 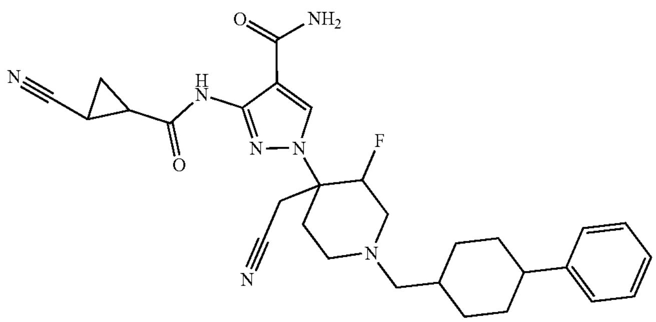 [SMILES: N#CCC1(n2cc(C(N)=O)c(NC(=O)C3CC3C#N)n2)CCN(CC2CCC(c3ccccc3)CC2)CC1F] | 532 |
| 232 | R | 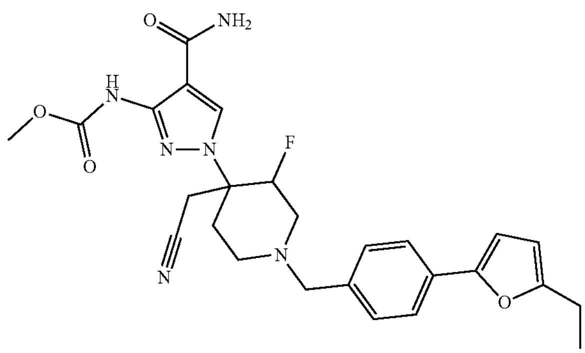 [SMILES: CCc1ccc(-c2ccc(CN3CCC(CC#N)(n4cc(C(N)=O)c(NC(=O)OC)n4)C(F)C3)cc2)o1] | 509 |
| 233 | I | 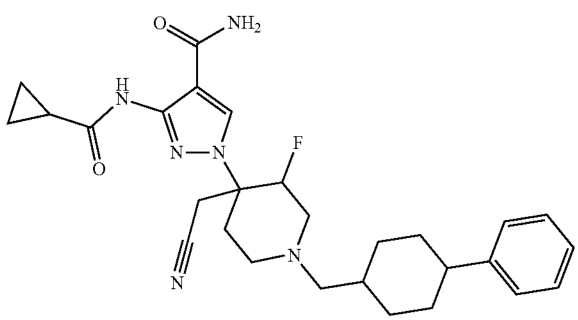 [SMILES: N#CCC1(n2cc(C(N)=O)c(NC(=O)C3CC3)n2)CCN(CC2CCC(c3ccccc3)CC2)CC1F] | 507 |
| 234 | I | 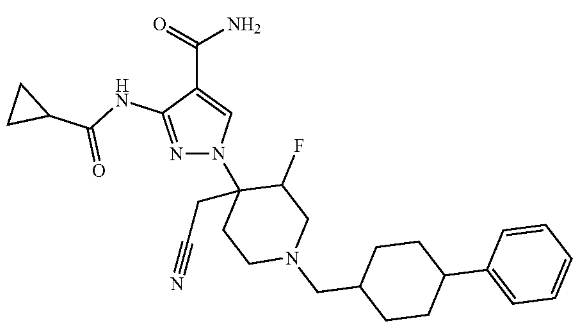 [SMILES: N#CCC1(n2cc(C(N)=O)c(NC(=O)C3CC3)n2)CCN(CC2CCC(c3ccccc3)CC2)CC1F] | 507 |

TABLE 2-continued

LCMS Procedures.

| Example | General Procedure | Structure | m/z |
|---|---|---|---|
| 235 | R | 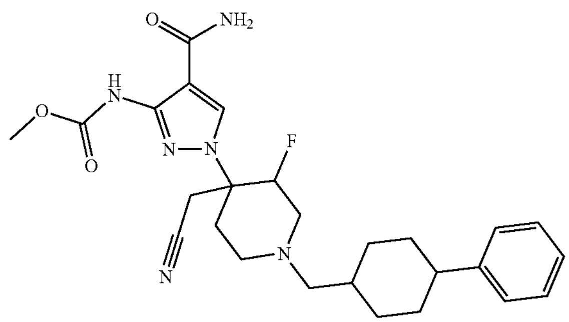 [SMILES: COC(=O)Nc1nn(C2(CC#N)CCN(CC3CCC(c4ccccc4)CC3)CC2F)cc1C(N)=O] | 497 |
| 236 | R | 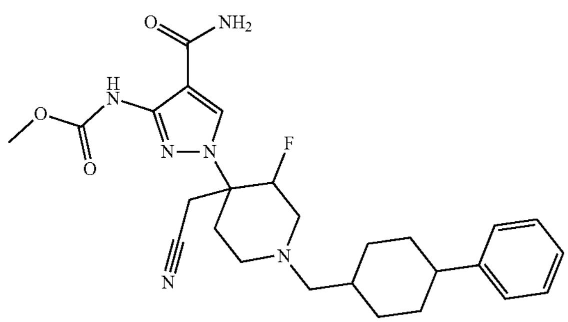 [SMILES: COC(=O)Nc1nn(C2(CC#N)CCN(CC3CCC(c4ccccc4)CC3)CC2F)cc1C(N)=O] | 497 |
| 237 | R | 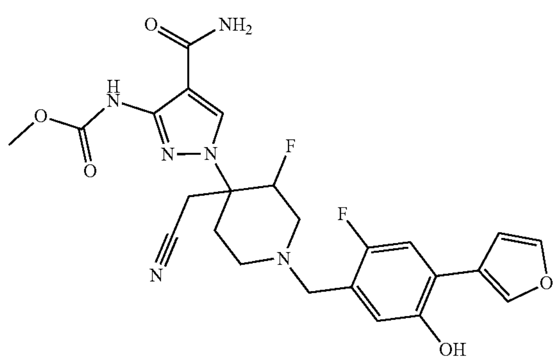 [SMILES: COC(=O)Nc1nn(C2(CC#N)CCN(Cc3cc(O)c(-c4ccoc4)cc3F)CC2F)cc1C(N)=O] | 515 |
| 238 | R | 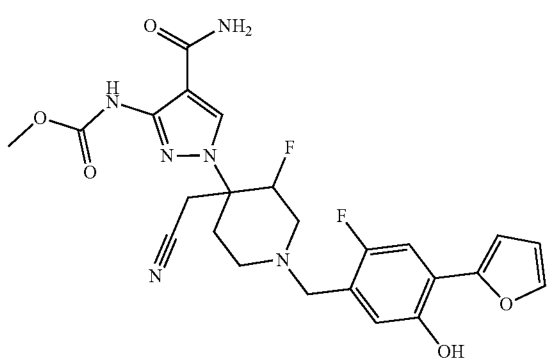 [SMILES: COC(=O)Nc1nn(C2(CC#N)CCN(Cc3cc(O)c(-c4ccco4)cc3F)CC2F)cc1C(N)=O] | 515 |

TABLE 2-continued

LCMS Procedures.

| Example | General Procedure | Structure | m/z |
|---------|-------------------|-----------|-----|
| 239 | R | 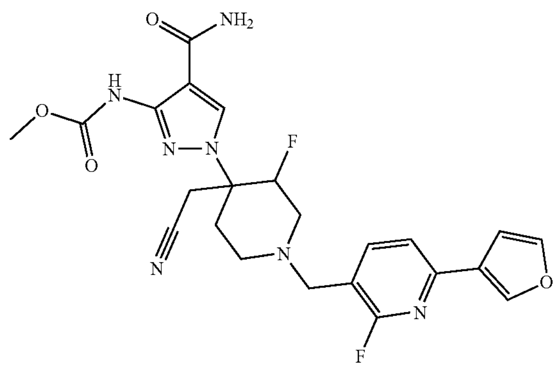 [SMILES: COC(=O)Nc1nn(C2(CC#N)CCN(Cc3ccc(-c4ccoc4)nc3F)CC2F)cc1C(N)=O] | 500 |
| 240 | I | 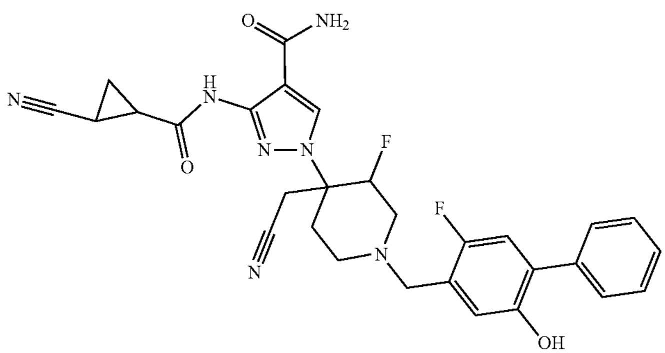 [SMILES: N#CCC1(n2cc(C(N)=O)c(NC(=O)C3CC3C#N)n2)CCN(Cc2cc(O)c(-c3ccccc3)cc2F)CC1F] | 560 |
| 241 | R | 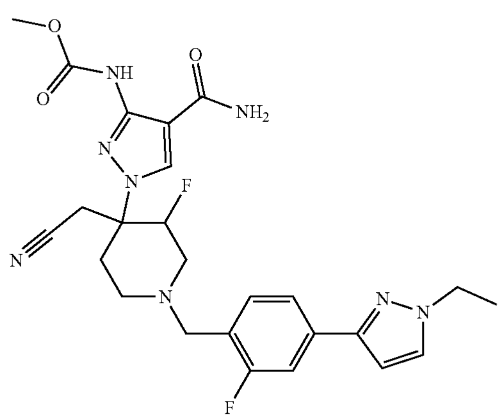 [SMILES: CCn1ccc(-c2ccc(CN3CCC(CC#N)(n4cc(C(N)=O)c(NC(=O)OC)n4)C(F)C3)c(F)c2)n1] | 527 |

TABLE 2-continued

LCMS Procedures.

| Example | General Procedure | Structure | m/z |
|---|---|---|---|
| 242 | I | 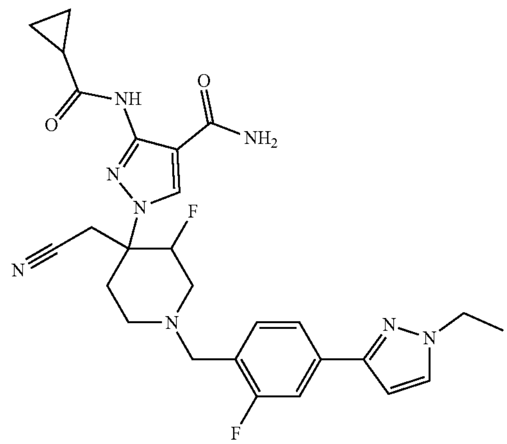 [SMILES: CCn1ccc(-c2ccc(CN3CCC(CC#N)(n4cc(C(N)=O)c(NC(=O)C5CC5)n4)C(F)C3)c(F)c2)n1] | 537 |
| 243 | Q | 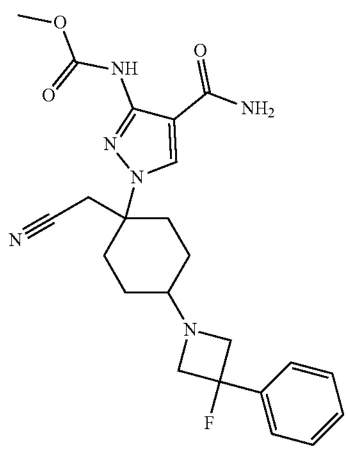 [SMILES: COC(=O)Nc1nn(C2(CC#N)CCC(N3CC(F)(c4ccccc4)C3)CC2)cc1C(N)=O] | 455 |
| 244 | R | 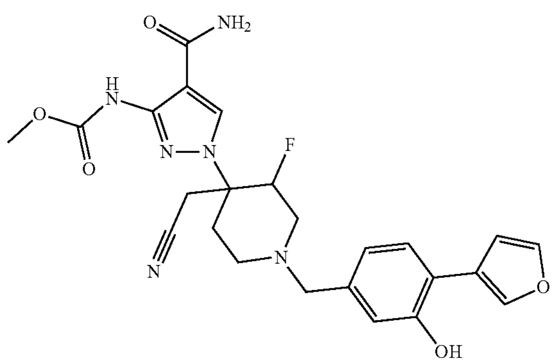 [SMILES: COC(=O)Nc1nn(C2(CC#N)CCN(Cc3ccc(-c4ccoc4)c(O)c3)CC2F)cc1C(N)=O] | 497 |

TABLE 2-continued
LCMS Procedures.
| Example | General Procedure | Structure | m/z |
|---|---|---|---|
| 245 | A | 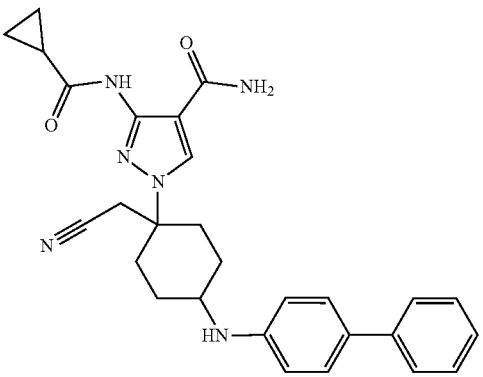 [SMILES: N#CCC1(n2cc(C(N)=O)c(NC(=O)C3CC3)n2)CCC(Nc2ccc(-c3ccccc3)cc2)CC1] | 483 |
| 246 | R | 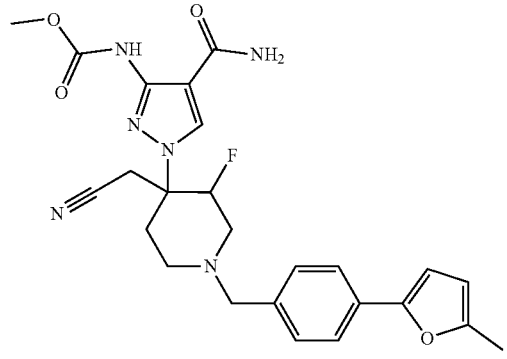 | 495 |
| 247 | R | 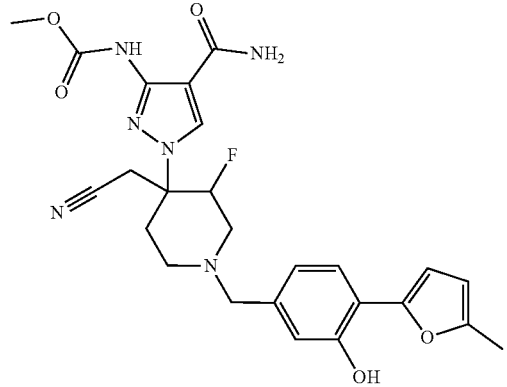 | 511 |
| 248 | R | 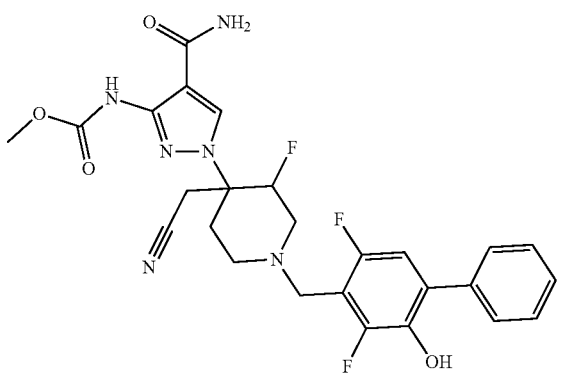 [SMILES: COC(=O)Nc1nn(C2(CC#N)CCN(Cc3c(F)cc(-c4ccccc4)c(O)c3F)CC2F)cc1C(N)=O] | 543 |

TABLE 2-continued
LCMS Procedures.
| Example | General Procedure | Structure | m/z |
|---------|-------------------|-----------|-----|
| 249 | R | 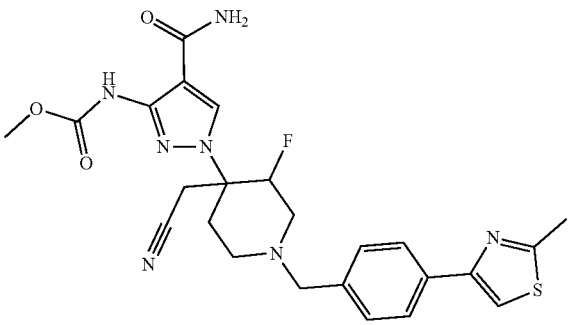 | 512 |
| 250 | I | 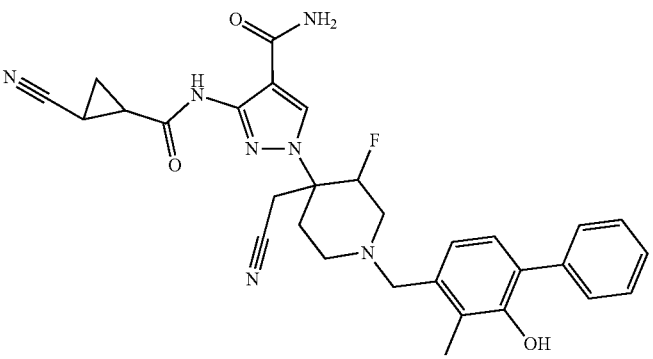 [SMILES: Cc1c(CN2CCC(CC#N)(n3cc(C(N)=O)c(NC(=O)C4CC4C#N)n3)C(F)C2)ccc(-c2ccccc2)c1O] | 556 |
| 251 | R | 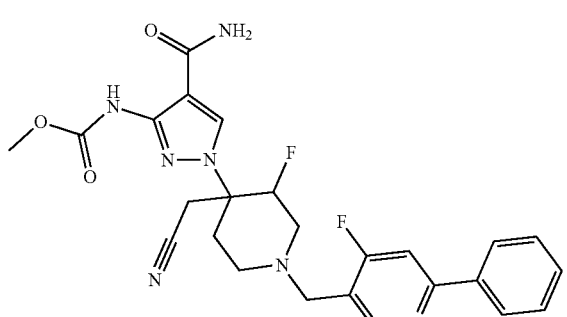 | 510 |
| 252 | R | 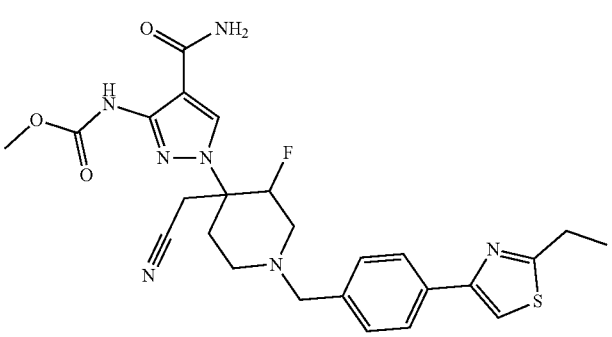 [SMILES: CCc1nc(-c2ccc(CN3CCC(CC#N)(n4cc(C(N)=O)c(NC(=O)OC)n4)C(F)C3)cc2)cs1] | 526 |

TABLE 2-continued
| | | LCMS Procedures. | |
|---|---|---|---|
| Example | General Procedure | Structure | m/z |
| 253 | E | 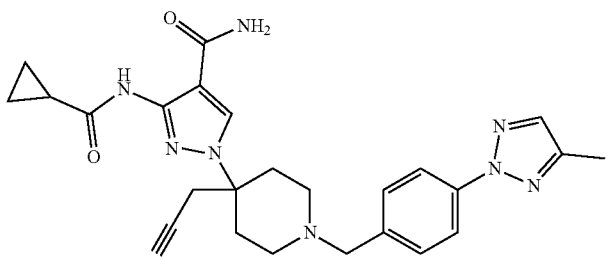 | 488 |
| 254 | I | 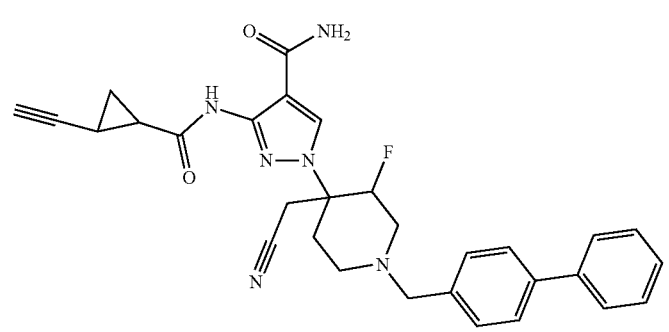 [SMILES: C#CC1CC1C(=O)Nc1nn(C2(CC#N)CCN(Cc3ccc(-c4ccccc4)cc3)CC2F)cc1C(N)=O] | 525 |
| 255 | I | 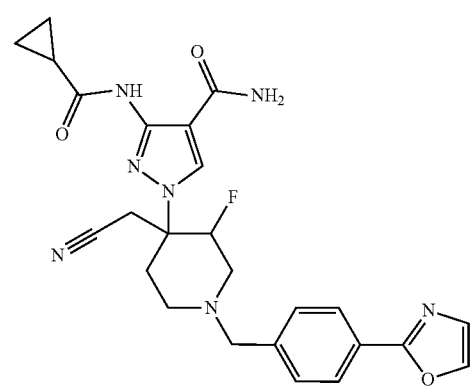 [SMILES: N#CCC1(n2cc(C(N)=O)c(NC(=O)C3CC3)n2)CCN(Cc2ccc(-c3ncco3)cc2)CC1F] | 492 |
| 256 | R | 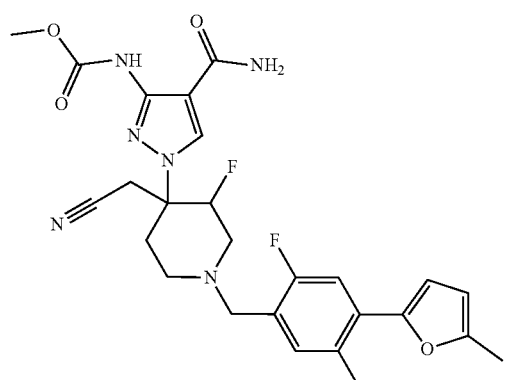 | 529 |

TABLE 2-continued

LCMS Procedures.

| Example | General Procedure | Structure | m/z |
|---------|-------------------|-----------|-----|
| 257 | R | 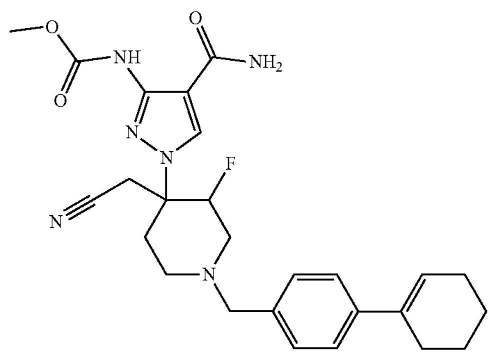 [SMILES: COC(=O)Nc1nn(C2(CC#N)CCN(Cc3ccc(C4=CCCCC4)cc3)CC2F)cc1C(N)=O] | 495 |
| 258 | R | 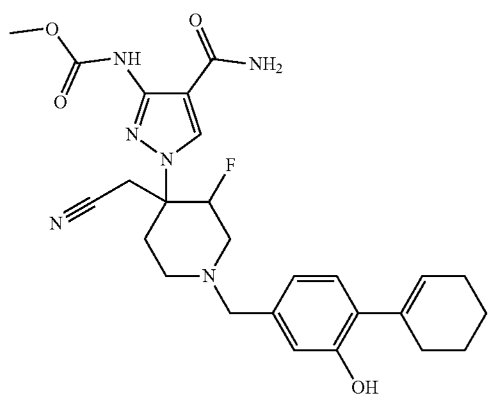 [SMILES: COC(=O)Nc1nn(C2(CC#N)CCN(Cc3ccc(C4=CCCCC4)c(O)c3)CC2F)cc1C(N)=O] | 511 |
| 259 | I | 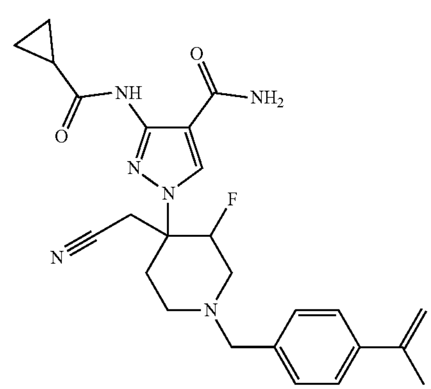 [SMILES: C=C(C)c1ccc(CN2CCC(CC#N)(n3cc(C(N)=O)c(NC(=O)C4CC4)n3)C(F)C2)cc1] | 465 |
| 260 | I | 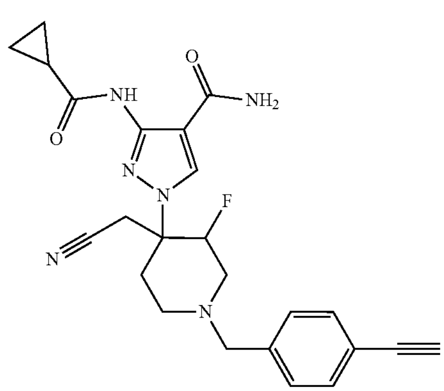 [SMILES: C#Cc1ccc(CN2CCC(CC#N)(n3cc(C(N)=O)c(NC(=O)C4CC4)n3)C(F)C2)cc1] | 449 |

TABLE 2-continued
LCMS Procedures.
| Example | General Procedure | Structure | m/z |
|---|---|---|---|
| 261 | I | 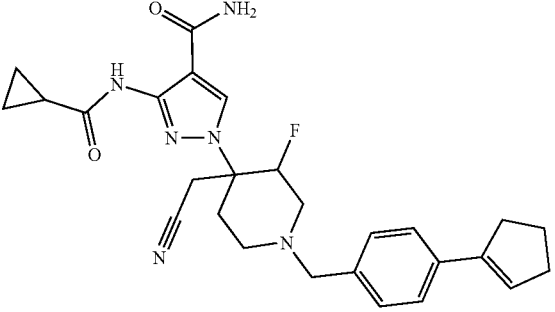 [SMILES: N#CCC1(n2cc(C(N)=O)c(NC(=O)C3CC3)n2)CCN(Cc2ccc(C3=CCCC3)cc2)CC1F] | 491 |
| 262 | Q | 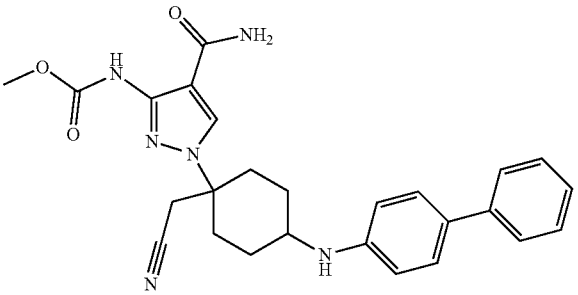 [SMILES: COC(=O)Nc1nn(C2(CC#N)CCC(Nc3ccc(-c4ccccc4)cc3)CC2)cc1C(N)=O] | 473 |
| 263 | R | 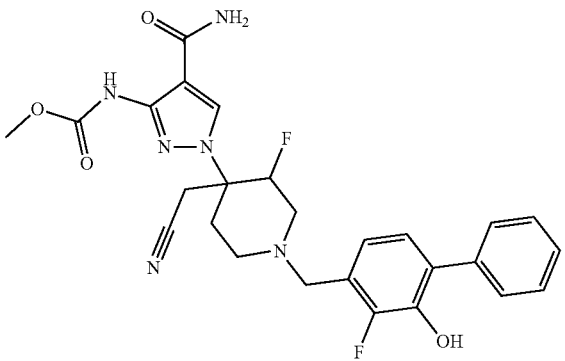 [SMILES: COC(=O)Nc1nn(C2(CC#N)CCN(Cc3ccc(-c4ccccc4)c(O)c3F)CC2F)cc1C(N)=O] | 525 |
| 264 | R | 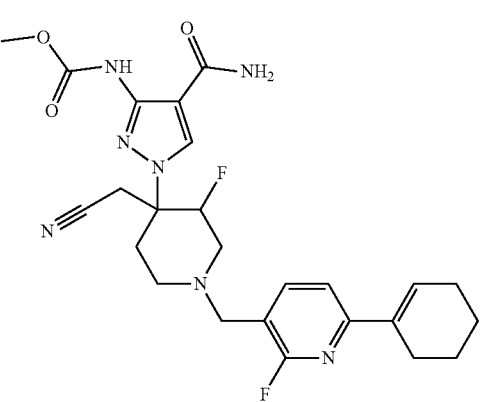 [SMILES: COC(=O)Nc1nn(C2(CC#N)CCN(Cc3ccc(C4=CCCCC4)nc3F)CC2F)cc1C(N)=O] | 514 |

TABLE 2-continued
LCMS Procedures.
| Example | General Procedure | Structure | m/z |
|---|---|---|---|
| 265 | F | 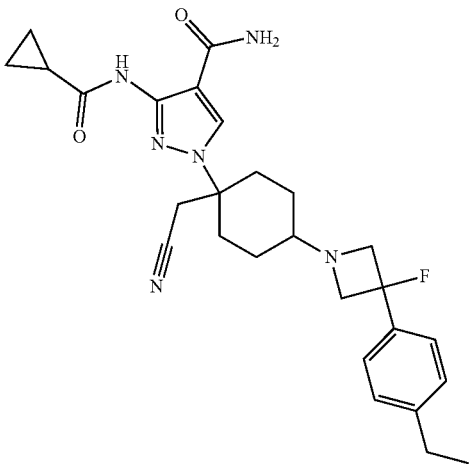 [SMILES: CCc1ccc(C2(F)CN(C3CCC(CC#N)(n4cc(C(N)=O)c(NC(=O)C5CC5)n4)CC3)C2)cc1] | 493 |
| 266 | Q | 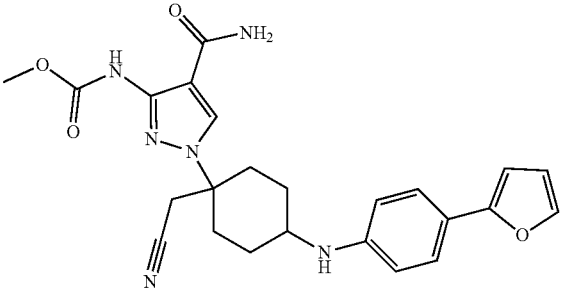 [SMILES: COC(=O)Nc1nn(C2(CC#N)CCC(Nc3ccc(-c4ccco4)cc3)CC2)cc1C(N)=O] | 463 |
| 267 | R | 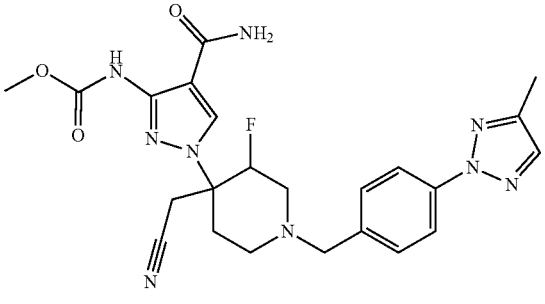 [SMILES: COC(=O)Nc1nn(C2(CC#N)CCN(Cc3ccc(-n4ncc(C)n4)cc3)CC2F)cc1C(N)=O] | 496 |
| 268 | R | 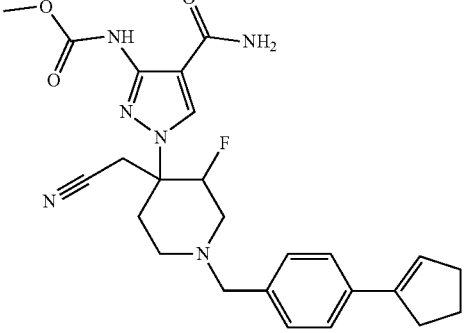 | 481 |

TABLE 2-continued
LCMS Procedures.
| Example | General Procedure | Structure | m/z |
|---|---|---|---|
| 269 | R | 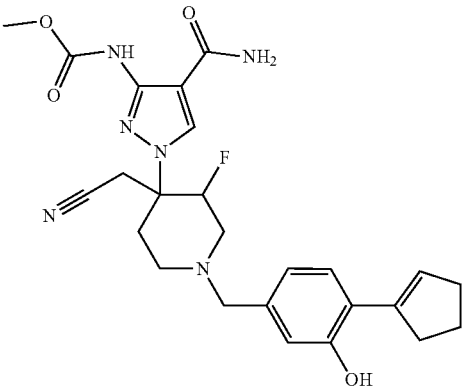 [SMILES: COC(=O)Nc1nn(C2(CC#N)CCN(Cc3ccc(C4=CCCC4)c(O)c3)CC2F)cc1C(N)=O] | 497 |
| 270 | R | 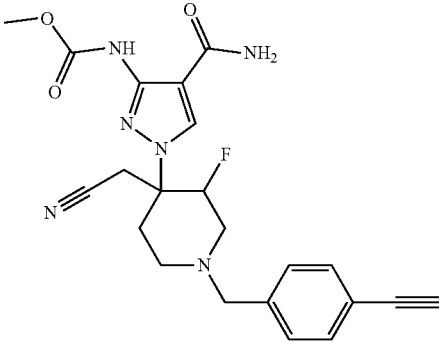 [SMILES: C#Cc1ccc(CN2CCC(CC#N)(n3cc(C(N)=O)c(NC(=O)OC)n3)C(F)C2)cc1] | 439 |
| 271 | I | 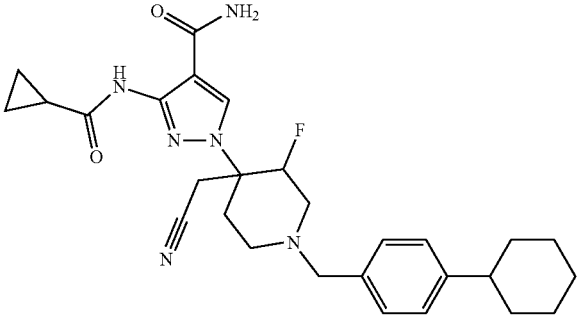 [SMILES: N#CCC1(n2cc(C(N)=O)c(NC(=O)C3CC3)n2)CCN(Cc2ccc(C3CCCCC3)cc2)CC1F] | 507 |
| 272 | R | 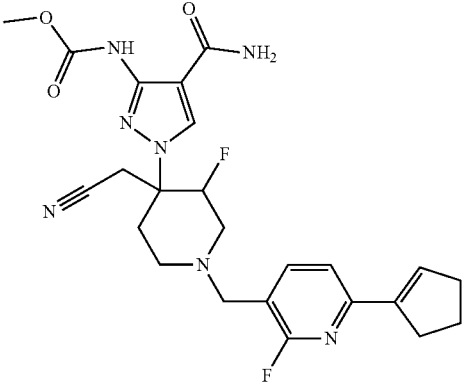 [SMILES: COC(=O)Nc1nn(C2(CC#N)CCN(Cc3ccc(C4=CCCC4)nc3F)CC2F)cc1C(N)=O] | 500 |

TABLE 2-continued

LCMS Procedures.

| Example | General Procedure | Structure | m/z |
|---|---|---|---|
| 273 | R | 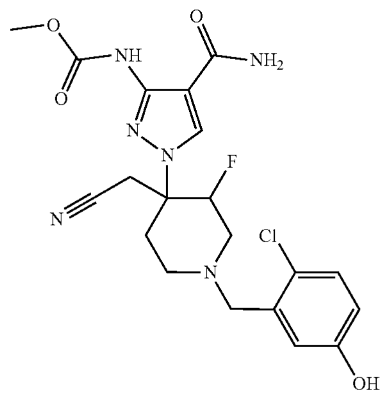 [SMILES: COC(=O)Nc1nn(C2(CC#N)CCN(Cc3cc(O)ccc3Cl)CC2F)cc1C(N)=O] | 465 |
| 274 | R | 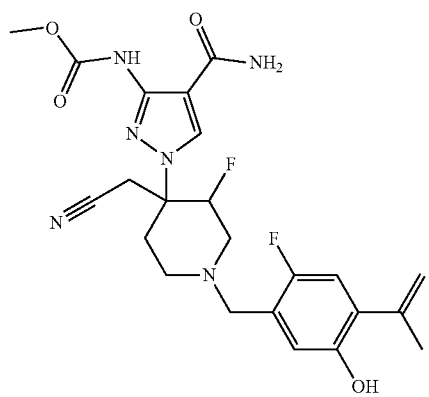 [SMILES: C=C(C)c1cc(F)c(CN2CCC(CC#N)(n3cc(C(N)=O)c(NC(=O)OC)n3)C(F)C2)cc1O] | 489 |
| 275 | A | 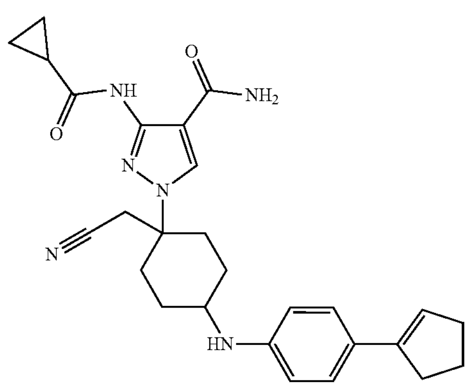 [SMILES: N#CCC1(n2cc(C(N)=O)c(NC(=O)C3CC3)n2)CCC(Nc2ccc(C3=CCCC3)cc2)CC1] | 473 |
| 276 | A | 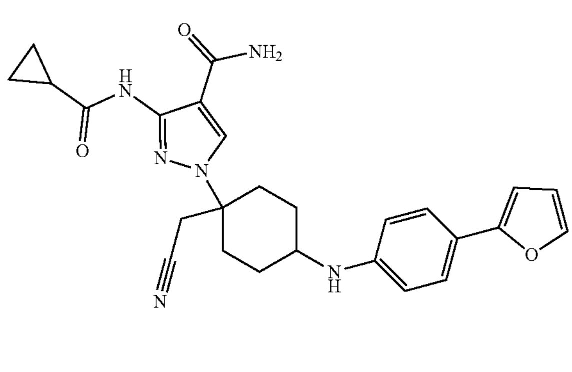 [SMILES: N#CCC1(n2cc(C(N)=O)c(NC(=O)C3CC3)n2)CCC(Nc2ccc(-c3ccco3)cc2)CC1] | 473 |

TABLE 2-continued

LCMS Procedures.

| Example | General Procedure | Structure | m/z |
|---|---|---|---|
| 277 | E | 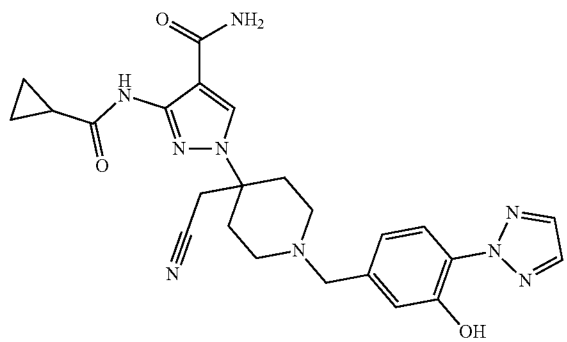 [SMILES: N#CCC1(n2cc(C(N)=O)c(NC(=O)C3CC3)n2)CCN(Cc2ccc(-n3nccn3)c(O)c2)CC1] | 490 |
| 278 | R | 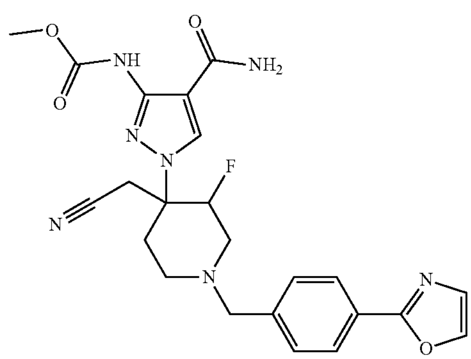 [SMILES: COC(=O)Nc1nn(C2(CC#N)CCN(Cc3ccc(-c4ncco4)cc3)CC2F)cc1C(N)=O] | 482 |
| 279 | A | 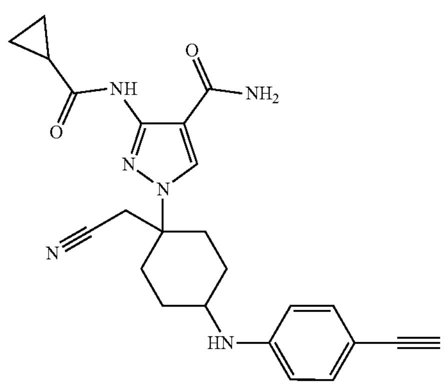 [SMILES: C#Cc1ccc(NC2CCC(CC#N)(n3cc(C(N)=O)c(NC(=O)C4CC4)n3)CC2)cc1] | 431 |
| 280 | I | 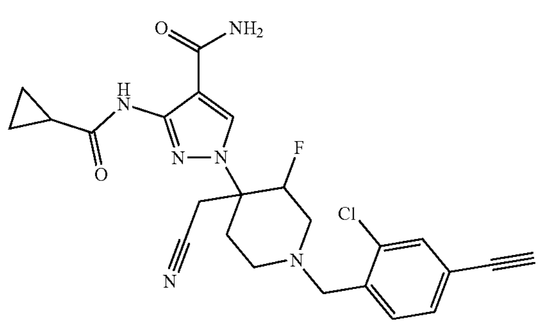 [SMILES: C#Cc1ccc(CN2CCC(CC#N)(n3cc(C(N)=O)c(NC(=O)C4CC4)n3)C(F)C2)c(Cl)c1] | 483 |

TABLE 2-continued

LCMS Procedures.

| Example | General Procedure | Structure | m/z |
|---|---|---|---|
| 281 | R | 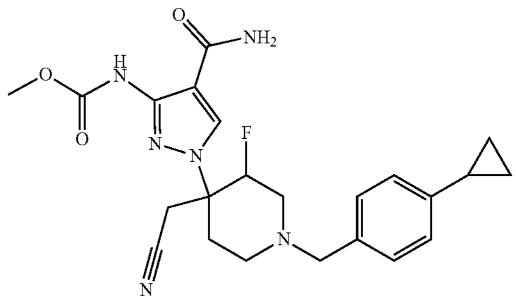 [SMILES: COC(=O)Nc1nn(C2(CC#N)CCN(Cc3ccc(C4CC4)cc3)CC2F)cc1C(N)=O] | 455 |
| 282 | A | 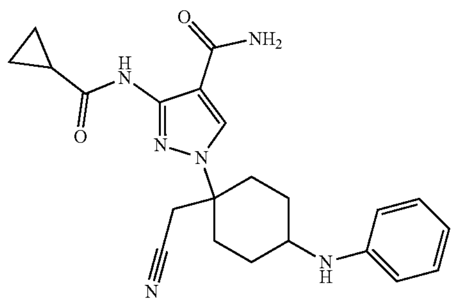 [SMILES: N#CCC1(n2cc(C(N)=O)c(NC(=O)C3CC3)n2)CCC(Nc2ccccc2)CC1] | 407 |
| 283 | R | 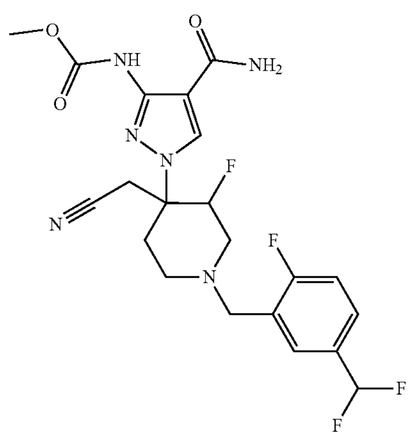 [SMILES: COC(=O)Nc1nn(C2(CC#N)CCN(Cc3cc(C(F)F)ccc3F)CC2F)cc1C(N)=O] | 483 |
| 284 | R | 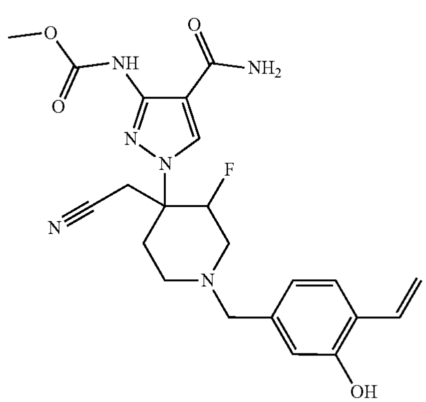 [SMILES: C=Cc1ccc(CN2CCC(CC#N)(n3cc(C(N)=O)c(NC(=O)OC)n3)C(F)C2)cc1O] | 457 |

TABLE 2-continued

LCMS Procedures.

| Example | General Procedure | Structure | m/z |
|---|---|---|---|
| 285 | R | (structure) | 475 |
| 286 | I | (structure) | 508 |
| 287 | R | (structure) | 498 |
| 288 | A | (structure) | 474 |

TABLE 2-continued

LCMS Procedures.

| Example | General Procedure | Structure | m/z |
|---|---|---|---|
| 289 | R | 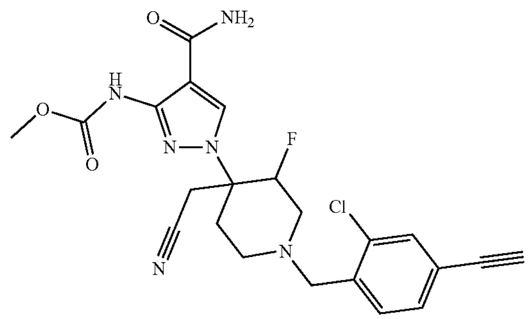 [SMILES: C#Cc1ccc(CN2CCC(CC#N)(n3cc(C(N)=O)c(NC(=O)OC)n3)C(F)C2)c(Cl)c1] | 473 |
| 290 | A | 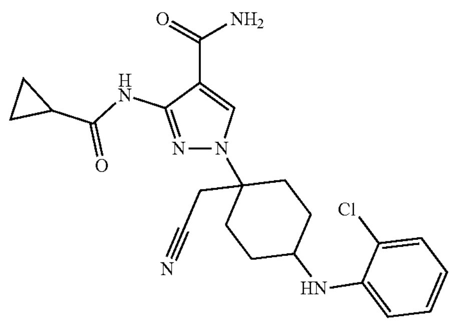 [SMILES: N#CCC1(n2cc(C(N)=O)c(NC(=O)C3CC3)n2)CCC(Nc2ccccc2Cl)CC1] | 441 |
| 291 | S | 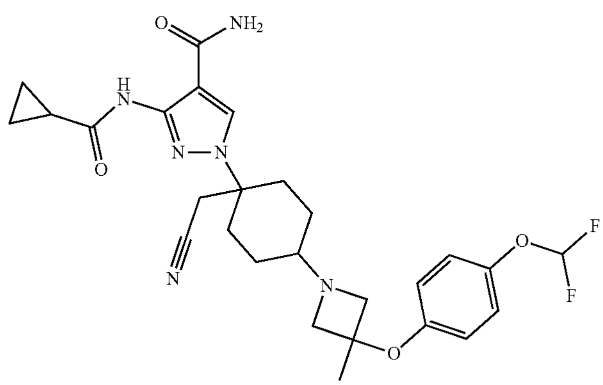 [SMILES: CC1(Oc2ccc(OC(F)F)cc2)CN(C2CCC(CC#N)(n3cc(C(N)=O)c(NC(=O)C4CC4)n3)CC2)C1] | 543 |
| 292 | R | 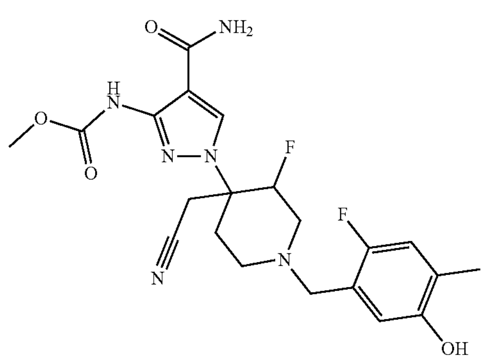 | 463 |

TABLE 2-continued

LCMS Procedures.

| Example | General Procedure | Structure | m/z |
|---|---|---|---|
| 293 | R | 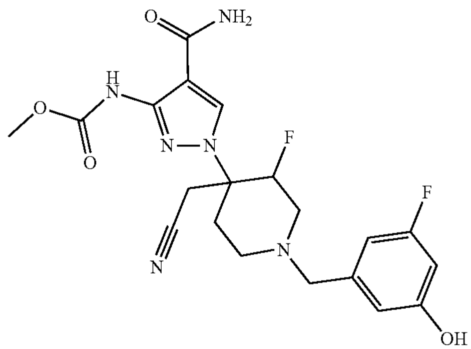 [SMILES: COC(=O)Nc1nn(C2(CC#N)CCN(Cc3cc(O)cc(F)c3)CC2F)cc1C(N)=O] | 449 |
| 294 | S | 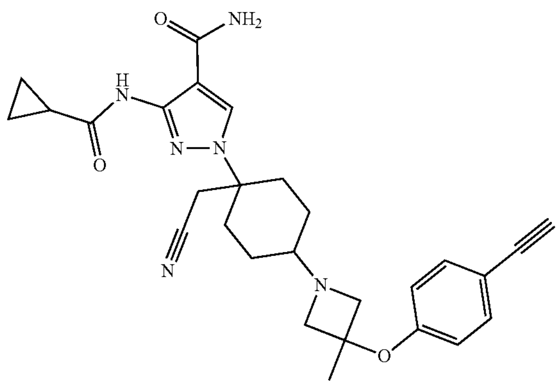 [SMILES: C#Cc1ccc(OC2(C)CN(C3CCC(CC#N)(n4cc(C(N)=O)c(NC(=O)C5CC5)n4)CC3)C2)cc1] | 501 |
| 295 | S | 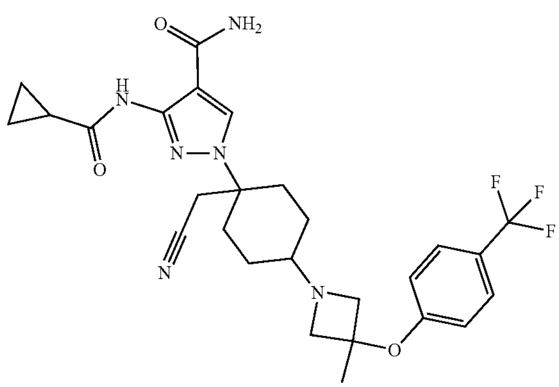 [SMILES: CC1(Oc2ccc(C(F)(F)F)cc2)CN(C2CCC(CC#N)(n3cc(C(N)=O)c(NC(=O)C4CC4)n3)CC2)C1] | 545 |
| 296 | R | 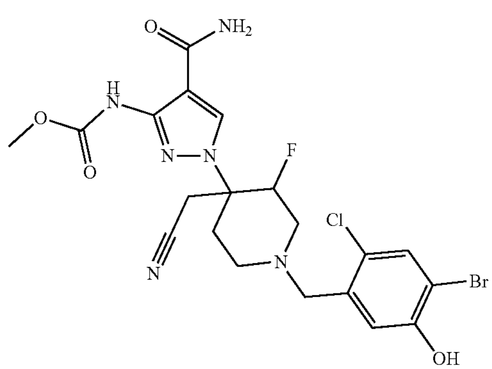 [SMILES: COC(=O)Nc1nn(C2(CC#N)CCN(Cc3cc(O)c(Br)cc3Cl)CC2F)cc1C(N)=O] | 545 |

TABLE 2-continued
LCMS Procedures.
| Example | General Procedure | Structure | m/z |
|---|---|---|---|
| 297 | R | 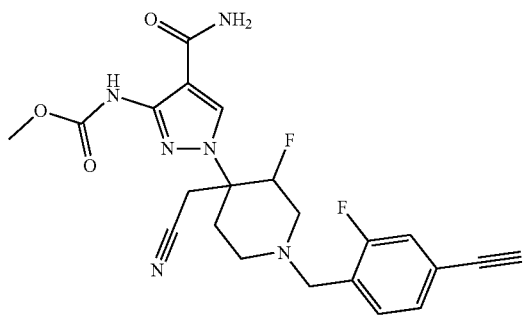 [SMILES: C#Cc1ccc(CN2CCC(CC#N)(n3cc(C(N)=O)c(NC(=O)OC)n3)C(F)C2)c(F)c1] | 457 |
| 298 | T | 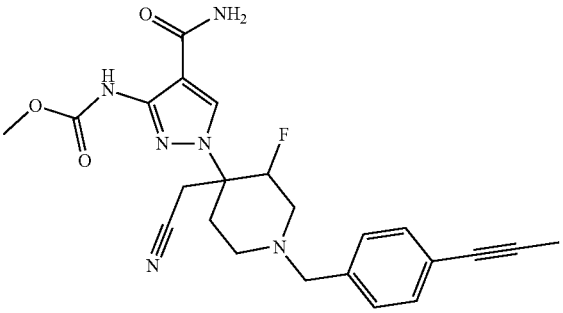 [SMILES: CC#Cc1ccc(CN2CCC(CC#N)(n3cc(C(N)=O)c(NC(=O)OC)n3)C(F)C2)cc1] | 453 |
| 299 | U | 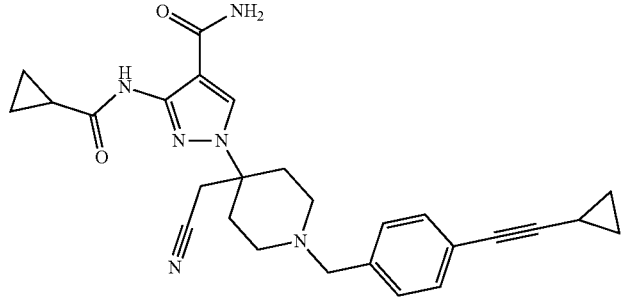 [SMILES: N#CCC1(n2cc(C(N)=O)c(NC(=O)C3CC3)n2)CCN(Cc2ccc(C#CC3CC3)cc2)CC1] | 471 |
| 300 | S | 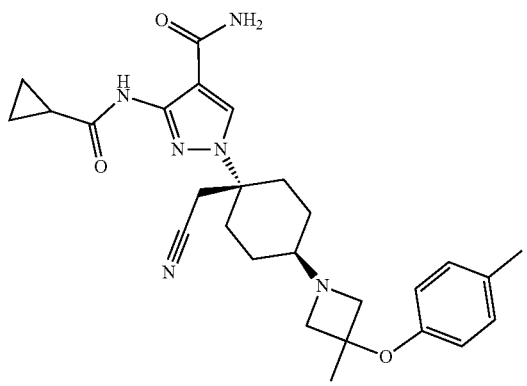 [SMILES: Cc1ccc(OC2(C)CN([C@H]3CC[C@](CC#N)(n4cc(C(N)=O)c(NC(=O)C5CC5)n4)CC3)C2)cc1] | 491 |

TABLE 2-continued
LCMS Procedures.
| Example | General Procedure | Structure | m/z |
|---|---|---|---|
| 301 | V | 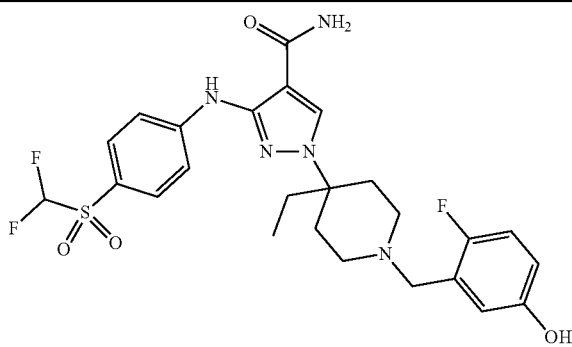 | 552 |
| 302 | X | 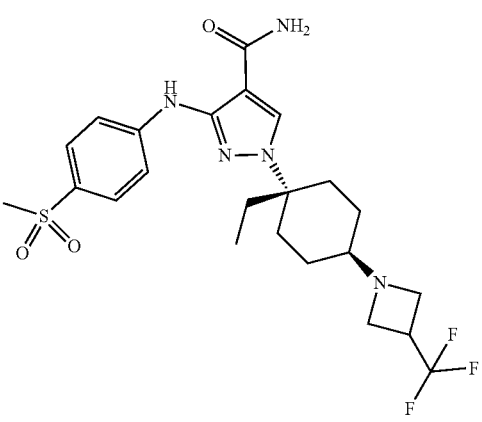 [SMILES: CC[C@]1(n2cc(C(N)=O)c(Nc3ccc(S(C)(=O)=O)cc3)n2)CC[C@H](N2CC(C(F)(F)F)C2)CC1] | 514 |
| 303 | Y | 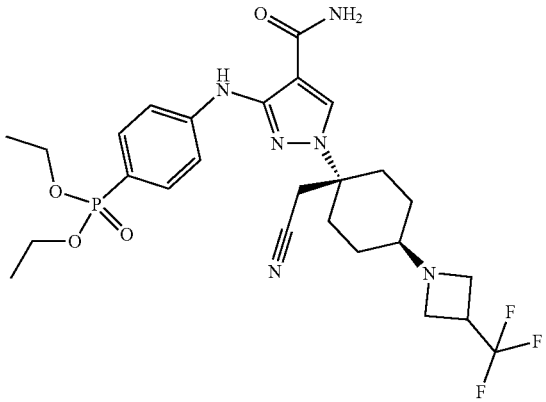 [SMILES: CCOP(=O)(OCC)c1ccc(Nc2nn([C@]3(CC#N)CC[C@@H](N4CC(C(F)(F)F)C4)CC3)cc2C(N)=O)cc1] | 583 |
| 304 | W | 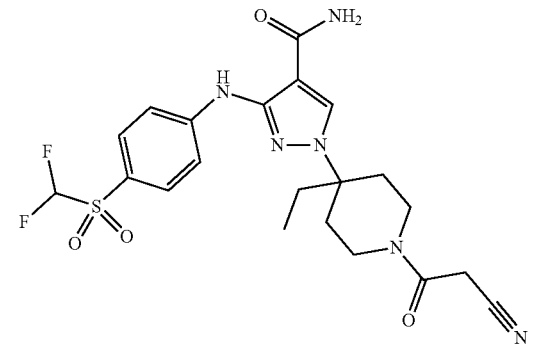 [SMILES: CCC1(n2cc(C(N)=O)c(Nc3ccc(S(=O)(=O)C(F)F)cc3)n2)CCN(C(=O)CC#N)CC1] | 495 |

Using procedures similar to those described herein, the following compounds of Formula (I) can also be prepared, and stereoisomers and salts thereof.
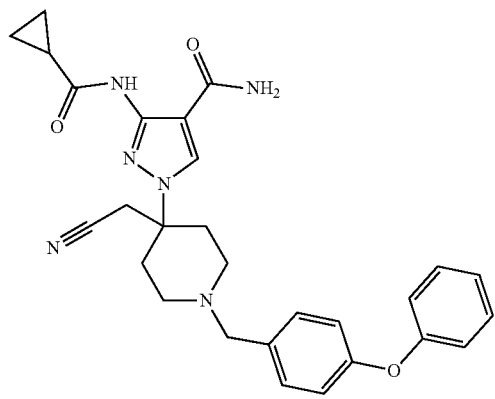
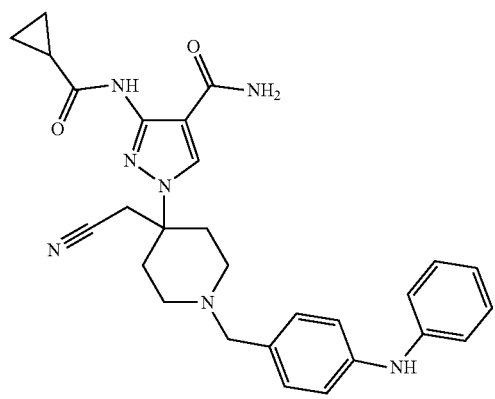
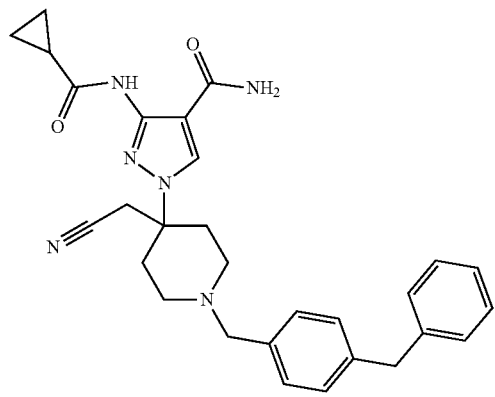
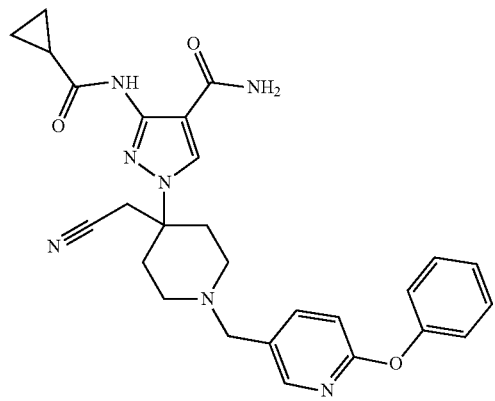
-continued
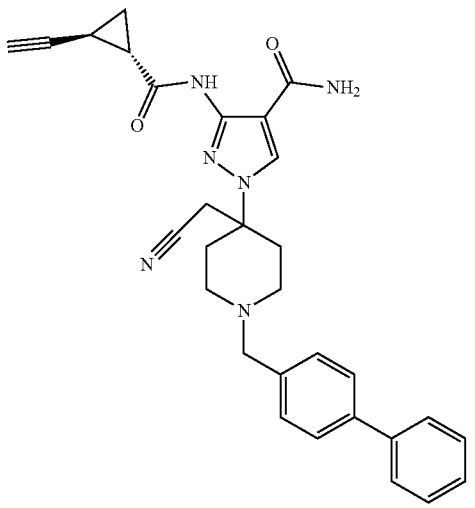
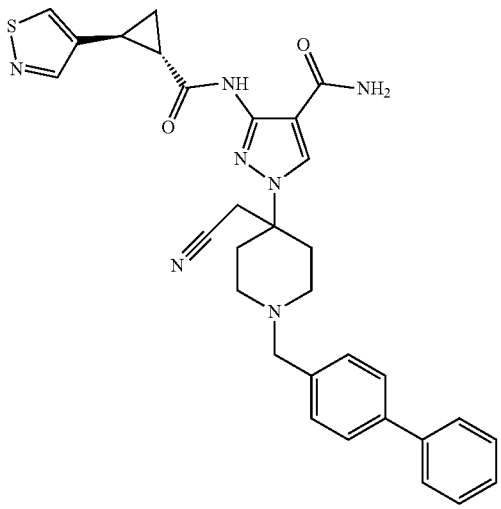
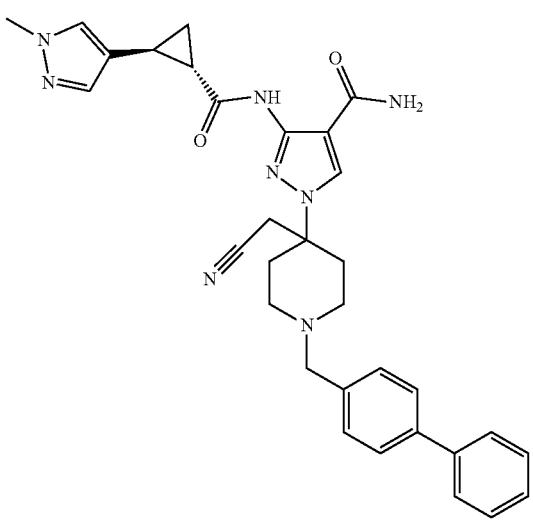

593
-continued
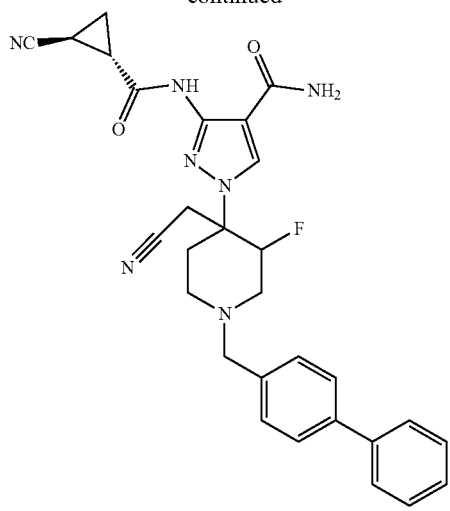
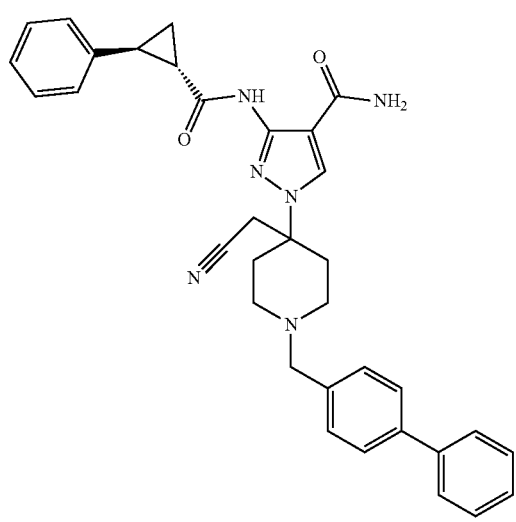
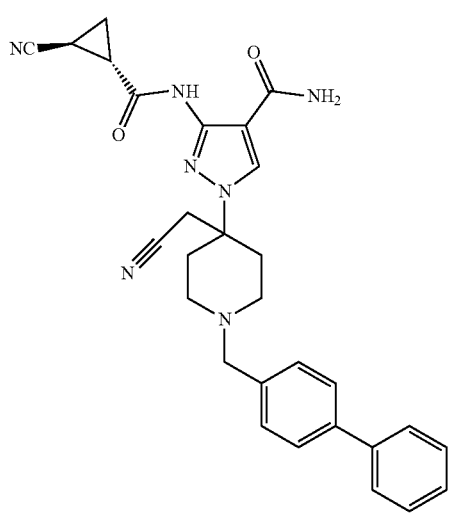
594
-continued
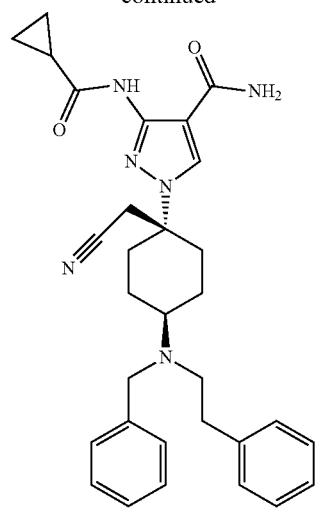
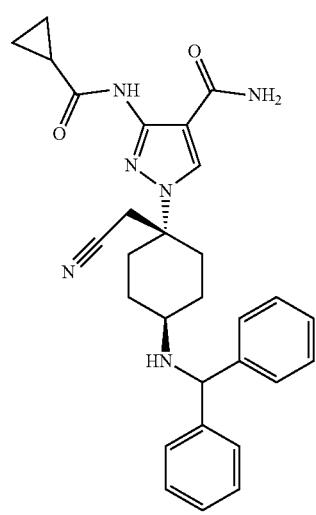
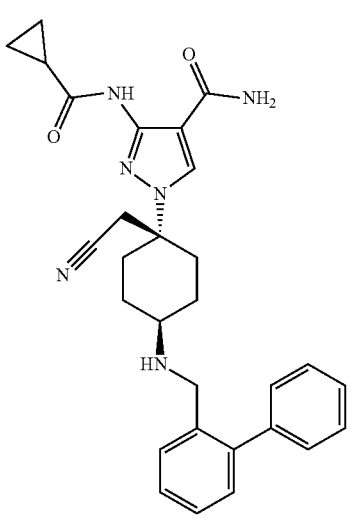

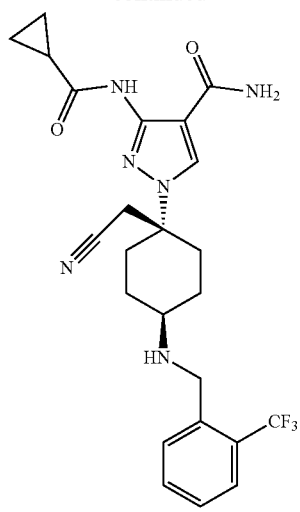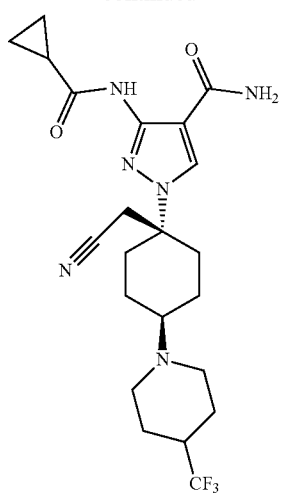

597
-continued

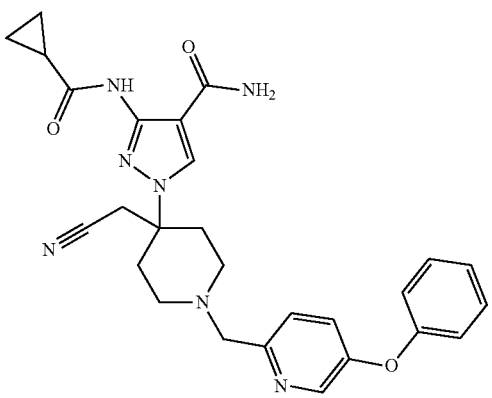

598
-continued

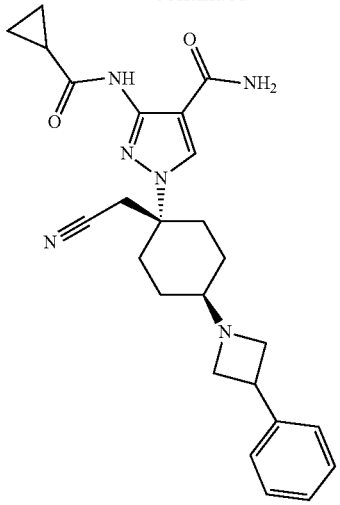

and

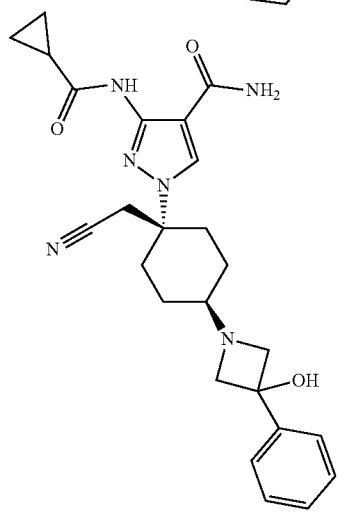

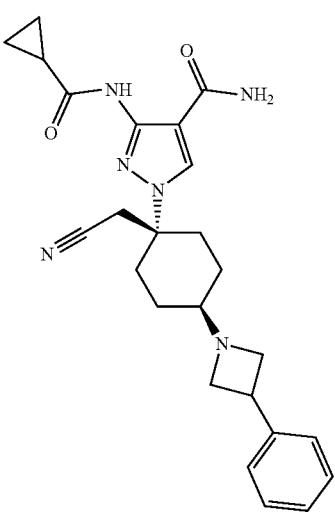

Enzymatic Assays

JAK Enzyme Assays were carried out as follows:

The activity of the isolated recombinant JAK1 and JAK2 kinase domain was measured by monitoring phosphorylation of a peptide derived from JAK3 (Val-Ala-Leu-Val-Asp-Gly-Tyr-Phe-Arg-Leu-Thr-Thr, fluorescently labeled on the N-terminus with 5-carboxyfluorescein) using the Caliper LabChip® technology (Caliper Life Sciences, Hopkinton, Mass.). To determine inhibition constants ($K_i$) compounds were diluted serially in DMSO and added to 50 μL kinase reactions containing purified enzyme (1.5 nM JAK1, or 0.2 nM JAK2), 100 mM HEPES buffer (pH 7.2), 0.015% Brij-35, 1.5 μM peptide substrate, ATP (25 μM), 10 mM $MgCl_2$, 4 mM DTT at a final DMSO concentration of 2%. Reactions were incubated at 22° C. in 384-well polypropylene microtiter plates for 30 minutes and then stopped by addition of 25 μL of an EDTA containing solution (100 mM HEPES buffer (pH 7.2), 0.015% Brij-35, 150 mM EDTA), resulting in a final EDTA concentration of 50 mM. After termination of the kinase reaction, the proportion of phosphorylated product was determined as a fraction of total peptide substrate using the Caliper LabChip® 3000 according to the manufacturer's specifications. $K_i$ values were then determined using the Morrison tight binding model (Morrison, J. F., Biochim. Biophys. Acta. 185:269-296 (1969); William, J. W. and Morrison, J. F., Meth. Enzymol., 63:437-467 (1979)) modified for ATP-competitive inhibition [$K_i = K_{i,app}/(1+[ATP]/K_{m,app})$].

JAK1 Pathway Assay in Cell Lines was carried out as follows:

Inhibitor potency ($EC_{50}$) was determined in cell-based assays designed to measure JAK1 dependent STAT phosphorylation. As noted above, inhibition of IL-4, IL-13, and IL-9 signalling by blocking the Jak/Stat signaling pathway can alleviate asthmatic symptoms in pre-clinical lung inflammation models (Mathew et al., 2001, J Exp Med 193 (9): 1087-1096; Kudlacz et. al., 2008, Eur J. Pharmacol 582 (1-3): 154-161).

In one assay approach, TF-1 human erythroleukemia cells obtained from the American Type Culture Collection (ATCC; Manassas, Va.) were used to measure JAK1-dependent STAT6 phosphorylation downstream of IL-13 stimulation. Prior to use in the assays, TF-1 cells were starved of GM-CSF overnight in OptiMEM medium (Life Technologies, Grand Island, N.Y.) supplemented with 0.5% charcoal/dextran stripped fetal bovine serum (FBS), 0.1 mM non-essential amino acids (NEAA), and 1 mM sodium pyruvate. The assays were run in 384-well plates in serum-free OptiMEM medium using 300,000 cells per well. In a second assay approach, BEAS-2B human bronchial epithelial cells obtained from ATCC were plated at 100,000 cells per well of a 96-well plate one day prior to the experiment. The BEAS-2B assay was run in complete growth medium (bronchial epithelial basal medium plus bulletkit; Lonza; Basel, Switzerland).

Test compounds were serially diluted 1:2 in DMSO and then diluted 1:50 in medium just before use. Diluted compounds were added to the cells, for a final DMSO concentration of 0.2%, and incubated for 30 min (for the TF-1 assay) or 1 hr (for the BEAS-2B assay) at 37° C. Then, cells were stimulated with human recombinant cytokine at their respective $EC_{90}$ concentrations, as previously determined for each individual lot. Cells were stimulated with IL-13 (R&D Systems, Minneapolis, Minn.) for 15 min at 37° C. The TF-1 cell reactions were stopped by the direct addition of 10× lysis buffer (Cell Signaling Technologies, Danvers, Mass.), whereas the BEAS-2B cell incubations were halted by the removal of medium and addition of 1× lysis buffer. The resultant samples were frozen in the plates at −80° C. Compound mediated inhibition of STATE phosphorylation was measured in the cell lysates using MesoScale Discovery (MSD) technology (Gaithersburg, Md.). $EC_{50}$ values were determined as the concentration of compound required for 50% inhibition of STAT phosphorylation relative to that measured for the DMSO control.

Table 3 provides JAK1 $K_i$, JAK2 $K_1$ and IL-13-pSTAT6 $IC_{50}$ information for the noted Examples.

TABLE 3

| Example | JAK1 $K_i$ (uM) | JAK2 $K_i$ (uM) | IL-13 p-STAT6 BEAS-2B $IC_{50}$ (uM) |
|---|---|---|---|
| 1 | >0.5621 | 0.2525 | >1 |
| 2 | 0.0012 | 0.0061 | 0.373 |
| 3 | 0.0064 | 0.0157 | |
| 4 | 0.0082 | 0.0345 | |
| 5 | 0.0228 | 0.1892 | |
| 6 | 0.0008 | 0.0036 | 0.031 |
| 7 | >0.5621 | >0.3188 | |

TABLE 3-continued

| Example | JAK1 $K_i$ (uM) | JAK2 $K_i$ (uM) | IL-13 p-STAT6 BEAS-2B $IC_{50}$ (uM) |
|---|---|---|---|
| 8 | 0.0017 | 0.0110 | 0.194 |
| 9 | 0.0022 | 0.0243 | 0.436 |
| 10 | >0.5621 | >0.3188 | >1 |
| 11 | 0.0004 | 0.0010 | 0.383 |
| 12 | 0.0013 | 0.0068 | 0.103 |
| 13 | 0.0006 | 0.0022 | 0.037 |
| 14 | 0.0002 | 0.0004 | 0.016 |
| 15 | 0.0042 | 0.0307 | 0.282 |
| 16 | 0.0005 | 0.0024 | 0.085 |
| 17 | 0.0040 | 0.0694 | 0.948 |
| 18 | 0.0308 | 0.2351 | |
| 19 | 0.0693 | >0.3188 | |
| 20 | 0.4473 | >0.3188 | |
| 21 | 0.0023 | 0.0484 | >1 |
| 22 | 0.0374 | 0.1511 | |
| 23 | 0.0045 | 0.0194 | 0.250 |
| 24 | 0.0356 | 0.0767 | |
| 25 | 0.0812 | >0.3188 | |
| 26 | 0.0115 | 0.2027 | |
| 27 | 0.1024 | 0.7813 | |
| 28 | 0.0121 | 0.0309 | |
| 29 | 0.0101 | 0.0119 | |
| 30 | 0.0086 | 0.0532 | |
| 31 | 0.0964 | 0.1892 | |
| 32 | 0.0718 | 0.1964 | |
| 33 | 0.0156 | 0.0765 | |
| 34 | 0.0248 | 0.2760 | |
| 35 | 0.0202 | 0.2749 | |
| 36 | >0.5621 | >0.3188 | |
| 37 | 0.0346 | 0.2680 | |
| 38 | 0.0081 | 0.1068 | |
| 39 | 0.0982 | >0.3188 | |
| 40 | 0.0079 | 0.0967 | |
| 41 | 0.0538 | >0.3188 | |
| 42 | 0.0078 | 0.0949 | |
| 43 | 0.0258 | 0.1695 | |
| 44 | 0.0276 | 0.1736 | |
| 45 | 0.0019 | 0.0085 | >1 |
| 46 | 0.0414 | 0.2841 | |
| 47 | 0.0341 | 0.2497 | |
| 48 | 0.0277 | 0.1887 | |
| 49 | 0.0233 | 0.1903 | |
| 50 | 0.0062 | 0.0664 | |
| 51 | 0.0065 | 0.0537 | |
| 52 | 0.0023 | 0.0209 | 0.102 |
| 53 | 0.0071 | 0.1006 | |
| 54 | 0.0107 | 0.1016 | |
| 55 | 0.0032 | 0.0314 | 0.098 |
| 56 | 0.0024 | 0.0243 | 0.363 |
| 57 | 0.0039 | 0.0490 | 0.128 |
| 58 | 0.0044 | 0.0426 | 0.287 |
| 59 | 0.0047 | 0.0359 | |
| 60 | 0.0039 | 0.0234 | 0.094 |
| 61 | 0.0083 | 0.1176 | |
| 62 | 0.0276 | 0.2848 | |
| 63 | 0.0144 | 0.1335 | |
| 64 | 0.0073 | 0.0835 | >1 |
| 65 | 0.0137 | 0.1228 | |
| 66 | 0.0040 | 0.0502 | 0.910 |
| 67 | 0.1002 | >0.3188 | |
| 68 | 0.0390 | >0.3188 | |
| 69 | 0.0152 | 0.1236 | |
| 70 | 0.0310 | >0.3188 | |
| 71 | 0.0341 | >0.3188 | |
| 72 | 0.0083 | 0.0313 | |
| 73 | 0.0573 | 0.2722 | |
| 74 | 0.0061 | 0.0587 | |
| 75 | 0.0027 | 0.0140 | >1 |
| 76 | 0.0039 | 0.0369 | >1 |
| 77 | 0.0026 | 0.0447 | 0.227 |
| 78 | 0.0029 | 0.0049 | >1 |
| 79 | 0.0030 | 0.0142 | >1 |
| 80 | 0.0012 | 0.0036 | >1 |
| 81 | 0.0044 | 0.0384 | >1 |
| 82 | 0.0049 | 0.0143 | 0.688 |

TABLE 3-continued

| Example | JAK1 $K_i$ (uM) | JAK2 $K_i$ (uM) | IL-13 p-STAT6 BEAS-2B $IC_{50}$ (uM) |
|---|---|---|---|
| 83 | 0.0161 | 0.3128 | |
| 84 | 0.0850 | >0.3188 | |
| 85 | 0.0451 | 0.1698 | |
| 86 | 0.0997 | >0.3188 | |
| 87 | 0.0022 | 0.0251 | 0.350 |
| 88 | 0.0263 | 0.1502 | |
| 89 | 0.0007 | 0.0068 | 0.119 |
| 90 | 0.0072 | 0.1334 | |
| 91 | 0.0083 | 0.1730 | |
| 92 | 0.0109 | 0.0881 | |
| 93 | 0.0721 | >0.3188 | |
| 94 | 0.0041 | 0.0218 | >1 |
| 95 | 0.0012 | 0.0063 | 0.275 |
| 96 | 0.0241 | 0.1133 | |
| 97 | 0.0410 | 0.1630 | |
| 98 | 0.0746 | 0.1519 | |
| 99 | 0.0922 | >0.3188 | |
| 100 | >0.5621 | >0.3188 | |
| 101 | >0.5621 | >0.3188 | |
| 102 | 0.0033 | 0.0318 | 0.933 |
| 103 | 0.0380 | >0.3188 | |
| 104 | >0.5621 | >0.3188 | |
| 105 | >0.5621 | >0.3188 | |
| 106 | 0.0233 | 0.3328 | |
| 107 | 0.0033 | 0.0431 | >1 |
| 108 | 0.4659 | 0.2048 | |
| 109 | >0.5621 | >0.3188 | |
| 110 | 0.0053 | 0.2542 | |
| 111 | 0.0095 | 0.0873 | |
| 112 | >0.5621 | >0.3188 | |
| 113 | 0.0144 | 0.1871 | |
| 114 | >0.5621 | >0.3188 | |
| 115 | 0.0219 | 0.2998 | |
| 116 | 0.1639 | >0.3188 | |
| 117 | 0.0037 | 0.0547 | 0.611 |
| 118 | >0.5621 | >0.3188 | |
| 119 | 0.4368 | >0.3188 | |
| 120 | 0.0120 | 0.1146 | |
| 121 | 0.0146 | 0.2819 | |
| 122 | 0.5621 | >0.3188 | |
| 123 | >0.5621 | >0.3188 | |
| 124 | 0.0327 | 0.2725 | |
| 125 | 0.0073 | 0.0783 | |
| 126 | 0.1879 | >0.3188 | |
| 127 | >0.5621 | >0.3188 | |
| 128 | 0.0046 | 0.0464 | 0.349 |
| 129 | 0.0033 | 0.0163 | 0.393 |
| 130 | >0.5621 | >0.3188 | |
| 131 | 0.0028 | 0.0187 | 0.334 |
| 132 | 0.2170 | >0.3188 | |
| 133 | 0.0025 | 0.0156 | 0.162 |
| 134 | >0.5621 | >0.3188 | |
| 135 | 0.0024 | 0.0243 | 0.170 |
| 136 | 0.4629 | >0.3188 | |
| 137 | 0.0027 | 0.0217 | >1 |
| 138 | >0.5621 | >0.3188 | |
| 139 | 0.0004 | 0.0010 | 0.104 |
| 140 | 0.0006 | 0.0044 | 0.049 |
| 141 | 0.0008 | 0.0034 | 0.062 |
| 142 | 0.0017 | 0.0129 | 0.060 |
| 143 | 0.0007 | 0.0055 | 0.049 |
| 144 | 0.0088 | 0.0635 | |
| 145 | 0.0031 | 0.0155 | >1 |
| 146 | 0.0011 | 0.0082 | 0.095 |
| 147 | 0.0021 | 0.0320 | 0.051 |
| 148 | 0.0018 | 0.0212 | 0.048 |
| 149 | 0.0007 | 0.0047 | 0.041 |
| 150 | 0.0159 | 0.2075 | |
| 151 | 0.0034 | 0.1543 | 0.286 |
| 152 | 0.0013 | 0.0078 | 0.126 |
| 153 | 0.0011 | 0.0308 | 0.103 |
| 154 | 0.0015 | 0.0087 | 0.116 |
| 155 | 0.0006 | 0.0073 | 0.060 |
| 156 | 0.0006 | 0.0043 | 0.209 |
| 157 | 0.0016 | 0.0137 | 0.104 |
| 158 | 0.0080 | 0.0394 | |
| 159 | 0.0190 | 0.1012 | |
| 160 | 0.0032 | 0.0120 | 0.186 |
| 161 | 0.0055 | 0.0353 | 1.014 |
| 162 | 0.0031 | 0.0106 | 0.293 |
| 163 | 0.0021 | 0.0185 | 0.103 |
| 164 | 0.0027 | 0.0090 | 0.275 |
| 165 | 0.0271 | 0.2112 | |
| 166 | 0.0022 | 0.0800 | 0.068 |
| 167 | 0.0023 | 0.0287 | 0.833 |
| 168 | 0.0075 | 0.0933 | |
| 169 | 0.0037 | 0.0483 | >1 |
| 170 | 0.0067 | 0.0709 | |
| 171 | 0.0066 | 0.0303 | |
| 172 | >0.5621 | >0.3188 | |
| 173 | 0.0087 | 0.0713 | |
| 174 | >0.5621 | >0.3188 | |
| 175 | 0.0141 | 0.3210 | |
| 176 | 0.3022 | >0.3188 | |
| 177 | 0.0187 | 0.2255 | |
| 178 | 0.0047 | 0.0184 | 0.167 |
| 179 | >0.5621 | >0.3188 | |
| 180 | 0.0055 | 0.0173 | 0.168 |
| 181 | >0.5621 | >0.3188 | |
| 182 | 0.0047 | 0.0507 | 0.675 |
| 183 | 0.0883 | >0.3188 | |
| 184 | 0.0904 | 0.1595 | 0.177 |
| 185 | 0.0023 | | 0.209 |
| 186 | 0.00024 | 0.001 | 0.068 |
| 187 | 0.00052 | 0.0031 | 0.074 |
| 188 | 0.0006 | 0.0014 | 0.034 |
| 189 | 0.00033 | 0.0013 | 0.038 |
| 190 | 0.0011 | 0.011 | 0.093 |
| 191 | 0.0002 | 0.00032 | 0.082 |
| 192 | 0.00035 | 0.0012 | 0.028 |
| 193 | 0.00033 | 0.00026 | 0.048 |
| 194 | 0.00063 | 0.0022 | 0.05 |
| 195 | 0.00011 | 0.00015 | 0.015 |
| 196 | 0.00026 | 0.00027 | 0.03 |
| 197 | 0.0012 | 0.022 | 0.065 |
| 198 | 0.0012 | 0.0038 | 0.074 |
| 199 | 0.00052 | 0.00055 | 0.064 |
| 200 | 0.00051 | 0.00096 | 0.039 |
| 201 | 0.00024 | 0.00023 | 0.023 |
| 202 | 0.00055 | 0.00074 | 0.074 |
| 203 | 0.00025 | 0.00022 | 0.015 |
| 204 | 0.001 | 0.0018 | 0.05 |
| 205 | 0.00089 | 0.0059 | 0.082 |
| 206 | 0.00018 | 0.0003 | 0.033 |
| 207 | 0.00011 | 0.00013 | 0.029 |
| 208 | 0.00017 | 0.00021 | 0.028 |
| 209 | 0.00049 | 0.0038 | 0.098 |
| 210 | 0.0021 | 0.0051 | 0.075 |
| 211 | 0.00074 | 0.0046 | 0.026 |
| 212 | 0.00022 | 0.0003 | 0.027 |
| 213 | 0.00037 | 0.00028 | 0.022 |
| 214 | 0.00031 | 0.00062 | 0.042 |
| 215 | 0.00024 | 0.00025 | 0.012 |
| 216 | 0.00074 | 0.0007 | 0.04 |
| 217 | 0.00066 | 0.00049 | 0.056 |
| 218 | 0.00035 | 0.00059 | 0.028 |
| 219 | 0.0017 | 0.0036 | 0.068 |
| 220 | 0.00027 | 0.00044 | 0.015 |
| 221 | 0.0003 | 0.0017 | 0.09 |
| 222 | 0.00018 | 0.00043 | 0.052 |
| 223 | 0.00038 | 0.00034 | 0.012 |
| 224 | 0.00016 | 0.00015 | 0.019 |
| 225 | 0.00062 | 0.0013 | 0.044 |
| 226 | 0.00037 | 0.00056 | 0.049 |
| 227 | 0.00031 | 0.00063 | 0.054 |
| 228 | 0.0015 | 0.0077 | 0.077 |
| 229 | 0.00048 | 0.00077 | 0.025 |
| 230 | 0.00051 | 0.0018 | 0.06 |
| 231 | 0.00036 | 0.0083 | 0.019 |
| 232 | 0.00032 | 0.00089 | 0.02 |

TABLE 3-continued

| Example | JAK1 K$_i$ (uM) | JAK2 K$_i$ (uM) | IL-13 p-STAT6 BEAS-2B IC$_{50}$ (uM) |
|---|---|---|---|
| 233 | 0.0003 | 0.00045 | 0.039 |
| 234 | 0.00027 | 0.001 | 0.031 |
| 235 | 0.00032 | 0.00067 | 0.026 |
| 236 | 0.00021 | 0.0014 | 0.019 |
| 237 | 0.00022 | 0.0003 | 0.027 |
| 238 | 0.00029 | 0.00035 | 0.018 |
| 239 | 0.00051 | 0.00089 | 0.067 |
| 240 | 0.00019 | 0.00029 | 0.071 |
| 241 | 0.00054 | 0.00051 | 0.029 |
| 242 | 0.0006 | 0.00051 | 0.055 |
| 243 | 0.0027 | 0.014 | 0.1 |
| 244 | 0.0002 | 0.00037 | 0.067 |
| 245 | 0.00023 | 0.00092 | 0.014 |
| 246 | 0.00035 | 0.00052 | 0.019 |
| 247 | 0.00035 | 0.00043 | 0.026 |
| 248 | 0.00028 | 0.00025 | 0.03 |
| 249 | 0.00052 | 0.00056 | 0.026 |
| 250 | 0.00031 | 0.00084 | 0.08 |
| 251 | 0.00034 | 0.0003 | 0.03 |
| 252 | 0.0003 | 0.00052 | 0.022 |
| 253 | 0.001 | 0.0056 | 0.056 |
| 254 | 0.00043 | 0.00082 | 0.043 |
| 255 | 0.0012 | 0.00096 | 0.07 |
| 256 | 0.00015 | 0.00089 | 0.047 |
| 257 | 0.00073 | 0.0013 | 0.052 |
| 258 | 0.00034 | 0.00029 | 0.034 |
| 259 | 0.00084 | 0.0018 | 0.05 |
| 260 | 0.00025 | 0.00035 | 0.032 |
| 261 | 0.00056 | 0.00082 | 0.021 |
| 262 | 0.0012 | 0.0037 | 0.057 |
| 263 | 0.0003 | 0.00024 | 0.025 |
| 264 | 0.00079 | 0.0014 | 0.088 |
| 265 | 0.0011 | 0.0042 | 0.088 |
| 266 | 0.00077 | 0.005 | 0.057 |
| 267 | 0.00086 | 0.00084 | 0.051 |
| 268 | 0.0009 | 0.0019 | 0.043 |
| 269 | 0.0006 | 0.00055 | 0.035 |
| 270 | 0.00041 | 0.0009 | 0.021 |
| 271 | 0.0026 | 0.015 | 0.083 |
| 272 | 0.00068 | 0.0016 | 0.067 |
| 273 | 0.00033 | 0.00031 | 0.075 |
| 274 | 0.00058 | 0.00061 | 0.038 |
| 275 | 0.0011 | 0.0081 | 0.052 |
| 276 | 0.00025 | 0.0022 | 0.009 |
| 277 | 0.00074 | 0.0019 | 0.04 |
| 278 | 0.0011 | 0.0013 | 0.045 |
| 279 | 0.0012 | 0.014 | 0.092 |
| 280 | 0.0003 | 0.0004 | 0.016 |
| 281 | 0.0011 | 0.0022 | 0.036 |
| 282 | 0.00062 | 0.0096 | 0.048 |
| 283 | 0.0014 | 0.0029 | 0.077 |
| 284 | 0.0003 | 0.0005 | 0.048 |
| 285 | 0.00019 | 0.00023 | 0.022 |
| 286 | 0.00043 | 0.0004 | 0.052 |
| 287 | 0.00035 | 0.00043 | 0.032 |
| 288 | 0.00028 | 0.0044 | 0.041 |
| 289 | 0.00026 | 0.00055 | 0.015 |
| 290 | 0.0011 | 0.013 | 0.082 |
| 291 | 0.00086 | 0.0021 | 0.054 |
| 292 | 0.00055 | 0.0007 | 0.049 |
| 293 | 0.0003 | 0.00034 | 0.055 |
| 294 | 0.00074 | 0.0011 | 0.047 |
| 295 | 0.002 | 0.0029 | 0.085 |
| 296 | 0.00056 | 0.00059 | 0.052 |
| 297 | 0.00053 | 0.00076 | 0.062 |
| 298 | 0.0006 | 0.00058 | 0.029 |
| 299 | 0.0011 | 0.003 | 0.085 |
| 300 | 0.0015 | 0.0013 | 0.043 |
| 301 | 0.0015 | 0.002 | 0.1 |
| 302 | 0.00094 | 0.002 | 0.043 |
| 303 | 0.00039 | 0.00066 | 0.034 |
| 304 | 0.00049 | 0.0028 | 0.220 |

What is claimed is:

1. A compound of Formula (I):

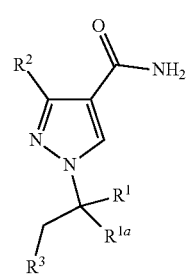

or a pharmaceutically acceptable salt thereof, wherein:

$R^1$ and $R^{1a}$ taken together with the atom to which they are attached form a 3-10 membered carbocycle optionally substituted with $R^a$ and optionally substituted with $R^b$; or $R^1$ and $R^{1a}$ taken together with the atom to which they are attached form a 3-15 membered heterocycle optionally substituted with RC and optionally substituted with $R^d$;

$R^2$ is

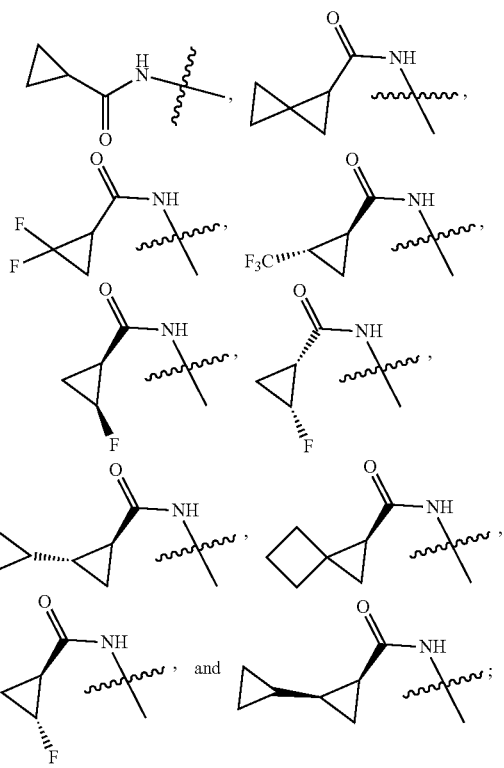

$R^3$ is —CH$_3$ or —CN;
$R^a$ is —NR$^r$R$^5$ or —OR$^r$;
each $R^b$ is independently selected from the group consisting of halo, cyano, hydroxy, oxo, C$_1$-C$_6$alkyl, C$_1$-C$_6$alkoxy, —NH$_2$, —NHCH$_3$, —N(CH$_3$)$_2$, —SH, and —SCH$_3$, wherein any C$_1$-C$_6$alkyl, and C$_1$-C$_6$alkoxy is optionally substituted with halo, cyano, hydroxy, oxo, C$_1$-$_3$alkyl, C$_1$-C$_3$alkoxy, —NH$_2$, —NHCH$_3$, —N(CH$_3$)$_2$, —SH, or —SCH$_3$ wherein any C$_1$-C$_3$alkyl and C$_1$-C$_3$alkoxy is optionally substituted with halo, hydroxy, cyano or oxo;

$R^c$ is —$OR'''$, —$SR'''$, —$NR'''R''$, —$C(O)R'''$, —$C(O)OR'''$, —$C(O)NR'''R''$, —$NR'''C(O)R''$, —$S(O)_{1-2}R'''$, —$NR'''S(O)_{1-2}R''V$, —$S(O)_{1-2}NR'''R''$, $C_1$-$C_6$alkyl, $C_2$-$C_6$alkenyl, $C_2$-$C_6$alkynyl, 3-10 membered carbocyclyl, 3-10 membered heterocyclyl, 6-10 membered aryl, or 5-10 membered heteroaryl, wherein any $C_1$-$C_6$alkyl, $C_2$-$C_6$alkenyl, $C_2$-$C_6$alkynyl of $R^c$ is optionally substituted with $R^x$;

each $R^d$ is independently selected from the group consisting of halo, cyano, $C_1$-$C_6$alkyl, and $C_1$-$C_6$alkoxy wherein any $C_1$-$C_6$alkyl, and $C_1$-$C_6$alkoxy is optionally substituted with halo, hydroxy, cyano or oxo;

$R^g$ is H, hydroxy, $C_1$-$C_6$alkyl, $C_1$-$C_6$alkoxy, —$NR^tR^u$, or a 3-10 membered carbocyclyl that is optionally substituted with halo, hydroxy, cyano, oxo, $C_1$-$C_3$alkyl, $C_2$-$C_3$alkynyl, 6-10 membered aryl, 5-6 membered heteroaryl, or 3-5 membered carbocyclyl, wherein any $C_1$-$C_3$alkyl, 6-10 membered aryl, 5-6 membered heteroaryl, or 3-5 membered carbocyclyl is optionally substituted with halo, hydroxy, cyano, or $C_1$-$C_3$alkyl;

$R'''$ and $R''$ are independently selected from the group consisting of hydrogen, 3-6 membered heterocyclyl, 3-6 membered carbocyclyl, 6-10 membered aryl, 5-10 membered heteroaryl, and $C_1$-$C_6$alkyl, wherein any 3-6 membered heterocyclyl, 3-6 membered carbocyclyl, 6-10 membered aryl, 5-10 membered heteroaryl, and $C_1$-$C_6$alkyl of $R'''$ and $R''$ is optionally substituted with $R^w$; or $R'''$ and $R''$ are taken together with the atom to which they are attached to form a 3-8 membered heterocyclyl that is optionally substituted with $R^w$;

each $R^r$ and $R^s$ is independently selected from the group consisting of hydrogen, 3-6 membered heterocyclyl, 3-6 membered carbocyclyl, 6-10 membered aryl, 5-10 membered heteroaryl and $C_1$-$C_3$alkyl, wherein any 3-6 membered heterocyclyl, 3-6 membered carbocyclyl, 6-10 membered aryl, 5-10 membered heteroaryl and $C_1$-$C_3$alkyl of $R^r$ and $R^s$ is optionally substituted with $R^v$; or $R^r$ and $R^s$ are taken together with the atom to which they are attached to form a 3-8 membered heterocyclyl or 5-10 membered heteroaryl, which 3-8 membered heterocyclyl and 5-10 membered heteroaryl is optionally substituted with $R^v$;

$R^t$ and $R^u$ are independently selected from the group consisting of hydrogen, 3-6 membered heterocyclyl, 3-6 membered carbocyclyl, 6-10 membered aryl, 5-10 membered heteroaryl and $C_1$-$C_3$alkyl, wherein any 3-6 membered heterocyclyl, 3-6 membered carbocyclyl, 6-10 membered aryl, 5-10 membered heteroaryl and $C_1$-$C_3$alkyl of $R^t$ and $R^u$ is optionally substituted with halo, hydroxy, cyano or oxo; or $R^t$ and $R^u$ are taken together with the atom to which they are attached to form a 3-6 membered heterocyclyl, optionally substituted with halo, hydroxy, cyano or oxo, or $C_1$-$C_6$alkyl that is optionally substituted with halo, hydroxy, cyano or oxo;

each $R^v$ is independently selected from the group consisting of halo, hydroxy, cyano, oxo, 6-10 membered aryl, 5-10 membered heteroaryl, $C_1$-$C_6$alkyl, $C_2$-$C_3$alkenyl, $C_2$-$C_3$alkynyl, 3-6 membered carbocyclyl, 3-6 membered heterocyclyl, (6-10 membered aryl)—O—, (5-10 membered heteroaryl)—O—, (3-6 membered carbocyclyl)—O—, (3-6 membered heterocyclyl)—O—, and $C_1$-$C_6$alkoxy, wherein any 6-10 membered aryl, 5-10 membered heteroaryl, $C_1$-$C_6$alkyl, 3-6 membered carbocyclyl, 3-6 membered heterocyclyl, (6-10 membered aryl)—O—, (5-10 membered heteroaryl)—O—, (3-6 membered carbocyclyl)—O—, (3-6 membered heterocyclyl)—O—, and $C_1$-$C_6$alkoxy of $R^v$ is optionally substituted with halo, hydroxy, cyano, $C_1$-$C_6$alkyl, $C_2$-$C_3$alkynyl, oxo, 3-6 membered carbocycle, 3-6 membered heterocyclyl, $C_1$-$C_6$alkoxy, 5-10 membered heteroaryl or 6-10 membered aryl, each of which is optionally substituted with halo, hydroxy, cyano, oxo $C_1$-$C_3$alkyl or $C_1$-$C_3$alkoxy;

each $R^w$ is independently selected from the group consisting of halo, hydroxy, cyano, oxo, 6-10 membered aryl, 5-10 membered heteroaryl, $C_1$-$C_6$alkyl, 3-6 membered carbocyclyl, 3-6 membered heterocyclyl and $C_1$-$C_6$alkoxy, wherein any 6-10 membered aryl, 5-10 membered heteroaryl, $C_1$-$C_6$alkyl, 3-6 membered carbocyclyl, 3-6 membered heterocyclyl and $C_1$-$C_6$alkoxy of $R^w$ is optionally substituted with halo, hydroxy, cyano, $C_1$-$C_6$alkyl, oxo, 3-6 membered carbocyclyl, 3-6 membered heterocyclyl $C_1$-$C_6$alkoxy, 5-10 membered heteroaryl, or 6-10 membered aryl, each optionally substituted with halo, hydroxy, cyano, oxo, $C_1$-$C_3$alkyl or $C_1$-$C_3$alkoxy; and each $R^x$ is independently selected from the group consisting of halo, hydroxy, cyano, nitro, oxo, —$OR'''$, —$SR'''$, —$NR'''R''$, —$C(O)R'''$, —$C(O)OR'''$, —$C(O)NR'''R''$, —$NR'''C(O)R''$, —$S(O)_{1-2}R'''$, —$NR'''S(O)_{1-2}R''$, —$S(O)_{1-2}NR'''R''$, 3-10 membered carbocyclyl, 3-15 membered heterocyclyl, 6-10 membered aryl, and 5-15 membered heteroaryl, wherein any 3-10 membered carbocyclyl, 3-15 membered heterocyclyl, 6-10 membered aryl, and 5-15 membered heteroaryl, is optionally substituted with halo, hydroxy, cyano, nitro, $C_2$-$C_6$alkenyl, $C_2$-$C_6$alkynyl, —$OR'''$, —$SR'''$, —$NR'''R''$, —$C(O)R'''$, —$C(O)OR'''$, —$C(O)NR'''R''$, —$NR'''C(O)R''$, —$S(O)_{1-2}R'''$, —$NR'''S(O)_{1-2}R''$, —$S(O)_{1-2}NR'''R''$, $C_1$-$C_6$alkyl, oxo, 3-10 membered carbocyclyl, 3-10 membered heterocyclyl, 6-10 membered aryl, or 5-10 membered heteroaryl, wherein any $C_1$-$C_6$alkyl, $C_2$-$C_6$alkenyl, $C_2$-$C_6$alkynyl, 3-10 membered carbocyclyl, 3-10 membered heterocyclyl, 6-10 membered aryl, and 5-10 membered heteroaryl is optionally substituted with halo, hydroxy, cyano, oxo, —$OR'''$, —$NR'''R''$, —$C(O)R'''$, —$C(O)OR'''$, —$C(O)NR'''R''$, 3-6 membered carbocyclyl, 6-10 membered aryl, or $C_1$-$C_6$alkyl that is optionally substituted with halo, hydroxy, cyano, oxo or $C_1$-$C_6$alkoxy.

2. A compound of claim 1 or a pharmaceutically acceptable salt thereof, wherein $R^3$ is —CN.

3. The compound of claim 1 or a pharmaceutically acceptable salt thereof, wherein $R^2$ is cyclopropylcarbonylamino.

4. The compound of claim 1 or a pharmaceutically acceptable salt thereof, wherein the group

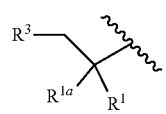

is selected from the group consisting of:
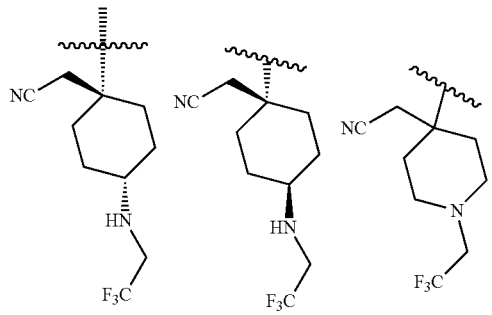
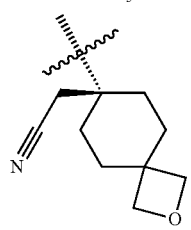
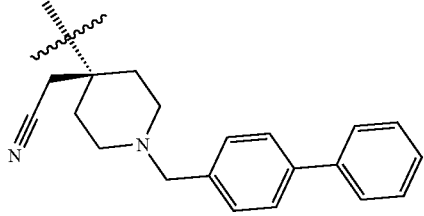
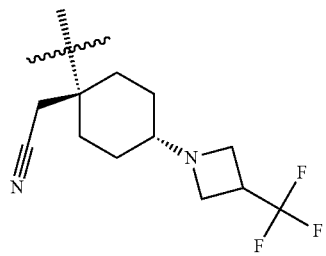
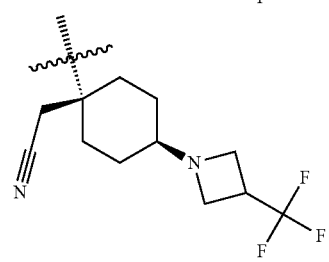
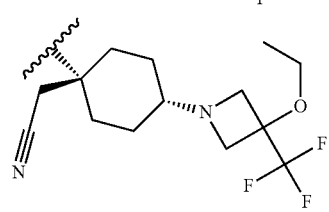
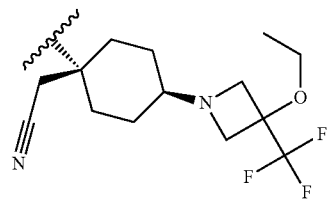
-continued
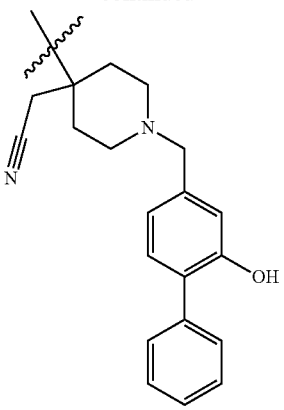
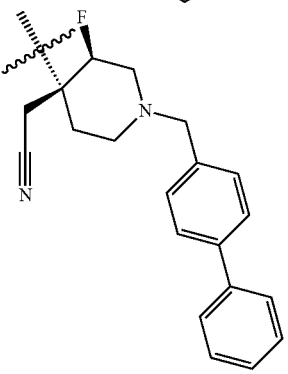
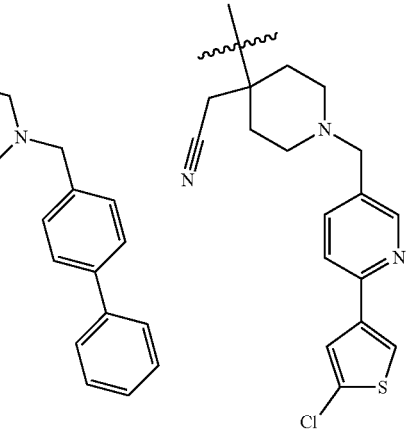
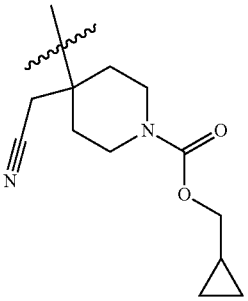
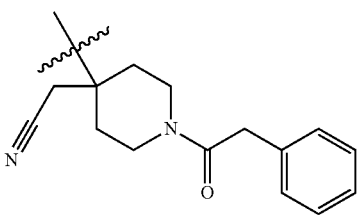

609
-continued
610
-continued
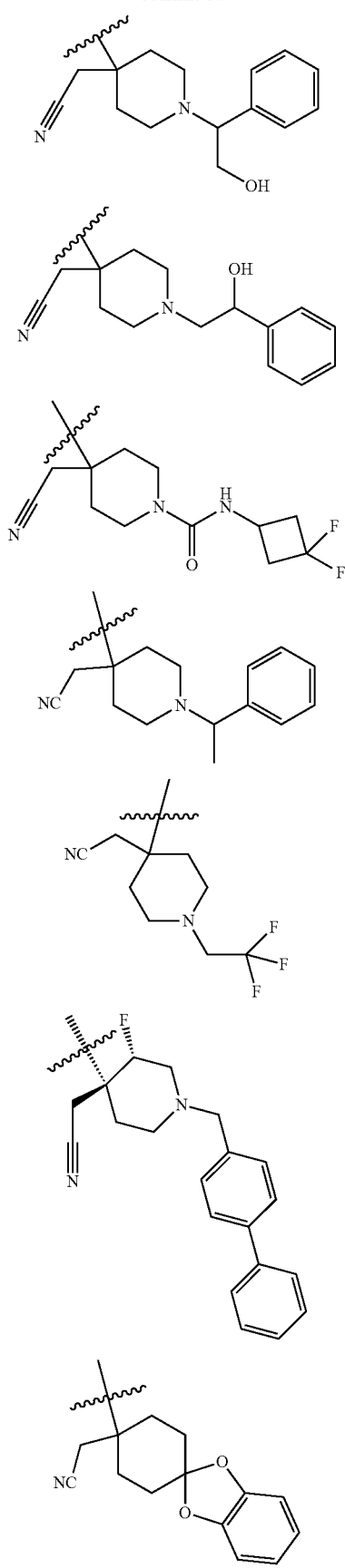
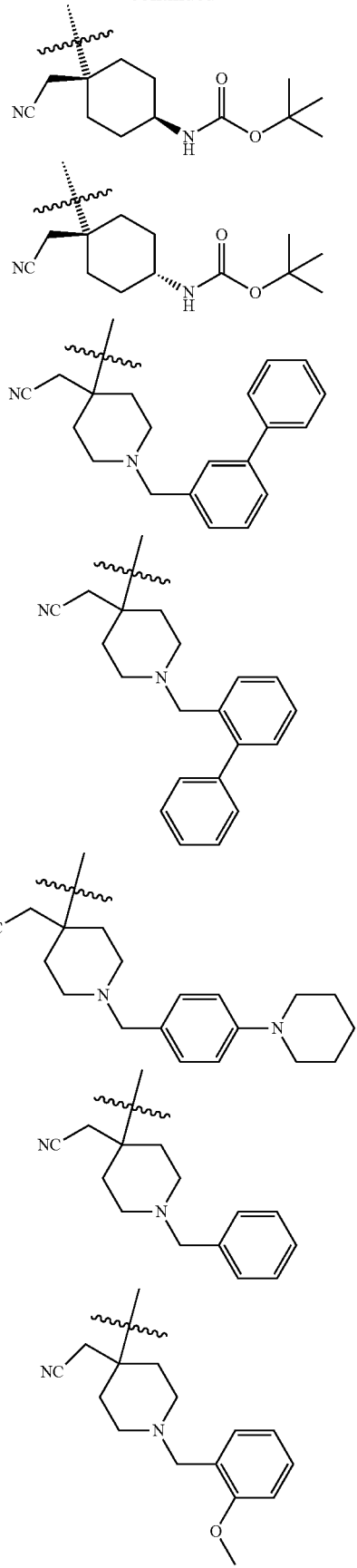

611
-continued
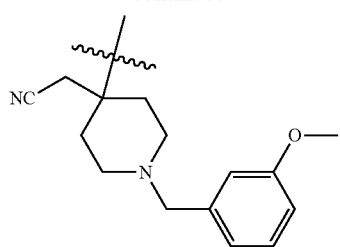
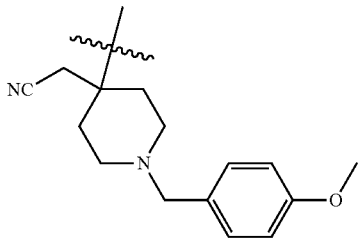
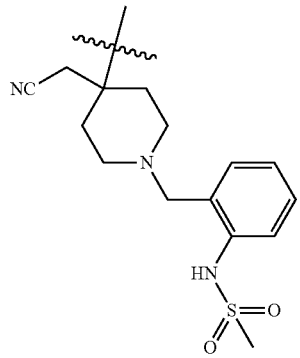
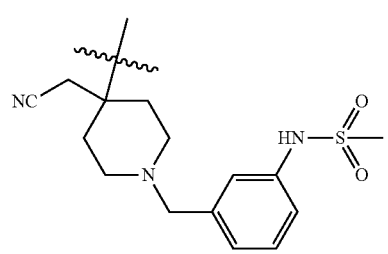
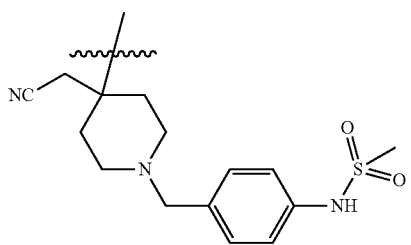
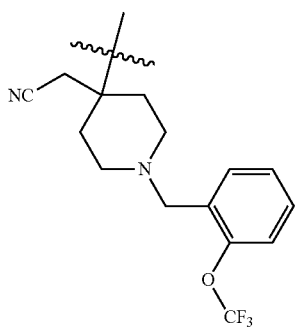
612
-continued
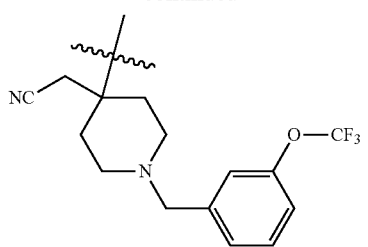
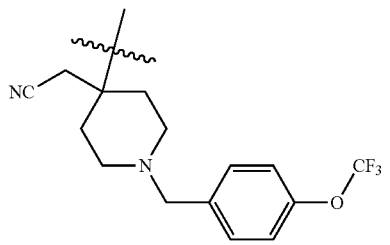
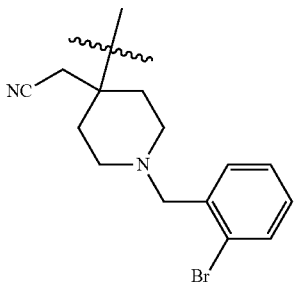
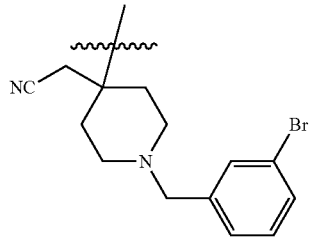
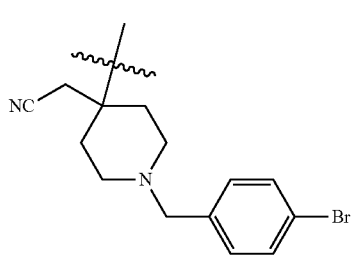
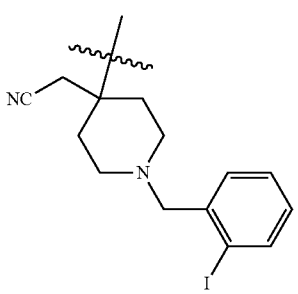

| 613 | 614 |
|---|---|
| -continued | -continued |
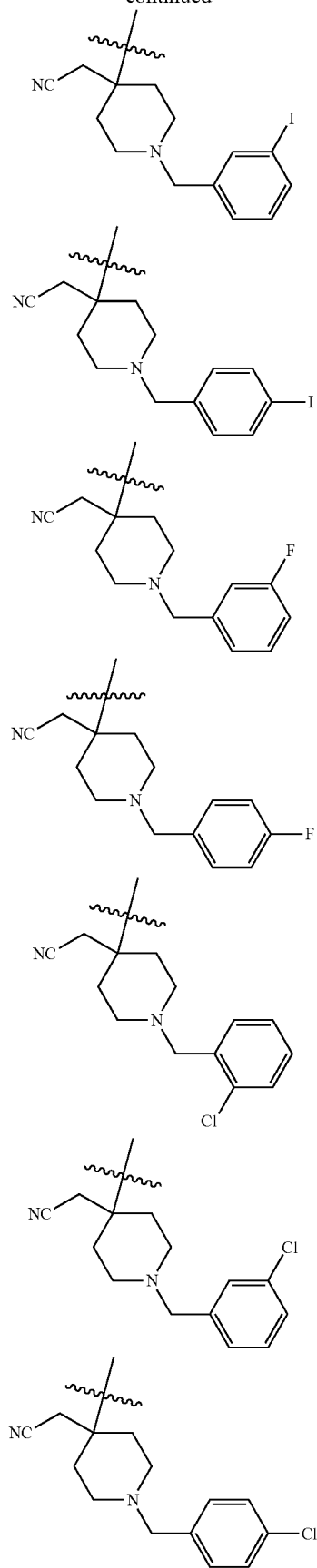
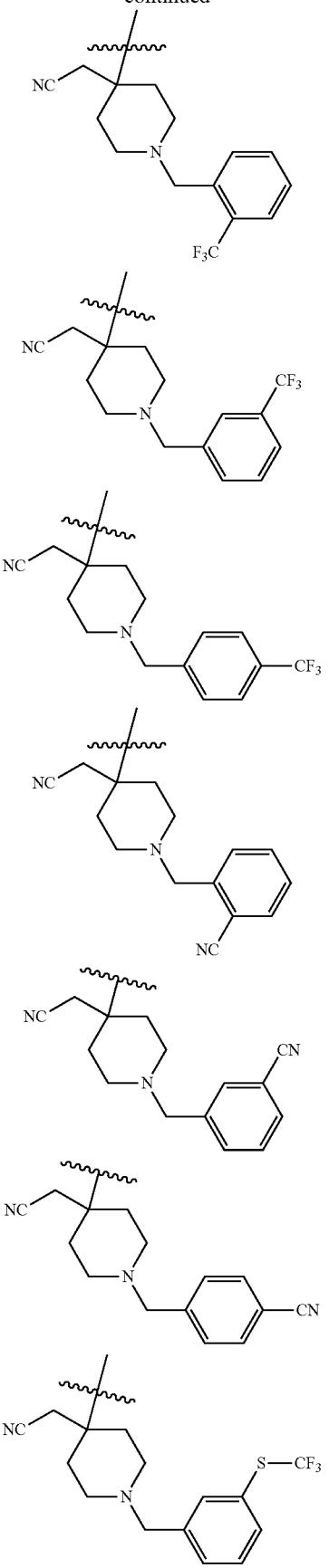

615
-continued
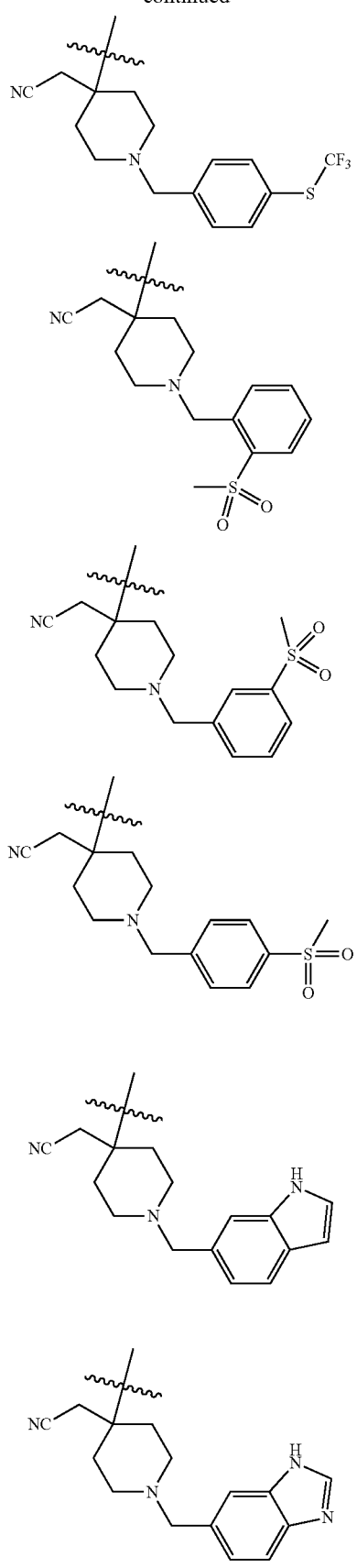
616
-continued
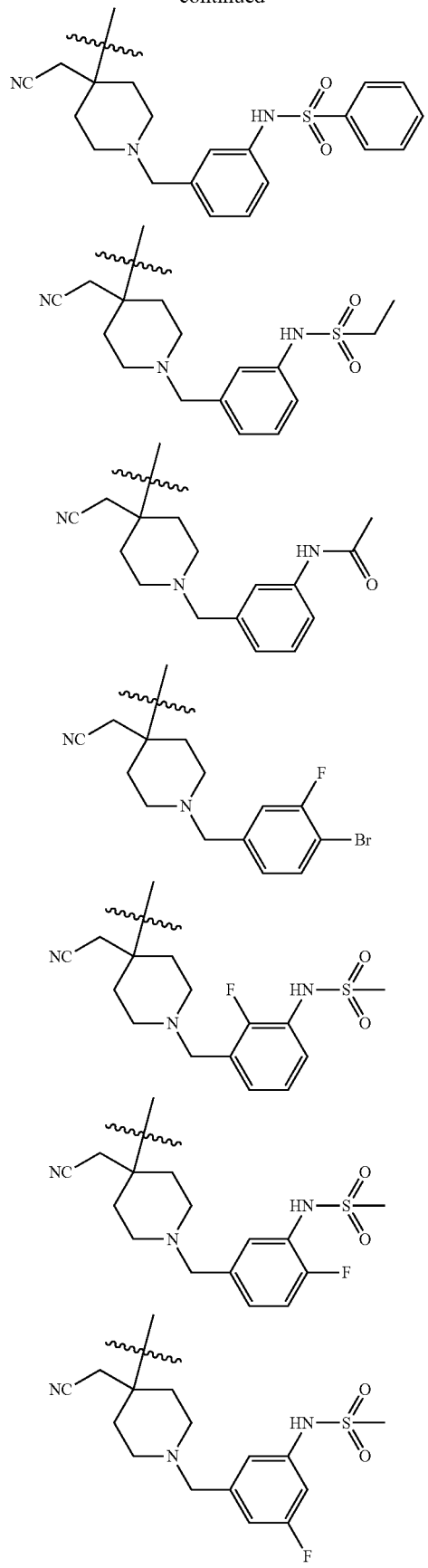

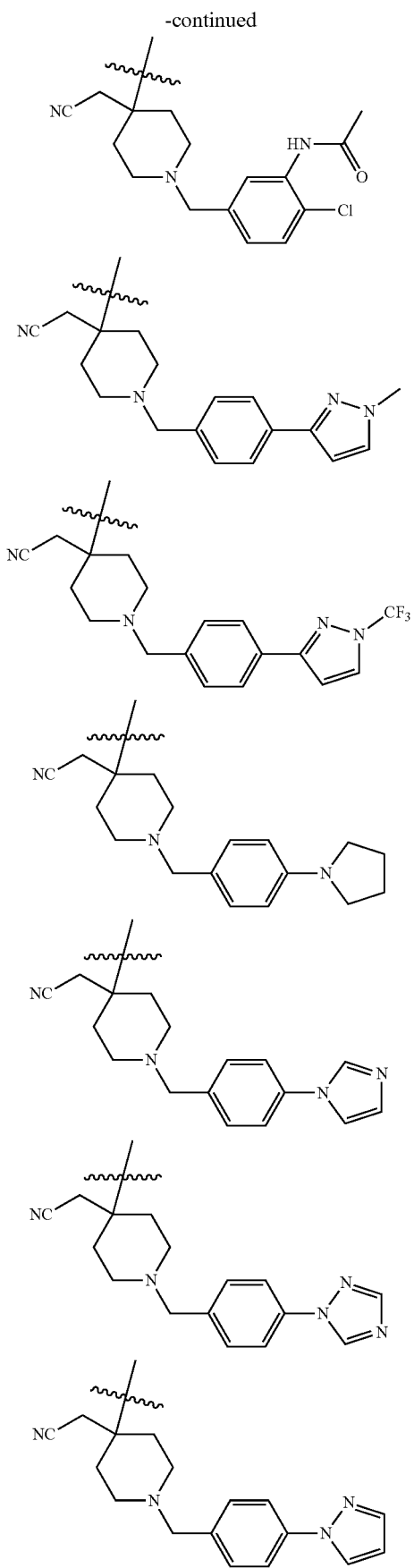
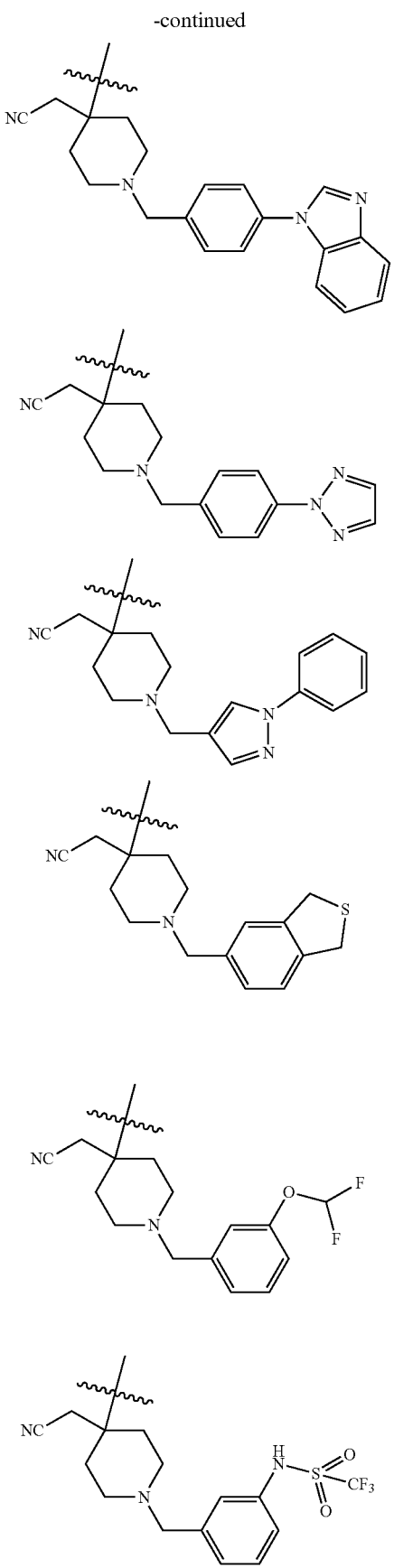

619
-continued
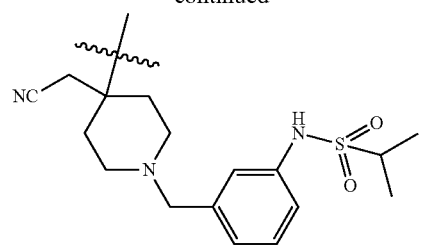
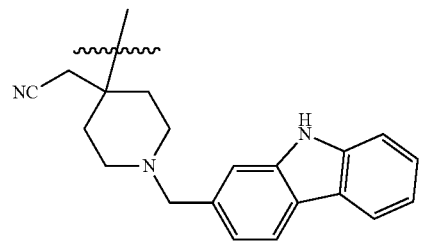
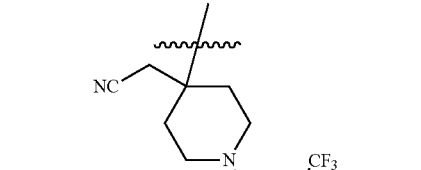
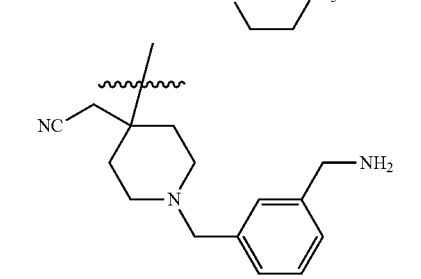
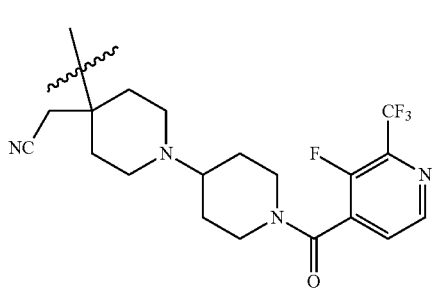
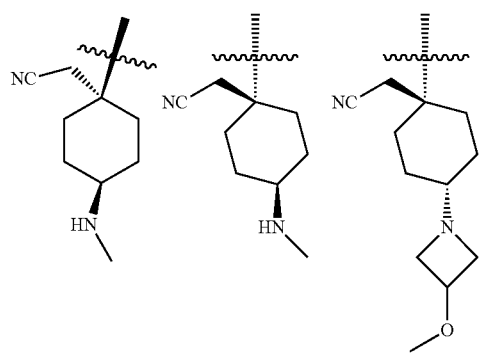
620
-continued
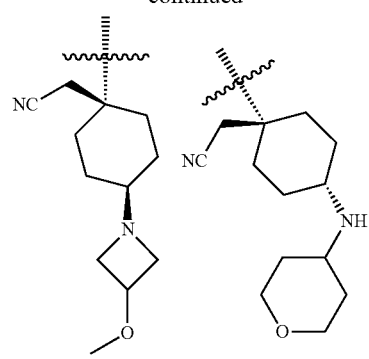
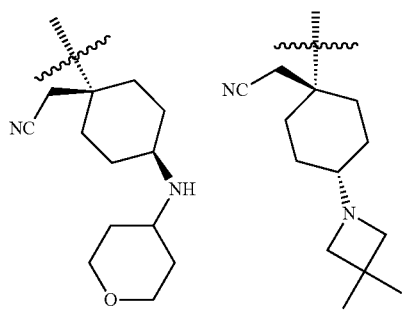
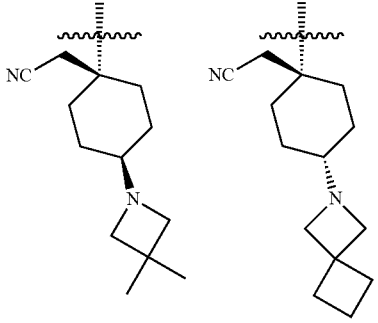
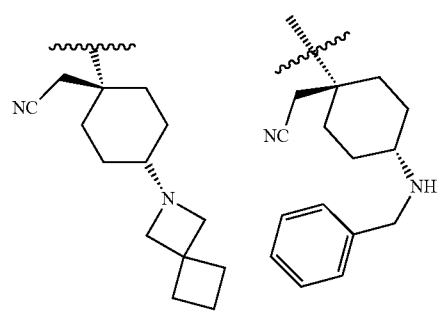
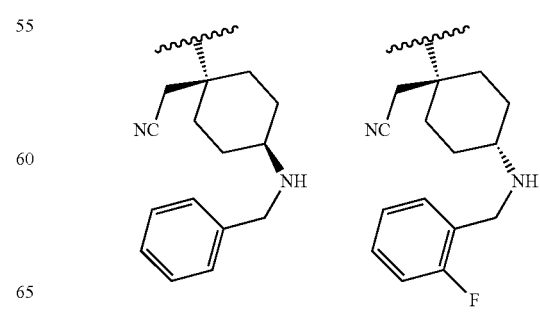

621
-continued
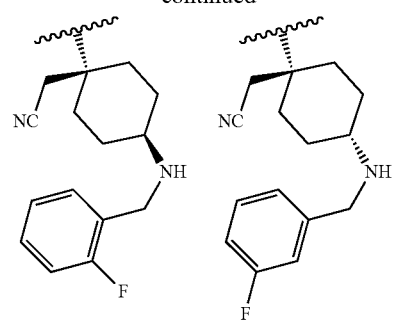
622
-continued
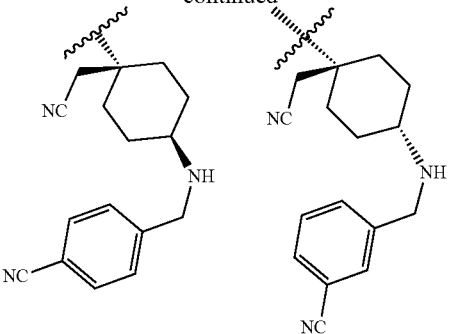
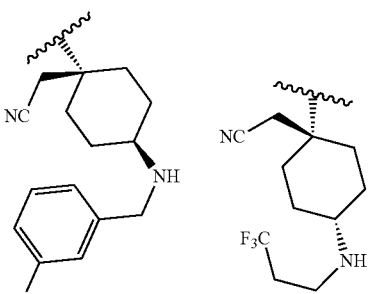
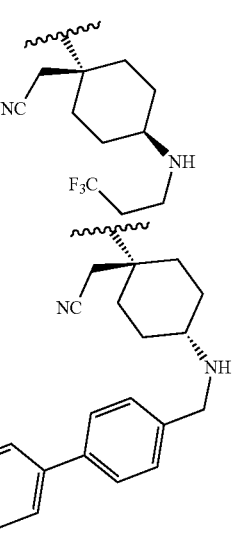
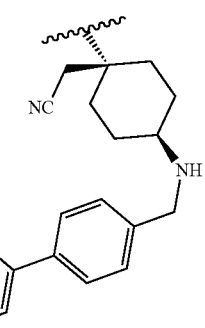
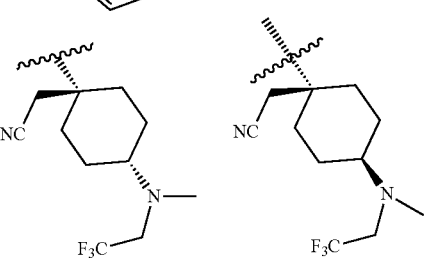

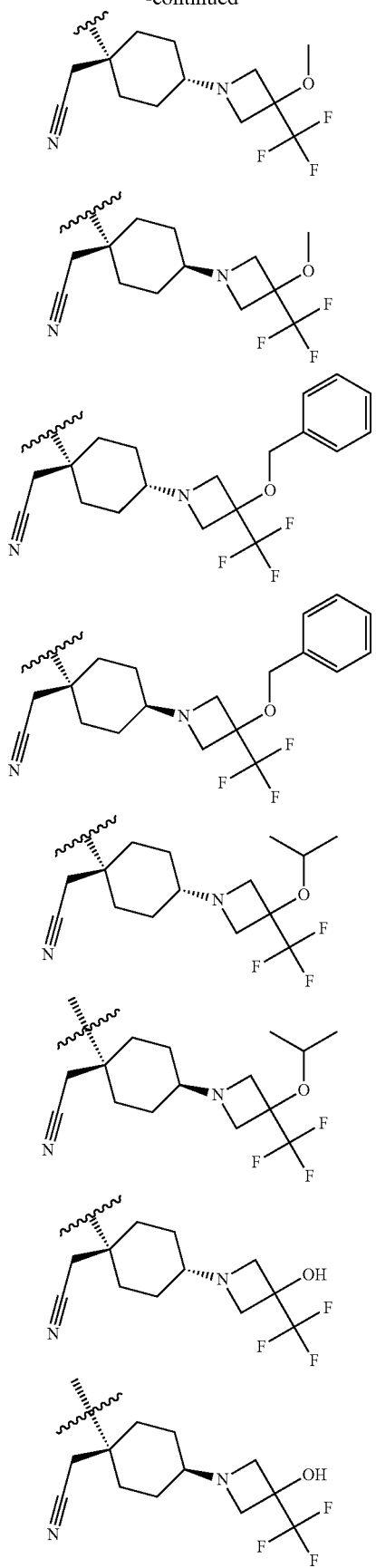
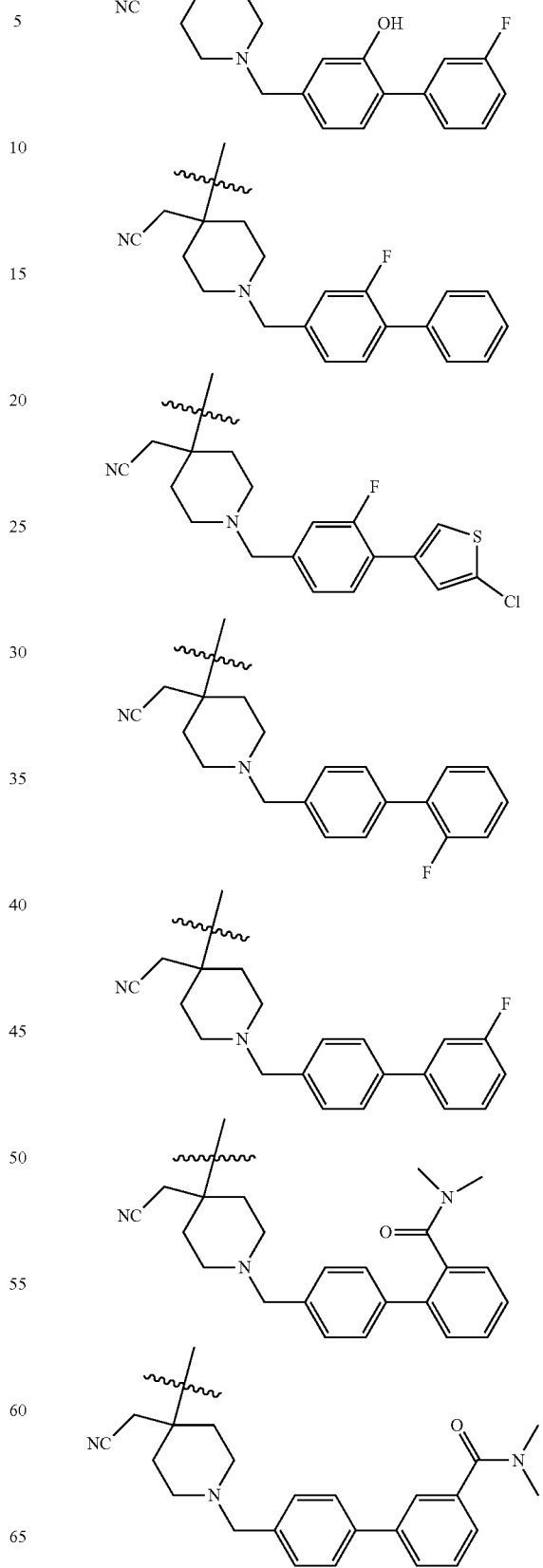

625
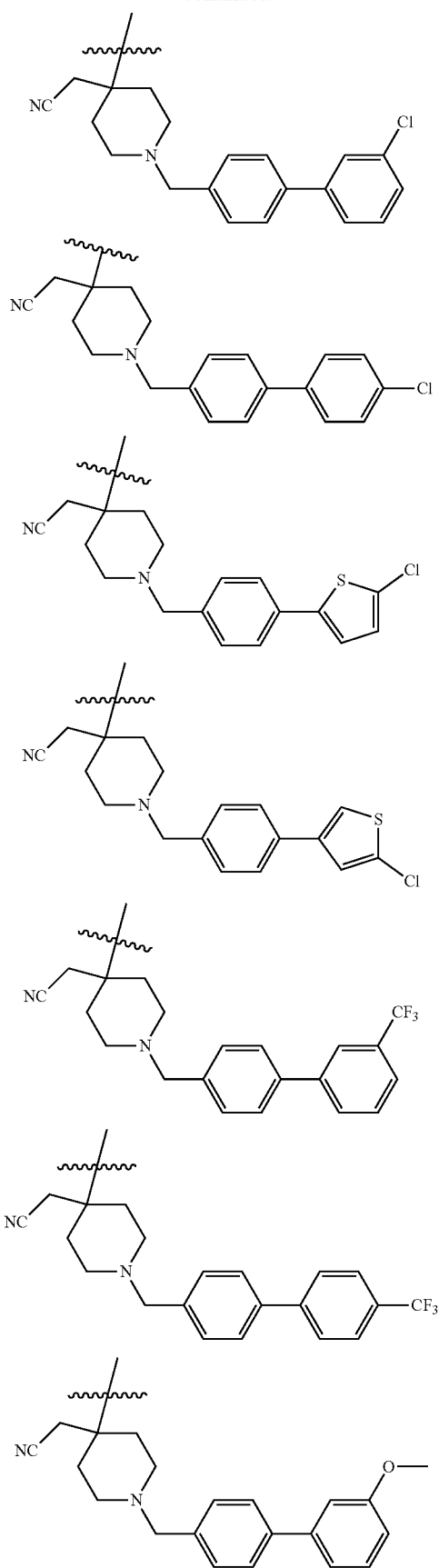
626
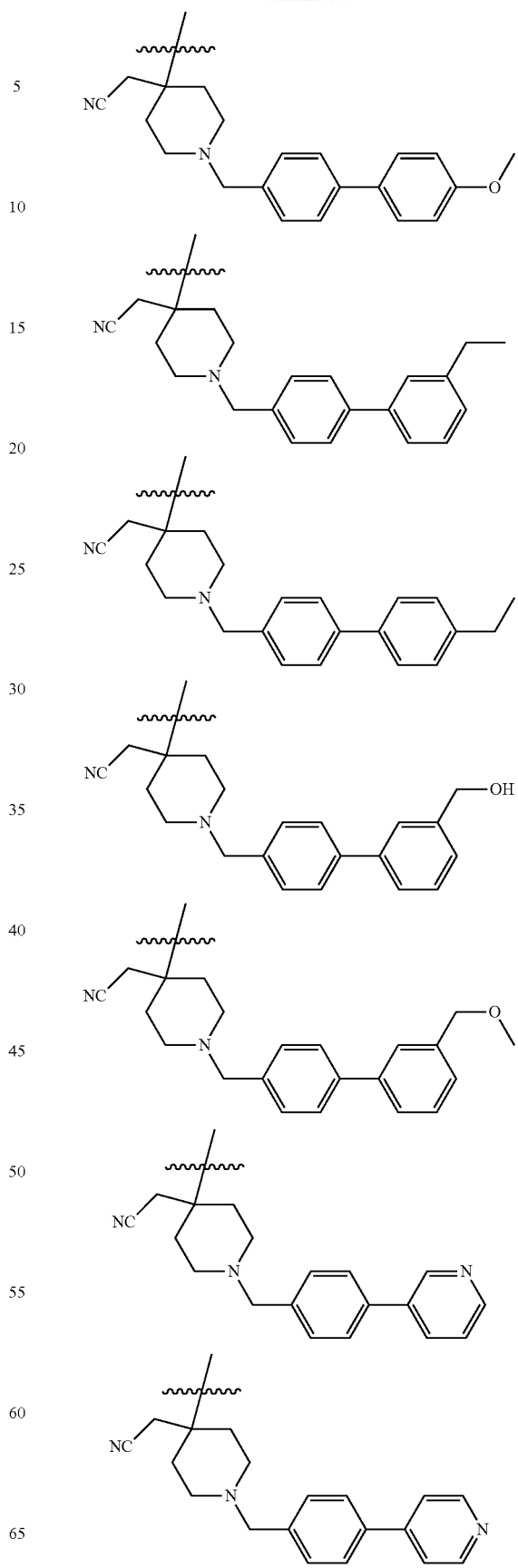

627
-continued
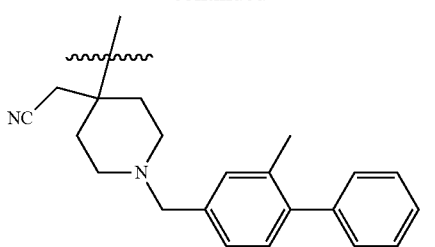
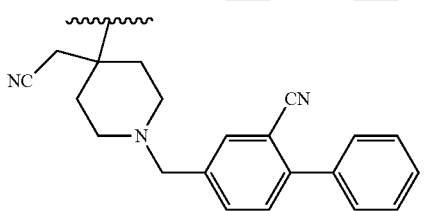
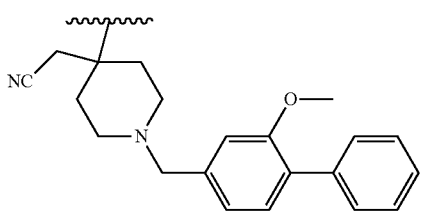
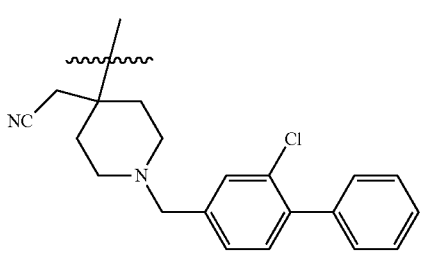
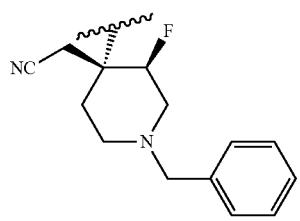
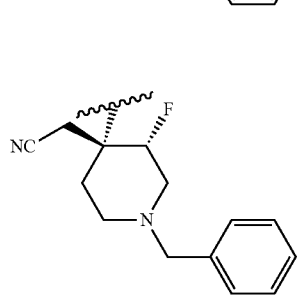
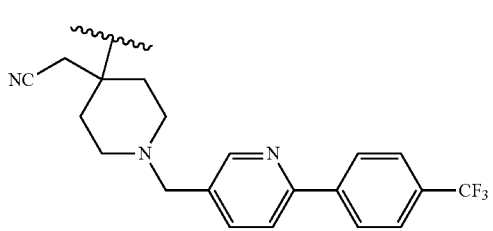
628
-continued
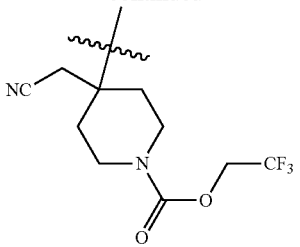
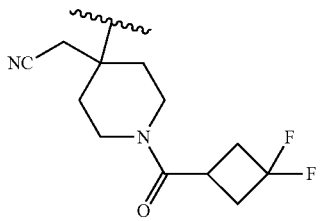
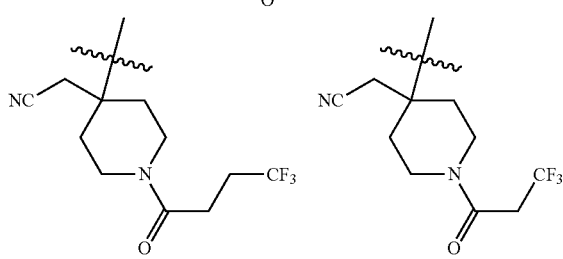
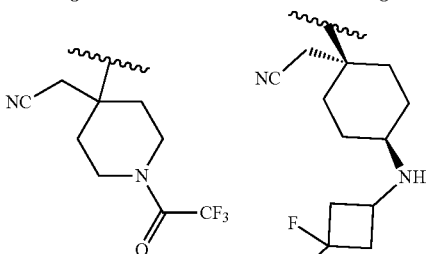
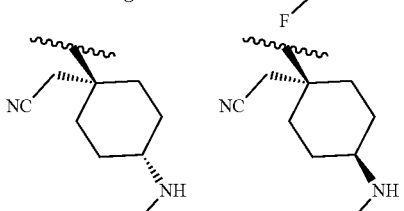
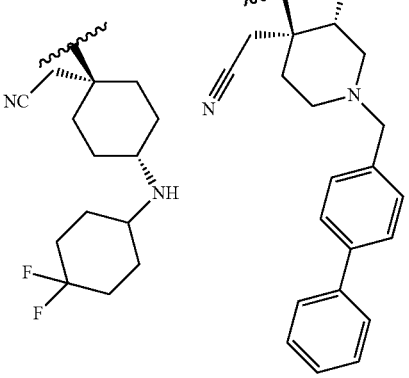

-continued
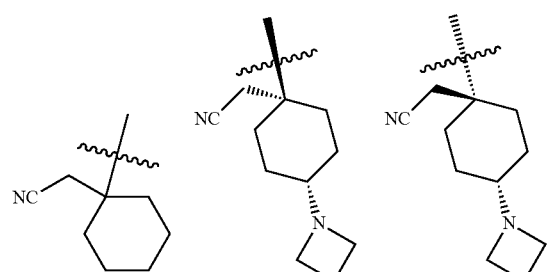
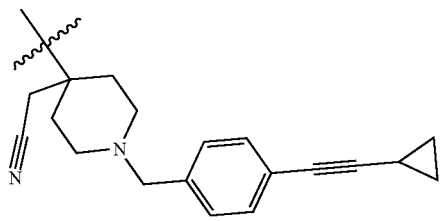
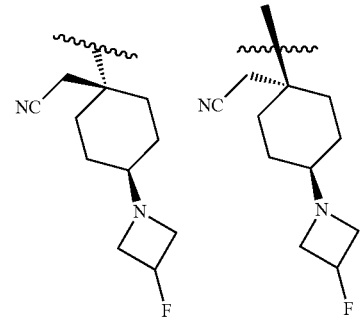
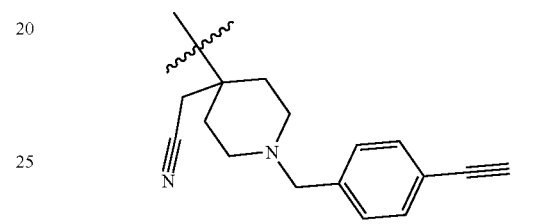
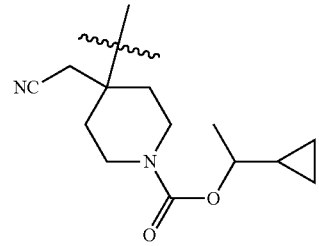
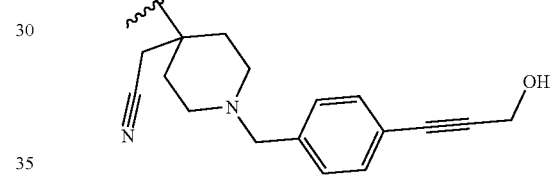
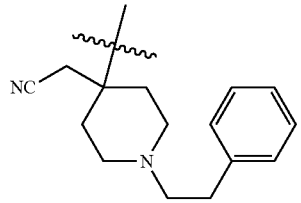
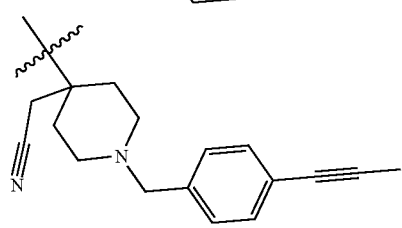
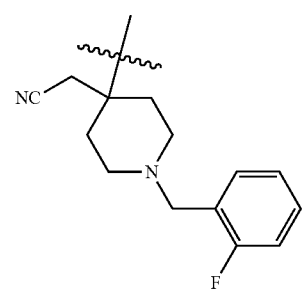
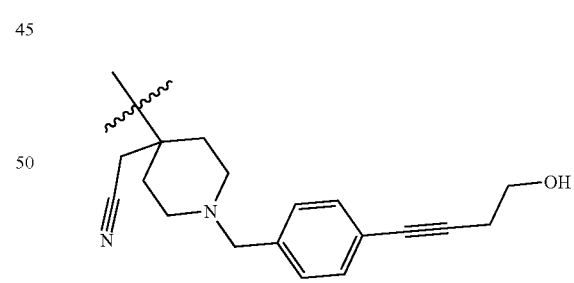
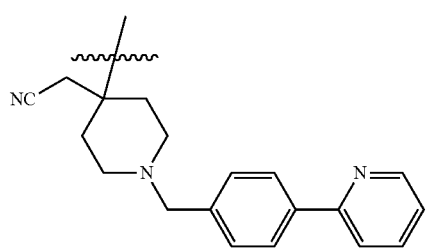
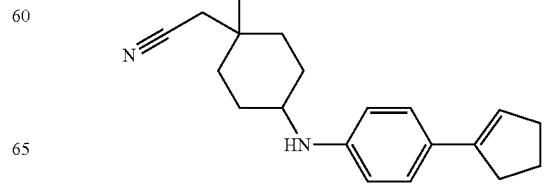

631
-continued
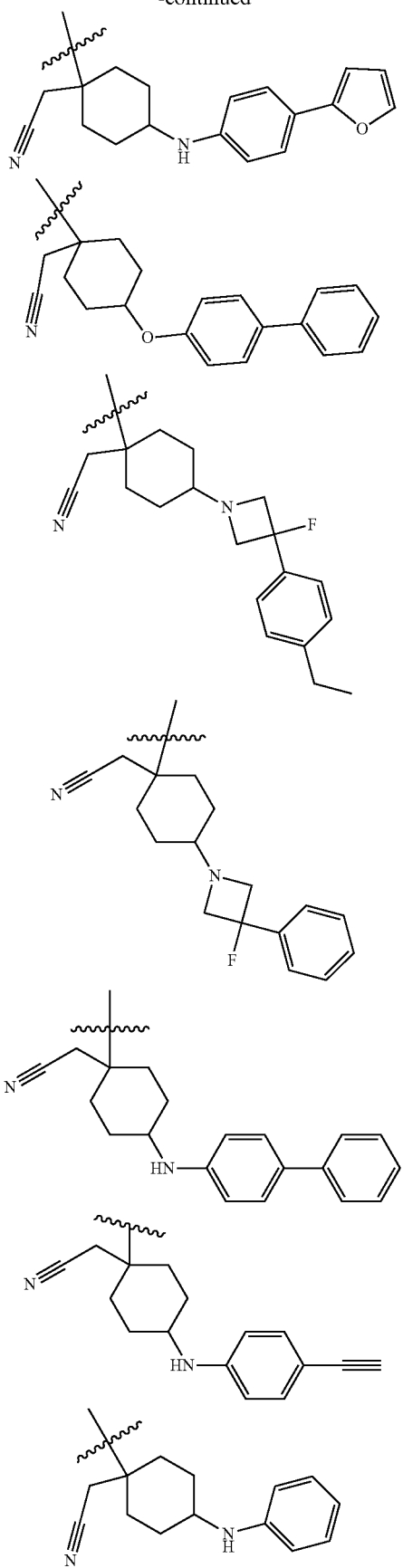
632
-continued
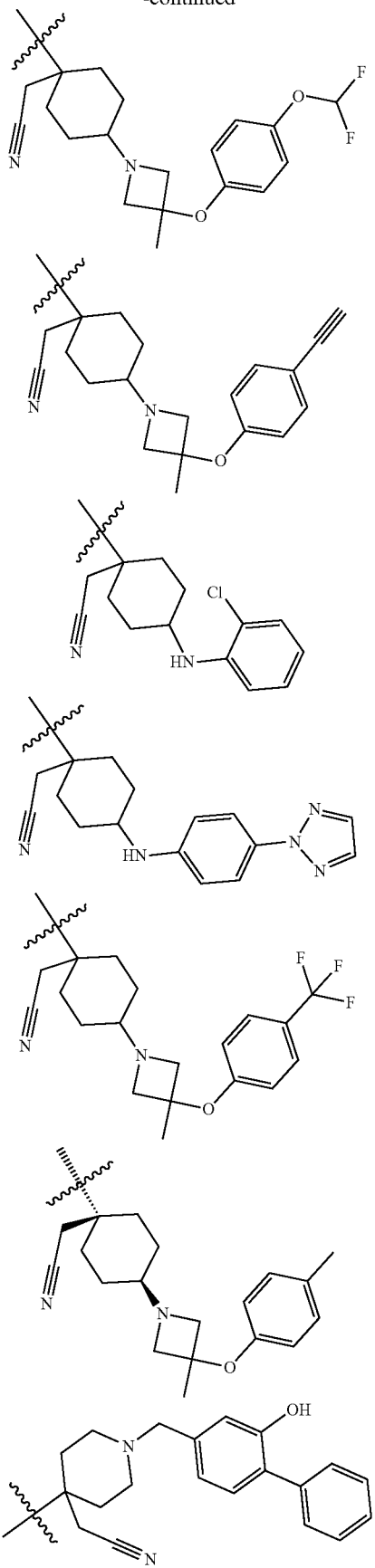

633
-continued
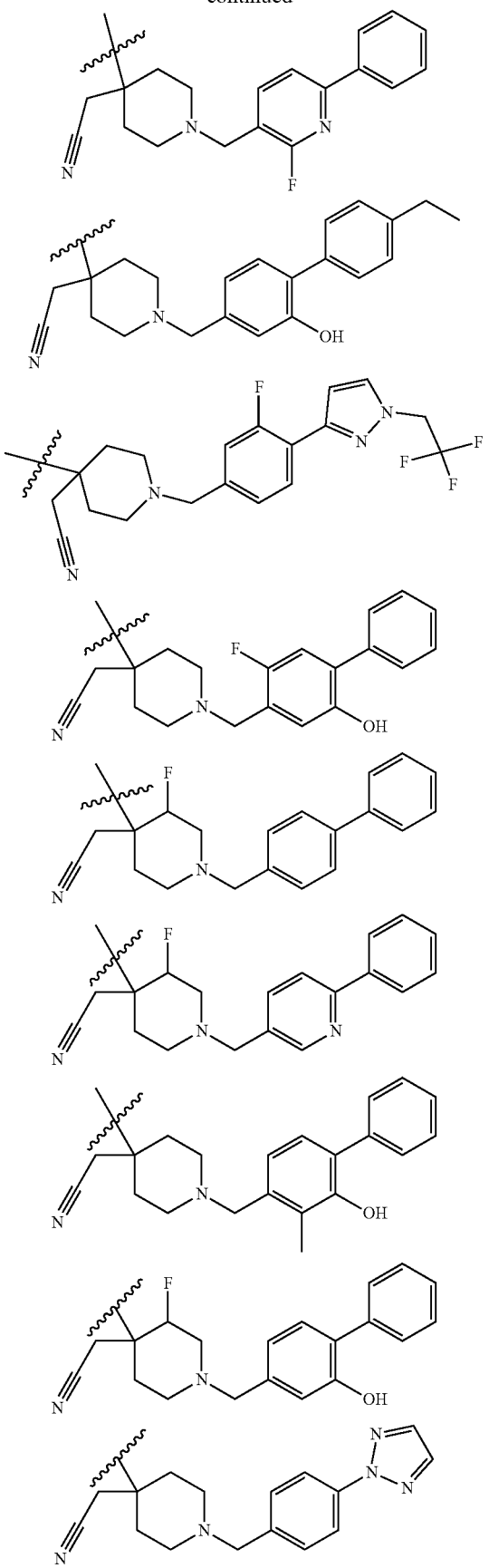
634
-continued
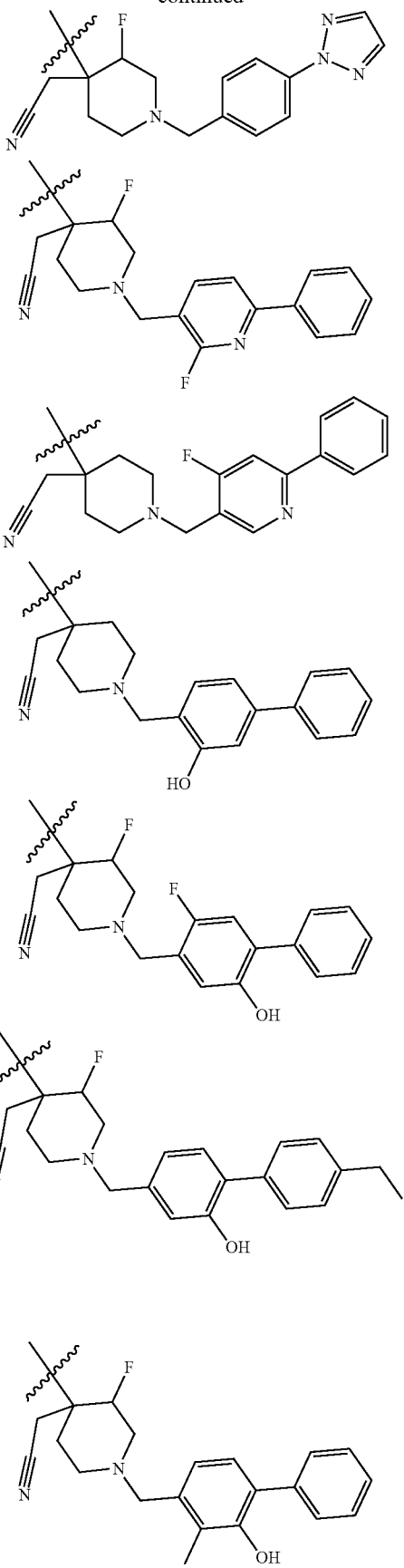

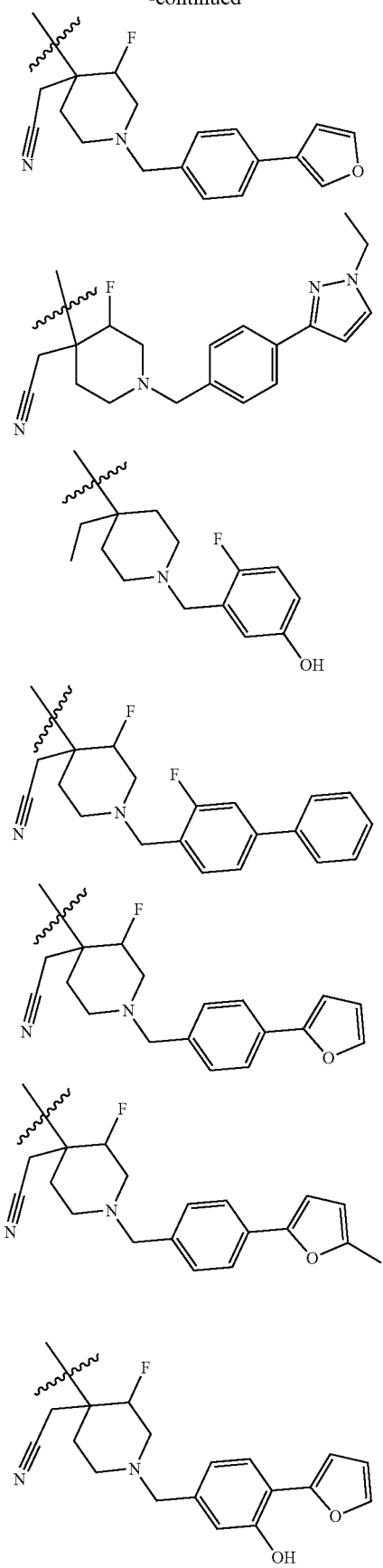
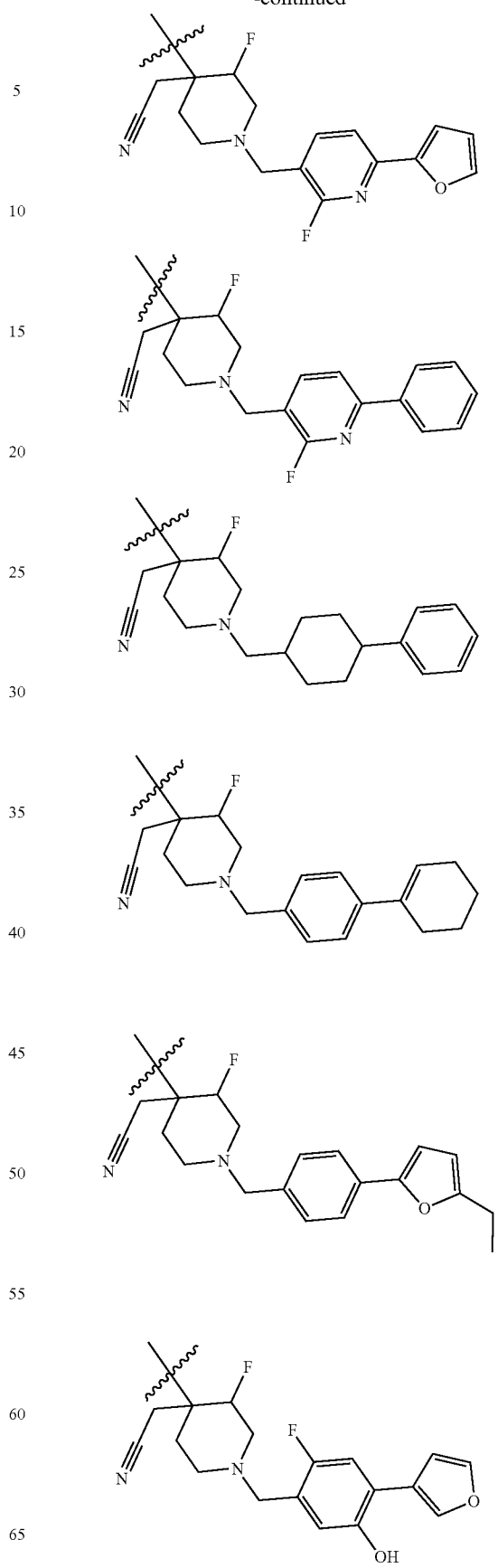

637
-continued
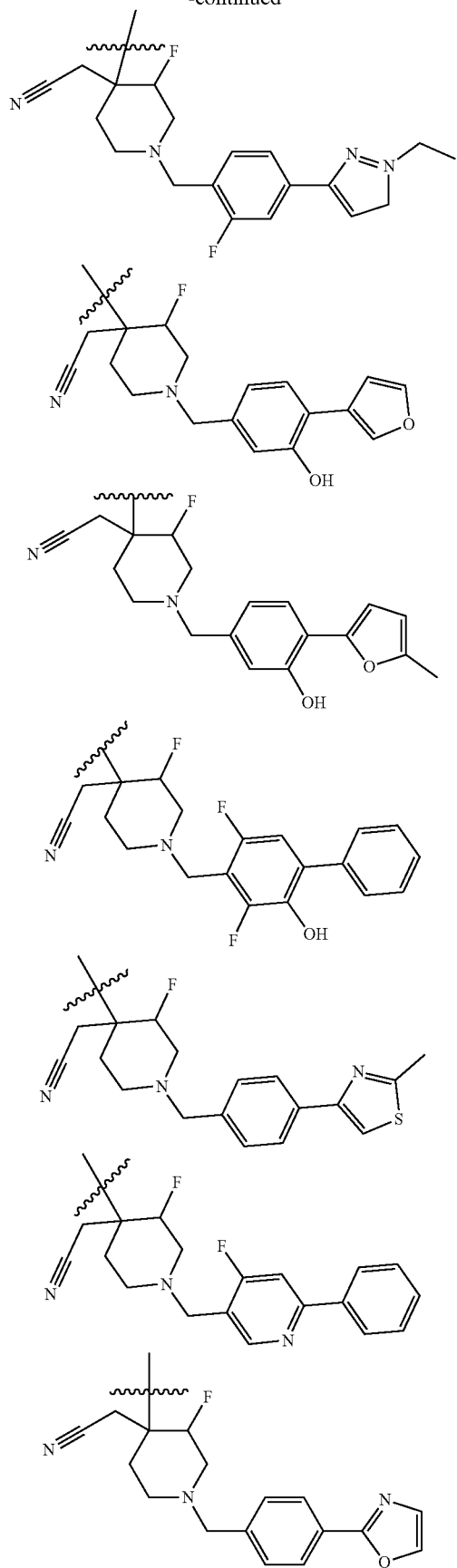
638
-continued
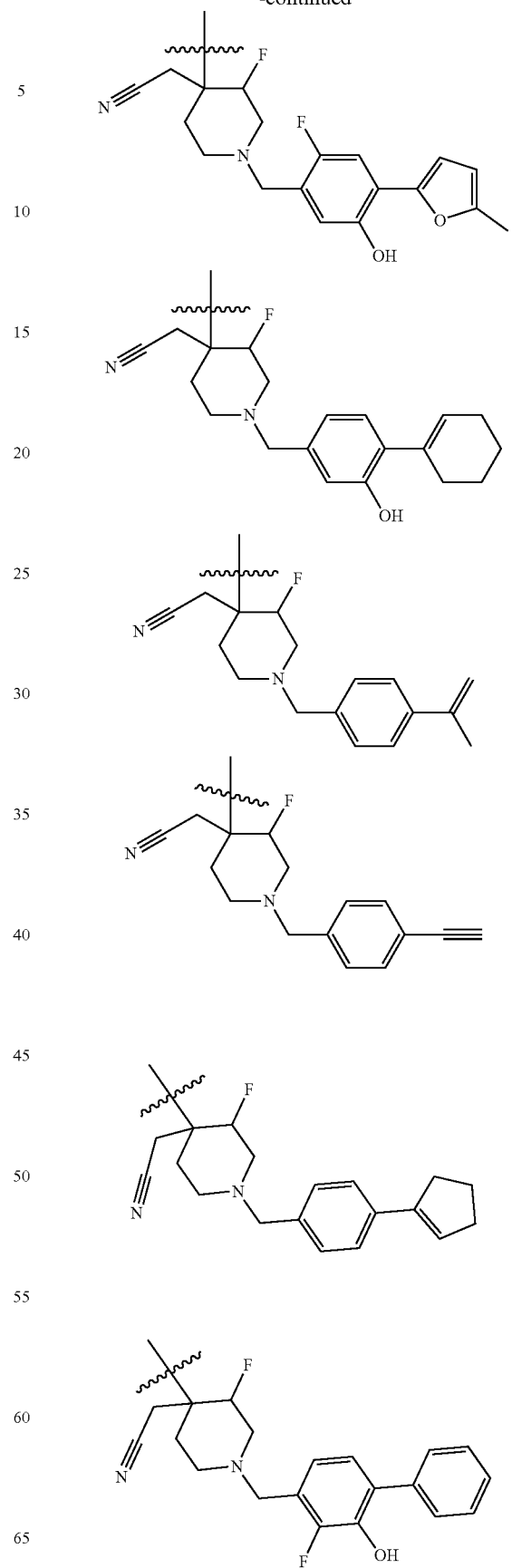

639
-continued
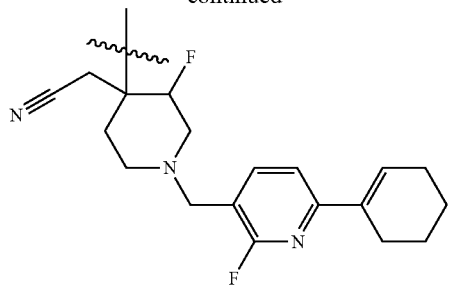
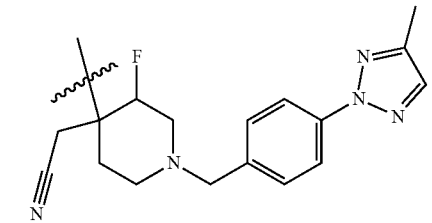
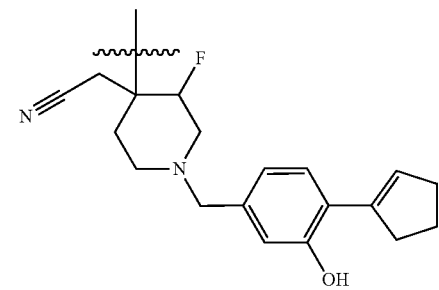
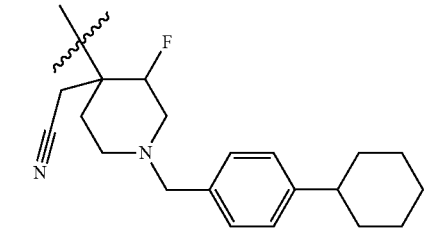
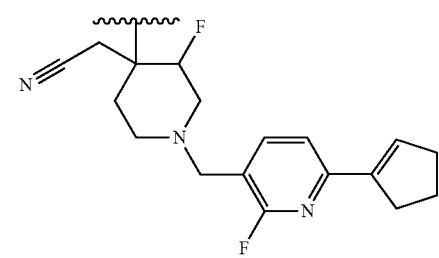
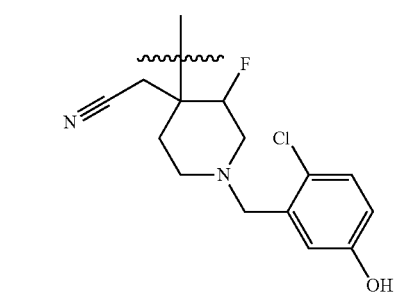
640
-continued
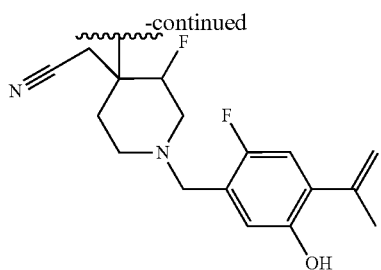
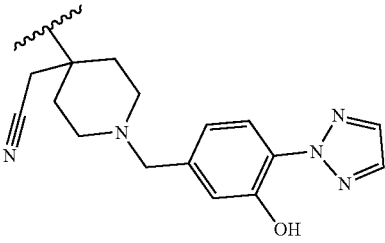
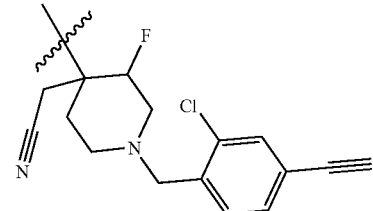
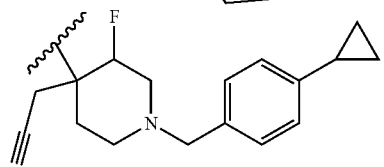
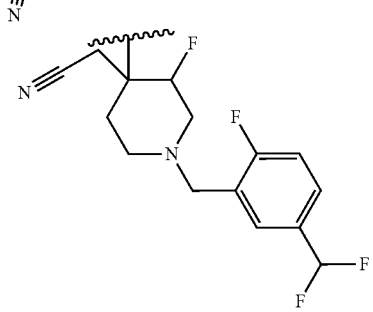
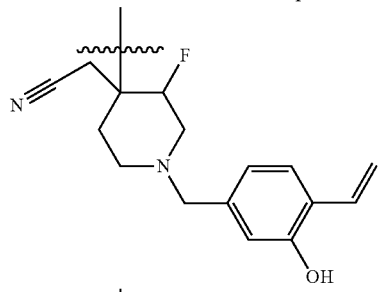
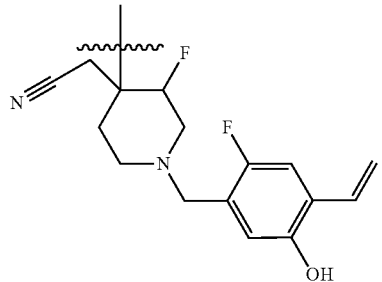

-continued
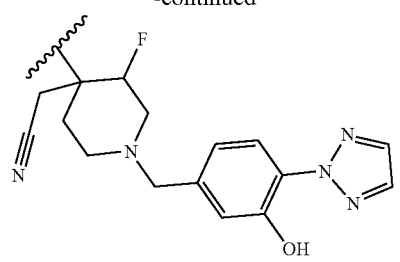
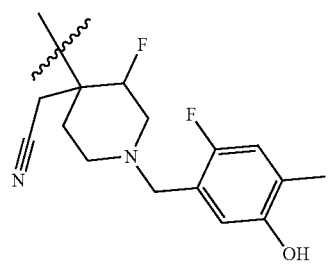
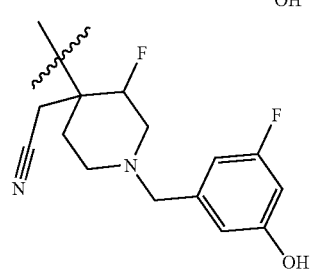
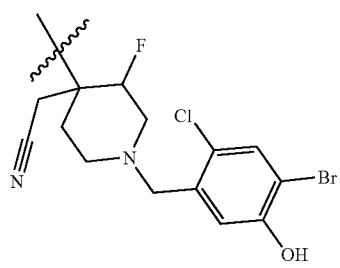
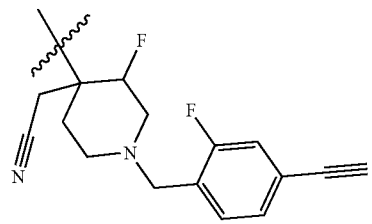
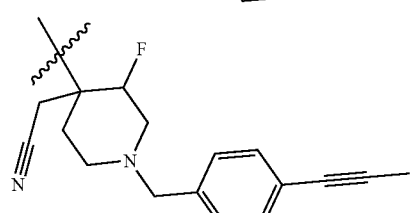
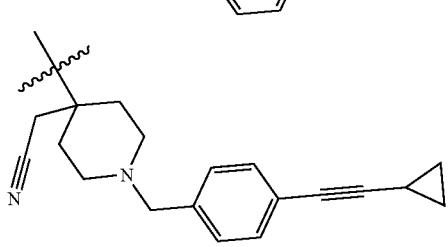
-continued
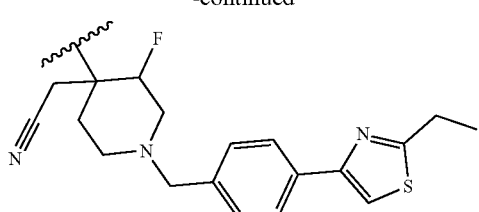
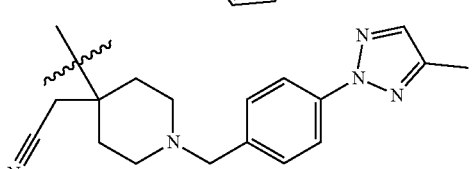
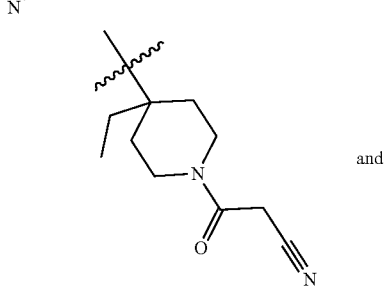
and
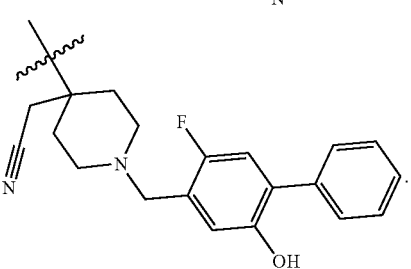
5. The compound of claim 1 or a pharmaceutically acceptable salt thereof, wherein $R^c$ is selected from the group consisting of:
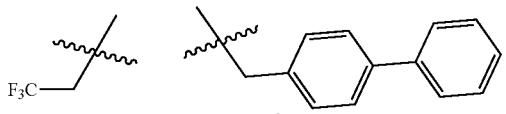
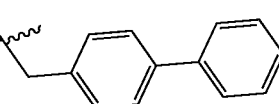
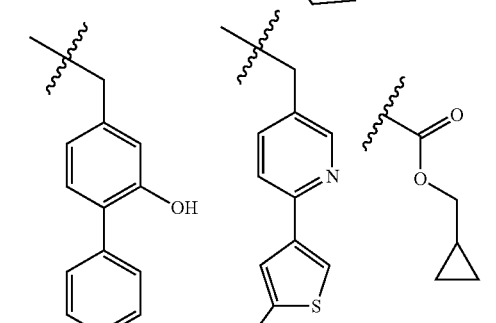
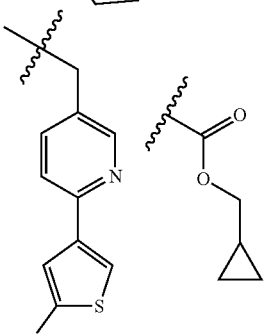
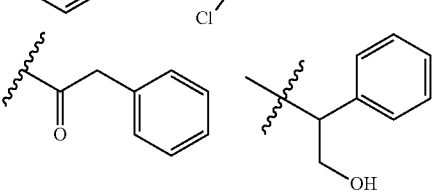
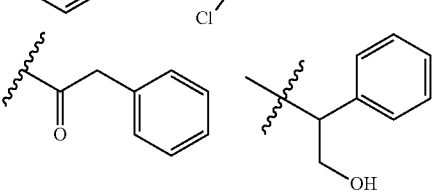

-continued
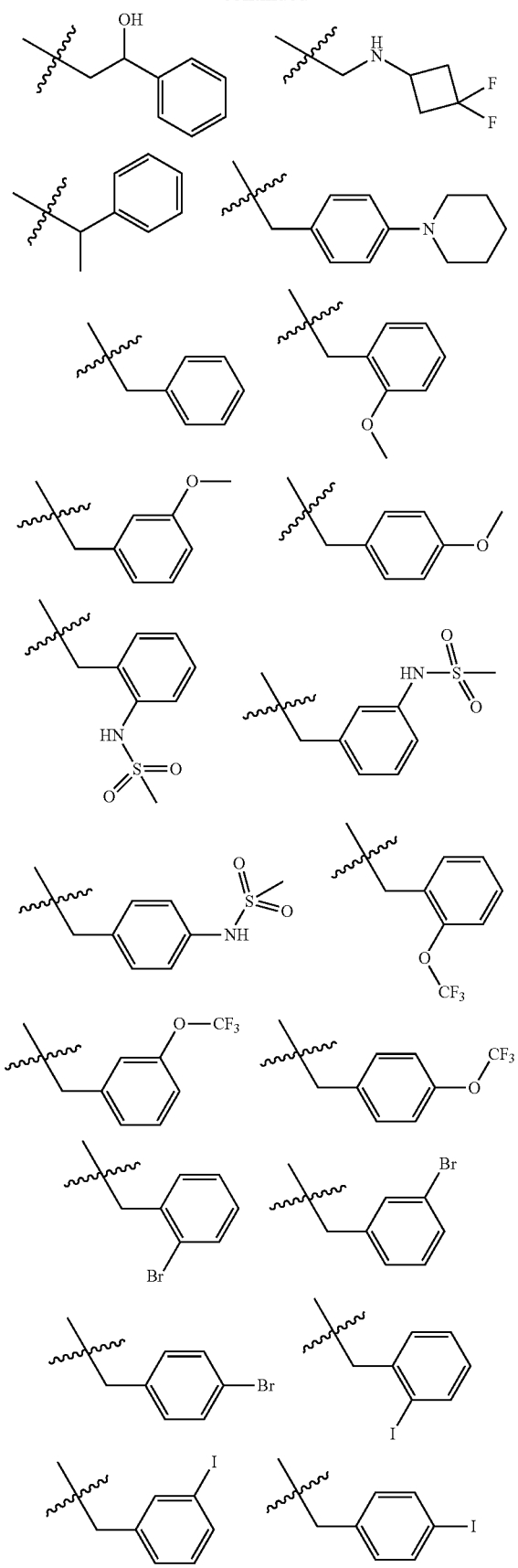
-continued
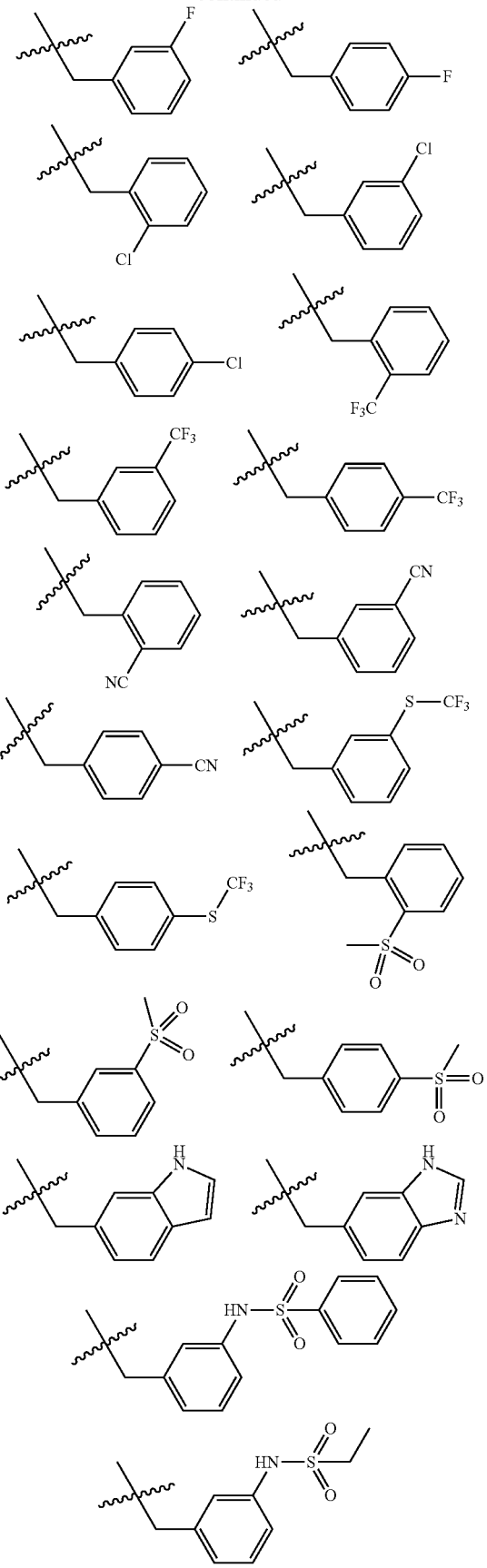

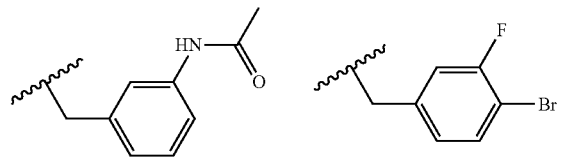
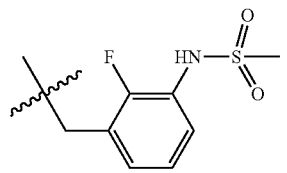
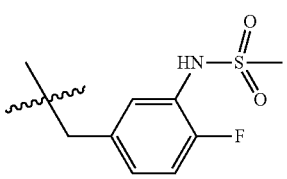
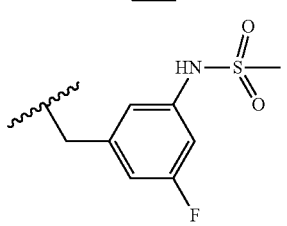
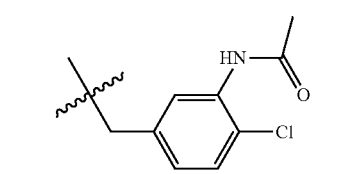
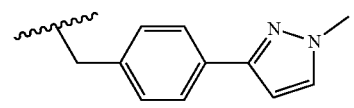
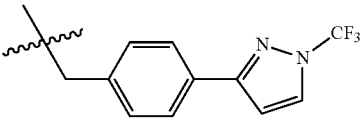
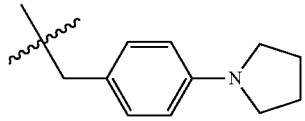
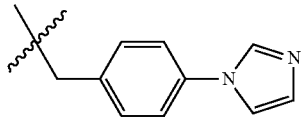
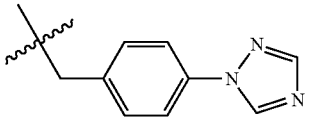
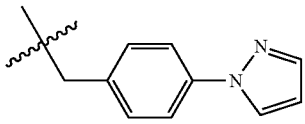
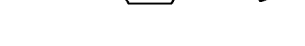
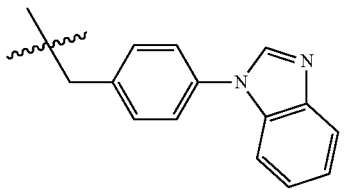
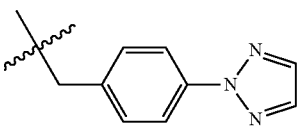
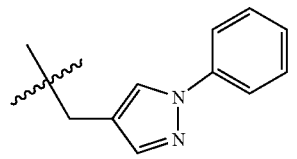
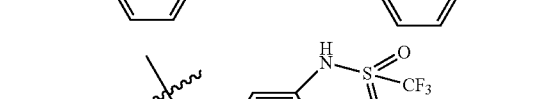
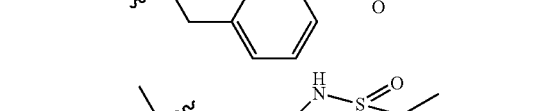
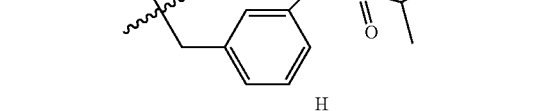
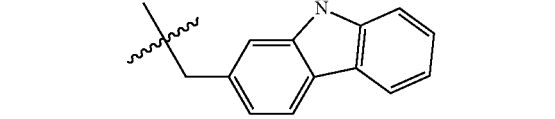
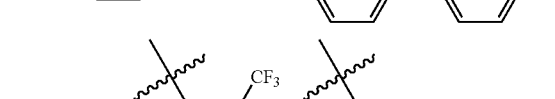
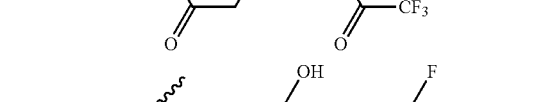
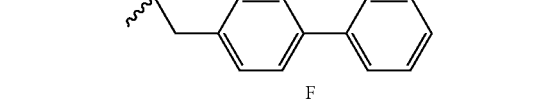
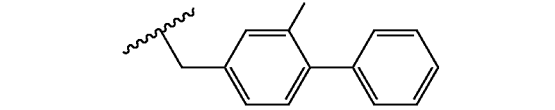
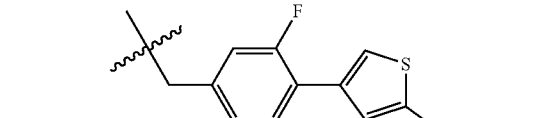

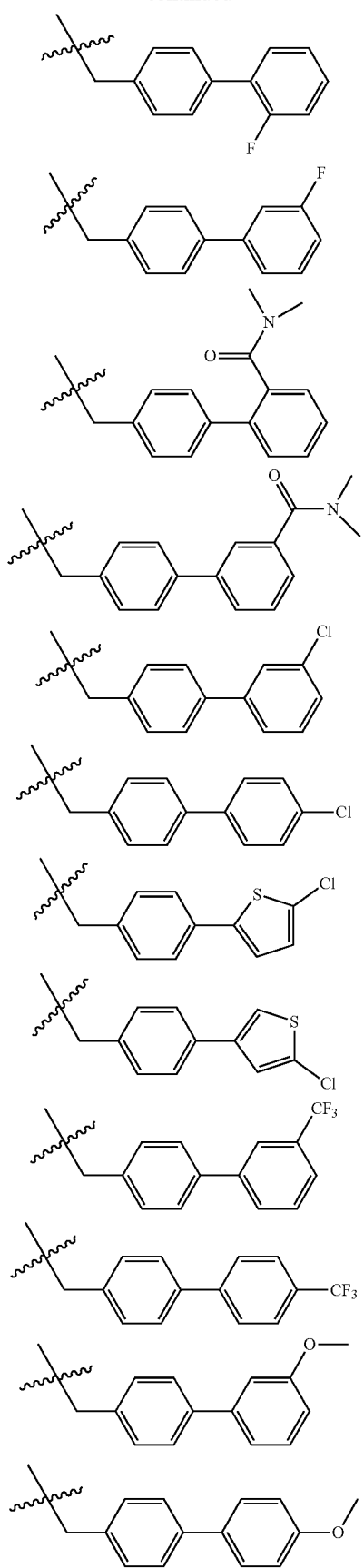
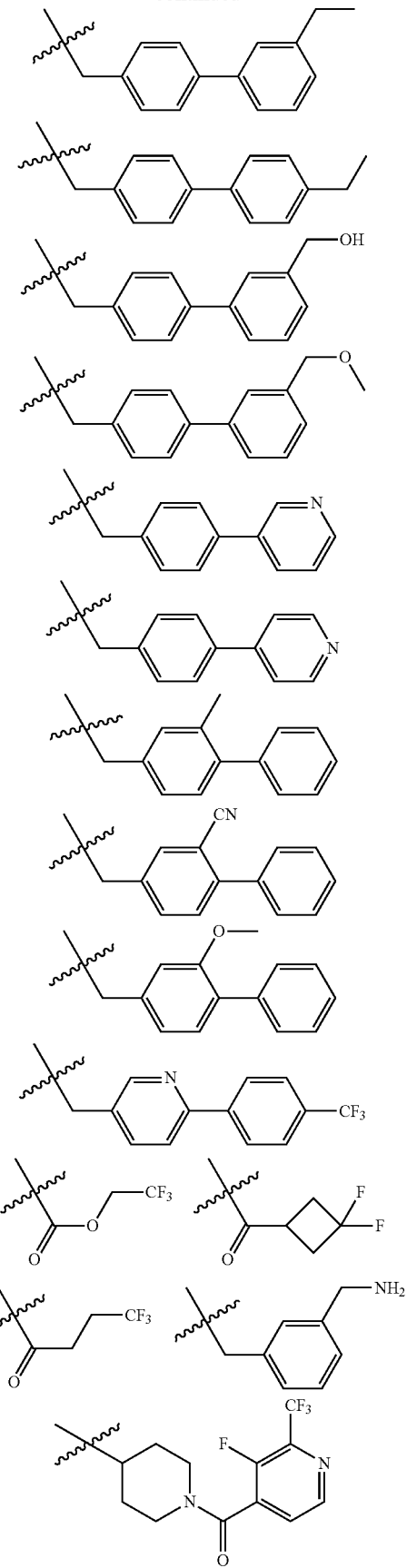

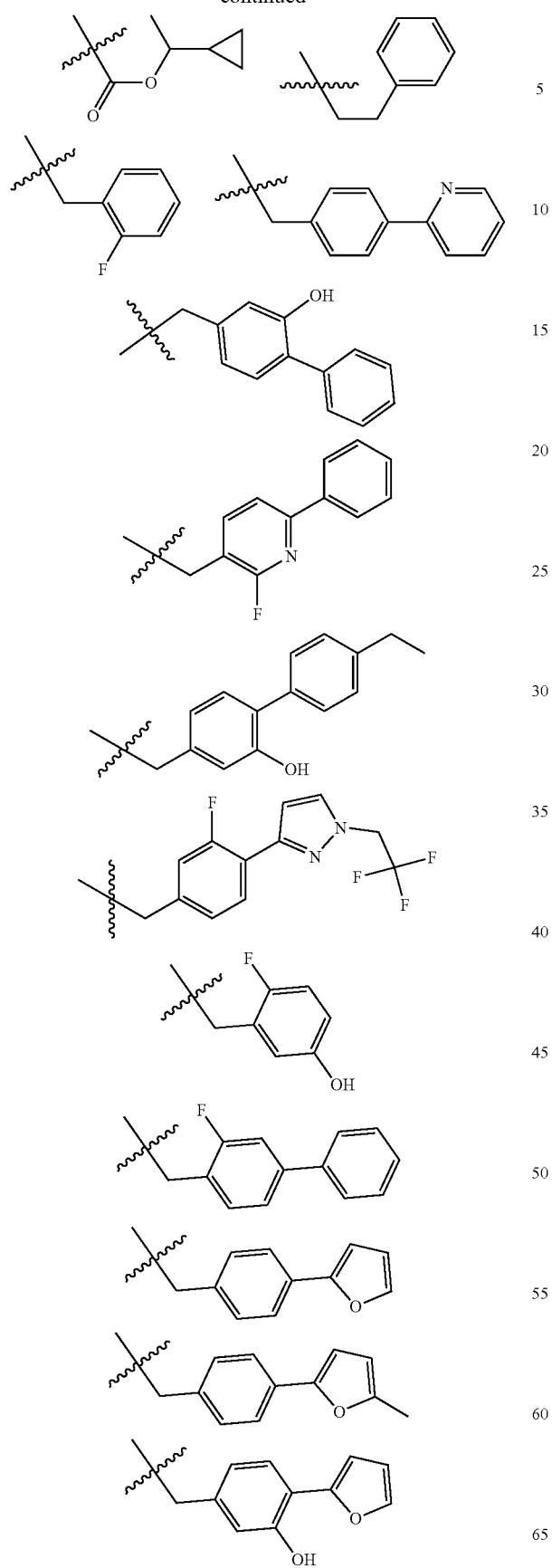
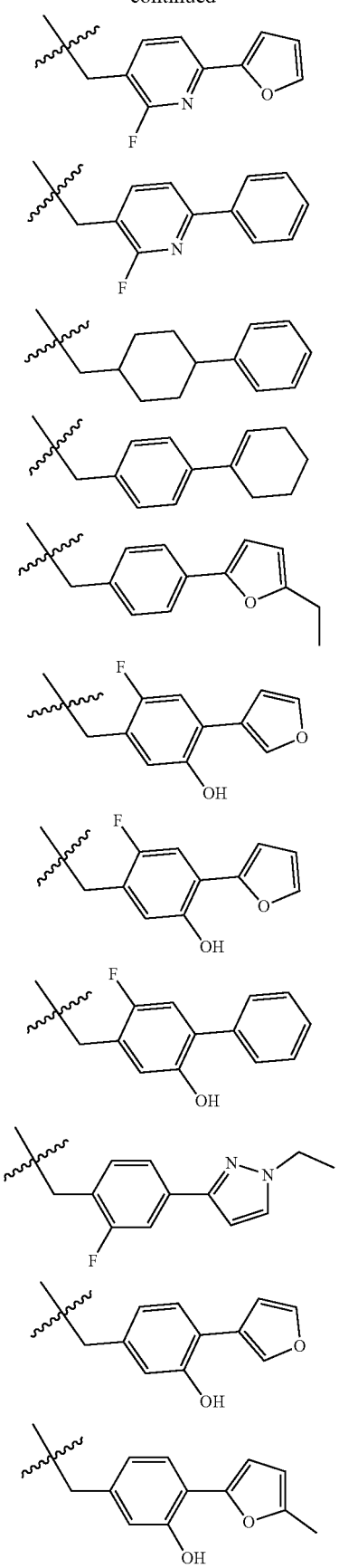

651
-continued
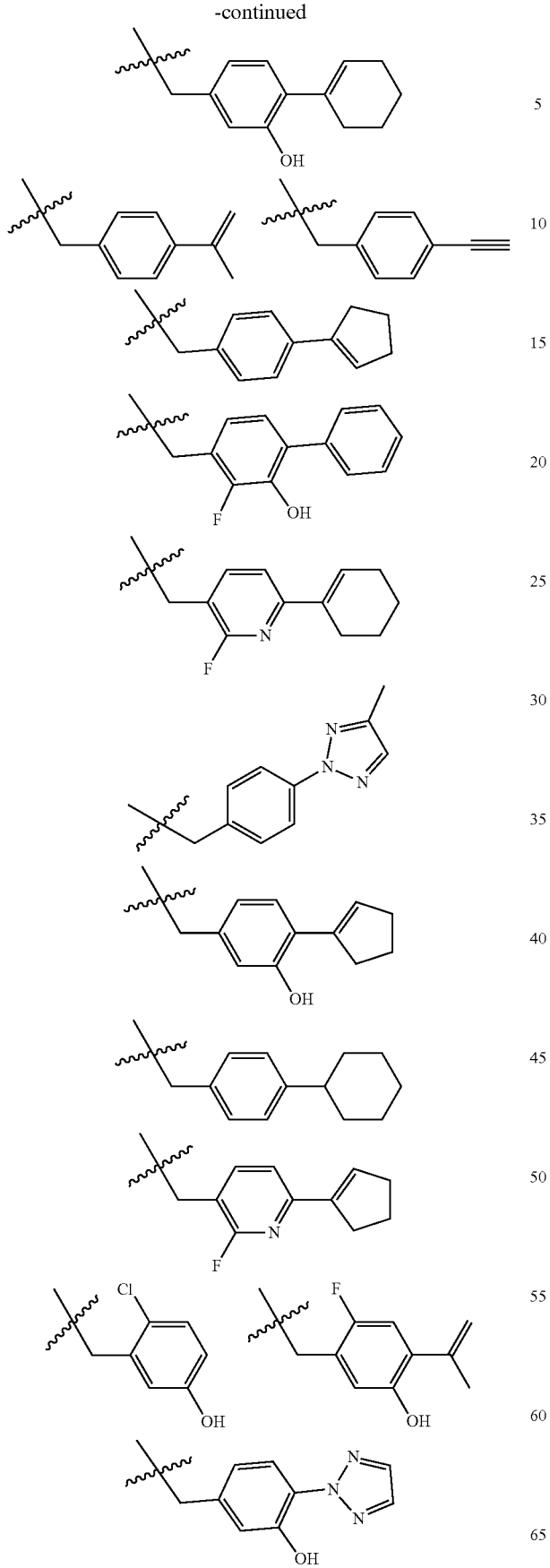
652
-continued
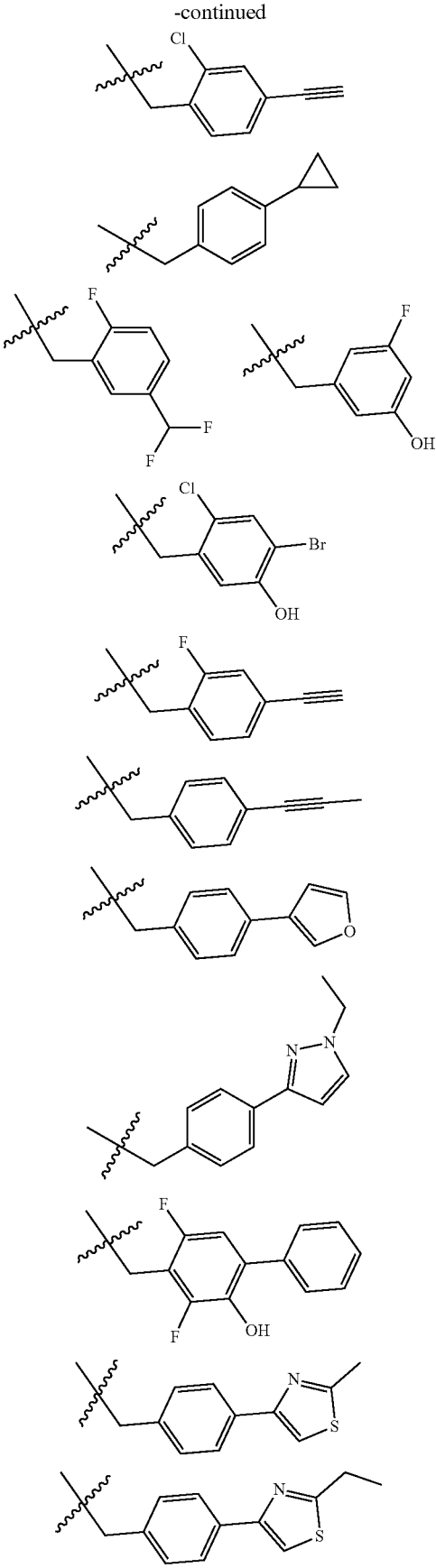

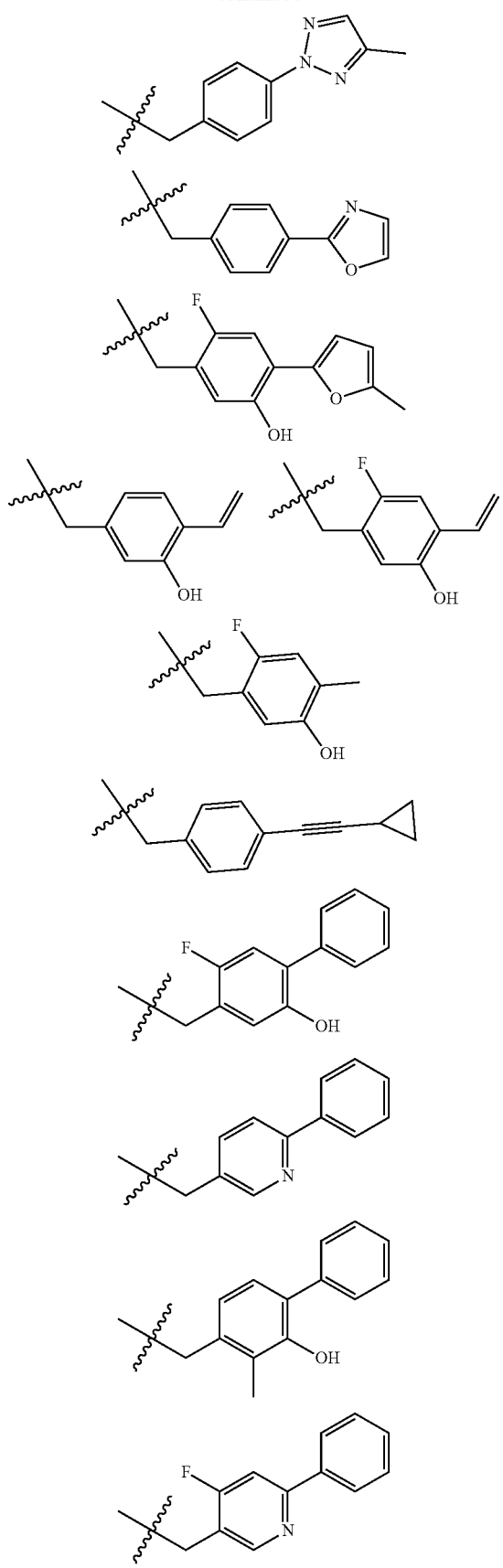
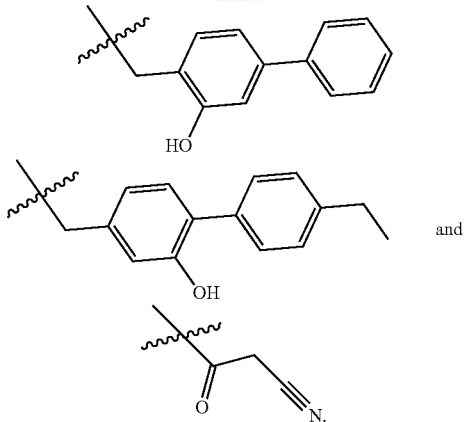
6. A compound or a pharmaceutically acceptable salt thereof, selected from the group consisting of:
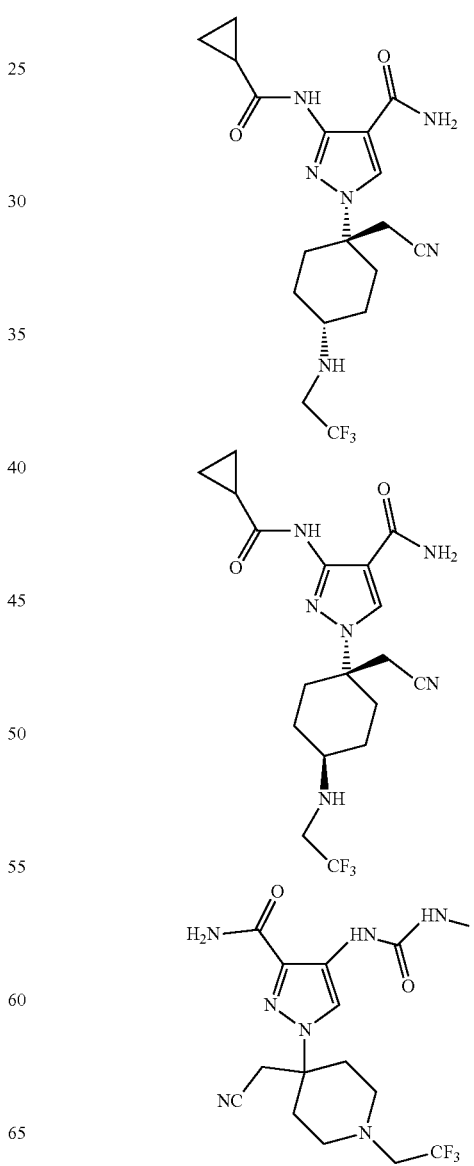

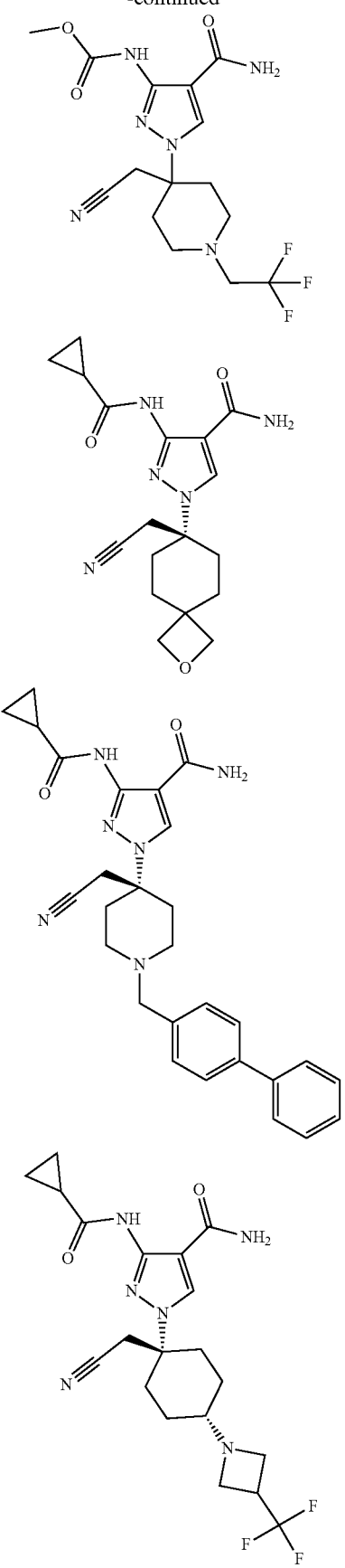
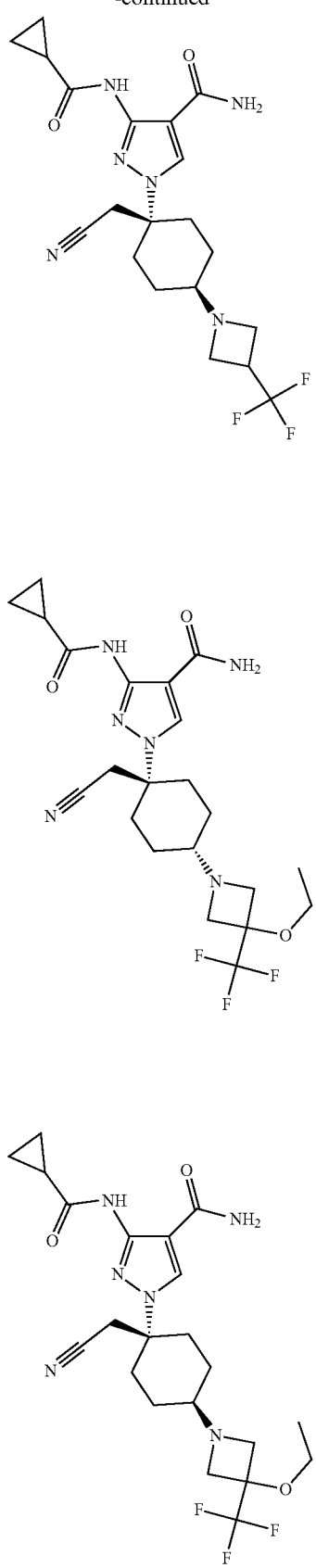

657
-continued
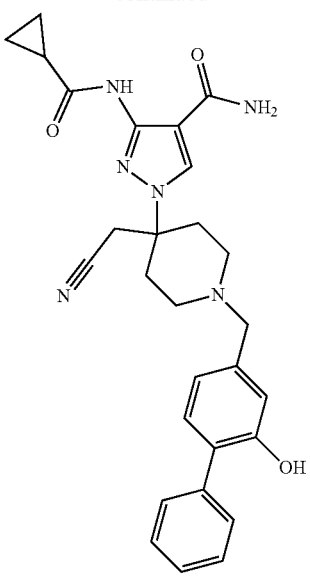
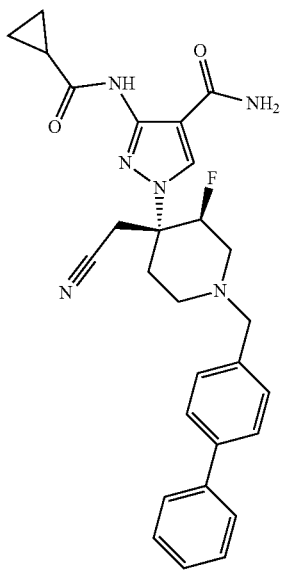
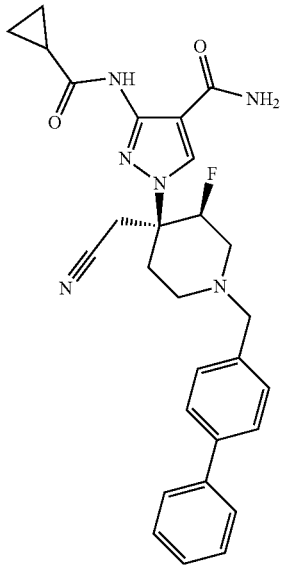
658
-continued
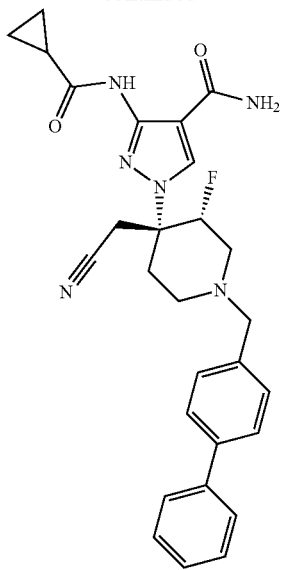
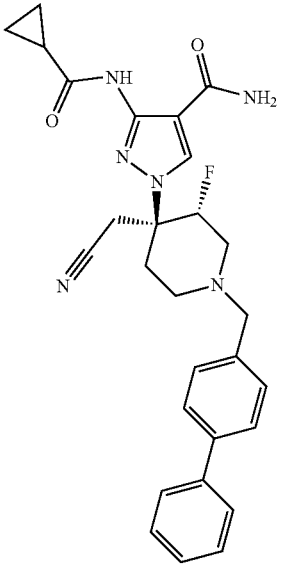
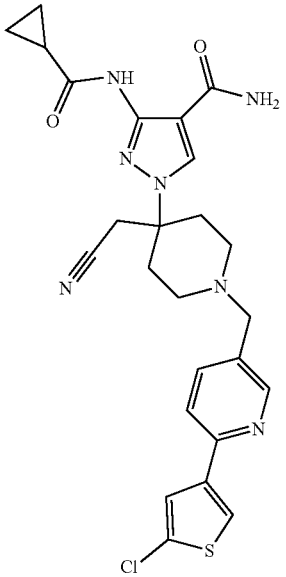

659
-continued
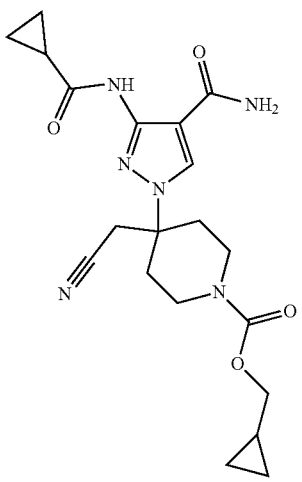
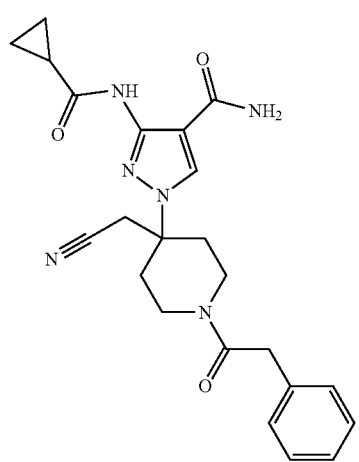
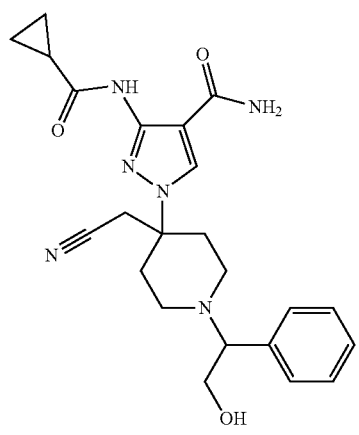
660
-continued
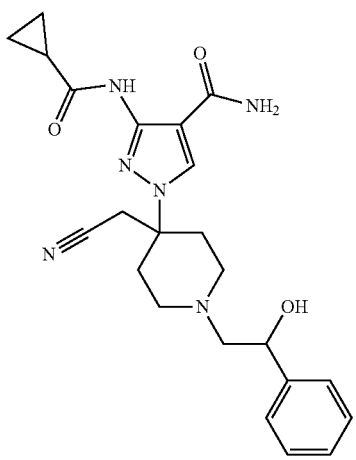
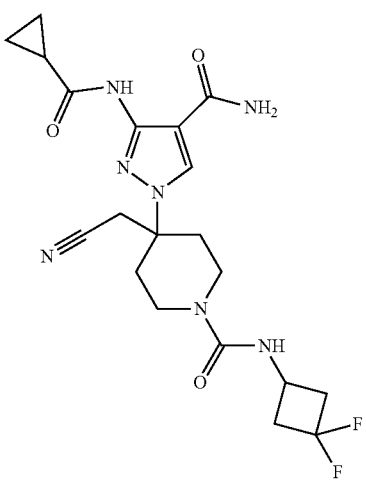
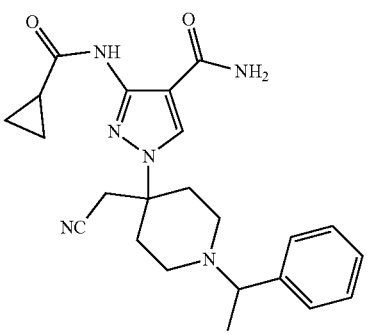
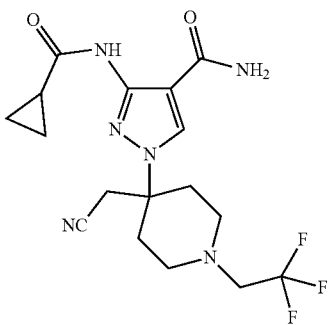

661
-continued
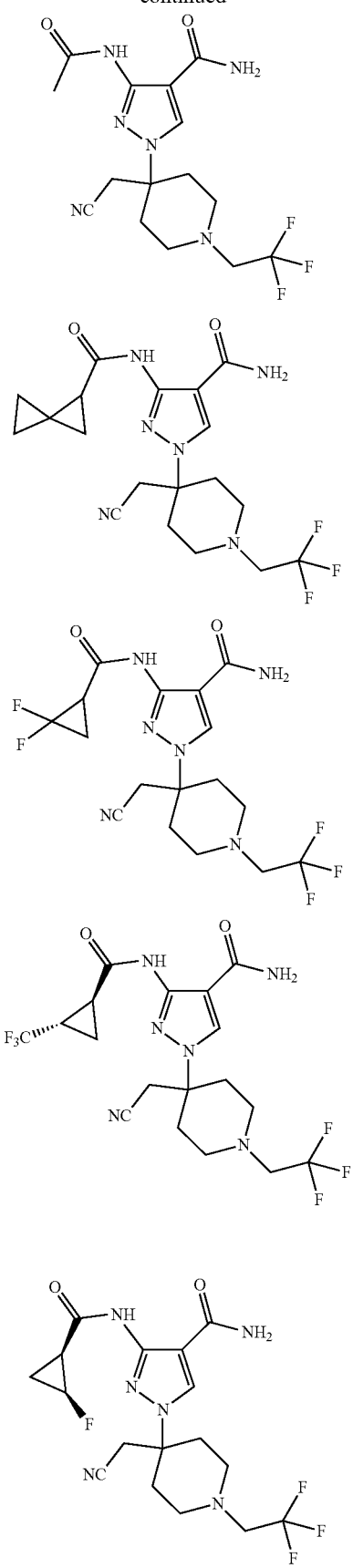
662
-continued
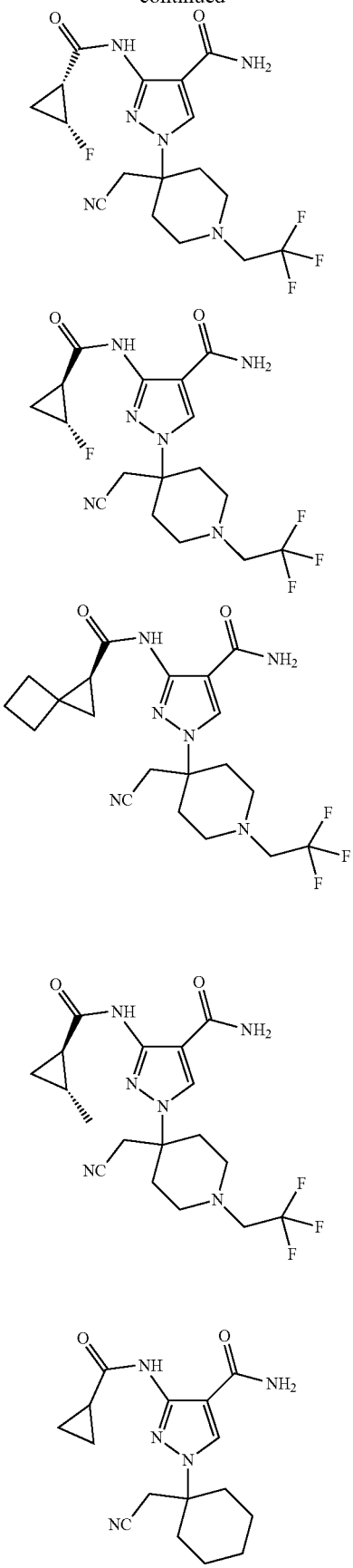

663
-continued
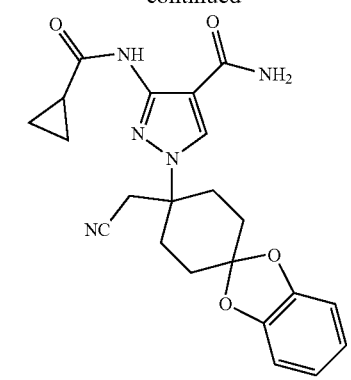
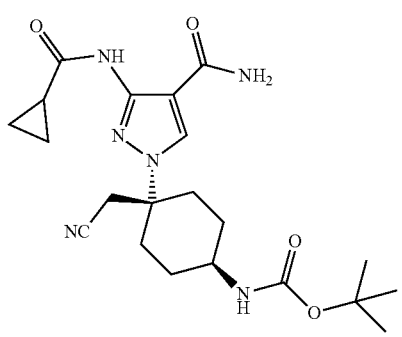
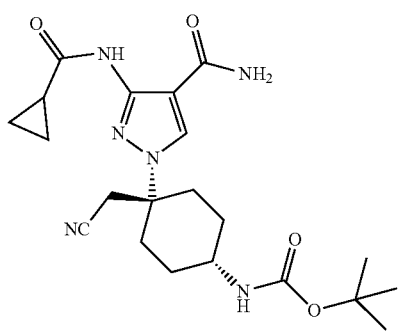
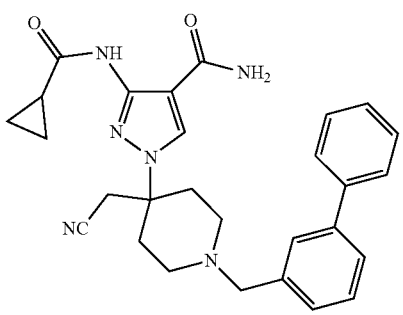
664
-continued
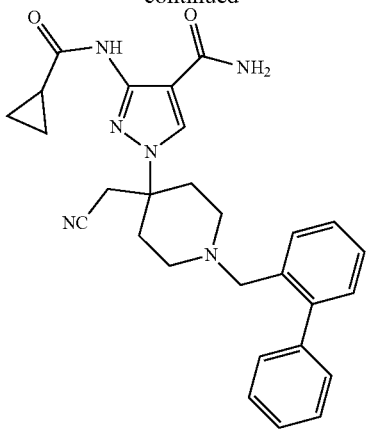
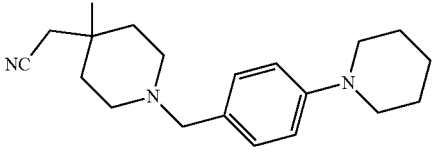
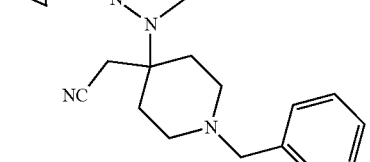
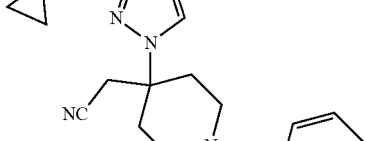
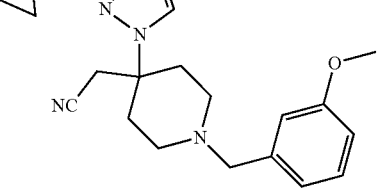

665
-continued
666
-continued
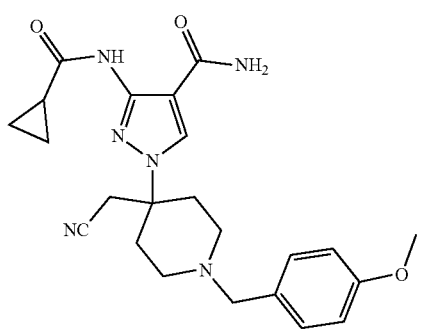
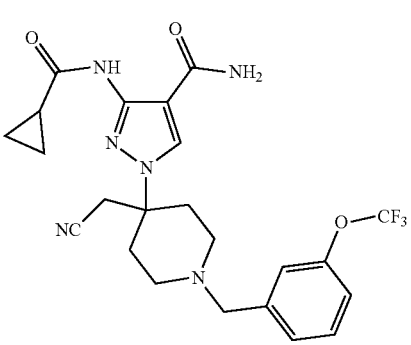
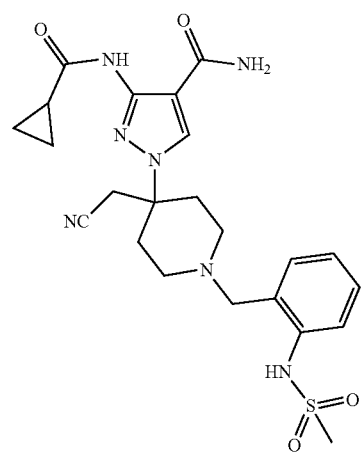
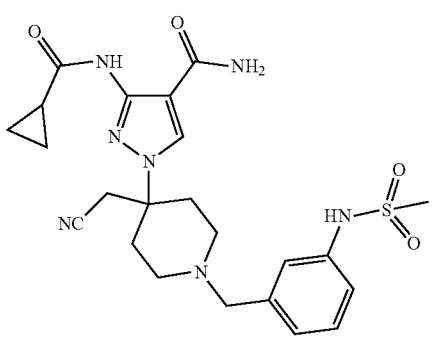
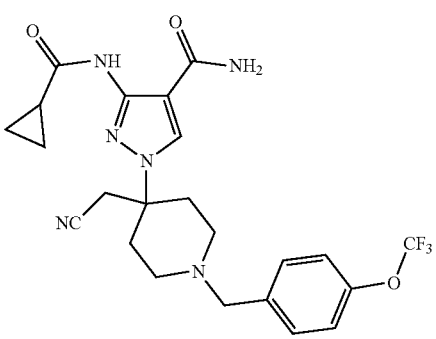
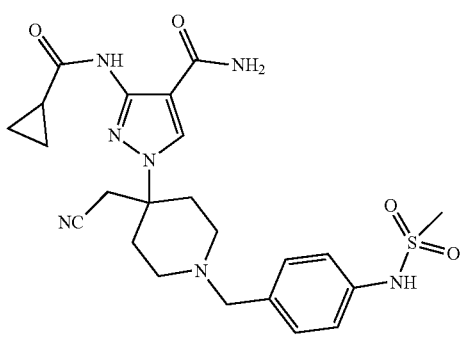
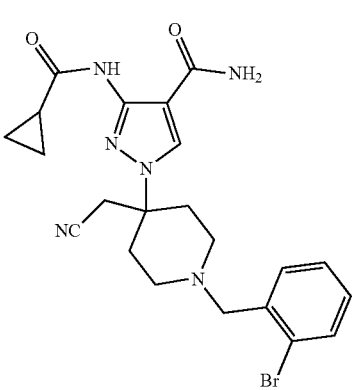

667
-continued
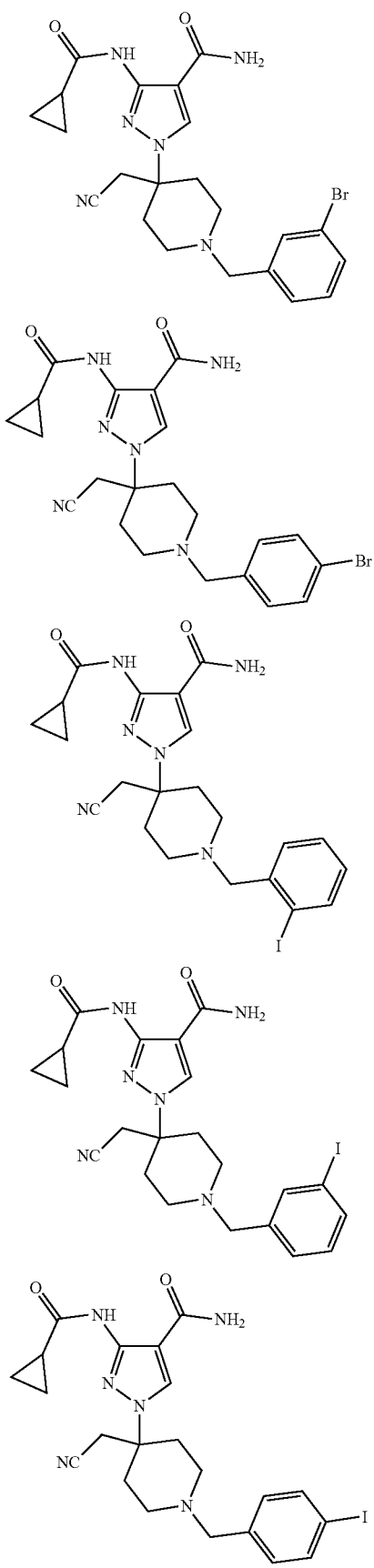
668
-continued
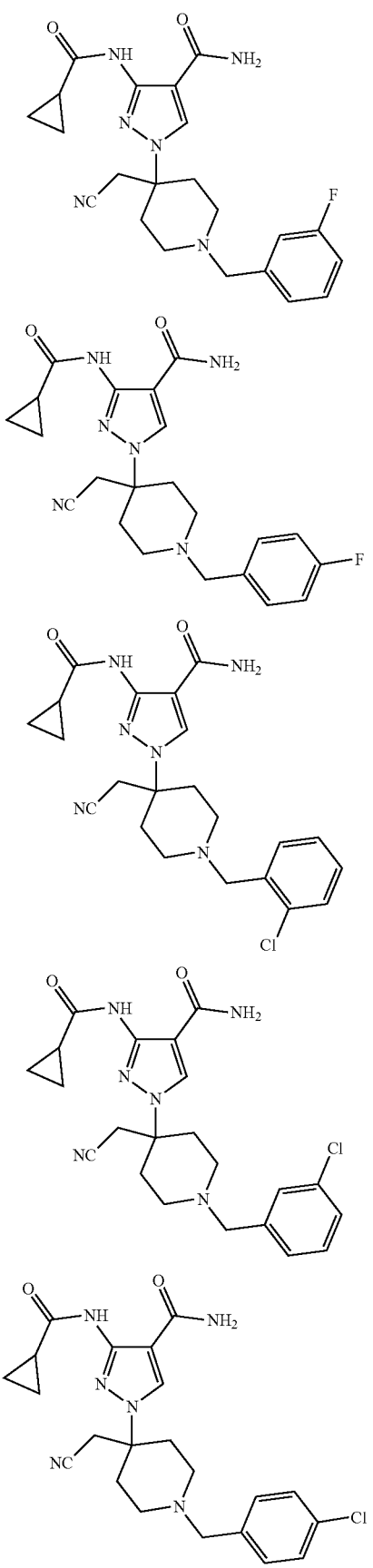

669
-continued
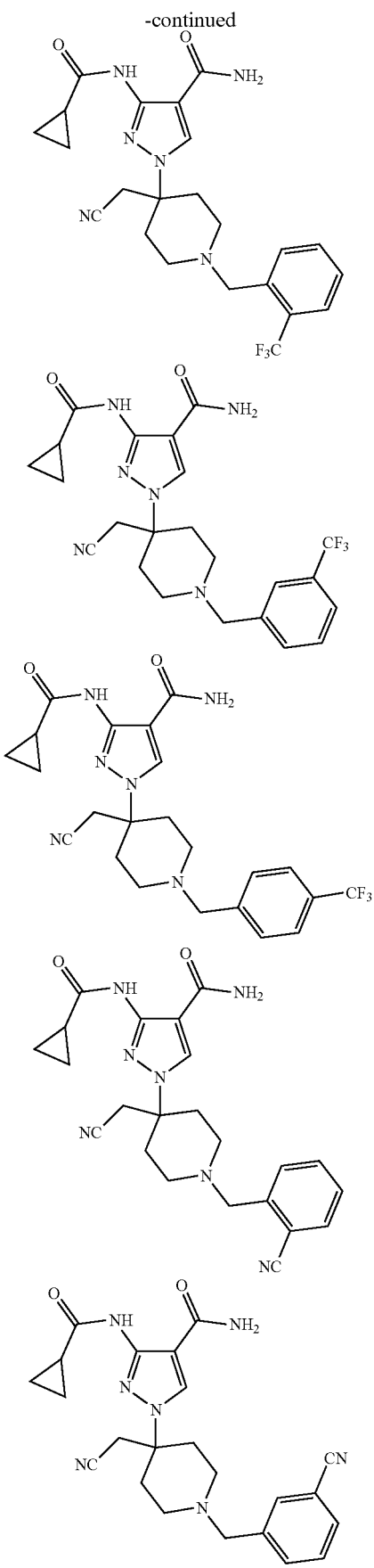
670
-continued
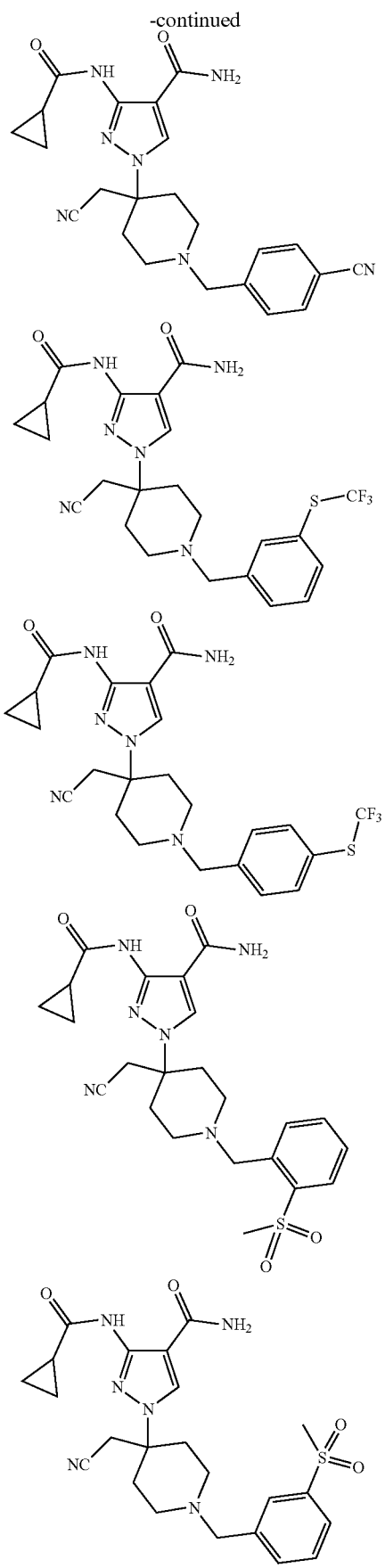

671
-continued
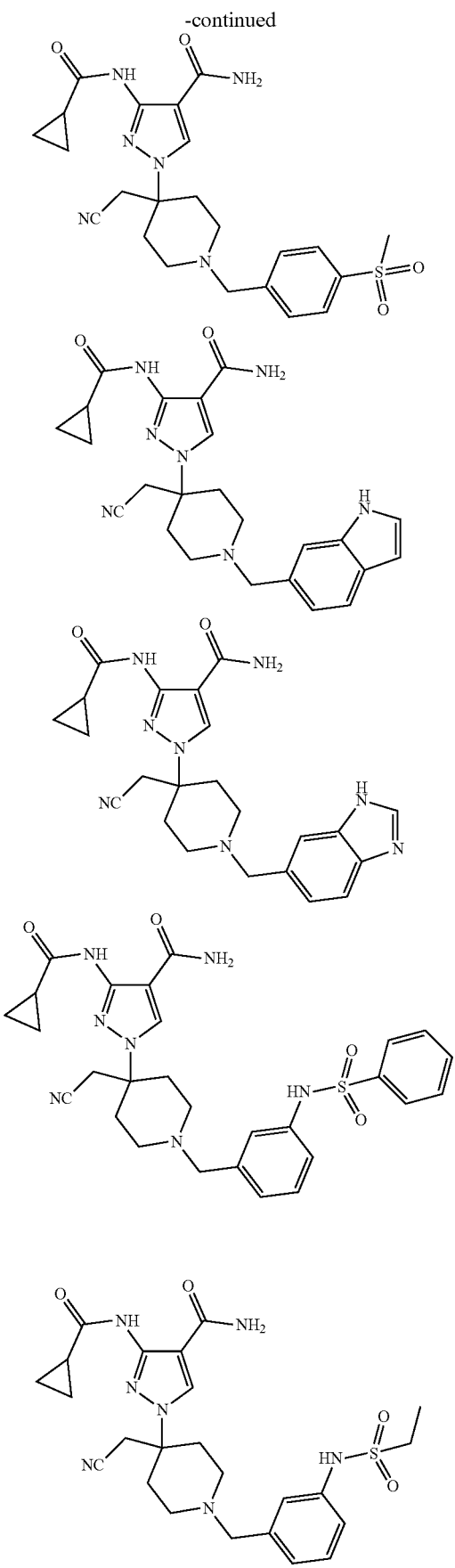
672
-continued
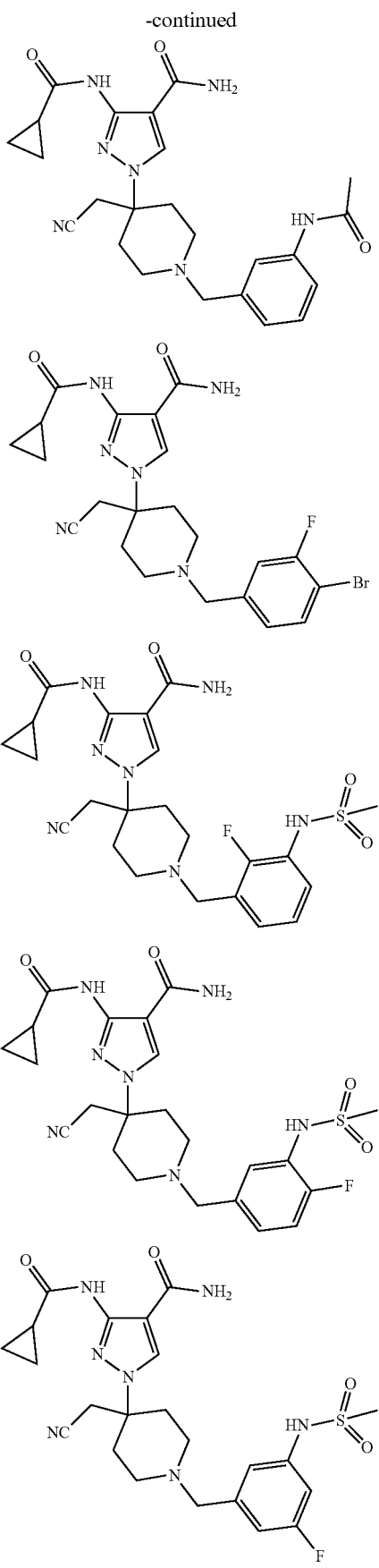

673
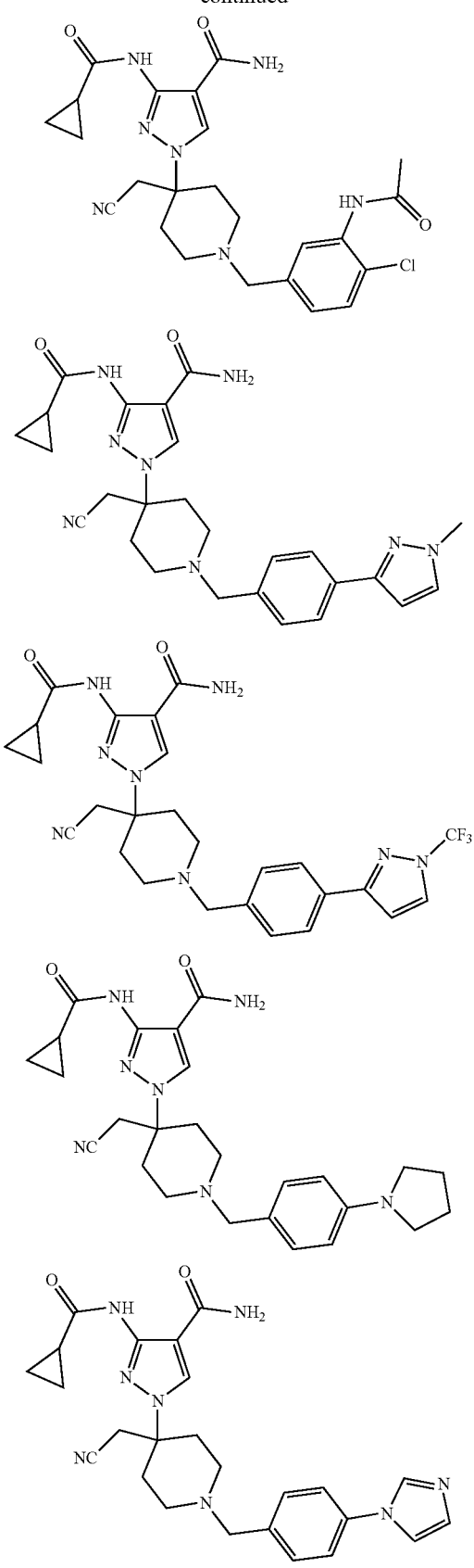
674
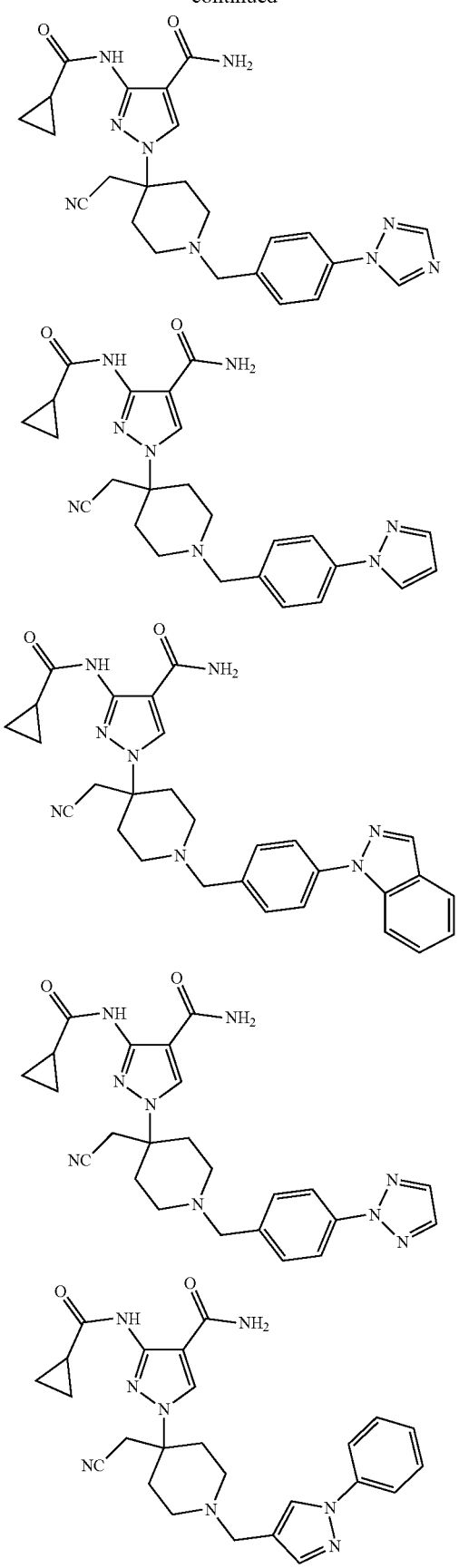

675
-continued
676
-continued
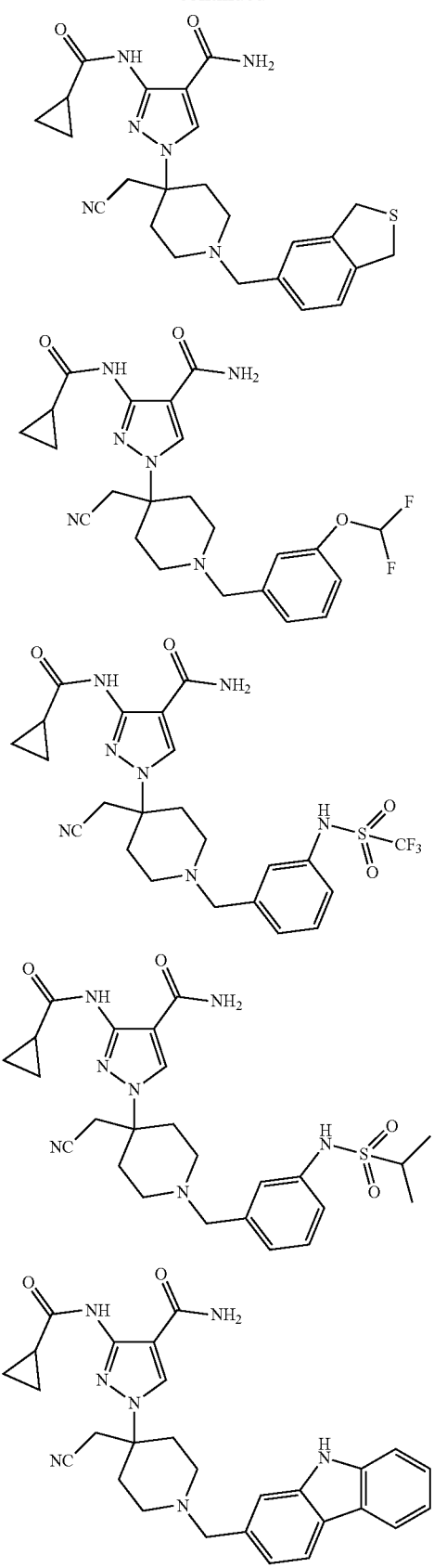
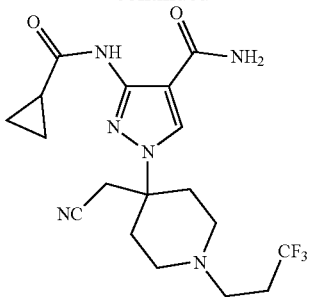
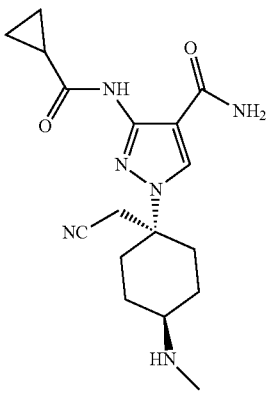

| 677 -continued | 678 -continued |
|---|---|
| 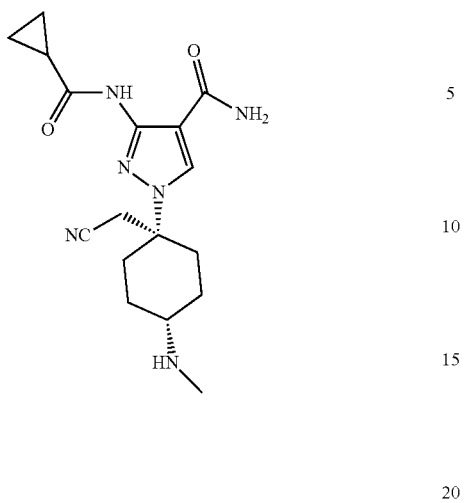 | 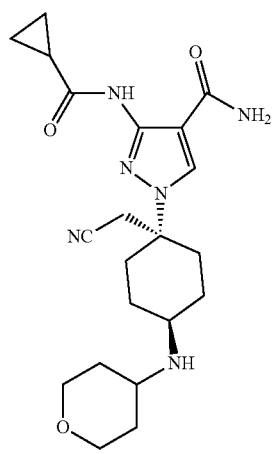 |
| 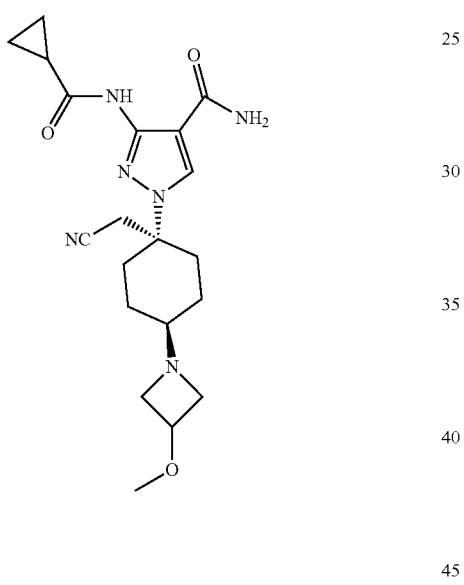 | 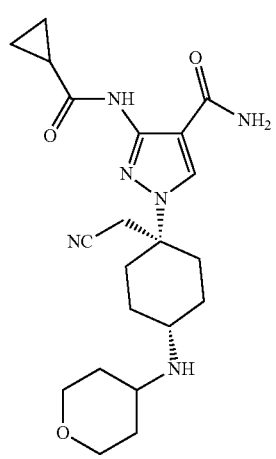 |
| 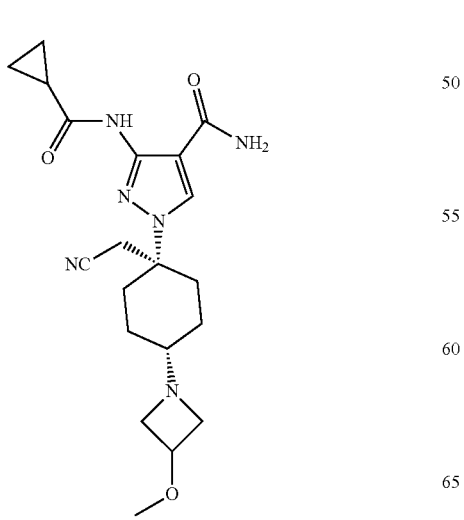 | 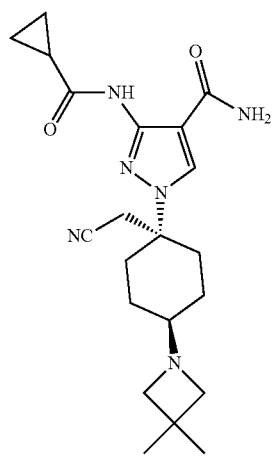 |

679
-continued
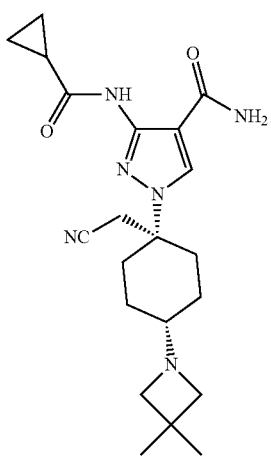
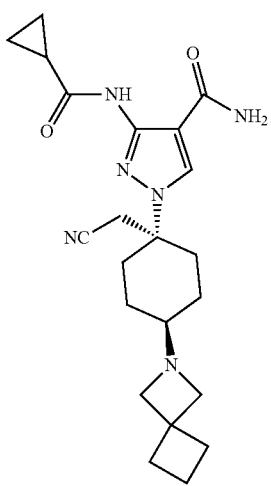
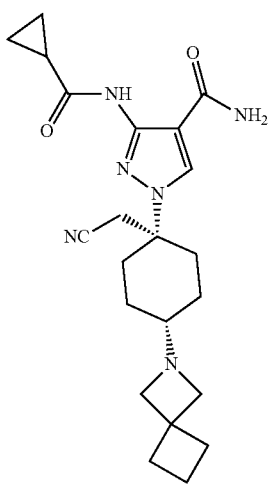
680
-continued
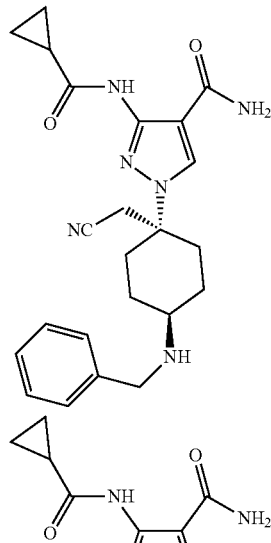
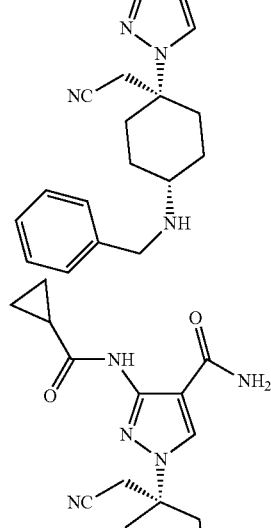
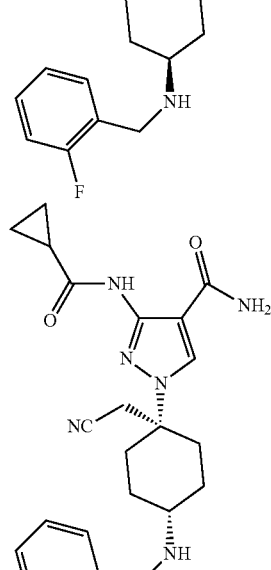
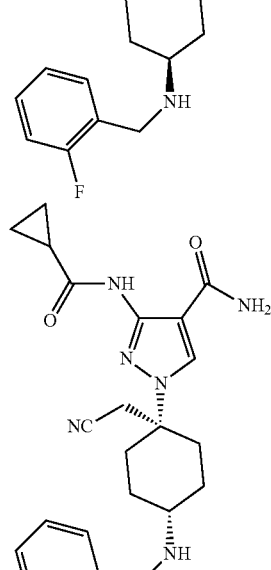

681
-continued
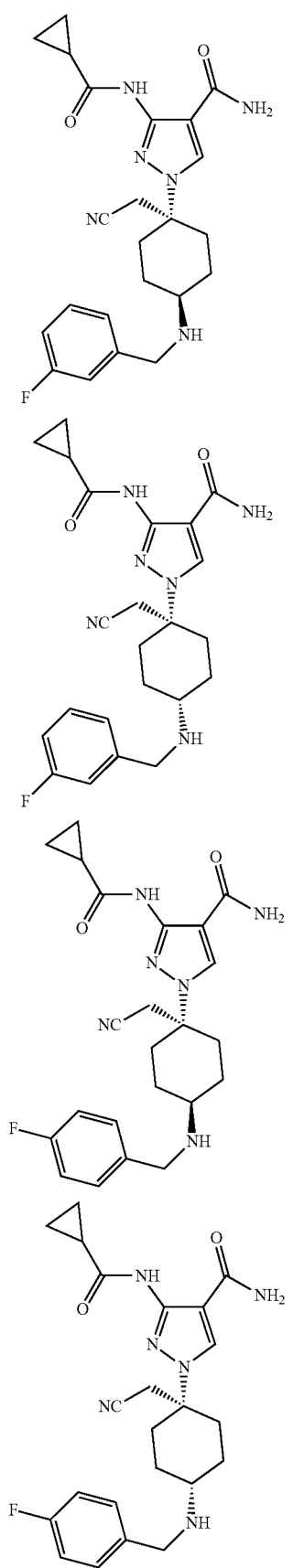
682
-continued
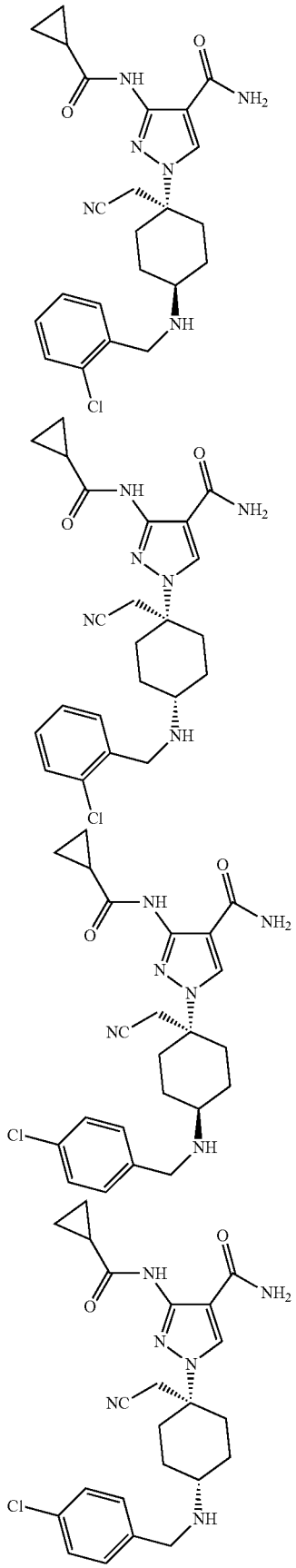

683
-continued
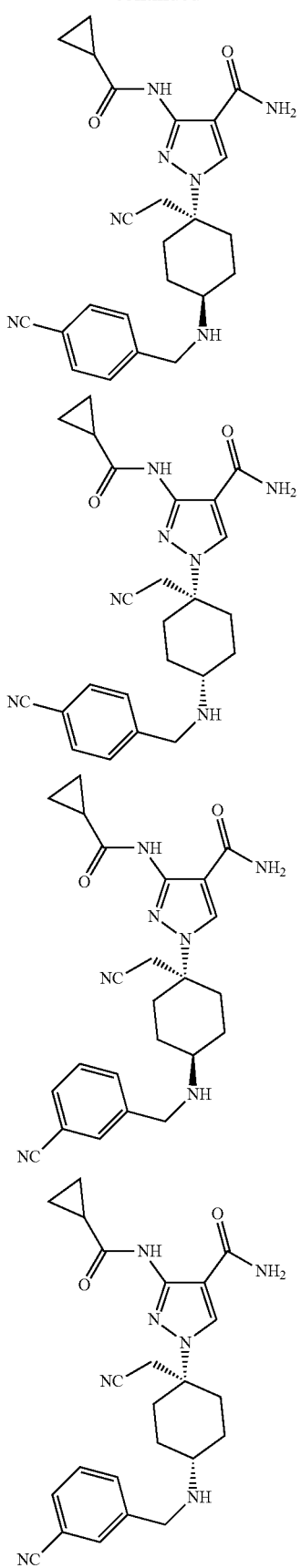
684
-continued
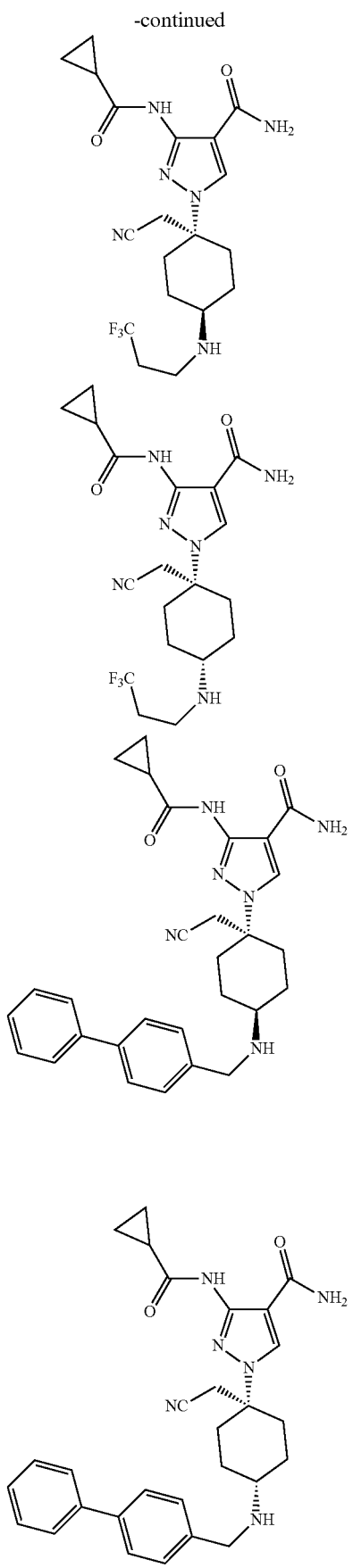

685
-continued
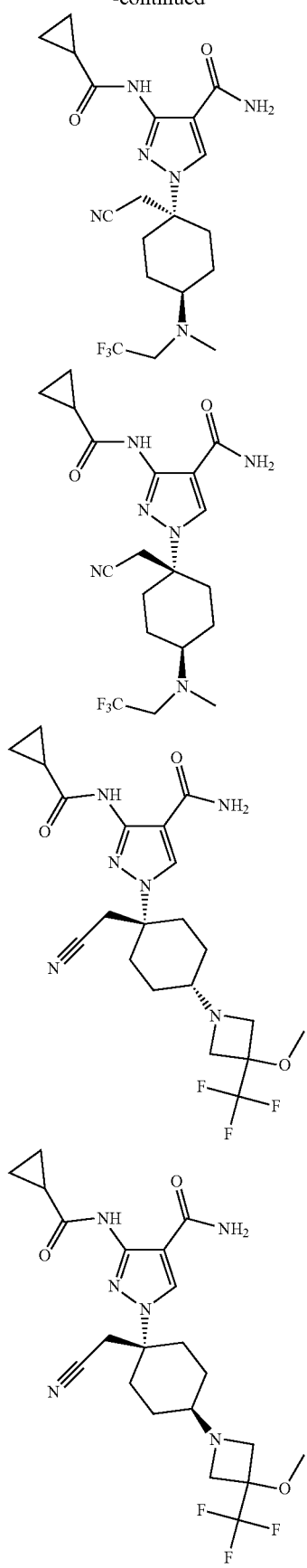
686
-continued
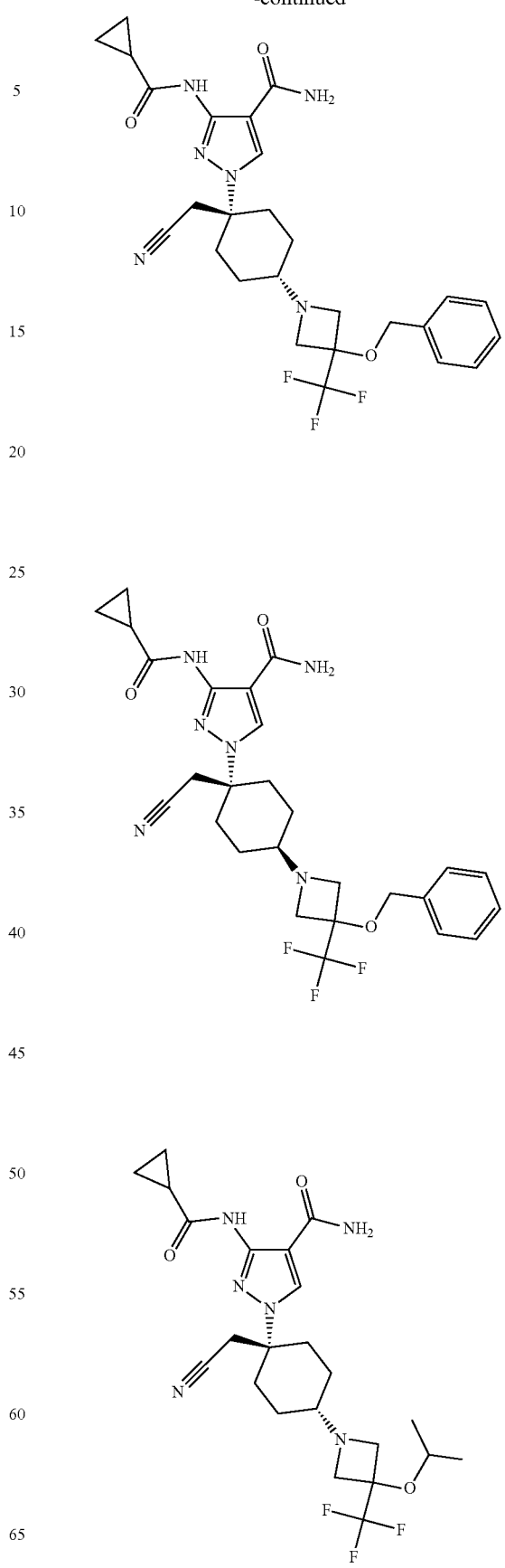

687
-continued
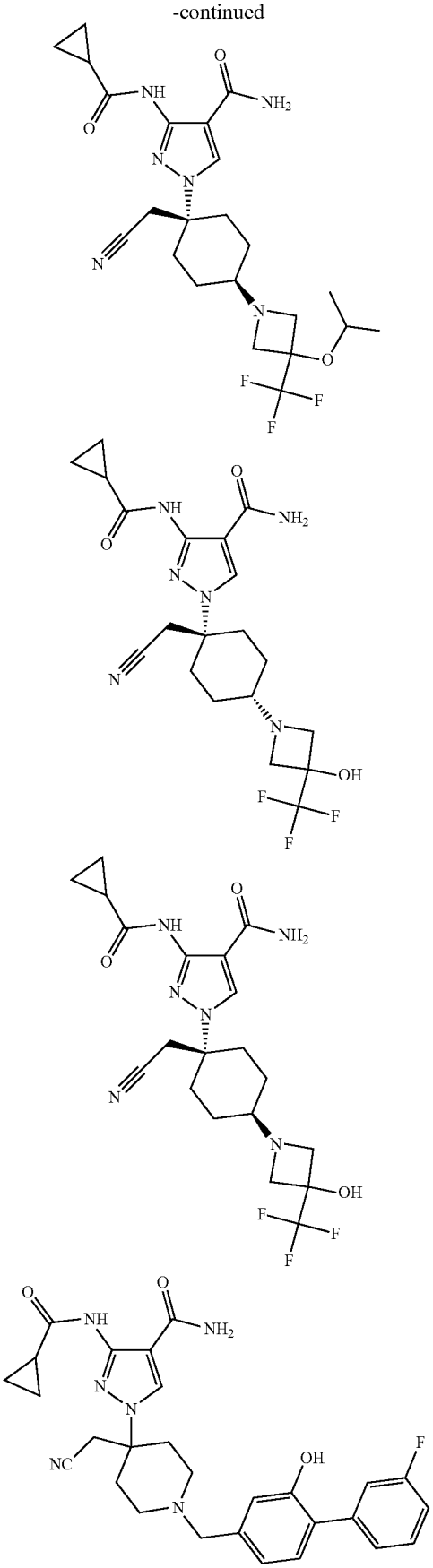
688
-continued
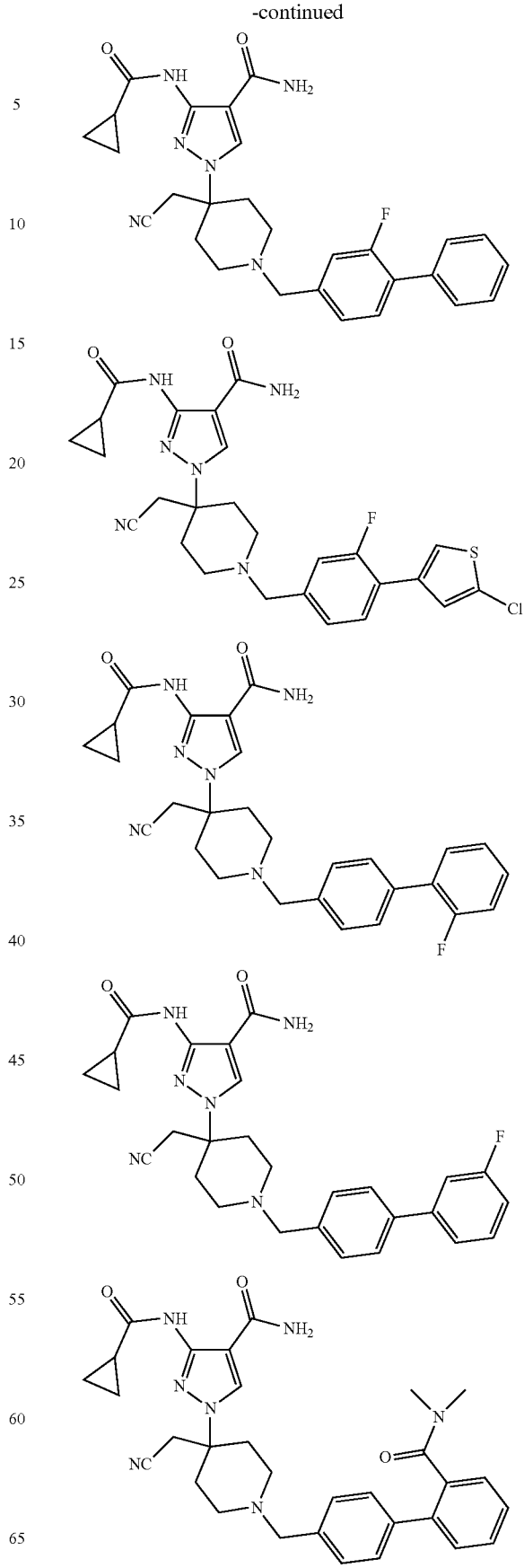

689
-continued
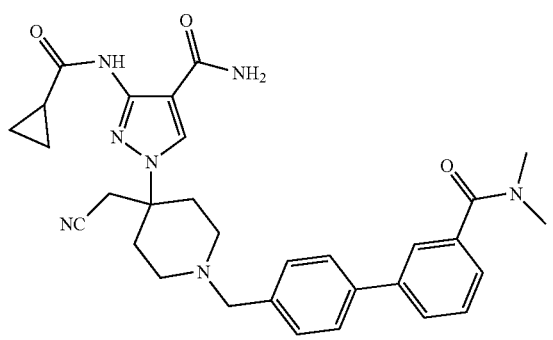
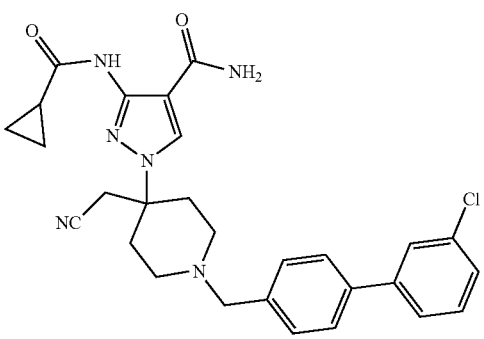
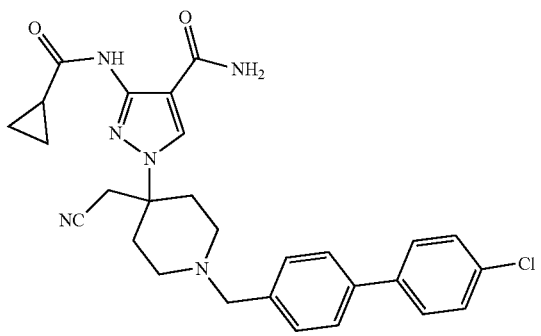
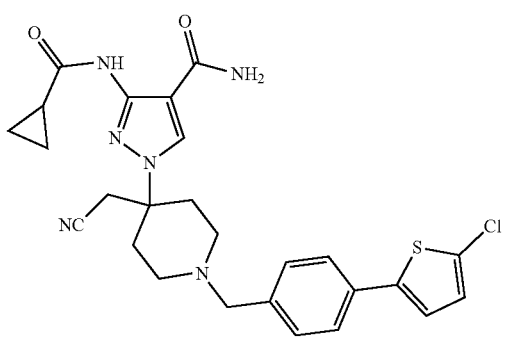
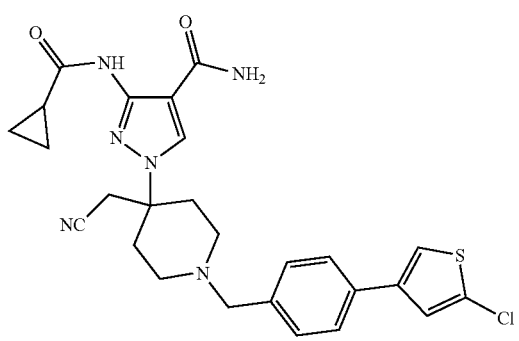
690
-continued
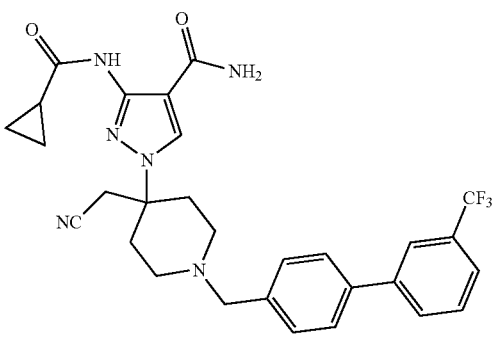
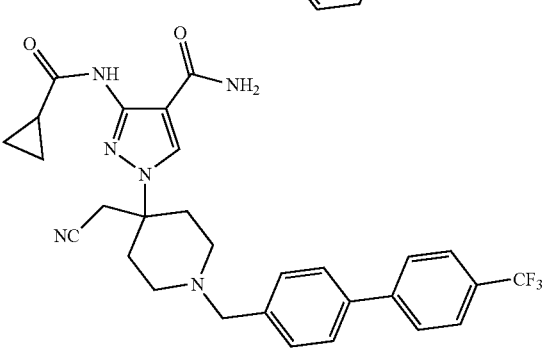
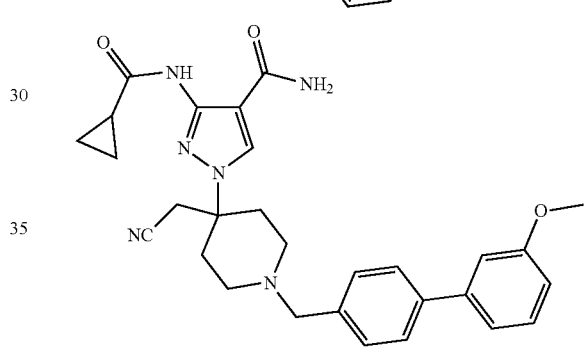
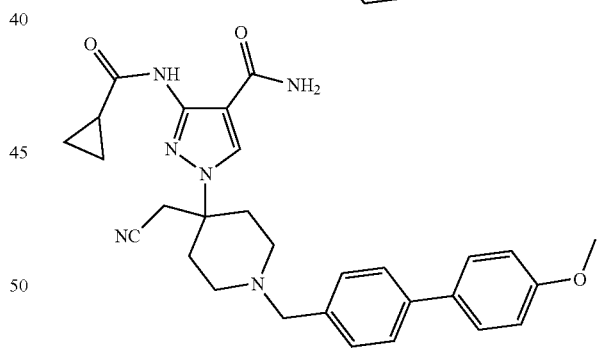
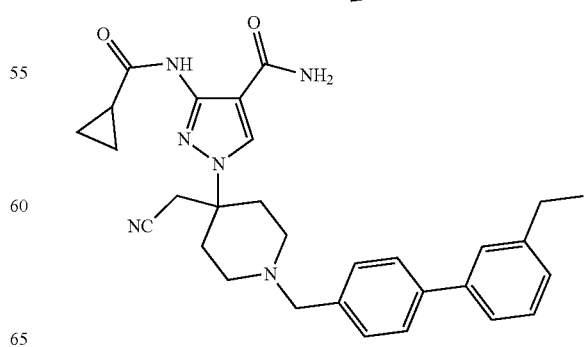

691
-continued
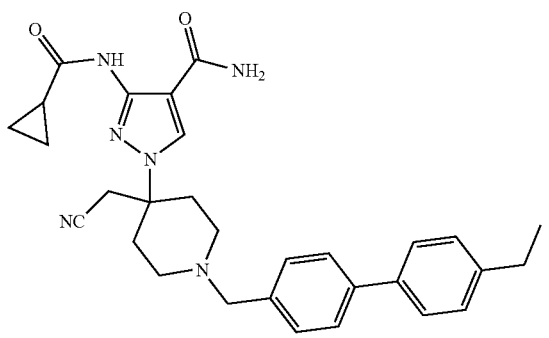
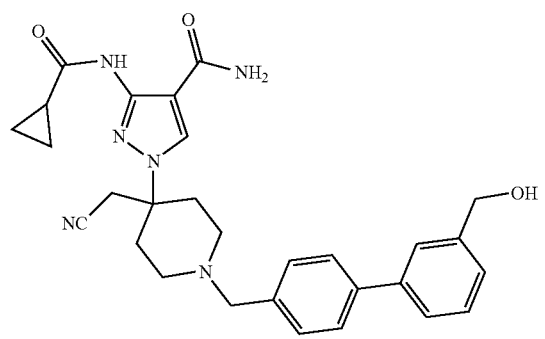
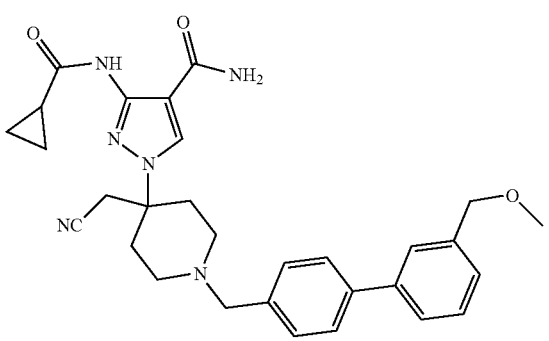
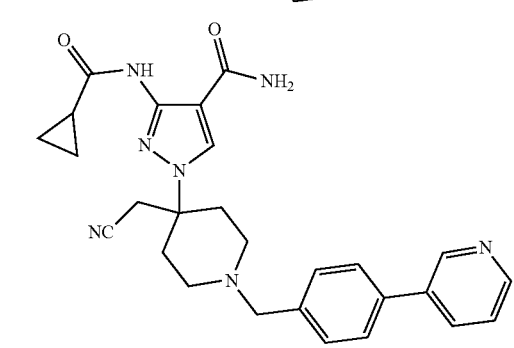
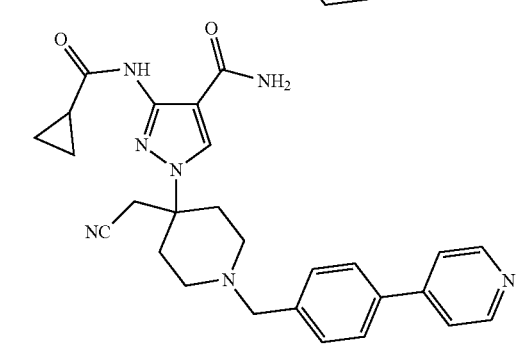
692
-continued
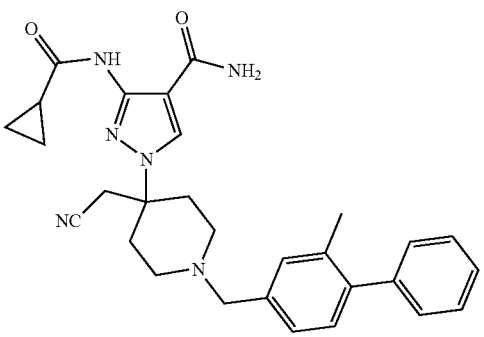
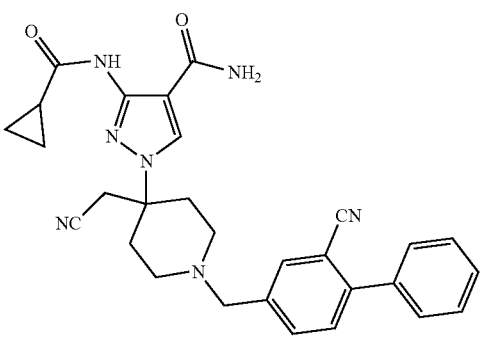
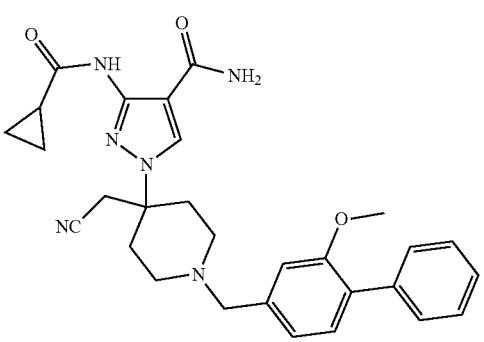
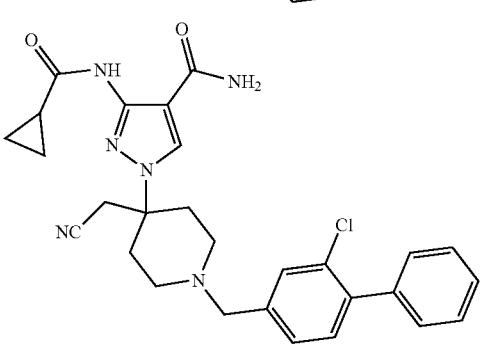
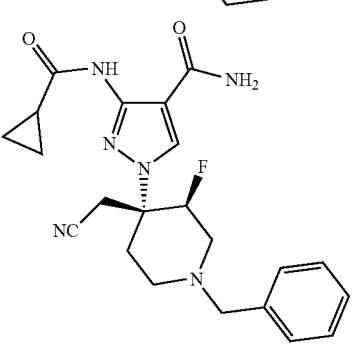

693
-continued
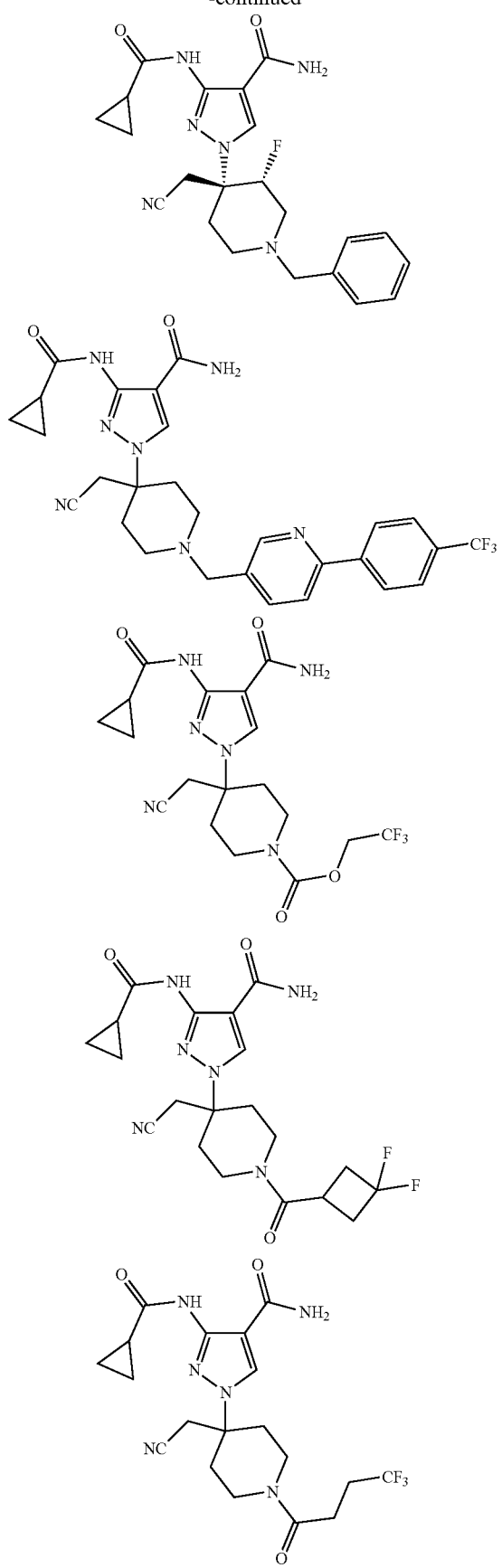
694
-continued
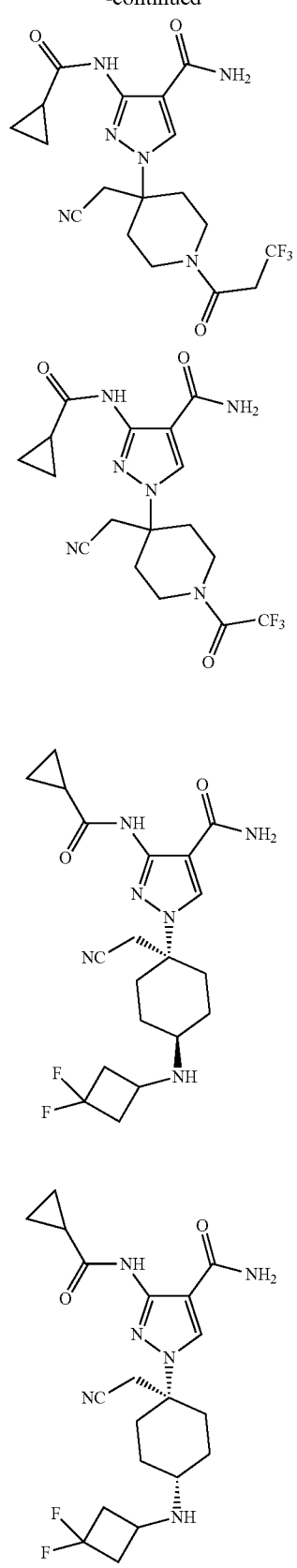

695
-continued
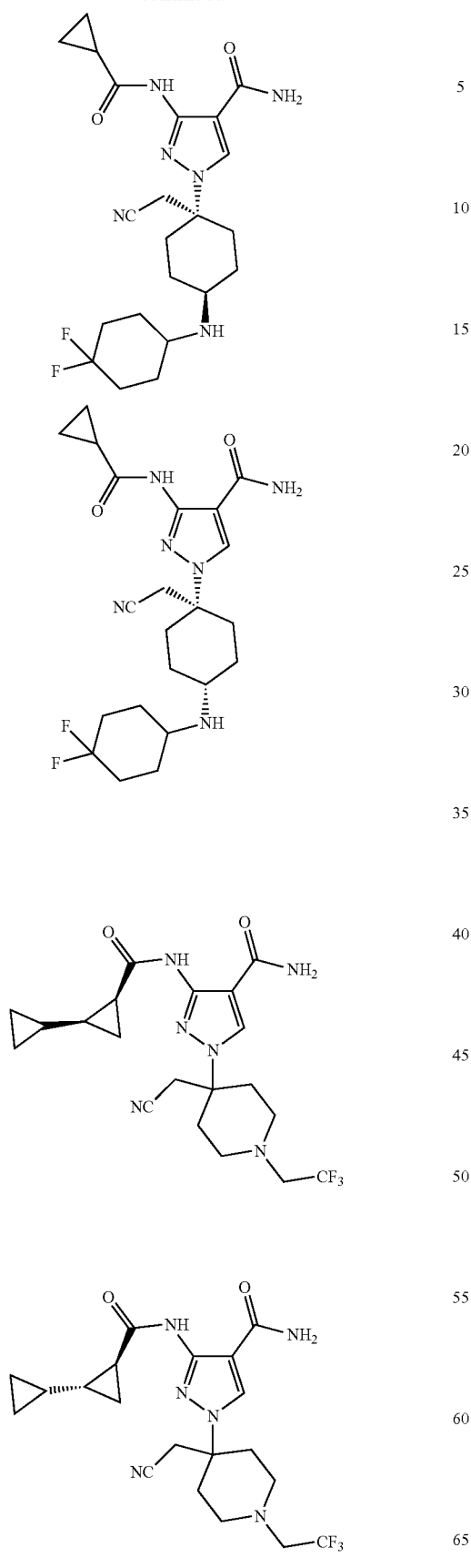
696
-continued
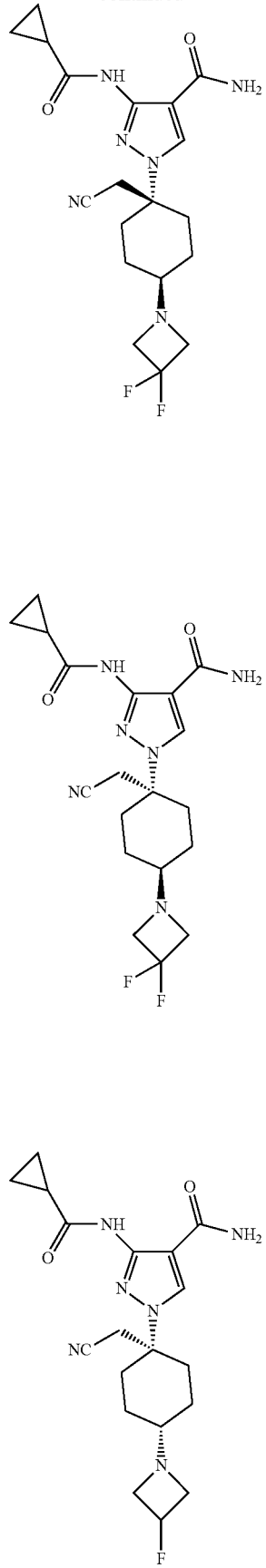

697
-continued
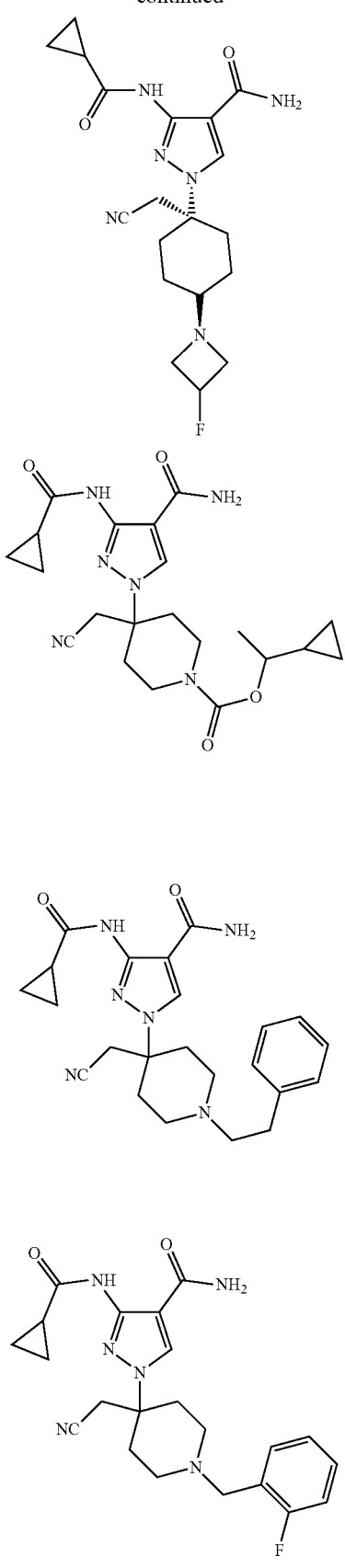
698
-continued
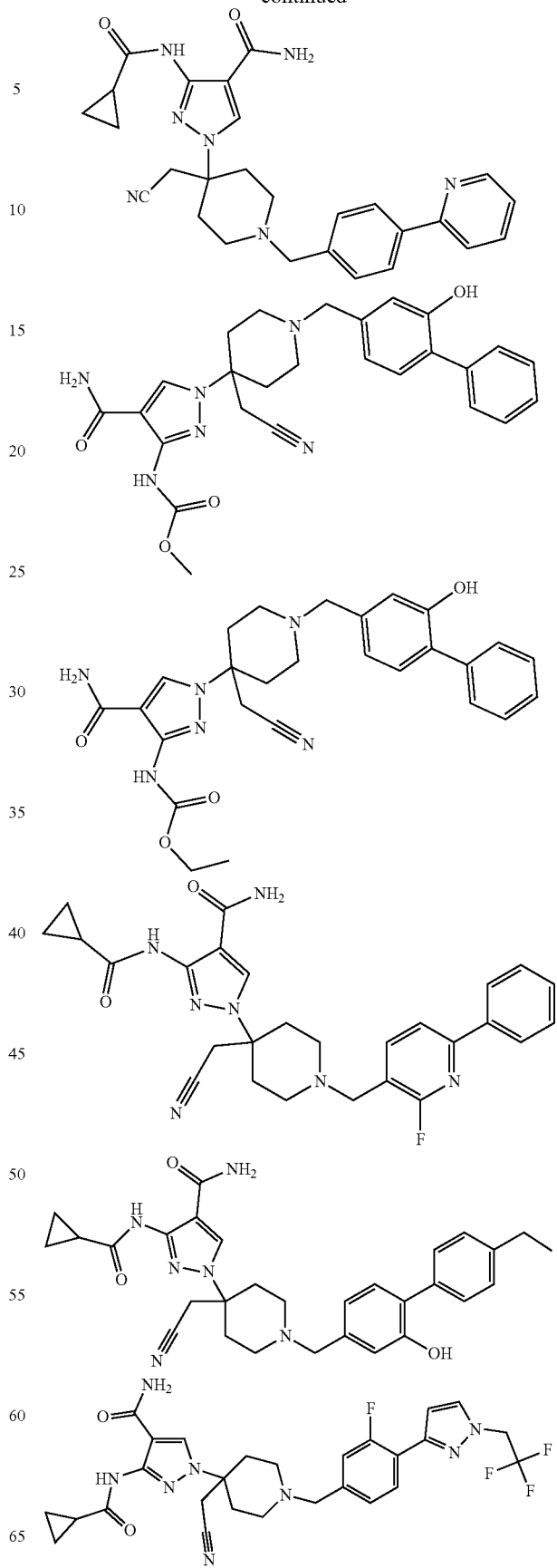

699
-continued
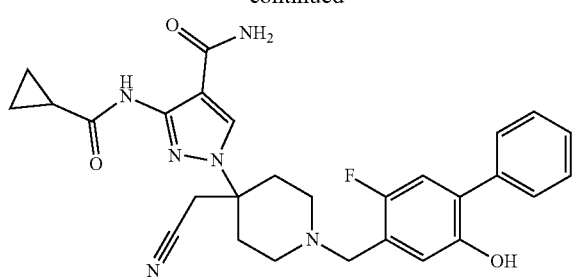
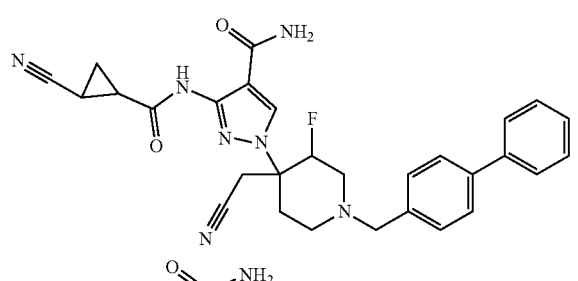
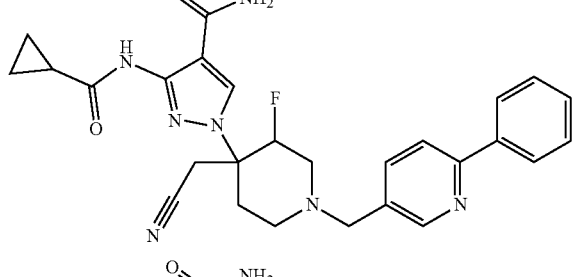
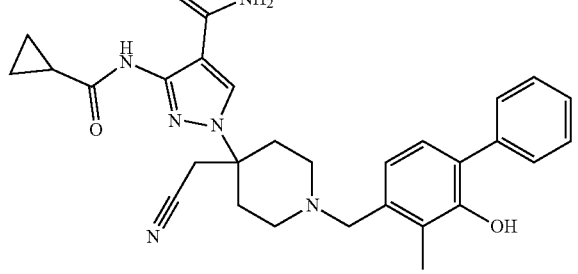
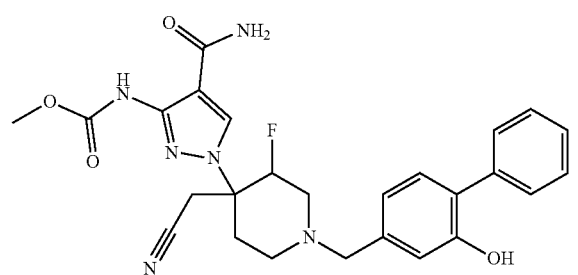
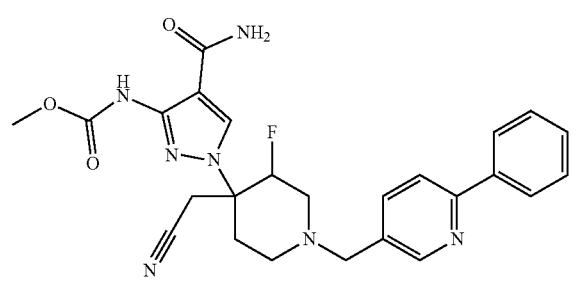
700
-continued
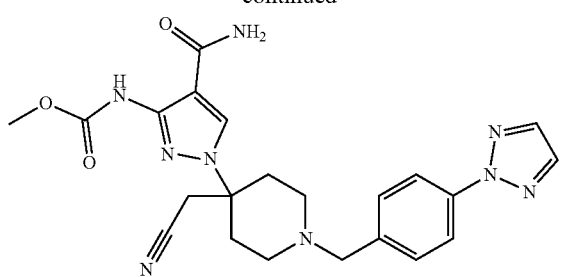
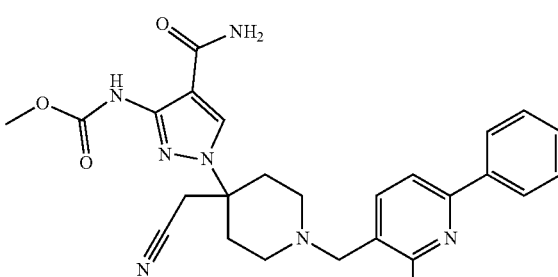
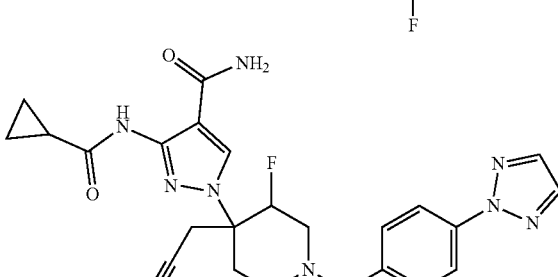
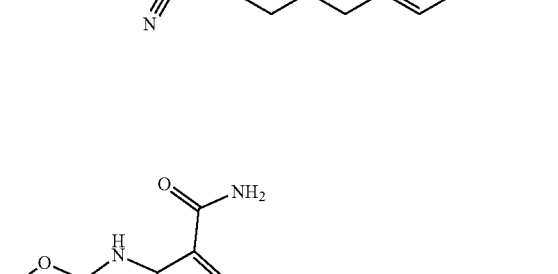
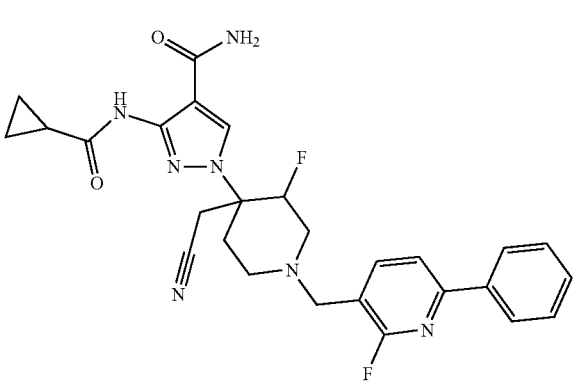

701
-continued
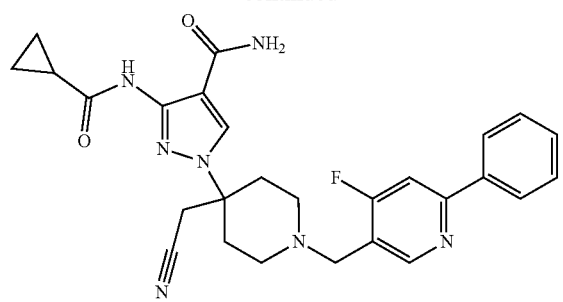
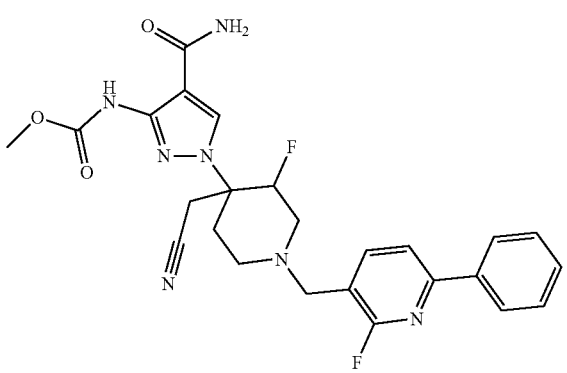
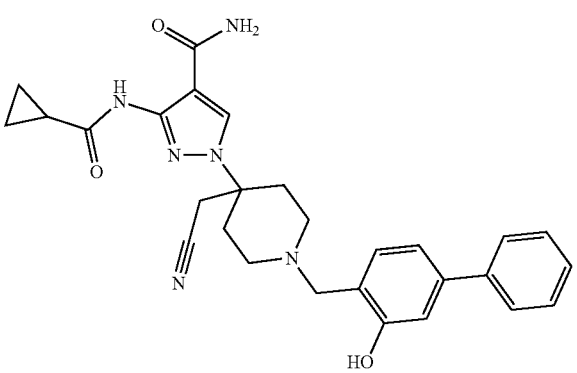
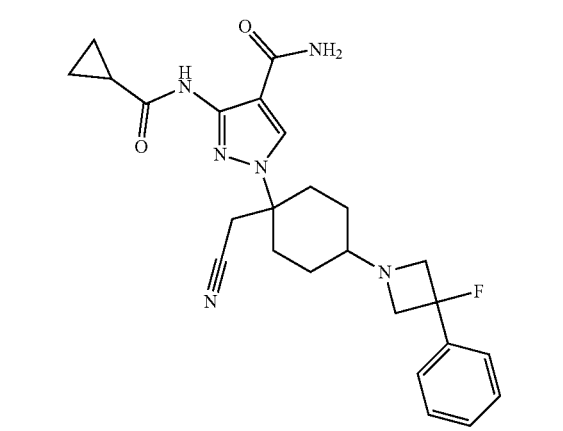
702
-continued
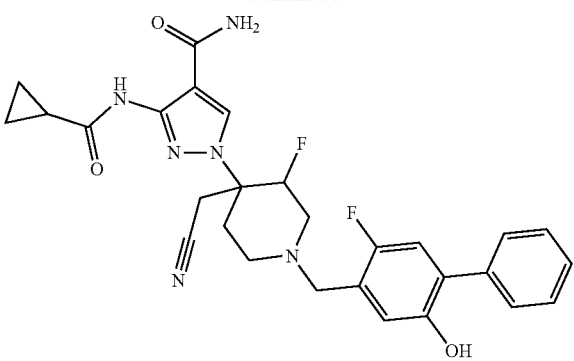
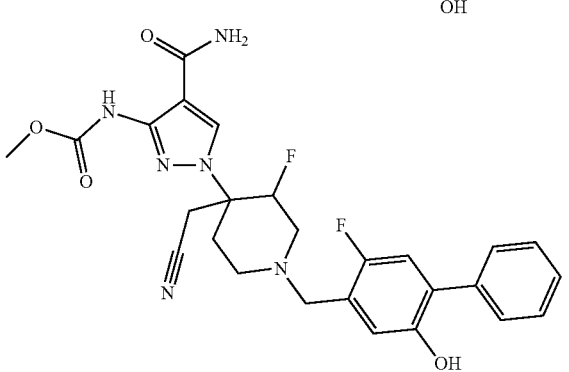
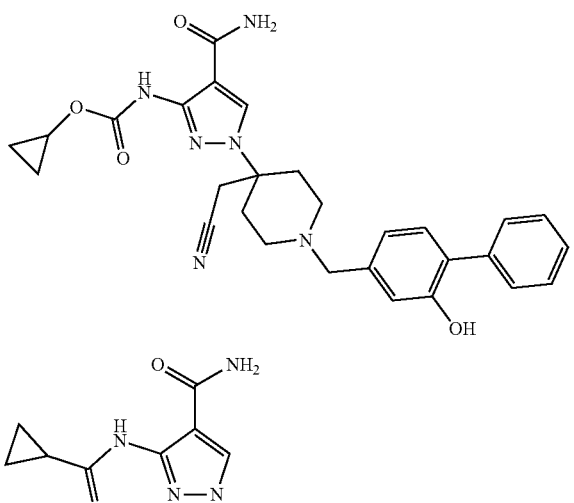
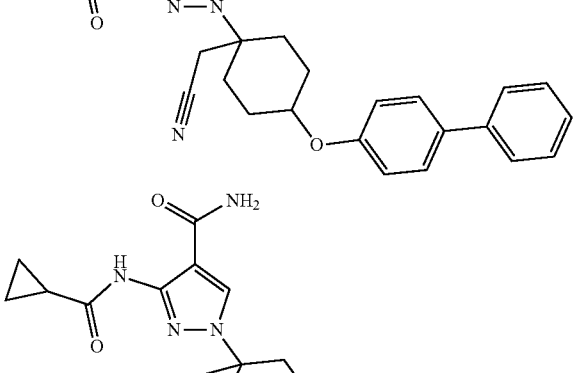
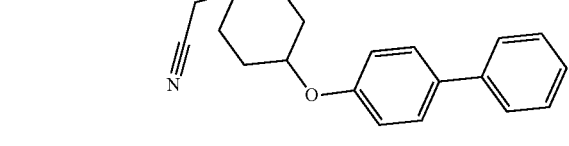

703
-continued
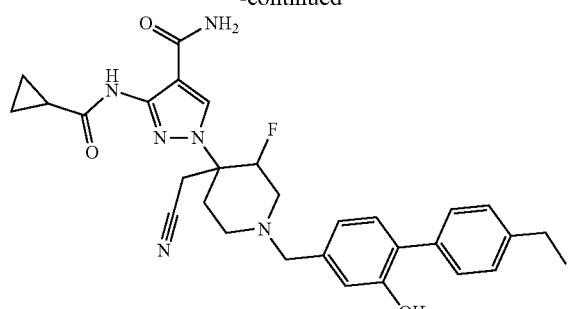
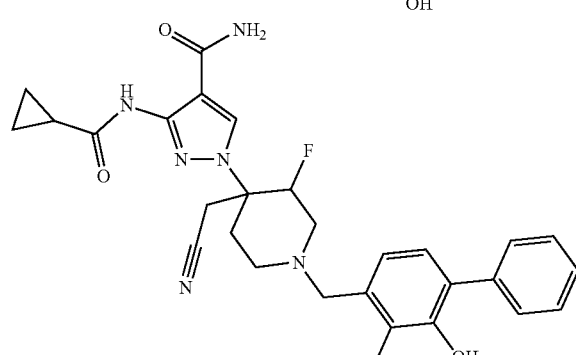
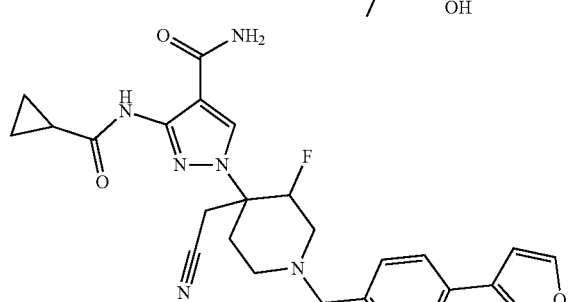
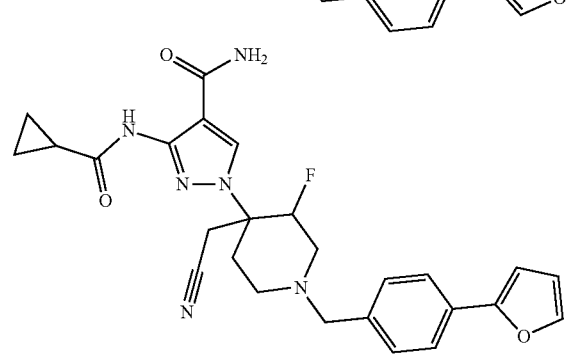
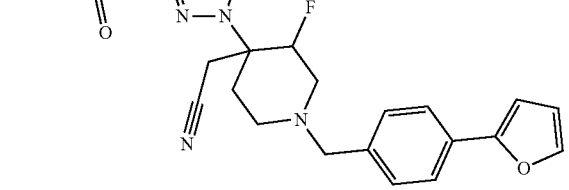
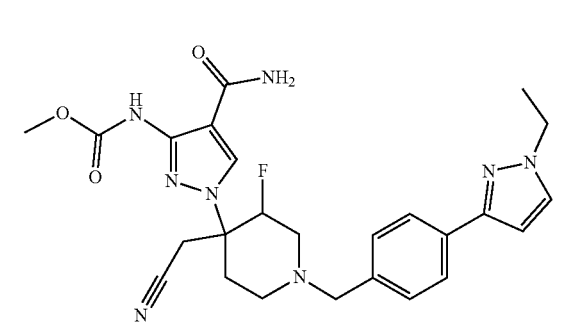
704
-continued
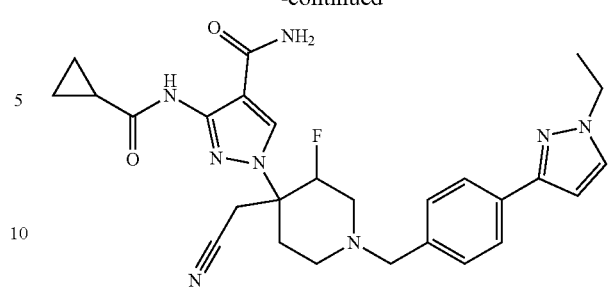
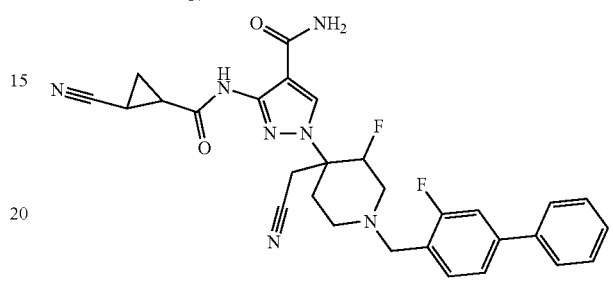
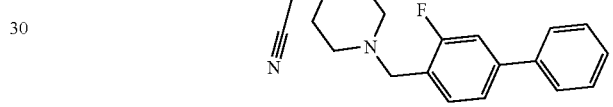
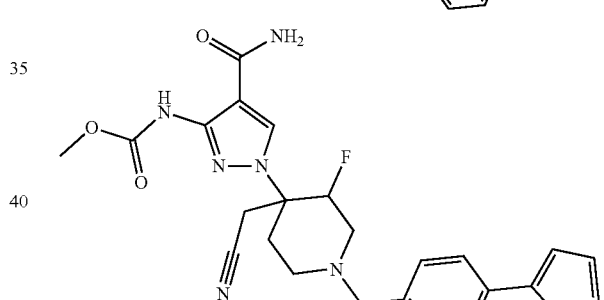
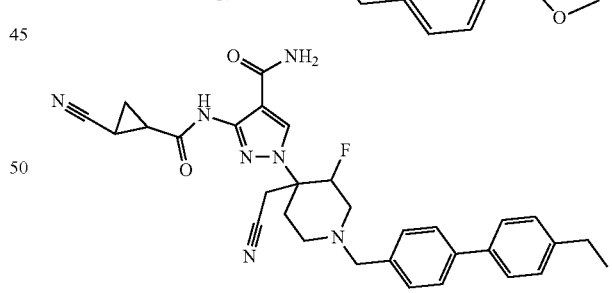
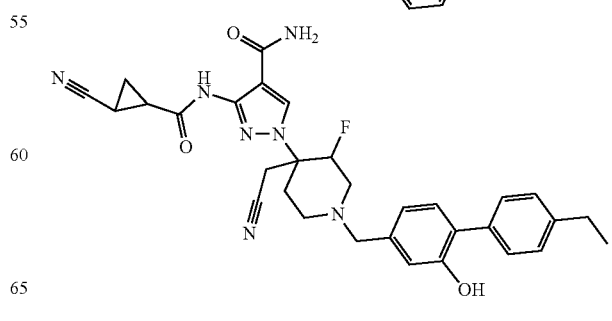

705
-continued
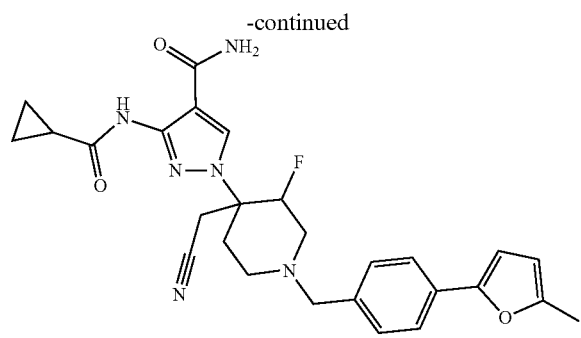
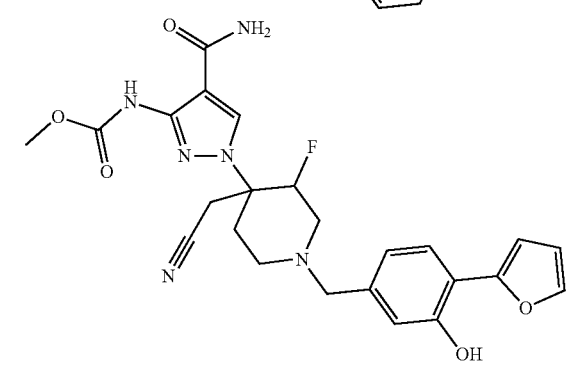
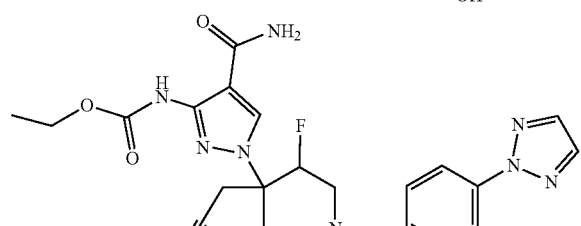
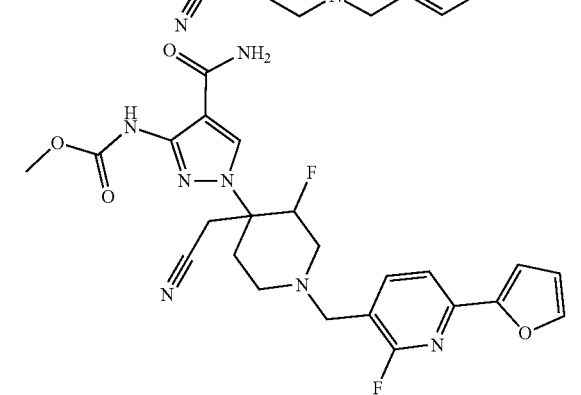
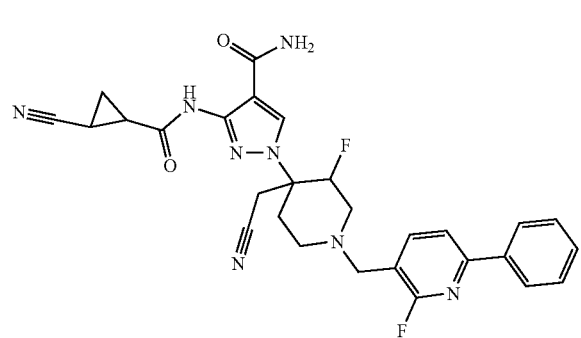
706
-continued
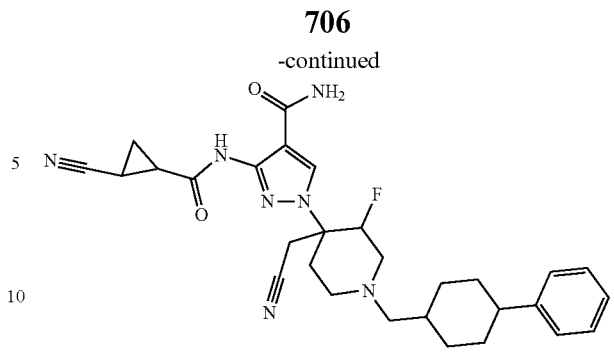
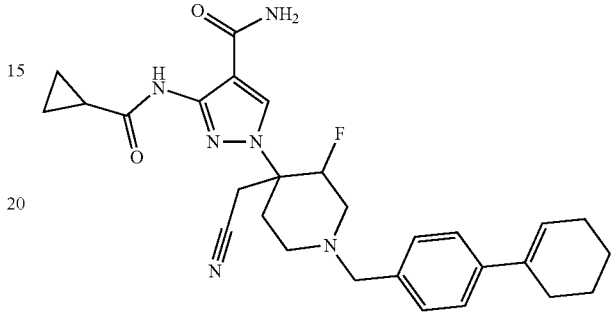
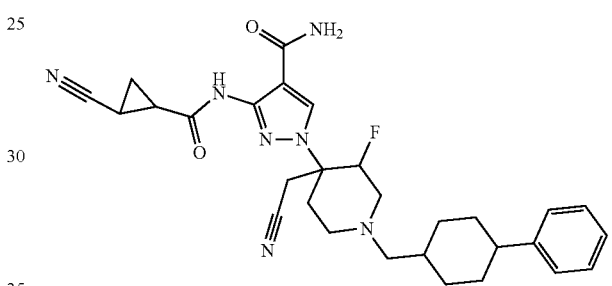
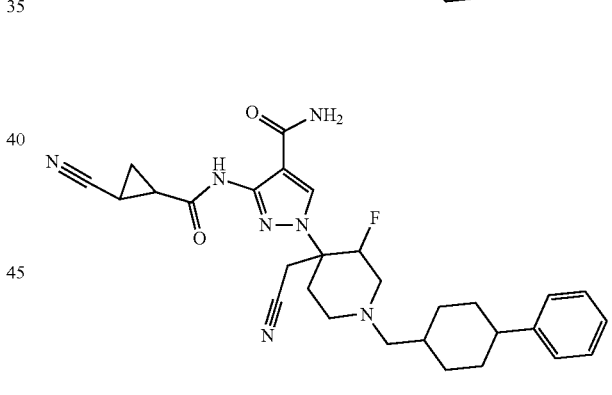
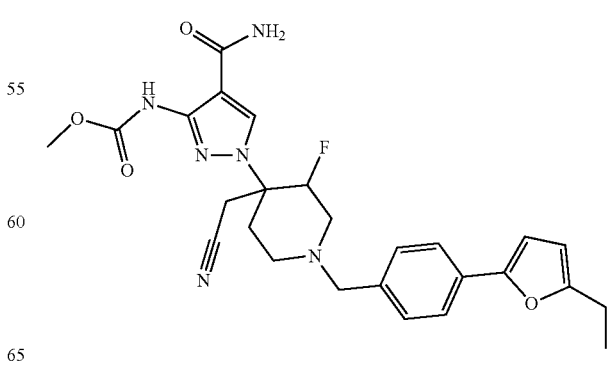

707
-continued
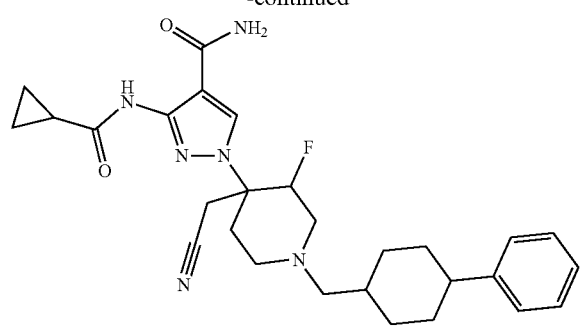
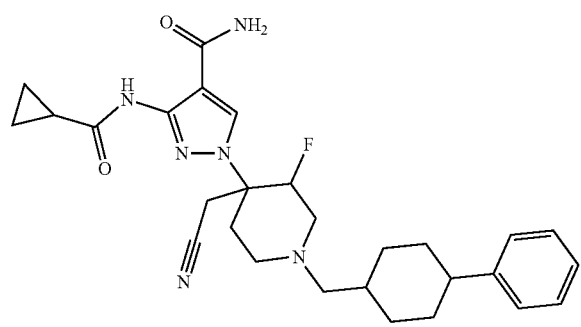
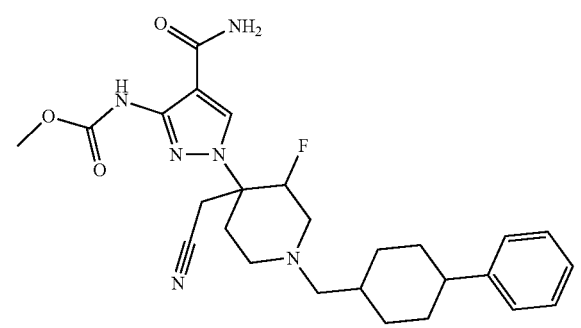
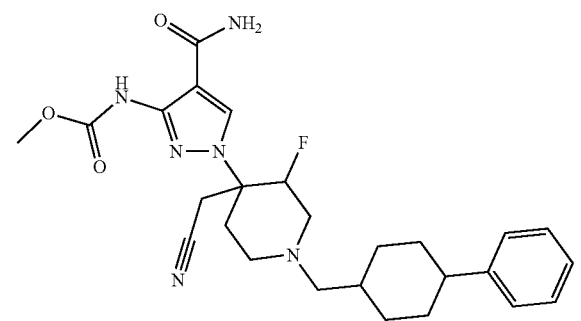
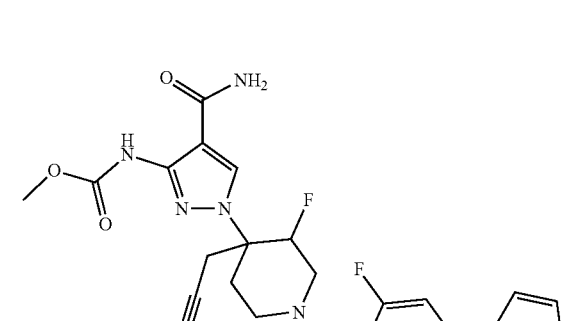
708
-continued
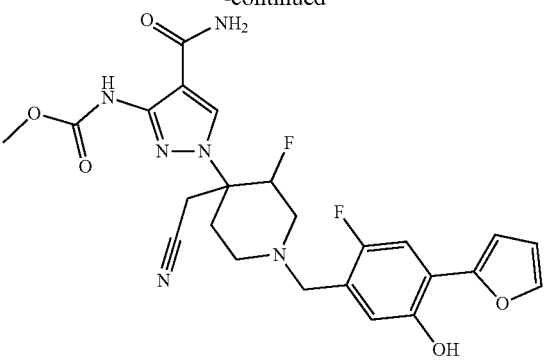
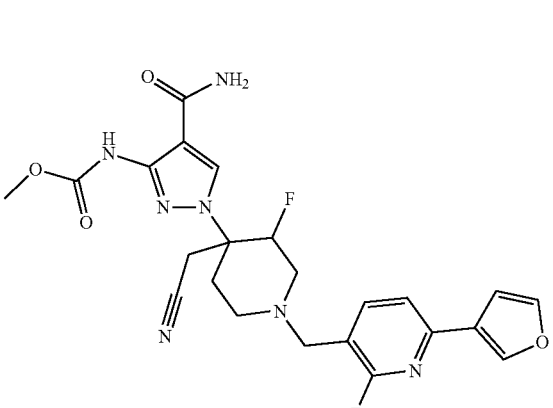
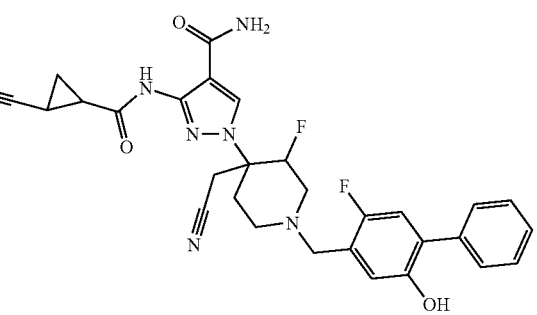
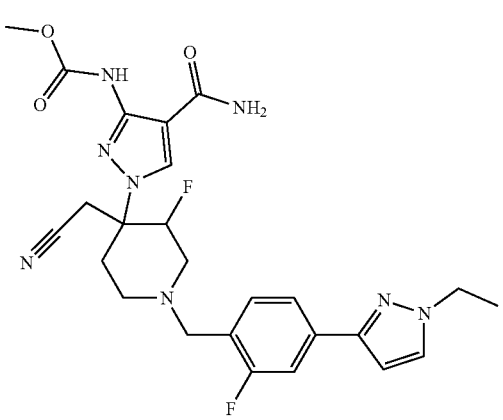

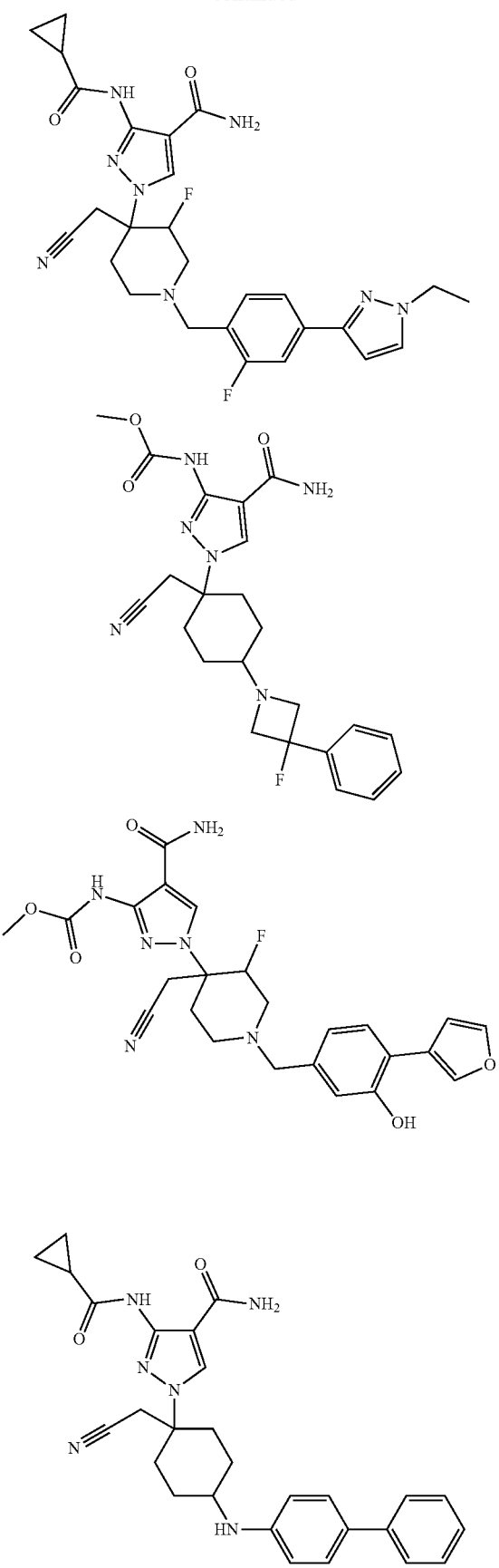
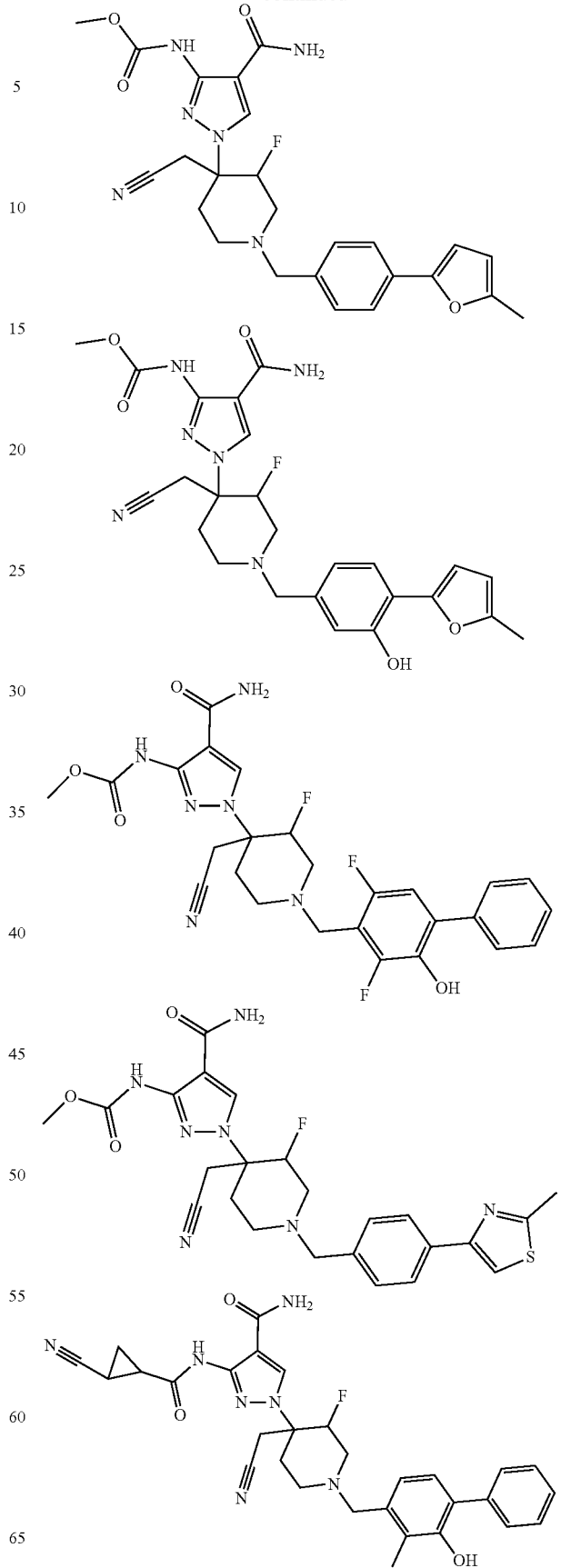

711
-continued
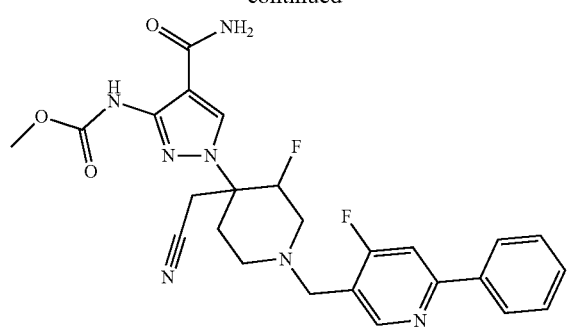
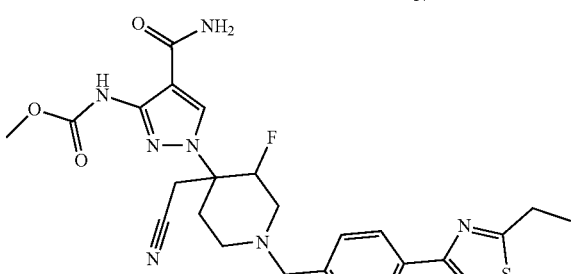
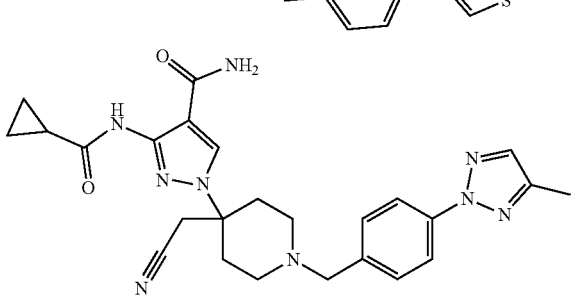
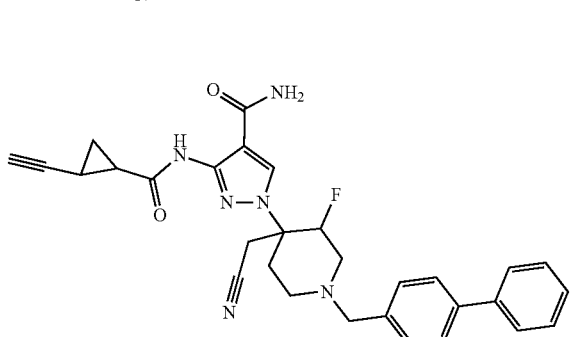
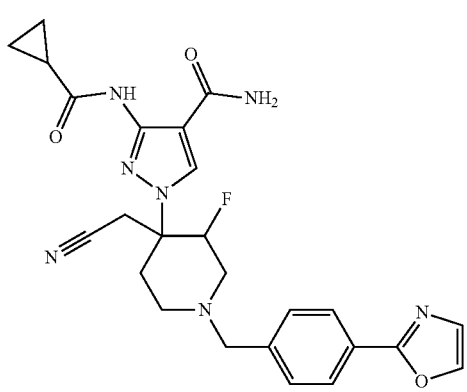
712
-continued
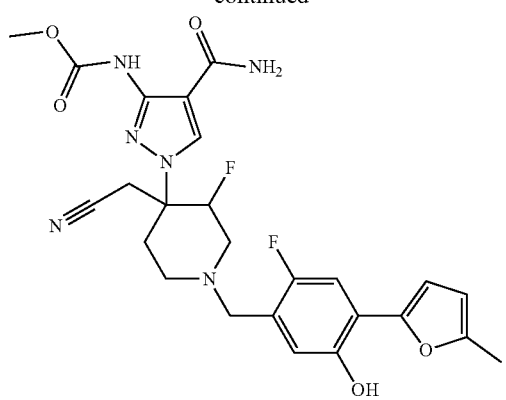
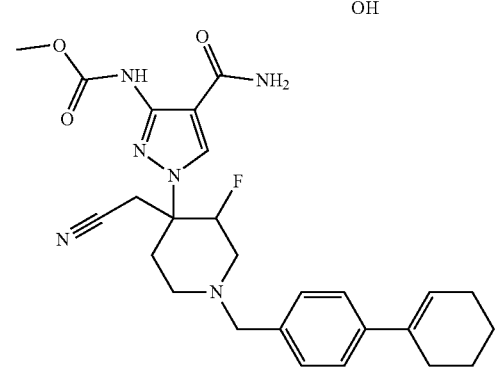
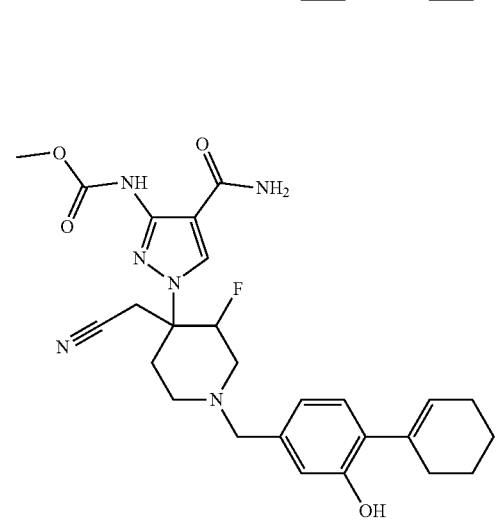
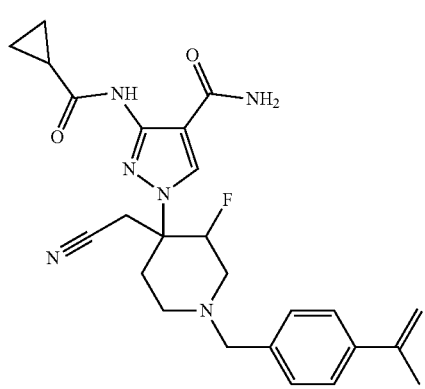

713
-continued
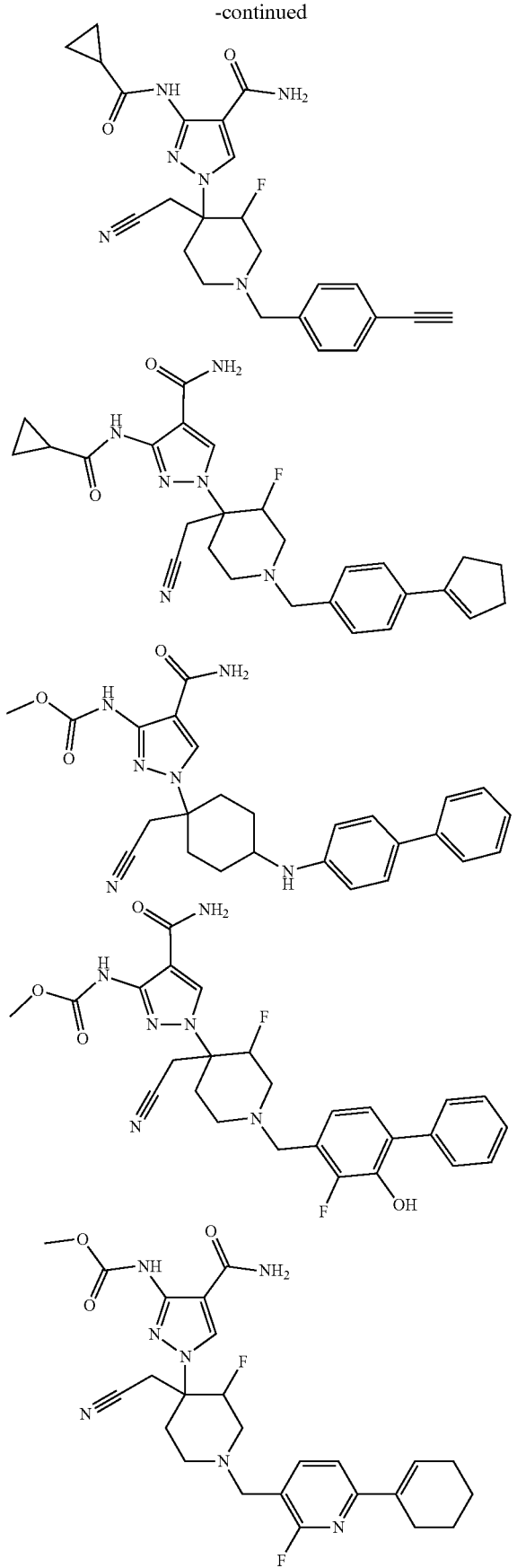
714
-continued
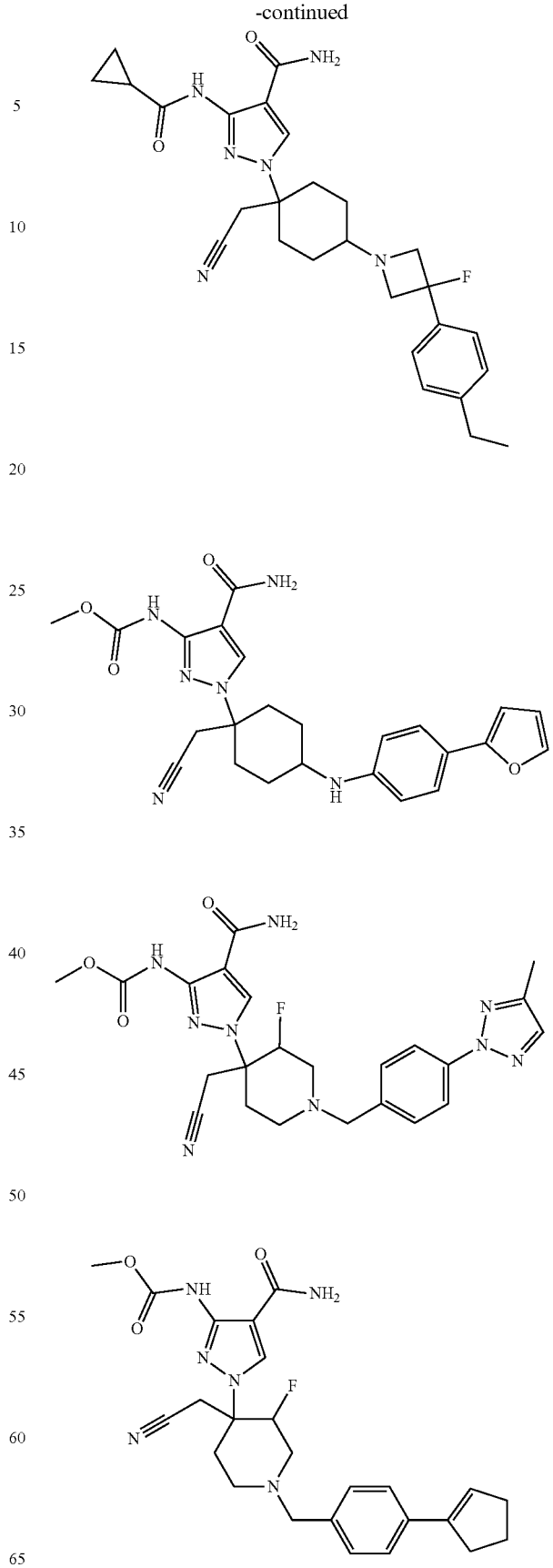

715
-continued
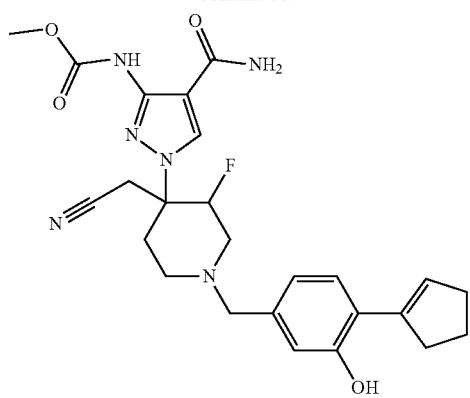
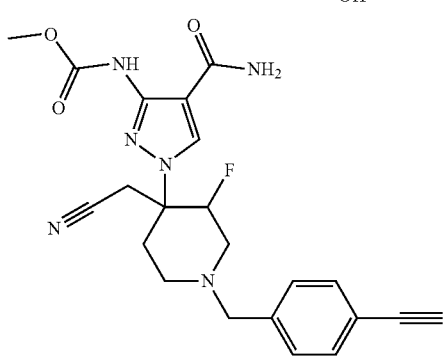
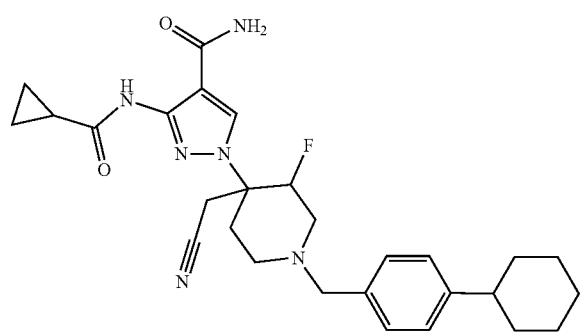
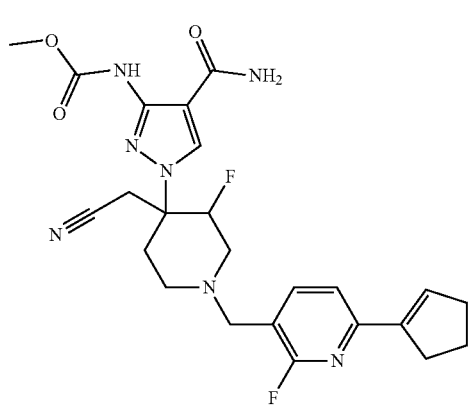
716
-continued
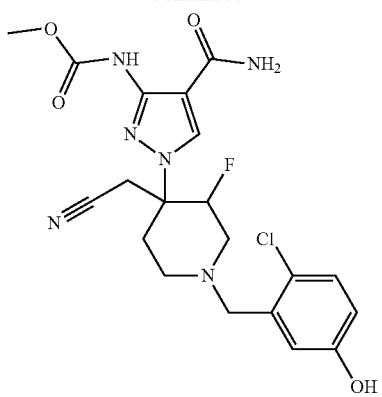
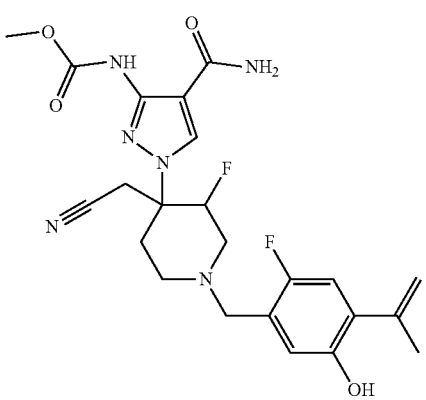
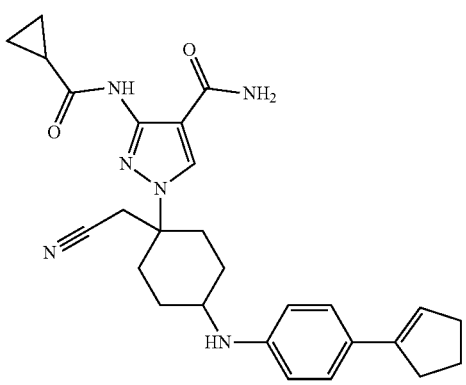
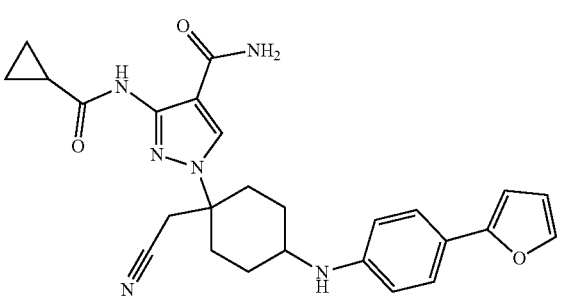

717
-continued
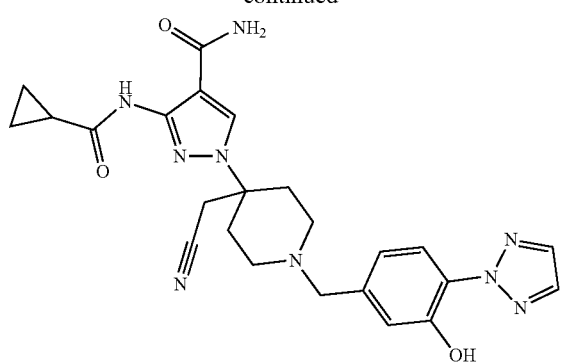
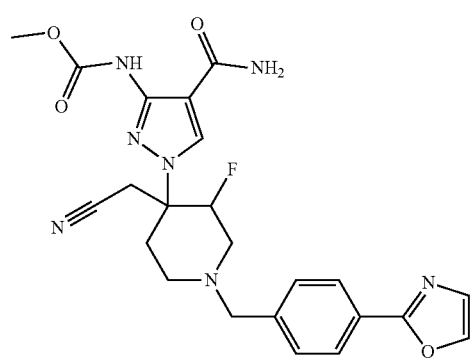
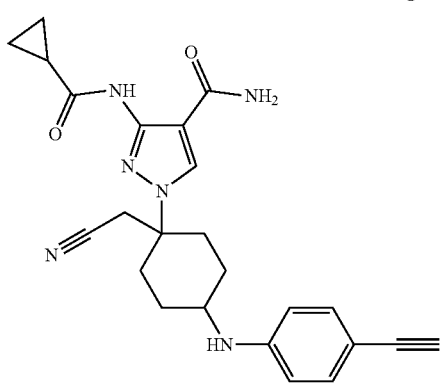
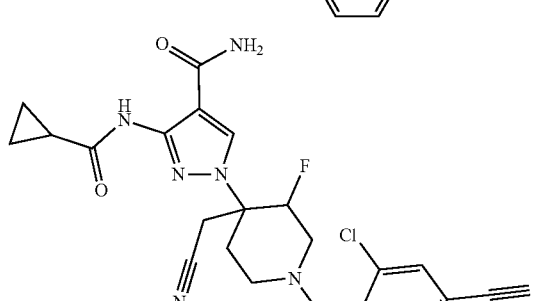
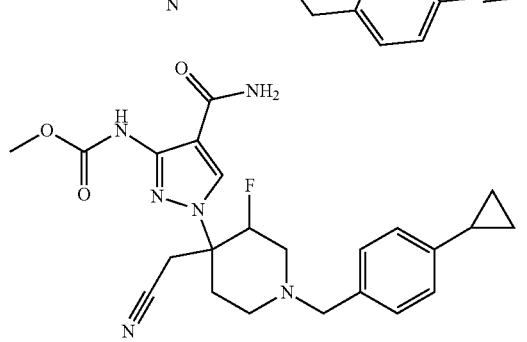
718
-continued
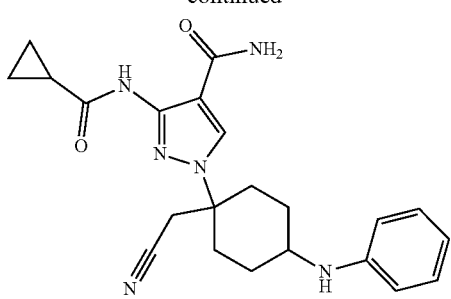
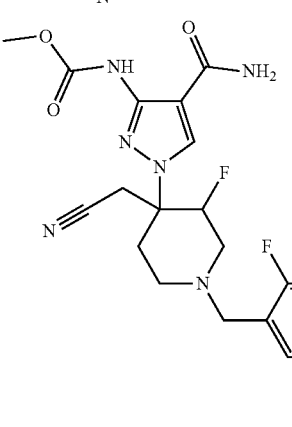
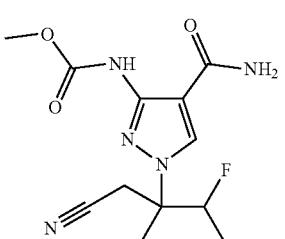
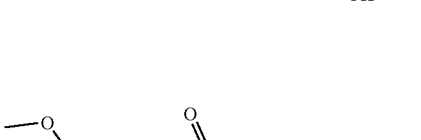
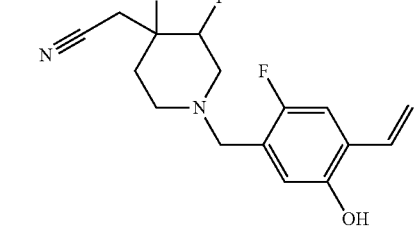

719
-continued
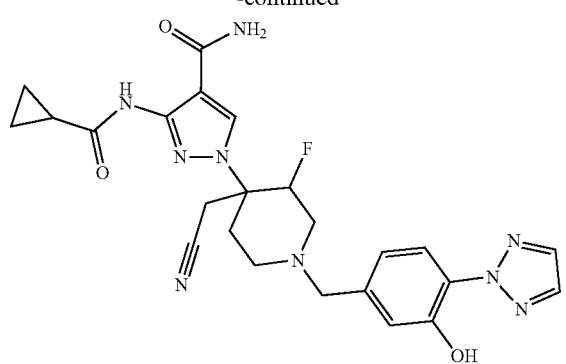
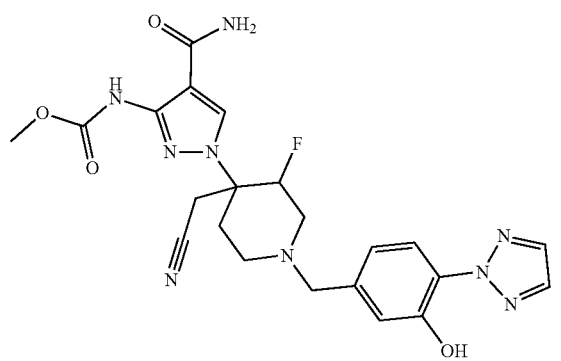
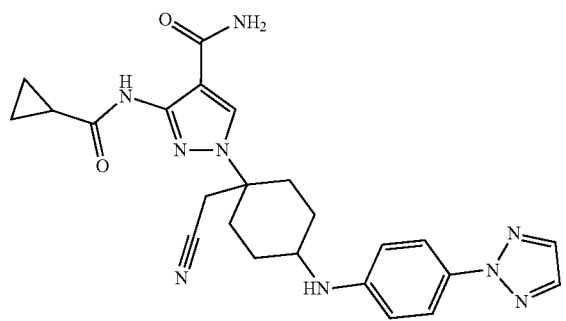
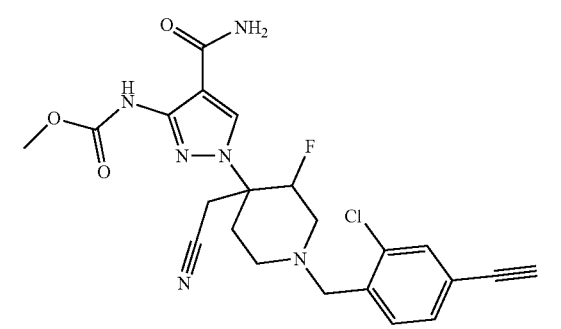
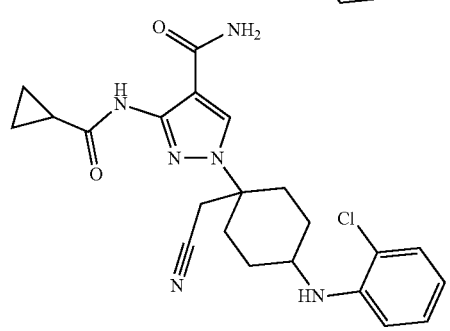
720
-continued
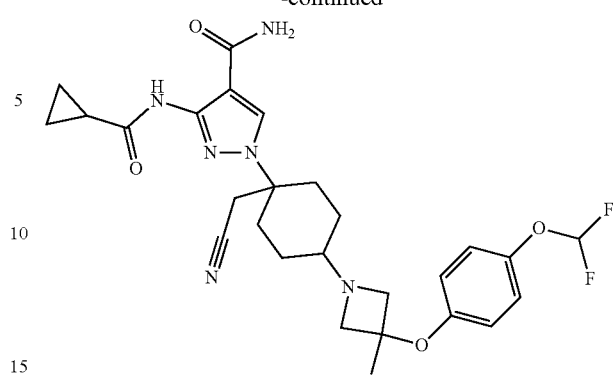
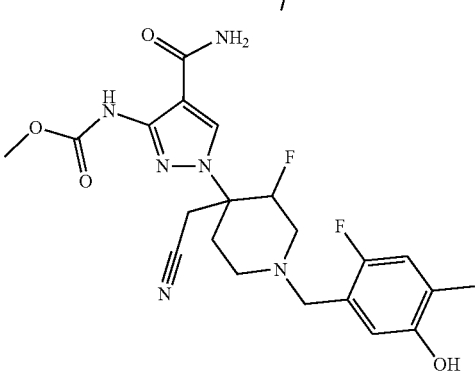
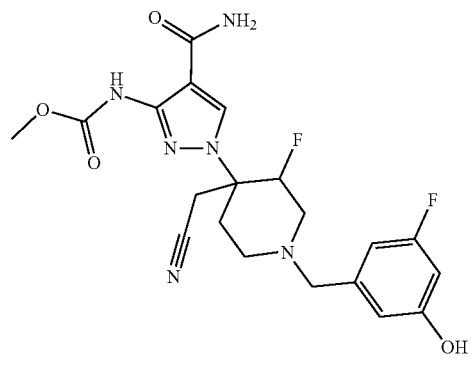
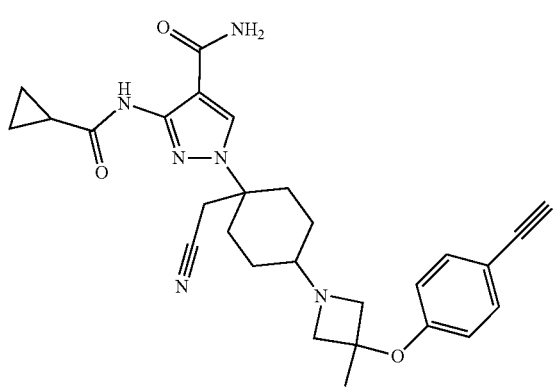

721
-continued
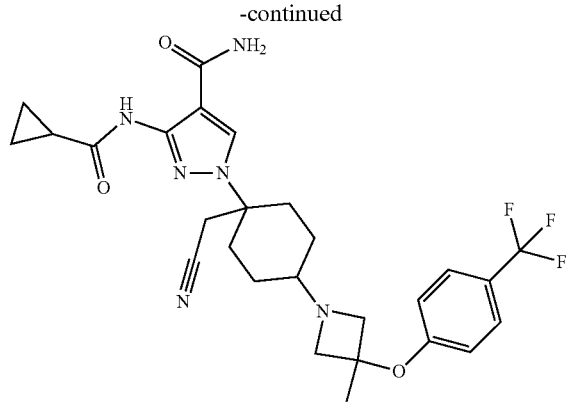
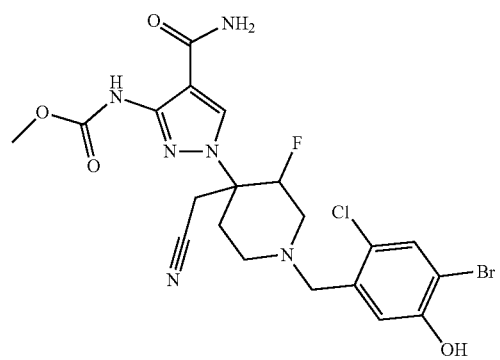
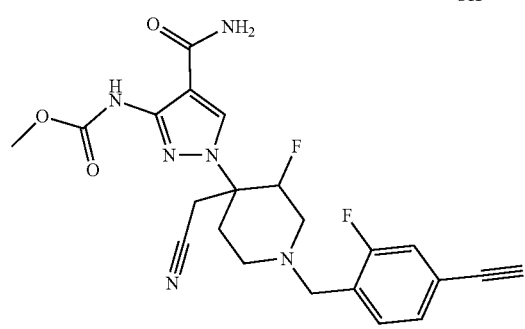
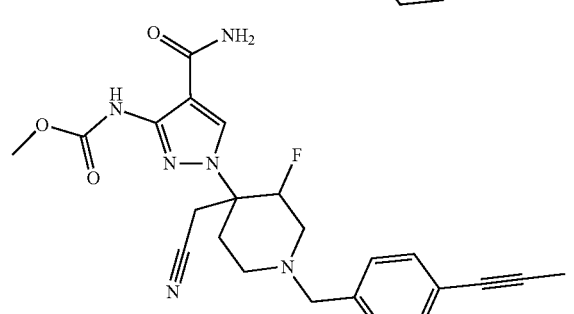
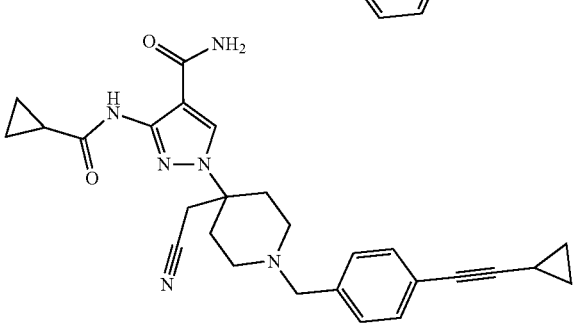
722
-continued
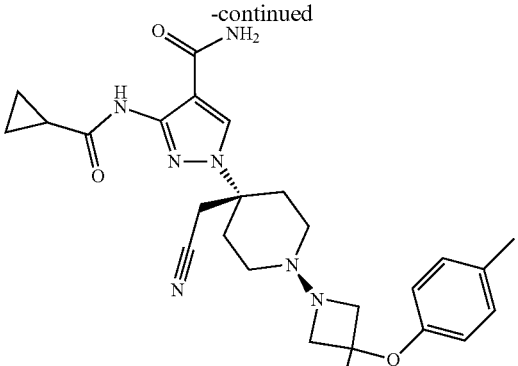
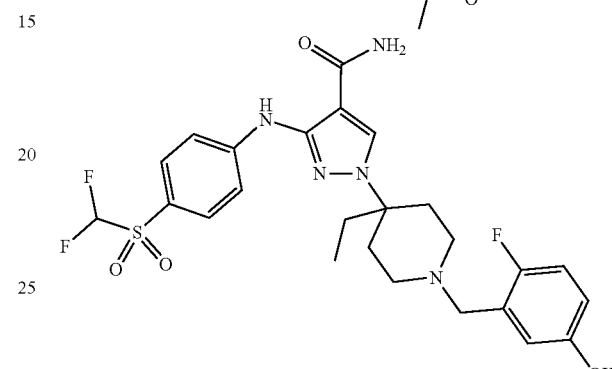
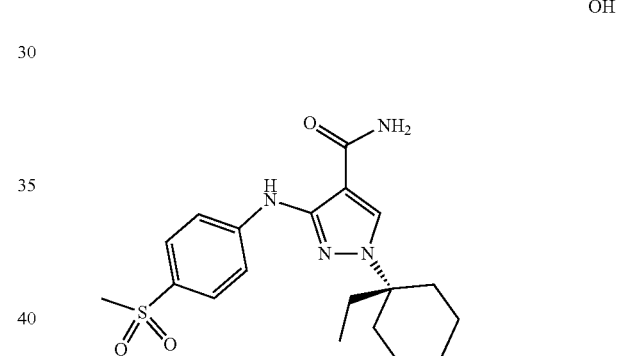
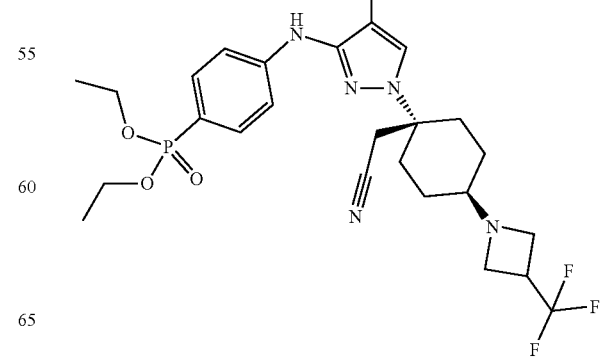

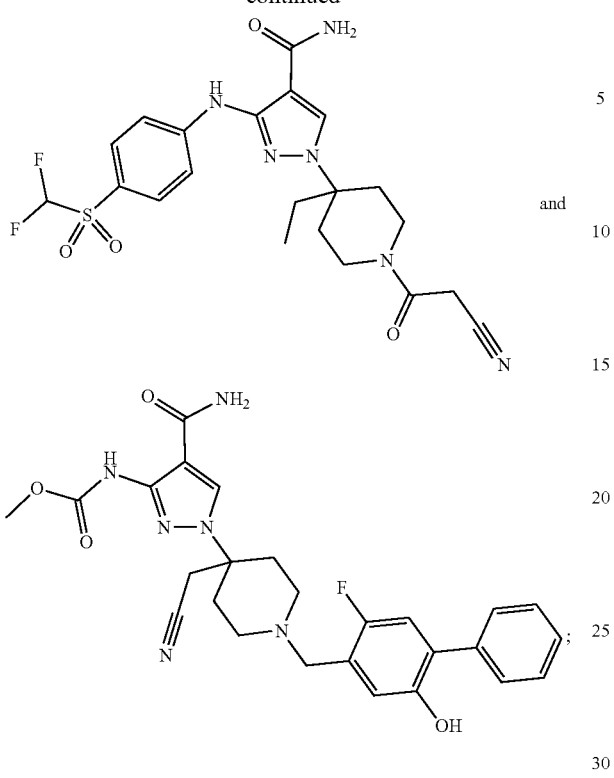
or a pharmaceutically acceptable salt thereof.
7. The compound of claim 6 or a pharmaceutically acceptable salt thereof, selected from the group consisting of:
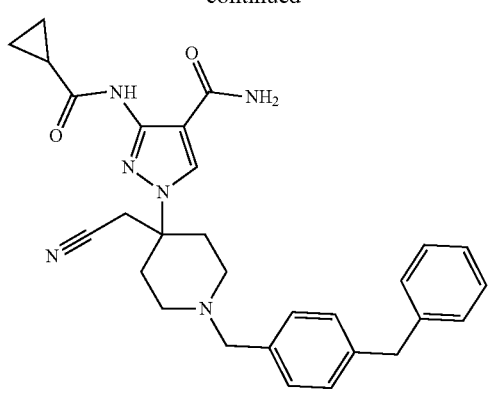
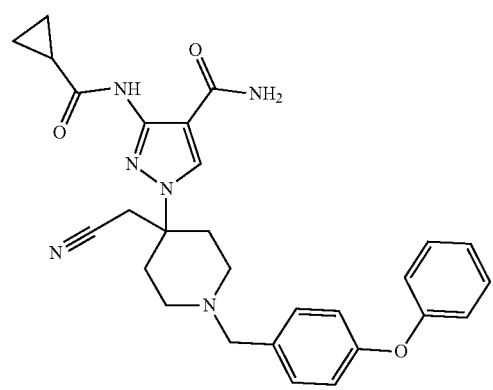
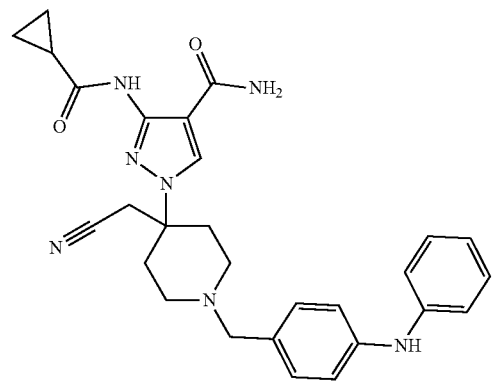
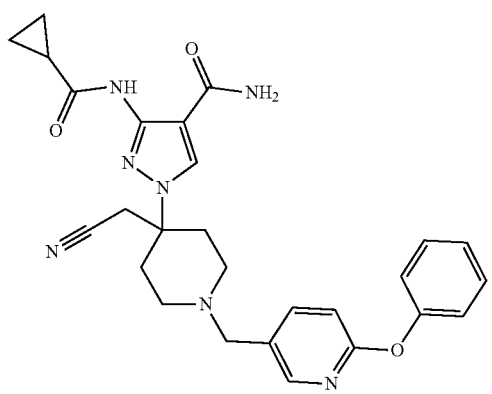
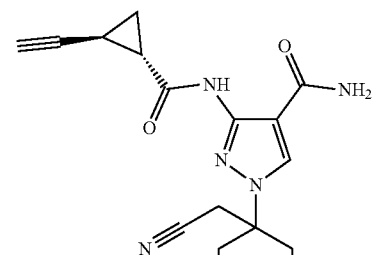
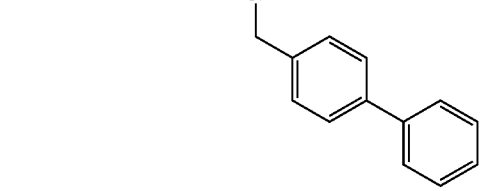

725
-continued
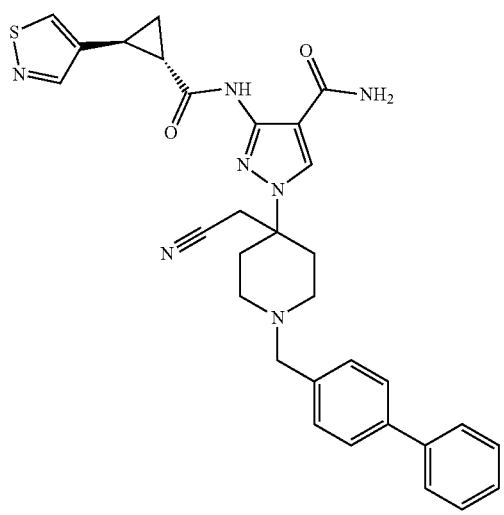
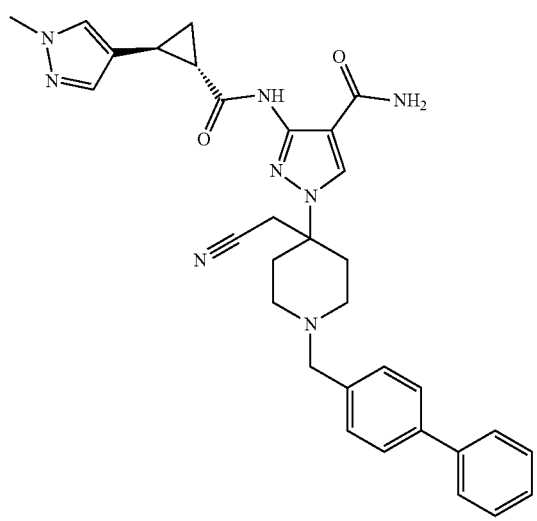
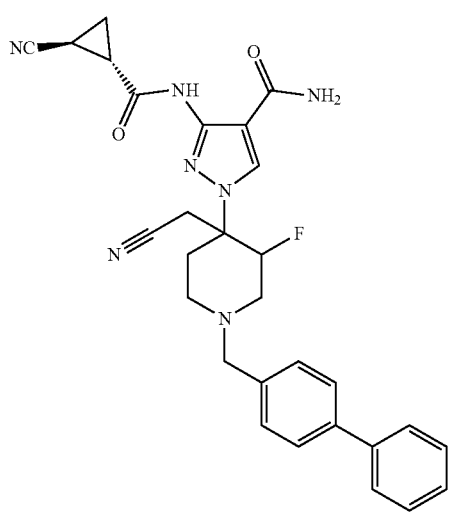
726
-continued
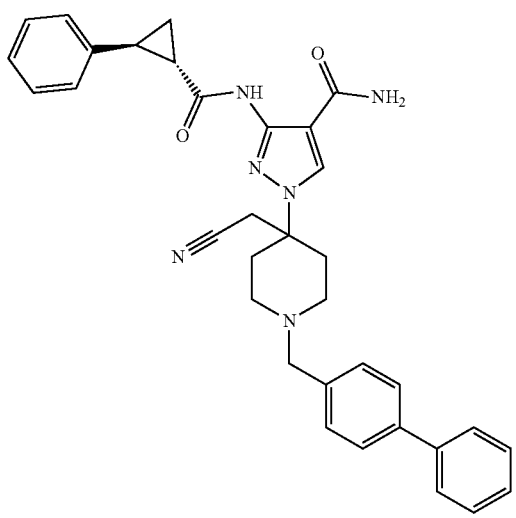
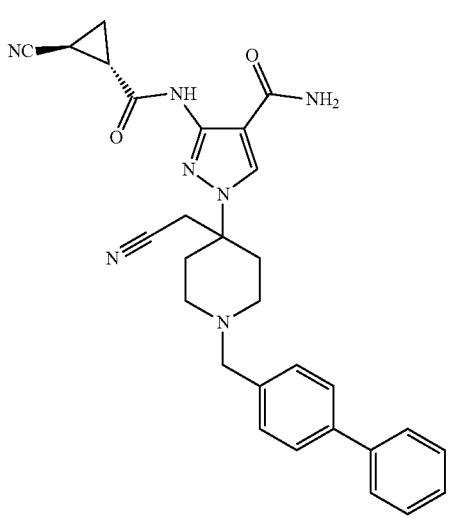
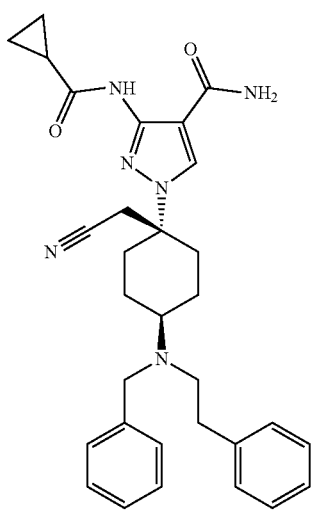

727
-continued
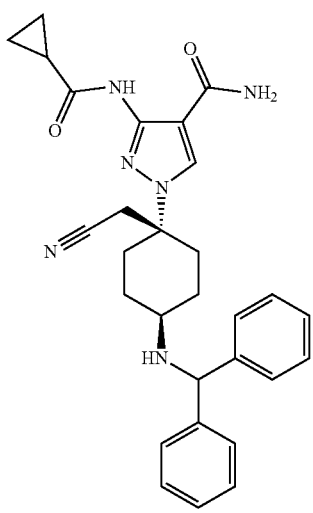
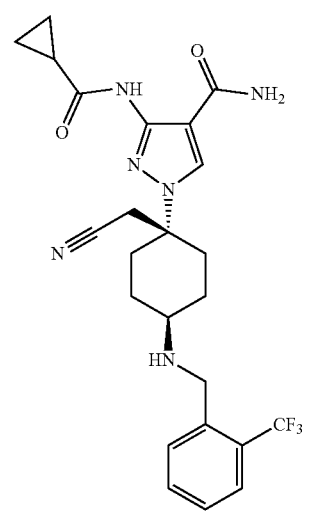
728
-continued
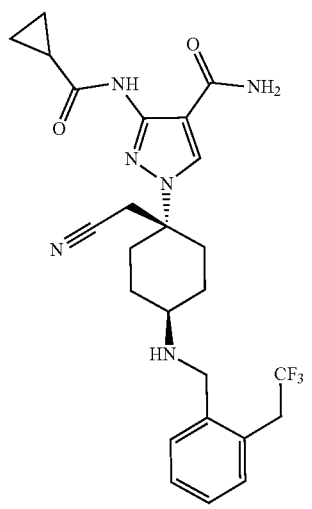
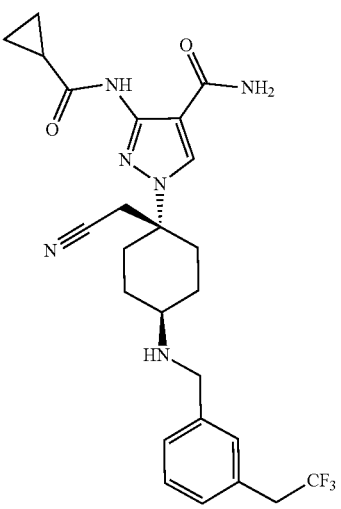
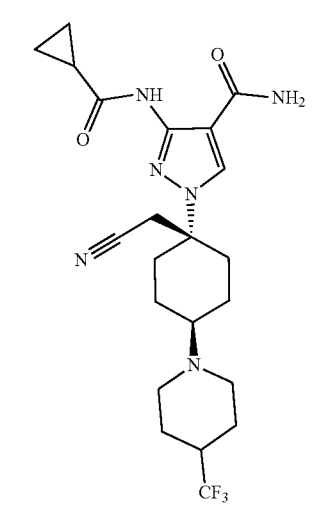

729
-continued
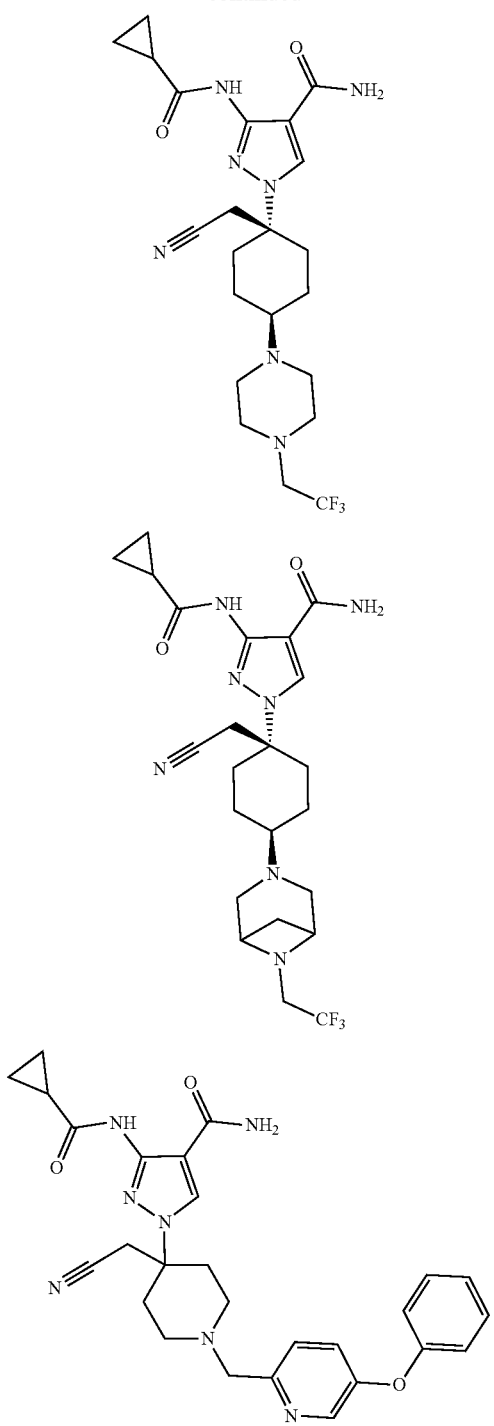
730
-continued
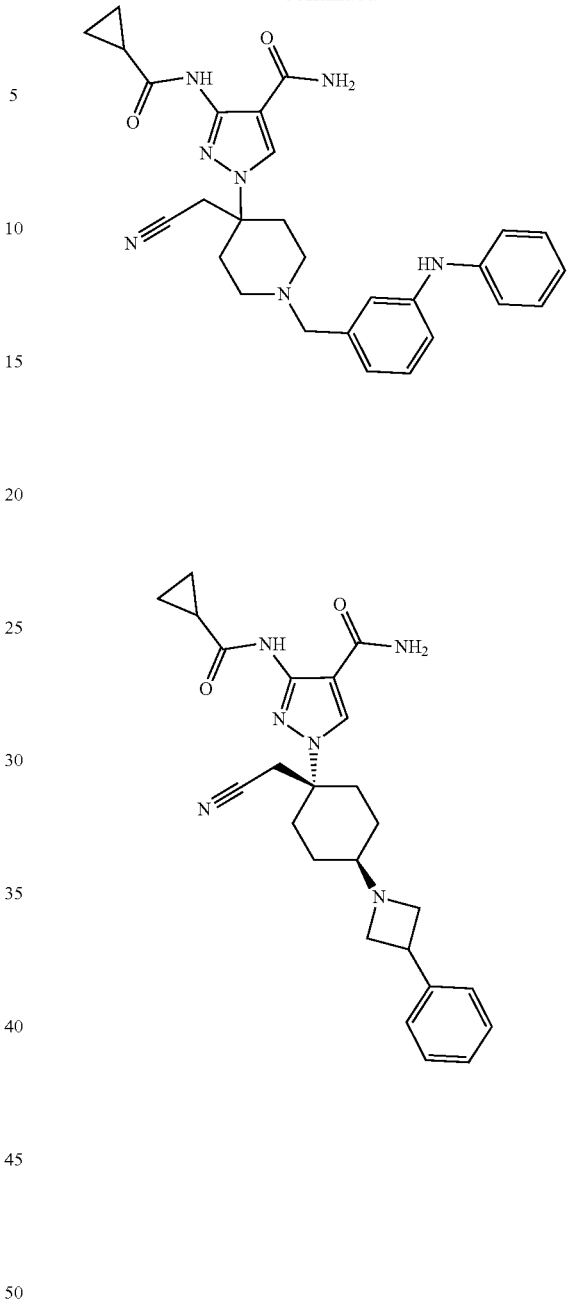
8. A pharmaceutical composition comprising a compound of claim 1 or a pharmaceutically acceptable salt thereof, and a pharmaceutically acceptable carrier, diluent or excipient.
* * * * *